US008513164B2

(12) United States Patent
Knappik et al.

(10) Patent No.: US 8,513,164 B2
(45) **Date of Patent: *Aug. 20, 2013**

(54) PROTEIN (POLY)PEPTIDES LIBRARIES

(75) Inventors: Achim Knappik, Gräfelfing (DE); Peter Pack, München (DE); Liming Ge, München (DE); Simon Moroney, München (DE); Andreas Plückthun, Zürich (CH)

(73) Assignee: MorphoSys AG, Martinsried/Planegg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/642,593

(22) Filed: Dec. 21, 2006

(65) Prior Publication Data

US 2008/0026948 A1 Jan. 31, 2008

Related U.S. Application Data

(60) Division of application No. 10/834,397, filed on Apr. 29, 2004, which is a division of application No. 09/490,324, filed on Jan. 24, 2000, now Pat. No. 6,828,422, which is a continuation of application No. PCT/EP96/03647, filed on Aug. 19, 1996.

(30) Foreign Application Priority Data

Aug. 18, 1995 (EP) .................................... 95113021

(51) Int. Cl.
*C40B 20/06* (2006.01)
*C40B 30/04* (2006.01)

(52) U.S. Cl.
USPC ................ 506/5; 506/2; 530/387.1; 530/350; 435/7.1

(58) Field of Classification Search
USPC ................ 506/5, 2; 530/387.1, 350; 435/7.1
See application file for complete search history.

(56) References Cited

U.S. PATENT DOCUMENTS

| | | | | |
|---|---|---|---|---|
| 4,395,750 | A | 7/1983 | Scheidemann | |
| 5,091,513 | A * | 2/1992 | Huston et al. | 530/387.3 |
| 5,395,750 | A | 3/1995 | Dillon | |
| 5,476,786 | A | 12/1995 | Huston | |
| 5,482,858 | A | 1/1996 | Huston | |
| 5,565,332 | A * | 10/1996 | Hoogenboom et al. | 435/69.1 |
| 5,580,717 | A | 12/1996 | Dower | |
| 5,693,493 | A | 12/1997 | Robinson et al. | |
| 5,693,761 | A | 12/1997 | Queen et al. | |
| 5,780,225 | A | 7/1998 | Wigler | |
| 5,840,479 | A | 11/1998 | Little et al. | |
| 5,855,885 | A | 1/1999 | Smith | |
| 5,859,205 | A * | 1/1999 | Adair et al. | 530/387.3 |
| 5,885,793 | A | 3/1999 | Griffiths | |
| 5,969,108 | A | 10/1999 | McCafferty | |
| 5,977,322 | A * | 11/1999 | Marks et al. | 530/388.85 |
| 6,096,551 | A | 8/2000 | Barbas | |
| 6,248,516 | B1 | 6/2001 | Winter | |
| 6,291,158 | B1 | 9/2001 | Winter | |
| 6,291,159 | B1 | 9/2001 | Winter | |
| 6,291,160 | B1 | 9/2001 | Lerner | |
| 6,291,161 | B1 | 9/2001 | Lerner | |
| 6,300,064 | B1 | 10/2001 | Knappik | |
| 6,303,313 | B1 | 10/2001 | Wigler | |
| 6,696,248 | B1 | 2/2004 | Knappik | |
| 6,706,484 | B1 | 3/2004 | Knappik et al. | |
| 6,828,422 | B1 | 12/2004 | Achim | |
| 7,264,963 | B1 | 9/2007 | Knappik | |
| 2006/0018898 | A1 * | 1/2006 | Waldmann et al. | 424/130.1 |

FOREIGN PATENT DOCUMENTS

| | | |
|---|---|---|
| EP | 0368684 | 5/1990 |
| WO | 9306213 | 4/1993 |
| WO | 9511998 | 5/1995 |
| WO | 9522625 | 8/1995 |

OTHER PUBLICATIONS de Kruif et al., J. Mol. Biol., 248:97-105 (1995).*
Sonderlind et al, Nature Biotechnology (2000), 18(8), 852-856.*
Jones et al ,Nature, vol. 321, 1986, pp. 522-525.*
Schier et al , J. Mot, Biol. (1996) 263, 551-567.*
Nissum et al., Antibody fragments from a 'single pot' phage display library as immunochemical reagents, EMBO Journal vol. 13 No. 3 pp. 692-698 (1994).
Maneewannakul (Plasmid 1994 vol. 31, 300-307).
Winter Making antibodies by phage display technology, annual review of immunology, Annual Reviews Inc, US, vol. 12, 1994, pp. 433-455, XP000564245 ISSN: 0732-0582.
Collett A binarly plasmid system for shuffling combinatorial antibodies libraries PNAC, vol. 89, No. 21, Nov. 1, 1992, p. 10026-10030.
Knappik and Pluckthun Engineered turns of a recombinant antibody improve ist in vivo folding, Protein Engineering, 8(1), 81-89 (1995).
Deng, S.J. Selection of antibody single-chain variable fragments with improved carbohydrate binding by phage display. J. Biol. Chem. 269, 9533 (1994).
Cox A directory of human germ-line Vk segments reveals a strong bias in their usage, Eur. J. Immunol. 1994, 24:827-836.
Tomlinson The repertoire of human germline Vh sequences reveals about 50 groups of Vh segments with different hypervariable loops, J. Mol. Biol. (1992) 227, 776-799.
Foote Antibody framework residues affecting the conformation of the hypervariable loops, J. Mol. Biol. 224, 487-499 (1992).
Gram In vitro and affinity maturation of antibodies from a naive conbinatorial immunoglobulin library, PNAS, 89 (8), 3576-3580 (1992).
Waterhouse Combinatorial infection and in vivo recombination: as strategy for making large phage antibody repertoires, Nucl. Acids Res. 21(9), 2265-2266 (1993).
Williams Cloning and sequences of human Vlambda gene segments, Eur. J. Immunol. 23, 1456-1461 (1993).
Marks By passing immunization: building high affinity antibodies by chain shuffling, 1992 Biotechnology 10:779-783.
Hoogenboom, Building antibodies from their genes, 1992 Immunlogical review, 130: 41-68.
Griffiths isolation of high affinity human antibodies directly from large synthetic repertoires, 1994 EMBO J. 13:3245-3260.

(Continued)

*Primary Examiner* — Teresa D. Wessendorf

(57) ABSTRACT

The present invention relates to a method of identifying one or more genes encoding one or more proteins having an optimized property. In particular, the method comprises expressing a collection of genes and screening for a desired property, identifying a plurality of genes having the desired property, and replacing one or more one or more sub-sequences of each of said genes with a different, compatible genetic sub-sequence, and screening again in order to identify genes encoding proteins having an optimized property.

8 Claims, 220 Drawing Sheets

(56) References Cited

OTHER PUBLICATIONS

Figure 1:
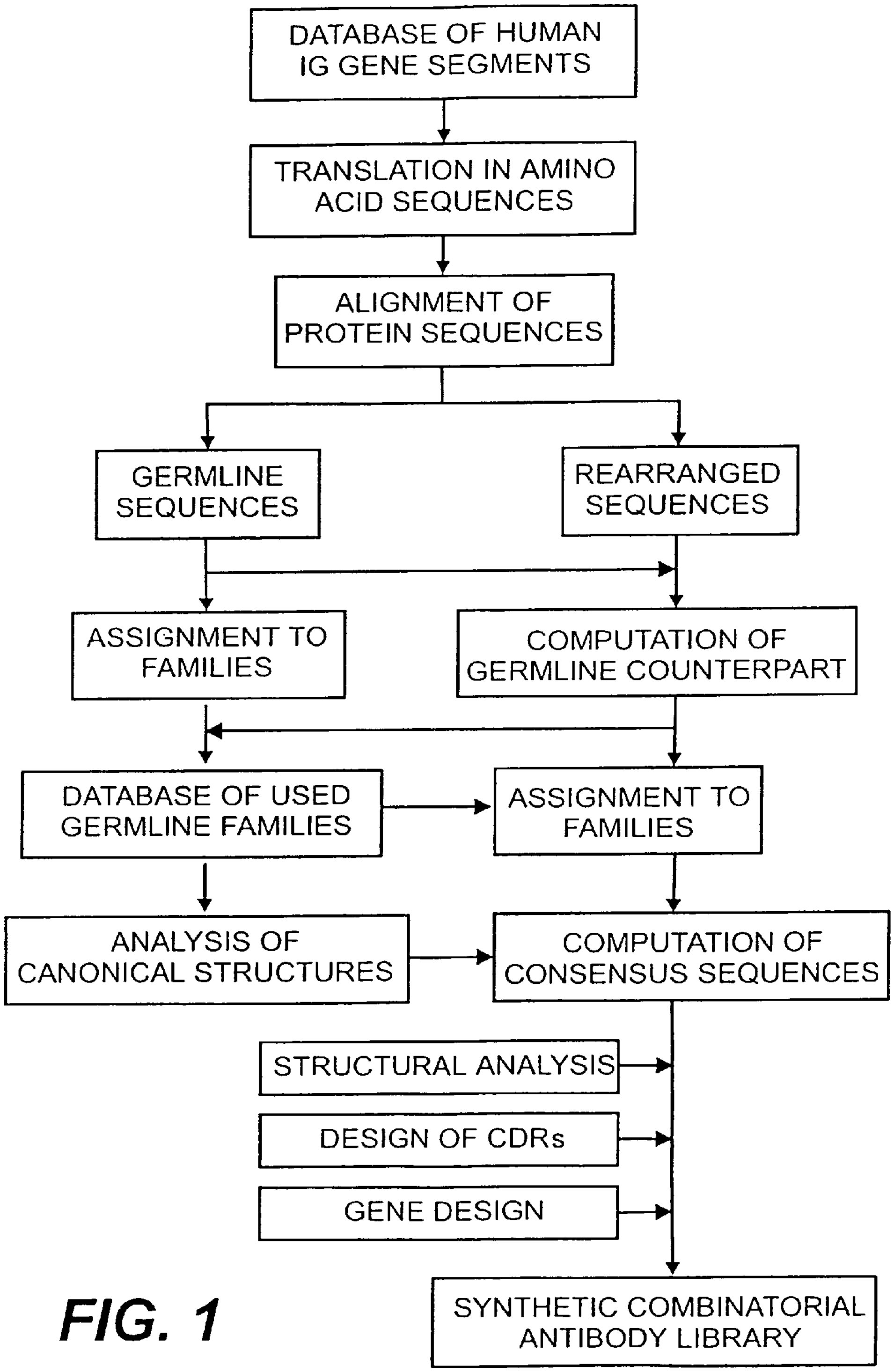
Figure 7E:
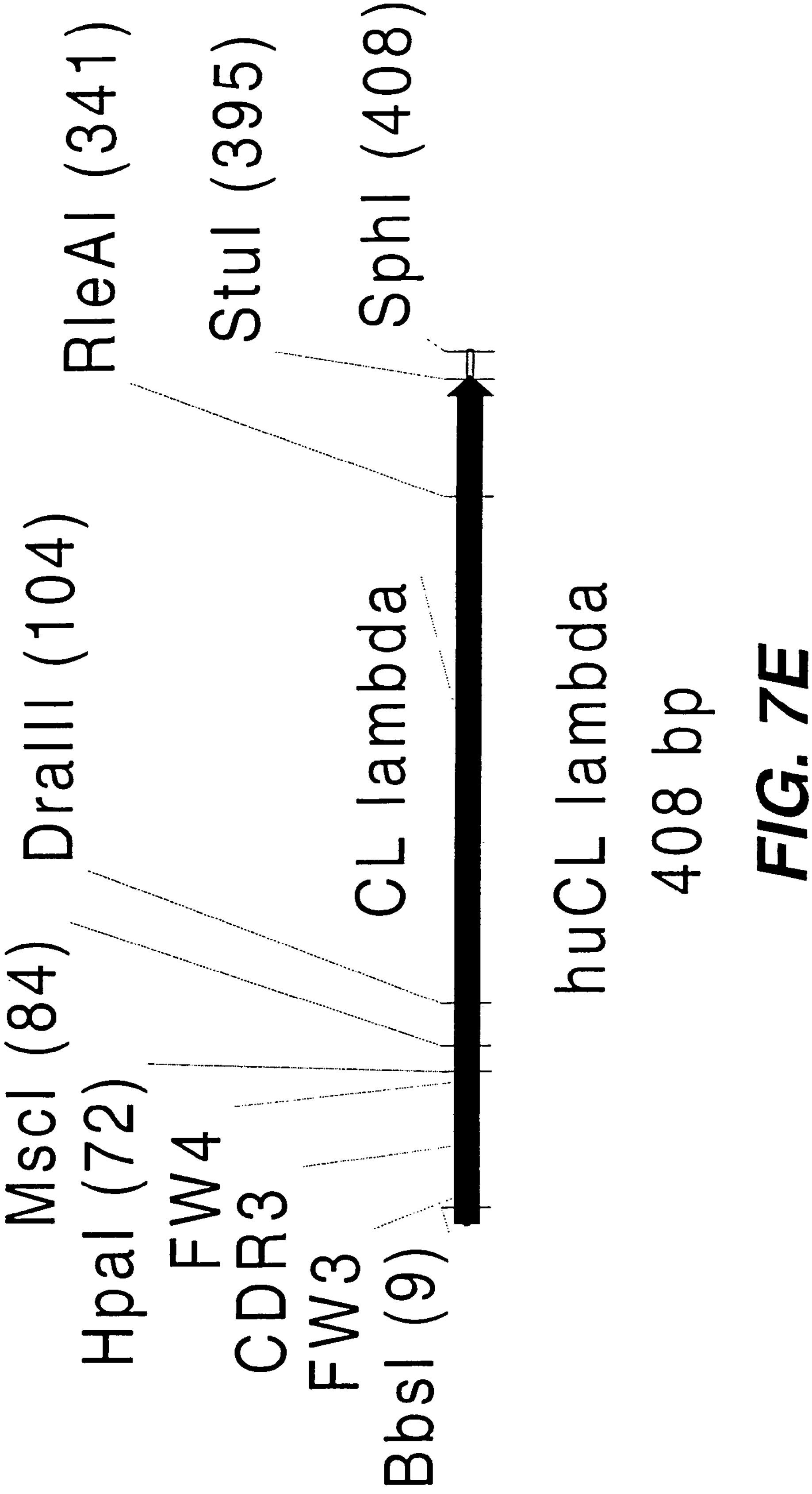

Winter and Milstein, Man made antibodies, 1991 Nature 349:293-299.
Anderson DE, et al.: "Hypervariable epitope constructs as a means of accounting for epitope variability", Vaccine. Jun. 1994;12(8):736-40.
Davis Julian, et al.: "An antibody VH domain with a Iox-Cre site integrated into ist coding region: bacterial recombination with a single polypeptide chain", FEBS Letter 377 (1995) 92-96.
Krawinkel Ulrich, et al.: "Recombination between antibody heavy chain variable-region genes: Evidence for gene conversion" , Proc Nat. Acad. Sci. USA, vol. 80, pp. 4997-5001, Aug. 1983.
Prak Eline L., et al.: "Light Chain Replacement: A New Model for Antibody Gene Rearrangement", 1995.
John De Kruif et al., "Selection and Application of Human Single Chain Fv Antibody Fragments from a semi-synthetic Phage Antibody Display Library with Designed CDR3 Regions", J. Mol. Biol. (1995) 248, pp. 97-105.
Robert Schier et al., "Identification of functional and structural amino-acid residues by parsimonious mutagenesis", Gene, 169, 1996, pp. 147-155.
Lisa J. Garrard et al., "Selection of an anti-IGF-1 Fab from a Fab phage library created by mutagenesis of multiple CDR loops", Gene, 128, 1993, pp. 103-109.
Carlos F. Barbas, III, "Semisynthetic combinatorial antibody libraries: A Chemical solution to the diversity problem", Proc. Natl. Acad. Sci. USA, vol. 89, May 1992, p. 4457-4461.

* cited by examiner

| | framework 1 | | | | | | | | | | | | | | | | | | | | | | | CDRI | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C |
| Vk1 | D | I | Q | M | T | Q | S | P | S | S | L | S | A | S | V | G | D | R | V | T | I | T | C | R | A | S | Q | - | - | - |
| Vk2 | D | I | V | M | T | Q | S | P | L | S | L | P | V | T | P | G | E | P | A | S | I | S | C | R | S | S | Q | S | L | L |
| Vk3 | D | I | V | L | T | Q | S | P | A | T | L | S | L | S | P | G | E | R | A | T | L | S | C | R | A | S | Q | S | - | - |
| Vk4 | D | I | V | M | T | Q | S | P | D | S | L | A | V | S | L | G | E | R | A | T | I | N | C | R | S | S | Q | S | V | L |

| | CDRI | | | | | | | | | | framework 2 | | | | | | | | | | | | | | | CDR II | | | | |
|---|---|---|---|---|---|---|---|---|---|---|---|---|---|---|---|---|---|---|---|---|---|---|---|---|---|---|---|---|---|---|
| | D | E | F | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 |
| Vk5 | - | - | - | G | I | S | S | Y | L | A | W | Y | Q | Q | K | P | G | K | A | P | K | L | L | I | Y | A | A | S | S | L |
| Vk6 | H | S | - | N | G | Y | N | Y | L | D | W | Y | L | Q | K | P | G | Q | S | P | Q | L | L | I | Y | L | G | S | N | R |
| Vk7 | - | - | - | V | S | S | S | Y | L | A | W | Y | Q | Q | K | P | G | Q | A | P | R | L | L | I | Y | G | A | S | S | R |
| Vk8 | Y | S | S | N | N | K | N | Y | L | A | W | Y | Q | Q | K | P | G | Q | P | P | K | L | L | I | Y | W | A | S | T | R |

FIG. 2A

| | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|
| | CDRII | | framework 3 | | | | | | | | | | | | | | | | | | | | | | | | | | | |
| Vk1 | Q | S | G | V | P | S | R | F | S | G | S | G | S | G | T | D | F | T | L | T | I | S | S | L | Q | P | E | D | F | A |
| Vk2 | A | S | G | V | P | D | R | F | S | G | S | G | S | G | T | D | F | T | L | K | I | S | R | V | E | A | E | D | V | G |
| Vk3 | A | T | G | V | P | A | R | F | S | G | S | G | S | G | T | D | F | T | L | T | I | S | S | L | E | P | E | D | F | A |
| Vk4 | E | S | G | V | P | D | R | F | S | G | S | G | S | G | T | D | F | T | L | T | I | S | S | L | Q | A | E | D | V | A |

| | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 |
|---|---|---|---|---|---|---|---|---|---|---|---|---|---|---|---|---|---|---|---|---|---|---|---|---|---|
| | framework 3 | | | | | CDRIII | | | | | | | framework 4 | | | | | | | | | | | | |
| Vk1 | T | Y | Y | C | Q | Q | H | Y | T | T | P | P | T | F | G | Q | G | T | K | V | E | I | K | R | T |
| Vk2 | V | Y | Y | C | Q | Q | H | Y | T | T | P | P | T | F | G | Q | G | T | K | V | E | I | K | R | T |
| Vk3 | V | Y | Y | C | Q | Q | H | Y | T | T | P | P | T | F | G | Q | G | T | K | V | E | I | K | R | T |
| Vk4 | V | Y | Y | C | Q | Q | H | Y | T | T | P | P | T | F | G | Q | G | T | K | V | E | I | K | R | T |

FIG. 2B

| | framework 1 | | | | | | | | | | | | | | | | | | | | | | | CDRI | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | D | E | 28 |
| vλ1 | Q | S | V | L | T | Q | P | P | S | - | V | S | G | A | P | G | Q | R | V | T | I | S | C | S | G | S | S | S | N | I |
| vλ2 | Q | S | A | L | T | Q | P | A | S | - | V | S | G | S | P | G | Q | S | I | T | I | S | C | T | G | T | S | S | D | V |
| vλ3 | S | Y | E | L | T | Q | P | P | S | - | V | S | V | A | P | G | Q | T | A | R | I | S | C | S | G | D | A | - | - | L |

| | CDRI | | | | | | framework 2 | | | | | | | | | | | | | | | CDR II | | | | | | | |
|---|---|---|---|---|---|---|---|---|---|---|---|---|---|---|---|---|---|---|---|---|---|---|---|---|---|---|---|---|---|---|
| | 29 | 30 | 31 | A | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 |
| vλ1 | G | S | N | - | Y | V | S | W | Y | Q | Q | L | P | G | T | A | P | K | L | L | I | Y | D | N | N | Q | R | P | S | G |
| vλ2 | G | G | Y | N | Y | V | S | W | Y | Q | Q | H | P | G | K | A | P | K | L | M | I | Y | D | V | S | N | R | P | S | G |
| vλ3 | G | D | K | - | Y | A | S | W | Y | Q | Q | K | P | G | Q | A | P | V | L | V | I | Y | D | D | S | D | R | P | S | G |

FIG. 2C

| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 |
|---|---|---|---|---|---|---|---|---|---|---|---|---|---|---|---|---|---|---|---|---|---|---|---|---|---|---|---|---|---|---|
| | framework 3 | | | | | | | | | | | | | | | | | | | | | | | | | | | | | |
| vλ1 | V | P | D | R | F | S | G | S | K | S | G | T | S | A | S | L | A | I | T | G | L | Q | S | E | D | E | A | D | Y | Y |
| vλ2 | V | S | N | R | F | S | G | S | K | S | G | N | T | A | S | L | T | I | S | G | L | Q | A | E | D | E | A | D | Y | Y |
| vλ3 | I | P | E | R | F | S | G | S | N | S | G | N | T | A | T | L | T | I | S | G | T | Q | A | E | D | E | A | D | Y | Y |

| | 88 | 89 | 90 | 91 | 92 | 93 | 94 | 95 | 96 | 97 | 98 | 99 | 100 | 101 | 102 | 103 | 104 | 105 | 106 | A | 107 |
|---|---|---|---|---|---|---|---|---|---|---|---|---|---|---|---|---|---|---|---|---|---|
| | | CDRIII | | | | | | | | framework 4 | | | | | | | | | | | |
| vλ1 | C | Q | Q | H | Y | T | T | P | P | V | F | G | G | G | T | K | L | T | V | L | G |
| vλ2 | C | Q | Q | H | Y | T | T | P | P | V | F | G | G | G | T | K | L | T | V | L | G |
| vλ3 | C | Q | Q | H | Y | T | T | P | P | V | F | G | G | G | T | K | L | T | V | L | G |

FIG. 2D

| | framework 1 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| VH1A | Q | V | Q | L | V | Q | S | G | A | E | V | K | K | P | G | S | S | V | K | V | S | C | K | A | S | G | G | T | F | S |
| VH1B | Q | V | Q | L | V | Q | S | G | A | E | V | K | K | P | G | A | S | V | K | V | S | C | K | A | S | G | Y | T | F | T |
| VH2 | Q | V | Q | L | K | E | S | G | P | A | L | V | K | P | T | Q | T | L | T | L | T | C | T | F | S | G | F | S | L | S |
| VH3 | E | V | Q | L | V | E | S | G | G | G | L | V | Q | P | G | G | S | L | R | L | S | C | A | A | S | G | F | T | F | S |
| VH4 | Q | V | Q | L | Q | E | S | G | P | G | L | V | K | P | S | E | T | L | S | L | T | C | T | V | S | G | G | S | I | S |
| VH5 | E | V | Q | L | V | Q | S | G | A | E | V | K | K | P | G | E | S | L | K | I | S | C | K | G | S | G | Y | S | F | T |
| VH6 | Q | V | Q | L | Q | Q | S | G | P | G | L | V | K | P | S | Q | T | L | S | L | T | C | A | I | S | G | D | S | V | S |

| | CDRI | | | | | | | | framework 2 | | | | | | | | | | | | | | | | CDR II | | | | | | | |
|---|---|---|---|---|---|---|---|---|---|---|---|---|---|---|---|---|---|---|---|---|---|---|---|---|---|---|---|---|---|---|---|---|
| | 31 | A | B | 32 | 33 | 34 | 35 | 36 | 37 | 38 | 39 | 40 | 41 | 42 | 43 | 44 | 45 | 46 | 47 | 48 | 49 | 50 | 51 | 52 | A | B | C | 53 | 54 | 55 | 56 | 57 |
| VH1A | S | - | - | Y | A | I | S | W | V | R | Q | A | P | G | Q | G | L | E | W | M | G | G | I | I | P | - | - | I | F | G | T | A |
| VH1B | S | - | - | Y | Y | M | H | W | V | R | Q | A | P | G | Q | G | L | E | W | M | G | W | I | N | P | - | - | N | S | G | G | T |
| VH2 | T | S | G | V | G | V | G | W | I | R | Q | P | P | G | K | A | L | E | W | L | A | L | I | D | - | - | - | W | D | D | D | K |
| VH3 | S | - | - | Y | A | M | S | W | V | R | Q | A | P | G | K | G | L | E | W | V | S | A | I | S | G | - | - | S | G | G | S | T |
| VH4 | S | - | - | Y | Y | W | S | W | I | R | Q | P | P | G | K | G | L | E | W | I | G | Y | I | Y | - | - | - | Y | S | G | S | T |
| VH5 | S | - | - | Y | W | I | G | W | V | R | Q | M | P | G | K | G | L | E | W | M | G | I | I | Y | P | - | - | G | D | S | D | T |

FIG. 2E

| | |
|---|---|
| VH6 | S N S A A W N W I R Q S P G R G L E W L G R T Y Y R - S K W Y N |

| | CDRII | | | | | | | | | | framework 3 | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C | 83 | 84 | 85 |
| VH1A | N | Y | A | Q | K | F | Q | G | R | V | T | I | T | A | D | E | S | T | S | T | A | Y | M | E | L | S | S | L | R | S | E |
| VH1B | N | Y | A | Q | K | F | Q | G | R | V | T | M | T | R | D | T | S | I | S | T | A | Y | M | E | L | S | S | L | R | S | E |
| VH2 | Y | Y | S | T | S | L | K | T | R | L | T | I | S | K | D | T | S | K | N | Q | V | V | L | T | M | T | N | M | D | P | V |
| VH3 | Y | Y | A | D | S | V | K | G | R | F | T | I | S | R | D | N | S | K | N | T | L | Y | L | Q | M | N | S | L | R | A | E |
| VH4 | N | Y | N | P | S | L | K | S | R | V | T | I | S | V | D | T | S | K | N | Q | F | S | L | K | L | S | S | V | T | A | A |
| VH5 | R | Y | S | P | S | F | Q | G | Q | V | T | I | S | A | D | K | S | I | S | T | A | Y | L | Q | W | S | S | L | K | A | S |
| VH6 | D | Y | A | V | S | V | K | S | R | I | T | I | N | P | D | T | S | K | N | Q | F | S | L | Q | L | N | S | V | T | P | E |

| | framework 3 | | | | | | | | | | CDRIII | | | | | | | | | | | | | framework 4 | | | | | | | |
|---|---|---|---|---|---|---|---|---|---|---|---|---|---|---|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 99 | 100 | A | B | C | 101 | 102 | 103 | 104 | 105 | 106 | 107 | 108 | 109 | 110 | 111 | 112 | 113 |
| VH1A | D | T | A | V | Y | Y | C | A | R | W | G | G | D | G | F | Y | A | M | D | Y | W | G | Q | G | T | L | V | T | V | S | S |
| VH1B | D | T | A | V | Y | Y | C | A | R | W | G | G | D | G | F | Y | A | M | D | Y | W | G | Q | G | T | L | V | T | V | S | S |
| VH2 | D | T | A | T | Y | Y | C | A | R | W | G | G | D | G | F | Y | A | M | D | Y | W | G | Q | G | T | L | V | T | V | S | S |
| VH3 | D | T | A | V | Y | Y | C | A | R | W | G | G | D | G | F | Y | A | M | D | Y | W | G | Q | G | T | L | V | T | V | S | S |
| VH4 | D | T | A | V | Y | Y | C | A | R | W | G | G | D | G | F | Y | A | M | D | Y | W | G | Q | G | T | L | V | T | V | S | S |

FIG. 2F

| | |
|---|---|
| VH5 | D T A M Y Y C A R W G G D G F Y A M D Y W G Q G T L V T V S S |
| VH6 | D T A V Y Y C A R W G G D G F Y A M D Y W G Q G T L V T V S S |

FIG. 2G

```
 D  I  Q  M   T  Q  S   P  S  S   L  S  A  S   V  G  D
 EcoRV                 BanII
~~~~~~                ~~~~~~~~
GATATCCAGA TGACCCAGAG CCCGTCTAGC CTGAGCGCGA GCGTGGGTGA
CTATAGGTCT ACTGGGTCTC GGGCAGATCG GACTCGCGCT CGCACCCACT

  R  V  T   I  T  C  R   A  S  Q   G  I  S   S  Y  L
                 PstI
                ~~~~~~~~
TCGTGTGACC ATTACCTGCA GAGCGAGCCA GGGCATTAGC AGCTATCTGG
AGCACACTGG TAATGGACGT CTCGCTCGGT CCCGTAATCG TCGATAGACC

A  W  Y  Q   Q  K  P   G  K  A  P   K  L  L   I  Y  A
    KpnI          SexAI                 AseI
   ~~~~~~~       ~~~~~~~~~            ~~~~~~~~
CGTGGTACCA GCAGAAACCA GGTAAAGCAC CGAAACTATT AATTTATGCA
GCACCATGGT CGTCTTTGGT CCATTTCGTG GCTTTGATAA TTAAATACGT

 A  S  S  L   Q  S  G   V  P  S   R  F  S  G   S  G  S
                      SanDI                     BamHI
                    ~~~~~~~~~                   ~~~~~~
GCCAGCAGCT TGCAAAGCGG GGTCCCGTCC CGTTTTAGCG GCTCTGGATC
CGGTCGTCGA ACGTTTCGCC CCAGGGCAGG GCAAAATCGC CGAGACCTAG
```

FIG. 3A

```
  G  T  D   F  T  L  T   I  S  S   L  Q  P   E  D  F
                                             Eco57I
                                             ~~~~~~~~
BamHI                                           BbsI
~                                              ~~~~~~
CGGCACTGAT TTTACCCTGA CCATTAGCAG CCTGCAACCT GAAGACTTTG
GCCGTGACTA AAATGGGACT GGTAATCGTC GGACGTTGGA CTTCTGAAAC

A  T  Y  Y   C  Q  Q   H  Y  T  T   P  P  T   F  G  Q
                                                 MscI
                                                ~~~~~~~
CGACCTATTA TTGCCAGCAG CATTATACCA CCCCGCCGAC CTTTGGCCAG
GCTGGATAAT AACGGTCGTC GTAATATGGT GGGGCGGCTG GAAACCGGTC

 G  T  K  V   E  I  K   R  T
                         BsiWI
                        ~~~~~
GGTACGAAAG TTGAAATTAA ACGTACG
CCATGCTTTC AACTTTAATT TGCATGC
```

FIG. 3B

```
 D  I  V  M   T  Q  S   P  L  S   L  P  V  T   P  G  E
 EcoRV                BanII
~~~~~~~              ~~~~~~~~
GATATCGTGA TGACCCAGAG CCCACTGAGC CTGCCAGTGA CTCCGGGCGA
CTATAGCACT ACTGGGTCTC GGGTGACTCG GACGGTCACT GAGGCCCGCT

  P  A  S   I  S  C  R   S  S  Q   S  L  L   H  S  N
                  PstI
                ~~~~~~~~
GCCTGCGAGC ATTAGCTGCA GAAGCAGCCA AAGCCTGCTG CATAGCAACG
CGGACGCTCG TAATCGACGT CTTCGTCGGT TTCGGACGAC GTATCGTTGC

G  Y  N  Y   L  D  W   Y  L  Q  K   P  G  Q   S  P  Q
                   KpnI            SexAI
                 ~~~~~~~~        ~~~~~~~~
GCTATAACTA TCTGGATTGG TACCTTCAAA AACCAGGTCA AAGCCCGCAG
CGATATTGAT AGACCTAACC ATGGAAGTTT TTGGTCCAGT TTCGGGCGTC
```

FIG. 3C

```
 L  L  I  Y   L  G  S   N  R  A   S  G  V  P   D  R  F
   AseI                                 SanDI
  ~~~~~~~                              ~~~~~~~~~
CTATTAATTT ATCTGGGCAG CAACCGTGCC AGTGGGGTCC CGGATCGTTT
GATAATTAAA TAGACCCGTC GTTGGCACGG TCACCCCAGG GCCTAGCAAA

  S  G  S   G  S  G  T   D  F  T   L  K  I   S  R  V
           BamHI
          ~~~~~~~
TAGCGGCTCT GGATCCGGCA CCGATTTTAC CCTGAAAATT AGCCGTGTGG
ATCGCCGAGA CCTAGGCCGT GGCTAAAATG GGACTTTTAA TCGGCACACC

E  A  E  D   V  G  V   Y  Y  C  Q   Q  H  Y   T  T  P
   Eco57I
   ~~~~~~~
      BbsI
     ~~~~~~~~
AAGCTGAAGA CGTGGGCGTG TATTATTGCC AGCAGCATTA TACCACCCCG
TTCGACTTCT GCACCCGCAC ATAATAACGG TCGTCGTAAT ATGGTGGGGC
```

FIG. 3D

```
P  T  F  G   Q  G  T   K  V  E   I  K  R  T
         MscI                         BsiWI
        ~~~~~~~~                     ~~~~~~
CCGACCTTTG GCCAGGGTAC GAAAGTTGAA ATTAAACGTA CG
GGCTGGAAAC CGGTCCCATG CTTTCAACTT TAATTTGCAT GC
```

FIG. 3E

```
 D  I  V  L   T  Q  S   P  A  T   L  S  L  S   P  G  E
 EcoRV             BanII
~~~~~~            ~~~~~~~~
GATATCGTGC TGACCCAGAG CCCGGCGACC CTGAGCCTGT CTCCGGGCGA
CTATAGCACG ACTGGGTCTC GGGCCGCTGG GACTCGGACA GAGGCCCGCT

  R  A  T   L  S  C  R   A  S  Q   S  V  S   S  S  Y
                 PstI
                ~~~~~~~~
ACGTGCGACC CTGAGCTGCA GAGCGAGCCA GAGCGTGAGC AGCAGCTATC
TGCACGCTGG GACTCGACGT CTCGCTCGGT CTCGCACTCG TCGTCGATAG

L  A  W  Y   Q  Q  K   P  G  Q  A   P  R  L   L  I  Y
      KpnI              SexAI                AseI
     ~~~~~~~~          ~~~~~~~~~            ~~~~~~~
```

FIG. 3F

```
TGGCGTGGTA CCAGCAGAAA CCAGGTCAAG CACCGCGTCT ATTAATTTAT
ACCGCACCAT GGTCGTCTTT GGTCCAGTTC GTGGCGCAGA TAATTAAATA

 G  A  S  S   R  A  T   G  V  P   A  R  F  S   G  S  G
                         SanDI                    BamHI
                        ~~~~~~~~                     ~~
GGCGCGAGCA GCCGTGCAAC TGGGGTCCCG GCGCGTTTTA GCGGCTCTGG
CCGCGCTCGT CGGCACGTTG ACCCCAGGGC CGCGCAAAAT CGCCGAGACC

  S  G  T   D  F  T  L   T  I  S   S  L  E   P  E  D
                                              Eco57I
                                              ~~~~~~
BamHI                                             BbsI
~~~~                                            ~~~~~~
ATCCGGCACG GATTTTACCC TGACCATTAG CAGCCTGGAA CCTGAAGACT
TAGGCCGTGC CTAAAATGGG ACTGGTAATC GTCGGACCTT GGACTTCTGA
```

FIG. 3G

```
F  A  V  Y   Y  C  Q   Q  H  Y  T   T  P  P   T  F  G
                                                 MscI
                                                 ~~~~
TTGCGGTGTA TTATTGCCAG CAGCATTATA CCACCCCGCC GACCTTTGGC
AACGCCACAT AATAACGGTC GTCGTAATAT GGTGGGGCGG CTGGAAACCG

 Q  G  T  K   V  E  I   K  R  T
MscI                    BsiWI
~~                     ~~~~~~
CAGGGTACGA AAGTTGAAAT TAAACGTACG
GTCCCATGCT TTCAACTTTA ATTTGCATGC
```

FIG. 3H

```
 D  I  V  M   T  Q  S   P  D  S   L  A  V  S   L  G  E
 EcoRV                 BanII
~~~~~~~               ~~~~~~~~
GATATCGTGA TGACCCAGAG CCCGGATAGC CTGGCGGTGA GCCTGGGCGA
CTATAGCACT ACTGGGTCTC GGGCCTATCG GACCGCCACT CGGACCCGCT

  R  A  T   I  N  C  R   S  S  Q   S  V  L   Y  S  S
                 PstI
                ~~~~~~~~
ACGTGCGACC ATTAACTGCA GAAGCAGCCA GAGCGTGCTG TATAGCAGCA
TGCACGCTGG TAATTGACGT CTTCGTCGGT CTCGCACGAC ATATCGTCGT

N  N  K  N   Y  L  A   W  Y  Q  Q   K  P  G   Q  P  P
                        KpnI            SexAI
                       ~~~~~~~        ~~~~~~~~~
ACAACAAAAA CTATCTGGCG TGGTACCAGC AGAAACCAGG TCAGCCGCCG
TGTTGTTTTT GATAGACCGC ACCATGGTCG TCTTTGGTCC AGTCGGCGGC
```

FIG. 3I

```
 K  L  L  I   Y  W  A   S  T  R   E  S  G  V   P  D  R
     AseI                                   SanDI
    ~~~~~~~~                               ~~~~~~~~~
AAACTATTAA TTTATTGGGC ATCCACCCGT GAAAGCGGGG TCCCGGATCG
TTTGATAATT AAATAACCCG TAGGTGGGCA CTTTCGCCCC AGGGCCTAGC

  F  S  G   S  G  S  G   T  D  F   T  L  T   I  S  S
                BamHI
               ~~~~~~~
TTTTAGCGGC TCTGGATCCG GCACTGATTT TACCCTGACC ATTTCGTCCC
AAAATCGCCG AGACCTAGGC CGTGACTAAA ATGGGACTGG TAAAGCAGGG

L  Q  A  E   D  V  A   V  Y  Y  C   Q  Q  H   Y  T  T
     Eco57I
     ~~~~~~~~
        BbsI
       ~~~~~~~~
```

FIG. 3J

```
TGCAAGCTGA AGACGTGGCG GTGTATTATT GCCAGCAGCA TTATACCACC
ACGTTCGACT TCTGCACCGC CACATAATAA CGGTCGTCGT AATATGGTGG

 P  P  T  F   G  Q  G   T  K  V   E  I  K  R   T
             MscI                           BsiWI
            ~~~~~~                         ~~~~~~
CCGCCGACCT TTGGCCAGGG TACGAAAGTT GAAATTAAAC GTACG
GGCGGCTGGA AACCGGTCCC ATGCTTTCAA CTTTAATTTG CATGC
```

FIG. 3K

```
 Q  S  V  L   T  Q  P   P  S  V   S  G  A  P   G  Q  R
                                        SexAI
                                       ~~~~~~~~~
CAGAGCGTGC TGACCCAGCC GCCTTCAGTG AGTGGCGCAC CAGGTCAGCG
GTCTCGCACG ACTGGGTCGG CGGAAGTCAC TCACCGCGTG GTCCAGTCGC
                        Eco57I
                        ~~~~~~~

  V  T  I   S  C  S  G   S  S  S   N  I  G   S  N  Y
          BssSI
         ~~~~~~~~
TGTGACCATC TCGTGTAGCG GCAGCAGCAG CAACATTGGC AGCAACTATG
ACACTGGTAG AGCACATCGC CGTCGTCGTC GTTGTAACCG TCGTTGATAC

V  S  W  Y   Q  Q  L   P  G  T  A   P  K  L   L  I  Y
      KpnI              XmaI    BbeI
     ~~~~~~~~          ~~~~~~~  ~~~~~~~~
TGAGCTGGTA CCAGCAGTTG CCCGGGACGG CGCCGAAACT GCTGATTTAT
ACTCGACCAT GGTCGTCAAC GGGCCCTGCC GCGGCTTTGA CGACTAAATA
```

FIG. 4A

```
 D  N  N  Q   R  P  S   G  V  P   D  R  F  S   G  S  K
                 Bsu36I                          BamHI
                 ~~~~~~~~~                      ~~~~~~~
GATAACAACC AGCGTCCCTC AGGCGTGCCG GATCGTTTTA GCGGATCCAA
CTATTGTTGG TCGCAGGGAG TCCGCACGGC CTAGCAAAAT CGCCTAGGTT

  S  G  T   S  A  S  L   A  I  T   G  L  Q   S  E  D
                                                 BbsI
                                               ~~~~~~~
AAGCGGCACC AGCGCGAGCC TTGCGATTAC GGGCCTGCAA AGCGAAGACG
TTCGCCGTGG TCGCGCTCGG AACGCTAATG CCCGGACGTT TCGCTTCTGC

E  A  D  Y   Y  C  Q   Q  H  Y  T   T  P  P   V  F  G
AAGCGGATTA TTATTGCCAG CAGCATTATA CCACCCCGCC TGTGTTTGGC
TTCGCCTAAT AATAACGGTC GTCGTAATAT GGTGGGGCGG ACACAAACCG
```

FIG. 4B

```
 G  G  T  K   L  T  V   L  G
             HpaI        MscI
            ~~~~~~~      ~~~
GGCGGCACGA AGTTAACCGT TCTTGGC
CCGCCGTGCT TCAATTGGCA AGAACCG
```

FIG. 4C

```
 Q  S  A  L   T  Q  P   A  S  V   S  G  S  P   G  Q  S
                                              SexAI
                                             ~~~~~~~~~
CAGAGCGCAC TGACCCAGCC AGCTTCAGTG AGCGGCTCAC CAGGTCAGAG
GTCTCGCGTG ACTGGGTCGG TCGAAGTCAC TCGCCGAGTG GTCCAGTCTC
                        Eco57I
                        ~~~~~~

  I  T  I   S  C  T  G   T  S  S   D  V  G   G  Y  N
           BssSI
          ~~~~~~~~
CATTACCATC TCGTGTACGG GTACTAGCAG CGATGTGGGC GGCTATAACT
GTAATGGTAG AGCACATGCC CATGATCGTC GCTACACCCG CCGATATTGA

Y  V  S  W   Y  Q  Q   H  P  G  K   A  P  K   L  M  I
           KpnI            XmaI       BbeI
          ~~~~~~~~        ~~~~~~~    ~~~~~~~
ATGTGAGCTG GTACCAGCAG CATCCCGGGA AGGCGCCGAA ACTGATGATT
TACACTCGAC CATGGTCGTC GTAGGGCCCT TCCGCGGCTT TGACTACTAA
```

*FIG. 4D*

```
 Y  D  V  S   N  R  P   S  G  V   S  N  R  F   S  G  S
                  Bsu36I                          BamHI
                  ~~~~~~~~~                       ~~~~~
TATGATGTGA GCAACCGTCC CTCAGGCGTG AGCAACCGTT TTAGCGGATC
ATACTACACT CGTTGGCAGG GAGTCCGCAC TCGTTGGCAA AATCGCCTAG

  K  S  G   N  T  A  S   L  T  I   S  G  L   Q  A  E
BamHI                                               BbsI
~                                                   ~~~~
CAAAAGCGGC AACACCGCGA GCCTGACCAT TAGCGGCCTG CAAGCGGAAG
GTTTTCGCCG TTGTGGCGCT CGGACTGGTA ATCGCCGGAC GTTCGCCTTC

D  E  A  D   Y  Y  C   Q  Q  H  Y   T  T  P   P  V  F
BbsI
~~
ACGAAGCGGA TTATTATTGC CAGCAGCATT ATACCACCCC GCCTGTGTTT
TGCTTCGCCT AATAATAACG GTCGTCGTAA TATGGTGGGG CGGACACAAA
```

*FIG. 4E*

```
 G  G  G  T   K  L  T   V  L  G
                HpaI         MscI
               ~~~~~~        ~~~~
GGCGGCGGCA CGAAGTTAAC CGTTCTTGGC
CCGCCGCCGT GCTTCAATTG GCAAGAACCG
```

FIG. 4F

```
 S  Y  E  L   T  Q  P   P  S  V   S  V  A  P   G  Q  T
                                             SexAI
                                           ~~~~~~~~~
AGCTATGAAC TGACCCAGCC GCCTTCAGTG AGCGTTGCAC CAGGTCAGAC
TCGATACTTG ACTGGGTCGG CGGAAGTCAC TCGCAACGTG GTCCAGTCTG
                        Eco57I
                        ~~~~~~~

  A  R  I   S  C  S  G   D  A  L   G  D  K   Y  A  S
            BssSI
          ~~~~~~~~
CGCGCGTATC TCGTGTAGCG GCGATGCGCT GGGCGATAAA TACGCGAGCT
GCGCGCATAG AGCACATCGC CGCTACGCGA CCCGCTATTT ATGCGCTCGA

W  Y  Q  Q   K  P  G   Q  A  P  V   L  V  I   Y  D  D
 KpnI           XmaI     BbeI
~~~~~~~       ~~~~~~~   ~~~~~~~
```

*FIG. 4G*

```
GGTACCAGCA GAAACCCGGG CAGGCGCCAG TTCTGGTGAT TTATGATGAT
CCATGGTCGT CTTTGGGCCC GTCCGCGGTC AAGACCACTA AATACTACTA


 S  D  R  P   S  G  I   P  E  R   F  S  G  S   N  S  G
           Bsu36I                          BamHI
           ~~~~~~~~                       ~~~~~~~~
TCTGACCGTC CCTCAGGCAT CCCGGAACGC TTTAGCGGAT CCAACAGCGG
AGACTGGCAG GGAGTCCGTA GGGCCTTGCG AAATCGCCTA GGTTGTCGCC

  N  T  A   T  L  T  I   S  G  T   Q  A  E   D  E  A
                                            BbsI
                                           ~~~~~~~~
```

*FIG. 4H*

```
CAACACCGCG ACCCTGACCA TTAGCGGCAC TCAGGCGGAA GACGAAGCGG
GTTGTGGCGC TGGGACTGGT AATCGCCGTG AGTCCGCCTT CTGCTTCGCC

D  Y  Y  C   Q  Q  H   Y  T  T  P   P  V  F   G  G  G
ATTATTATTG CCAGCAGCAT TATACCACCC CGCCTGTGTT TGGCGGCGGC
TAATAATAAC GGTCGTCGTA ATATGGTGGG GCGGACACAA ACCGCCGCCG

 T  K  L  T   V  L  G
     HpaI         MscI
    ~~~~~~~~      ~~~~
ACGAAGTTAA CCGTTCTTGG C
TGCTTCAATT GGCAAGAACC G
```

FIG. 4I

```
 Q  V  Q  L   V  Q  S   G  A  E   V  K  K  P   G  S  S
      MfeI
     ~~~~~~~~
CAGGTGCAAT TGGTTCAGTC TGGCGCGGAA GTGAAAAAAC CGGGCAGCAG
GTCCACGTTA ACCAAGTCAG ACCGCGCCTT CACTTTTTTG GCCCGTCGTC

  V  K  V   S  C  K  A   S  G  G   T  F  S   S  Y  A
                         BspEI
                        ~~~~~~~
CGTGAAAGTG AGCTGCAAAG CCTCCGGAGG CACTTTTAGC AGCTATGCGA
GCACTTTCAC TCGACGTTTC GGAGGCCTCC GTGAAAATCG TCGATACGCT

I  S  W  V   R  Q  A   P  G  Q  G   L  E  W   M  G  G
                BstXI            XhoI
             ~~~~~~~~~~~~~~     ~~~~~~~
TTAGCTGGGT GCGCCAAGCC CCTGGGCAGG GTCTCGAGTG GATGGGCGGC
AATCGACCCA CGCGGTTCGG GGACCCGTCC CAGAGCTCAC CTACCCGCCG
```

*FIG. 5A*

```
 I  I  P  I   F  G  T   A  N  Y   A  Q  K  F   Q  G  R
ATTATTCCGA TTTTTGGCAC GGCGAACTAC GCGCAGAAGT TTCAGGGCCG
TAATAAGGCT AAAAACCGTG CCGCTTGATG CGCGTCTTCA AAGTCCCGGC

  V  T  I   T  A  D  E   S  T  S   T  A  Y   M  E  L
BstEII
~~~~~~~~
GGTGACCATT ACCGCGGATG AAAGCACCAG CACCGCGTAT ATGGAACTGA
CCACTGGTAA TGGCGCCTAC TTTCGTGGTC GTGGCGCATA TACCTTGACT

S  S  L  R   S  E  D   T  A  V  Y   Y  C  A   R  W  G
                        EagI             BssHII
                       ~~~~~~~           ~~~~~~~~
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
```

FIG. 5B

```
 G  D  G  F   Y  A  M   D  Y  W   G  Q  G  T   L  V  T
                                     StyI
                                    ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V  S  S
     BlpI
    ~~~~~~~
GGTTAGCTCA G
CCAATCGAGT C
```

FIG. 5C

```
 Q  V  Q  L   V  Q  S   G  A  E   V  K  K  P   G  A  S
      MfeI
     ~~~~~~~~
CAGGTGCAAT TGGTTCAGAG CGGCGCGGAA GTGAAAAAAC CGGGCGCGAG
GTCCACGTTA ACCAAGTCTC GCCGCGCCTT CACTTTTTTG GCCCGCGCTC

  V  K  V   S  C  K  A   S  G  Y   T  F  T   S  Y  Y
                         BspEI
                        ~~~~~~~
CGTGAAAGTG AGCTGCAAAG CCTCCGGATA TACCTTTACC AGCTATTATA
GCACTTTCAC TCGACGTTTC GGAGGCCTAT ATGGAAATGG TCGATAATAT

M  H  W  V   R  Q  A   P  G  Q  G   L  E  W   M  G  W
                BstXI               XhoI
              ~~~~~~~~~~~~~~      ~~~~~~~
TGCACTGGGT CCGCCAAGCC CCTGGGCAGG GTCTCGAGTG GATGGGCTGG
ACGTGACCCA GGCGGTTCGG GGACCCGTCC CAGAGCTCAC CTACCCGACC
```

FIG. 5D

```
 I  N  P  N   S  G  G   T  N  Y   A  Q  K  F   Q  G  R
ATTAACCCGA ATAGCGGCGG CACGAACTAC GCGCAGAAGT TTCAGGGCCG
TAATTGGGCT TATCGCCGCC GTGCTTGATG CGCGTCTTCA AAGTCCCGGC

  V  T  M   T  R  D  T   S  I  S   T  A  Y   M  E  L
BstEII
~~~~~~~
GGTGACCATG ACCCGTGATA CCAGCATTAG CACCGCGTAT ATGGAACTGA
CCACTGGTAC TGGGCACTAT GGTCGTAATC GTGGCGCATA TACCTTGACT

S  S  L  R   S  E  D   T  A  V  Y   Y  C  A   R  W  G
                        EagI            BssHII
                       ~~~~~~          ~~~~~~~
GCAGCCTGCG TAGCGAAGAT ACGGCCGTGT ATTATTGCGC GCGTTGGGGC
CGTCGGACGC ATCGCTTCTA TGCCGGCACA TAATAACGCG CGCAACCCCG
```

*FIG. 5E*

```
 G  D  G  F   Y  A  M   D  Y  W   G  Q  G  T   L  V  T
                                     StyI
                                    ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V  S  S
     BlpI
    ~~~~~~~
GGTTAGCTCA G
CCAATCGAGT C
```

FIG. 5F

```
Q  V  Q  L   K  E  S   G  P  A   L  V  K  P   T  Q  T
      MfeI
     ~~~~~~~~
CAGGTGCAAT TGAAAGAAAG CGGCCCGGCC CTGGTGAAAC CGACCCAAAC
GTCCACGTTA ACTTTCTTTC GCCGGGCCGG GACCACTTTG GCTGGGTTTG

 L  T  L   T  C  T  F   S  G  F   S  L  S   T  S  G
                        BspEI
                       ~~~~~~~
CCTGACCCTG ACCTGTACCT TTTCCGGATT TAGCCTGTCC ACGTCTGGCG
GGACTGGGAC TGGACATGGA AAAGGCCTAA ATCGGACAGG TGCAGACCGC

V  G  V  G   W  I  R   Q  P  P  G   K  A  L   E  W  L
                        BstXI              XhoI
                     ~~~~~~~~~~~~~~~~    ~~~~~~~~
TTGGCGTGGG CTGGATTCGC CAGCCGCCTG GGAAAGCCCT CGAGTGGCTG
AACCGCACCC GACCTAAGCG GTCGGCGGAC CCTTTCGGGA GCTCACCGAC
```

FIG. 5G

```
 A  L  I  D   W  D  D   D  K  Y   Y  S  T  S   L  K  T
                                                 MluI
                                                   ~~
GCTCTGATTG ATTGGGATGA TGATAAGTAT TATAGCACCA GCCTGAAAAC
CGAGACTAAC TAACCCTACT ACTATTCATA ATATCGTGGT CGGACTTTTG

  R  L  T   I  S  K  D   T  S  K   N  Q  V   V  L  T
MluI                       NspV
~~~~                      ~~~~~~~
GCGTCTGACC ATTAGCAAAG ATACTTCGAA AAATCAGGTG GTGCTGACTA
CGCAGACTGG TAATCGTTTC TATGAAGCTT TTTAGTCCAC CACGACTGAT

M  T  N  M   D  P  V   D  T  A  T   Y  Y  C   A  R  W
                                        BssHII
                                        ~~~~~~~~
TGACCAACAT GGACCCGGTG GATACGGCCA CCTATTATTG CGCGCGTTGG
ACTGGTTGTA CCTGGGCCAC CTATGCCGGT GGATAATAAC GCGCGCAACC
```

FIG. 5H

```
 G  G  D  G   F  Y  A   M  D  Y   W  G  Q  G   T  L  V
                                        StyI
                                       ~~~~~~~~
GGCGGCGATG GCTTTTATGC GATGGATTAT TGGGGCCAAG GCACCCTGGT
CCGCCGCTAC CGAAAATACG CTACCTAATA ACCCCGGTTC CGTGGGACCA

  T  V  S   S
      BlpI
     ~~~~~~~
GACGGTTAGC TCAG
CTGCCAATCG AGTC
```

FIG. 5I

```
  E  V  Q  L   V  E  S   G  G  G   L  V  Q  P   G  G  S
       MfeI
      ~~~~~~~~
GAAGTGCAAT TGGTGGAAAG CGGCGGCGGC CTGGTGCAAC CGGGCGGCAG
CTTCACGTTA ACCACCTTTC GCCGCCGCCG GACCACGTTG GCCCGCCGTC

   L  R  L   S  C  A  A   S  G  F   T  F  S   S  Y  A
                         BspEI
                        ~~~~~~
CCTGCGTCTG AGCTGCGCGG CCTCCGGATT TACCTTTAGC AGCTATGCGA
GGACGCAGAC TCGACGCGCC GGAGGCCTAA ATGGAAATCG TCGATACGCT

 M  S  W  V   R  Q  A   P  G  K  G   L  E  W   V  S  A
                 BstXI              XhoI
              ~~~~~~~~~~~~~~       ~~~~~~
TGAGCTGGGT GCGCCAAGCC CCTGGGAAGG GTCTCGAGTG GGTGAGCGCG
ACTCGACCCA CGCGGTTCGG GGACCCTTCC CAGAGCTCAC CCACTCGCGC
```

FIG. 5J

```
 I  S  G  S   G  G  S   T  Y  Y   A  D  S  V   K  G  R
ATTAGCGGTA GCGGCGGCAG CACCTATTAT GCGGATAGCG TGAAAGGCCG
TAATCGCCAT CGCCGCCGTC GTGGATAATA CGCCTATCGC ACTTTCCGGC

  F  T  I   S  R  D  N   S  K  N   T  L  Y   L  Q  M
             PmlI        NspV
            ~~~~~~      ~~~~~~~
TTTTACCATT TCACGTGATA ATTCGAAAAA CACCCTGTAT CTGCAAATGA
AAAATGGTAA AGTGCACTAT TAAGCTTTTT GTGGGACATA GACGTTTACT

N  S  L  R   A  E  D   T  A  V  Y   Y  C  A   R  W  G
                         EagI           BssHII
                        ~~~~~~~        ~~~~~~~~
ACAGCCTGCG TGCGGAAGAT ACGGCCGTGT ATTATTGCGC GCGTTGGGGC
TGTCGGACGC ACGCCTTCTA TGCCGGCACA TAATAACGCG CGCAACCCCG
```

FIG. 5K

```
 G  D  G  F   Y  A  M   D  Y  W   G  Q  G  T   L  V  T
                                     StyI
                                   ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

 V  S  S
     BlpI
   ~~~~~~~
GGTTAGCTCA G
CCAATCGAGT C
```

FIG. 5L

```
 Q  V  Q  L   Q  E  S   G  P  G   L  V  K  P   S  E  T
     MfeI
    ~~~~~~~~
CAGGTGCAAT TGCAAGAAAG TGGTCCGGGC CTGGTGAAAC CGAGCGAAAC
GTCCACGTTA ACGTTCTTTC ACCAGGCCCG GACCACTTTG GCTCGCTTTG

  L  S  L   T  C  T  V   S  G  G   S  I  S   S  Y  Y
                          BspEI
                         ~~~~~~~
CCTGAGCCTG ACCTGCACCG TTTCCGGAGG CAGCATTAGC AGCTATTATT
GGACTCGGAC TGGACGTGGC AAAGGCCTCC GTCGTAATCG TCGATAATAA

W  S  W  I   R  Q  P   P  G  K  G   L  E  W   I  G  Y
                 BstXI                XhoI

             ~~~~~~~~~~~~~~           ~~~~~~
```

FIG. 5M

```
GGAGCTGGAT TCGCCAGCCG CCTGGGAAGG GTCTCGAGTG GATTGGCTAT
CCTCGACCTA AGCGGTCGGC GGACCCTTCC CAGAGCTCAC CTAACCGATA

 I  Y  Y  S   G  S  T   N  Y  N   P  S  L  K   S  R  V
                                                  BstEII
                                                     ~~~
ATTTATTATA GCGGCAGCAC CAACTATAAT CCGAGCCTGA AAAGCCGGGT
TAAATAATAT CGCCGTCGTG GTTGATATTA GGCTCGGACT TTTCGGCCCA

  T  I  S   V  D  T  S   K  N  Q   F  S  L   K  L  S
BstEII              NspV
~~~~               ~~~~~~~~
GACCATTAGC GTTGATACTT CGAAAAACCA GTTTAGCCTG AAACTGAGCA
CTGGTAATCG CAACTATGAA GCTTTTTGGT CAAATCGGAC TTTGACTCGT

S  V  T  A   A  D  T   A  V  Y  Y   C  A  R   W  G  G
                    EagI              BssHII
                   ~~~~~~~~           ~~~~~~~
```

FIG. 5N

```
GCGTGACGGC GGCGGATACG GCCGTGTATT ATTGCGCGCG TTGGGGCGGC
CGCACTGCCG CCGCCTATGC CGGCACATAA TAACGCGCGC AACCCCGCCG

 D  G  F  Y   A  M  D   Y  W  G   Q  G  T  L   V  T  V
                                  StyI
                                ~~~~~~~~
GATGGCTTTT ATGCGATGGA TTATTGGGGC CAAGGCACCC TGGTGACGGT
CTACCGAAAA TACGCTACCT AATAACCCCG GTTCCGTGGG ACCACTGCCA

  S  S
   BlpI
  ~~~~~~
TAGCTCAG
ATCGAGTC
```

FIG. 5O

```
  E  V  Q  L   V  Q  S   G  A  E   V  K  K  P   G  E  S
        MfeI
      ~~~~~~~~
GAAGTGCAAT TGGTTCAGAG CGGCGCGGAA GTGAAAAAAC CGGGCGAAAG
CTTCACGTTA ACCAAGTCTC GCCGCGCCTT CACTTTTTTG GCCCGCTTTC

   L  K  I   S  C  K  G   S  G  Y   S  F  T   S  Y  W
                          BspEI
                         ~~~~~~~
CCTGAAAATT AGCTGCAAAG GTTCCGGATA TTCCTTTACG AGCTATTGGA
GGACTTTTAA TCGACGTTTC CAAGGCCTAT AAGGAAATGC TCGATAACCT

 I  G  W  V   R  Q  M   P  G  K  G   L  E  W   M  G  I
                BstXI              XhoI
             ~~~~~~~~~~~~~~      ~~~~~~~
TTGGCTGGGT GCGCCAGATG CCTGGGAAGG GTCTCGAGTG GATGGGCATT
AACCGACCCA CGCGGTCTAC GGACCCTTCC CAGAGCTCAC CTACCCGTAA
```

FIG. 5P

```
 I  Y  P  G   D  S  D   T  R  Y   S  P  S  F   Q  G  Q
ATTTATCCGG GCGATAGCGA TACCCGTTAT TCTCCGAGCT TTCAGGGCCA
TAAATAGGCC CGCTATCGCT ATGGGCAATA AGAGGCTCGA AAGTCCCGGT

  V  T  I   S  A  D  K   S  I  S   T  A  Y   L  Q  W
BstEII
~~~~~~~~
GGTGACCATT AGCGCGGATA AAAGCATTAG CACCGCGTAT CTTCAATGGA
CCACTGGTAA TCGCGCCTAT TTTCGTAATC GTGGCGCATA GAAGTTACCT

S  S  L  K   A  S  D   T  A  M  Y   Y  C  A   R  W  G
                                       BssHII
                                       ~~~~~~~~
GCAGCCTGAA AGCGAGCGAT ACGGCCATGT ATTATTGCGC GCGTTGGGGC
CGTCGGACTT TCGCTCGCTA TGCCGGTACA TAATAACGCG CGCAACCCCG
```

FIG.5Q

```
 G  D  G  F   Y  A  M   D  Y  W   G  Q  G  T   L  V  T
                                     StyI
                                    ~~~~~~~
GGCGATGGCT TTTATGCGAT GGATTATTGG GGCCAAGGCA CCCTGGTGAC
CCGCTACCGA AAATACGCTA CCTAATAACC CCGGTTCCGT GGGACCACTG

  V  S  S
     BlpI
    ~~~~~~~
GGTTAGCTCA G
CCAATCGAGT C
```

FIG.5R

```
 Q  V  Q  L   Q  Q  S   G  P  G   L  V  K  P   S  Q  T
      MfeI
     ~~~~~~~~
CAGGTGCAAT TGCAACAGTC TGGTCCGGGC CTGGTGAAAC CGAGCCAAAC
GTCCACGTTA ACGTTGTCAG ACCAGGCCCG GACCACTTTG GCTCGGTTTG

  L  S  L   T  C  A  I   S  G  D   S  V  S   S  N  S
                          BspEI
                         ~~~~~~
CCTGAGCCTG ACCTGTGCGA TTTCCGGAGA TAGCGTGAGC AGCAACAGCG
GGACTCGGAC TGGACACGCT AAAGGCCTCT ATCGCACTCG TCGTTGTCGC

 A  A  W  N   W  I  R   Q  S  P  G   R  G  L   E  W  L
                          BstXI            XhoI
                      ~~~~~~~~~~~~~~~   ~~~~~~~~
CGGCGTGGAA CTGGATTCGC CAGTCTCCTG GGCGTGGCCT CGAGTGGCTG
GCCGCACCTT GACCTAAGCG GTCAGAGGAC CCGCACCGGA GCTCACCGAC
```

FIG. 5S

```
 G  R  T  Y   Y  R  S   K  W  Y   N  D  Y  A   V  S  V
GGCCGTACCT ATTATCGTAG CAAATGGTAT AACGATTATG CGGTGAGCGT
CCGGCATGGA TAATAGCATC GTTTACCATA TTGCTAATAC GCCACTCGCA

  K  S  R   I  T  I  N   P  D  T   S  K  N   Q  F  S
             BsaBI                 NspV
         ~~~~~~~~~~~~~            ~~~~~~~
GAAAAGCCGG ATTACCATCA ACCCGGATAC TTCGAAAAAC CAGTTTAGCC
CTTTTCGGCC TAATGGTAGT TGGGCCTATG AAGCTTTTTG GTCAAATCGG

L  Q  L  N   S  V  T   P  E  D  T   A  V  Y   Y  C  A
                                   EagI           BssHII
                                  ~~~~~~~          ~~~~~~
TGCAACTGAA CAGCGTGACC CCGGAAGATA CGGCCGTGTA TTATTGCGCG
ACGTTGACTT GTCGCACTGG GGCCTTCTAT GCCGGCACAT AATAACGCGC
```

FIG. 5T

```
 R  W  G  G   D  G  F   Y  A  M   D  Y  W  G   Q  G  T
BssHII                                          StyI
~                                              ~~~~~~
CGTTGGGGCG GCGATGGCTT TTATGCGATG GATTATTGGG GCCAAGGCAC
GCAACCCCGC CGCTACCGAA AATACGCTAC CTAATAACCC CGGTTCCGTG

  L  V  T   V  S  S
                 BlpI
                ~~~~~~
CCTGGTGACG GTTAGCTCAG
GGACCACTGC CAATCGAGTC
```

FIG. 5U

O1K1 5'- GAATGCATACGCTGATATCCAGATGACCCAGAG-CCCGTCTAGCCTGAGC -3'
O1K2 5'- CGCTCTGCAGGTAATGGTCACACGATCACCCAC-GCTCGCGCTCAGGCTAGACGGGC -3'
O1K3 5'- GACCATTACCTGCAGAGCGAGCCAGGGCATTAG-CAGCTATCTGGCGTGGTACCAGCAG -3'
O1K4 5'- CTTTGCAAGCTGCTGGCTGCATAAATTAATAGT-TTCGGTGCTTTACCTGGTTTCTGCTGGTACCACGCCAG -3'
O1K5 5'- CAGCCAGCAGCTTGCAAAGCGGGGTCCCGTCCC-GTTTTAGCGGCTCTGGATCCGGCACTGATTTTAC -3'
O1K6 5'- GATAATAGGTCGCAAAGTCTTCAGGTTGCAGGC-TGCTAATGGTCAGGGTAAAATCAGTGCCGGATCC -3'
O2K1 5'- CGATATCGTGATGACCCAGAGCCCACTGAGCCT-GCCAGTGACTCCGGGCGAGCC -3'
O2K2 5'- GCCGTTGCTATGCAGCAGGCTTTGGCTGCTTCT-GCAGCTAATGCTCGCAGGCTCGCCCGGAGTCAC -3'
O2K3 5'- CTGCTGCATAGCAACGGCTATAACTATCTGGAT-TGGTACCTTCAAAAACCAGGTCAAAGCCC -3'
O2K4 5'- CGATCCGGGACCCCACTGGCACGGTTGCTGCCC-AGATAAATTAATAGCTGCGGGCTTTGACCTGGTTTTTG -3'
O2K5 5'- AGTGGGGTCCCGGATCGTTTTAGCGGCTCTGGA-TCCGGCACCGATTTTACCCTGAAAATTAGCCGTGTG -3'
O2K6 5'- CCATGCAATAATACACGCCCACGTCTTCAGCTT-CCACACGGCTAATTTTCAGGG -3'
O3K1 5'- GAATGCATACGCTGATATCGTGCTGACCCAGAG CCCGG -3'
O3K2 5'- CGCTCTGCAGCTCAGGGTCGCACGTTCGCCCGG-AGACAGGCTCAGGGTCGCCGGGCTCTGGGTCAGC -3'
O3K3 5'- CCCTGAGCTGCAGAGCGAGCCAGAGCGTGAGCA-GCAGCTATCTGGCGTGGTACCAG -3'

*FIG. 6A*

O3K4 5'- GCACGGCTGCTCGCGCCATAAATTAATAGACGC-GGTGCTTGACCTGGTTTCTGCTGGTACCACGCCAGATAG -3'

O3K5 5'- GCGCGAGCAGCCGTGCAACTGGGGTCCCGGCGC-GTTTTAGCGGCTCTGGATCCGGCACGGATTTTAC -3'

O3K6 5'- GATAATACACCGCAAAGTCTTCAGGTTCCAGGC-TGCTAATGGTCAGGGTAAAATCCGTGCCGGATC -3'

O4K1 5'- GAATGCATACGCTGATATCGTGATGACCCAGAG-CCCGGATAGCCTGGCG -3'

O4K2 5'- GCTTCTGCAGTTAATGGTCGCACGTTCGCCCAG-GCTCACCGCCAGGCTATCCGGGC -3'

O4K3 5'- CGACCATTAACTGCAGAAGCAGCCAGAGCGTGC-TGTATAGCAGCAACAACAAAAACTATCTGGCGTGGTACCAG

3'

O4K4 5'- GATGCCCAATAAATTAATAGTTTCGGCGGCTGA-CCTGGTTTCTGCTGGTACCACGCCAGATAG -3'

O4K5 5'- AAACTATTAATTTATTGGGCATCCACCCGTGAA-AGCGGGGTCCCGGATCGTTTTAGCGGCTCTGGATCCGGCAC-

3'

O4K6 5'- GATAATACACCGCCACGTCTTCAGCTTGCAGGG-ACGAAATGGTCAGGGTAAAATCAGTGCCGGATCCAGAGCC-

3'

O1L1 5'- GAATGCATACGCTCAGAGCGTGCTGACCCAGCC-GCCTTCAGTGAGTGG -3'

O1L2 5'- CAATGTTGCTGCTGCTGCCGCTACACGAGATGG-TCACACGCTGACCTGGTGCGCCACTCACTGAAGGCGGC -3'

O1L3 5'- GGCAGCAGCAGCAACATTGGCAGCAACTATGTG-AGCTGGTACCAGCAGTTGCCCGGGAC -3'

O1L4 5'- CCGGCACGCCTGAGGGACGCTGGTTGTTATCAT-AAATCAGCAGTTTCGGCGCCGTCCCGGGCAACTGC -3

O1L5 5'- CCCTCAGGCGTGCCGGATCGTTTTAGCGGATCC-AAAAGCGGCACCAGCGCGAGCCTTGCG -3'

*FIG. 6B*

O1L6 5'- CCGCTTCGTCTTCGCTTTGCAGGCCCGTAATCG-
CAAGGCTCGCGCTGG -3'
O2L1 5'- GAATGCATACGCTCAGAGCGCACTGACCCAGCC-
AGCTTCAGTGAGCGGC -3'
O2L2 5'- CGCTGCTAGTACCCGTACACGAGATGGTAATGC-
TCTGACCTGGTGAGCCGCTCACTGAAGCTGG -3'
O2L3 5'- GTACGGGTACTAGCAGCGATGTGGGCGGCTATA-
ACTATGTGAGCTGGTACCAGCAGCATCCCGG -3'
O2L4 5'- CGCCTGAGGGACGGTTGCTCACATCATAAATCA-
TCAGTTTCGGCGCCTTCCCGGGATGCTGCTGGTAC -3'
O2L5 5'- CAACCGTCCCTCAGGCGTGAGCAACCGTTTTAG-
CGGATCCAAAAGCGGCAACACCGCGAGCC -3'
O2L6 5'- CCGCTTCGTCTTCCGCTTGCAGGCCGCTAATGG-
TCAGGCTCGCGGTGTTGCCG -3'
O3L1 5'- GAATGCATACGCTAGCTATGAACTGACCCAGCC-
GCCTTCAGTGAGCG -3'
O3L2 5'- CGCCCAGCGCATCGCCGCTACACGAGATACGCG-
CGGTCTGACCTGGTGCAACGCTCACTGAAGGCGGC -3'
O3L3 5'- GGCGATGCGCTGGGCGATAAATACGCGAGCTGG-
TACCAGCAGAAACCCGGGCAGGCGC -3'
O3L4 5'- GCGTTCCGGGATGCCTGAGGGACGGTCAGAATC-
ATCATAAATCACCAGAACTGGCGCCTGCCCGGGTTTC -3'
O3L5 5'- CAGGCATCCCGGAACGCTTTAGCGGATCCAACA-
GCGGCAACACCGCGACCCTGACCATTAGCGG -3'
O3L6 5'- CCGCTTCGTCTTCCGCCTGAGTGCCGCTAATGG-
TCAGGGTC -3'
O1246H1 5'- GCTCTTCACCCCTGTTACCAAAGCCCAG-
GTGCAATTG -3'
O1AH2 5'- GGCTTTGCAGCTCACTTTCACGCTGCTGCCCGGT-
TTTTTCACTTCCGCGCCAGACTGAACCAATTGCACCTGGGC-
TTTG -3'

*FIG. 6C*

O1AH3 5'- GAAAGTGAGCTGCAAAGCCTCCGGAGGCACTTT-
TAGCAGCTATGCGATTAGCTGGGTGCGCCAAGCCCCTGGGCAG
GGTC -3'
O1AH4 5'- GCCCTGAAACTTCTGCGCGTAGTTCGCCGTGCCA-
AAAATCGGAATAATGCCGCCCATCCACTCGAGACCCTGCCC-
AGGGGC -3'
O1AH5 5'- GCGCAGAAGTTTCAGGGCCGGGTGACCATTACC-
GCGGATGAAAGCACCAGCACCGCGTATATGGAACTGAGCAGCC
TGCG -3'
O1ABH6 5'- GCGCGCAATAATACACGGCCGTATCTTCGCT-
ACGCAGGCTGCTCAGTTCC -3'
O1BH2 5'- GGCTTTGCAGCTCACTTTCACGCTCGCGCCCGGT-
TTTTTCACTTCCGCGCCGCTCTGAACCAATTGCACCTGGGC-
TTTG -3'
O1BH3 5'- GAAAGTGAGCTGCAAAGCCTCCGGATATACCTT-
TACCAGCTATTATATGCACTGGGTCCGCCAAGCCCCTGGGCAG
GGTC -3'
O1BH4 5'- GCCCTGAAACTTCTGCGCGTAGTTCGTGCCGCC-
GCTATTCGGGTTAATCCAGCCCATCCACTCGAGACCCTGCCCA
GGGGC -3'
O1BH5 5'- GCGCAGAAGTTTCAGGGCCGGGTGACCATGACC-
CGTGATACCAGCATTAGCACCGCGTATATGGAACTGAGCAGCC
TGCG -3'
O2H2 5'- GGTACAGGTCAGGGTCAGGGTTTGGGTCGGTTT-
CACCAGGGCCGGGCCGCTTTCTTTCAATTGCACCTGGGCTTTG
-3'
O2H3 5'- CTGACCCTGACCTGTACCTTTTCCGGATTTAGC-
CTGTCCACGTCTGGCGTTGGCGTGGGCTGGATTCGCCAGCCGC
CTGGGAAAG -3
O2H4 5'- GCGTTTTCAGGCTGGTGCTATAATACTTATCAT-
CATCCCAATCAATCAGAGCCAGCCACTCGAGGGCTTTCCCAGG
CGGCTGG -3'

*FIG. 6D*

O2H5 5'- GCACCAGCCTGAAAACGCGTCTGACCATTAGCA-AAGATACTTCGAAAAATCAGGTGGTGCTGACTATGACCAACATGG -3'
O2H6 5'- GCGCGCAATAATAGGTGGCCGTATCCACCGGGT-CCATGTTGGTCATAGTCAGC -3'
O3H1 5'- CGAAGTGCAATTGGTGGAAAGCGGCGGCGGCCT-GGTGCAACCGGGCGGCAG -3'
O3H2 5'- CATAGCTGCTAAAGGTAAATCCGGAGGCCGCGC-AGCTCAGACGCAGGCTGCCGCCCGGTTGCAC -3'
O3H3 5'- GATTTACCTTTAGCAGCTATGCGATGAGCTGGG-TGCGCCAAGCCCCTGGGAAGGGTCTCGAGTGGGTGAG -3'
O3H4 5'- GGCCTTTCACGCTATCCGCATAATAGGTGCTGC-CGCCGCTACCGCTAATCGCGCTCACCCACTCGAGACCC -3'
O3H5 5'- CGGATAGCGTGAAAGGCCGTTTTACCATTTCAC-GTGATAATTCGAAAAACACCCTGTATCTGCAAATGAACAG-3'
O3H6 5'- CACGCGCGCAATAATACACGGCCGTATCTTCCG-CACGCAGGCTGTTCATTTGCAGATACAGG -3'
O4H2 5'- GGTCAGGCTCAGGGTTTCGCTCGGTTTCACCAG-GCCCGGACCACTTTCTTGCAATTGCACCTGGGCTTTG -3'
O4H3 5'- GAAACCCTGAGCCTGACCTGCACCGTTTCCGGAGG-CAGCATTAGCAGCTATTATTGGAGCTGGATTCGCCAGCCGC -3'
O4H4 5'- GATTATAGTTGGTGCTGCCGCTATAATAAATAT-AGCCAATCCACTCGAGACCCTTCCCAGGCGGCTGGCGAATCCAG -3'
O4H5 5'- CGGCAGCACCAACTATAATCCGAGCCTGAAAAG-CCGGGTGACCATTAGCGTTGATACTTCGAAAAACCAGTTTAGCCTG -3'
O4H6 5'- GCGCGCAATAATACACGGCCGTATCCGCCGCCG-TCACGCTGCTCAGTTTCAGGCTAAACTGGTTTTTCG -3'

FIG. 6E

O5H1 5'- GCTCTTCACCCCTGTTACCAAAGCCGAAGTGCA
ATTG -3'
O5H2 5'- CCTTTGCAGCTAATTTTCAGGCTTTCGCCCGGT-
TTTTTCACTTCCGCGCCGCTCTGAACCAATTGCACTTCGGCTT
TGG -3'
O5H3 5'- CCTGAAAATTAGCTGCAAAGGTTCCGGATATTC-
CTTTACGAGCTATTGGATTGGCTGGGTGCGCCAGATGCCTGG
-3'
O5H4 5'- CGGAGAATAACGGGTATCGCTATCGCCCGGATA-
AATAATGCCCATCCACTCGAGACCCTTCCCAGGCATCTGGCGC
AC -3'
O5H5 5'- CGATACCCGTTATTCTCCGAGCTTTCAGGGCCA-
GGTGACCATTAGCGCGGATAAAAGCATTAGCACCGCGTATCTT
C -3'
O5H6 5'- GCGCGCAATAATACATGGCCGTATCGCTCGCTT-
TCAGGCTGCTCCATTGAAGATACGCGGTGCTAATG -3'
O6H2 5'- GAAATCGCACAGGTCAGGCTCAGGGTTTGGCTC-
GGTTTCACCAGGCCCGGACCAGACTGTTGCAATTGCACCTGG-
GCTTTG -3'
O6H3 5'- GCCTGACCTGTGCGATTTCCGGAGATAGCGTGA-
GCAGCAACAGCGCGGCGTGGAACTGGATTCGCCAGTCTCCTGG
GCG -3'
O6H4 5'- CACCGCATAATCGTTATACCATTTGCTACGATA-
ATAGGTACGGCCCAGCCACTCGAGGCCACGCCCAGGAGACTG
GCG -3'
O6H5 5'- GGTATAACGATTATGCGGTGAGCGTGAAAAGCC-
GGATTACCATCAACCCGGATACTTCGAAAAACCAGTTTAGCCT
GC -3'
O6H6 5'- GCGCGCAATAATACACGGCCGTATCTTCCGGGG-
TCACGCTGTTCAGTTGCAGGCTAAACTGGTTTTTC -3'
OCLK1 5'- GGCTGAAGACGTGGGCGTGTATTATTGCCAGCA-
GCATTATACCACCCCGCCGACCTTTGGCCAGGGTAC -3'

*FIG. 6F*

OCLK2 5'- GCGAAAAATAAACACGCTCGGAGCAGCCACCG-TACGTTTAATTTCAACTTTCGTACCCTGGCCAAAGGTC -3'
OCLK3 5'- GAGCGTGTTTATTTTTCCGCCGAGCGATGAACA-ACTGAAAAGCGGCACGGCGAGCGTGGTGTGCCTGCTG -3'
OCLK4 5'- CAGCGCGTTGTCTACTTTCCACTGAACTTTCGC-TTCACGCGGATAAAAGTTGTTCAGCAGGCACACCACGC -3'
OCLK5 5'- GAAAGTAGACAACGCGCTGCAAAGCGGCAACAG-CCAGGAAAGCGTGACCGAACAGGATAGCAAAGATAG -3'
OCLK6 5'- GTTTTTCATAATCCGCTTTGCTCAGGGTCAGGG-TGCTGCTCAGAGAATAGGTGCTATCTTTGCTATCCTGTTCG -3'
OCLK7 5'- GCAAAGCGGATTATGAAAAACATAAAGTGTATG-CGTGCGAAGTGACCCATCAAGGTCTGAGCAGCCCGGTG -3'
OCLK8 5'- GGCATGCTTATCAGGCCTCGCCACGATTAAAAG-ATTTAGTCACCGGGCTGCTCAGAC -3'
OCH1 5'- GGCGTCTAGAGGCCAAGGCACCCTGGTGACGGT-TAGCTCAGCGTCGAC -3'
OCH2 5'- GTGCTTTTGCTGCTCGGAGCCAGCGGAAACACG-CTTGGACCTTTGGTCGACGCTGAGCTAACC -3'
OCH3 5'- CTCCGAGCAGCAAAAGCACCAGCGGCGGCACGG-CTGCCCTGGGCTGCCTGGTTAAAGATTATTTCC -3'
OCH4 5'- CTGGTCAGCGCCCCGCTGTTCCAGCTCACGGTG-ACTGGTTCCGGGAAATAATCTTTAACCAGGCA -3'
OCH5 5'- AGCGGGGCGCTGACCAGCGGCGTGCATACCTTT-CCGGCGGTGCTGCAAAGCAGCGGCCTG -3'
OCH6 5'- GTGCCTAAGCTGCTGCTCGGCACGGTCACAACG-CTGCTCAGGCTATACAGGCCGCTGCTTTGCAG -3'
OCH7 5'- GAGCAGCAGCTTAGGCACTCAGACCTATATTTG-CAACGTGAACCATAAACCGAGCAACACC -3'
OCH8 5'- GCGCGAATTCGCTTTTCGGTTCCACTTTTTTAT-CCACTTTGGTGTTGCTCGGTTTATGG -3'

*FIG. 6G*

```
        V  A   A  P  S   V  F  I   F  P  P  S   D  E  Q
 BsiWI
~~~~~~
CGTACGGTGG CTGCTCCGAG CGTGTTTATT TTTCCGCCGA GCGATGAACA
GCATGCCACC GACGAGGCTC GCACAAATAA AAAGGCGGCT CGCTACTTGT

 L  K  S   G  T  A  S   V  V  C   L  L  N   N  F  Y
ACTGAAAAGC GGCACGGCGA GCGTGGTGTG CCTGCTGAAC AACTTTTATC
TGACTTTTCG CCGTGCCGCT CGCACCACAC GGACGACTTG TTGAAAATAG

P  R  E  A   K  V  Q   W  K  V  D   N  A  L   Q  S  G
CGCGTGAAGC GAAAGTTCAG TGGAAAGTAG ACAACGCGCT GCAAAGCGGC
GCGCACTTCG CTTTCAAGTC ACCTTTCATC TGTTGCGCGA CGTTTCGCCG

 N  S  Q  E   S  V  T   E  Q  D   S  K  D  S   T  Y  S
AACAGCCAGG AAAGCGTGAC CGAACAGGAT AGCAAAGATA GCACCTATTC
TTGTCGGTCC TTTCGCACTG GCTTGTCCTA TCGTTTCTAT CGTGGATAAG
```

FIG. 7A

```
L  S  S   T  L  T  L   S  K  A   D  Y  E   K  H  K
TCTGAGCAGC ACCCTGACCC TGAGCAAAGC GGATTATGAA AAACATAAAG
AGACTCGTCG TGGGACTGGG ACTCGTTTCG CCTAATACTT TTTGTATTTC

V  Y  A  C   E  V  T   H  Q  G  L   S  S  P   V  T  K
TGTATGCGTG CGAAGTGACC CATCAAGGTC TGAGCAGCCC GGTGACTAAA
ACATACGCAC GCTTCACTGG GTAGTTCCAG ACTCGTCGGG CCACTGATTT

 S  F  N  R   G  E  A   *
                StuI        SphI
              ~~~~~~~     ~~~~~~
TCTTTTAATC GTGGCGAGGC CTGATAAGCA TGC
AGAAAATTAG CACCGCTCCG GACTATTCGT ACG
```

FIG. 7B

```
      A   S    T  K  G   P  S  V  F   P  L  A   P  S  S
 BlpI   SalI
~~~~~~~~~~~~~~~
GCTCAGCGTC GACCAAAGGT CCAAGCGTGT TTCCGCTGGC TCCGAGCAGC
CGAGTCGCAG CTGGTTTCCA GGTTCGCACA AAGGCGACCG AGGCTCGTCG

 K  S  T  S   G  G  T   A  A  L   G  C  L  V   K  D  Y
AAAAGCACCA GCGGCGGCAC GGCTGCCCTG GGCTGCCTGG TTAAAGATTA
TTTTCGTGGT CGCCGCCGTG CCGACGGGAC CCGACGGACC AATTTCTAAT

  F  P  E   P  V  T  V   S  W  N   S  G  A   L  T  S
TTTCCCGGAA CCAGTCACCG TGAGCTGGAA CAGCGGGGCG CTGACCAGCG
AAAGGGCCTT GGTCAGTGGC ACTCGACCTT GTCGCCCCGC GACTGGTCGC

G  V  H  T   F  P  A   V  L  Q  S   S  G  L   Y  S  L
GCGTGCATAC CTTTCCGGCG GTGCTGCAAA GCAGCGGCCT GTATAGCCTG
CGCACGTATG GAAAGGCCGC CACGACGTTT CGTCGCCGGA CATATCGGAC
```

FIG. 7C

```
 S  S  V  V   T  V  P   S  S  S   L  G  T  Q   T  Y  I
AGCAGCGTTG TGACCGTGCC GAGCAGCAGC TTAGGCACTC AGACCTATAT
TCGTCGCAAC ACTGGCACGG CTCGTCGTCG AATCCGTGAG TCTGGATATA

  C  N  V   N  H  K  P   S  N  T   K  V  D   K  K  V
TTGCAACGTG AACCATAAAC CGAGCAACAC CAAAGTGGAT AAAAAAGTGG
AACGTTGCAC TTGGTATTTG GCTCGTTGTG GTTTCACCTA TTTTTTCACC

E  P  K  S   E  F  *
             EcoRI    HindIII
            ~~~~~~     ~~~~~~
AACCGAAAAG CGAATTCTGA TAAGCTT
TTGGCTTTTC GCTTAAGACT ATTCGAA
```

FIG. 7D

```
      BbsI
      ~~~~~~~
  1   GAAGACGAAG CGGATTATTA TTGCCAGCAG CATTATACCA CCCCGCCTGT
      CTTCTGCTTC GCCTAATAAT AACGGTCGTC GTAATATGGT GGGGCGGACA

                          HpaI          MscI          DraIII
                         ~~~~~~~~     ~~~~~~~           ~~~
 51   GTTTGGCGGC GGCACGAAGT TAACCGTTCT TGGCCAGCCG AAAGCCGCAC
      CAAACCGCCG CCGTGCTTCA ATTGGCAAGA ACCGGTCGGC TTTCGGCGTG

      DraIII
      ~~~~~~
101   CGAGTGTGAC GCTGTTTCCG CCGAGCAGCG AAGAATTGCA GGCGAACAAA
      GCTCACACTG CGACAAAGGC GGCTCGTCGC TTCTTAACGT CCGCTTGTTT

151   GCGACCCTGG TGTGCCTGAT TAGCGACTTT TATCCGGGAG CCGTGACAGT
      CGCTGGGACC ACACGGACTA ATCGCTGAAA ATAGGCCCTC GGCACTGTCA
```

FIG. 7F

```
201  GGCCTGGAAG GCAGATAGCA GCCCCGTCAA GGCGGGAGTG GAGACCACCA
     CCGGACCTTC CGTCTATCGT CGGGGCAGTT CCGCCCTCAC CTCTGGTGGT

251  CACCCTCCAA ACAAAGCAAC AACAAGTACG CGGCCAGCAG CTATCTGAGC
     GTGGGAGGTT TGTTTCGTTG TTGTTCATGC GCCGGTCGTC GATAGACTCG

                                RleAI
                               ~~~~~~~
301  CTGACGCCTG AGCAGTGGAA GTCCCACAGA AGCTACAGCT GCCAGGTCAC
     GACTGCGGAC TCGTCACCTT CAGGGTGTCT TCGATGTCGA CGGTCCAGTG

                                                  StuI
                                                 ~~~~~~~
```

FIG. 7G

```
351  GCATGAGGGG AGCACCGTGG AAAAAACCGT TGCGCCGACT GAGGCCTGAT
     CGTACTCCCC TCGTGGCACC TTTTTTGGCA ACGCGGCTGA CTCCGGACTA

        SphI
       ~~~~~~
401  AAGCATGC
     TTCGTACG
```

FIG. 7H

M24: assembly PCR

M24-A:

GAAGACAAGCGGATTATTATTGCCAGCAGCATTATACCACCCCGCCTGTGTTTGGCGGCG-
GCACGAAGTTAACCGTTC

M24-B:

CAATTCTTCGCTGCTCGGCGGAAACAGCGTCACACTCGGTGCGGCTTTCGGCTGGCCAA-
GAACGGTTAACTTCGTGCCGC

M24-C:

CGCCGAGCAGCGAAGAATTGCAGGCGAACAAAGCGACCCTGGTGTGCCTGATTAGCGACT-
TTTATCCGGGAGCCGTGACA

FIG. 7I

M24-D:

TGTTTGGAGGGTGTGGTGGTCTCCACTCCCGCCTTGACGGGGCTGCTATCTGCCTTCCAG-
GCCACTGTCACGGCTCCCGG

M24-E:

CCACACCCTCCAAACAAAGCAACAACAAGTACGCGGCCAGCAGCTATCTGAGCCTGACGC-
CTGAGCAGTGGAAGTCCCACAGAAGCTACAGCTG

M24-F:

GCATGCTTATCAGGCCTCAGTCGGCGCAACGGTTTTTCCACGGTGCTCCCCTCATGCGT-
GACCTGGCAGCTGTAGCTTC

*FIG. 7J*

```
 M  K  Q  S   T  I  A   L  A  L   L  P  L  L   F  T  P
                                         SapI
                                        ~~~~~~~~~
ATGAAACAAA GCACTATTGC ACTGGCACTC TTACCGTTGC TCTTCACCCC
TACTTTGTTT CGTGATAACG TGACCGTGAG AATGGCAACG AGAAGTGGGG

  V  T  K   A  D  Y  K   D  E  V   Q  L  V   E  S  G
                                  MfeI
                                 ~~~~~~~
TGTTACCAAA GCCGACTACA AAGATGAAGT GCAATTGGTG GAAAGCGGCG
ACAATGGTTT CGGCTGATGT TTCTACTTCA CGTTAACCAC CTTTCGCCGC

G  G  L  V   Q  P  G   G  S  L  R   L  S  C   A  A  S
                                                BspEI
                                                  ~~~
GCGGCCTGGT GCAACCGGGC GGCAGCCTGC GTCTGAGCTG CGCGGCCTCC
CGCCGGACCA CGTTGGCCCG CCGTCGGACG CAGACTCGAC GCGCCGGAGG

 G  F  T  F   S  S  Y   A  M  S   W  V  R  Q   A  P  G
BspEI                                         BstXI
~~~                                     ~~~~~~~~~~~~~~
GGATTTACCT TTAGCAGCTA TGCGATGAGC TGGGTGCGCC AAGCCCCTGG

CCTAAATGGA AATCGTCGAT ACGCTACTCG ACCCACGCGG TTCGGGGACC
```

FIG. 8A

```
K  G  L   E  W  V  S   A  I  S   G  S  G   G  S  T
          XhoI
         ~~~~~~~~
GAAGGGTCTC GAGTGGGTGA GCGCGATTAG CGGTAGCGGC GGCAGCACCT
CTTCCCAGAG CTCACCCACT CGCGCTAATC GCCATCGCCG CCGTCGTGGA

Y  Y  A  D   S  V  K   G  R  F  T   I  S  R   D  N  S
                                         PmlI       NspV
                                       ~~~~~~~~     ~~~~
ATTATGCGGA TAGCGTGAAA GGCCGTTTTA CCATTTCACG TGATAATTCG
TAATACGCCT ATCGCACTTT CCGGCAAAAT GGTAAAGTGC ACTATTAAGC

 K  N  T  L   Y  L  Q   M  N  S   L  R  A  E   D  T  A
NspV                                                EagI
~~                                                  ~~~~
AAAAACACCC TGTATCTGCA AATGAACAGC CTGCGTGCGG AAGATACGGC
TTTTTGTGGG ACATAGACGT TTACTTGTCG GACGCACGCC TTCTATGCCG

  V  Y  Y   C  A  R  W   G  G  D   G  F  Y   A  M  D
EagI        BssHII
~~          ~~~~~~~
CGTGTATTAT TGCGCGCGTT GGGGCGGCGA TGGCTTTTAT GCGATGGATT
```

FIG. 8B

```
GCACATAATAACGCGCGCAA CCCCGCCGCT ACCGAAAATA CGCTACCTAA
Y  W  G  Q   G  T  L   V  T  V  S   S  A  G   G  G  S
        StyI                             BlpI
       ~~~~~~~                         ~~~~~~~
ATTGGGGCCA AGGCACCCTG GTGACGGTTA GCTCAGCGGG TGGCGGTTCT
TAACCCCGGT TCCGTGGGAC CACTGCCAAT CGAGTCGCCC ACCGCCAAGA

 G  G  G  G   S  G  G   G  G  S   G  G  G  G   S  D  I
                                                 EcoRV
                                                 ~~~~~
GGCGGCGGTG GGAGCGGTGG CGGTGGTTCT GGCGGTGGTG GTTCCGATAT
CCGCCGCCAC CCTCGCCACC GCCACCAAGA CCGCCACCAC CAAGGCTATA

  V  M  T   Q  S  P  L   S  L  P   V  T  P   G  E  P
EcoRV          BanII
~             ~~~~~~
CGTGATGACC CAGAGCCCAC TGAGCCTGCC AGTGACTCCG GGCGAGCCTG
GCACTACTGG GTCTCGGGTG ACTCGGACGG TCACTGAGGC CCGCTCGGAC

A  S  I  S   C  R  S   S  Q  S  L   L  H  S   N  G  Y
            PstI
           ~~~~~~
CGAGCATTAG CTGCAGAAGC AGCCAAAGCC TGCTGCATAG CAACGGCTAT
GCTCGTAATC GACGTCTTCG TCGGTTTCGG ACGACGTATC GTTGCCGATA
```

FIG. 8C

```
N  Y  L  D   W  Y  L   Q  K  P   G  Q  S  P   Q  L  L
                  KpnI           SexAI               AseI
                 ~~~~~~~        ~~~~~~~~~              ~~~
AACTATCTGG ATTGGTACCT TCAAAAACCA GGTCAAAGCC CGCAGCTATT
TTGATAGACC TAACCATGGA AGTTTTTGGT CCAGTTTCGG GCGTCGATAA

  I  Y  L   G  S  N  R   A  S  G   V  P  D   R  F  S
AseI                                Eco0109I
~~~                                  ~~~~~~~~~
AATTTATCTG GGCAGCAACC GTGCCAGTGG GGTCCCGGAT CGTTTTAGCG
TTAAATAGAC CCGTCGTTGG CACGGTCACC CCAGGGCCTA GCAAAATCGC

G  S  G  S   G  T  D   F  T  L  K   I  S  R   V  E  A
      BamHI
     ~~~~~~~~
GCTCTGGATC CGGCACCGAT TTTACCCTGA AAATTAGCCG TGTGGAAGCT
CGAGACCTAG GCCGTGGCTA AAATGGGACT TTTAATCGGC ACACCTTCGA

 E  D  V  G   V  Y  Y   C  Q  Q   H  Y  T  T   P  P  T
 BbsI
~~~~~~~
GAAGACGTGG GCGTGTATTA TTGCCAGCAG CATTATACCA CCCCGCCGAC
CTTCTGCACC CGCACATAAT AACGGTCGTC GTAATATGGT GGGGCGGCTG
```

*FIG. 8D*

```
F  G  Q  G  T  K  V  E  I  K  R  T  E  F
   MscI                          BsiWI EcoRI
   ~~~~~~                        ~~~~~~~~~~~~~
CTTTGGCCAG GGTACGAAAG TTGAAATTAA ACGTACGGAA TTC
GAAACCGGTC CCATGCTTTC AACTTTAATT TGCATGCCTT AAG
```

*FIG. 8E*

| | 92 | 93 | 94 | 95 | 96 | 97 | 98 | 99 | 100 | 100A | 100B | 100C | 100D | 100E | 101 | 102 | 103 |
|---|---|---|---|---|---|---|---|---|---|---|---|---|---|---|---|---|---|
| A | C | A | R | W | G | G | D | G | F | Y | A | - | - | M | D | Y | W |
| B | C | A | R | F | G | K | M | N | Y | - | - | - | - | - | D | Y | W |
| | C | A | R | H | R | T | E | W | H | - | - | - | - | - | D | Y | W |
| | C | A | R | V | R | E | L | Y | H | - | - | - | - | - | D | Y | W |
| | C | A | R | K | F | L | K | A | R | - | - | - | - | - | D | Y | W |
| | C | A | R | W | N | T | T | G | Y | - | - | - | - | - | D | Y | W |
| | C | A | R | I | N | E | A | Q | P | - | - | - | - | - | D | Y | W |
| | C | A | R | T | A | I | T | R | - | - | - | - | - | - | D | Y | W |
| | C | A | R | W | Y | N | R | N | S | - | - | - | - | - | D | Y | W |
| | C | A | R | S | V | G | D | S | K | - | - | - | - | - | D | Y | W |
| | C | A | R | S | K | T | F | A | A | - | - | - | - | - | D | Y | W |
| | C | A | R | V | A | P | Q | Y | D | - | - | - | - | - | D | Y | W |
| | C | A | R | M | Q | S | E | W | M | - | - | - | - | - | D | Y | W |

FIG. 10A

C

| | | | | | | | | | | | | | | | | |
|---|---|---|---|---|---|---|---|---|---|---|---|---|---|---|---|---|
| C | A | R | Y | F | V | H | F | L | Y | T | M | V | M | D | V | W |
| C | A | R | M | A | L | R | A | S | G | K | Y | I | M | D | V | W |
| C | A | R | K | N | Q | M | V | F | H | A | R | K | F | D | V | W |
| C | A | R | T | Q | S | F | W | E | Q | Q | K | V | M | D | Y | W |
| C | A | R | Y | P | Y | R | S | N | F | F | M | P | M | D | V | W |
| C | A | R | * | G | S | G | S | E | H | W | S | I | F | D | V | W |
| C | A | R | R | N | P | W | N | V | N | Y | L | H | F | D | V | W |
| C | A | R | M | K | P | M | L | N | R | D | G | T | M | D | V | W |
| C | A | R | K | G | S | E | F | L | E | T | D | V | M | D | Y | W |
| C | A | R | S | W | T | N | D | K | P | N | F | I | M | D | V | W |
| C | A | R | Y | A | G | T | T | F | K | Q | G | P | M | D | Y | W |

FIG. 10B

| 92 | 93 | 94 | 95 | 96 | 97 | 98 | 99 | 100 | 100A | 100B | 100C | 100D | 100E | 101 | 102 | 103 | Frequency |
|---|---|---|---|---|---|---|---|---|---|---|---|---|---|---|---|---|---|
| C | A | R | K | R | M | M | Q | N | P | R | F | R | F | D | V | W | 1 |
| C | A | R | R | S | K | Q | K | R | K | M | R | R | F | D | V | W | 3 |
| C | A | R | R | N | G | K | R | H | L | R | H | R | F | D | V | W | 1 |
| C | A | R | R | K | M | R | K | R | I | K | R | R | F | D | V | W | 2 |
| C | A | R | Y | R | K | I | M | K | W | K | N | S | F | D | V | W | 1 |
| C | A | R | L | I | E | V | H | P | S | F | D | Q | M | D | V | W | 1 |
| C | A | R | R | K | P | M | F | L | K | K | A | V | F | D | V | W | 1 |
| C | A | R | R | K | F | H | R | Y | S | T | V | K | F | D | Y | W | 2 |
| C | A | R | R | K | T | M | R | S | R | V | K | Y | F | D | Y | W | 1 |
| C | A | R | K | K | R | S | W | R | R | M | D | R | F | D | V | W | 1 |
| C | A | R | R | N | P | R | R | G | R | M | N | R | F | D | V | W | 1 |
| C | A | R | K | G | K | K | K | F | A | R | P | R | F | D | V | W | 1 |
| C | A | R | R | M | V | H | K | G | K | R | K | I | F | D | V | W | 1 |
| C | A | R | R | K | H | I | T | Y | P | R | K | Q | F | D | V | W | 1 |
| C | A | R | R | W | T | K | R | R | S | F | A | R | F | D | V | W | 1 |
| C | A | R | K | K | L | K | Q | Y | T | F | S | R | F | D | Y | W | 1 |

FIG. 15

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | T | R | P | W | Q | A | T | R | K | G | F | D | V | W | 3 |
| C | A | R | N | Q | W | E | F | K | N | R | R | K | M | D | Y | W | 8 |
| C | A | R | K | R | W | M | W | P | I | G | K | R | F | D | Y | W | 7 |
| C | A | R | Y | S | L | W | R | L | D | E | Y | F | F | D | Y | W | 1 |
| C | A | R | V | P | W | G | D | F | W | S | W | H | M | D | V | W | 1 |
| C | A | R | N | G | L | E | P | R | H | R | K | M | M | D | Y | W | 1 |
| C | A | R | I | M | K | A | P | P | - | - | - | - | - | D | Y | W | 1 |
| C | A | R | R | K | T | W | H | W | F | Y | K | R | M | D | Y | W | 1 |
| C | A | R | W | K | D | M | W | S | Q | V | Y | V | M | D | Y | W | 1 |
| C | A | R | N | K | Q | Q | M | R | F | R | R | F | M | D | Y | W | 5 |
| C | A | R | N | M | L | A | L | S | R | G | K | E | M | D | V | W | 4 |
| C | A | R | N | M | R | L | M | R | M | R | K | N | F | D | V | W | 1 |

FIG. 20

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | Y | I | K | Q | A | K | R | K | L | A | F | D | Y | W | 4 |
| C | A | R | Y | N | R | H | A | W | Q | K | M | Q | F | D | Y | W | 3 |
| C | A | R | Y | V | K | Y | A | R | N | K | M | Q | F | D | Y | W | 2 |
| C | A | R | Y | K | R | G | A | W | M | K | T | M | F | D | V | W | 1 |
| C | A | R | R | K | P | L | R | R | I | M | K | W | F | D | Y | W | 1 |
| C | A | R | Y | R | K | R | A | S | R | Q | M | Q | F | D | Y | W | 1 |

FIG. 21

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | Q | R | Y | R | S | K | I | K | G | H | F | D | V | W | 16 |
| C | A | R | _ | W | R | D | F | N | S | Y | D | P | M | D | Y | W | 1 |
| C | A | R | M | A | D | L | D | N | Y | W | V | Q | F | D | Y | W | 1 |
| C | A | R | L | Q | A | Y | L | K | P | H | H | W | M | D | Y | W | 1 |
| C | A | R | R | L | I | E | Q | A | R | D | H | V | M | D | Y | W | 1 |
| C | A | R | S | W | H | N | S | Q | F | T | Q | S | F | D | V | W | 1 |
| C | A | R | V | D | H | F | Q | T | E | N | E | W | M | D | Y | W | 1 |
| C | A | R | D | W | P | T | L | I | F | W | Y | W | F | D | Y | W | 1 |

FIG. 22

| 92 | 93 | 94 | 95 | 96 | 97 | 98 | 99 | 100 | 100A | 100B | 100C | 100Ca | 100D | 100E | 101 | 102 | 103 | FREQUENCY |
|---|---|---|---|---|---|---|---|---|---|---|---|---|---|---|---|---|---|---|
| C | A | R | G | F | G | F | T | E | - | - | - | - | - | - | D | Y | W | 4 |
| C | A | R | Q | F | D | E | D | S | F | V | R | - | R | F | D | V | W | 4 |
| C | A | R | I | L | K | E | S | S | K | S | R | - | Q | M | D | V | W | 2 |
| C | A | R | E | Q | D | E | Y | G | A | I | R | - | I | M | D | Y | W | 1 |
| C | A | R | N | H | F | E | A | S | W | P | R | R | Q | M | D | V | W | 1 |
| C | A | R | E | N | E | W | V | D | M | I | L | - | D | M | D | Y | W | 2 |
| C | A | R | Q | Y | S | E | T | R | W | V | R | - | K | F | D | Y | W | 1 |
| C | A | R | Q | F | K | E | S | K | T | R | R | - | K | F | D | V | W | 13 |
| C | A | R | K | K | T | Q | Y | V | H | D | W | - | R | M | D | V | W | 3 |
| C | A | R | R | W | R | E | T | K | S | K | R | - | F | F | D | V | W | 1 |
| C | A | R | D | Y | I | M | E | F | - | - | - | - | - | - | D | Y | W | 1 |
| C | A | R | Q | F | E | E | T | K | Q | R | R | - | L | M | D | Y | W | 1 |

FIG. 23

| 92 | 93 | 94 | 95 | 96 | 97 | 98 | 99 | 100 | 100A | 100B | 100C | 100D | 100E | 101 | 102 | 103 | FREQUENCY |
|---|---|---|---|---|---|---|---|---|---|---|---|---|---|---|---|---|---|
| C | A | R | D | Q | G | F | Y | A | I | D | Y | V | M | D | Y | W | 5 |
| C | A | R | V | F | T | Y | M | Y | N | Y | F | R | F | D | V | W | 1 |
| C | A | R | V | F | F | E | Q | M | E | V | V | R | M | D | V | W | 1 |
| C | A | R | E | K | E | Y | R | L | S | W | S | Q | M | D | Y | W | 1 |
| C | A | R | Y | P | S | R | W | A | P | N | W | Y | M | D | Y | W | 1 |
| C | A | R | D | G | G | F | K | P | L | T | H | F | F | D | V | W | 1 |

FIG. 24

| unique restriction site | Isoschizomers |
|---|---|
| AatII | / |
| AflII | BfrI, BspTI, Bst98I |
| AscI | / |
| AseI | VspI, AsnI, PshBI |
| BamHI | BstI |
| BbeI | EheI, KasI, NarI |
| BbsI | BpuAI, BpiI |
| BglII | / |
| BlpI | Bpu1102I,CelII, BlpI |
| BsaBI | MamI, Bsh1365I, BsrBRI |
| BsiWI | Pfl23II, SplI, SunI |
| BspEI | AccIII, BseAI, BsiMI, Kpn2I, MroI |
| BsrGI | Bsp1407I, SspBI |
| BssHII | PauI |
| BstEII | BstPI, Eco91I, Eco0651 |
| BstXI | / |
| Bsu36I | AocI, CvnI, Eco81I |
| DraIII | / |
| DsmAI | |
| EagI | BstZI, EclXI, Eco52I, XmaIII |
| Eco57I | / |
| EcoO109I | DraII |
| EcoRI | / |
| EcoRV | Eco32I |
| FseI | / |
| HindIII | / |
| HpaI | / |
| KpnI | Acc65I, Asp718I |
| MluI | / |
| MscI | BalI, MluNI |

FIG. 25B

| unique restriction site | Isoschizomers |
|---|---|
| MunI | MfeI |
| NheI | / |
| NsiI | Ppu10I, EcoT22I, Mph1103I |
| NspV | Bsp119I, BstBI, Csp45I, LspI, SfuI |
| PacI | / |
| PmeI | / |
| PmlI | BbrPI, Eco72I, PmaCI |
| Psp5II | PpuMI |
| PstI | / |
| RsrII | (RsriI), CpoI, CspI |
| SanDI | / |
| SapI | / |
| SexAI | / |
| SpeI | / |
| SfiI | / |
| SphI | BbuI, PaeI,NspI |
| StuI | AatI, Eco147I |
| StyI | Eco130I, EcoT14I |
| XbaI | BspLU11II |
| XhoI | PaeR7I |
| XmaI | AvaI, SmaI, Cfr9I, PspAI |

*FIG. 25C*

| No | module/flanking restriction sites | functional element | sites to be removed | sites to be inserted | template | reference |
|---|---|---|---|---|---|---|
| M1 | AatII-lacp/o-XbaI | lac promotor/operator | 2x VspI (AseI) | AatII | vector pASK30 | Skerra et al. (1991) Bio/Technology 9, 273-278 |
| M2 | BglII-lox-AatII | Cre/lox recombination site | 2x VspI (AseI) | lox, BglII | (synthetic) | Hoess et al. (1986) Nucleic Acids Res. 2287-2300 |
| M3 | XbaI-lox'-SphI | Cre/lox' recombination site | none | lox', SphI | (synthetic) | see M2 |
| M7-I | EcoRI-gIIIlong-HindIII | gIIIp of filamentous phage with N-terminal myctail/amber codon | SphI, BamHI | none | vector pIG10 | Ge et al., (1994) Expressing antibodies in E. coli. In: Antibody engineering: A practical approach. IRL Press, New York, pp 229-266 |

FIG. 26A

| | | | | | | |
|---|---|---|---|---|---|---|
| M7-II | EcoRI-gIIIss-HindIII | truncated gIIIp of filamentous phage with N-terminal Gly-Ser linker | SphI | | vector pIG10 | see M7-I |
| M7-III | EcoRI-gIIIss-HindIII | truncated gIIIp of filamentous phage with N-terminal myctail/amber codon | SphI, BbsI | | vector pIG10 | see M7-I |
| M8 | SphI-lox-HindIII | Cre/lox recombination site | none | lox | (synthetic) | see M3 |
| M9-II | HindIII-lpp-PacI | lpp-terminator | none | PacI, FseI | (synthetic) | see M1 |
| M10-II | PacI/FseI-bla-BsrGI | beta-lactamase/bla (ampR) | VspI, Eco57I, BssSI | PacI, FseI, BsrGI | pASK30 | see M1 |
| M11-II | BsrGI-f1 ori-NheI | origin of single-stranded replication | DraIII (BanII not removed) | BsrGI, NheI | pASK30 | see M1 |
| M11-III | BsrGI-f1 ori-NheI | origin of single-stranded replication | DraIII, BanII | BsrGI, NheI | pASK30 | see M1 |

FIG. 26B

| | | | | | | |
|---|---|---|---|---|---|---|
| M12 | NheI-p15A-BglII | origin of double-stranded replication | BssSI, VspI, NspV | NheI, BglII | pACYC184 | Rose, R.E. (1988) Nucleic Acids Res. 16, 355 |
| M13 | BglII-lox-BglII | Cre/lox recombination site | none | BglII, lox, XmnI | (synthetic) | see M3 |
| M14-Ext2 | BglII-ColEI-NheI | origin of double-stranded replication | Eco57I (BssSI not removed) | BglII, NheI | pUC19 | Yanisch-Peron, C. (1985) Gene 33,103-119 |
| M17 | AatII-cat-BglII | chloramphenicol-acetyltransferase/ cat (camR) | BspEI, MscI, StyI/NcoI | | pACYC184 | Cardoso, M. & Schwarz,S. (1992) J. Appl. Bacteriol.72, 289-293 |
| M19 | XbaI-phoA-EcoRI | signal sequence of phosphatase A | (synthetic) | | (synthetic) | see M1 |
| M20 | XbaI-phoA-FLAG-EcoRI | signal sequence of phosphatase A + FLAG detection tag | (synthetic) | | (synthetic) | Knappik, A & Plückthun, A. (1994) BioTechniques 17, 754-761 |

*FIG. 26C*

| | | | | | | |
|---|---|---|---|---|---|---|
| M21 | XbaI-stII-SapI | heat-stable enterotoxin II signal sequence | (synthetic) | | (synthetic) | Lee et al. (1983) Infect. Immunol 264-268 |
| M41 | AflII-lacI-NheI | lac-repressor | BstXI, MluI,BbsI, BanII, BstEII, HpaI, BbeI, VspI | | pASK30 | see M1 |
| M42 | EcoRI-Histail-HindIII | poly-histidine tail | (synthetic) | | (synthetic) | Lindner et al., (1992) Methods: a companion to methods in enzymology 4, 41-56 |

FIG. 26D

```
          HindIII                 PacI                     BsrGI
          ~~~~~~~~             ~~~~~~~~~                  ~~~~~~~
  1   ACATGTAAGC TTCCCCCCCC CCTTAATTAA CCCCCCCCCC TGTACACCCC
      TGTACATTCG AAGGGGGGGG GGAATTAATT GGGGGGGGGG ACATGTGGGG

           NheI                 BglII                AatII    XbaI
          ~~~~~~~~             ~~~~~~~            ~~~~~~~~       ~
 51   CCCCCCGCTA GCCCCCCCCC CCAGATCTCC CCCCCCCCGA CGTCCCCCCT
      GGGGGGCGAT CGGGGGGGGG GGTCTAGAGG GGGGGGGGCT GCAGGGGGGA

      XbaI              SphI                    EcoRI AatII
      ~~~~~           ~~~~~~~~                ~~~~~~~~~~~~
101   CTAGACCCCC CCCCCGCATG CCCCCCCCCC CGAATTCGAC GTC
      GATCTGGGGG GGGGGCGTAC GGGGGGGGGG GCTTAAGCTG CAG
```

FIG. 27B

```
  1  CAGGTGGCAC TTTTCGGGGA AATGTGCGCG GAACCCCTAT TTGTTTATTT
     GTCCACCGTG AAAAGCCCCT TTACACGCGC CTTGGGGATA AACAAATAAA

 51  TTCTAAATAC ATTCAAATAT GTATCCGCTC ATGAGACAAT AACCCTGATA
     AAGATTTATG TAAGTTTATA CATAGGCGAG TACTCTGTTA TTGGGACTAT

101  AATGCTTCAA TAATATTGAA AAAGGAAGAG TATGAGTATT CAACATTTCC
     TTACGAAGTT ATTATAACTT TTTCCTTCTC ATACTCATAA GTTGTAAAGG

151  GTGTCGCCCT TATTCCCTTT TTTGCGGCAT TTTGCCTTCC TGTTTTTGCT
     CACAGCGGGA ATAAGGGAAA AAACGCCGTA AAACGGAAGG ACAAAAACGA

                                      Eco57I
                                      ~~~~~~~
201  CACCCAGAAA CGCTGGTGAA AGTAAAAGAT GCTGAAGATC AGTTGGGTGC
     GTGGGTCTTT GCGACCACTT TCATTTTCTA CGACTTCTAG TCAACCCACG
                                                     BssSI
                                                         ~

251  ACGAGTGGGT TACATCGAAC TGGATCTCAA CAGCGGTAAG ATCCTTGAGA
     TGCTCACCCA ATGTAGCTTG ACCTAGAGTT GTCGCCATTC TAGGAACTCT
     BssSI
     ~~~~~
```

FIG. 28B

```
                      XmnI
                 ~~~~~~~~~~~~
301  GTTTTCGCCC CGAAGAACGT TTTCCAATGA TGAGCACTTT TAAAGTTCTG
     CAAAAGCGGG GCTTCTTGCA AAAGGTTACT ACTCGTGAAA ATTTCAAGAC

351  CTATGTGGCG CGGTATTATC CCGTATTGAC GCCGGGCAAG AGCAACTCGG
     GATACACCGC GCCATAATAG GGCATAACTG CGGCCCGTTC TCGTTGAGCC

401  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

451  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

501  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

551  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

601  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

651  GACGAGCGTG ACACCACGAT GCCTGTAGCA ATGGCAACAA CGTTGCGCAA
```

*FIG. 28C*

```
      CTGCTCGCAC TGTGGTGCTA CGGACATCGT TACCGTTGTT GCAACGCGTT

                                                   AseI
                                                  ~~~~~~~
701   ACTATTAACT GGCGAACTAC TTACTCTAGC TTCCCGGCAA CAATTAATAG
      TGATAATTGA CCGCTTGATG AATGAGATCG AAGGGCCGTT GTTAATTATC

751   ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

801   CCGGCTGGCT GGTTTATTGC TGATAAATCT GGAGCCGGTG AGCGTGGGTC
      GGCCGACCGA CCAAATAACG ACTATTTAGA CCTCGGCCAC TCGCACCCAG

851   TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

901   TAGTTATCTA CACGACGGGG AGTCAGGCAA CTATGGATGA ACGAAATAGA
      ATCAATAGAT GTGCTGCCCC TCAGTCCGTT GATACCTACT TGCTTTATCT

951   CAGATCGCTG AGATAGGTGC CTCACTGATT AAGCATTGGT AACTGTCAGA
      GTCTAGCGAC TCTATCCACG GAGTGACTAA TTCGTAACCA TTGACAGTCT

1001  CCAAGTTTAC TCATATATAC TTTAGATTGA TTTAAAACTT CATTTTTAAT
      GGTTCAAATG AGTATATATG AAATCTAACT AAATTTTGAA GTAAAAATTA
```

FIG. 28D

```
1051   TTAAAAGGAT  CTAGGTGAAG  ATCCTTTTTG  ATAATCTCAT  GACCAAAATC
       AATTTTCCTA  GATCCACTTC  TAGGAAAAAC  TATTAGAGTA  CTGGTTTTAG

1101   CCTTAACGTG  AGTTTTCGTT  CCACTGAGCG  TCAGACCCCG  TAGAAAAGAT
       GGAATTGCAC  TCAAAAGCAA  GGTGACTCGC  AGTCTGGGGC  ATCTTTTCTA

1151   CAAAGGATCT  TCTTGAGATC  CTTTTTTTCT  GCGCGTAATC  TGCTGCTTGC
       GTTTCCTAGA  AGAACTCTAG  GAAAAAAAGA  CGCGCATTAG  ACGACGAACG

1201   AAACAAAAAA  ACCACCGCTA  CCAGCGGTGG  TTTGTTTGCC  GGATCAAGAG
       TTTGTTTTTT  TGGTGGCGAT  GGTCGCCACC  AAACAAACGG  CCTAGTTCTC

1251   CTACCAACTC  TTTTTCCGAA  GGTAACTGGC  TTCAGCAGAG  CGCAGATACC
       GATGGTTGAG  AAAAAGGCTT  CCATTGACCG  AAGTCGTCTC  GCGTCTATGG
                                                Eco57I
                                                ~~~~~~~

1301   AAATACTGTC  CTTCTAGTGT  AGCCGTAGTT  AGGCCACCAC  TTCAAGAACT
       TTTATGACAG  GAAGATCACA  TCGGCATCAA  TCCGGTGGTG  AAGTTCTTGA

1351   CTGTAGCACC  GCCTACATAC  CTCGCTCTGC  TAATCCTGTT  ACCAGTGGCT
       GACATCGTGG  CGGATGTATG  GAGCGAGACG  ATTAGGACAA  TGGTCACCGA
```

FIG. 28E

```
1401   GCTGCCAGTG GCGATAAGTC GTGTCTTACC GGGTTGGACT CAAGACGATA
       CGACGGTCAC CGCTATTCAG CACAGAATGG CCCAACCTGA GTTCTGCTAT

1451   GTTACCGGAT AAGGCGCAGC GGTCGGGCTG AACGGGGGGT TCGTGCACAC
       CAATGGCCTA TTCCGCGTCG CCAGCCCGAC TTGCCCCCCA AGCACGTGTG

1501   AGCCCAGCTT GGAGCGAACG ACCTACACCG AACTGAGATA CCTACAGCGT
       TCGGGTCGAA CCTCGCTTGC TGGATGTGGC TTGACTCTAT GGATGTCGCA

1551   GAGCTATGAG AAAGCGCCAC GCTTCCCGAA GGGAGAAAGG CGGACAGGTA
       CTCGATACTC TTTCGCGGTG CGAAGGGCTT CCCTCTTTCC GCCTGTCCAT

1601   TCCGGTAAGC GGCAGGGTCG GAACAGGAGA GCGCACGAGG GAGCTTCCAG
       AGGCCATTCG CCGTCCCAGC CTTGTCCTCT CGCGTGCTCC CTCGAAGGTC
                                           BssSI
                                          ~~~~~~~

1651   GGGGAAACGC CTGGTATCTT TATAGTCCTG TCGGGTTTCG CCACCTCTGA
       CCCCTTTGCG GACCATAGAA ATATCAGGAC AGCCCAAAGC GGTGGAGACT

1701   CTTGAGCGTC GATTTTTGTG ATGCTCGTCA GGGGGGCGGA GCCTATGGAA
       GAACTCGCAG CTAAAAACAC TACGAGCAGT CCCCCCGCCT CGGATACCTT

1751   AAACGCCAGC AACGCGGCCT TTTTACGGTT CCTGGCCTTT TGCTGGCCTT
```

FIG. 28F

```
      TTTGCGGTCG TTGCGCCGGA AAAATGCCAA GGACCGGAAA ACGACCGGAA

                   HindIII                PacI               BsrGI
                   ~~~~~~~             ~~~~~~~~~~              ~~~~
1801  TTGCTCACAT GTAAGCTTCC CCCCCCCCTT AATTAACCCC CCCCCCTGTA
      AACGAGTGTA CATTCGAAGG GGGGGGGGAA TTAATTGGGG GGGGGGACAT

      BsrGI          NheI              BglII                AatII
      ~~             ~~~~~~~        ~~~~~~~~              ~~~~~~~
1851  CACCCCCCCC CCGCTAGCCC CCCCCCCCAG ATCTCCCCCC CCCCGACGTC
      GTGGGGGGGG GGCGATCGGG GGGGGGGGTC TAGAGGGGGG GGGGCTGCAG

            XbaI               SphI                 EcoRI
          ~~~~~~~~           ~~~~~~~            ~~~~~~~~
1901  CCCCCTCTAG ACCCCCCCCC CGCATGCCCC CCCCCCCGAA TTCACGT
      GGGGGAGATC TGGGGGGGGG GCGTACGGGG GGGGGGGCTT AAGTGCA
```

FIG. 28G

```
       AatII
       ~~~~~~~
  1    GACGTCTTAA TGTGAGTTAG CTCACTCATT AGGCACCCCA GGCTTTACAC
       CTGCAGAATT ACACTCAATC GAGTGAGTAA TCCGTGGGGT CCGAAATGTG

 51    TTTATGCTTC CGGCTCGTAT GTTGTGTGGA ATTGTGAGCG GATAACAATT
       AAATACGAAG GCCGAGCATA CAACACACCT TAACACTCGC CTATTGTTAA

                                                 XbaI
                                                ~~~~~~
101    TCACACAGGA AACAGCTATG ACCATGATTA CGAATTTCTA GA
       AGTGTGTCCT TTGTCGATAC TGGTACTAAT GCTTAAAGAT CT
```

FIG. 29B

```
          EcoRI
          ~~~~~~
  1   GAATTCGAGC AGAAGCTGAT CTCTGAGGAG GATCTGTAGG GTGGTGGCTC
      CTTAAGCTCG TCTTCGACTA GAGACTCCTC CTAGACATCC CACCACCGAG

 51   TGGTTCCGGT GATTTTGATT ATGAAAAGAT GGCAAACGCT AATAAGGGGG
      ACCAAGGCCA CTAAAACTAA TACTTTTCTA CCGTTTGCGA TTATTCCCCC

101   CTATGACCGA AAATGCCGAT GAAAACGCGC TACAGTCTGA CGCTAAAGGC
      GATACTGGCT TTTACGGCTA CTTTTGCGCG ATGTCAGACT GCGATTTCCG

151   AAACTTGATT CTGTCGCTAC TGATTACGGT GCTGCTATCG ATGGTTTCAT
      TTTGAACTAA GACAGCGATG ACTAATGCCA CGACGATAGC TACCAAAGTA

201   TGGTGACGTT TCCGGCCTTG CTAATGGTAA TGGTGCTACT GGTGATTTTG
      ACCACTGCAA AGGCCGGAAC GATTACCATT ACCACGATGA CCACTAAAAC

251   CTGGCTCTAA TTCCCAAATG GCTCAAGTCG GTGACGGTGA TAATTCACCT
      GACCGAGATT AAGGGTTTAC CGAGTTCAGC CACTGCCACT ATTAAGTGGA

                   XmnI
              ~~~~~~~~~~~~
301   TTAATGAATA ATTTCCGTCA ATATTTACCT TCCCTCCCTC AATCGGTTGA
      AATTACTTAT TAAAGGCAGT TATAAATGGA AGGGAGGGAG TTAGCCAACT
```

FIG. 30B

```
351  ATGTCGCCCT TTTGTCTTTG GCGCTGGTAA ACCATATGAA TTTTCTATTG
     TACAGCGGGA AAACAGAAAC CGCGACCATT TGGTATACTT AAAAGATAAC

401  ATTGTGACAA AATAAACTTA TTCCGTGGTG TCTTTGCGTT TCTTTTATAT
     TAACACTGTT TTATTTGAAT AAGGCACCAC AGAAACGCAA AGAAAATATA

451  GTTGCCACCT TTATGTATGT ATTTTCTACG TTTGCTAACA TACTGCGTAA
     CAACGGTGGA AATACATACA TAAAAGATGC AAACGATTGT ATGACGCATT

                     HindIII
                      ~~~~~~
501  TAAGGAGTCT TGATAAGCTT
     ATTCCTCAGA ACTATTCGAA
```

FIG. 30C

```
                 HindIII
                 ~~~~~~~
  1   GGGGGGGGGG AAGCTTGACC TGTGAAGTGA AAAATGGCGC AGATTGTGCG
      CCCCCCCCCC TTCGAACTGG ACACTTCACT TTTTACCGCG TCTAACACGC

                             PacI                   FseI
                            ~~~~~~~~~            ~~~~~~~~~~
 51   ACATTTTTTT TGTCTGCCGT TTAATTAAAG GGGGGGGGGG GCCGGCCTGG
      TGTAAAAAAA ACAGACGGCA AATTAATTTC CCCCCCCCCC CGGCCGGACC

               BsrGI
             ~~~~~~~~
101   GGGGGGGTGT ACAGGGGGGG GGG
      CCCCCCCACA TGTCCCCCCC CCC
```

FIG. 31B

```
           NheI
           ~~~~~~~
  1    GCTAGCACGC GCCCTGTAGC GGCGCATTAA GCGCGGCGGG TGTGGTGGTT
       CGATCGTGCG CGGGACATCG CCGCGTAATT CGCGCCGCCC ACACCACCAA

 51    ACGCGCAGCG TGACCGCTAC ACTTGCCAGC GCCCTAGCGC CCGCTCCTTT
       TGCGCGTCGC ACTGGCGATG TGAACGGTCG CGGGATCGCG GGCGAGGAAA

101    CGCTTTCTTC CCTTCCTTTC TCGCCACGTT CGCCGGCTTT CCCCGTCAAG
       GCGAAAGAAG GGAAGGAAAG AGCGGTGCAA GCGGCCGAAA GGGGCAGTTC

151    CTCTAAATCG GGGCATCCCT TTAGGGTTCC GATTTAGTGC TTTACGGCAC
       GAGATTTAGC CCCGTAGGGA AATCCCAAGG CTAAATCACG AAATGCCGTG

201    CTCGACCCCA AAAAACTTGA TTAGGGTGAT GGTTCTCGTA GTGGGCCATC
       GAGCTGGGGT TTTTTGAACT AATCCCACTA CCAAGAGCAT CACCCGGTAG

251    GCCCTGATAG ACGGTTTTTC GCCCTTTGAC GTTGGAGTCC ACGTTCTTTA
       CGGGACTATC TGCCAAAAAG CGGGAAACTG CAACCTCAGG TGCAAGAAAT

301    ATAGTGGACT CTTGTTCCAA ACTGGAACAA CACTCAACCC TATCTCGGTC
       TATCACCTGA GAACAAGGTT TGACCTTGTT GTGAGTTGGG ATAGAGCCAG

351    TATTCTTTTG ATTTATAAGG GATTTTGCCG ATTTCGGCCT ATTGGTTAAA
```

FIG. 32B

```
       ATAAGAAAAC TAAATATTCC CTAAAACGGC TAAAGCCGGA TAACCAATTT

401    AAATGAGCTG ATTTAACAAA AATTTAACGC GAATTTTAAC AAAATATTAA
       TTTACTCGAC TAAATTGTTT TTAAATTGCG CTTAAAATTG TTTTATAATT

                        BsrGI
                      ~~~~~~
451    CGTTTACAAT TTCATGTACA
       GCAAATGTTA AAGTACATGT
```

FIG. 32C

M14-EXT2
733 bp

```
      BglII
     ~~~~~~~
  1  AGATCTGACC AAAATCCCTT AACGTGAGTT TTCGTTCCAC TGAGCGTCAG
     TCTAGACTGG TTTTAGGGAA TTGCACTCAA AAGCAAGGTG ACTCGCAGTC

 51  ACCCCGTAGA AAAGATCAAA GGATCTTCTT GAGATCCTTT TTTTCTGCGC
     TGGGGCATCT TTTCTAGTTT CCTAGAAGAA CTCTAGGAAA AAAAGACGCG

101  GTAATCTGCT GCTTGCAAAC AAAAAAACCA CCGCTACCAG CGGTGGTTTG
     CATTAGACGA CGAACGTTTG TTTTTTTGGT GGCGATGGTC GCCACCAAAC

151  TTTGCCGGAT CAAGAGCTAC CAACTCTTTT TCCGAAGGTA ACTGGCTACA
     AAACGGCCTA GTTCTCGATG GTTGAGAAAA AGGCTTCCAT TGACCGATGT

201  GCAGAGCGCA GATACCAAAT ACTGTTCTTC TAGTGTAGCC GTAGTTAGGC
     CGTCTCGCGT CTATGGTTTA TGACAAGAAG ATCACATCGG CATCAATCCG

251  CACCACTTCA AGAACTCTGT AGCACCGCCT ACATACCTCG CTCTGCTAAT
     GTGGTGAAGT TCTTGAGACA TCGTGGCGGA TGTATGGAGC GAGACGATTA

301  CCTGTTACCA GTGGCTGCTG CCAGTGGCGA TAAGTCGTGT CTTACCGGGT
     GGACAATGGT CACCGACGAC GGTCACCGCT ATTCAGCACA GAATGGCCCA

351  TGGACTCAAG ACGATAGTTA CCGGATAAGG CGCAGCGGTC GGGCTGAACG
```

FIG. 33B

```
     ACCTGAGTTC TGCTATCAAT GGCCTATTCC GCGTCGCCAG CCCGACTTGC

401  GGGGGTTCGT GCACACAGCC CAGCTTGGAG CGAACGACCT ACACCGAACT
     CCCCCAAGCA CGTGTGTCGG GTCGAACCTC GCTTGCTGGA TGTGGCTTGA

451  GAGATACCTA CAGCGTGAGC TATGAGAAAG CGCCACGCTT CCCGAAGGGA
     CTCTATGGAT GTCGCAGTCG ATACTCTTTC GCGGTGCGAA GGGCTTCCCT

501  GAAAGGCGGA CAGGTATCCG GTAAGCGGCA GGGTCGGAAC AGGAGAGCGC
     CTTTCCGCCT GTCCATAGGC CATTCGCCGT CCCAGCCTTG TCCTCTCGCG
                                                     BssSI
                                                         ~

551  ACGAGGGAGC TTCCAGGGGG AAACGCCTGG TATCTTTATA GTCCTGTCGG
     TGCTCCCTCG AAGGTCCCCC TTTGCGGACC ATAGAAATAT CAGGACAGCC
     BssSI
     ~~~~~

601  GTTTCGCCAC CTCTGACTTG AGCGTCGATT TTTGTGATGC TCGTCAGGGG
     CAAAGCGGTG GAGACTGAAC TCGCAGCTAA AAACACTACG AGCAGTCCCC

651  GGCGGAGCCT ATGGAAAAAC GCCAGCAACG CGGCCTTTTT ACGGTTCCTG
     CCGCCTCGGA TACCTTTTTG CGGTCGTTGC GCCGGAAAAA TGCCAAGGAC
```

FIG. 33C

```
                                              NheI
                                            ~~~~~~~
701  GCCTTTTGCT GGCCTTTCGC TCACATGGCT AGC
     CGGAAAACGA CCGGAAAACG AGTGTACCGA TCG
```

FIG. 33D

M17
813 bp

```
       AatII
      ~~~~~~
  1   GGGACGTCGG GTGAGGTTCC AACTTTCACC ATAATGAAAT AAGATCACTA
      CCCTGCAGCC CACTCCAAGG TTGAAAGTGG TATTACTTTA TTCTAGTGAT

 51   CCGGGCGTAT TTTTTGAGTT ATCGAGATTT TCAGGAGCTA AGGAAGCTAA
      GGCCCGCATA AAAAACTCAA TAGCTCTAAA AGTCCTCGAT TCCTTCGATT

101   AATGGAGAAA AAAATCACTG GATATACCAC CGTTGATATA TCCCAATGGC
      TTACCTCTTT TTTTAGTGAC CTATATGGTG GCAACTATAT AGGGTTACCG

151   ATCGTAAAGA ACATTTTGAG GCATTTCAGT CAGTTGCTCA ATGTACCTAT
      TAGCATTTCT TGTAAAACTC CGTAAAGTCA GTCAACGAGT TACATGGATA

201   AACCAGACCG TTCAGCTGGA TATTACGGCC TTTTTAAAGA CCGTAAAGAA
      TTGGTCTGGC AAGTCGACCT ATAATGCCGG AAAAATTTCT GGCATTTCTT

251   AAATAAGCAC AAGTTTTATC CGGCCTTTAT TCACATTCTT GCCCGCCTGA
      TTTATTCGTG TTCAAAATAG GCCGGAAATA AGTGTAAGAA CGGGCGGACT

301   TGAATGCTCA CCCGGAGTTC CGTATGGCAA TGAAAGACGG TGAGCTGGTG
      ACTTACGAGT GGGCCTCAAG GCATACCGTT ACTTTCTGCC ACTCGACCAC

351   ATATGGGATA GTGTTCACCC TTGTTACACC GTTTTCCATG AGCAAACTGA
```

FIG. 34B

```
       TATACCCTAT CACAAGTGGG AACAATGTGG CAAAAGGTAC TCGTTTGACT

401    AACGTTTTCA TCGCTCTGGA GTGAATACCA CGACGATTTC CGGCAGTTTC
       TTGCAAAAGT AGCGAGACCT CACTTATGGT GCTGCTAAAG GCCGTCAAAG

451    TACACATATA TTCGCAAGAT GTGGCGTGTT ACGGTGAAAA CCTGGCCTAT
       ATGTGTATAT AAGCGTTCTA CACCGCACAA TGCCACTTTT GGACCGGATA

501    TTCCCTAAAG GGTTTATTGA GAATATGTTT TTCGTCTCAG CCAATCCCTG
       AAGGGATTTC CCAAATAACT CTTATACAAA AAGCAGAGTC GGTTAGGGAC

551    GGTGAGTTTC ACCAGTTTTG ATTTAAACGT AGCCAATATG GACAACTTCT
       CCACTCAAAG TGGTCAAAAC TAAATTTGCA TCGGTTATAC CTGTTGAAGA

601    TCGCCCCCGT TTTCACTATG GGCAAATATT ATACGCAAGG CGACAAGGTG
       AGCGGGGGCA AAAGTGATAC CCGTTTATAA TATGCGTTCC GCTGTTCCAC

651    CTGATGCCGC TGGCGATTCA GGTTCATCAT GCCGTTTGTG ATGGCTTCCA
       GACTACGGCG ACCGCTAAGT CCAAGTAGTA CGGCAAACAC TACCGAAGGT

701    TGTCGGCAGA ATGCTTAATG AATTACAACA GTACTGCGAT GAGTGGCAGG
       ACAGCCGTCT TACGAATTAC TTAATGTTGT CATGACGCTA CTCACCGTCC

751    GCGGGGCGTA ATTTTTTTAA GGCAGTTATT GGGTGCCCTT AAACGCCTGG
```

FIG. 34C

```
     CGCCCCGCAT TAAAAAAATT CCGTCAATAA CCCACGGGAA TTTGCGGACC

          BglII
         ~~~~~~
801  TGCTAGATCT TCC
     ACGATCTAGA AGG
```

FIG. 34D

```
      EcoRI
      ~~~~~
  1   AATTCGAGCA GAAGCTGATC TCTGAGGAGG ATCTGTAGGG TGGTGGCTCT
      TTAAGCTCGT CTTCGACTAG AGACTCCTCC TAGACATCCC ACCACCGAGA

 51   GGTTCCGGTG ATTTTGATTA TGAAAAGATG GCAAACGCTA ATAAGGGGGC
      CCAAGGCCAC TAAAACTAAT ACTTTTCTAC CGTTTGCGAT TATTCCCCCG

101   TATGACCGAA AATGCCGATG AAAACGCGCT ACAGTCTGAC GCTAAAGGCA
      ATACTGGCTT TTACGGCTAC TTTTGCGCGA TGTCAGACTG CGATTTCCGT

151   AACTTGATTC TGTCGCTACT GATTACGGTG CTGCTATCGA TGGTTTCATT
      TTGAACTAAG ACAGCGATGA CTAATGCCAC GACGATAGCT ACCAAAGTAA

201   GGTGACGTTT CCGGCCTTGC TAATGGTAAT GGTGCTACTG GTGATTTTGC
      CCACTGCAAA GGCCGGAACG ATTACCATTA CCACGATGAC CACTAAAACG

251   TGGCTCTAAT TCCCAAATGG CTCAAGTCGG TGACGGTGAT AATTCACCTT
      ACCGAGATTA AGGGTTTACC GAGTTCAGCC ACTGCCACTA TTAAGTGGAA

              XmnI
          ~~~~~~~~~~~~
301   TAATGAATAA TTTCCGTCAA TATTTACCTT CCCTCCCTCA ATCGGTTGAA
      ATTACTTATT AAAGGCAGTT ATAAATGGAA GGGAGGGAGT TAGCCAACTT
```

FIG. 35B

```
351  TGTCGCCCTT TTGTCTTTGG CGCTGGTAAA CCATATGAAT TTTCTATTGA
     ACAGCGGGAA AACAGAAACC GCGACCATTT GGTATACTTA AAAGATAACT

401  TTGTGACAAA ATAAACTTAT TCCGTGGTGT CTTTGCGTTT CTTTTATATG
     AACACTGTTT TATTTGAATA AGGCACCACA GAAACGCAAA GAAAATATAC

451  TTGCCACCTT TATGTATGTA TTTTCTACGT TTGCTAACAT ACTGCGTAAT
     AACGGTGGAA ATACATACAT AAAAGATGCA AACGATTGTA TGACGCATTA

                 HindIII
                 ~~~~~~
501  AAGGAGTCTT GATAAGCTTG ACCTGTGAAG TGAAAAATGG CGCAGATTGT
     TTCCTCAGAA CTATTCGAAC TGGACACTTC ACTTTTTACC GCGTCTAACA

                                PacI                FseI
                             ~~~~~~~~~~          ~~~~~~~~~
551  GCGACATTTT TTTTGTCTGC CGTTTAATTA AAGGGGGGGG GGGGCCGGCC
     CGCTGTAAAA AAAACAGACG GCAAATTAAT TTCCCCCCCC CCCCGGCCGG

               BsrG1
               ~~~~~~
601  TGGGGGGGGG TGTACATGAA ATTGTAAACG TTAATATTTT GTTAAAATTC
     ACCCCCCCCC ACATGTACTT TAACATTTGC AATTATAAAA CAATTTTAAG
```

FIG. 35C

```
651   GCGTTAAATT TTTGTTAAAT CAGCTCATTT TTTAACCAAT AGGCCGAAAT
      CGCAATTTAA AAACAATTTA GTCGAGTAAA AAATTGGTTA TCCGGCTTTA

701   CGGCAAAATC CCTTATAAAT CAAAAGAATA GACCGAGATA GGGTTGAGTG
      GCCGTTTTAG GGAATATTTA GTTTTCTTAT CTGGCTCTAT CCCAACTCAC

751   TTGTTCCAGT TTGGAACAAG AGTCCACTAT TAAAGAACGT GGACTCCAAC
      AACAAGGTCA AACCTTGTTC TCAGGTGATA ATTTCTTGCA CCTGAGGTTG

801   GTCAAAGGGC GAAAAACCGT CTATCAGGGC GATGGCCCAC TACGAGAACC
      CAGTTTCCCG CTTTTTGGCA GATAGTCCCG CTACCGGGTG ATGCTCTTGG

851   ATCACCCTAA TCAAGTTTTT TGGGGTCGAG GTGCCGTAAA GCACTAAATC
      TAGTGGGATT AGTTCAAAAA ACCCCAGCTC CACGGCATTT CGTGATTTAG

                  BanII
                 ~~~~~~~
901   GGAACCCTAA AGGGAGCCCC CGATTTAGAG CTTGACGGGG AAAGCCGGCG
      CCTTGGGATT TCCCTCGGGG GCTAAATCTC GAACTGCCCC TTTCGGCCGC

951   AACGTGGCGA GAAAGGAAGG GAAGAAAGCG AAAGGAGCGG GCGCTAGGGC
      TTGCACCGCT CTTTCCTTCC CTTCTTTCGC TTTCCTCGCC CGCGATCCCG
```

FIG. 35D

```
1001  GCTGGCAAGT GTAGCGGTCA CGCTGCGCGT AACCACCACA CCCGCCGCGC
      CGACCGTTCA CATCGCCAGT GCGACGCGCA TTGGTGGTGT GGGCGGCGCG

                               NheI
                              ~~~~~~~
1051  TTAATGCGCC GCTACAGGGC GCGTGCTAGC CATGTGAGCA AAAGGCCAGC
      AATTACGCGG CGATGTCCCG CGCACGATCG GTACACTCGT TTTCCGGTCG

1101  AAAAGGCCAG GAACCGTAAA AAGGCCGCGT TGCTGGCGTT TTTCCATAGG
      TTTTCCGGTC CTTGGCATTT TTCCGGCGCA ACGACCGCAA AAAGGTATCC

1151  CTCCGCCCCC CTGACGAGCA TCACAAAAAT CGACGCTCAA GTCAGAGGTG
      GAGGCGGGGG GACTGCCCGT AGTGTTTTTA GCTGCGAGTT CAGTCTCCAC

1201  GCGAAACCCG ACAGGACTAT AAAGATACCA GGCGTTTCCC CCTGGAAGCT
      CGCTTTGGGC TGTCCTGATA TTTCTATGGT CCGCAAAGGG GGACCTTCGA

        BssSI
      ~~~~~~~
1251  CCCTCGTGCG CTCTCCTGTT CCGACCCTGC CGCTTACCGG ATACCTGTCC
      GGGAGCACGC GAGAGGACAA GGCTGGGACG GCGAATGGCC TATGGACAGG

1301  GCCTTTCTCC CTTCGGGAAG CGTGGCGCTT TCTCATAGCT CACGCTGTAG
      CGGAAAGAGG GAAGCCCTTC GCACCGCGAA AGAGTATCGA GTGCGACATC
```

FIG. 35E

```
1351  GTATCTCAGT TCGGTGTAGG TCGTTCGCTC CAAGCTGGGC TGTGTGCACG
      CATAGAGTCA AGCCACATCC AGCAAGCGAG GTTCGACCCG ACACACGTGC

1401  AACCCCCCGT TCAGCCCGAC CGCTGCGCCT TATCCGGTAA CTATCGTCTT
      TTGGGGGGCA AGTCGGGCTG GCGACGCGGA ATAGGCCATT GATAGCAGAA

1451  GAGTCCAACC CGGTAAGACA CGACTTATCG CCACTGGCAG CAGCCACTGG
      CTCAGGTTGG GCCATTCTGT GCTGAATAGC GGTGACCGTC GTCGGTGACC

1501  TAACAGGATT AGCAGAGCGA GGTATGTAGG CGGTGCTACA GAGTTCTTGA
      ATTGTCCTAA TCGTCTCGCT CCATACATCC GCCACGATGT CTCAAGAACT

1551  AGTGGTGGCC TAACTACGGC TACACTAGAA GAACAGTATT TGGTATCTGC
      TCACCACCGG ATTGATGCCG ATGTGATCTT CTTGTCATAA ACCATAGACG

1601  GCTCTGCTGT AGCCAGTTAC CTTCGGAAAA AGAGTTGGTA GCTCTTGATC
      CGAGACGACA TCGGTCAATG GAAGCCTTTT TCTCAACCAT CGAGAACTAG

1651  CGGCAAACAA ACCACCGCTG GTAGCGGTGG TTTTTTTGTT TGCAAGCAGC
      GCCGTTTGTT TGGTGGCGAC CATCGCCACC AAAAAAACAA ACGTTCGTCG

1701  AGATTACGCG CAGAAAAAAA GGATCTCAAG AAGATCCTTT GATCTTTTCT
      TCTAATGCGC GTCTTTTTTT CCTAGAGTTC TTCTAGGAAA CTAGAAAAGA
```

*FIG. 35F*

```
1751  ACGGGGTCTG ACGCTCAGTG GAACGAAAAC TCACGTTAAG GGATTTTGGT
      TGCCCCAGAC TGCGAGTCAC CTTGCTTTTG AGTGCAATTC CCTAAAACCA

        BglII
      ~~~~~~
1801  CAGATCTAGC ACCAGGCGTT TAAGGGCACC AATAACTGCC TTAAAAAAAT
      GTCTAGATCG TGGTCCGCAA ATTCCCGTGG TTATTGACGG AATTTTTTTA

1851  TACGCCCCGC CCTGCCACTC ATCGCAGTAC TGTTGTAATT CATTAAGCAT
      ATGCGGGGCG GGACGGTGAG TAGCGTCATG ACAACATTAA GTAATTCGTA

1901  TCTGCCGACA TGGAAGCCAT CACAAACGGC ATGATGAACC TGAATCGCCA
      AGACGGCTGT ACCTTCGGTA GTGTTTGCCG TACTACTTGG ACTTAGCGGT

1951  GCGGCATCAG CACCTTGTCG CCTTGCGTAT AATATTTGCC CATAGTGAAA
      CGCCGTAGTC GTGGAACAGC GGAACGCATA TTATAAACGG GTATCACTTT

2001  ACGGGGGCGA AGAAGTTGTC CATATTGGCT ACGTTTAAAT CAAAACTGGT
      TGCCCCCGCT TCTTCAACAG GTATAACCGA TGCAAATTTA GTTTTGACCA

2051  GAAACTCACC CAGGGATTGG CTGAGACGAA AAACATATTC TCAATAAACC
      CTTTGAGTGG GTCCCTAACC GACTCTGCTT TTTGTATAAG AGTTATTTGG
```

FIG. 35G

```
2101  CTTTAGGGAA ATAGGCCAGG TTTTCACCGT AACACGCCAC ATCTTGCGAA
      GAAATCCCTT TATCCGGTCC AAAAGTGGCA TTGTGCGGTG TAGAACGCTT

2151  TATATGTGTA GAAACTGCCG GAAATCGTCG TGGTATTCAC TCCAGAGCGA
      ATATACACAT CTTTGACGGC CTTTAGCAGC ACCATAAGTG AGGTCTCGCT

2201  TGAAAACGTT TCAGTTTGCT CATGGAAAAC GGTGTAACAA GGGTGAACAC
      ACTTTTGCAA AGTCAAACGA GTACCTTTTG CCACATTGTT CCCACTTGTG

2251  TATCCCATAT CACCAGCTCA CCGTCTTTCA TTGCCATACG GAACTCCGGG
      ATAGGGTATA GTGGTCGAGT GGCAGAAAGT AACGGTATGC CTTGAGGCCC

2301  TGAGCATTCA TCAGGCGGGC AAGAATGTGA ATAAAGGCCG GATAAAACTT
      ACTCGTAAGT AGTCCGCCCG TTCTTACACT TATTTCCGGC CTATTTTGAA

2351  GTGCTTATTT TTCTTTACGG TCTTTAAAAA GGCCGTAATA TCCAGCTGAA
      CACGAATAAA AAGAAATGCC AGAAATTTTT CCGGCATTAT AGGTCGACTT

2401  CGGTCTGGTT ATAGGTACAT TGAGCAACTG ACTGAAATGC CTCAAAATGT
      GCCAGACCAA TATCCATGTA ACTCGTTGAC TGACTTTACG GAGTTTTACA

2451  TCTTTACGAT GCCATTGGGA TATATCAACG GTGGTATATC CAGTGATTTT
      AGAAATGCTA CGGTAACCCT ATATAGTTGC CACCATATAG GTCACTAAAA
```

FIG. 35H

```
2501  TTTCTCCATT TTAGCTTCCT TAGCTCCTGA AAATCTCGAT AACTCAAAAA
      AAAGAGGTAA AATCGAAGGA ATCGAGGACT TTTAGAGCTA TTGAGTTTTT

2551  ATACGCCCGG TAGTGATCTT ATTTCATTAT GGTGAAAGTT GGAACCTCAC
      TATGCGGGCC ATCACTAGAA TAAAGTAATA CCACTTTCAA CCTTGGAGTG

         AatII
        ~~~~~~
2601  CCGACGTCTA ATGTGAGTTA GCTCACTCAT TAGGCACCCC AGGCTTTACA
      GGCTGCAGAT TACACTCAAT CGAGTGAGTA ATCCGTGGGG TCCGAAATGT

2651  CTTTATGCTT CCGGCTCGTA TGTTGTGTGG AATTGTGAGC GGATAACAAT
      GAAATACGAA GGCCGAGCAT ACAACACACC TTAACACTCG CCTATTGTTA

                                           XbaI   SphI
                                          ~~~~~~~~~~~~~~
2701  TTCACACAGG AAACAGCTAT GACCATGATT ACGAATTTCT AGAGCATGCG
      AAGTGTGTCC TTTGTCGATA CTGGTACTAA TGCTTAAAGA TCTCGTACGC

      EcoRI

2751  GGGGG
      CCCCC
```

FIG. 35I

```
M 2:

     AatII
     ~~~~~~
  1  GACGTCTTAA TGTGAGTTAG CTCACTCATT AGGCACCCCA GGCTTTACAC
     CTGCAGAATT ACACTCAATC GAGTGAGTAA TCCGTGGGGT CCGAAATGTG

 51  TTTATGCTTC CGGCTCGTAT GTTGTGTGGA ATTGTGAGCG GATAACAATT
     AAATACGAAG GCCGAGCATA CAACACACCT TAACACTCGC CTATTGTTAA

                                            XmnI
                                      ~~~~~~~~~~~~
                                 XbaI
                              ~~~~~~~~
101  TCACACAGGA AACAGCTATG ACCATGTCTA GAATAACTTC GTATAATGTA
     AGTGTGTCCT TTGTCGATAC TGGTACAGAT CTTATTGAAG CATATTACAT

                      SphI
                    ~~~~~~
151  CGCTATACGA AGTTATCGCA TGC
     GCGATATGCT TCAATAGCGT ACG
```

FIG. 35K

```
M 3:

    BglII                                               AatII
    ~~~~~~                                             ~~~~~~
1   AGATCTCATA ACTTCGTATA ATGTATGCTA TACGAAGTTA TGACGTC
    TCTAGAGTAT TGAAGCATAT TACATACGAT ATGCTTCAAT ACTGCAG
```

FIG. 35M

M7-I (long)
1255 bp

```
M 7-I (long):

     EcoRI
    -------
  1 GAATTCGGTG GTGGTGGATC TGCGTGCGCT GAAACGGTTG AAAGTTGTTT
    CTTAAGCCAC CACCACCTAG ACGCACGCGA CTTTGCCAAC TTTCAACAAA

 51 AGCAAAATCC CATACAGAAA ATTCATTTAC TAACGTCTGG AAAGACGACA
    TCGTTTTAGG GTATGTCTTT TAAGTAAATG ATTGCAGACC TTTCTGCTGT

101 AAACTTTAGA TCGTTACGCT AACTATGAGG GCTGTCTGTG GAATGCTACA
    TTTGAAATCT AGCAATGCGA TTGATACTCC CGACAGACAC CTTACGATGT

151 GGCGTTGTAG TTTGTACTGG TGACGAAACT CAGTGTTACG GTACATGGGT
    CCGCAACATC AAACATGACC ACTGCTTTGA GTCACAATGC CATGTACCCA

201 TCCTATTGGG CTTGCTATCC CTGAAAATGA GGGTGGTGGC TCTGAGGGTG
    AGGATAACCC GAACGATAGG GACTTTTACT CCCACCACCG AGACTCCCAC

251 GCGGTTCTGA GGGTGGCGGT TCTGAGGGTG GCGGTACTAA ACCTCCTGAG
    CGCCAAGACT CCCACCGCCA AGACTCCCAC CGCCATGATT TGGAGGACTC

301 TACGGTGATA CACCTATTCC GGGCTATACT TATATCAACC CTCTCGACGG
    ATGCCACTAT GTGGATAAGG CCCGATATGA ATATAGTTGG GAGAGCTGCC
```

*FIG. 35O*

```
351  CACTTATCCG CCTGGTACTG AGCAAAACCC CGCTAATCCT AATCCTTCTC
     GTGAATAGGC GGACCATGAC TCGTTTTGGG GCGATTAGGA TTAGGAAGAG

401  TTGAGGAGTC TCAGCCTCTT AATACTTTCA TGTTTCAGAA TAATAGGTTC
     AACTCCTCAG AGTCGGAGAA TTATGAAAGT ACAAAGTCTT ATTATCCAAG

451  CGAAATAGGC AGGGGGCATT AACTGTTTAT ACGGGCACTG TTACTCAAGG
     GCTTTATCCG TCCCCCGTAA TTGACAAATA TGCCCGTGAC AATGAGTTCC

501  CACTGACCCC GTTAAAACTT ATTACCAGTA CACTCCTGTA TCATCAAAAG
     GTGACTGGGG CAATTTTGAA TAATGGTCAT GTGAGGACAT AGTAGTTTTC

551  CCATGTATGA CGCTTACTGG AACGGTAAAT TCAGAGACTG CGCTTTCCAT
     GGTACATACT GCGAATGACC TTGCCATTTA AGTCTCTGAC GCGAAAGGTA

601  TCTGGCTTTA ATGAGGGTTT ATTTGTTTGT GAATATCAAG GCCAATCGTC
     AGACCGAAAT TACTCCCAAA TAAACAAACA CTTATAGTTC CGGTTAGCAG

651  TGACCTGCCT CAACCTCCTG TCAATGCTGG CGGCGGCTCT GGTGGTGGTT
     ACTGGACGGA GTTGGAGGAC AGTTACGACC GCCGCCGAGA CCACCACCAA

701  CTGGTGGCGG CTCTGAGGGT GGTGGCTCTG AGGGTGGCGG TTCTGAGGGT
     GACCACCGCC GAGACTCCCA CCACCGAGAC TCCCACCGCC AAGACTCCCA
```

FIG. 35P

```
751   GGCGGCTCTG AGGGAGGCGG TTCCGGTGGT GGCTCTGGTT CCGGTGATTT
      CCGCCGAGAC TCCCTCCGCC AAGGCCACCA CCGAGACCAA GGCCACTAAA

801   TGATTATGAA AAGATGGCAA ACGCTAATAA GGGGGCTATG ACCGAAAATG
      ACTAATACTT TTCTACCGTT TGCGATTATT CCCCCGATAC TGGCTTTTAC

851   CCGATGAAAA CGCGCTACAG TCTGACGCTA AAGGCAAACT TGATTCTGTC
      GGCTACTTTT GCGCGATGTC AGACTGCGAT TTCCGTTTGA ACTAAGACAG

901   GCTACTGATT ACGGTGCTGC TATCGATGGT TTCATTGGTG ACGTTTCCGG
      CGATGACTAA TGCCACGACG ATAGCTACCA AAGTAACCAC TGCAAAGGCC

951   CCTTGCTAAT GGTAATGGTG CTACTGGTGA TTTTGCTGGC TCTAATTCCC
      GGAACGATTA CCATTACCAC GATGACCACT AAAACGACCG AGATTAAGGG

                                                    XmnI
                                                 ~~~~~~~~~~
1001  AAATGGCTCA AGTCGGTGAA GGTGATAATT CACCTTTAAT GAATAATTTC
      TTTACCGAGT TCAGCCACTT CCACTATTAA GTGGAAATTA CTTATTAAAG

1051  CGTCAATATT TACCTTCCAT CCCTCAATCG GTTGAATGTC GCCCTTTTGT
      GCAGTTATAA ATGGAAGGTA GGGAGTTAGC CAACTTACAG CGGGAAAACA
```

FIG. 35Q

```
1101  CTTTGGCGCT GGTAAACCCT ATGAATTTTC TATTGATTGT GACAAAATAA
      GAAACCGCGA CCATTTGGGA TACTTAAAAG ATAACTAACA CTGTTTTATT

1151  ACTTATTCCG TGGTGTCTTT GCGTTTCTTT TATATGTTGC CACCTTTATG
      TGAATAAGGC ACCACAGAAA CGCAAAGAAA ATATACAACG GTGGAAATAC

                                                    HindIII
                                                          ~
1201  TATGTATTTT CTACGTTTGC TAACATACTG CGTAATAAGG AGTCTTGATA
      ATACATAAAA GATGCAAACG ATTGTATGAC GCATTATTCC TCAGAACTAT

      HindI
      ~~~~
1251  AGCTT
      TCGAA
```

FIG. 35R

```
M 7-II (ss-TAG):

      EcoRI
     -------
  1  CGGGAATTCG GAGGCGGTTC CGGTGGTGGC TCTGGTTCCG GTGATTTTGA
     GCCCTTAAGC CTCCGCCAAG GCCACCACCG AGACCAAGGC CACTAAAACT

 51  TTATGAAAAG ATGGCAAACG CTAATAAGGG GGCTATGACC GAAAATGCCG
     AATACTTTTC TACCGTTTGC GATTATTCCC CCGATACTGG CTTTTACGGC

101  ATGAAAAACGC GCTACAGTCT GACGCTAAAG GCAAACTTGA TTCTGTCGCT
     TACTTTTGCG CGATGTCAGA CTGCGATTTC CGTTTGAACT AAGACAGCGA

151  ACTGATTACG GTGCTGCTAT CGATGGTTTC ATTGGTGACG TTTCCGGCCT
     TGACTAATGC CACGACGATA GCTACCAAAG TAACCACTGC AAAGGCCGGA

201  TGCTAATGGT AATGGTGCTA CTGGTGATTT TGCTGGCTCT AATTCCCAAA
     ACGATTACCA TTACCACGAT GACCACTAAA ACGACCGAGA TTAAGGGTTT

                                                XmnI
                                           -----------
251  TGGCTCAAGT CGGTGACGGT GATAATTCAC CTTTAATGAA TAATTTCCGT
     ACCGAGTTCA GCCACTGCCA CTATTAAGTG GAAATTACTT ATTAAAGGCA
```

*FIG. 35T*

```
301  CAATATTTAC CTTCCCTCCC TCAATCGGTT GAATGTCGCC CTTTTGTCTT
     GTTATAAATG GAAGGGAGGG AGTTAGCCAA CTTACAGCGG GAAAACAGAA

351  TGGCGCTGGT AAACCATATG AATTTTCTAT TGATTGTGAC AAAATAAACT
     ACCGCGACCA TTTGGTATAC TTAAAAGATA ACTAACACTG TTTTATTTGA

401  TATTCCGTGG TGTCTTTGCG TTTCTTTTAT ATGTTGCCAC CTTTATGTAT
     ATAAGGCACC ACAGAAACGC AAAGAAAATA TACAACGGTG GAAATACATA

                                                 HindIII
                                                    ~~~~
451  GTATTTTCTA CGTTTGCTAA CATACTGCGT AATAAGGAGT CTTGATAAGC
     CATAAAAGAT GCAAACGATT GTATGACGCA TTATTCCTCA GAACTATTCG

     Hi
     ~
501  TT
     AA
```

*FIG. 35U*

```
M 8:

     SphI                                             HindIII
    ~~~~~~~                                            ~~~~~~
1   GCATGCCATA ACTTCGTATA ATGTACGCTA TACGAAGTTA TAAGCTT
    CGTACGGTAT TGAAGCATAT TACATGCGAT ATGCTTCAAT ATTCGAA
```

FIG. 35W

M10-11
1163 bp

```
M 10-II:

         BsrGI
        --------
  1   GGGGGTGTAC ATTCAAATAT GTATCCGCTC ATGAGACAAT AACCCTGATA
      CCCCCACATG TAAGTTTATA CATAGGCGAG TACTCTGTTA TTGGGACTAT

 51   AATGCTTCAA TAATATTGAA AAAGGAAGAG TATGAGTATT CAACATTTCC
      TTACGAAGTT ATTATAACTT TTTCCTTCTC ATACTCATAA GTTGTAAAGG

101   GTGTCGCCCT TATTCCCTTT TTTGCGGCAT TTTGCCTTCC TGTTTTTGCT
      CACAGCGGGA ATAAGGGAAA AAACGCCGTA AAACGGAAGG ACAAAAACGA

151   CACCCAGAAA CGCTGGTGAA AGTAAAAGAT GCTGAGGATC AGTTGGGTGC
      GTGGGTCTTT GCGACCACTT TCATTTTCTA CGACTCCTAG TCAACCCACG

201   GCGAGTGGGT TACATCGAAC TGGATCTCAA CAGCGGTAAG ATCCTTGAGA
      CGCTCACCCA ATGTAGCTTG ACCTAGAGTT GTCGCCATTC TAGGAACTCT

                       XmnI
                   -----------
251   GTTTTCGCCC CGAAGAACGT TTTCCAATGA TGAGCACTTT TAAAGTTCTG
      CAAAAGCGGG GCTTCTTGCA AAAGGTTACT ACTCGTGAAA ATTTCAAGAC
```

FIG. 35Y

```
301  CTATGTGGCG CGGTATTATC CCGTATTGAC GCCGGGCAAG AGCAACTCGG
     GATACACCGC GCCATAATAG GGCATAACTG CGGCCCGTTC TCGTTGAGCC

351  TCGCCGCATA CACTATTCTC AGAATGACTT GGTTGAGTAC TCACCAGTCA
     AGCGGCGTAT GTGATAAGAG TCTTACTGAA CCAACTCATG AGTGGTCAGT

401  CAGAAAAGCA TCTTACGGAT GGCATGACAG TAAGAGAATT ATGCAGTGCT
     GTCTTTTCGT AGAATGCCTA CCGTACTGTC ATTCTCTTAA TACGTCACGA

451  GCCATAACCA TGAGTGATAA CACTGCGGCC AACTTACTTC TGACAACGAT
     CGGTATTGGT ACTCACTATT GTGACGCCGG TTGAATGAAG ACTGTTGCTA

501  CGGAGGACCG AAGGAGCTAA CCGCTTTTTT GCACAACATG GGGGATCATG
     GCCTCCTGGC TTCCTCGATT GGCGAAAAAA CGTGTTGTAC CCCCTAGTAC

551  TAACTCGCCT TGATCGTTGG GAACCGGAGC TGAATGAAGC CATACCAAAC
     ATTGAGCGGA ACTAGCAACC CTTGGCCTCG ACTTACTTCG GTATGGTTTG

601  GACGAGCGTG ACACCACGAT GCCTGTAGCA ATGGCAACAA CGTTGCGCAA
     CTGCTCGCAC TGTGGTGCTA CGGACATCGT TACCGTTGTT GCAACGCGTT

651  ACTATTAACT GGCGAACTAC TTACTCTAGC TTCCCGGCAA CAGTTAATAG
     TGATAATTGA CCGCTTGATG AATGAGATCG AAGGGCCGTT GTCAATTATC
```

FIG. 35Z

```
701   ACTGGATGGA GGCGGATAAA GTTGCAGGAC CACTTCTGCG CTCGGCCCTT
      TGACCTACCT CCGCCTATTT CAACGTCCTG GTGAAGACGC GAGCCGGGAA

751   CCGGCTGGCT GGTTTATTGC TGATAAATCT GGAGCCGGTG AGCGTGGGTC
      GGCCGACCGA CCAAATAACG ACTATTTAGA CCTCGGCCAC TCGCACCCAG

801   TCGCGGTATC ATTGCAGCAC TGGGGCCAGA TGGTAAGCCC TCCCGTATCG
      AGCGCCATAG TAACGTCGTG ACCCCGGTCT ACCATTCGGG AGGGCATAGC

851   TAGTTATCTA CACGACGGGG AGTCAGGCAA CTATGGATGA ACGAAATAGA
      ATCAATAGAT GTGCTGCCCC TCAGTCCGTT GATACCTACT TGCTTTATCT

901   CAGATCGCTG AGATAGGTGC CTCACTGATT AAGCATTGGG TAACTGTCAG
      GTCTAGCGAC TCTATCCACG GAGTGACTAA TTCGTAACCC ATTGACAGTC

951   ACCAAGTTTA CTCATATATA CTTTAGATTG ATTTAAAACT TCATTTTTAA
      TGGTTCAAAT GAGTATATAT GAAATCTAAC TAAATTTTGA AGTAAAAATT

1001  TTTAAAAGGA TCTAGGTGAA GATCCTTTTT GATAATCTCA TGACCAAAAT
      AAATTTTCCT AGATCCACTT CTAGGAAAAA CTATTAGAGT ACTGGTTTTA

1051  CCCTTAACGT GAGTTTTCGT TCCACTGAGC GTCAGACCCC GTAGAAAAGA
      GGGAATTGCA CTCAAAAGCA AGGTGACTCG CAGTCTGGGG CATCTTTTCT
```

FIG. 35AA

```
                                                    FseI        PacI
                                              ~~~~~~~~~~          ~~
1101  TCAAAGGATC TTCTTGAGAT CCTTTTTGAT AATGGCCGGC CCCCCCCCTT
      AGTTTCCTAG AAGAACTCTA GGAAAAACTA TTACCGGCCG GGGGGGGGAA

      PacI
      ~~~~~~~
1151  AATTAAGGGG GGG
      TTAATTCCCC CCC
```

FIG. 35BB

M11-II:

```
         NheI
         ~~~~~~
  1      GCTAGCACGC GCCCTGTAGC GGCGCATTAA GCGCGGCGGG TGTGGTGGTT
         CGATCGTGCG CGGGACATCG CCGCGTAATT CGCGCCGCCC ACACCACCAA

 51      ACGCGCAGCG TGACCGCTAC ACTTGCCAGC GCCCTAGCGC CCGCTCCTTT
         TGCGCGTCGC ACTGGCGATG TGAACGGTCG CGGGATCGCG GGCGAGGAAA

101      CGCTTTCTTC CCTTCCTTTC TCGCCACGTT CGCCGGCTTT CCCCGTCAAG
         GCGAAAGAAG GGAAGGAAAG AGCGGTGCAA GCGGCCGAAA GGGGCAGTTC

                    BanII
                   ~~~~~~
151      CTCTAAATCG GGGGCTCCCT TTAGGGTTCC GATTTAGTGC TTTACGGCAC
         GAGATTTAGC CCCCGAGGGA AATCCCAAGG CTAAATCACG AAATGCCGTG

201      CTCGACCCCA AAAAACTTGA TTAGGGTGAT GGTTCTCGTA GTGGGCCATC
         GAGCTGGGGT TTTTTGAACT AATCCCACTA CCAAGAGCAT CACCCGGTAG

251      GCCCTGATAG ACGGTTTTTC GCCCTTTGAC GTTGGAGTCC ACGTTCTTTA
         CGGGACTATC TGCCAAAAAG CGGGAAACTG CAACCTCAGG TGCAAGAAAT
```

FIG. 35DD

```
301  ATAGTGGACT CTTGTTCCAA ACTGGAACAA CACTCAACCC TATCTCGGTC
     TATCACCTGA GAACAAGGTT TGACCTTGTT GTGAGTTGGG ATAGAGCCAG

351  TATTCTTTTG ATTTATAAGG GATTTTGCCG ATTTCGGCCT ATTGGTTAAA
     ATAAGAAAAC TAAATATTCC CTAAAACGGC TAAAGCCGGA TAACCAATTT

401  AAATGAGCTG ATTTAACAAA AATTTAACGC GAATTTTAAC AAAATATTAA
     TTTACTCGAC TAAATTGTTT TTAAATTGCG CTTAAAATTG TTTTATAATT

                        BsrGI
                      ~~~~~~~
451  CGTTTACAAT TTCATGTACA
     GCAAATGTTA AAGTACATGT
```

*FIG. 35EE*

```
M 12:
      BglII
      ~~~~~~
  1   AGATCTAATA AGATGATCTT CTTGAGATCG TTTTGGTCTG CGCGTAATCT
      TCTAGATTAT TCTACTAGAA GAACTCTAGC AAAACCAGAC GCGCATTAGA

 51   CTTGCTCTGA AAACGAAAAA ACCGCCTTGC AGGGCGGTTT TTCGTAGGTT
      GAACGAGACT TTTGCTTTTT TGGCGGAACG TCCCGCCAAA AAGCATCCAA

101   CTCTGAGCTA CCAACTCTTT GAACCGAGGT AACTGGCTTG GAGGAGCGCA
      GAGACTCGAT GGTTGAGAAA CTTGGCTCCA TTGACCGAAC CTCCTCGCGT

151   GTCACTAAAA CTTGTCCTTT CAGTTTAGCC TTAACCGGCG CATGACTTCA
      CAGTGATTTT GAACAGGAAA GTCAAATCGG AATTGGCCGC GTACTGAAGT

201   AGACTAACTC CTCTAAATCA ATTACCAGTG GCTGCTGCCA GTGGTGCTTT
      TCTGATTGAG GAGATTTAGT TAATGGTCAC CGACGACGGT CACCACGAAA

251   TGCATGTCTT TCCGGGTTGG ACTCAAGACG ATAGTTACCG GATAAGGCGC
      ACGTACAGAA AGGCCCAACC TGAGTTCTGC TATCAATGGC CTATTCCGCG

301   AGCGGTCGGA CTGAACGGGG GGTTCGTGCA TACAGTCCAG CTTGGAGCGA
      TCGCCAGCCT GACTTGCCCC CCAAGCACGT ATGTCAGGTC GAACCTCGCT
```

FIG. 35GG

```
351   ACTGCCTACC CGGAACTGAG TGTCAGGCGT GGAATGAGAC AAACGCGGCC
      TGACGGATGG GCCTTGACTC ACAGTCCGCA CCTTACTCTG TTTGCGCCGG

                          AgeI
                        ~~~~~~~~
401   ATAACAGCGG AATGACACCG GTAAACCGAA AGGCAGGAAC AGGAGAGCGC
      TATTGTCGCC TTACTGTGGC CATTTGGCTT TCCGTCCTTG TCCTCTCGCG

451   AGGAGGGAGC CGCCAGGGGG AAACGCCTGG TATCTTTATA GTCCTGTCGG
      TCCTCCCTCG GCGGTCCCCC TTTGCGGACC ATAGAAATAT CAGGACAGCC

501   GTTTCGCCAC CACTGATTTG AGCGTCAGAT TTCGTGATGC TTGTCAGGGG
      CAAAGCGGTG GTGACTAAAC TCGCAGTCTA AAGCACTACG AACAGTCCCC

551   GGCGGAGCCT ATGGAAAAAC GGCTTTGCCG CGGCCCTCTC ACTTCCCTGT
      CCGCCTCGGA TACCTTTTTG CCGAAACGGC GCCGGGAGAG TGAAGGGACA

601   TAAGTATCTT CCTGGCATCT TCCAGGAAAT CTCCGCCCCG TTCGTAAGCC
      ATTCATAGAA GGACCGTAGA AGGTCCTTTA GAGGCGGGGC AAGCATTCGG

651   ATTTCCGCTC GCCGCAGTCG AACGACCGAG CGTAGCGAGT CAGTGAGCGA
      TAAAGGCGAG CGGCGTCAGC TTGCTGGCTC GCATCGCTCA GTCACTCGCT
```

FIG. 35HH

```
                                                    AgeI
                                                   ~~~~~~~
701  GGAAGCGGAA TATATCCTGT ATCACATATT CTGCTGACGC ACCGGTGCAG
     CCTTCGCCTT ATATAGGACA TAGTGTATAA GACGACTGCG TGGCCACGTC

                             XmnI
                          ~~~~~~~~~~~
751  CCTTTTTTCT CCTGCCACAT GAAGCACTTC ACTGACACCC TCATCAGTGC
     GGAAAAAAGA GGACGGTGTA CTTCGTGAAG TGACTGTGGG AGTAGTCACG

                                  NheI
                                ~~~~~~~
801  CAACATAGTA AGCCAGTATA CACTCCGCTA GC
     GTTGTATCAT TCGGTCATAT GTGAGGCGAT CG
```

FIG. 35II

```
M 13:

 BglII                                            XmnI      BglII
-------                                         -----------------
1  AGATCTCATA ACTTCGTATA ATGTATGCTA TACGAAGTTA TTCAGATCT
   TCTAGAGTAT TGAAGCATAT TACATACGAT ATGCTTCAAT AAGTCTAGA
```

FIG. 35KK

M19
96 bp

```
M 19:

     XbaI  SphI
    ~~~~~~~~~~~~~~
 1  TCTAGAGCAT GCGTAGGAGA AAATAAAATG AAACAAAGCA CTATTGCACT
    AGATCTCGTA CGCATCCTCT TTTATTTTAC TTTGTTTCGT GATAACGTGA

                     SapI                         EcoRI
                  ~~~~~~~~~                     ~~~~~~
51  GGCACTCTTA CCGTTGCTCT TCACCCCTGT TACCAAAGCC GAATTC
    CCGTGAGAAT GGCAACGAGA AGTGGGGACA ATGGTTTCGG CTTAAG
```

*FIG. 35MM*

```
M 20:

      XbaI  SphI
     ~~~~~~~~~~~~~~
  1  TCTAGAGCAT GCGTAGGAGA AAATAAAATG AAACAAAGCA CTATTGCACT
     AGATCTCGTA CGCATCCTCT TTTATTTTAC TTTGTTTCGT GATAACGTGA

                          SapI
                        ~~~~~~~~~
 51  GGCACTCTTA CCGTTGCTCT TCACCCCTGT TACCAAAGCC GACTACAAAG
     CCGTGAGAAT GGCAACGAGA AGTGGGGACA ATGGTTTCGG CTGATGTTTC

                MunI   EcoRI
               ~~~~~~~~~~~~~~
101  ATGAAGTGCA ATTGGAATTC
     TACTTCACGT TAACCTTAAG
```

FIG. 35OO

M21
96 bp

```
M 21:

    XbaI
   ~~~~~~~
1  TCTAGAGGTT GAGGTGATTT TATGAAAAAG AATATCGCAT TTCTTCTTGC
   AGATCTCCAA CTCCACTAAA ATACTTTTTC TTATAGCGTA AAGAAGAACG

                                      NsiI      EcoRI
                                   ~~~~~~~~    ~~~~~~
51 ATCTATGTTC GTTTTTTCTA TTGCTACAAA TGCATACGCT GAATTC
   TAGATACAAG CAAAAAAGAT AACGATGTTT ACGTATGCGA CTTAAG
```

FIG. 35QQ

M41
1221 bp

```
M 41:

      NheI
     -------
  1  GCTAGCATCG AATGGCGCAA AACCTTTCGC GGTATGGCAT GATAGCGCCC
     CGATCGTAGC TTACCGCGTT TTGGAAAGCG CCATACCGTA CTATCGCGGG

 51  GGAAGAGAGT CAATTCAGGG TGGTGAATGT GAAACCAGTA ACGTTATACG
     CCTTCTCTCA GTTAAGTCCC ACCACTTACA CTTTGGTCAT TGCAATATGC

101  ATGTCGCAGA GTATGCCGGT GTCTCTTATC AGACCGTTTC CCGCGTGGTG
     TACAGCGTCT CATACGGCCA CAGAGAATAG TCTGGCAAAG GGCGCACCAC

151  AACCAGGCCA GCCACGTTTC TGCGAAAACG CGGGAAAAAG TGGAAGCGGC
     TTGGTCCGGT CGGTGCAAAG ACGCTTTTGC GCCCTTTTTC ACCTTCGCCG

201  GATGGCGGAG CTGAATTACA TTCCTAACCG CGTGGCACAA CAACTGGCGG
     CTACCGCCTC GACTTAATGT AAGGATTGGC GCACCGTGTT GTTGACCGCC

251  GCAAACAGTC GTTGCTGATT GGCGTTGCCA CCTCCAGTCT GGCCCTGCAC
     CGTTTGTCAG CAACGACTAA CCGCAACGGT GGAGGTCAGA CCGGGACGTG

301  GCGCCGTCGC AAATTGTCGC GGCGATTAAA TCTCGCGCCG ATCAACTGGG
     CGCGGCAGCG TTTAACAGCG CCGCTAATTT AGAGCGCGGC TAGTTGACCC
```

FIG. 35SS

```
351  TGCCAGCGTG GTCGTGTCGA TGGTAGAACG AAGCGGCGTC GAAGCCTGTA
     ACGGTCGCAC CAGCACAGCT ACCATCTTGC TTCGCCGCAG CTTCGGACAT

401  AAGCGGCGGT GCACAATCTT CTCGCGCAAC GTGTCAGTGG GCTGATTATT
     TTCGCCGCCA CGTGTTAGAA GAGCGCGTTG CACAGTCACC CGACTAATAA

451  AACTATCCGC TGGATGACCA GGATGCTATT GCTGTGGAAG CTGCCTGCAC
     TTGATAGGCG ACCTACTGGT CCTACGATAA CGACACCTTC GACGGACGTG

501  TAATGTTCCG GCGTTATTTC TTGATGTCTC TGACCAGACA CCCATCAACA
     ATTACAAGGC CGCAATAAAG AACTACAGAG ACTGGTCTGT GGGTAGTTGT

551  GTATTATTTT CTCCCATGAG GACGGTACGC GACTGGGCGT GGAGCATCTG
     CATAATAAAA GAGGGTACTC CTGCCATGCG CTGACCCGCA CCTCGTAGAC

601  GTCGCATTGG GCCACCAGCA AATCGCGCTG TTAGCTGGCC CATTAAGTTC
     CAGCGTAACC CGGTGGTCGT TTAGCGCGAC AATCGACCGG GTAATTCAAG

651  TGTCTCGGCG CGTCTGCGTC TGGCTGGCTG GCATAAATAT CTCACTCGCA
     ACAGAGCCGC GCAGACGCAG ACCGACCGAC CGTATTTATA GAGTGAGCGT

701  ATCAAATTCA GCCGATAGCG GAACGGGAAG GCGACTGGAG TGCCATGTCC
     TAGTTTAAGT CGGCTATCGC CTTGCCCTTC CGCTGACCTC ACGGTACAGG
```

*FIG. 35TT*

```
751   GGTTTTCAAC AAACCATGCA AATGCTGAAT GAGGGCATCG TTCCCACTGC
      CCAAAAGTTG TTTGGTACGT TTACGACTTA CTCCCGTAGC AAGGGTGACG

801   GATGCTGGTT GCCAACGATC AGATGGCGCT GGGCGCAATG CGTGCCATTA
      CTACGACCAA CGGTTGCTAG TCTACCGCGA CCCGCGTTAC GCACGGTAAT

851   CCGAGTCCGG GCTGCGCGTT GGTGCGGACA TCTCGGTAGT GGGATACGAC
      GGCTCAGGCC CGACGCGCAA CCACGCCTGT AGAGCCATCA CCCTATGCTG

901   GATACCGAGG ACAGCTCATG TTATATCCCG CCGCTGACCA CCATCAAACA
      CTATGGCTCC TGTCGAGTAC AATATAGGGC GGCGACTGGT GGTAGTTTGT

951   GGATTTTCGC CTGCTGGGGC AAACCAGCGT GGACCGCTTG CTGCAACTCT
      CCTAAAAGCG GACGACCCCG TTTGGTCGCA CCTGGCGAAC GACGTTGAGA

1001  CTCAGGGCCA GGCGGTGAAG GGCAATCAGC TGTTGCCCGT CTCACTGGTG
      GAGTCCCGGT CCGCCACTTC CCGTTAGTCG ACAACGGGCA GAGTGACCAC

1051  AAAAGAAAAA CCACCCTGGC TCCCAATACG CAAACCGCCT CTCCCCGCGC
      TTTTCTTTTT GGTGGGACCG AGGGTTATGC GTTTGGCGGA GAGGGGCGCG

1101  GTTGGCCGAT TCACTGATGC AGCTGGCACG ACAGGTTTCC CGACTGGAAA
      CAACCGGCTA AGTGACTACG TCGACCGTGC TGTCCAAAGG GCTGACCTTT
```

FIG. 35UU

```
1151  GCGGGCAGTG AGGCTACCCG ATAAAAGCGG CTTCCTGACA GGAGGCCGTT
      CGCCCGTCAC TCCGATGGGC TATTTTCGCC GAAGGACTGT CCTCCGGCAA

                       AflII
                      ~~~~~~~
1201  TTGTTTTGCA GCCCACTTAA G
      AACAAAACGT CGGGTGAATT C
```

FIG. 35VV

```
pCALO-1:
      BglII
      ~~~~~~
  1   GATCTAGCAC CAGGCGTTTA AGGGCACCAA TAACTGCCTT AAAAAAATTA
      CTAGATCGTG GTCCGCAAAT TCCCGTGGTT ATTGACGGAA TTTTTTTAAT

 51   CGCCCCGCCC TGCCACTCAT CGCAGTACTG TTGTAATTCA TTAAGCATTC
      GCGGGGCGGG ACGGTGAGTA GCGTCATGAC AACATTAAGT AATTCGTAAG

101   TGCCGACATG GAAGCCATCA CAAACGGCAT GATGAACCTG AATCGCCAGC
      ACGGCTGTAC CTTCGGTAGT GTTTGCCGTA CTACTTGGAC TTAGCGGTCG

151   GGCATCAGCA CCTTGTCGCC TTGCGTATAA TATTTGCCCA TAGTGAAAAC
      CCGTAGTCGT GGAACAGCGG AACGCATATT ATAAACGGGT ATCACTTTTG

201   GGGGGCGAAG AAGTTGTCCA TATTGGCTAC GTTTAAATCA AAACTGGTGA
      CCCCCGCTTC TTCAACAGGT ATAACCGATG CAAATTTAGT TTTGACCACT

251   AACTCACCCA GGGATTGGCT GAGACGAAAA ACATATTCTC AATAAACCCT
      TTGAGTGGGT CCCTAACCGA CTCTGCTTTT TGTATAAGAG TTATTTGGGA

301   TTAGGGAAAT AGGCCAGGTT TTCACCGTAA CACGCCACAT CTTGCGAATA
      AATCCCTTTA TCCGGTCCAA AAGTGGCATT GTGCGGTGTA GAACGCTTAT
```

FIG. 35XX

```
351  TATGTGTAGA AACTGCCGGA AATCGTCGTG GTATTCACTC CAGAGCGATG
     ATACACATCT TTGACGGCCT TTAGCAGCAC CATAAGTGAG GTCTCGCTAC

401  AAAACGTTTC AGTTTGCTCA TGGAAAACGG TGTAACAAGG GTGAACACTA
     TTTTGCAAAG TCAAACGAGT ACCTTTTGCC ACATTGTTCC CACTTGTGAT

451  TCCCATATCA CCAGCTCACC GTCTTTCATT GCCATACGGA ACTCCGGGTG
     AGGGTATAGT GGTCGAGTGG CAGAAAGTAA CGGTATGCCT TGAGGCCCAC

501  AGCATTCATC AGGCGGGCAA GAATGTGAAT AAAGGCCGGA TAAAACTTGT
     TCGTAAGTAG TCCGCCCGTT CTTACACTTA TTTCCGGCCT ATTTTGAACA

551  GCTTATTTTT CTTTACGGTC TTTAAAAAGG CCGTAATATC CAGCTGAACG
     CGAATAAAAA GAAATGCCAG AAATTTTTCC GGCATTATAG GTCGACTTGC

601  GTCTGGTTAT AGGTACATTG AGCAACTGAC TGAAATGCCT CAAAATGTTC
     CAGACCAATA TCCATGTAAC TCGTTGACTG ACTTTACGGA GTTTTACAAG

651  TTTACGATGC CATTGGGATA TATCAACGGT GGTATATCCA GTGATTTTTT
     AAATGCTACG GTAACCCTAT ATAGTTGCCA CCATATAGGT CACTAAAAAA

701  TCTCCATTTT AGCTTCCTTA GCTCCTGAAA ATCTCGATAA CTCAAAAAAT
     AGAGGTAAAA TCGAAGGAAT CGAGGACTTT TAGAGCTATT GAGTTTTTTA
```

FIG. 35YY

```
751   ACGCCCGGTA GTGATCTTAT TTCATTATGG TGAAAGTTGG AACCTCACCC
      TGCGGGCCAT CACTAGAATA AAGTAATACC ACTTTCAACC TTGGAGTGGG

       AatII
      ~~~~~~
801   GACGTCTAAT GTGAGTTAGC TCACTCATTA GGCACCCCAG GCTTTACACT
      CTGCAGATTA CACTCAATCG AGTGAGTAAT CCGTGGGGTC CGAAATGTGA

851   TTATGCTTCC GGCTCGTATG TTGTGTGGAA TTGTGAGCGG ATAACAATTT
      AATACGAAGG CCGAGCATAC AACACACCTT AACACTCGCC TATTGTTAAA

                                          XbaI
                                        ~~~~~~~
901   CACACAGGAA ACAGCTATGA CCATGATTAC GAATTTCTAG ACCCCCCCCC
      GTGTGTCCTT TGTCGATACT GGTACTAATG CTTAAAGATC TGGGGGGGGG

        SphI                                       HindIII
      ~~~~~~~                                      ~~~~~~
951   CGCATGCCAT AACTTCGTAT AATGTACGCT ATACGAAGTT ATAAGCTTGA
      GCGTACGGTA TTGAAGCATA TTACATGCGA TATGCTTCAA TATTCGAACT

1001  CCTGTGAAGT GAAAAATGGC GCAGATTGTG CGACATTTTT TTTGTCTGCC
      GGACACTTCA CTTTTTACCG CGTCTAACAC GCTGTAAAAA AAACAGACGG
```

FIG. 35ZZ

```
                PacI                         FseI                         BsrGI
              ~~~~~~~~~                    ~~~~~~~~~                    ~~~~~~~~
1051   GTTTAATTAA AGGGGGGGGG GGGCCGGCCT GGGGGGGGGT GTACATGAAA
       CAAATTAATT TCCCCCCCCC CCCGGCCGGA CCCCCCCCCA CATGTACTTT

1101   TTGTAAACGT TAATATTTTG TTAAAATTCG CGTTAAATTT TTGTTAAATC
       AACATTTGCA ATTATAAAAC AATTTTAAGC GCAATTTAAA AACAATTTAG

1151   AGCTCATTTT TTAACCAATA GGCCGAAATC GGCAAAATCC CTTATAAATC
       TCGAGTAAAA AATTGGTTAT CCGGCTTTAG CCGTTTTAGG GAATATTTAG

1201   AAAAGAATAG ACCGAGATAG GGTTGAGTGT TGTTCCAGTT TGGAACAAGA
       TTTTCTTATC TGGCTCTATC CCAACTCACA ACAAGGTCAA ACCTTGTTCT

1251   GTCCACTATT AAAGAACGTG GACTCCAACG TCAAAGGGCG AAAAACCGTC
       CAGGTGATAA TTTCTTGCAC CTGAGGTTGC AGTTTCCCGC TTTTTGGCAG

1301   TATCAGGGCG ATGGCCCACT ACGAGAACCA TCACCCTAAT CAAGTTTTTT
       ATAGTCCCGC TACCGGGTGA TGCTCTTGGT AGTGGGATTA GTTCAAAAAA

                                                          BanII
                                                         ~~~~~~
1351   GGGGTCGAGG TGCCGTAAAG CACTAAATCG GAACCCTAAA GGGAGCCCCC
       CCCCAGCTCC ACGGCATTTC GTGATTTAGC CTTGGGATTT CCCTCGGGGG
```

*FIG. 35AAA*

```
1401  GATTTAGAGC TTGACGGGGA AAGCCGGCGA ACGTGGCGAG AAAGGAAGGG
      CTAAATCTCG AACTGCCCCT TTCGGCCGCT TGCACCGCTC TTTCCTTCCC

1451  AAGAAAGCGA AAGGAGCGGG CGCTAGGGCG CTGGCAAGTG TAGCGGTCAC
      TTCTTTCGCT TTCCTCGCCC GCGATCCCGC GACCGTTCAC ATCGCCAGTG

1501  GCTGCGCGTA ACCACCACAC CCGCCGCGCT TAATGCGCCG CTACAGGGCG
      CGACGCGCAT TGGTGGTGTG GGCGGCGCGA ATTACGCGGC GATGTCCCGC

          NheI
        ~~~~~~
1551  CGTGCTAGCG GAGTGTATAC TGGCTTACTA TGTTGGCACT GATGAGGGTG
      GCACGATCGC CTCACATATG ACCGAATGAT ACAACCGTGA CTACTCCCAC

               XmnI                                 AgeI
          ~~~~~~~~~~~~                            ~~~~~~~~
1601  TCAGTGAAGT GCTTCATGTG GCAGGAGAAA AAAGGCTGCA CCGGTGCGTC
      AGTCACTTCA CGAAGTACAC CGTCCTCTTT TTTCCGACGT GGCCACGCAG

1651  AGCAGAATAT GTGATACAGG ATATATTCCG CTTCCTCGCT CACTGACTCG
      TCGTCTTATA CACTATGTCC TATATAAGGC GAAGGAGCGA GTGACTGAGC

1701  CTACGCTCGG TCGTTCGACT GCGGCGAGCG GAAATGGCTT ACGAACGGGG
```

FIG. 35BBB

```
      GATGCGAGCC AGCAAGCTGA CGCCGCTCGC CTTTACCGAA TGCTTGCCCC

1751  CGGAGATTTC CTGGAAGATG CCAGGAAGAT ACTTAACAGG GAAGTGAGAG
      GCCTCTAAAG GACCTTCTAC GGTCCTTCTA TGAATTGTCC CTTCACTCTC

1801  GGCCGCGGCA AAGCCGTTTT TCCATAGGCT CCGCCCCCCT GACAAGCATC
      CCGGCGCCGT TTCGGCAAAA AGGTATCCGA GGCGGGGGGA CTGTTCGTAG

1851  ACGAAATCTG ACGCTCAAAT CAGTGGTGGC GAAACCCGAC AGGACTATAA
      TGCTTTAGAC TGCGAGTTTA GTCACCACCG CTTTGGGCTG TCCTGATATT

1901  AGATACCAGG CGTTTCCCCC TGGCGGCTCC CTCCTGCGCT CTCCTGTTCC
      TCTATGGTCC GCAAAGGGGG ACCGCCGAGG GAGGACGCGA GAGGACAAGG

                   AgeI
                  ~~~~~~
1951  TGCCTTTCGG TTTACCGGTG TCATTCCGCT GTTATGGCCG CGTTTGTCTC
      ACGGAAAGCC AAATGGCCAC AGTAAGGCGA CAATACCGGC GCAAACAGAG

2001  ATTCCACGCC TGACACTCAG TTCCGGGTAG GCAGTTCGCT CCAAGCTGGA
      TAAGGTGCGG ACTGTGAGTC AAGGCCCATC CGTCAAGCGA GGTTCGACCT

2051  CTGTATGCAC GAACCCCCCG TTCAGTCCGA CCGCTGCGCC TTATCCGGTA
      GACATACGTG CTTGGGGGGC AAGTCAGGCT GGCGACGCGG AATAGGCCAT
```

FIG. 35CCC

```
2101  ACTATCGTCT TGAGTCCAAC CCGGAAAGAC ATGCAAAAGC ACCACTGGCA
      TGATAGCAGA ACTCAGGTTG GGCCTTTCTG TACGTTTTCG TGGTGACCGT

2151  GCAGCCACTG GTAATTGATT TAGAGGAGTT AGTCTTGAAG TCATGCGCCG
      CGTCGGTGAC CATTAACTAA ATCTCCTCAA TCAGAACTTC AGTACGCGGC

2201  GTTAAGGCTA AACTGAAAGG ACAAGTTTTA GTGACTGCGC TCCTCCAAGC
      CAATTCCGAT TTGACTTTCC TGTTCAAAAT CACTGACGCG AGGAGGTTCG

2251  CAGTTACCTC GGTTCAAAGA GTTGGTAGCT CAGAGAACCT ACGAAAAACC
      GTCAATGGAG CCAAGTTTCT CAACCATCGA GTCTCTTGGA TGCTTTTTGG

2301  GCCCTGCAAG GCGGTTTTTT CGTTTTCAGA GCAAGAGATT ACGCGCAGAC
      CGGGACGTTC CGCCAAAAAA GCAAAAGTCT CGTTCTCTAA TGCGCGTCTG

                                 BglII
                                     ~
2351  CAAAACGATC TCAAGAAGAT CATCTTATTA
      GTTTTGCTAG AGTTCTTCTA GTAGAATAAT
```

FIG. 35DDD

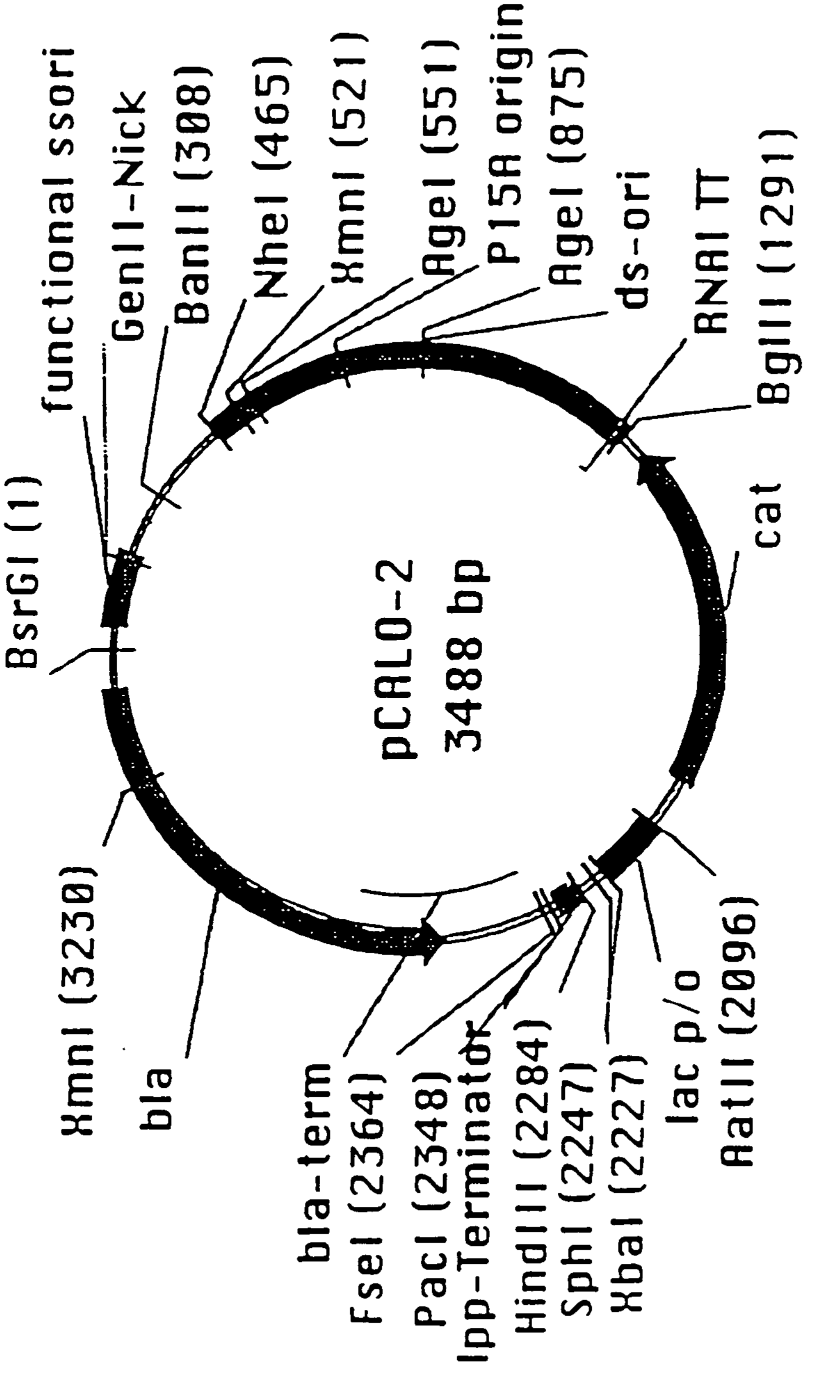
FIG. 35EEE

```
pCALO-2:
    BsrGI
    ~~~~~
  1 GTACATGAAA TTGTAAACGT TAATATTTTG TTAAAATTCG CGTTAAATTT
    CATGTACTTT AACATTTGCA ATTATAAAAC AATTTTAAGC GCAATTTAAA

 51 TTGTTAAATC AGCTCATTTT TTAACCAATA GGCCGAAATC GGCAAAATCC
    AACAATTTAG TCGAGTAAAA AATTGGTTAT CCGGCTTTAG CCGTTTTAGG

101 CTTATAAATC AAAAGAATAG ACCGAGATAG GGTTGAGTGT TGTTCCAGTT
    GAATATTTAG TTTTCTTATC TGGCTCTATC CCAACTCACA ACAAGGTCAA

151 TGGAACAAGA GTCCACTATT AAAGAACGTG GACTCCAACG TCAAAGGGCG
    ACCTTGTTCT CAGGTGATAA TTTCTTGCAC CTGAGGTTGC AGTTTCCCGC

201 AAAAACCGTC TATCAGGGCG ATGGCCCACT ACGAGAACCA TCACCCTAAT
    TTTTTGGCAG ATAGTCCCGC TACCGGGTGA TGCTCTTGGT AGTGGGATTA

251 CAAGTTTTTT GGGGTCGAGG TGCCGTAAAG CACTAAATCG GAACCCTAAA
    GTTCAAAAAA CCCCAGCTCC ACGGCATTTC GTGATTTAGC CTTGGGATTT

       BanII
      ~~~~~~
301 GGGAGCCCCC GATTTAGAGC TTGACGGGGA AAGCCGGCGA ACGTGGCGAG
```

FIG. 35FFF

```
     CCCTCGGGGG CTAAATCTCG AACTGCCCCT TTCGGCCGCT TGCACCGCTC

351  AAAGGAAGGG AAGAAAGCGA AAGGAGCGGG CGCTAGGGCG CTGGCAAGTG
     TTTCCTTCCC TTCTTTCGCT TTCCTCGCCC GCGATCCCGC GACCGTTCAC

401  TAGCGGTCAC GCTGCGCGTA ACCACCACAC CCGCCGCGCT TAATGCGCCG
     ATCGCCAGTG CGACGCGCAT TGGTGGTGTG GGCGGCGCGA ATTACGCGGC

                  NheI
                 ~~~~~~~
451  CTACAGGGCG CGTGCTAGCG GAGTGTATAC TGGCTTACTA TGTTGGCACT
     GATGTCCCGC GCACGATCGC CTCACATATG ACCGAATGAT ACAACCGTGA

                      XmnI                             AgeI
                   ~~~~~~~~~~~~                           ~
501  GATGAGGGTG TCAGTGAAGT GCTTCATGTG GCAGGAGAAA AAAGGCTGCA
     CTACTCCCAC AGTCACTTCA CGAAGTACAC CGTCCTCTTT TTTCCGACGT

     AgeI
     ~~~~~
551  CCGGTGCGTC AGCAGAATAT GTGATACAGG ATATATTCCG CTTCCTCGCT
     GGCCACGCAG TCGTCTTATA CACTATGTCC TATATAAGGC GAAGGAGCGA

601  CACTGACTCG CTACGCTCGG TCGTTCGACT GCGGCGAGCG GAAATGGCTT
```

FIG. 35GGG

```
     GTGACTGAGC GATGCGAGCC AGCAAGCTGA CGCCGCTCGC CTTTACCGAA

651  ACGAACGGGG CGGAGATTTC CTGGAAGATG CCAGGAAGAT ACTTAACAGG
     TGCTTGCCCC GCCTCTAAAG GACCTTCTAC GGTCCTTCTA TGAATTGTCC

701  GAAGTGAGAG GGCCGCGGCA AAGCCGTTTT TCCATAGGCT CCGCCCCCCT
     CTTCACTCTC CCGGCGCCGT TTCGGCAAAA AGGTATCCGA GGCGGGGGGA

751  GACAAGCATC ACGAAATCTG ACGCTCAAAT CAGTGGTGGC GAAACCCGAC
     CTGTTCGTAG TGCTTTAGAC TGCGAGTTTA GTCACCACCG CTTTGGGCTG

801  AGGACTATAA AGATACCAGG CGTTTCCCCC TGGCGGCTCC CTCCTGCGCT
     TCCTGATATT TCTATGGTCC GCAAAGGGGG ACCGCCGAGG GAGGACGCGA

                             AgeI
                            ~~~~~~
851  CTCCTGTTCC TGCCTTTCGG TTTACCGGTG TCATTCCGCT GTTATGGCCG
     GAGGACAAGG ACGGAAAGCC AAATGGCCAC AGTAAGGCGA CAATACCGGC

901  CGTTTGTCTC ATTCCACGCC TGACACTCAG TTCCGGGTAG GCAGTTCGCT
     GCAAACAGAG TAAGGTGCGG ACTGTGAGTC AAGGCCCATC CGTCAAGCGA

951  CCAAGCTGGA CTGTATGCAC GAACCCCCCG TTCAGTCCGA CCGCTGCGCC
     GGTTCGACCT GACATACGTG CTTGGGGGGC AAGTCAGGCT GGCGACGCGG
```

FIG. 35HHH

```
1001  TTATCCGGTA ACTATCGTCT TGAGTCCAAC CCGGAAAGAC ATGCAAAAGC
      AATAGGCCAT TGATAGCAGA ACTCAGGTTG GGCCTTTCTG TACGTTTTCG

1051  ACCACTGGCA GCAGCCACTG GTAATTGATT TAGAGGAGTT AGTCTTGAAG
      TGGTGACCGT CGTCGGTGAC CATTAACTAA ATCTCCTCAA TCAGAACTTC

1101  TCATGCGCCG GTTAAGGCTA AACTGAAAGG ACAAGTTTTA GTGACTGCGC
      AGTACGCGGC CAATTCCGAT TTGACTTTCC TGTTCAAAAT CACTGACGCG

1151  TCCTCCAAGC CAGTTACCTC GGTTCAAAGA GTTGGTAGCT CAGAGAACCT
      AGGAGGTTCG GTCAATGGAG CCAAGTTTCT CAACCATCGA GTCTCTTGGA

1201  ACGAAAAACC GCCCTGCAAG GCGGTTTTTT CGTTTTCAGA GCAAGAGATT
      TGCTTTTTGG CGGGACGTTC CGCCAAAAAA GCAAAAGTCT CGTTCTCTAA

                                                  BglII
                                                ~~~~~~~~
1251  ACGCGCAGAC CAAAACGATC TCAAGAAGAT CATCTTATTA GATCTAGCAC
      TGCGCGTCTG GTTTTGCTAG AGTTCTTCTA GTAGAATAAT CTAGATCGTG

1301  CAGGCGTTTA AGGGCACCAA TAACTGCCTT AAAAAAATTA CGCCCCGCCC
      GTCCGCAAAT TCCCGTGGTT ATTGACGGAA TTTTTTTAAT GCGGGGCGGG
```

FIG. 35III

```
1351  TGCCACTCAT CGCAGTACTG TTGTAATTCA TTAAGCATTC TGCCGACATG
      ACGGTGAGTA GCGTCATGAC AACATTAAGT AATTCGTAAG ACGGCTGTAC

1401  GAAGCCATCA CAAACGGCAT GATGAACCTG AATCGCCAGC GGCATCAGCA
      CTTCGGTAGT GTTTGCCGTA CTACTTGGAC TTAGCGGTCG CCGTAGTCGT

1451  CCTTGTCGCC TTGCGTATAA TATTTGCCCA TAGTGAAAAC GGGGGCGAAG
      GGAACAGCGG AACGCATATT ATAAACGGGT ATCACTTTTG CCCCCGCTTC

1501  AAGTTGTCCA TATTGGCTAC GTTTAAATCA AAACTGGTGA AACTCACCCA
      TTCAACAGGT ATAACCGATG CAAATTTAGT TTTGACCACT TTGAGTGGGT

1551  GGGATTGGCT GAGACGAAAA ACATATTCTC AATAAACCCT TTAGGGAAAT
      CCCTAACCGA CTCTGCTTTT TGTATAAGAG TTATTTGGGA AATCCCTTTA

1601  AGGCCAGGTT TTCACCGTAA CACGCCACAT CTTGCGAATA TATGTGTAGA
      TCCGGTCCAA AAGTGGCATT GTGCGGTGTA GAACGCTTAT ATACACATCT

1651  AACTGCCGGA AATCGTCGTG GTATTCACTC CAGAGCGATG AAAACGTTTC
      TTGACGGCCT TTAGCAGCAC CATAAGTGAG GTCTCGCTAC TTTTGCAAAG

1701  AGTTTGCTCA TGGAAAACGG TGTAACAAGG GTGAACACTA TCCCATATCA
      TCAAACGAGT ACCTTTTGCC ACATTGTTCC CACTTGTGAT AGGGTATAGT
```

FIG. 35JJJ

```
1751  CCAGCTCACC GTCTTTCATT GCCATACGGA ACTCCGGGTG AGCATTCATC
      GGTCGAGTGG CAGAAAGTAA CGGTATGCCT TGAGGCCCAC TCGTAAGTAG

1801  AGGCGGGCAA GAATGTGAAT AAAGGCCGGA TAAAACTTGT GCTTATTTTT
      TCCGCCCGTT CTTACACTTA TTTCCGGCCT ATTTTGAACA CGAATAAAAA

1851  CTTTACGGTC TTTAAAAAGG CCGTAATATC CAGCTGAACG GTCTGGTTAT
      GAAATGCCAG AAATTTTTCC GGCATTATAG GTCGACTTGC CAGACCAATA

1901  AGGTACATTG AGCAACTGAC TGAAATGCCT CAAAATGTTC TTTACGATGC
      TCCATGTAAC TCGTTGACTG ACTTTACGGA GTTTTACAAG AAATGCTACG

1951  CATTGGGATA TATCAACGGT GGTATATCCA GTGATTTTTT TCTCCATTTT
      GTAACCCTAT ATAGTTGCCA CCATATAGGT CACTAAAAAA AGAGGTAAAA

2001  AGCTTCCTTA GCTCCTGAAA ATCTCGATAA CTCAAAAAAT ACGCCCGGTA
      TCGAAGGAAT CGAGGACTTT TAGAGCTATT GAGTTTTTTA TGCGGGCCAT

                                                  AatII
                                                 ~~~~~~
2051  GTGATCTTAT TTCATTATGG TGAAAGTTGG AACCTCACCC GACGTCTAAT
      CACTAGAATA AAGTAATACC ACTTTCAACC TTGGAGTGGG CTGCAGATTA

2101  GTGAGTTAGC TCACTCATTA GGCACCCCAG GCTTTACACT TTATGCTTCC
```

*FIG. 35KKK*

```
      CACTCAATCG AGTGAGTAAT CCGTGGGGTC CGAAATGTGA AATACGAAGG

2151  GGCTCGTATG TTGTGTGGAA TTGTGAGCGG ATAACAATTT CACACAGGAA
      CCGAGCATAC AACACACCTT AACACTCGCC TATTGTTAAA GTGTGTCCTT

                                XbaI                  SphI
                              ~~~~~~~~              ~~~~~~~
2201  ACAGCTATGA CCATGATTAC GAATTTCTAG ACCCCCCCCC CGCATGCCAT
      TGTCGATACT GGTACTAATG CTTAAAGATC TGGGGGGGGG GCGTACGGTA

                                           HindIII
                                           ~~~~~~~
2251  AACTTCGTAT AATGTACGCT ATACGAAGTT ATAAGCTTGA CCTGTGAAGT
      TTGAAGCATA TTACATGCGA TATGCTTCAA TATTCGAACT GGACACTTCA

                                                     PacI
                                                  ~~~~~~~~~
2301  GAAAAATGGC GCAGATTGTG CGACATTTTT TTTGTCTGCC GTTTAATTAA
      CTTTTTACCG CGTCTAACAC GCTGTAAAAA AAACAGACGG CAAATTAATT

              FseI
           ~~~~~~~~~~
2351  GGGGGGGGGC CGGCCATTAT CAAAAAGGAT CTCAAGAAGA TCCTTTGATC
      CCCCCCCCCG GCCGGTAATA GTTTTTCCTA GAGTTCTTCT AGGAAACTAG
```

FIG. 35LLL

```
2401  TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA

2451  TTTGGTCATG AGATTATCAA AAAGGATCTT CACCTAGATC CTTTTAAATT
      AAACCAGTAC TCTAATAGTT TTTCCTAGAA GTGGATCTAG GAAAATTTAA

2501  AAAAATGAAG TTTTAAATCA ATCTAAAGTA TATATGAGTA AACTTGGTCT
      TTTTTACTTC AAAATTTAGT TAGATTTCAT ATATACTCAT TTGAACCAGA

2551  GACAGTTACC CAATGCTTAA TCAGTGAGGC ACCTATCTCA GCGATCTGTC
      CTGTCAATGG GTTACGAATT AGTCACTCCG TGGATAGAGT CGCTAGACAG

2601  TATTTCGTTC ATCCATAGTT GCCTGACTCC CCGTCGTGTA GATAACTACG
      ATAAAGCAAG TAGGTATCAA CGGACTGAGG GGCAGCACAT CTATTGATGC

2651  ATACGGGAGG GCTTACCATC TGGCCCCAGT GCTGCAATGA TACCGCGAGA
      TATGCCCTCC CGAATGGTAG ACCGGGGTCA CGACGTTACT ATGGCGCTCT

2701  CCCACGCTCA CCGGCTCCAG ATTTATCAGC AATAAACCAG CCAGCCGGAA
      GGGTGCGAGT GGCCGAGGTC TAAATAGTCG TTATTTGGTC GGTCGGCCTT

2751  GGGCCGAGCG CAGAAGTGGT CCTGCAACTT TATCCGCCTC CATCCAGTCT
      CCCGGCTCGC GTCTTCACCA GGACGTTGAA ATAGGCGGAG GTAGGTCAGA
```

FIG. 35MMM

```
2801  ATTAACTGTT GCCGGGAAGC TAGAGTAAGT AGTTCGCCAG TTAATAGTTT
      TAATTGACAA CGGCCCTTCG ATCTCATTCA TCAAGCGGTC AATTATCAAA

2851  GCGCAACGTT GTTGCCATTG CTACAGGCAT CGTGGTGTCA CGCTCGTCGT
      CGCGTTGCAA CAACGGTAAC GATGTCCGTA GCACCACAGT GCGAGCAGCA

2901  TTGGTATGGC TTCATTCAGC TCCGGTTCCC AACGATCAAG GCGAGTTACA
      AACCATACCG AAGTAAGTCG AGGCCAAGGG TTGCTAGTTC CGCTCAATGT

2951  TGATCCCCCA TGTTGTGCAA AAAAGCGGTT AGCTCCTTCG GTCCTCCGAT
      ACTAGGGGGT ACAACACGTT TTTTCGCCAA TCGAGGAAGC CAGGAGGCTA

3001  CGTTGTCAGA AGTAAGTTGG CCGCAGTGTT ATCACTCATG GTTATGGCAG
      GCAACAGTCT TCATTCAACC GGCGTCACAA TAGTGAGTAC CAATACCGTC

3051  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

3101  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

3151  GAGTTGCTCT TGCCCGGCGT CAATACGGGA TAATACCGCG CCACATAGCA
      CTCAACGAGA ACGGGCCGCA GTTATGCCCT ATTATGGCGC GGTGTATCGT
```

*FIG. 35NNN*

```
                                   XmnI
                                 ~~~~~~~~~~~~
3201  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

3251  TCAAGGATCT TACCGCTGTT GAGATCCAGT TCGATGTAAC CCACTCGCGC
      AGTTCCTAGA ATGGCGACAA CTCTAGGTCA AGCTACATTG GGTGAGCGCG

3301  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

3351  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

3401  AAATGTTGAA TACTCATACT CTTCCTTTTT CAATATTATT GAAGCATTTA
      TTTACAACTT ATGAGTATGA GAAGGAAAAA GTTATAATAA CTTCGTAAAT

                                        BsrGI

3451  TCAGGGTTAT TGTCTCATGA GCGGATACAT ATTTGAAT
      AGTCCCAATA ACAGAGTACT CGCCTATGTA TAAACTTA
```

FIG. 35OOO

Figure 35A:
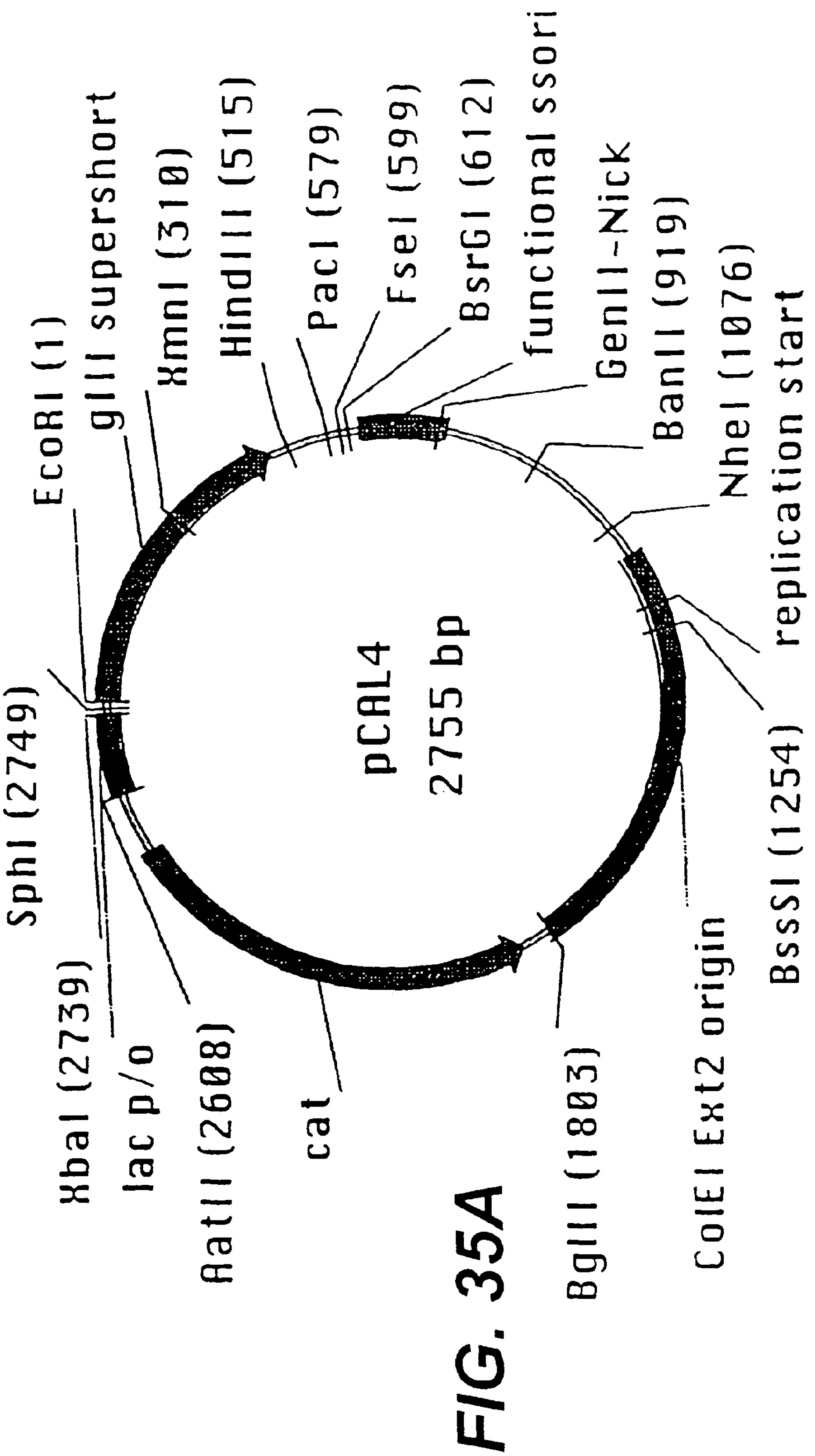
Figure 35J:
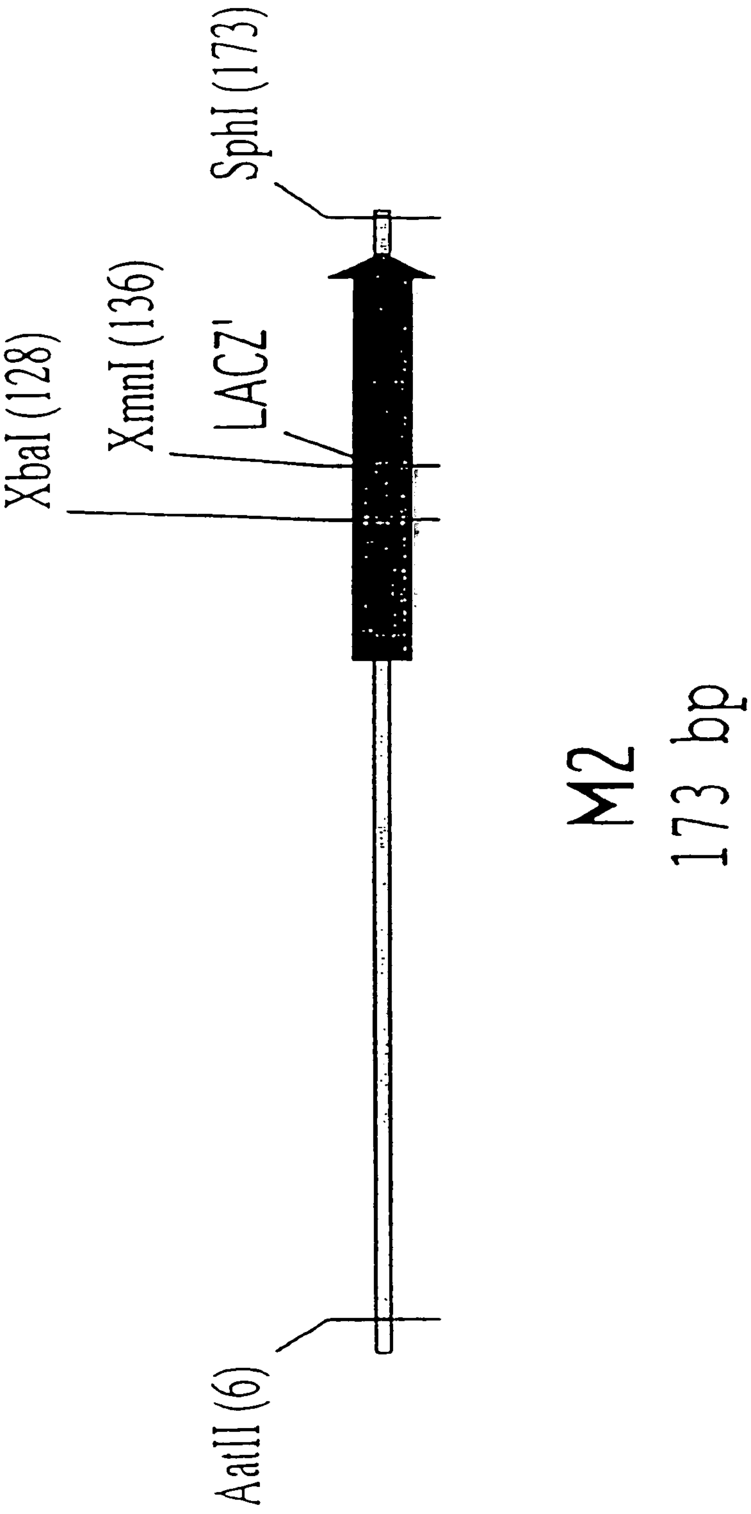
Figure 35L:
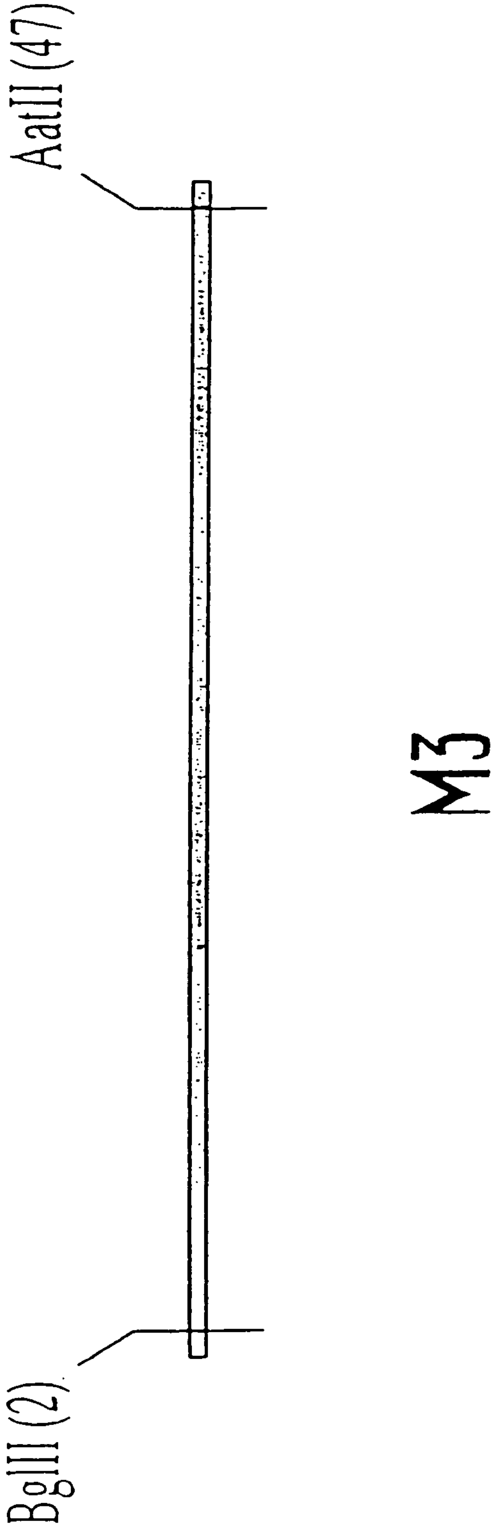
Figure 35N:
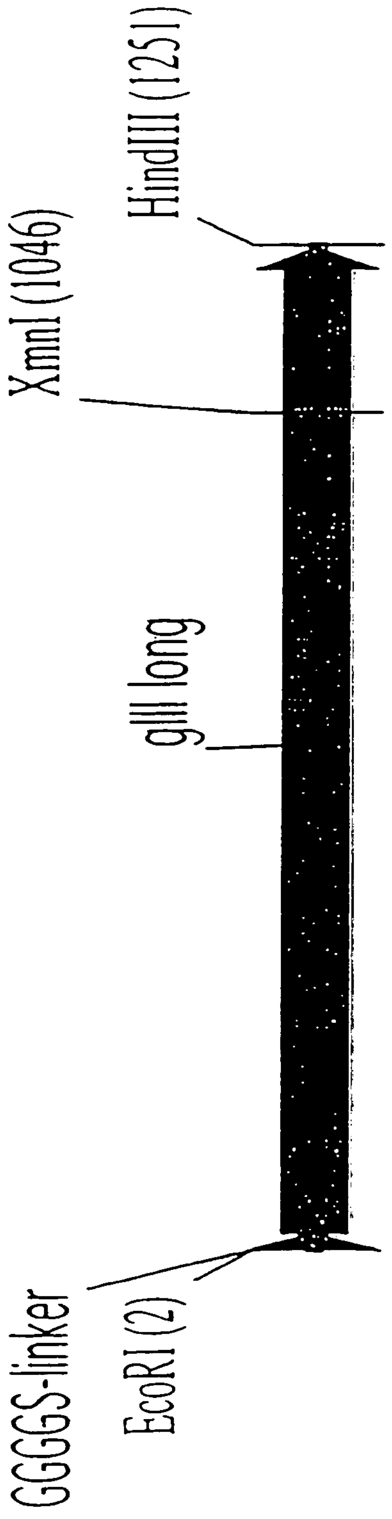
Figure 35S:
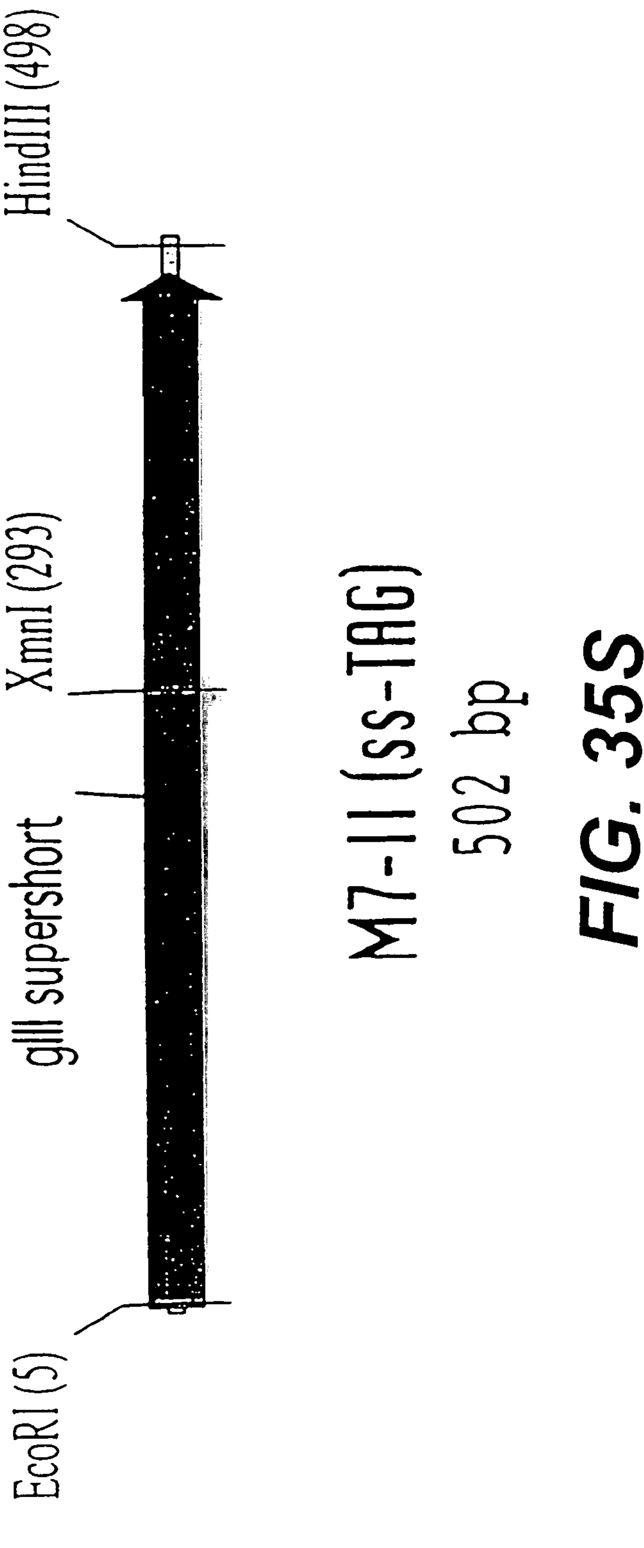
Figure 35V:
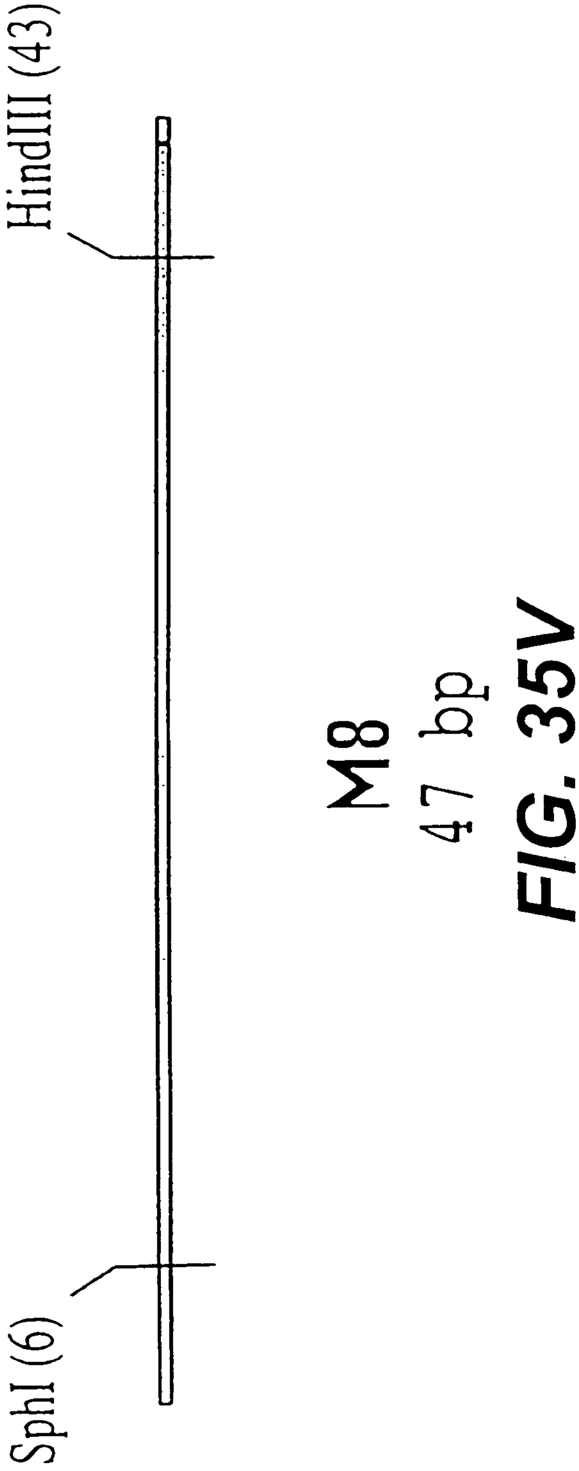
Figure 35X:
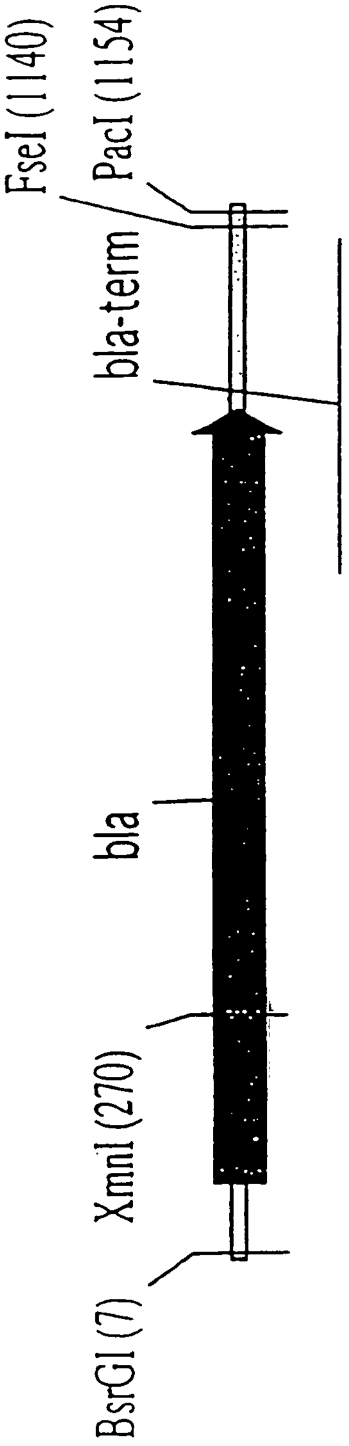
Figure 35C:
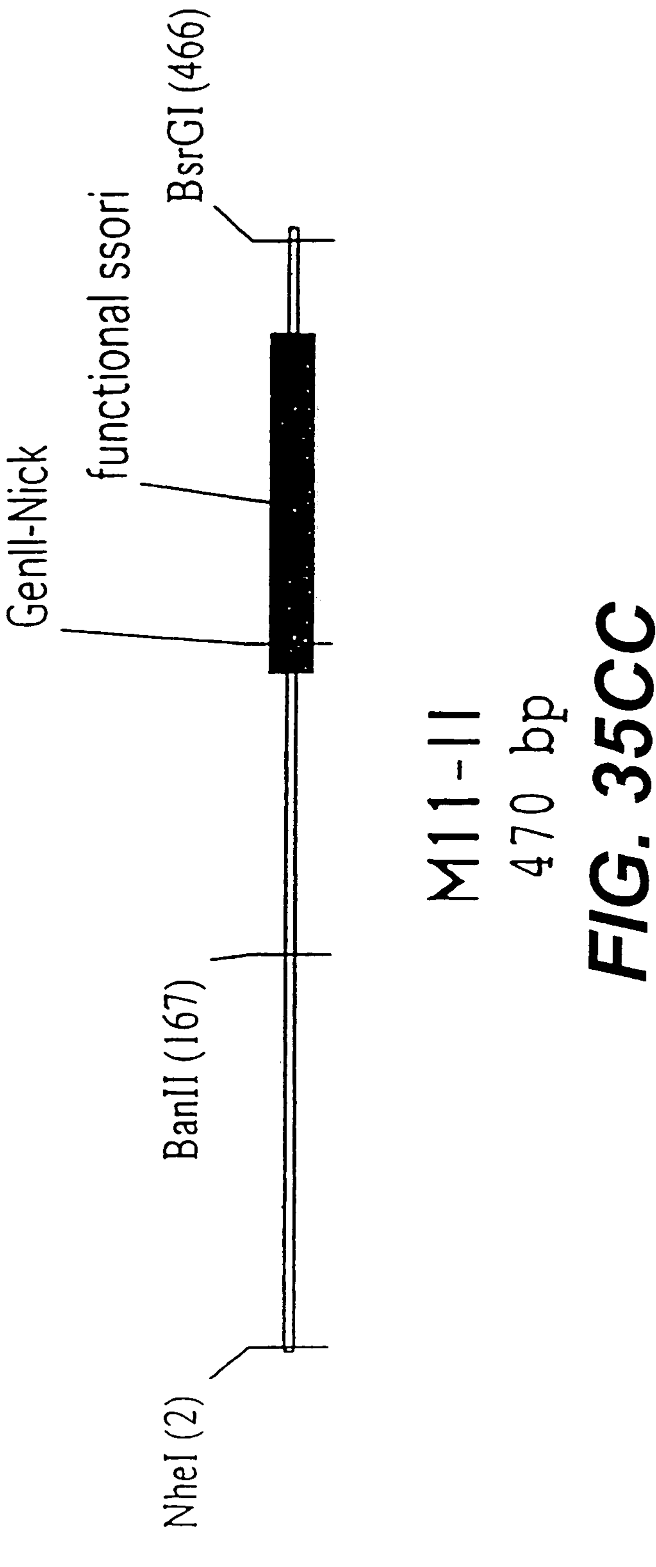
Figure 35F:
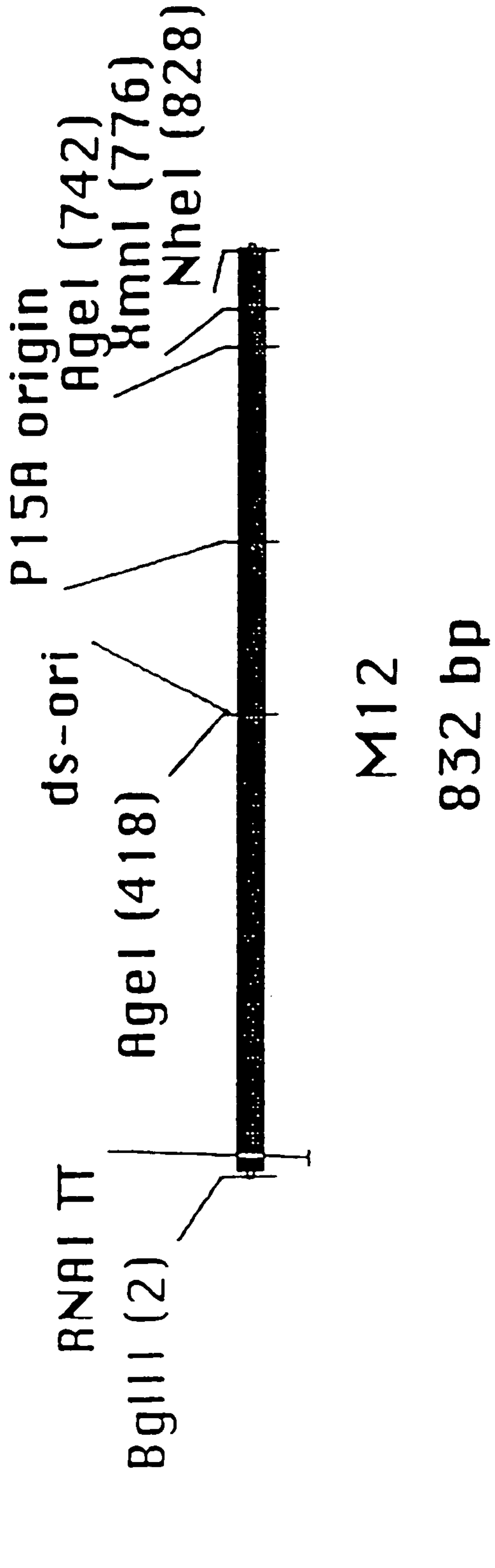
Figure 35J:
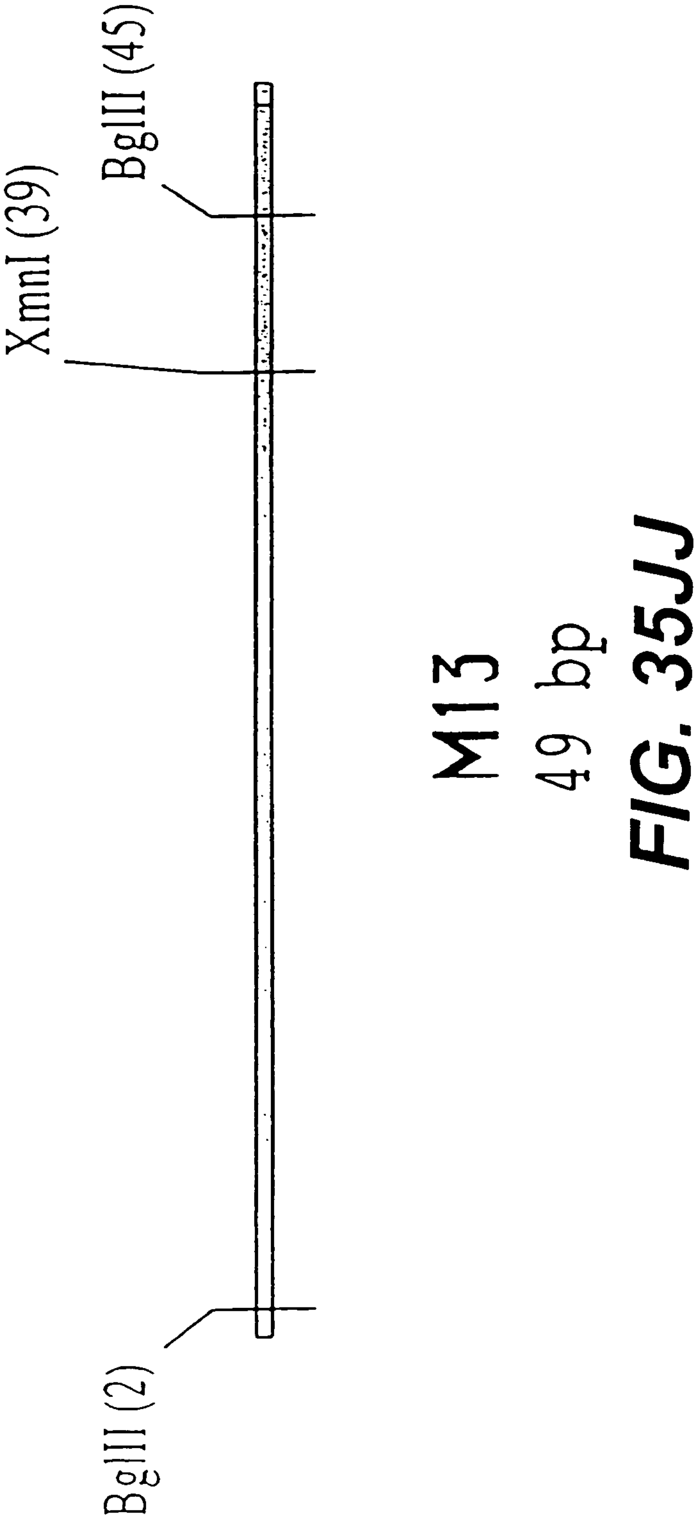
Figure 35L:
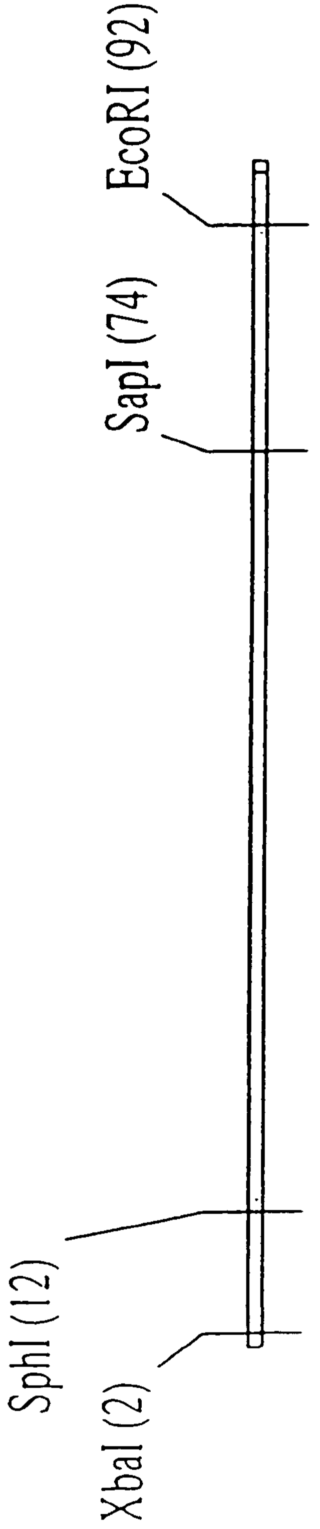
Figure 35N:
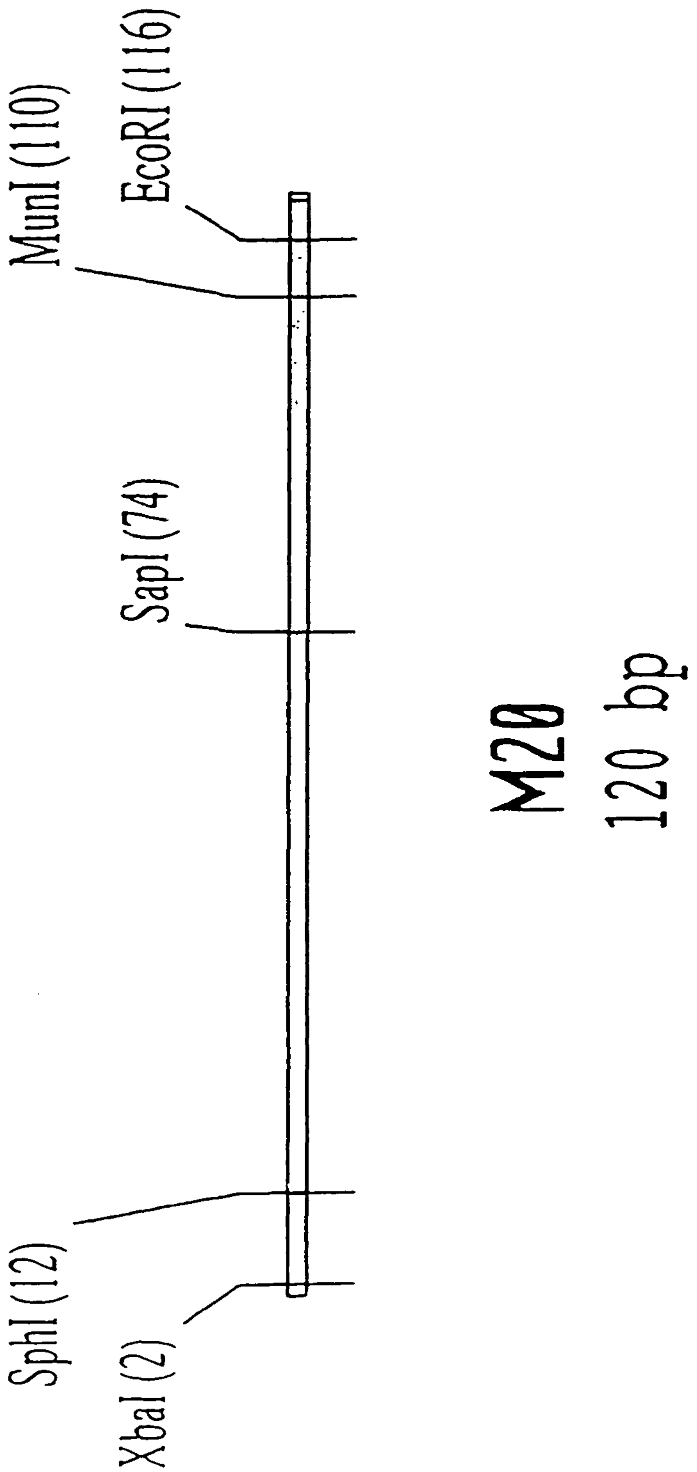
Figure 35P:
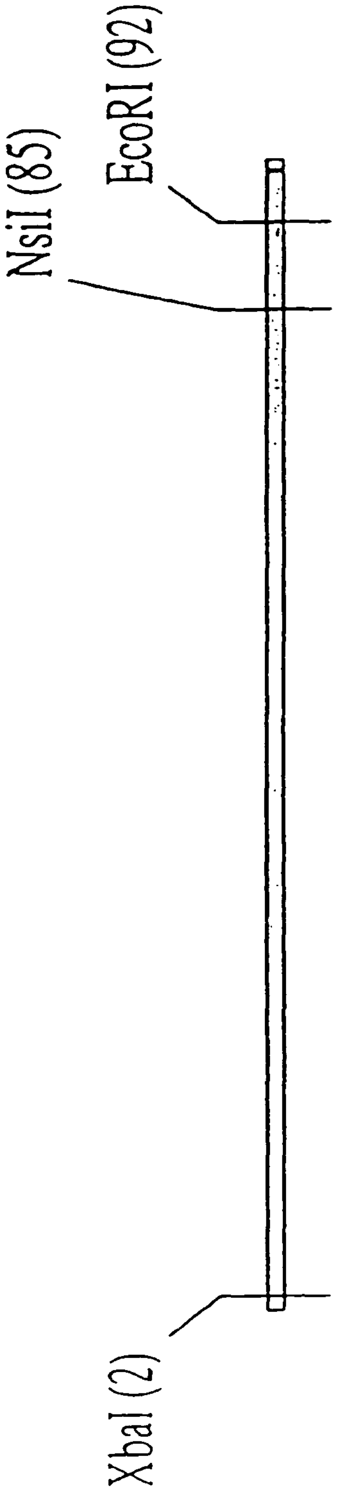
Figure 35R:
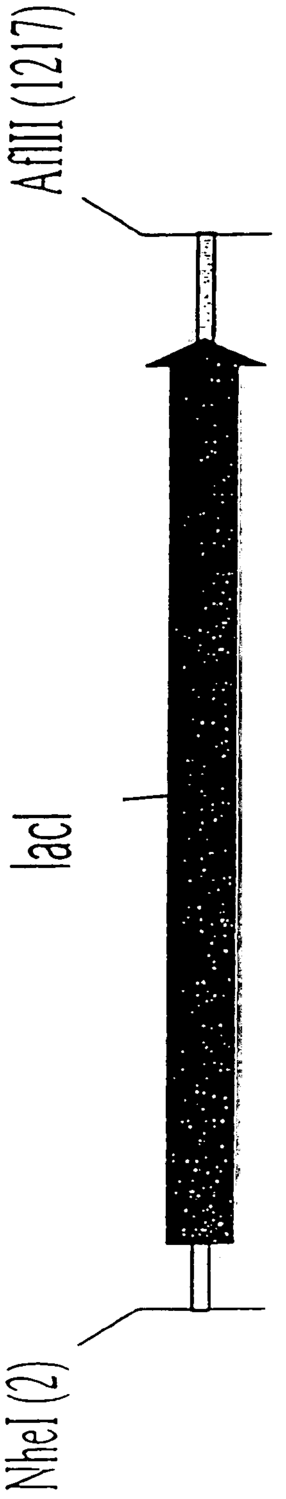
Figure 35W:
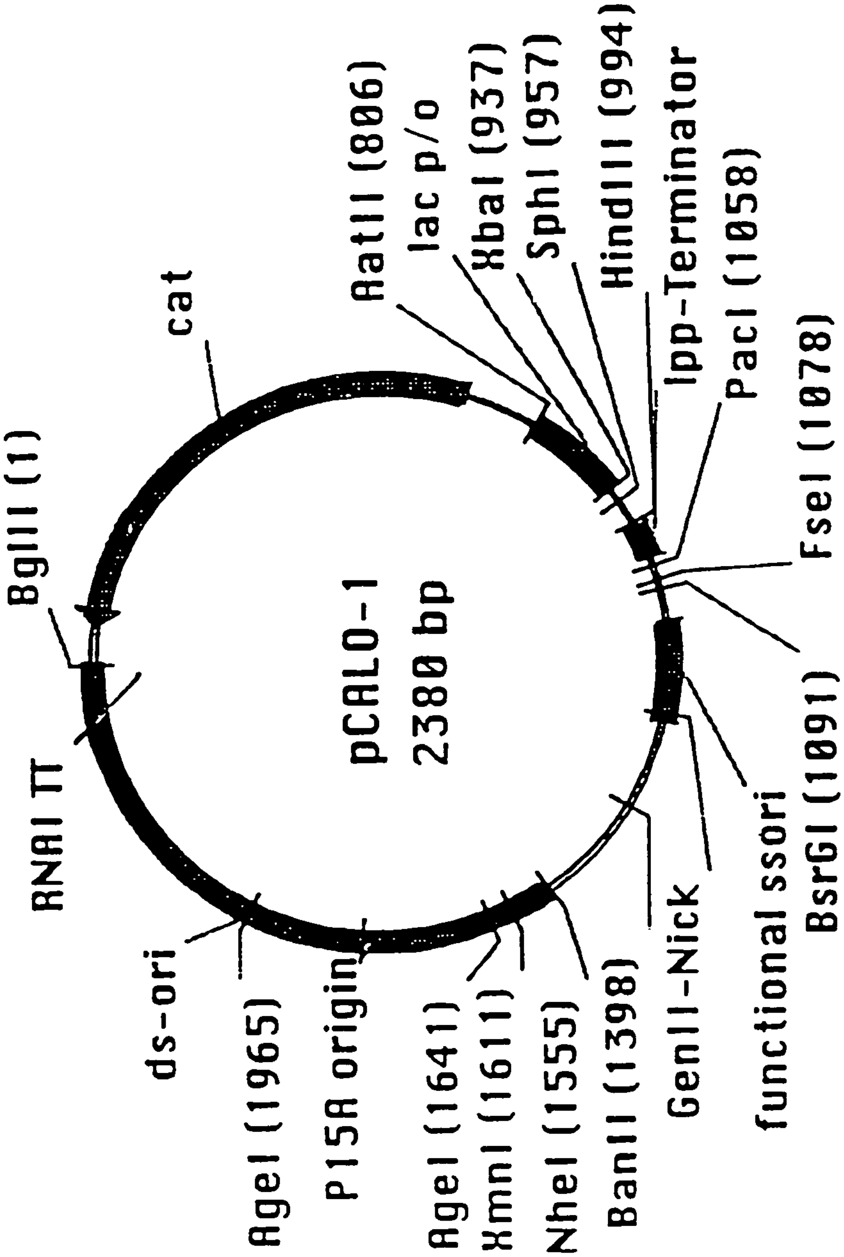
Figure 36A:
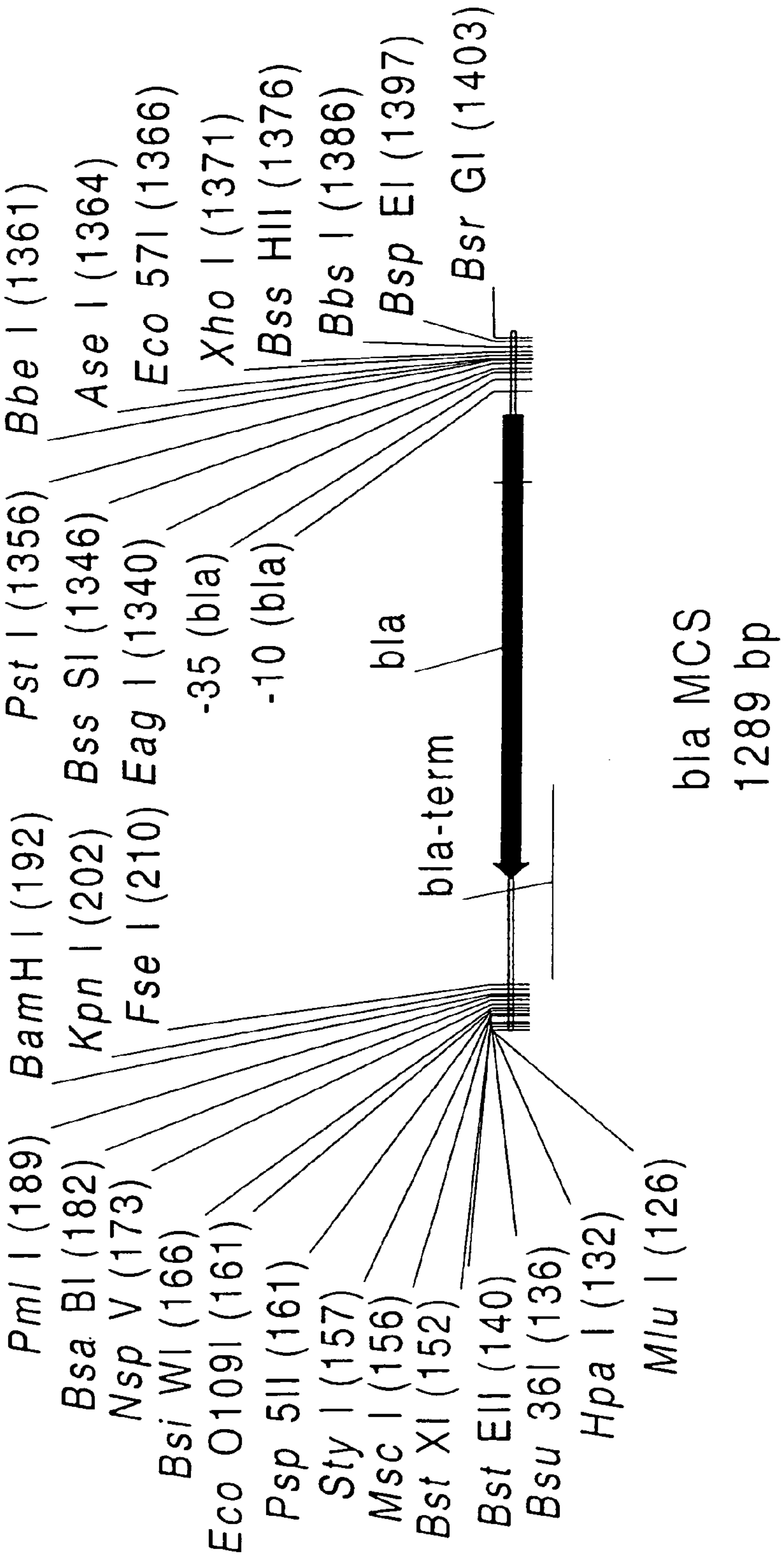
Figure 37A:
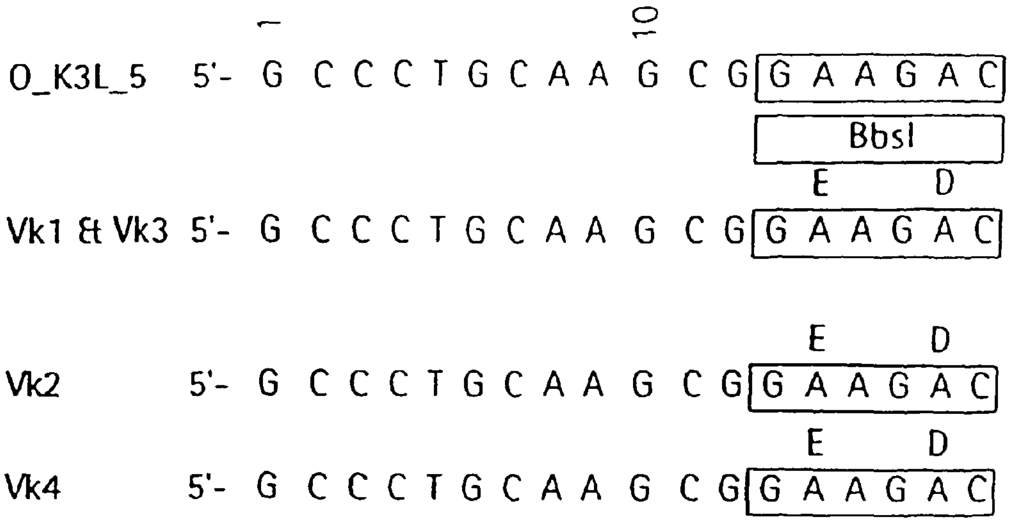
Figure 37B:
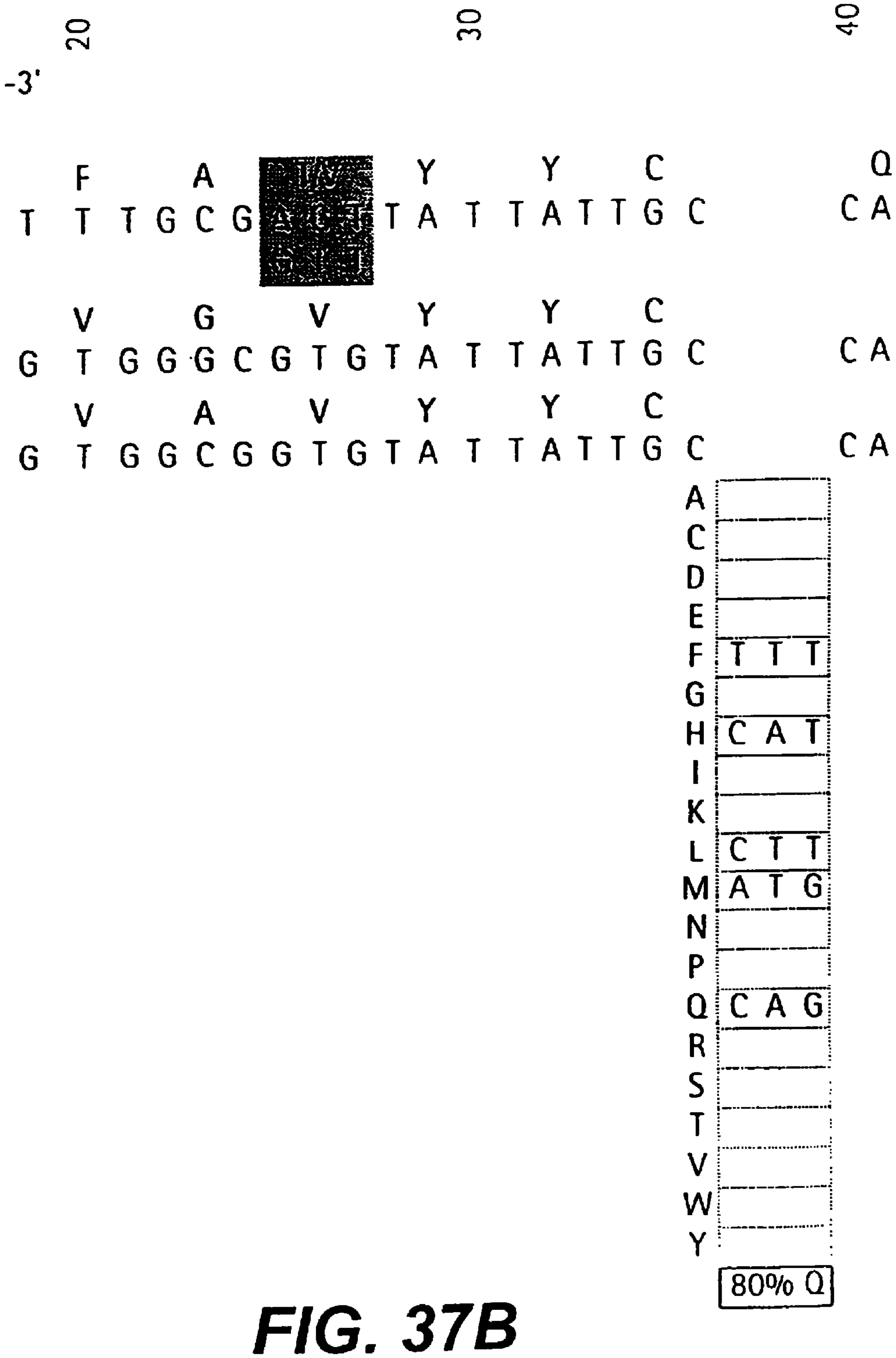
Figure 37D:
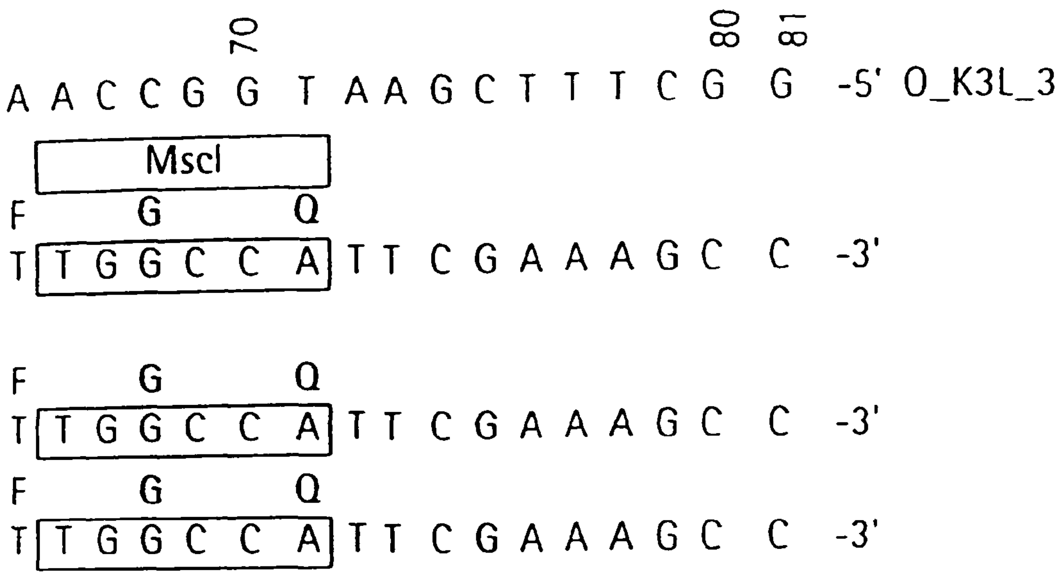
Figure 38A:
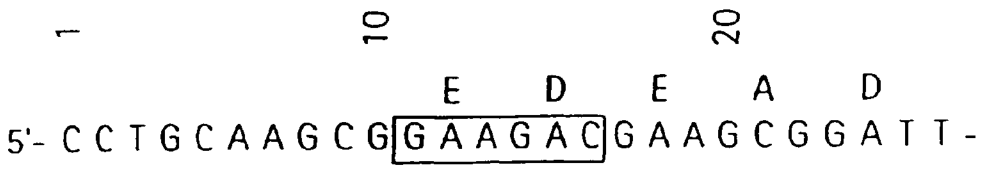
Figure 38B:
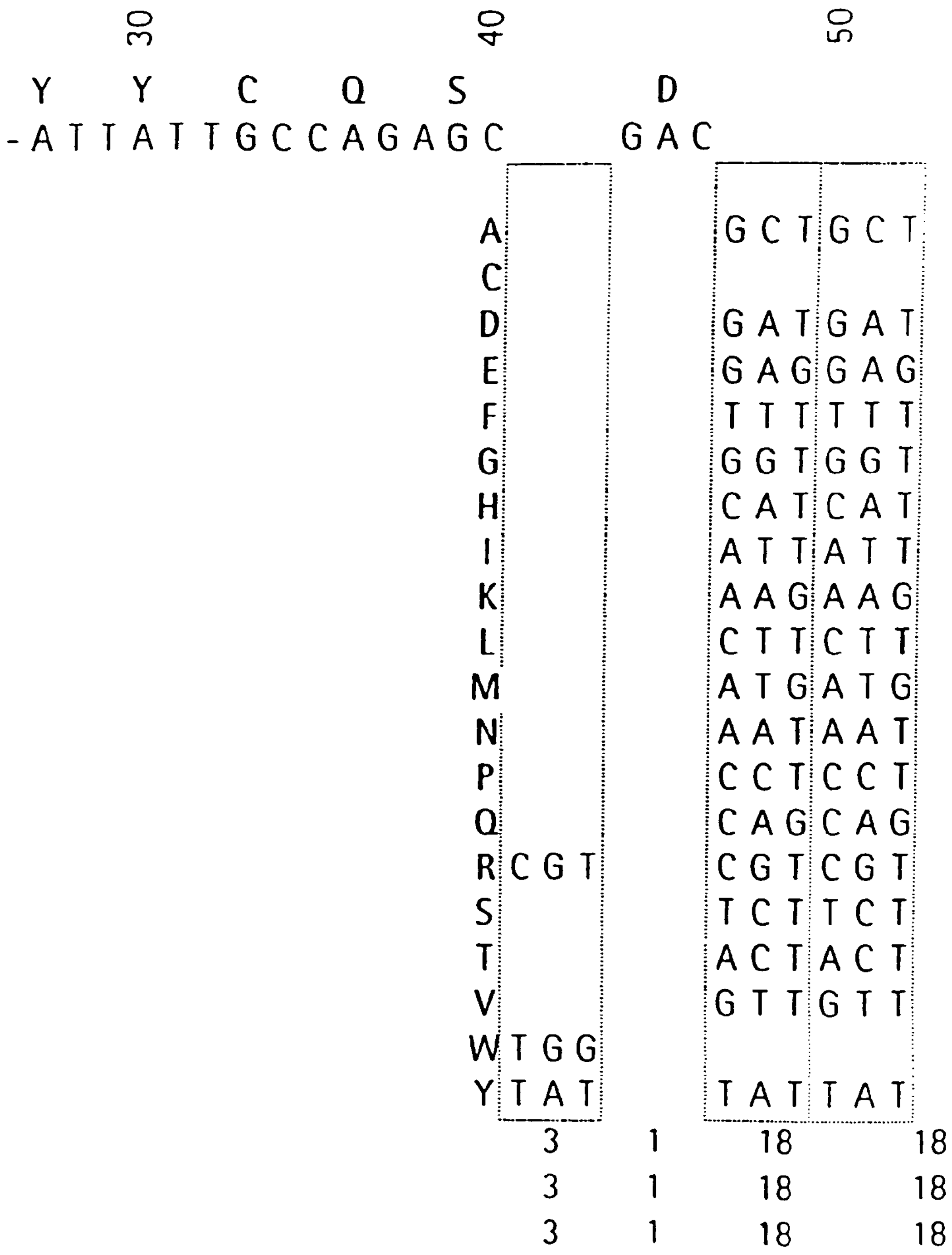

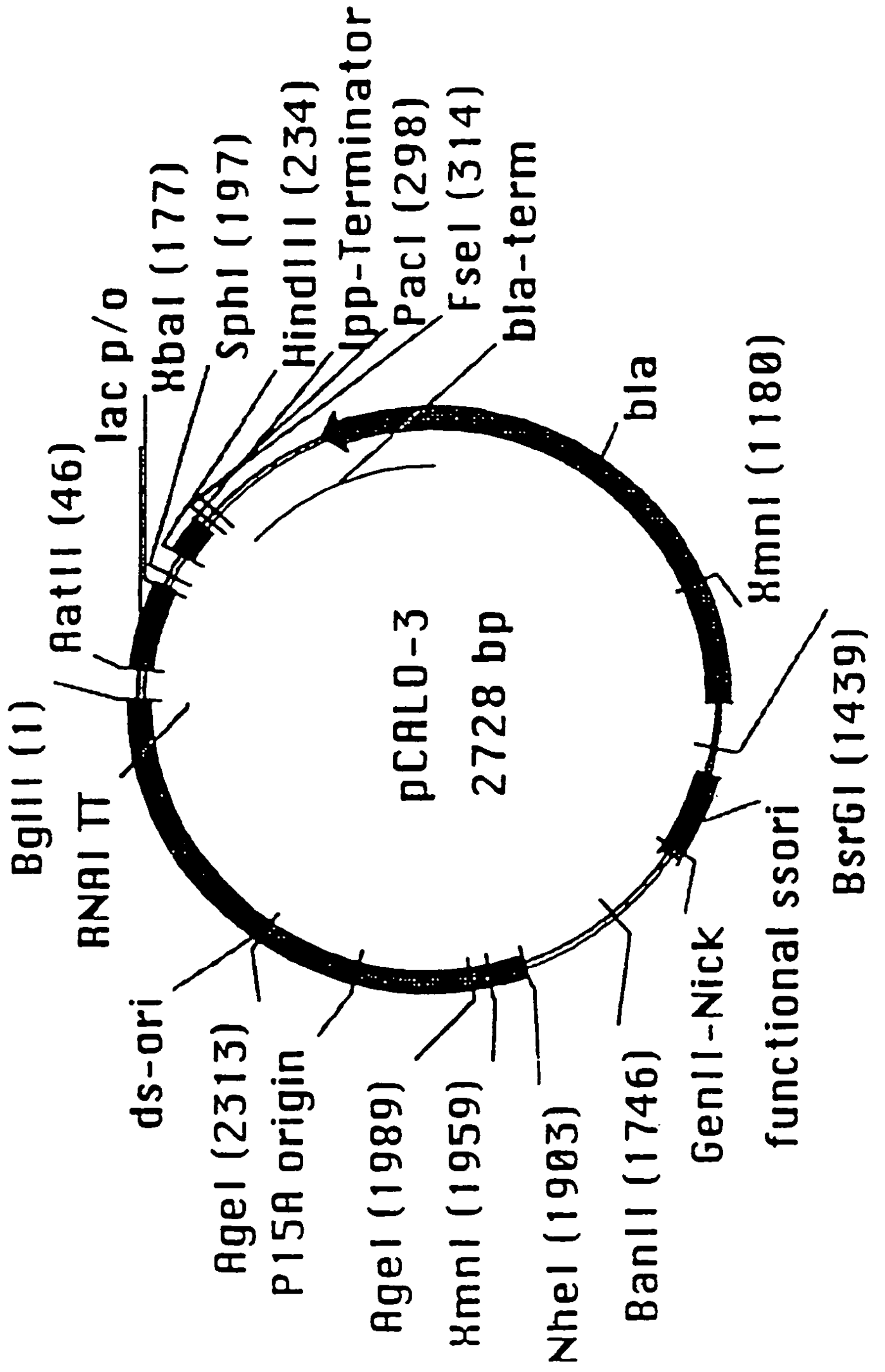
FIG. 35PPP

```
pCALO-3:
    BglII                                                  AatII
    ~~~~~~                                                ~~~~~~~
  1 GATCTCATAA CTTCGTATAA TGTATGCTAT ACGAAGTTAT GACGTCTAAT
    CTAGAGTATT GAAGCATATT ACATACGATA TGCTTCAATA CTGCAGATTA

 51 GTGAGTTAGC TCACTCATTA GGCACCCCAG GCTTTACACT TTATGCTTCC
    CACTCAATCG AGTGAGTAAT CCGTGGGGTC CGAAATGTGA AATACGAAGG

101 GGCTCGTATG TTGTGTGGAA TTGTGAGCGG ATAACAATTT CACACAGGAA
    CCGAGCATAC AACACACCTT AACACTCGCC TATTGTTAAA GTGTGTCCTT

                                 XbaI                SphI
                               ~~~~~~~~            ~~~~~~~
151 ACAGCTATGA CCATGATTAC GAATTTCTAG ACCCCCCCCC CGCATGCCAT
    TGTCGATACT GGTACTAATG CTTAAAGATC TGGGGGGGGG GCGTACGGTA

                                       HindIII
                                       ~~~~~~~
201 AACTTCGTAT AATGTACGCT ATACGAAGTT ATAAGCTTGA CCTGTGAAGT
    TTGAAGCATA TTACATGCGA TATGCTTCAA TATTCGAACT GGACACTTCA

                                                  PacI
```

FIG. 35QQQ

```
                                                               ~~~~~~~~~
251   GAAAAATGGC GCAGATTGTG CGACATTTTT TTTGTCTGCC GTTTAATTAA
      CTTTTTACCG CGTCTAACAC GCTGTAAAAA AAACAGACGG CAAATTAATT

               FseI
             ~~~~~~~~~~
301   GGGGGGGGGC CGGCCATTAT CAAAAAGGAT CTCAAGAAGA TCCTTTGATC
      CCCCCCCCCG GCCGGTAATA GTTTTTCCTA GAGTTCTTCT AGGAAACTAG

351   TTTTCTACGG GGTCTGACGC TCAGTGGAAC GAAAACTCAC GTTAAGGGAT
      AAAAGATGCC CCAGACTGCG AGTCACCTTG CTTTTGAGTG CAATTCCCTA

401   TTTGGTCATG AGATTATCAA AAAGGATCTT CACCTAGATC CTTTTAAATT
      AAACCAGTAC TCTAATAGTT TTTCCTAGAA GTGGATCTAG GAAAATTTAA

451   AAAAATGAAG TTTTAAATCA ATCTAAAGTA TATATGAGTA AACTTGGTCT
      TTTTTACTTC AAAATTTAGT TAGATTTCAT ATATACTCAT TTGAACCAGA

501   GACAGTTACC CAATGCTTAA TCAGTGAGGC ACCTATCTCA GCGATCTGTC
      CTGTCAATGG GTTACGAATT AGTCACTCCG TGGATAGAGT CGCTAGACAG

551   TATTTCGTTC ATCCATAGTT GCCTGACTCC CCGTCGTGTA GATAACTACG
      ATAAAGCAAG TAGGTATCAA CGGACTGAGG GGCAGCACAT CTATTGATGC
```

*FIG. 35RRR*

```
601  ATACGGGAGG GCTTACCATC TGGCCCCAGT GCTGCAATGA TACCGCGAGA
     TATGCCCTCC CGAATGGTAG ACCGGGGTCA CGACGTTACT ATGGCGCTCT

651  CCCACGCTCA CCGGCTCCAG ATTTATCAGC AATAAACCAG CCAGCCGGAA
     GGGTGCGAGT GGCCGAGGTC TAAATAGTCG TTATTTGGTC GGTCGGCCTT

701  GGGCCGAGCG CAGAAGTGGT CCTGCAACTT TATCCGCCTC CATCCAGTCT
     CCCGGCTCGC GTCTTCACCA GGACGTTGAA ATAGGCGGAG GTAGGTCAGA

751  ATTAACTGTT GCCGGGAAGC TAGAGTAAGT AGTTCGCCAG TTAATAGTTT
     TAATTGACAA CGGCCCTTCG ATCTCATTCA TCAAGCGGTC AATTATCAAA

801  GCGCAACGTT GTTGCCATTG CTACAGGCAT CGTGGTGTCA CGCTCGTCGT
     CGCGTTGCAA CAACGGTAAC GATGTCCGTA GCACCACAGT GCGAGCAGCA

851  TTGGTATGGC TTCATTCAGC TCCGGTTCCC AACGATCAAG GCGAGTTACA
     AACCATACCG AAGTAAGTCG AGGCCAAGGG TTGCTAGTTC CGCTCAATGT

901  TGATCCCCCA TGTTGTGCAA AAAAGCGGTT AGCTCCTTCG GTCCTCCGAT
     ACTAGGGGGT ACAACACGTT TTTTCGCCAA TCGAGGAAGC CAGGAGGCTA

951  CGTTGTCAGA AGTAAGTTGG CCGCAGTGTT ATCACTCATG GTTATGGCAG
     GCAACAGTCT TCATTCAACC GGCGTCACAA TAGTGAGTAC CAATACCGTC
```

FIG. 35SSS

```
1001  CACTGCATAA TTCTCTTACT GTCATGCCAT CCGTAAGATG CTTTTCTGTG
      GTGACGTATT AAGAGAATGA CAGTACGGTA GGCATTCTAC GAAAAGACAC

1051  ACTGGTGAGT ACTCAACCAA GTCATTCTGA GAATAGTGTA TGCGGCGACC
      TGACCACTCA TGAGTTGGTT CAGTAAGACT CTTATCACAT ACGCCGCTGG

1101  GAGTTGCTCT TGCCCGGCGT CAATACGGGA TAATACCGCG CCACATAGCA
      CTCAACGAGA ACGGGCCGCA GTTATGCCCT ATTATGGCGC GGTGTATCGT

                                 XmnI
                             ~~~~~~~~~~~~
1151  GAACTTTAAA AGTGCTCATC ATTGGAAAAC GTTCTTCGGG GCGAAAACTC
      CTTGAAATTT TCACGAGTAG TAACCTTTTG CAAGAAGCCC CGCTTTTGAG

1201  TCAAGGATCT TACCGCTGTT GAGATCCAGT TCGATGTAAC CCACTCGCGC
      AGTTCCTAGA ATGGCGACAA CTCTAGGTCA AGCTACATTG GGTGAGCGCG

1251  ACCCAACTGA TCCTCAGCAT CTTTTACTTT CACCAGCGTT TCTGGGTGAG
      TGGGTTGACT AGGAGTCGTA GAAAATGAAA GTGGTCGCAA AGACCCACTC

1301  CAAAAACAGG AAGGCAAAAT GCCGCAAAAA AGGGAATAAG GGCGACACGG
      GTTTTTGTCC TTCCGTTTTA CGGCGTTTTT TCCCTTATTC CCGCTGTGCC

1351  AAATGTTGAA TACTCATACT CTTCCTTTTT CAATATTATT GAAGCATTTA
```

FIG. 35TTT

```
      TTTACAACTT ATGAGTATGA GAAGGAAAAA GTTATAATAA CTTCGTAAAT

                                              BsrGI
                                             ~~~~~~~~
1401  TCAGGGTTAT TGTCTCATGA GCGGATACAT ATTTGAATGT ACATGAAATT
      AGTCCCAATA ACAGAGTACT CGCCTATGTA TAAACTTACA TGTACTTTAA

1451  GTAAACGTTA ATATTTTGTT AAAATTCGCG TTAAATTTTT GTTAAATCAG
      CATTTGCAAT TATAAAACAA TTTTAAGCGC AATTTAAAAA CAATTTAGTC

1501  CTCATTTTTT AACCAATAGG CCGAAATCGG CAAAATCCCT TATAAATCAA
      GAGTAAAAAA TTGGTTATCC GGCTTTAGCC GTTTTAGGGA ATATTTAGTT

1551  AAGAATAGAC CGAGATAGGG TTGAGTGTTG TTCCAGTTTG GAACAAGAGT
      TTCTTATCTG GCTCTATCCC AACTCACAAC AAGGTCAAAC CTTGTTCTCA

1601  CCACTATTAA AGAACGTGGA CTCCAACGTC AAAGGGCGAA AAACCGTCTA
      GGTGATAATT TCTTGCACCT GAGGTTGCAG TTTCCCGCTT TTTGGCAGAT

1651  TCAGGGCGAT GGCCCACTAC GAGAACCATC ACCCTAATCA AGTTTTTTGG
      AGTCCCGCTA CCGGGTGATG CTCTTGGTAG TGGGATTAGT TCAAAAAACC

                                                  BanII
                                                 ~~~~~~
```

FIG. 35UUU

```
1701  GGTCGAGGTG CCGTAAAGCA CTAAATCGGA ACCCTAAAGG GAGCCCCCGA
      CCAGCTCCAC GGCATTTCGT GATTTAGCCT TGGGATTTCC CTCGGGGGCT

1751  TTTAGAGCTT GACGGGGAAA GCCGGCGAAC GTGGCGAGAA AGGAAGGGAA
      AAATCTCGAA CTGCCCCTTT CGGCCGCTTG CACCGCTCTT TCCTTCCCTT

1801  GAAAGCGAAA GGAGCGGGCG CTAGGGCGCT GGCAAGTGTA GCGGTCACGC
      CTTTCGCTTT CCTCGCCCGC GATCCCGCGA CCGTTCACAT CGCCAGTGCG

1851  TGCGCGTAAC CACCACACCC GCCGCGCTTA ATGCGCCGCT ACAGGGCGCG
      ACGCGCATTG GTGGTGTGGG CGGCGCGAAT TACGCGGCGA TGTCCCGCGC

        NheI
       ~~~~~~
1901  TGCTAGCGGA GTGTATACTG GCTTACTATG TTGGCACTGA TGAGGGTGTC
      ACGATCGCCT CACATATGAC CGAATGATAC AACCGTGACT ACTCCCACAG

             XmnI                          AgeI
         ~~~~~~~~~~~~                    ~~~~~~~~
1951  AGTGAAGTGC TTCATGTGGC AGGAGAAAAA AGGCTGCACC GGTGCGTCAG
      TCACTTCACG AAGTACACCG TCCTCTTTTT TCCGACGTGG CCACGCAGTC

2001  CAGAATATGT GATACAGGAT ATATTCCGCT TCCTCGCTCA CTGACTCGCT
      GTCTTATACA CTATGTCCTA TATAAGGCGA AGGAGCGAGT GACTGAGCGA
```

FIG. 35VVV

```
2051  ACGCTCGGTC GTTCGACTGC GGCGAGCGGA AATGGCTTAC GAACGGGGCG
      TGCGAGCCAG CAAGCTGACG CCGCTCGCCT TTACCGAATG CTTGCCCCGC

2101  GAGATTTCCT GGAAGATGCC AGGAAGATAC TTAACAGGGA AGTGAGAGGG
      CTCTAAAGGA CCTTCTACGG TCCTTCTATG AATTGTCCCT TCACTCTCCC

2151  CCGCGGCAAA GCCGTTTTTC CATAGGCTCC GCCCCCCTGA CAAGCATCAC
      GGCGCCGTTT CGGCAAAAAG GTATCCGAGG CGGGGGGACT GTTCGTAGTG

2201  GAAATCTGAC GCTCAAATCA GTGGTGGCGA AACCCGACAG GACTATAAAG
      CTTTAGACTG CGAGTTTAGT CACCACCGCT TTGGGCTGTC CTGATATTTC

2251  ATACCAGGCG TTTCCCCCTG GCGGCTCCCT CCTGCGCTCT CCTGTTCCTG
      TATGGTCCGC AAAGGGGGAC CGCCGAGGGA GGACGCGAGA GGACAAGGAC

                  AgeI
                 ~~~~~~~
2301  CCTTTCGGTT TACCGGTGTC ATTCCGCTGT TATGGCCGCG TTTGTCTCAT
      GGAAAGCCAA ATGGCCACAG TAAGGCGACA ATACCGGCGC AAACAGAGTA

2351  TCCACGCCTG ACACTCAGTT CCGGGTAGGC AGTTCGCTCC AAGCTGGACT
      AGGTGCGGAC TGTGAGTCAA GGCCCATCCG TCAAGCGAGG TTCGACCTGA
```

FIG. 35WWW

```
2401  GTATGCACGA ACCCCCCGTT CAGTCCGACC GCTGCGCCTT ATCCGGTAAC
      CATACGTGCT TGGGGGGCAA GTCAGGCTGG CGACGCGGAA TAGGCCATTG

2451  TATCGTCTTG AGTCCAACCC GGAAAGACAT GCAAAAGCAC CACTGGCAGC
      ATAGCAGAAC TCAGGTTGGG CCTTTCTGTA CGTTTTCGTG GTGACCGTCG

2501  AGCCACTGGT AATTGATTTA GAGGAGTTAG TCTTGAAGTC ATGCGCCGGT
      TCGGTGACCA TTAACTAAAT CTCCTCAATC AGAACTTCAG TACGCGGCCA

2551  TAAGGCTAAA CTGAAAGGAC AAGTTTTAGT GACTGCGCTC CTCCAAGCCA
      ATTCCGATTT GACTTTCCTG TTCAAAATCA CTGACGCGAG GAGGTTCGGT

2601  GTTACCTCGG TTCAAAGAGT TGGTAGCTCA GAGAACCTAC GAAAAACCGC
      CAATGGAGCC AAGTTTCTCA ACCATCGAGT CTCTTGGATG CTTTTTGGCG

2651  CCTGCAAGGC GGTTTTTTCG TTTTCAGAGC AAGAGATTAC GCGCAGACCA
      GGACGTTCCG CCAAAAAAGC AAAAGTCTCG TTCTCTAATG CGCGTCTGGT

                                  BglII

2701  AAACGATCTC AAGAAGATCA TCTTATTA
      TTTGCTAGAG TTCTTCTAGT AGAATAAT
```

*FIG. 35XXX*

M1: PCR using template

NoVspAatII: TAGACGTC

M2: synthesis

BloxA-A: TATGAGATCTCATAACTTCGTATAATGTACGCTATACG-AAGTTAT

BloxA-B: TAATAACTTCGTATAGCATACATTATACGAAGTTATG-AGATCTCA

M3: PCR, NoVspAatII as second oligo

XloxS-muta: CATTTTTTGCCCTCGTTATCTACGCATGCGATAACTTCGTA-TAGCGTACATTATACGAAGTTATTCTAGACATGGTCATAGCTGTTTCCTG

M7-I: PCR gIIINEW-fow: GGGGGGAATTCGGTGGTGGTGGATCTGCGTGCGCTG-AAACGGTTGAAAGTTG gIIINEW-rev: CCCCCCCAAGCTTATCAAGACTCCTTATTACG

M7-II: PCR gIIIss-fow: GGGGGGGGAATTCGGAGGCGGTTCCGGTGGTGGC

M7-III: PCR gIIIsupernew-fow: GGGGGGGGAATTCGAGCAGAAGCTGATCTCT-GAGGAGGATCTGTAGGGTGGTGGCTCTGGTTCCGGTGATTTTG

FIG. 35YYY

M8: synthesis lox514-A: CCATAACTTCGTATAATGTACGCTATACGAAGTTATA lox514-B: AGCTTATAACTTCGTATAGCGTACATTATACGAAGT-TATGGCATG M9II: synthesis M9II-fow: AGCTTGACCTGTGAAGTGAAAAATGGCGCAGATT-GTGCGACATTTTTTTTGTCTGCCGTTTAATTAAAGGGGGGGT M9II-rev: GTACACCCCCCCCAGGCCGGCCCCCCCCCCCTTTAA-TTAAACGGCAGACAAAAAAAATGTCGCACAATCTGCG M10II: assembly PCR with template bla-fow: GGGGGGGTGTACATTCAAATATGTATCCGCTCATG bla-seq4: GGGTTACATCGAACTGGATCTC bla1-muta: CCAGTTCGATGTAACCCACTCGCGCACCCAACTGATC-CTCAGCATCTTTTACTTTCACC blaII-muta: ACTCTAGCTTCCCGGCAACAGTTAATAGACTGGATG-GAGGCGG bla-NEW: CTGTTGCCGGGAAGCTAGAGTAAG bla-rev: CCCCCCCTTAATTAAGGGGGGGGCCGGCCATTATCAAA-AAGGATCTCAAGAAGATCC M11II/III: PCR, site-directed mutagenesis

FIG. 35ZZZ f1-fow: GGGGGGGGGCTAGCACGCGCCCTGTAGCGGCGCATTAA f1-rev: CCCCCCCTGTACATGAAATTGTAAACGTTAATATTTTG f1-t133.muta: GGGCGATGGCCCACTACGAGAACCATCACCCTAATC M12: assembly PCR using template p15-fow: GGGGGGAGATCTAATAAGATGATCTTCTTGAG p15-NEWI: GAGTTGGTAGCTCAGAGAACCTACGAAAAACCGCCCTG-
CAAGGCG p15-NEWII: GTAGGTTCTCTGAGCTACCAACTC p15-NEWIII: GTTTCCCCCTGGCGGCTCCCTCCTGCGCTCTCCTGTTCCT-
GCC p15-NEWIV: AGGAGGGAGCCGCCAGGGGGAAAC p15-rev: GACATCAGCGCTAGCGGAGTGTATAC M13: synthesis BloxXB-A: GATCTCATAACTTCGTATAATGTATGCTATACGAAGTTA-
TTCA BloxXB-B: GATCTGAATAACTTCGTATAGCATACATTATACGAAGTTA-
TGAGA M14-Ext2: PCR, site-directed mutagenesis ColEXT2-fow: GGGGGGGAGATCTGACCAAAATCCCTTAACGTGAG Col-mutal: GGTATCTGCGCTCTGCTGTAGCCAGTTACCTTCGG

*FIG. 35AAAA*

Col-rev: CCCCCCCGCTAGCCATGTGAGCAAAAGGCCAGCAA

M17: assembly PCR using template

CAT-1: GGGACGTCGGGTGAGGTTCCAAC

CAT-2: CCATACGGAACTCCGGGTGAGCATTCATC

CAT-3: CCGGAGTTCCGTATGG

CAT-4: ACGTTTAAATCAAAACTGG

CAT-5: CCAGTTTTGATTTAAACGTAGCCAATATGGACAACTTCTTC-GCCCCCGTTTTCACTATGGGCAAATATT

CAT-6: GGAAGATCTAGCACCAGGCGTTTAAG

M41: assembly PCR using template

LAC1: GAGGCCGGCCATCGAATGGCGCAAAAC

LAC2: CGCGTACCGTCCTCATGGGAGAAAATAATAC

LAC3: CCATGAGGACGGTACGCGACTGGGCGTGGAGCATCTGGTCGCA-TTGGGTCACCAGCAAATCCGCTGTTAGCTGGCCCATTAAG

LAC4: GTCAGCGGCGGGATATAACATGAGCTGTCCTCGGTATCGTCG

LAC5: GTTATATCCCGCCGCTGACCACCATCAAAC

LAC6: CATCAGTGAATCGGCCAACGCGCGGGGAGAGGCGGTTTGCGT4TTG-GGAGCCAGGGTGGTTTTTC

LAC7: GGTTAATTAACCTCACTGCCCGCTTTCCAGTCGGGAAACCTGTCGTGCC-AGCTGCATCAGTGAATCGGCCAAC

M41-MCS-fow: CTAGACTAGTGTTTAAACCGGACCGGGGGGGGGCTT-AAGGGGGGGGGGGG

*FIG. 35BBBB*

M41-MCS-rev: CTAGCCCCCCCCCCCCTTAAGCCCCCCCCCGGTCCGGT-TTAAACACTAGT

M41-fow: CTAGACTAGTGTTTAAACCGGACCGGGGGGGGGCTTAA-GGGCGGGGGGGG

M41-rev: CCCCCCCTTAAGTGGGCTGCAAAACAAAACGGCCTCC-TGTCAGGAAGCCGCTTTTATCGGGTAGCCTCACTGCCCGCTTTCC

M41-A2: GTTGTTGTGCCACGCGGTTAGGAATGTAATTCAGCTCCGC

M41-B1: AACCGCGTGGCACAACAAC

M41-B2: CTTCGTTCTACCATCGACACGACCACGCTGGCACCCAGTTG

M41-C1: GTGTCGATGGTAGAACGAAG

M41-CII: CCACAGCAATAGCATCCTGGTCATCCAGCGGATAGTT-AATAATCAGCCCACTGACACGTTGCGCGAG

M41-DI: GACCAGGATGCTATTGCTGTGG

M41-DII: CAGCGCGATTTGCTGGTGGCCCAATGCGACCAGATGC

M41-EI: CACCAGCAAATCGCGCTG

M41-EII: CCCGGACTCGGTAATGGCACGCATTGCGCCCAGCGCC

M41-FI: GCCATTACCGAGTCCGGG

M42: synthesis

Eco-H5-Hind-fow: AATTCCACCATCATCACCATTGACGTCTA

Eco-H5-Hind-rev: AGCTTAGACGTCAATGGTGATGATGGTGG

FIG. 35CCCC

```
                                                       StyI
                                                      ~~~~~~~
                                                         Psp5II
                                                         ~~~~~~~~
      MluI      Bsu36I              BstXI            EcoO109I
      ~~~~~     ~~~~~~~~~    ~~~~~~~~~~~~~~          ~~~~~~~~
           HpaI        BstEII              MscI               BsiWI NspV
          ~~~~~~~      ~~~~~~~~        ~~~~~~~~          ~~~~~~~~~~~~~
126   CGCGTTAACC TCAGGTGACC AAGCCCCTGG CCAAGGTCCC GTACGTTCGA
      GCGCAATTGG AGTCCACTGG TTCGGGGACC GGTTCCAGGG CATGCAAGCT

                   PmlI
                 ~~~~~~
      NspVBsaBI         BamHI  KpnI       FseI
      ~~~~~~~~~~~~~    ~~~~~~~~~~~~~~  ~~~~~~~~~~
176   AGATTACCAT CACGTGGATC CGGTACCAGG CCGGCCATTA TCAAAAAGGA
      TCTAATGGTA GTGCACCTAG GCCATGGTCC GGCCGGTAAT AGTTTTTCCT

226   TCTCAAGAAG ATCCTTTGAT CTTTTCTACG GGGTCTGACG CTCAGTGGAA
      AGAGTTCTTC TAGGAAACTA GAAAAGATGC CCCAGACTGC GAGTCACCTT

276   CGAAAACTCA CGTTAAGGGA TTTTGGTCAT GAGATTATCA AAAAGGATCT
      GCTTTTGAGT GCAATTCCCT AAAACCAGTA CTCTAATAGT TTTTCCTAGA
```

FIG. 36B

```
326   TCACCTAGAT CCTTTTAAAT TAAAAATGAA GTTTTAAATC AATCTAAAGT
      AGTGGATCTA GGAAAATTTA ATTTTTACTT CAAAATTTAG TTAGATTTCA

376   ATATATGAGT AAACTTGGTC TGACAGTTAC CAATGCTTAA TCAGTGAGGC
      TATATACTCA TTTGAACCAG ACTGTCAATG GTTACGAATT AGTCACTCCG

426   ACCTATCTCA GCGATCTGTC TATTTCGTTC ATCCATAGTT GCCTGACTCC
      TGGATAGAGT CGCTAGACAG ATAAAGCAAG TAGGTATCAA CGGACTGAGG

476   CCGTCGTGTA GATAACTACG ATACGGGAGG GCTTACCATC TGGCCCCAGT
      GGCAGCACAT CTATTGATGC TATGCCCTCC CGAATGGTAG ACCGGGGTCA

526   GCTGCAATGA TACCGCGAGA CCCACGCTCA CCGGCTCCAG ATTTATCAGC
      CGACGTTACT ATGGCGCTCT GGGTGCGAGT GGCCGAGGTC TAAATAGTCG

576   AATAAACCAG CCAGCCGGAA GGGCCGAGCG CAGAAGTGGT CCTGCAACTT
      TTATTTGGTC GGTCGGCCTT CCCGGCTCGC GTCTTCACCA GGACGTTGAA

626   TATCCGCCTC CATCCAGTCT ATTAACTGTT GCCGGGAAGC TAGAGTAAGT
      ATAGGCGGAG GTAGGTCAGA TAATTGACAA CGGCCCTTCG ATCTCATTCA

676   AGTTCGCCAG TTAATAGTTT GCGCAACGTT GTTGCCATTG CTACAGGCAT
      TCAAGCGGTC AATTATCAAA CGCGTTGCAA CAACGGTAAC GATGTCCGTA
```

FIG. 36C

```
726   CGTGGTGTCA CGCTCGTCGT TTGGTATGGC TTCATTCAGC TCCGGTTCCC
      GCACCACAGT GCGAGCAGCA AACCATACCG AAGTAAGTCG AGGCCAAGGG

776   AACGATCAAG GCGAGTTACA TGATCCCCCA TGTTGTGCAA AAAAGCGGTT
      TTGCTAGTTC CGCTCAATGT ACTAGGGGGT ACAACACGTT TTTTCGCCAA

826   AGCTCCTTCG GTCCTCCGAT CGTTGTCAGA AGTAAGTTGG CCGCAGTGTT
      TCGAGGAAGC CAGGAGGCTA GCAACAGTCT TCATTCAACC GGCGTCACAA

876   ATCACTCATG GTTATGGCAG CACTGCATAA TTCTCTTACT GTCATGCCAT
      TAGTGAGTAC CAATACCGTC GTGACGTATT AAGAGAATGA CAGTACGGTA

926   CCGTAAGATG CTTTTCTGTG ACTGGTGAGT ACTCAACCAA GTCATTCTGA
      GGCATTCTAC GAAAAGACAC TGACCACTCA TGAGTTGGTT CAGTAAGACT

976   GAATAGTGTA TGCGGCGACC GAGTTGCTCT TGCCCGGCGT CAATACGGGA
      CTTATCACAT ACGCCGCTGG CTCAACGAGA ACGGGCCGCA GTTATGCCCT

1026  TAATACCGCG CCACATAGCA GAACTTTAAA AGTGCTCATC ATTGGAAAAC
      ATTATGGCGC GGTGTATCGT CTTGAAATTT TCACGAGTAG TAACCTTTTG

1076  GTTCTTCGGG GCGAAAACTC TCAAGGATCT TACCGCTGTT GAGATCCAGT
      CAAGAAGCCC CGCTTTTGAG AGTTCCTAGA ATGGCGACAA CTCTAGGTCA
```

FIG. 36D

```
1126  TCGATGTAAC CCACTCGTGC ACCCAACTGA TCTTCAGCAT CTTTTACTTT
      AGCTACATTG GGTGAGCACG TGGGTTGACT AGAAGTCGTA GAAAATGAAA
                  BssSI                  Eco57I
                 ~~~~~~~                ~~~~~~~

1176  CACCAGCGTT TCTGGGTGAG CAAAAACAGG AAGGCAAAAT GCCGCAAAAA
      GTGGTCGCAA AGACCCACTC GTTTTTGTCC TTCCGTTTTA CGGCGTTTTT

1226  AGGGAATAAG GGCGACACGG AAATGTTGAA TACTCATACT CTTCCTTTTT
      TCCCTTATTC CCGCTGTGCC TTTACAACTT ATGAGTATGA GAAGGAAAAA

1276  CAATATTATT GAAGCATTTA TCAGGGTTAT TGTCTCATGA GCGGATACAT
      GTTATAATAA CTTCGTAAAT AGTCCCAATA ACAGAGTACT CGCCTATGTA

                                 PstI                  XhoI
                               ~~~~~~~~               ~~~~~~
                  EagI   BssSI          BbeI  AseI    BssHII
                 ~~~~~~~~~~~~~~        ~~~~~~~~~~~~~~      ~
1326  ATTTGAATGT ACTCGGCCGC ACGAGCTGCA GGCGCCATTA ATGGCTCGAG
      TAAACTTACA TGAGCCGGCG TGCTCGACGT CCGCGGTAAT TACCGAGCTC

      BssHII                BspEI BsrGI
      ~~~~~                ~~~~~~~~~~~~~~
```

FIG. 36E

```
1376   CGCGCTTCAG CGCTTTGTCT TCCGGATGTA CATGAAATT
       GCGCGAAGTC GCGAAACAGA AGGCCTACAT GTACTTTAA
          Eco57I        BbsI
          ~~~~~~~     ~~~~~~~~
```

FIG. 36F

```
                               1              10
O_K3L_5   5'- G C C C T G C A A G C G G A A G A C
                                        Bbsl
                                         E     D
Vk1 & Vk3 5'- G C C C T G C A A G C G G A A G A C

                                         E     D
Vk2       5'- G C C C T G C A A G C G G A A G A C
                                         E     D
Vk4       5'- G C C C T G C A A G C G G A A G A C
```

50 60

3'- G G A

T
G A C C T

T
G A C C T

T
G A C C T

| | | | | | |
|---|---|---|---|---|---|
| G C T | | | G C T | | G C T |
| | | | | | |
| G A T | G A T | G A T | G A T | | G A T |
| G A G | | | G A G | | G A G |
| T T T | | | T T T | | T T T |
| G G T | G G T | G G T | G G T | | G G T |
| C A T | | | C A T | | C A T |
| A T T | | | A T T | | A T T |
| A A G | | | A A G | | A A G |
| C T T | | | C T T | | C T T |
| A T G | | | A T G | | A T G |
| A A T | A A T | A A T | A A T | | A A T |
| | | | C C T | C C T | C C T |
| C A G | | | C A G | | C A G |
| C G T | | | C G T | | C G T |
| T C T | T C T | T C T | T C T | T C T | T C T |
| A C T | | | A C T | | A C T |
| G T T | | | G T T | | G T T |
| T G G | | | T G G | | T G G |
| T A T | T A T | | T A T | | T A T |
| 50% Y | | | | 80% P | |

*FIG. 37C*

```
                     E   D   E   A   D
5'- C C T G C A A G C G G A A G A C G A A G C G G A T T -
```
(with positions 1, 10, 20 marked above, and GAAGAC boxed)

```
              30              40              50
          Y  Y  C  Q  S           D
        -ATTATTGCCAGAGC       GAC
                          A              GCT GCT
                          C
                          D              GAT GAT
                          E              GAG GAG
                          F              TTT TTT
                          G              GGT GGT
                          H              CAT CAT
                          I              ATT ATT
                          K              AAG AAG
                          L              CTT CTT
                          M              ATG ATG
                          N              AAT AAT
                          P              CCT CCT
                          Q              CAG CAG
                          R  CGT         CGT CGT
                          S              TCT TCT
                          T              ACT ACT
                          V              GTT GTT
                          W  TGG
                          Y  TAT         TAT TAT
                             3     1     18   18
                             3     1     18   18
                             3     1     18   18
```

60 70 80

G G G T K L

GGCGGCGGCACGAAGTTA

| | | gap | gap | | |
|---|---|---|---|---|---|
| - | GCT | GCT | GCT | GCT | |
| | GAT | GAT | GAT | GAT | |
| | GAG | GAG | GAG | GAG | |
| | TTT | TTT | TTT | TTT | |
| | GGT | GGT | GGT | GGT | |
| | CAT | CAT | CAT | CAT | |
| | ATT | ATT | ATT | ATT | |
| | AAG | AAG | AAG | AAG | |
| | CTT | CTT | CTT | CTT | |
| | ATG | ATG | ATG | ATG | |
| | AAT | AAT | AAT | AAT | |
| | CCT | CCT | CCT | CCT | |
| | CAG | CAG | CAG | CAG | |
| | CGT | CGT | CGT | CGT | |
| | TCT | TCT | TCT | TCT | |
| | ACT | ACT | ACT | ACT | |
| | GTT | GTT | GTT | GTT | |
| | | | | TGG | |
| | TAT | TAT | TAT | TAT | Variability |
| | 18 | | | 19 | 3.32E+05 |
| | 18 | 18 | | 19 | 5.98E+06 |
| | 18 | 18 | 18 | 19 | 1.08E+08 |

| % soluble | κ1 | κ2 | κ3 | κ4 | λ1 | λ2 | λ3 |
|---|---|---|---|---|---|---|---|
| H1A | 61% | 58% | 52% | 42% | 90% | 61% | 60% |
| H1B | 39% | 48% | 66% | 48% | 47% | 39% | 36% |
| H2 | 47% | 57% | 46% | 49% | 37% | 36% | 45% |
| H3 | 85% | 67% | 76% | 61% | 80% | 71% | 83% |
| H4 | 69% | 52% | 51% | 44% | 45% | 33% | 42% |
| H5 | 49% | 49% | 46% | 67% | 54% | 46% | 47% |
| H6 | 90% | 58% | 54% | 47% | 45% | 50% | 51% |

| Total amount compared to H3κ2 | κ1 | κ2 | κ3 | κ4 | λ1 | λ2 | λ3 |
|---|---|---|---|---|---|---|---|
| H1A | 289% | 94% | 166% | 272% | 20% | 150% | 78% |
| H1B | 219% | 122% | 89% | 139% | 117% | 158% | 101% |
| H2 | 186% | 223% | 208% | 182% | 126% | 60% | 97% |
| H3 | 50% | | 71% | 54% | 59% | 130% | 47% |
| H4 | 37% | 55% | 60% | 77% | 195% | 107% | 251% |
| H5 | 98% | 201% | 167% | 83% | 93% | 128% | 115% |
| H6 | 65% | 117% | 89% | 109% | 299% | 215% | 278% |

FIG. 40A

| Soluble amount compared to H3κ2 | κ1 | κ2 | κ3 | κ4 | λ1 | λ2 | λ3 |
|---|---|---|---|---|---|---|---|
| H1A | 191% | 88% | 121% | 122% | 26% | 211% | 76% |
| H1B | 124% | 95% | 83% | 107% | 79% | 142% | 59% |
| H2 | 126% | 204% | 139% | 130% | 66% | 50% | 70% |
| H3 | 63% | - | 81% | 49% | 69% | 143% | 61% |
| H4 | 40% | 47% | 49% | 54% | 95% | 55% | 125% |
| H5 | 69% | 158% | 116% | 80% | 72% | 84% | 84% |
| H6 | 85% | 122% | 87% | 77% | 162% | 162% | 212% |

| | McPC |
|---|---|
| soluble | 38% |
| %H3k2 total | 117% |
| %H3k2 soluble | 69% |

FIG. 40B

SEQUENCE LISTING

```
<160> NUMBER OF SEQ ID NOS: 372

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 1

Ala Gly Gly Gly Ser Gly Gly Gly Gly Ser Gly Gly Gly Gly Ser Gly
  1               5                  10                  15

Gly Gly Gly Ser
             20


<210> SEQ ID NO 2
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

tcagcgggtg gcggttctgg cggcggtggg agcggtggcg gtggttctgg cggtggtggt     60

tccgatatcg gtccacgtac gg                                              82


<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

aattccgtac gtggaccgat atcggaacca ccaccgccag aaccaccgcc accgctccca     60

ccgccgccag aaccgccacc cgc                                             83


<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (28)..(30)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (31)..(33)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (34)..(36)
<223> OTHER INFORMATION: region represents a variable trinucleotide
      combination capable of coding any natural occurring amino acid
      other than Cys
```

<220> FEATURE:
<221> NAME/KEY: modified_base
<222> LOCATION: (37)..(39)
<223> OTHER INFORMATION: region represents a variable trinucleotide combination capable of coding any natural occurring amino acid other than Cys
<220> FEATURE:
<221> NAME/KEY: modified_base
<222> LOCATION: (40)..(42)
<223> OTHER INFORMATION: region represents a variable trinucleotide combination capable of coding any natural occurring amino acid other than Cys
<220> FEATURE:
<221> NAME/KEY: modified_base
<222> LOCATION: (43)..(45)
<223> OTHER INFORMATION: region represents a variable trinucleotide combination capable of coding any natural occurring amino acid other than Cys

<400> SEQUENCE: 4
gatacggccg tgtattattg cgcgcgtnnn nnnnnnnnnn nnnnngatta ttggggccaa 60
ggcaccctg 69

<210> SEQ ID NO 5
<211> LENGTH: 84
<212> TYPE: DNA
<213> ORGANISM: Artificial Sequence
<220> FEATURE:
<223> OTHER INFORMATION: Description of Artificial Sequence: Synthetic oligonucleotide template
<220> FEATURE:
<221> NAME/KEY: modified_base
<222> LOCATION: (28)..(30)
<223> OTHER INFORMATION: region represents a variable trinucleotide combination capable of coding any natural occurring amino acid other than Cys
<220> FEATURE:
<221> NAME/KEY: modified_base
<222> LOCATION: (31)..(33)
<223> OTHER INFORMATION: region represents a variable trinucleotide combination capable of coding any natural occurring amino acid other than Cys
<220> FEATURE:
<221> NAME/KEY: modified_base
<222> LOCATION: (34)..(36)
<223> OTHER INFORMATION: region represents a variable trinucleotide combination capable of coding any natural occurring amino acid other than Cys
<220> FEATURE:
<221> NAME/KEY: modified_base
<222> LOCATION: (37)..(39)
<223> OTHER INFORMATION: region represents a variable trinucleotide combination capable of coding any natural occurring amino acid other than Cys
<220> FEATURE:
<221> NAME/KEY: modified_base
<222> LOCATION: (40)..(42)
<223> OTHER INFORMATION: region represents a variable trinucleotide combination capable of coding any natural occurring amino acid other than Cys
<220> FEATURE:
<221> NAME/KEY: modified_base
<222> LOCATION: (43)..(45)
<223> OTHER INFORMATION: region represents a variable trinucleotide combination capable of coding any natural occurring amino acid other than Cys
<220> FEATURE:
<221> NAME/KEY: modified_base
<222> LOCATION: (46)..(48)
<223> OTHER INFORMATION: region represents a variable trinucleotide combination capable of coding any natural occurring amino acid other than Cys
<220> FEATURE:
<221> NAME/KEY: modified_base
<222> LOCATION: (49)..(51)
<223> OTHER INFORMATION: region represents a variable trinucleotide combination capable of coding any natural occurring amino acid other than Cys
<220> FEATURE:
<221> NAME/KEY: modified_base
<222> LOCATION: (52)..(54)
<223> OTHER INFORMATION: region represents a variable trinucleotide combination capable of coding any natural occurring amino acid other than Cys
<220> FEATURE:
<221> NAME/KEY: modified_base
<222> LOCATION: (55)..(57)
<223> OTHER INFORMATION: region represents a variable trinucleotide combination capable of coding any natural occurring amino acid other than Cys

<400> SEQUENCE: 5
gatacggccg tgtattattg cgcgcgtnnn nnnnnnnnnn nnnnnnnnnn nnnnnnnwtk 60
gatkwttggg gccaaggcac cctg 84

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gatacggccg tgtattattg c 21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
cagggtgcct tggcccc 17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gcagaaggcg aacgtcc 17

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide template
<220> FEATURE:
<221> NAME/KEY: modified_base
<222> LOCATION: (42)..(44)
<223> OTHER INFORMATION: region represents a variable trinucleotide combination capable of coding any natural occurring amino acid other than Cys
<220> FEATURE:
<221> NAME/KEY: modified_base
<222> LOCATION: (45)..(47)
<223> OTHER INFORMATION: region represents a variable trinucleotide combination capable of coding any natural occurring amino acid other than Cys
<220> FEATURE:

<221> NAME/KEY: modified_base
<222> LOCATION: (48)..(50)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (51)..(53)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (57)..(59)
<223> OTHER INFORMATION: region represents a variable trinucleotide
      combination capable of coding any natural occurring amino acid
      other than Cys

<400> SEQUENCE: 9
tggaagctga agacgtgggc gtgtattatt gccagcagbv tnnnnnnnnn nnnccgnnnt     60
ttggccaggg tacgaaagtt                                                 80

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aactttcgta ccctggcc                                                   18

<210> SEQ ID NO 11
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide template
<220> FEATURE:
<221> NAME/KEY: modified_base
<222> LOCATION: (21)..(23)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (27)..(29)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (30)..(32)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (33)..(35)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (42)..(44)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (48)..(50)
<223> OTHER INFORMATION: region represents a variable trinucleotide
      combination capable of coding any natural occurring amino acid other than Cys

<400> SEQUENCE: 11
agggtctcga gtgggtgagc nnnattnnnn nnnnnrvtrv tnnnaccnnn tatgcggata 60
gcgtgaaagg ccgttttacc atttcacgtg ataattcgaa aaacacca 108

<210> SEQ ID NO 12
<211> LENGTH: 105
<212> TYPE: DNA
<213> ORGANISM: Artificial Sequence
<220> FEATURE:
<223> OTHER INFORMATION: Description of Artificial Sequence: Synthetic oligonucleotide template
<220> FEATURE:
<221> NAME/KEY: modified_base
<222> LOCATION: (21)..(23)
<223> OTHER INFORMATION: region represents a variable trinucleotide combination capable of coding any natural occurring amino acid other than Cys
<220> FEATURE:
<221> NAME/KEY: modified_base
<222> LOCATION: (27)..(29)
<223> OTHER INFORMATION: region represents a variable trinucleotide combination capable of coding any natural occurring amino acid other than Cys
<220> FEATURE:
<221> NAME/KEY: modified_base
<222> LOCATION: (30)..(32)
<223> OTHER INFORMATION: region represents a variable trinucleotide combination capable of coding any natural occurring amino acid other than Cys
<220> FEATURE:
<221> NAME/KEY: modified_base
<222> LOCATION: (39)..(41)
<223> OTHER INFORMATION: region represents a variable trinucleotide combination capable of coding any natural occurring amino acid other than Cys
<220> FEATURE:
<221> NAME/KEY: modified_base
<222> LOCATION: (45)..(47)
<223> OTHER INFORMATION: region represents a variable trinucleotide combination capable of coding any natural occurring amino acid other than Cys

<400> SEQUENCE: 12
agggtctcga gtgggtgagc nnnattnnnn nnrvtrvtnn naccnnntat gcggatagcg 60
tgaaaggccg ttttaccatt tcacgtgata attcgaaaaa cacca 105

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tggtgttttt cgaattatca 20

<210> SEQ ID NO 14
<211> LENGTH: 108
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gly Gly Thr Lys Val Glu Ile Lys Arg
            100                 105


<210> SEQ ID NO 15
<211> LENGTH: 113
<212> TYPE: PRT
<213> ORGANISM: Homo sapiens

<400> SEQUENCE: 15

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg


<210> SEQ ID NO 16
<211> LENGTH: 109
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Tyr Thr Phe Gly Gln Gly Thr Lys Val Glu Ile Lys Arg
            100                 105


<210> SEQ ID NO 17
<211> LENGTH: 114
<212> TYPE: PRT
<213> ORGANISM: Homo sapiens
```

<400> SEQUENCE: 17

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Pro Thr Phe Gly Gln Gly Thr Lys Val Glu Ile
100 105 110

Lys Arg

<210> SEQ ID NO 18
<211> LENGTH: 112
<212> TYPE: PRT
<213> ORGANISM: Homo sapiens

<400> SEQUENCE: 18

Gln Ser Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ser Glu Asp Glu Ala Asp Tyr Tyr Cys Ala Thr Trp Asp Asp Ser Leu
85 90 95

Ser Gly Val Val Phe Gly Gly Gly Thr Lys Leu Thr Val Leu Gly Gln
100 105 110

<210> SEQ ID NO 19
<211> LENGTH: 112
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Ala Gly Ser
85 90 95

Ser Thr Val Val Phe Gly Gly Gly Thr Lys Leu Thr Val Leu Gly Gln
100 105 110

<210> SEQ ID NO 20
<211> LENGTH: 108
<212> TYPE: PRT
<213> ORGANISM: Homo sapiens

<400> SEQUENCE: 20

Tyr Glu Leu Thr Gln Pro Pro Ser Val Ser Val Ala Pro Gly Gln Thr
1 5 10 15

Ala Arg Ile Thr Cys Ser Gly Asp Ser Leu Gly Ser Lys Tyr Ala Ser
20 25 30

Trp Tyr Gln Gln Lys Pro Gly Gln Ala Pro Val Leu Val Ile Tyr Asp
35 40 45

Asp Asn Lys Arg Pro Ser Gly Ile Pro Glu Arg Phe Ser Gly Ser Asn
50 55 60

Ser Gly Asn Thr Ala Thr Leu Thr Ile Ser Gly Val Gln Ala Glu Asp
65 70 75 80

Glu Ala Asp Tyr Tyr Cys Gln Ser Trp Asp Ser Ser Gly Asn Val Val
85 90 95

Phe Gly Gly Gly Thr Lys Leu Thr Val Leu Gly Gln
100 105

<210> SEQ ID NO 21
<211> LENGTH: 119
<212> TYPE: PRT
<213> ORGANISM: Homo sapiens

<400> SEQUENCE: 21

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ala Pro Gly Tyr Cys Ser Gly Phe Asp Tyr Trp Gly Gln Gly
100 105 110

Thr Leu Val Thr Val Ser Ser
115

<210> SEQ ID NO 22
<211> LENGTH: 117
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met 35 40 45

Gly Trp Ile Asn Pro Asn Ser Gly Asn Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Ser Leu Arg Ser Asp Asp Thr Ala Val Tyr Tyr Cys
85 90 95

Ala Arg Asp Gly Asp Gly Gly Phe Asp Tyr Trp Gly Gln Gly Thr Leu
100 105 110

Val Thr Val Ser Ser
115

<210> SEQ ID NO 23
<211> LENGTH: 120
<212> TYPE: PRT
<213> ORGANISM: Homo sapiens

<400> SEQUENCE: 23

Glx Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

Gly Met Gly Val Ser Trp Ile Arg Gln Pro Pro Gly Lys Ala Leu Glu
35 40 45

Trp Leu Ala His Ile Asp Trp Asp Asp Asp Lys Tyr Tyr Ser Thr Ser
50 55 60

Leu Lys Ser Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Ile His Asn Ile Gly Glu Ala Phe Asp Val Trp Gly Gln
100 105 110

Gly Thr Leu Val Thr Val Ser Ser
115 120

<210> SEQ ID NO 24
<211> LENGTH: 117
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ser Val Ile Ser Tyr Asp Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Arg Gly Gly Ser Gly Asp Tyr Trp Gly Gln Gly Thr Leu
100 105 110

Val Thr Val Ser Ser
115

<210> SEQ ID NO 25
<211> LENGTH: 118
<212> TYPE: PRT
<213> ORGANISM: Homo sapiens

<400> SEQUENCE: 25

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Glu Ile Tyr His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Arg Gly Gly Gly Gly Val Phe Asp Tyr Trp Gly Gln Gly Thr
            100                 105                 110

Leu Val Thr Val Ser Ser
        115
```

<210> SEQ ID NO 26
<211> LENGTH: 119
<212> TYPE: PRT
<213> ORGANISM: Homo sapiens

<400> SEQUENCE: 26

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Gly Gly Gly Tyr Tyr Phe Asp Tyr Trp Gly Gln Gly
            100                 105                 110

Thr Leu Val Thr Val Ser Ser
        115
```

<210> SEQ ID NO 27
<211> LENGTH: 119
<212> TYPE: PRT
<213> ORGANISM: Homo sapiens

<400> SEQUENCE: 27

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
```

```
        35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Asp Pro Gly Gly Phe Asp Val Trp Gly Gln Gly
            100                 105                 110

Thr Leu Val Thr Val Ser Ser
        115


<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr
            100                 105


<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 29

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
            100                 105                 110
```

Arg Thr

<210> SEQ ID NO 30
<211> LENGTH: 110
<212> TYPE: PRT
<213> ORGANISM: Artificial Sequence
<220> FEATURE:
<223> OTHER INFORMATION: Description of Artificial Sequence: Synthetic consensus protein

<400> SEQUENCE: 30

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln His Tyr Thr Thr Pro
                 85                  90                  95

Pro Thr Phe Gly Gln Gly Thr Lys Val Glu Ile Lys Arg Thr
            100                 105                 110
```

<210> SEQ ID NO 31
<211> LENGTH: 115
<212> TYPE: PRT
<213> ORGANISM: Artificial Sequence
<220> FEATURE:
<223> OTHER INFORMATION: Description of Artificial Sequence: Synthetic consensus protein

<400> SEQUENCE: 31

```
Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
            100                 105                 110

Lys Arg Thr
        115
```

<210> SEQ ID NO 32
<211> LENGTH: 109
<212> TYPE: PRT
<213> ORGANISM: Artificial Sequence
<220> FEATURE:
<223> OTHER INFORMATION: Description of Artificial Sequence: Synthetic consensus protein

<400> SEQUENCE: 32

```
Gln Ser Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                 85                  90                  95

Pro Val Phe Gly Gly Gly Thr Lys Leu Thr Val Leu Gly
            100                 105


<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 33

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Gln His Tyr Thr Thr
                 85                  90                  95

Pro Pro Val Phe Gly Gly Gly Thr Lys Leu Thr Val Leu Gly
            100                 105                 110


<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 34

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80
```

```
Asp Glu Ala Asp Tyr Tyr Cys Gln Gln His Tyr Thr Thr Pro Pro Val
                85                  90                  95

Phe Gly Gly Gly Thr Lys Leu Thr Val Leu Gly
            100                 105


<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 35

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 36

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 37
<211> LENGTH: 121
<212> TYPE: PRT
```

<213> ORGANISM: Artificial Sequence
<220> FEATURE:
<223> OTHER INFORMATION: Description of Artificial Sequence: Synthetic
consensus protein

<400> SEQUENCE: 37

```
Gln Val Gln Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala Leu Ile Asp Trp Asp Asp Asp Lys Tyr Tyr Ser Thr Ser
     50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120
```

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
consensus protein

<400> SEQUENCE: 38

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
consensus protein

<400> SEQUENCE: 39

```
Gln Val Gln Leu Gln Glu Ser Gly Pro Gly Leu Val Lys Pro Ser Glu
  1               5                  10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Trp Gly Gly Asp Gly Phe Tyr Ala Met Asp Tyr Trp Gly Gln Gly
            100                 105                 110

Thr Leu Val Thr Val Ser Ser
        115


<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      consensus protein

<400> SEQUENCE: 41

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
```

-continued

```
 65                  70                  75                  80

Gln Phe Ser Leu Gln Leu Asn Ser Val Thr Pro Glu Asp Thr Ala Val
                85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120


<210> SEQ ID NO 42
<211> LENGTH: 327
<212> TYPE: DNA
<213> ORGANISM: Artificial Sequence
<220> FEATURE:
<223> OTHER INFORMATION: Description of Artificial Sequence: Synthetic
      V kappa consensus gene
<220> FEATURE:
<221> NAME/KEY: CDS
<222> LOCATION: (1)..(327)

<400> SEQUENCE: 42

gat atc cag atg acc cag agc ccg tct agc ctg agc gcg agc gtg ggt       48
Asp Ile Gln Met Thr Gln Ser Pro Ser Ser Leu Ser Ala Ser Val Gly
  1               5                  10                  15

gat cgt gtg acc att acc tgc aga gcg agc cag ggc att agc agc tat       96
Asp Arg Val Thr Ile Thr Cys Arg Ala Ser Gln Gly Ile Ser Ser Tyr
             20                  25                  30

ctg gcg tgg tac cag cag aaa cca ggt aaa gca ccg aaa cta tta att      144
Leu Ala Trp Tyr Gln Gln Lys Pro Gly Lys Ala Pro Lys Leu Leu Ile
         35                  40                  45

tat gca gcc agc agc ttg caa agc ggg gtc ccg tcc cgt ttt agc ggc      192
Tyr Ala Ala Ser Ser Leu Gln Ser Gly Val Pro Ser Arg Phe Ser Gly
     50                  55                  60

tct gga tcc ggc act gat ttt acc ctg acc att agc agc ctg caa cct      240
Ser Gly Ser Gly Thr Asp Phe Thr Leu Thr Ile Ser Ser Leu Gln Pro
 65                  70                  75                  80

gaa gac ttt gcg acc tat tat tgc cag cag cat tat acc acc ccg ccg      288
Glu Asp Phe Ala Thr Tyr Tyr Cys Gln Gln His Tyr Thr Thr Pro Pro
                85                  90                  95

acc ttt ggc cag ggt acg aaa gtt gaa att aaa cgt acg                  327
Thr Phe Gly Gln Gly Thr Lys Val Glu Ile Lys Arg Thr
            100                 105


<210> SEQ ID NO 43
<211> LENGTH: 109
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 43

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
```

```
                 85                  90                  95

Thr Phe Gly Gln Gly Thr Lys Val Glu Ile Lys Arg Thr
            100                 105


<210> SEQ ID NO 44
<211> LENGTH: 342
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(342)

<400> SEQUENCE: 44

gat atc gtg atg acc cag agc cca ctg agc ctg cca gtg act ccg ggc       48
Asp Ile Val Met Thr Gln Ser Pro Leu Ser Leu Pro Val Thr Pro Gly
  1               5                  10                  15

gag cct gcg agc att agc tgc aga agc agc caa agc ctg ctg cat agc       96
Glu Pro Ala Ser Ile Ser Cys Arg Ser Ser Gln Ser Leu Leu His Ser
             20                  25                  30

aac ggc tat aac tat ctg gat tgg tac ctt caa aaa cca ggt caa agc      144
Asn Gly Tyr Asn Tyr Leu Asp Trp Tyr Leu Gln Lys Pro Gly Gln Ser
         35                  40                  45

ccg cag cta tta att tat ctg ggc agc aac cgt gcc agt ggg gtc ccg      192
Pro Gln Leu Leu Ile Tyr Leu Gly Ser Asn Arg Ala Ser Gly Val Pro
     50                  55                  60

gat cgt ttt agc ggc tct gga tcc ggc acc gat ttt acc ctg aaa att      240
Asp Arg Phe Ser Gly Ser Gly Ser Gly Thr Asp Phe Thr Leu Lys Ile
 65                  70                  75                  80

agc cgt gtg gaa gct gaa gac gtg ggc gtg tat tat tgc cag cag cat      288
Ser Arg Val Glu Ala Glu Asp Val Gly Val Tyr Tyr Cys Gln Gln His
                 85                  90                  95

tat acc acc ccg ccg acc ttt ggc cag ggt acg aaa gtt gaa att aaa      336
Tyr Thr Thr Pro Pro Thr Phe Gly Gln Gly Thr Lys Val Glu Ile Lys
            100                 105                 110

cgt acg                                                              342
Arg Thr


<210> SEQ ID NO 45
<211> LENGTH: 114
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 45

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
```

-continued

```
            100                 105                 110

Arg Thr


<210> SEQ ID NO 46
<211> LENGTH: 330
<212> TYPE: DNA
<213> ORGANISM: Artificial Sequence
<220> FEATURE:
<223> OTHER INFORMATION: Description of Artificial Sequence: Synthetic V
      kappa consensus gene
<220> FEATURE:
<221> NAME/KEY: CDS
<222> LOCATION: (1)..(330)

<400> SEQUENCE: 46

gat atc gtg ctg acc cag agc ccg gcg acc ctg agc ctg tct ccg ggc       48
Asp Ile Val Leu Thr Gln Ser Pro Ala Thr Leu Ser Leu Ser Pro Gly
  1               5                  10                  15

gaa cgt gcg acc ctg agc tgc aga gcg agc cag agc gtg agc agc agc       96
Glu Arg Ala Thr Leu Ser Cys Arg Ala Ser Gln Ser Val Ser Ser Ser
            20                  25                  30

tat ctg gcg tgg tac cag cag aaa cca ggt caa gca ccg cgt cta tta      144
Tyr Leu Ala Trp Tyr Gln Gln Lys Pro Gly Gln Ala Pro Arg Leu Leu
        35                  40                  45

att tat ggc gcg agc agc cgt gca act ggg gtc ccg gcg cgt ttt agc      192
Ile Tyr Gly Ala Ser Ser Arg Ala Thr Gly Val Pro Ala Arg Phe Ser
     50                  55                  60

ggc tct gga tcc ggc acg gat ttt acc ctg acc att agc agc ctg gaa      240
Gly Ser Gly Ser Gly Thr Asp Phe Thr Leu Thr Ile Ser Ser Leu Glu
 65                  70                  75                  80

cct gaa gac ttt gcg gtg tat tat tgc cag cag cat tat acc acc ccg      288
Pro Glu Asp Phe Ala Val Tyr Tyr Cys Gln Gln His Tyr Thr Thr Pro
                 85                  90                  95

ccg acc ttt ggc cag ggt acg aaa gtt gaa att aaa cgt acg              330
Pro Thr Phe Gly Gln Gly Thr Lys Val Glu Ile Lys Arg Thr
            100                 105                 110


<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic V
      kappa consensus gene

<400> SEQUENCE: 47

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln His Tyr Thr Thr Pro
                 85                  90                  95

Pro Thr Phe Gly Gln Gly Thr Lys Val Glu Ile Lys Arg Thr
            100                 105                 110


<210> SEQ ID NO 48
```

<211> LENGTH: 345
<212> TYPE: DNA
<213> ORGANISM: Artificial Sequence
<220> FEATURE:
<223> OTHER INFORMATION: Description of Artificial Sequence: Synthetic V kappa consensus gene
<220> FEATURE:
<221> NAME/KEY: CDS
<222> LOCATION: (1)..(345)

<400> SEQUENCE: 48

```
gat atc gtg atg acc cag agc ccg gat agc ctg gcg gtg agc ctg ggc       48
Asp Ile Val Met Thr Gln Ser Pro Asp Ser Leu Ala Val Ser Leu Gly
  1               5                  10                  15

gaa cgt gcg acc att aac tgc aga agc agc cag agc gtg ctg tat agc       96
Glu Arg Ala Thr Ile Asn Cys Arg Ser Ser Gln Ser Val Leu Tyr Ser
             20                  25                  30

agc aac aac aaa aac tat ctg gcg tgg tac cag cag aaa cca ggt cag      144
Ser Asn Asn Lys Asn Tyr Leu Ala Trp Tyr Gln Gln Lys Pro Gly Gln
         35                  40                  45

ccg ccg aaa cta tta att tat tgg gca tcc acc cgt gaa agc ggg gtc      192
Pro Pro Lys Leu Leu Ile Tyr Trp Ala Ser Thr Arg Glu Ser Gly Val
     50                  55                  60

ccg gat cgt ttt agc ggc tct gga tcc ggc act gat ttt acc ctg acc      240
Pro Asp Arg Phe Ser Gly Ser Gly Ser Gly Thr Asp Phe Thr Leu Thr
 65                  70                  75                  80

att tcg tcc ctg caa gct gaa gac gtg gcg gtg tat tat tgc cag cag      288
Ile Ser Ser Leu Gln Ala Glu Asp Val Ala Val Tyr Tyr Cys Gln Gln
                 85                  90                  95

cat tat acc acc ccg ccg acc ttt ggc cag ggt acg aaa gtt gaa att      336
His Tyr Thr Thr Pro Pro Thr Phe Gly Gln Gly Thr Lys Val Glu Ile
             100                 105                 110

aaa cgt acg                                                          345
Lys Arg Thr
        115
```

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic V kappa consensus gene

<400> SEQUENCE: 49

```
Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Thr Thr Pro Pro Thr Phe Gly Gln Gly Thr Lys Val Glu Ile
             100                 105                 110

Lys Arg Thr
        115
```

<210> SEQ ID NO 50
<211> LENGTH: 327
<212> TYPE: DNA
<213> ORGANISM: Artificial Sequence
<220> FEATURE:
<223> OTHER INFORMATION: Description of Artificial Sequence: Synthetic V lambda consensus gene
<220> FEATURE:
<221> NAME/KEY: CDS
<222> LOCATION: (1)..(327)

<400> SEQUENCE: 50

```
cag agc gtg ctg acc cag ccg cct tca gtg agt ggc gca cca ggt cag       48
Gln Ser Val Leu Thr Gln Pro Pro Ser Val Ser Gly Ala Pro Gly Gln
  1               5                  10                  15

cgt gtg acc atc tcg tgt agc ggc agc agc agc aac att ggc agc aac       96
Arg Val Thr Ile Ser Cys Ser Gly Ser Ser Ser Asn Ile Gly Ser Asn
             20                  25                  30

tat gtg agc tgg tac cag cag ttg ccc ggg acg gcg ccg aaa ctg ctg      144
Tyr Val Ser Trp Tyr Gln Gln Leu Pro Gly Thr Ala Pro Lys Leu Leu
         35                  40                  45

att tat gat aac aac cag cgt ccc tca ggc gtg ccg gat cgt ttt agc      192
Ile Tyr Asp Asn Asn Gln Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag cag cat tat acc acc ccg      288
Ser Glu Asp Glu Ala Asp Tyr Tyr Cys Gln Gln His Tyr Thr Thr Pro
                 85                  90                  95

cct gtg ttt ggc ggc ggc acg aag tta acc gtt ctt ggc                  327
Pro Val Phe Gly Gly Gly Thr Lys Leu Thr Val Leu Gly
            100                 105
```

<210> SEQ ID NO 51
<211> LENGTH: 109
<212> TYPE: PRT
<213> ORGANISM: Artificial Sequence
<220> FEATURE:
<223> OTHER INFORMATION: Description of Artificial Sequence: Synthetic V lambda consensus gene

<400> SEQUENCE: 51

```
Gln Ser Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Tyr Val Ser Trp Tyr Gln Gln Leu Pro Gly Thr Ala Pro Lys Leu Leu
         35                  40                  45

Ile Tyr Asp Asn Asn Gln Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Gln His Tyr Thr Thr Pro
                 85                  90                  95

Pro Val Phe Gly Gly Gly Thr Lys Leu Thr Val Leu Gly
            100                 105
```

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic V lambda consensus gene
<220> FEATURE:
<221> NAME/KEY: CDS
<222> LOCATION: (1)..(330)

<400> SEQUENCE: 52

```
cag agc gca ctg acc cag cca gct tca gtg agc ggc tca cca ggt cag       48
Gln Ser Ala Leu Thr Gln Pro Ala Ser Val Ser Gly Ser Pro Gly Gln
  1               5                  10                  15

agc att acc atc tcg tgt acg ggt act agc agc gat gtg ggc ggc tat       96
Ser Ile Thr Ile Ser Cys Thr Gly Thr Ser Ser Asp Val Gly Gly Tyr
             20                  25                  30

aac tat gtg agc tgg tac cag cag cat ccc ggg aag gcg ccg aaa ctg      144
Asn Tyr Val Ser Trp Tyr Gln Gln His Pro Gly Lys Ala Pro Lys Leu
         35                  40                  45

atg att tat gat gtg agc aac cgt ccc tca ggc gtg agc aac cgt ttt      192
Met Ile Tyr Asp Val Ser Asn Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
 65                  70                  75                  80

caa gcg gaa gac gaa gcg gat tat tat tgc cag cag cat tat acc acc      288
Gln Ala Glu Asp Glu Ala Asp Tyr Tyr Cys Gln Gln His Tyr Thr Thr
                 85                  90                  95

ccg cct gtg ttt ggc ggc ggc acg aag tta acc gtt ctt ggc              330
Pro Pro Val Phe Gly Gly Gly Thr Lys Leu Thr Val Leu Gly
            100                 105                 110
```

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic V lambda consensus gene

<400> SEQUENCE: 53

```
Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Gln His Tyr Thr Thr
                 85                  90                  95

Pro Pro Val Phe Gly Gly Gly Thr Lys Leu Thr Val Leu Gly
            100                 105                 110
```

<210> SEQ ID NO 54
<211> LENGTH: 321
<212> TYPE: DNA
<213> ORGANISM: Artificial Sequence
<220> FEATURE:
<223> OTHER INFORMATION: Description of Artificial Sequence: Synthetic V lambda consensus gene
<220> FEATURE:
<221> NAME/KEY: CDS
<222> LOCATION: (1)..(321)

<400> SEQUENCE: 54

```
agc tat gaa ctg acc cag ccg cct tca gtg agc gtt gca cca ggt cag       48
Ser Tyr Glu Leu Thr Gln Pro Pro Ser Val Ser Val Ala Pro Gly Gln
  1               5                  10                  15

acc gcg cgt atc tcg tgt agc ggc gat gcg ctg ggc gat aaa tac gcg       96
Thr Ala Arg Ile Ser Cys Ser Gly Asp Ala Leu Gly Asp Lys Tyr Ala
             20                  25                  30

agc tgg tac cag cag aaa ccc ggg cag gcg cca gtt ctg gtg att tat      144
Ser Trp Tyr Gln Gln Lys Pro Gly Gln Ala Pro Val Leu Val Ile Tyr
         35                  40                  45

gat gat tct gac cgt ccc tca ggc atc ccg gaa cgc ttt agc gga tcc      192
Asp Asp Ser Asp Arg Pro Ser Gly Ile Pro Glu Arg Phe Ser Gly Ser
     50                  55                  60

aac agc ggc aac acc gcg acc ctg acc att agc ggc act cag gcg gaa      240
Asn Ser Gly Asn Thr Ala Thr Leu Thr Ile Ser Gly Thr Gln Ala Glu
 65                  70                  75                  80

gac gaa gcg gat tat tat tgc cag cag cat tat acc acc ccg cct gtg      288
Asp Glu Ala Asp Tyr Tyr Cys Gln Gln His Tyr Thr Thr Pro Pro Val
                 85                  90                  95

ttt ggc ggc ggc acg aag tta acc gtt ctt ggc                          321
Phe Gly Gly Gly Thr Lys Leu Thr Val Leu Gly
            100                 105


<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic V
      lambda consensus gene

<400> SEQUENCE: 55

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105


<210> SEQ ID NO 56
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 56

cag gtg caa ttg gtt cag tct ggc gcg gaa gtg aaa aaa ccg ggc agc       48
Gln Val Gln Leu Val Gln Ser Gly Ala Glu Val Lys Lys Pro Gly Ser
  1               5                  10                  15

agc gtg aaa gtg agc tgc aaa gcc tcc gga ggc act ttt agc agc tat       96
```

```
Ser Val Lys Val Ser Cys Lys Ala Ser Gly Gly Thr Phe Ser Ser Tyr
            20                  25                  30

gcg att agc tgg gtg cgc caa gcc cct ggg cag ggt ctc gag tgg atg      144
Ala Ile Ser Trp Val Arg Gln Ala Pro Gly Gln Gly Leu Glu Trp Met
        35                  40                  45

ggc ggc att att ccg att ttt ggc acg gcg aac tac gcg cag aag ttt      192
Gly Gly Ile Ile Pro Ile Phe Gly Thr Ala Asn Tyr Ala Gln Lys Phe
    50                  55                  60

cag ggc cgg gtg acc att acc gcg gat gaa agc acc agc acc gcg tat      240
Gln Gly Arg Val Thr Ile Thr Ala Asp Glu Ser Thr Ser Thr Ala Tyr
65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                85                  90                  95

gcg cgt tgg ggc ggc gat ggc ttt tat gcg atg gat tat tgg ggc caa      336
Ala Arg Trp Gly Gly Asp Gly Phe Tyr Ala Met Asp Tyr Trp Gly Gln
            100                 105                 110

ggc acc ctg gtg acg gtt agc tca g                                    361
Gly Thr Leu Val Thr Val Ser Ser
        115                 120


<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 58
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 58

cag gtg caa ttg gtt cag agc ggc gcg gaa gtg aaa aaa ccg ggc gcg       48
Gln Val Gln Leu Val Gln Ser Gly Ala Glu Val Lys Lys Pro Gly Ala
1               5                   10                  15
```

```
agc gtg aaa gtg agc tgc aaa gcc tcc gga tat acc ttt acc agc tat       96
Ser Val Lys Val Ser Cys Lys Ala Ser Gly Tyr Thr Phe Thr Ser Tyr
            20                  25                  30

tat atg cac tgg gtc cgc caa gcc cct ggg cag ggt ctc gag tgg atg      144
Tyr Met His Trp Val Arg Gln Ala Pro Gly Gln Gly Leu Glu Trp Met
        35                  40                  45

ggc tgg att aac ccg aat agc ggc ggc acg aac tac gcg cag aag ttt      192
Gly Trp Ile Asn Pro Asn Ser Gly Gly Thr Asn Tyr Ala Gln Lys Phe
    50                  55                  60

cag ggc cgg gtg acc atg acc cgt gat acc agc att agc acc gcg tat      240
Gln Gly Arg Val Thr Met Thr Arg Asp Thr Ser Ile Ser Thr Ala Tyr
 65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                85                  90                  95

gcg cgt tgg ggc ggc gat ggc ttt tat gcg atg gat tat tgg ggc caa      336
Ala Arg Trp Gly Gly Asp Gly Phe Tyr Ala Met Asp Tyr Trp Gly Gln
            100                 105                 110

ggc acc ctg gtg acg gtt agc tca g                                    361
Gly Thr Leu Val Thr Val Ser Ser
        115                 120


<210> SEQ ID NO 59
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 59

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 60
<211> LENGTH: 364
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(363)

<400> SEQUENCE: 60

cag gtg caa ttg aaa gaa agc ggc ccg gcc ctg gtg aaa ccg acc caa       48
Gln Val Gln Leu Lys Glu Ser Gly Pro Ala Leu Val Lys Pro Thr Gln
  1               5                  10                  15
```

```
acc ctg acc ctg acc tgt acc ttt tcc gga ttt agc ctg tcc acg tct       96
Thr Leu Thr Leu Thr Cys Thr Phe Ser Gly Phe Ser Leu Ser Thr Ser
            20                  25                  30

ggc gtt ggc gtg ggc tgg att cgc cag ccg cct ggg aaa gcc ctc gag      144
Gly Val Gly Val Gly Trp Ile Arg Gln Pro Pro Gly Lys Ala Leu Glu
        35                  40                  45

tgg ctg gct ctg att gat tgg gat gat gat aag tat tat agc acc agc      192
Trp Leu Ala Leu Ile Asp Trp Asp Asp Asp Lys Tyr Tyr Ser Thr Ser
    50                  55                  60

ctg aaa acg cgt ctg acc att agc aaa gat act tcg aaa aat cag gtg      240
Leu Lys Thr Arg Leu Thr Ile Ser Lys Asp Thr Ser Lys Asn Gln Val
65                  70                  75                  80

gtg ctg act atg acc aac atg gac ccg gtg gat acg gcc acc tat tat      288
Val Leu Thr Met Thr Asn Met Asp Pro Val Asp Thr Ala Thr Tyr Tyr
                85                  90                  95

tgc gcg cgt tgg ggc ggc gat ggc ttt tat gcg atg gat tat tgg ggc      336
Cys Ala Arg Trp Gly Gly Asp Gly Phe Tyr Ala Met Asp Tyr Trp Gly
            100                 105                 110

caa ggc acc ctg gtg acg gtt agc tca g                                364
Gln Gly Thr Leu Val Thr Val Ser Ser
        115                 120


<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 61

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Trp Gly Gly Asp Gly Phe Tyr Ala Met Asp Tyr Trp Gly
            100                 105                 110

Gln Gly Thr Leu Val Thr Val Ser Ser
        115                 120


<210> SEQ ID NO 62
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 62

gaa gtg caa ttg gtg gaa agc ggc ggc ggc ctg gtg caa ccg ggc ggc       48
Glu Val Gln Leu Val Glu Ser Gly Gly Gly Leu Val Gln Pro Gly Gly
```

-continued

```
  1               5                  10                  15

agc ctg cgt ctg agc tgc gcg gcc tcc gga ttt acc ttt agc agc tat       96
Ser Leu Arg Leu Ser Cys Ala Ala Ser Gly Phe Thr Phe Ser Ser Tyr
            20                  25                  30

gcg atg agc tgg gtg cgc caa gcc cct ggg aag ggt ctc gag tgg gtg      144
Ala Met Ser Trp Val Arg Gln Ala Pro Gly Lys Gly Leu Glu Trp Val
        35                  40                  45

agc gcg att agc ggt agc ggc ggc agc acc tat tat gcg gat agc gtg      192
Ser Ala Ile Ser Gly Ser Gly Gly Ser Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95

gcg cgt tgg ggc ggc gat ggc ttt tat gcg atg gat tat tgg ggc caa      336
Ala Arg Trp Gly Gly Asp Gly Phe Tyr Ala Met Asp Tyr Trp Gly Gln
            100                 105                 110

ggc acc ctg gtg acg gtt agc tca g                                    361
Gly Thr Leu Val Thr Val Ser Ser
        115                 120
```

<210> SEQ ID NO 63
<211> LENGTH: 120
<212> TYPE: PRT
<213> ORGANISM: Artificial Sequence
<220> FEATURE:
<223> OTHER INFORMATION: Description of Artificial Sequence: Synthetic V heavy chain gene sequence

<400> SEQUENCE: 63

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 64
<211> LENGTH: 358
<212> TYPE: DNA
<213> ORGANISM: Artificial Sequence
<220> FEATURE:
<223> OTHER INFORMATION: Description of Artificial Sequence: Synthetic V heavy chain gene sequence
<220> FEATURE:
<221> NAME/KEY: CDS
<222> LOCATION: (1)..(357)

<400> SEQUENCE: 64

```
cag gtg caa ttg caa gaa agt ggt ccg ggc ctg gtg aaa ccg agc gaa       48
```

```
Gln Val Gln Leu Gln Glu Ser Gly Pro Gly Leu Val Lys Pro Ser Glu
  1               5                  10                  15

acc ctg agc ctg acc tgc acc gtt tcc gga ggc agc att agc agc tat       96
Thr Leu Ser Leu Thr Cys Thr Val Ser Gly Gly Ser Ile Ser Ser Tyr
             20                  25                  30

tat tgg agc tgg att cgc cag ccg cct ggg aag ggt ctc gag tgg att      144
Tyr Trp Ser Trp Ile Arg Gln Pro Pro Gly Lys Gly Leu Glu Trp Ile
         35                  40                  45

ggc tat att tat tat agc ggc agc acc aac tat aat ccg agc ctg aaa      192
Gly Tyr Ile Tyr Tyr Ser Gly Ser Thr Asn Tyr Asn Pro Ser Leu Lys
     50                  55                  60

agc cgg gtg acc att agc gtt gat act tcg aaa aac cag ttt agc ctg      240
Ser Arg Val Thr Ile Ser Val Asp Thr Ser Lys Asn Gln Phe Ser Leu
 65                  70                  75                  80

aaa ctg agc agc gtg acg gcg gcg gat acg gcc gtg tat tat tgc gcg      288
Lys Leu Ser Ser Val Thr Ala Ala Asp Thr Ala Val Tyr Tyr Cys Ala
                 85                  90                  95

cgt tgg ggc ggc gat ggc ttt tat gcg atg gat tat tgg ggc caa ggc      336
Arg Trp Gly Gly Asp Gly Phe Tyr Ala Met Asp Tyr Trp Gly Gln Gly
            100                 105                 110

acc ctg gtg acg gtt agc tca g                                        358
Thr Leu Val Thr Val Ser Ser
        115


<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 65

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Trp Gly Gly Asp Gly Phe Tyr Ala Met Asp Tyr Trp Gly Gln Gly
            100                 105                 110

Thr Leu Val Thr Val Ser Ser
        115


<210> SEQ ID NO 66
<211> LENGTH: 361
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(360)

<400> SEQUENCE: 66
```

```
gaa gtg caa ttg gtt cag agc ggc gcg gaa gtg aaa aaa ccg ggc gaa       48
Glu Val Gln Leu Val Gln Ser Gly Ala Glu Val Lys Lys Pro Gly Glu
  1               5                  10                  15

agc ctg aaa att agc tgc aaa ggt tcc gga tat tcc ttt acg agc tat       96
Ser Leu Lys Ile Ser Cys Lys Gly Ser Gly Tyr Ser Phe Thr Ser Tyr
             20                  25                  30

tgg att ggc tgg gtg cgc cag atg cct ggg aag ggt ctc gag tgg atg      144
Trp Ile Gly Trp Val Arg Gln Met Pro Gly Lys Gly Leu Glu Trp Met
         35                  40                  45

ggc att att tat ccg ggc gat agc gat acc cgt tat tct ccg agc ttt      192
Gly Ile Ile Tyr Pro Gly Asp Ser Asp Thr Arg Tyr Ser Pro Ser Phe
     50                  55                  60

cag ggc cag gtg acc att agc gcg gat aaa agc att agc acc gcg tat      240
Gln Gly Gln Val Thr Ile Ser Ala Asp Lys Ser Ile Ser Thr Ala Tyr
 65                  70                  75                  80

ctt caa tgg agc agc ctg aaa gcg agc gat acg gcc atg tat tat tgc      288
Leu Gln Trp Ser Ser Leu Lys Ala Ser Asp Thr Ala Met Tyr Tyr Cys
                 85                  90                  95

gcg cgt tgg ggc ggc gat ggc ttt tat gcg atg gat tat tgg ggc caa      336
Ala Arg Trp Gly Gly Asp Gly Phe Tyr Ala Met Asp Tyr Trp Gly Gln
            100                 105                 110

ggc acc ctg gtg acg gtt agc tca g                                    361
Gly Thr Leu Val Thr Val Ser Ser
        115                 120


<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic V
      heavy chain gene sequence

<400> SEQUENCE: 67

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 68
<211> LENGTH: 370
<212> TYPE: DNA
<213> ORGANISM: Artificial Sequence
<220> FEATURE:
<223> OTHER INFORMATION: Description of Artificial Sequence: Synthetic V
      heavy chain gene sequence
<220> FEATURE:
<221> NAME/KEY: CDS
<222> LOCATION: (1)..(369)

<400> SEQUENCE: 68
```

```
cag gtg caa ttg caa cag tct ggt ccg ggc ctg gtg aaa ccg agc caa       48
Gln Val Gln Leu Gln Gln Ser Gly Pro Gly Leu Val Lys Pro Ser Gln
  1               5                  10                  15

acc ctg agc ctg acc tgt gcg att tcc gga gat agc gtg agc agc aac       96
Thr Leu Ser Leu Thr Cys Ala Ile Ser Gly Asp Ser Val Ser Ser Asn
             20                  25                  30

agc gcg gcg tgg aac tgg att cgc cag tct cct ggg cgt ggc ctc gag      144
Ser Ala Ala Trp Asn Trp Ile Arg Gln Ser Pro Gly Arg Gly Leu Glu
         35                  40                  45

tgg ctg ggc cgt acc tat tat cgt agc aaa tgg tat aac gat tat gcg      192
Trp Leu Gly Arg Thr Tyr Tyr Arg Ser Lys Trp Tyr Asn Asp Tyr Ala
     50                  55                  60

gtg agc gtg aaa agc cgg att acc atc aac ccg gat act tcg aaa aac      240
Val Ser Val Lys Ser Arg Ile Thr Ile Asn Pro Asp Thr Ser Lys Asn
 65                  70                  75                  80

cag ttt agc ctg caa ctg aac agc gtg acc ccg gaa gat acg gcc gtg      288
Gln Phe Ser Leu Gln Leu Asn Ser Val Thr Pro Glu Asp Thr Ala Val
                 85                  90                  95

tat tat tgc gcg cgt tgg ggc ggc gat ggc ttt tat gcg atg gat tat      336
Tyr Tyr Cys Ala Arg Trp Gly Gly Asp Gly Phe Tyr Ala Met Asp Tyr
            100                 105                 110

tgg ggc caa ggc acc ctg gtg acg gtt agc tca g                        370
Trp Gly Gln Gly Thr Leu Val Thr Val Ser Ser
        115                 120
```

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic V heavy chain gene sequence

<400> SEQUENCE: 69

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Trp Gly Gly Asp Gly Phe Tyr Ala Met Asp Tyr
            100                 105                 110

Trp Gly Gln Gly Thr Leu Val Thr Val Ser Ser
        115                 120
```

<210> SEQ ID NO 70
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70

```
gaatgcatac gctgatatcc agatgaccca gagcccgtct agcctgagc                 49
```

<210> SEQ ID NO 71
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
cgctctgcag gtaatggtca cacgatcacc cacgctcgcg ctcaggctag acgggc 56

<210> SEQ ID NO 72
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
gaccattacc tgcagagcga gccagggcat tagcagctat ctggcgtggt accagcag 58

<210> SEQ ID NO 73
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
ctttgcaagc tgctggctgc ataaattaat agtttcggtg ctttacctgg tttctgctgg 60
taccacgcca g 71

<210> SEQ ID NO 74
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
cagccagcag cttgcaaagc ggggtcccgt cccgttttag cggctctgga tccggcactg 60
attttac 67

<210> SEQ ID NO 75
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
gataataggt cgcaaagtct tcaggttgca ggctgctaat ggtcagggta aaatcagtgc 60
cggatcc 67

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
cgatatcgtg atgacccaga gcccactgag cctgccagtg actccgggcg agcc 54

<210> SEQ ID NO 77
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gccgttgcta tgcagcaggc tttggctgct tctgcagcta atgctcgcag gctcgcccgg 60
agtcac 66

<210> SEQ ID NO 78
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
ctgctgcata gcaacggcta taactatctg gattggtacc ttcaaaaacc aggtcaaagc 60
cc 62

<210> SEQ ID NO 79
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
cgatccggga ccccactggc acggttgctg cccagataaa ttaatagctg cgggctttga 60
cctggttttt g 71

<210> SEQ ID NO 80
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
agtggggtcc cggatcgttt tagcggctct ggatccggca ccgattttac cctgaaaatt 60
agccgtgtg 69

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
ccatgcaata atacacgccc acgtcttcag cttccacacg gctaattttc aggg 54

<210> SEQ ID NO 82

<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
gaatgcatac gctgatatcg tgctgaccca gagcccgg 38

<210> SEQ ID NO 83
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
cgctctgcag ctcagggtcg cacgttcgcc cggagacagg ctcagggtcg ccgggctctg 60
ggtcagc 67

<210> SEQ ID NO 84
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
ccctgagctg cagagcgagc cagagcgtga gcagcagcta tctggcgtgg taccag 56

<210> SEQ ID NO 85
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gcacggctgc tcgcgccata aattaataga cgcggtgctt gacctggttt ctgctggtac 60
cacgccagat ag 72

<210> SEQ ID NO 86
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
gcgcgagcag ccgtgcaact ggggtcccgg cgcgttttag cggctctgga tccggcacgg 60
attttac 67

<210> SEQ ID NO 87
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
gataatacac cgcaaagtct tcaggttcca ggctgctaat ggtcagggta aaatccgtgc 60
cggatc 66

<210> SEQ ID NO 88
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
gaatgcatac gctgatatcg tgatgaccca gagcccggat agcctggcg 49

<210> SEQ ID NO 89
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
gcttctgcag ttaatggtcg cacgttcgcc caggctcacc gccaggctat ccgggc 56

<210> SEQ ID NO 90
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
cgaccattaa ctgcagaagc agccagagcg tgctgtatag cagcaacaac aaaaactatc 60
tggcgtggta ccag 74

<210> SEQ ID NO 91
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
gatgcccaat aaattaatag tttcggcggc tgacctggtt tctgctggta ccacgccaga 60
tag 63

<210> SEQ ID NO 92
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
aaactattaa tttattgggc atccacccgt gaaagcgggg tcccggatcg ttttagcggc 60
tctggatccg gcac 74

<210> SEQ ID NO 93
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gataatacac cgccacgtct tcagcttgca gggacgaaat ggtcagggta aaatcagtgc 60
cggatccaga gcc 73

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
gaatgcatac gctcagagcg tgctgaccca gccgccttca gtgagtgg 48

<210> SEQ ID NO 95
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
caatgttgct gctgctgccg ctacacgaga tggtcacacg ctgacctggt gcgccactca 60
ctgaaggcgg c 71

<210> SEQ ID NO 96
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
ggcagcagca gcaacattgg cagcaactat gtgagctggt accagcagtt gcccgggac 59

<210> SEQ ID NO 97
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
ccggcacgcc tgagggacgc tggttgttat cataaatcag cagtttcggc gccgtcccgg 60
gcaactgc 68

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
ccctcaggcg tgccggatcg ttttagcgga tccaaaagcg gcaccagcgc gagccttgcg 60

<210> SEQ ID NO 99
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 99
ccgcttcgtc ttcgctttgc aggcccgtaa tcgcaaggct cgcgctgg 48

<210> SEQ ID NO 100
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 100
gaatgcatac gctcagagcg cactgaccca gccagcttca gtgagcggc 49

<210> SEQ ID NO 101
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cgctgctagt acccgtacac gagatggtaa tgctctgacc tggtgagccg ctcactgaag 60
ctgg 64

<210> SEQ ID NO 102
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
gtacgggtac tagcagcgat gtgggcggct ataactatgt gagctggtac cagcagcatc 60
ccgg 64

<210> SEQ ID NO 103
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
cgcctgaggg acggttgctc acatcataaa tcatcagttt cggcgccttc ccgggatgct 60
gctggtac 68

<210> SEQ ID NO 104
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
caaccgtccc tcaggcgtga gcaaccgttt tagcggatcc aaaagcggca acaccgcgag 60
cc 62

<210> SEQ ID NO 105
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
ccgcttcgtc ttccgcttgc aggccgctaa tggtcaggct cgcggtgttg ccg 53

<210> SEQ ID NO 106
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
gaatgcatac gctagctatg aactgaccca gccgccttca gtgagcg 47

<210> SEQ ID NO 107
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
cgcccagcgc atcgccgcta cacgagatac gcgcggtctg acctggtgca acgctcactg 60
aaggcggc 68

<210> SEQ ID NO 108
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
ggcgatgcgc tgggcgataa atacgcgagc tggtaccagc agaaacccgg gcaggcgc 58

<210> SEQ ID NO 109
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
gcgttccggg atgcctgagg gacggtcaga atcatcataa atcaccagaa ctggcgcctg 60
cccgggtttc 70

<210> SEQ ID NO 110
<211> LENGTH: 64
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 110
caggcatccc ggaacgcttt agcggatcca acagcggcaa caccgcgacc ctgaccatta 60
gcgg 64

<210> SEQ ID NO 111
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
ccgcttcgtc ttccgcctga gtgccgctaa tggtcagggt c 41

<210> SEQ ID NO 112
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
gctcttcacc cctgttacca aagcccaggt gcaattg 37

<210> SEQ ID NO 113
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
ggctttgcag ctcactttca cgctgctgcc cggttttttc acttccgcgc cagactgaac 60
caattgcacc tgggctttg 79

<210> SEQ ID NO 114
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
gaaagtgagc tgcaaagcct ccggaggcac ttttagcagc tatgcgatta gctgggtgcg 60
ccaagcccct gggcagggtc 80

<210> SEQ ID NO 115
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
gccctgaaac ttctgcgcgt agttcgccgt gccaaaaatc ggaataatgc cgcccatcca 60
ctcgagaccc tgcccagggg c 81

<210> SEQ ID NO 116
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
gcgcagaagt ttcagggccg ggtgaccatt accgcggatg aaagcaccag caccgcgtat 60
atggaactga gcagcctgcg 80

<210> SEQ ID NO 117
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
gcgcgcaata atacacggcc gtatcttcgc tacgcaggct gctcagttcc 50

<210> SEQ ID NO 118
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
ggctttgcag ctcactttca cgctcgcgcc cggtttttc acttccgcgc cgctctgaac 60
caattgcacc tgggctttg 79

<210> SEQ ID NO 119
<211> LENGTH: 80
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
gaaagtgagc tgcaaagcct ccggatatac ctttaccagc tattatatgc actgggtccg 60
ccaagcccct gggcagggtc 80

<210> SEQ ID NO 120
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
gccctgaaac ttctgcgcgt agttcgtgcc gccgctattc gggttaatcc agcccatcca 60
ctcgagaccc tgcccagggg c 81

<210> SEQ ID NO 121
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
gcgcagaagt ttcagggccg ggtgaccatg acccgtgata ccagcattag caccgcgtat 60
atggaactga gcagcctgcg 80

<210> SEQ ID NO 122
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
ggtacaggtc agggtcaggg tttgggtcgg tttcaccagg gccgggccgc tttctttcaa 60
ttgcacctgg gctttg 76

<210> SEQ ID NO 123
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
ctgaccctga cctgtacctt ttccggattt agcctgtcca cgtctggcgt tggcgtgggc 60
tggattcgcc agccgcctgg gaaag 85

<210> SEQ ID NO 124
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
gcgttttcag gctggtgcta taatacttat catcatccca atcaatcaga gccagccact 60
cgagggcttt cccaggcggc tgg 83

<210> SEQ ID NO 125
<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
gcaccagcct gaaaacgcgt ctgaccatta gcaaagatac ttcgaaaaat caggtggtgc 60
tgactatgac caacatgg 78

<210> SEQ ID NO 126
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
gcgcgcaata ataggtggcc gtatccaccg ggtccatgtt ggtcatagtc agc 53

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
cgaagtgcaa ttggtggaaa gcggcggcgg cctggtgcaa ccgggcggca g 51

<210> SEQ ID NO 128
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
catagctgct aaaggtaaat ccggaggccg cgcagctcag acgcaggctg ccgcccggtt 60
gcac 64

<210> SEQ ID NO 129
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
gatttacctt tagcagctat gcgatgagct gggtgcgcca agcccctggg aagggtctcg 60
agtgggtgag 70

<210> SEQ ID NO 130
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
ggcctttcac gctatccgca taataggtgc tgccgccgct accgctaatc gcgctcaccc 60
actcgagacc c 71

<210> SEQ ID NO 131
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 131
cggatagcgt gaaaggccgt tttaccattt cacgtgataa ttcgaaaaac accctgtatc 60
tgcaaatgaa cag 73

<210> SEQ ID NO 132
<211> LENGTH: 62
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 132
cacgcgcgca ataatacacg gccgtatctt ccgcacgcag gctgttcatt tgcagataca 60
gg 62

<210> SEQ ID NO 133
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 133
ggtcaggctc agggtttcgc tcggtttcac caggcccgga ccactttctt gcaattgcac 60
ctgggctttg 70

<210> SEQ ID NO 134
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
gaaaccctga gcctgacctg caccgtttcc ggaggcagca ttagcagcta ttattggagc 60
tggattcgcc agccgc 76

<210> SEQ ID NO 135
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
gattatagtt ggtgctgccg ctataataaa tatagccaat ccactcgaga cccttcccag 60
gcggctggcg aatccag 77

<210> SEQ ID NO 136
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
cggcagcacc aactataatc cgagcctgaa aagccgggtg accattagcg ttgatacttc 60
gaaaaaccag tttagcctg 79

<210> SEQ ID NO 137
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
gcgcgcaata atacacggcc gtatccgccg ccgtcacgct gctcagtttc aggctaaact 60
ggtttttcg 69

<210> SEQ ID NO 138
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
gctcttcacc cctgttacca aagccgaagt gcaattg 37

<210> SEQ ID NO 139
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
cctttgcagc taattttcag gctttcgccc ggttttttca cttccgcgcc gctctgaacc 60
aattgcactt cggctttgg 79

<210> SEQ ID NO 140
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
cctgaaaatt agctgcaaag gttccggata ttcctttacg agctattgga ttggctgggt 60
gcgccagatg cctgg 75

<210> SEQ ID NO 141
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
cggagaataa cgggtatcgc tatcgcccgg ataaataatg cccatccact cgagaccctt 60
cccaggcatc tggcgcac 78

<210> SEQ ID NO 142
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
cgatacccgt tattctccga gctttcaggg ccaggtgacc attagcgcgg ataaaagcat 60
tagcaccgcg tatcttc 77

<210> SEQ ID NO 143
<211> LENGTH: 68

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
gcgcgcaata atacatggcc gtatcgctcg ctttcaggct gctccattga agatacgcgg 60
tgctaatg 68

<210> SEQ ID NO 144
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
gaaatcgcac aggtcaggct cagggtttgg ctcggtttca ccaggcccgg accagactgt 60
tgcaattgca cctgggcttt g 81

<210> SEQ ID NO 145
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
gcctgacctg tgcgatttcc ggagatagcg tgagcagcaa cagcgcggcg tggaactgga 60
ttcgccagtc tcctgggcg 79

<210> SEQ ID NO 146
<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
caccgcataa tcgttatacc atttgctacg ataataggta cggcccagcc actcgaggcc 60
acgcccagga gactggcg 78

<210> SEQ ID NO 147
<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
ggtataacga ttatgcggtg agcgtgaaaa gccggattac catcaacccg gatacttcga 60
aaaaccagtt tagcctgc 78

<210> SEQ ID NO 148
<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
gcgcgcaata atacacggcc gtatcttccg gggtcacgct gttcagttgc aggctaaact 60
ggtttttc 68

<210> SEQ ID NO 149
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
ggctgaagac gtgggcgtgt attattgcca gcagcattat accaccccgc cgacctttgg 60
ccagggtac 69

<210> SEQ ID NO 150
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
gcggaaaaat aaacacgctc ggagcagcca ccgtacgttt aatttcaact ttcgtaccct 60
ggccaaaggt c 71

<210> SEQ ID NO 151
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
gagcgtgttt atttttccgc cgagcgatga acaactgaaa agcggcacgg cgagcgtggt 60
gtgcctgctg 70

<210> SEQ ID NO 152
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
cagcgcgttg tctactttcc actgaacttt cgcttcacgc ggataaaagt tgttcagcag 60
gcacaccacg c 71

<210> SEQ ID NO 153
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
gaaagtagac aacgcgctgc aaagcggcaa cagccaggaa agcgtgaccg aacaggatag 60
caaagatag 69

<210> SEQ ID NO 154
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
gtttttcata atccgctttg ctcagggtca gggtgctgct cagagaatag gtgctatctt 60
tgctatcctg ttcg 74

<210> SEQ ID NO 155
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
gcaaagcgga ttatgaaaaa cataaagtgt atgcgtgcga agtgacccat caaggtctga 60
gcagcccggt g 71

<210> SEQ ID NO 156
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
ggcatgctta tcaggcctcg ccacgattaa aagatttagt caccgggctg ctcagac 57

<210> SEQ ID NO 157
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
ggcgtctaga ggccaaggca ccctggtgac ggttagctca gcgtcgac 48

<210> SEQ ID NO 158
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
gtgcttttgc tgctcggagc cagcggaaac acgcttggac ctttggtcga cgctgagcta 60
acc 63

<210> SEQ ID NO 159
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
ctccgagcag caaaagcacc agcggcggca cggctgccct gggctgcctg gttaaagatt 60
atttcc 66

<210> SEQ ID NO 160
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
ctggtcagcg ccccgctgtt ccagctcacg gtgactggtt ccgggaaata atctttaacc 60
aggca 65

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
agcggggcgc tgaccagcgg cgtgcatacc tttccggcgg tgctgcaaag cagcggcctg 60

<210> SEQ ID NO 162
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
gtgcctaagc tgctgctcgg cacggtcaca acgctgctca ggctatacag gccgctgctt 60
tgcag 65

<210> SEQ ID NO 163
<211> LENGTH: 61
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
gagcagcagc ttaggcactc agacctatat ttgcaacgtg aaccataaac cgagcaacac 60
c 61

<210> SEQ ID NO 164
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
gcgcgaattc gcttttcggt tccacttttt tatccacttt ggtgttgctc ggtttatgg 59

<210> SEQ ID NO 165
<211> LENGTH: 333
<212> TYPE: DNA
<213> ORGANISM: Artificial Sequence
<220> FEATURE:
<223> OTHER INFORMATION: Description of Artificial Sequence: Synthetic C
kappa gene sequence
<220> FEATURE:
<221> NAME/KEY: CDS
<222> LOCATION: (7)..(321)

<400> SEQUENCE: 165

```
cgtacg gtg gct gct ccg agc gtg ttt att ttt ccg ccg agc gat gaa        48
       Val Ala Ala Pro Ser Val Phe Ile Phe Pro Pro Ser Asp Glu
         1               5                  10

caa ctg aaa agc ggc acg gcg agc gtg gtg tgc ctg ctg aac aac ttt       96
Gln Leu Lys Ser Gly Thr Ala Ser Val Val Cys Leu Leu Asn Asn Phe
 15                  20                  25                  30

tat ccg cgt gaa gcg aaa gtt cag tgg aaa gta gac aac gcg ctg caa      144
Tyr Pro Arg Glu Ala Lys Val Gln Trp Lys Val Asp Asn Ala Leu Gln
                 35                  40                  45

agc ggc aac agc cag gaa agc gtg acc gaa cag gat agc aaa gat agc      192
Ser Gly Asn Ser Gln Glu Ser Val Thr Glu Gln Asp Ser Lys Asp Ser
             50                  55                  60

acc tat tct ctg agc agc acc ctg acc ctg agc aaa gcg gat tat gaa      240
Thr Tyr Ser Leu Ser Ser Thr Leu Thr Leu Ser Lys Ala Asp Tyr Glu
         65                  70                  75

aaa cat aaa gtg tat gcg tgc gaa gtg acc cat caa ggt ctg agc agc      288
Lys His Lys Val Tyr Ala Cys Glu Val Thr His Gln Gly Leu Ser Ser
     80                  85                  90

ccg gtg act aaa tct ttt aat cgt ggc gag gcc tgataagcat gc           333
Pro Val Thr Lys Ser Phe Asn Arg Gly Glu Ala
 95                 100                 105
```

<210> SEQ ID NO 166
<211> LENGTH: 105
<212> TYPE: PRT
<213> ORGANISM: Artificial Sequence
<220> FEATURE:
<223> OTHER INFORMATION: Description of Artificial Sequence: Synthetic C
kappa gene sequence

<400> SEQUENCE: 166

```
Val Ala Ala Pro Ser Val Phe Ile Phe Pro Pro Ser Asp Glu Gln Leu
  1               5                  10                  15

Lys Ser Gly Thr Ala Ser Val Val Cys Leu Leu Asn Asn Phe Tyr Pro
             20                  25                  30

Arg Glu Ala Lys Val Gln Trp Lys Val Asp Asn Ala Leu Gln Ser Gly
         35                  40                  45

Asn Ser Gln Glu Ser Val Thr Glu Gln Asp Ser Lys Asp Ser Thr Tyr
     50                  55                  60

Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Ala
            100                 105
```

<210> SEQ ID NO 167
<211> LENGTH: 327
<212> TYPE: DNA
<213> ORGANISM: Artificial Sequence
<220> FEATURE:
<223> OTHER INFORMATION: Description of Artificial Sequence: Synthetic

```
      CH1 gene sequence
<220> FEATURE:
<221> NAME/KEY: CDS
<222> LOCATION: (6)..(317)

<400> SEQUENCE: 167

gctca gcg tcg acc aaa ggt cca agc gtg ttt ccg ctg gct ccg agc agc      50
      Ala Ser Thr Lys Gly Pro Ser Val Phe Pro Leu Ala Pro Ser Ser
        1               5                  10                  15

aaa agc acc agc ggc ggc acg gct gcc ctg ggc tgc ctg gtt aaa gat        98
Lys Ser Thr Ser Gly Gly Thr Ala Ala Leu Gly Cys Leu Val Lys Asp
                 20                  25                  30

tat ttc ccg gaa cca gtc acc gtg agc tgg aac agc ggg gcg ctg acc       146
Tyr Phe Pro Glu Pro Val Thr Val Ser Trp Asn Ser Gly Ala Leu Thr
             35                  40                  45

agc ggc gtg cat acc ttt ccg gcg gtg ctg caa agc agc ggc ctg tat       194
Ser Gly Val His Thr Phe Pro Ala Val Leu Gln Ser Ser Gly Leu Tyr
         50                  55                  60

agc ctg agc agc gtt gtg acc gtg ccg agc agc agc tta ggc act cag       242
Ser Leu Ser Ser Val Val Thr Val Pro Ser Ser Ser Leu Gly Thr Gln
     65                  70                  75

acc tat att tgc aac gtg aac cat aaa ccg agc aac acc aaa gtg gat       290
Thr Tyr Ile Cys Asn Val Asn His Lys Pro Ser Asn Thr Lys Val Asp
 80                  85                  90                  95

aaa aaa gtg gaa ccg aaa agc gaa ttc tgataagctt                        327
Lys Lys Val Glu Pro Lys Ser Glu Phe
            100


<210> SEQ ID NO 168
<211> LENGTH: 104
<212> TYPE: PRT
<213> ORGANISM: Artificial Sequence
<220> FEATURE:
<223> OTHER INFORMATION: Description of Artificial Sequence: Synthetic
      CH1 gene sequence

<400> SEQUENCE: 168

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Glu Phe
            100


<210> SEQ ID NO 169
<211> LENGTH: 408
<212> TYPE: DNA
<213> ORGANISM: Artificial Sequence
<220> FEATURE:
<223> OTHER INFORMATION: Description of Artificial Sequence: Synthetic
      C lambda gene segment
<220> FEATURE:
<221> NAME/KEY: CDS
<222> LOCATION: (85)..(396)

<400> SEQUENCE: 169
```

```
gaagacgaag cggattatta ttgccagcag cattatacca ccccgcctgt gtttggcggc     60

ggcacgaagt taaccgttct tggc cag ccg aaa gcc gca ccg agt gtg acg       111
                           Gln Pro Lys Ala Ala Pro Ser Val Thr
                             1               5

ctg ttt ccg ccg agc agc gaa gaa ttg cag gcg aac aaa gcg acc ctg      159
Leu Phe Pro Pro Ser Ser Glu Glu Leu Gln Ala Asn Lys Ala Thr Leu
 10                 15                  20                  25

gtg tgc ctg att agc gac ttt tat ccg gga gcc gtg aca gtg gcc tgg      207
Val Cys Leu Ile Ser Asp Phe Tyr Pro Gly Ala Val Thr Val Ala Trp
                30                  35                  40

aag gca gat agc agc ccc gtc aag gcg gga gtg gag acc acc aca ccc      255
Lys Ala Asp Ser Ser Pro Val Lys Ala Gly Val Glu Thr Thr Thr Pro
            45                  50                  55

tcc aaa caa agc aac aac aag tac gcg gcc agc agc tat ctg agc ctg      303
Ser Lys Gln Ser Asn Asn Lys Tyr Ala Ala Ser Ser Tyr Leu Ser Leu
        60                  65                  70

acg cct gag cag tgg aag tcc cac aga agc tac agc tgc cag gtc acg      351
Thr Pro Glu Gln Trp Lys Ser His Arg Ser Tyr Ser Cys Gln Val Thr
    75                  80                  85

cat gag ggg agc acc gtg gaa aaa acc gtt gcg ccg act gag gcc          396
His Glu Gly Ser Thr Val Glu Lys Thr Val Ala Pro Thr Glu Ala
 90                 95                  100

tgataagcat gc                                                        408


<210> SEQ ID NO 170
<211> LENGTH: 104
<212> TYPE: PRT
<213> ORGANISM: Artificial Sequence
<220> FEATURE:
<223> OTHER INFORMATION: Description of Artificial Sequence: Synthetic
      C lambda gene segment

<400> SEQUENCE: 170

Gln Pro Lys Ala Ala Pro Ser Val Thr Leu Phe Pro Pro Ser Ser Glu
  1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                85                  90                  95

Lys Thr Val Ala Pro Thr Glu Ala
            100


<210> SEQ ID NO 171
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171

gaagacaagc ggattattat tgccagcagc attataccac cccgcctgtg tttggcggcg     60

gcacgaagtt aaccgttc                                                   78
```

<210> SEQ ID NO 172
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
caattcttcg ctgctcggcg gaaacagcgt cacactcggt gcggctttcg gctggccaag 60
aacggttaac ttcgtgccgc 80

<210> SEQ ID NO 173
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
cgccgagcag cgaagaattg caggcgaaca aagcgaccct ggtgtgcctg attagcgact 60
tttatccggg agccgtgaca 80

<210> SEQ ID NO 174
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 174
tgtttggagg gtgtggtggt ctccactccc gccttgacgg ggctgctatc tgccttccag 60
gccactgtca cggctcccgg 80

<210> SEQ ID NO 175
<211> LENGTH: 94
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
ccacaccctc caaacaaagc aacaacaagt acgcggccag cagctatctg agcctgacgc 60
ctgagcagtg gaagtcccac agaagctaca gctg 94

<210> SEQ ID NO 176
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 176
gcatgcttat caggcctcag tcggcgcaac ggttttttcc acggtgctcc cctcatgcgt 60
gacctggcag ctgtagcttc 80

<210> SEQ ID NO 177
<211> LENGTH: 843
<212> TYPE: DNA
<213> ORGANISM: Artificial Sequence

```
<220> FEATURE:
<223> OTHER INFORMATION: Description of Artificial Sequence: Synthetic
      single chain  fragment VH3-V kappa 2
<220> FEATURE:
<221> NAME/KEY: CDS
<222> LOCATION: (1)..(843)

<400> SEQUENCE: 177

atg aaa caa agc act att gca ctg gca ctc tta ccg ttg ctc ttc acc       48
Met Lys Gln Ser Thr Ile Ala Leu Ala Leu Leu Pro Leu Leu Phe Thr
  1               5                  10                  15

cct gtt acc aaa gcc gac tac aaa gat gaa gtg caa ttg gtg gaa agc       96
Pro Val Thr Lys Ala Asp Tyr Lys Asp Glu Val Gln Leu Val Glu Ser
             20                  25                  30

ggc ggc ggc ctg gtg caa ccg ggc ggc agc ctg cgt ctg agc tgc gcg      144
Gly Gly Gly Leu Val Gln Pro Gly Gly Ser Leu Arg Leu Ser Cys Ala
         35                  40                  45

gcc tcc gga ttt acc ttt agc agc tat gcg atg agc tgg gtg cgc caa      192
Ala Ser Gly Phe Thr Phe Ser Ser Tyr Ala Met Ser Trp Val Arg Gln
     50                  55                  60

gcc cct ggg aag ggt ctc gag tgg gtg agc gcg att agc ggt agc ggc      240
Ala Pro Gly Lys Gly Leu Glu Trp Val Ser Ala Ile Ser Gly Ser Gly
 65                  70                  75                  80

ggc agc acc tat tat gcg gat agc gtg aaa ggc cgt ttt acc att tca      288
Gly Ser Thr Tyr Tyr Ala Asp Ser Val Lys Gly Arg Phe Thr Ile Ser
                 85                  90                  95

cgt gat aat tcg aaa aac acc ctg tat ctg caa atg aac agc ctg cgt      336
Arg Asp Asn Ser Lys Asn Thr Leu Tyr Leu Gln Met Asn Ser Leu Arg
            100                 105                 110

gcg gaa gat acg gcc gtg tat tat tgc gcg cgt tgg ggc ggc gat ggc      384
Ala Glu Asp Thr Ala Val Tyr Tyr Cys Ala Arg Trp Gly Gly Asp Gly
        115                 120                 125

ttt tat gcg atg gat tat tgg ggc caa ggc acc ctg gtg acg gtt agc      432
Phe Tyr Ala Met Asp Tyr Trp Gly Gln Gly Thr Leu Val Thr Val Ser
    130                 135                 140

tca gcg ggt ggc ggt tct ggc ggc ggt ggg agc ggt ggc ggt ggt tct      480
Ser Ala Gly Gly Gly Ser Gly Gly Gly Gly Ser Gly Gly Gly Gly Ser
145                 150                 155                 160

ggc ggt ggt ggt tcc gat atc gtg atg acc cag agc cca ctg agc ctg      528
Gly Gly Gly Gly Ser Asp Ile Val Met Thr Gln Ser Pro Leu Ser Leu
                165                 170                 175

cca gtg act ccg ggc gag cct gcg agc att agc tgc aga agc agc caa      576
Pro Val Thr Pro Gly Glu Pro Ala Ser Ile Ser Cys Arg Ser Ser Gln
            180                 185                 190

agc ctg ctg cat agc aac ggc tat aac tat ctg gat tgg tac ctt caa      624
Ser Leu Leu His Ser Asn Gly Tyr Asn Tyr Leu Asp Trp Tyr Leu Gln
        195                 200                 205

aaa cca ggt caa agc ccg cag cta tta att tat ctg ggc agc aac cgt      672
Lys Pro Gly Gln Ser Pro Gln Leu Leu Ile Tyr Leu Gly Ser Asn Arg
    210                 215                 220

gcc agt ggg gtc ccg gat cgt ttt agc ggc tct gga tcc ggc acc gat      720
Ala Ser Gly Val Pro Asp Arg Phe Ser Gly Ser Gly Ser Gly Thr Asp
225                 230                 235                 240

ttt acc ctg aaa att agc cgt gtg gaa gct gaa gac gtg ggc gtg tat      768
Phe Thr Leu Lys Ile Ser Arg Val Glu Ala Glu Asp Val Gly Val Tyr
                245                 250                 255

tat tgc cag cag cat tat acc acc ccg ccg acc ttt ggc cag ggt acg      816
Tyr Cys Gln Gln His Tyr Thr Thr Pro Pro Thr Phe Gly Gln Gly Thr
            260                 265                 270

aaa gtt gaa att aaa cgt acg gaa ttc                                  843
Lys Val Glu Ile Lys Arg Thr Glu Phe
        275                 280
```

<210> SEQ ID NO 178
<211> LENGTH: 281
<212> TYPE: PRT
<213> ORGANISM: Artificial Sequence
<220> FEATURE:
<223> OTHER INFORMATION: Description of Artificial Sequence: Synthetic
single chain fragment VH3-V kappa 2

<400> SEQUENCE: 178

```
Met Lys Gln Ser Thr Ile Ala Leu Ala Leu Leu Pro Leu Leu Phe Thr
  1               5                  10                  15

Pro Val Thr Lys Ala Asp Tyr Lys Asp Glu Val Gln Leu Val Glu Ser
             20                  25                  30

Gly Gly Gly Leu Val Gln Pro Gly Gly Ser Leu Arg Leu Ser Cys Ala
         35                  40                  45

Ala Ser Gly Phe Thr Phe Ser Ser Tyr Ala Met Ser Trp Val Arg Gln
     50                  55                  60

Ala Pro Gly Lys Gly Leu Glu Trp Val Ser Ala Ile Ser Gly Ser Gly
 65                  70                  75                  80

Gly Ser Thr Tyr Tyr Ala Asp Ser Val Lys Gly Arg Phe Thr Ile Ser
                 85                  90                  95

Arg Asp Asn Ser Lys Asn Thr Leu Tyr Leu Gln Met Asn Ser Leu Arg
            100                 105                 110

Ala Glu Asp Thr Ala Val Tyr Tyr Cys Ala Arg Trp Gly Gly Asp Gly
        115                 120                 125

Phe Tyr Ala Met Asp Tyr Trp Gly Gln Gly Thr Leu Val Thr Val Ser
    130                 135                 140

Ser Ala Gly Gly Gly Ser Gly Gly Gly Gly Ser Gly Gly Gly Gly Ser
145                 150                 155                 160

Gly Gly Gly Gly Ser Asp Ile Val Met Thr Gln Ser Pro Leu Ser Leu
                165                 170                 175

Pro Val Thr Pro Gly Glu Pro Ala Ser Ile Ser Cys Arg Ser Ser Gln
            180                 185                 190

Ser Leu Leu His Ser Asn Gly Tyr Asn Tyr Leu Asp Trp Tyr Leu Gln
        195                 200                 205

Lys Pro Gly Gln Ser Pro Gln Leu Leu Ile Tyr Leu Gly Ser Asn Arg
    210                 215                 220

Ala Ser Gly Val Pro Asp Arg Phe Ser Gly Ser Gly Ser Gly Thr Asp
225                 230                 235                 240

Phe Thr Leu Lys Ile Ser Arg Val Glu Ala Glu Asp Val Gly Val Tyr
                245                 250                 255

Tyr Cys Gln Gln His Tyr Thr Thr Pro Pro Thr Phe Gly Gln Gly Thr
            260                 265                 270

Lys Val Glu Ile Lys Arg Thr Glu Phe
        275                 280
```

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

```
Cys Ala Arg Trp Gly Gly Asp Gly Phe Tyr Ala Met Asp Tyr Trp
  1               5                  10                  15
```

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Cys Ala Arg Phe Gly Lys Met Asn Tyr Asp Tyr Trp
1 5 10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Cys Ala Arg His Arg Thr Glu Trp His Asp Tyr Trp
1 5 10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Cys Ala Arg Val Arg Glu Leu Tyr His Asp Tyr Trp
1 5 10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Cys Ala Arg Lys Phe Leu Lys Ala Arg Asp Tyr Trp
1 5 10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Cys Ala Arg Trp Asn Thr Thr Gly Tyr Asp Tyr Trp
1 5 10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Cys Ala Arg Ile Asn Glu Ala Gln Pro Asp Tyr Trp
1 5 10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Cys Ala Arg Thr Ala Ile Thr Arg Asp Tyr Trp
1 5 10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Cys Ala Arg Trp Tyr Asn Arg Asn Ser Asp Tyr Trp
1 5 10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Cys Ala Arg Ser Val Gly Asp Ser Lys Asp Tyr Trp
1 5 10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Cys Ala Arg Ser Lys Thr Phe Ala Ala Asp Tyr Trp
1 5 10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Cys Ala Arg Val Ala Pro Gln Tyr Asp Asp Tyr Trp
1 5 10

<210> SEQ ID NO 191
<211> LENGTH: 12
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 191

Cys Ala Arg Met Gln Ser Glu Trp Met Asp Tyr Trp
1 5 10

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Cys Ala Arg Tyr Phe Val His Phe Leu Tyr Thr Met Val Met Asp Val
1 5 10 15

Trp

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 193

Cys Ala Arg Met Ala Leu Arg Ala Ser Gly Lys Tyr Ile Met Asp Val
1 5 10 15

Trp

<210> SEQ ID NO 194
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Cys Ala Arg Lys Asn Gln Met Val Phe His Ala Arg Lys Phe Asp Val
1 5 10 15

Trp

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 195

Cys Ala Arg Thr Gln Ser Phe Trp Glu Gln Gln Lys Val Met Asp Tyr
1 5 10 15

Trp

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 196

Cys Ala Arg Tyr Pro Tyr Arg Ser Asn Phe Phe Met Pro Met Asp Val
1 5 10 15

Trp

<210> SEQ ID NO 197
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Cys Ala Arg Gly Ser Gly Ser Glu His Trp Ser Ile Phe Asp Val Trp
1 5 10 15

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Cys Ala Arg Arg Asn Pro Trp Asn Val Asn Tyr Leu His Phe Asp Val
1 5 10 15

Trp

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Cys Ala Arg Met Lys Pro Met Leu Asn Arg Asp Gly Thr Met Asp Val
1 5 10 15

Trp

<210> SEQ ID NO 200
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 200

Cys Ala Arg Lys Gly Ser Glu Phe Leu Glu Thr Asp Val Met Asp Tyr
1 5 10 15

Trp

<210> SEQ ID NO 201
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 201

Cys Ala Arg Ser Trp Thr Asn Asp Lys Pro Asn Phe Ile Met Asp Val
1 5 10 15

Trp

<210> SEQ ID NO 202
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Cys Ala Arg Tyr Ala Gly Thr Thr Phe Lys Gln Gly Pro Met Asp Tyr
1 5 10 15

Trp

<210> SEQ ID NO 203
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Cys Ala Arg Lys Arg Met Met Gln Asn Pro Arg Phe Arg Phe Asp Val
1 5 10 15

Trp

<210> SEQ ID NO 204
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Cys Ala Arg Arg Ser Lys Gln Lys Arg Lys Met Arg Arg Phe Asp Val
1 5 10 15

Trp

<210> SEQ ID NO 205
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Cys Ala Arg Arg Asn Gly Lys Arg His Leu Arg His Arg Phe Asp Val
1 5 10 15

Trp

<210> SEQ ID NO 206
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Cys Ala Arg Arg Lys Met Arg Lys Arg Ile Lys Arg Arg Phe Asp Val
1 5 10 15

Trp

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Cys Ala Arg Tyr Arg Lys Ile Met Lys Trp Lys Asn Ser Phe Asp Val
1 5 10 15

Trp

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Cys Ala Arg Leu Ile Glu Val His Pro Ser Phe Asp Gln Met Asp Val
1 5 10 15

Trp

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Cys Ala Arg Arg Lys Pro Met Phe Leu Lys Lys Ala Val Phe Asp Val
1 5 10 15

Trp

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Cys Ala Arg Arg Lys Phe His Arg Tyr Ser Thr Val Lys Phe Asp Tyr
1 5 10 15

Trp

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

```
Cys Ala Arg Arg Lys Thr Met Arg Ser Arg Val Lys Tyr Phe Asp Tyr
 1               5                  10                  15

Trp


<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Ala Arg Lys Lys Arg Ser Trp Arg Arg Met Asp Arg Phe Asp Val
 1               5                  10                  15

Trp


<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Ala Arg Arg Asn Pro Arg Arg Gly Arg Met Asn Arg Phe Asp Val
 1               5                  10                  15

Trp


<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Ala Arg Lys Gly Lys Lys Lys Phe Ala Arg Pro Arg Phe Asp Val
 1               5                  10                  15

Trp


<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Cys Ala Arg Arg Met Val His Lys Gly Lys Arg Lys Ile Phe Asp Val
 1               5                  10                  15

Trp


<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216
```

Cys Ala Arg Arg Lys His Ile Thr Tyr Pro Arg Lys Gln Phe Asp Val
1 5 10 15

Trp

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Cys Ala Arg Arg Trp Thr Lys Arg Arg Ser Phe Ala Arg Phe Asp Val
1 5 10 15

Trp

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Cys Ala Arg Lys Lys Leu Lys Gln Tyr Thr Phe Ser Arg Phe Asp Tyr
1 5 10 15

Trp

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Cys Ala Arg Thr Arg Pro Trp Gln Ala Thr Arg Lys Gly Phe Asp Val
1 5 10 15

Trp

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Cys Ala Arg Asn Gln Trp Glu Phe Lys Asn Arg Arg Lys Met Asp Tyr
1 5 10 15

Trp

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Cys Ala Arg Lys Arg Trp Met Trp Pro Ile Gly Lys Arg Phe Asp Tyr
1 5 10 15

Trp

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Cys Ala Arg Tyr Ser Leu Trp Arg Leu Asp Glu Tyr Phe Phe Asp Tyr
1 5 10 15

Trp

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Cys Ala Arg Val Pro Trp Gly Asp Phe Trp Ser Trp His Met Asp Val
1 5 10 15

Trp

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Cys Ala Arg Asn Gly Leu Glu Pro Arg His Arg Lys Met Met Asp Tyr
1 5 10 15

Trp

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Cys Ala Arg Ile Met Lys Ala Pro Pro Asp Tyr Trp
1 5 10

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Cys Ala Arg Arg Lys Thr Trp His Trp Phe Tyr Lys Arg Met Asp Tyr 1 5 10 15

Trp

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Cys Ala Arg Trp Lys Asp Met Trp Ser Gln Val Tyr Val Met Asp Tyr
1 5 10 15

Trp

<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Cys Ala Arg Asn Lys Gln Gln Met Arg Phe Arg Arg Phe Met Asp Tyr
1 5 10 15

Trp

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Cys Ala Arg Asn Met Leu Ala Leu Ser Arg Gly Lys Glu Met Asp Val
1 5 10 15

Trp

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Cys Ala Arg Asn Met Arg Leu Met Arg Met Arg Lys Asn Phe Asp Val
1 5 10 15

Trp

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Cys Ala Arg Tyr Ile Lys Gln Ala Lys Arg Lys Leu Ala Phe Asp Tyr

```
  1               5                   10                  15

Trp


<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Ala Arg Tyr Asn Arg His Ala Trp Gln Lys Met Gln Phe Asp Tyr
  1               5                   10                  15

Trp


<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Ala Arg Tyr Val Lys Tyr Ala Arg Asn Lys Met Gln Phe Asp Tyr
  1               5                   10                  15

Trp


<210> SEQ ID NO 234
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Ala Arg Tyr Lys Arg Gly Ala Trp Met Lys Thr Met Phe Asp Val
  1               5                   10                  15

Trp


<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Ala Arg Arg Lys Pro Leu Arg Arg Ile Met Lys Trp Phe Asp Tyr
  1               5                   10                  15

Trp


<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Ala Arg Tyr Arg Lys Arg Ala Ser Arg Gln Met Gln Phe Asp Tyr
```

1 5 10 15

Trp

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Cys Ala Arg Gln Arg Tyr Arg Ser Lys Ile Lys Gly His Phe Asp Val
1 5 10 15

Trp

<210> SEQ ID NO 238
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Cys Ala Arg Trp Arg Asp Phe Asn Ser Tyr Asp Pro Met Asp Tyr Trp
1 5 10 15

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Cys Ala Arg Met Ala Asp Leu Asp Asn Tyr Trp Val Gln Phe Asp Tyr
1 5 10 15

Trp

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Cys Ala Arg Leu Gln Ala Tyr Leu Lys Pro His His Trp Met Asp Tyr
1 5 10 15

Trp

<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Cys Ala Arg Arg Leu Ile Glu Gln Ala Arg Asp His Val Met Asp Tyr
1 5 10 15

Trp

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Cys Ala Arg Ser Trp His Asn Ser Gln Phe Thr Gln Ser Phe Asp Val
1 5 10 15

Trp

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Cys Ala Arg Val Asp His Phe Gln Thr Glu Asn Glu Trp Met Asp Tyr
1 5 10 15

Trp

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Cys Ala Arg Asp Trp Pro Thr Leu Ile Phe Trp Tyr Trp Phe Asp Tyr
1 5 10 15

Trp

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Cys Ala Arg Gly Phe Gly Phe Thr Glu Asp Tyr Trp
1 5 10

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Cys Ala Arg Gln Phe Asp Glu Asp Ser Phe Val Arg Arg Phe Asp Val
1 5 10 15

Trp

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Ala Arg Ile Leu Lys Glu Ser Ser Lys Ser Arg Gln Met Asp Val
1 5 10 15

Trp

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Ala Arg Glu Gln Asp Glu Tyr Gly Ala Ile Arg Ile Met Asp Tyr
1 5 10 15

Trp

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Ala Arg Asn His Phe Glu Ala Ser Trp Pro Arg Arg Gln Met Asp
1 5 10 15

Val Trp

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Ala Arg Glu Asn Glu Trp Val Asp Met Ile Leu Asp Met Asp Tyr
1 5 10 15

Trp

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Ala Arg Gln Tyr Ser Glu Thr Arg Trp Val Arg Lys Phe Asp Tyr
1 5 10 15

Trp

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Cys Ala Arg Gln Phe Lys Glu Ser Lys Thr Arg Arg Lys Phe Asp Val
1 5 10 15

Trp

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 253

Cys Ala Arg Lys Lys Thr Gln Tyr Val His Asp Trp Arg Met Asp Val
1 5 10 15

Trp

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Cys Ala Arg Arg Trp Arg Glu Thr Lys Ser Lys Arg Phe Phe Asp Val
1 5 10 15

Trp

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Cys Ala Arg Asp Tyr Ile Met Glu Phe Asp Tyr Trp
1 5 10

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Cys Ala Arg Gln Phe Glu Glu Thr Lys Gln Arg Arg Leu Met Asp Tyr
1 5 10 15

Trp

<210> SEQ ID NO 257

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Ala Arg Asp Gln Gly Phe Tyr Ala Ile Asp Tyr Val Met Asp Tyr
  1               5                  10                  15

Trp

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Ala Arg Val Phe Thr Tyr Met Tyr Asn Tyr Phe Arg Phe Asp Val
  1               5                  10                  15

Trp

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Ala Arg Val Phe Phe Glu Gln Met Glu Val Val Arg Met Asp Val
  1               5                  10                  15

Trp

<210> SEQ ID NO 260
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Ala Arg Glu Lys Glu Tyr Arg Leu Ser Trp Ser Gln Met Asp Tyr
  1               5                  10                  15

Trp

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Ala Arg Tyr Pro Ser Arg Trp Ala Pro Asn Trp Tyr Met Asp Tyr
  1               5                  10                  15

Trp

<210> SEQ ID NO 262

<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

```
Cys Ala Arg Asp Gly Gly Phe Lys Pro Leu Thr His Phe Phe Asp Val
  1               5                  10                  15

Trp
```

<210> SEQ ID NO 263
<211> LENGTH: 143
<212> TYPE: DNA
<213> ORGANISM: Artificial Sequence
<220> FEATURE:
<223> OTHER INFORMATION: Description of Artificial Sequence: Synthetic DNA cassette

<400> SEQUENCE: 263

```
acatgtaagc ttcccccccc ccttaattaa cccccccccc tgtacacccc ccccccgcta     60

gccccccccc ccagatctcc cccccccga cgtcccccct ctagaccccc cccccgcatg    120

cccccccccc cgaattcgac gtc                                           143
```

<210> SEQ ID NO 264
<211> LENGTH: 1947
<212> TYPE: DNA
<213> ORGANISM: Artificial Sequence
<220> FEATURE:
<223> OTHER INFORMATION: Description of Artificial Sequence: Synthetic vector
<220> FEATURE:
<221> NAME/KEY: CDS
<222> LOCATION: (132)..(989)

<400> SEQUENCE: 264

```
caggtggcac ttttcgggga aatgtgcgcg gaacccctat ttgtttattt ttctaaatac     60

attcaaatat gtatccgctc atgagacaat aaccctgata aatgcttcaa taatattgaa    120

aaaggaagag t atg agt att caa cat ttc cgt gtc gcc ctt att ccc ttt     170
             Met Ser Ile Gln His Phe Arg Val Ala Leu Ile Pro Phe
               1               5                  10

ttt gcg gca ttt tgc ctt cct gtt ttt gct cac cca gaa acg ctg gtg      218
Phe Ala Ala Phe Cys Leu Pro Val Phe Ala His Pro Glu Thr Leu Val
     15                  20                  25

aaa gta aaa gat gct gaa gat cag ttg ggt gca cga gtg ggt tac atc      266
Lys Val Lys Asp Ala Glu Asp Gln Leu Gly Ala Arg Val Gly Tyr Ile
 30                  35                  40                  45

gaa ctg gat ctc aac agc ggt aag atc ctt gag agt ttt cgc ccc gaa      314
Glu Leu Asp Leu Asn Ser Gly Lys Ile Leu Glu Ser Phe Arg Pro Glu
                 50                  55                  60

gaa cgt ttt cca atg atg agc act ttt aaa gtt ctg cta tgt ggc gcg      362
Glu Arg Phe Pro Met Met Ser Thr Phe Lys Val Leu Leu Cys Gly Ala
             65                  70                  75

gta tta tcc cgt att gac gcc ggg caa gag caa ctc ggt cgc cgc ata      410
Val Leu Ser Arg Ile Asp Ala Gly Gln Glu Gln Leu Gly Arg Arg Ile
         80                  85                  90

cac tat tct cag aat gac ttg gtt gag tac tca cca gtc aca gaa aag      458
His Tyr Ser Gln Asn Asp Leu Val Glu Tyr Ser Pro Val Thr Glu Lys
     95                 100                 105

cat ctt acg gat ggc atg aca gta aga gaa tta tgc agt gct gcc ata      506
His Leu Thr Asp Gly Met Thr Val Arg Glu Leu Cys Ser Ala Ala Ile
110                 115                 120                 125
```

```
acc atg agt gat aac act gcg gcc aac tta ctt ctg aca acg atc gga      554
Thr Met Ser Asp Asn Thr Ala Ala Asn Leu Leu Leu Thr Thr Ile Gly
                130                 135                 140

gga ccg aag gag cta acc gct ttt ttg cac aac atg ggg gat cat gta      602
Gly Pro Lys Glu Leu Thr Ala Phe Leu His Asn Met Gly Asp His Val
            145                 150                 155

act cgc ctt gat cgt tgg gaa ccg gag ctg aat gaa gcc ata cca aac      650
Thr Arg Leu Asp Arg Trp Glu Pro Glu Leu Asn Glu Ala Ile Pro Asn
        160                 165                 170

gac gag cgt gac acc acg atg cct gta gca atg gca aca acg ttg cgc      698
Asp Glu Arg Asp Thr Thr Met Pro Val Ala Met Ala Thr Thr Leu Arg
    175                 180                 185

aaa cta tta act ggc gaa cta ctt act cta gct tcc cgg caa caa tta      746
Lys Leu Leu Thr Gly Glu Leu Leu Thr Leu Ala Ser Arg Gln Gln Leu
190                 195                 200                 205

ata gac tgg atg gag gcg gat aaa gtt gca gga cca ctt ctg cgc tcg      794
Ile Asp Trp Met Glu Ala Asp Lys Val Ala Gly Pro Leu Leu Arg Ser
                210                 215                 220

gcc ctt ccg gct ggc tgg ttt att gct gat aaa tct gga gcc ggt gag      842
Ala Leu Pro Ala Gly Trp Phe Ile Ala Asp Lys Ser Gly Ala Gly Glu
            225                 230                 235

cgt ggg tct cgc ggt atc att gca gca ctg ggg cca gat ggt aag ccc      890
Arg Gly Ser Arg Gly Ile Ile Ala Ala Leu Gly Pro Asp Gly Lys Pro
        240                 245                 250

tcc cgt atc gta gtt atc tac acg acg ggg agt cag gca act atg gat      938
Ser Arg Ile Val Val Ile Tyr Thr Thr Gly Ser Gln Ala Thr Met Asp
    255                 260                 265

gaa cga aat aga cag atc gct gag ata ggt gcc tca ctg att aag cat      986
Glu Arg Asn Arg Gln Ile Ala Glu Ile Gly Ala Ser Leu Ile Lys His
270                 275                 280                 285

tgg taactgtcag accaagttta ctcatatata ctttagattg atttaaaact          1039
Trp

tcatttttaa tttaaaagga tctaggtgaa gatccttttt gataatctca tgaccaaaat   1099

cccttaacgt gagttttcgt tccactgagc gtcagacccc gtagaaaaga tcaaaggatc   1159

ttcttgagat cctttttttc tgcgcgtaat ctgctgcttg caaacaaaaa aaccaccgct   1219

accagcggtg gtttgtttgc cggatcaaga gctaccaact ctttttccga aggtaactgg   1279

cttcagcaga gcgcagatac caaatactgt ccttctagtg tagccgtagt taggccacca   1339

cttcaagaac tctgtagcac cgcctacata cctcgctctg ctaatcctgt taccagtggc   1399

tgctgccagt ggcgataagt cgtgtcttac cgggttggac tcaagacgat agttaccgga   1459

taaggcgcag cggtcgggct gaacgggggg ttcgtgcaca cagcccagct tggagcgaac   1519

gacctacacc gaactgagat acctacagcg tgagctatga gaaagcgcca cgcttcccga   1579

agggagaaag gcggacaggt atccggtaag cggcagggtc ggaacaggag agcgcacgag   1639

ggagcttcca gggggaaacg cctggtatct ttatagtcct gtcgggtttc gccacctctg   1699

acttgagcgt cgatttttgt gatgctcgtc aggggggcgg agcctatgga aaaacgccag   1759

caacgcggcc tttttacggt tcctggcctt ttgctggcct tttgctcaca tgtaagcttc   1819

ccccccccct taattaaccc cccccctgt acacccccccc cccgctagcc ccccccccca   1879

gatctccccc cccccgacgt cccccctcta gacccccccc ccgcatgccc ccccccccga   1939

attcacgt                                                            1947
```

<210> SEQ ID NO 265
<211> LENGTH: 286
<212> TYPE: PRT

<213> ORGANISM: Artificial Sequence
<220> FEATURE:
<223> OTHER INFORMATION: Description of Artificial Sequence: Synthetic
vector

<400> SEQUENCE: 265

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

<210> SEQ ID NO 266
<211> LENGTH: 142
<212> TYPE: DNA
<213> ORGANISM: Artificial Sequence
<220> FEATURE:
<223> OTHER INFORMATION: Description of Artificial Sequence: Synthetic
DNA cassette

<400> SEQUENCE: 266

```
gacgtcttaa tgtgagttag ctcactcatt aggcacccca ggctttacac tttatgcttc      60

cggctcgtat gttgtgtgga attgtgagcg gataacaatt tcacacagga aacagctatg     120

accatgatta cgaatttcta ga                                              142
```

<210> SEQ ID NO 267

<211> LENGTH: 520
<212> TYPE: DNA
<213> ORGANISM: Artificial Sequence
<220> FEATURE:
<223> OTHER INFORMATION: Description of Artificial Sequence: Synthetic
vector
<220> FEATURE:
<221> NAME/KEY: CDS
<222> LOCATION: (1)..(510)

<400> SEQUENCE: 267

```
gaa ttc gag cag aag ctg atc tct gag gag gat ctg tag ggt ggt ggc       48
Glu Phe Glu Gln Lys Leu Ile Ser Glu Glu Asp Leu     Gly Gly Gly
  1               5                  10                  15

tct ggt tcc ggt gat ttt gat tat gaa aag atg gca aac gct aat aag       96
Ser Gly Ser Gly Asp Phe Asp Tyr Glu Lys Met Ala Asn Ala Asn Lys
                 20                  25                  30

ggg gct atg acc gaa aat gcc gat gaa aac gcg cta cag tct gac gct      144
Gly Ala Met Thr Glu Asn Ala Asp Glu Asn Ala Leu Gln Ser Asp Ala
             35                  40                  45

aaa ggc aaa ctt gat tct gtc gct act gat tac ggt gct gct atc gat      192
Lys Gly Lys Leu Asp Ser Val Ala Thr Asp Tyr Gly Ala Ala Ile Asp
         50                  55                  60

ggt ttc att ggt gac gtt tcc ggc ctt gct aat ggt aat ggt gct act      240
Gly Phe Ile Gly Asp Val Ser Gly Leu Ala Asn Gly Asn Gly Ala Thr
     65                  70                  75

ggt gat ttt gct ggc tct aat tcc caa atg gct caa gtc ggt gac ggt      288
Gly Asp Phe Ala Gly Ser Asn Ser Gln Met Ala Gln Val Gly Asp Gly
 80                  85                  90                  95

gat aat tca cct tta atg aat aat ttc cgt caa tat tta cct tcc ctc      336
Asp Asn Ser Pro Leu Met Asn Asn Phe Arg Gln Tyr Leu Pro Ser Leu
                100                 105                 110

cct caa tcg gtt gaa tgt cgc cct ttt gtc ttt ggc gct ggt aaa cca      384
Pro Gln Ser Val Glu Cys Arg Pro Phe Val Phe Gly Ala Gly Lys Pro
            115                 120                 125

tat gaa ttt tct att gat tgt gac aaa ata aac tta ttc cgt ggt gtc      432
Tyr Glu Phe Ser Ile Asp Cys Asp Lys Ile Asn Leu Phe Arg Gly Val
        130                 135                 140

ttt gcg ttt ctt tta tat gtt gcc acc ttt atg tat gta ttt tct acg      480
Phe Ala Phe Leu Leu Tyr Val Ala Thr Phe Met Tyr Val Phe Ser Thr
    145                 150                 155

ttt gct aac ata ctg cgt aat aag gag tct tgataagctt                   520
Phe Ala Asn Ile Leu Arg Asn Lys Glu Ser
160                 165
```

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
vector

<400> SEQUENCE: 268

```
Glu Phe Glu Gln Lys Leu Ile Ser Glu Glu Asp Leu
  1               5                  10
```

<210> SEQ ID NO 269
<211> LENGTH: 123
<212> TYPE: DNA
<213> ORGANISM: Artificial Sequence
<220> FEATURE:
<223> OTHER INFORMATION: Description of Artificial Sequence: Synthetic
DNA cassette

<400> SEQUENCE: 269
gggggggggg aagcttgacc tgtgaagtga aaaatggcgc agattgtgcg acattttttt 60
tgtctgccgt ttaattaaag gggggggggg gccggcctgg gggggggtgt acaggggggg 120
ggg 123

<210> SEQ ID NO 270
<211> LENGTH: 470
<212> TYPE: DNA
<213> ORGANISM: Artificial Sequence
<220> FEATURE:
<223> OTHER INFORMATION: Description of Artificial Sequence: Synthetic DNA cassette

<400> SEQUENCE: 270
gctagcacgc gccctgtagc ggcgcattaa gcgcggcggg tgtggtggtt acgcgcagcg 60
tgaccgctac acttgccagc gccctagcgc ccgctccttt cgctttcttc ccttcctttc 120
tcgccacgtt cgccggcttt ccccgtcaag ctctaaatcg ggcatccct ttagggttcc 180 gatttagtgc tttacggcac ctcgacccca aaaaacttga ttagggtgat ggttctcgta 240
gtgggccatc gccctgatag acggtttttc gccctttgac gttggagtcc acgttcttta 300
atagtggact cttgttccaa actggaacaa cactcaaccc tatctcggtc tattcttttg 360
atttataagg gattttgccg atttcggcct attggttaaa aaatgagctg atttaacaaa 420
aatttaacgc gaattttaac aaaatattaa cgtttacaat ttcatgtaca 470

<210> SEQ ID NO 271
<211> LENGTH: 733
<212> TYPE: DNA
<213> ORGANISM: Artificial Sequence
<220> FEATURE:
<223> OTHER INFORMATION: Description of Artificial Sequence: Synthetic DNA cassette

<400> SEQUENCE: 271
agatctgacc aaaatccctt aacgtgagtt ttcgttccac tgagcgtcag accccgtaga 60
aaagatcaaa ggatcttctt gagatccttt ttttctgcgc gtaatctgct gcttgcaaac 120
aaaaaaacca ccgctaccag cggtggtttg tttgccggat caagagctac caactctttt 180
tccgaaggta actggctaca gcagagcgca gataccaaat actgttcttc tagtgtagcc 240
gtagttaggc caccacttca agaactctgt agcaccgcct acatacctcg ctctgctaat 300
cctgttacca gtggctgctg ccagtggcga taagtcgtgt cttaccgggt tggactcaag 360
acgatagtta ccggataagg cgcagcggtc gggctgaacg gggggttcgt gcacacagcc 420
cagcttggag cgaacgacct acaccgaact gagataccta cagcgtgagc tatgagaaag 480
cgccacgctt cccgaaggga gaaaggcgga caggtatccg gtaagcggca gggtcggaac 540
aggagagcgc acgagggagc ttccaggggg aaacgcctgg tatctttata gtcctgtcgg 600
gtttcgccac ctctgacttg agcgtcgatt tttgtgatgc tcgtcagggg ggcggagcct 660
atggaaaaac gccagcaacg cggccttttt acggttcctg gccttttgct ggccttttgc 720
tcacatggct agc 733

<210> SEQ ID NO 272
<211> LENGTH: 813
<212> TYPE: DNA
<213> ORGANISM: Artificial Sequence
<220> FEATURE:
<223> OTHER INFORMATION: Description of Artificial Sequence: Synthetic vector
<220> FEATURE:

```
<221> NAME/KEY: CDS
<222> LOCATION: (102)..(758)

<400> SEQUENCE: 272

gggacgtcgg gtgaggttcc aactttcacc ataatgaaat aagatcacta ccgggcgtat     60

tttttgagtt atcgagattt tcaggagcta aggaagctaa a atg gag aaa aaa atc    116
                                            Met Glu Lys Lys Ile
                                            1               5

act gga tat acc acc gtt gat ata tcc caa tgg cat cgt aaa gaa cat      164
Thr Gly Tyr Thr Thr Val Asp Ile Ser Gln Trp His Arg Lys Glu His
                10                  15                  20

ttt gag gca ttt cag tca gtt gct caa tgt acc tat aac cag acc gtt      212
Phe Glu Ala Phe Gln Ser Val Ala Gln Cys Thr Tyr Asn Gln Thr Val
            25                  30                  35

cag ctg gat att acg gcc ttt tta aag acc gta aag aaa aat aag cac      260
Gln Leu Asp Ile Thr Ala Phe Leu Lys Thr Val Lys Lys Asn Lys His
        40                  45                  50

aag ttt tat ccg gcc ttt att cac att ctt gcc cgc ctg atg aat gct      308
Lys Phe Tyr Pro Ala Phe Ile His Ile Leu Ala Arg Leu Met Asn Ala
    55                  60                  65

cac ccg gag ttc cgt atg gca atg aaa gac ggt gag ctg gtg ata tgg      356
His Pro Glu Phe Arg Met Ala Met Lys Asp Gly Glu Leu Val Ile Trp
 70                  75                  80                  85

gat agt gtt cac cct tgt tac acc gtt ttc cat gag caa act gaa acg      404
Asp Ser Val His Pro Cys Tyr Thr Val Phe His Glu Gln Thr Glu Thr
                90                  95                  100

ttt tca tcg ctc tgg agt gaa tac cac gac gat ttc cgg cag ttt cta      452
Phe Ser Ser Leu Trp Ser Glu Tyr His Asp Asp Phe Arg Gln Phe Leu
            105                 110                 115

cac ata tat tcg caa gat gtg gcg tgt tac ggt gaa aac ctg gcc tat      500
His Ile Tyr Ser Gln Asp Val Ala Cys Tyr Gly Glu Asn Leu Ala Tyr
        120                 125                 130

ttc cct aaa ggg ttt att gag aat atg ttt ttc gtc tca gcc aat ccc      548
Phe Pro Lys Gly Phe Ile Glu Asn Met Phe Phe Val Ser Ala Asn Pro
    135                 140                 145

tgg gtg agt ttc acc agt ttt gat tta aac gta gcc aat atg gac aac      596
Trp Val Ser Phe Thr Ser Phe Asp Leu Asn Val Ala Asn Met Asp Asn
150                 155                 160                 165

ttc ttc gcc ccc gtt ttc act atg ggc aaa tat tat acg caa ggc gac      644
Phe Phe Ala Pro Val Phe Thr Met Gly Lys Tyr Tyr Thr Gln Gly Asp
                170                 175                 180

aag gtg ctg atg ccg ctg gcg att cag gtt cat cat gcc gtt tgt gat      692
Lys Val Leu Met Pro Leu Ala Ile Gln Val His His Ala Val Cys Asp
            185                 190                 195

ggc ttc cat gtc ggc aga atg ctt aat gaa tta caa cag tac tgc gat      740
Gly Phe His Val Gly Arg Met Leu Asn Glu Leu Gln Gln Tyr Cys Asp
        200                 205                 210

gag tgg cag ggc ggg gcg taattttttt aaggcagtta ttgggtgccc             788
Glu Trp Gln Gly Gly Ala
    215

ttaaacgcct ggtgctagat cttcc                                          813


<210> SEQ ID NO 273
<211> LENGTH: 219
<212> TYPE: PRT
<213> ORGANISM: Artificial Sequence
<220> FEATURE:
<223> OTHER INFORMATION: Description of Artificial Sequence: Synthetic
      vector

<400> SEQUENCE: 273
```

```
Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

<210> SEQ ID NO 274
<211> LENGTH: 2755
<212> TYPE: DNA
<213> ORGANISM: Artificial Sequence
<220> FEATURE:
<223> OTHER INFORMATION: Description of Artificial Sequence: Synthetic
      vector
<220> FEATURE:
<221> NAME/KEY: CDS
<222> LOCATION: (3)..(509)

<400> SEQUENCE: 274

```
aa ttc gag cag aag ctg atc tct gag gag gat ctg tag ggt ggt ggc        47
   Phe Glu Gln Lys Leu Ile Ser Glu Glu Asp Leu     Gly Gly Gly
     1               5                  10

tct ggt tcc ggt gat ttt gat tat gaa aag atg gca aac gct aat aag       95
Ser Gly Ser Gly Asp Phe Asp Tyr Glu Lys Met Ala Asn Ala Asn Lys
 15                  20                  25                  30

ggg gct atg acc gaa aat gcc gat gaa aac gcg cta cag tct gac gct      143
Gly Ala Met Thr Glu Asn Ala Asp Glu Asn Ala Leu Gln Ser Asp Ala
                 35                  40                  45

aaa ggc aaa ctt gat tct gtc gct act gat tac ggt gct gct atc gat      191
Lys Gly Lys Leu Asp Ser Val Ala Thr Asp Tyr Gly Ala Ala Ile Asp
             50                  55                  60

ggt ttc att ggt gac gtt tcc ggc ctt gct aat ggt aat ggt gct act      239
Gly Phe Ile Gly Asp Val Ser Gly Leu Ala Asn Gly Asn Gly Ala Thr
         65                  70                  75

ggt gat ttt gct ggc tct aat tcc caa atg gct caa gtc ggt gac ggt      287
Gly Asp Phe Ala Gly Ser Asn Ser Gln Met Ala Gln Val Gly Asp Gly
     80                  85                  90
```

-continued

```
gat aat tca cct tta atg aat aat ttc cgt caa tat tta cct tcc ctc      335
Asp Asn Ser Pro Leu Met Asn Asn Phe Arg Gln Tyr Leu Pro Ser Leu
 95                 100                 105                 110

cct caa tcg gtt gaa tgt cgc cct ttt gtc ttt ggc gct ggt aaa cca      383
Pro Gln Ser Val Glu Cys Arg Pro Phe Val Phe Gly Ala Gly Lys Pro
                115                 120                 125

tat gaa ttt tct att gat tgt gac aaa ata aac tta ttc cgt ggt gtc      431
Tyr Glu Phe Ser Ile Asp Cys Asp Lys Ile Asn Leu Phe Arg Gly Val
            130                 135                 140

ttt gcg ttt ctt tta tat gtt gcc acc ttt atg tat gta ttt tct acg      479
Phe Ala Phe Leu Leu Tyr Val Ala Thr Phe Met Tyr Val Phe Ser Thr
        145                 150                 155

ttt gct aac ata ctg cgt aat aag gag tct tgataagctt gacctgtgaa        529
Phe Ala Asn Ile Leu Arg Asn Lys Glu Ser
    160                 165

gtgaaaaatg gcgcagattg tgcgacattt tttttgtctg ccgtttaatt aaaggggggg    589

gggggccggc ctgggggggg gtgtacatga aattgtaaac gttaatattt tgttaaaatt    649

cgcgttaaat ttttgttaaa tcagctcatt ttttaaccaa taggccgaaa tcggcaaaat    709

cccttataaa tcaaaagaat agaccgagat agggttgagt gttgttccag tttggaacaa    769

gagtccacta ttaaagaacg tggactccaa cgtcaaaggg cgaaaaaccg tctatcaggg    829

cgatggccca ctacgagaac catcacccta atcaagtttt ttggggtcga ggtgccgtaa    889

agcactaaat cggaacccta aagggagccc ccgatttaga gcttgacggg gaaagccggc    949

gaacgtggcg agaaaggaag ggaagaaagc gaaaggagcg ggcgctaggg cgctggcaag   1009

tgtagcggtc acgctgcgcg taaccaccac acccgccgcg cttaatgcgc cgctacaggg   1069

cgcgtgctag ccatgtgagc aaaaggccag caaaaggcca ggaaccgtaa aaaggccgcg   1129

ttgctggcgt ttttccatag gctccgcccc cctgacgagc atcacaaaaa tcgacgctca   1189

agtcagaggt ggcgaaaccc gacaggacta taaagatacc aggcgtttcc ccctggaagc   1249

tccctcgtgc gctctcctgt tccgaccctg ccgcttaccg gatacctgtc cgcctttctc   1309

ccttcgggaa gcgtggcgct ttctcatagc tcacgctgta ggtatctcag ttcggtgtag   1369

gtcgttcgct ccaagctggg ctgtgtgcac gaaccccccg ttcagcccga ccgctgcgcc   1429

ttatccggta actatcgtct tgagtccaac ccggtaagac acgacttatc gccactggca   1489

gcagccactg gtaacaggat tagcagagcg aggtatgtag gcggtgctac agagttcttg   1549

aagtggtggc ctaactacgg ctacactaga agaacagtat ttggtatctg cgctctgctg   1609

tagccagtta ccttcggaaa aagagttggt agctcttgat ccggcaaaca aaccaccgct   1669

ggtagcggtg gtttttttgt ttgcaagcag cagattacgc gcagaaaaaa aggatctcaa   1729

gaagatcctt tgatcttttc tacggggtct gacgctcagt ggaacgaaaa ctcacgttaa   1789

gggattttgg tcagatctag caccaggcgt ttaagggcac caataactgc cttaaaaaaa   1849

ttacgccccg ccctgccact catcgcagta ctgttgtaat tcattaagca ttctgccgac   1909

atggaagcca tcacaaacgg catgatgaac ctgaatcgcc agcggcatca gcaccttgtc   1969

gccttgcgta taatatttgc ccatagtgaa aacgggggcg aagaagttgt ccatattggc   2029

tacgtttaaa tcaaaactgg tgaaactcac ccagggattg gctgagacga aaaacatatt   2089

ctcaataaac cctttaggga aataggccag gttttcaccg taacacgcca catcttgcga   2149

atatatgtgt agaaactgcc ggaaatcgtc gtggtattca ctccagagcg atgaaaacgt   2209

ttcagtttgc tcatggaaaa cggtgtaaca agggtgaaca ctatcccata tcaccagctc   2269

accgtctttc attgccatac ggaactccgg gtgagcattc atcaggcggg caagaatgtg   2329
```

-continued

```
aataaaggcc ggataaaact tgtgcttatt tttctttacg gtctttaaaa aggccgtaat   2389

atccagctga acggtctggt tataggtaca ttgagcaact gactgaaatg cctcaaaatg   2449

ttctttacga tgccattggg atatatcaac ggtggtatat ccagtgattt ttttctccat   2509

tttagcttcc ttagctcctg aaaatctcga taactcaaaa aatacgcccg gtagtgatct   2569

tatttcatta tggtgaaagt tggaacctca cccgacgtct aatgtgagtt agctcactca   2629

ttaggcaccc caggctttac actttatgct tccggctcgt atgttgtgtg gaattgtgag   2689

cggataacaa tttcacacag gaaacagcta tgaccatgat tacgaatttc tagagcatgc   2749

gggggg                                                              2755


<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      vector

<400> SEQUENCE: 275

Phe Glu Gln Lys Leu Ile Ser Glu Glu Asp Leu
  1               5                  10


<210> SEQ ID NO 276
<211> LENGTH: 219
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 276

Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205
```

```
Gln Gln Tyr Cys Asp Glu Trp Gln Gly Gly Ala
    210                 215


<210> SEQ ID NO 277
<211> LENGTH: 173
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 277

gacgtcttaa tgtgagttag ctcactcatt aggcacccca ggctttacac tttatgcttc     60

cggctcgtat gttgtgtgga attgtgagcg gataacaatt tcacacagga aacagctatg    120

accatgtcta gaataacttc gtataatgta cgctatacga agttatcgca tgc          173


<210> SEQ ID NO 278
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 278

agatctcata acttcgtata atgtatgcta tacgaagtta tgacgtc                   47


<210> SEQ ID NO 279
<211> LENGTH: 1255
<212> TYPE: DNA
<213> ORGANISM: Artificial Sequence
<220> FEATURE:
<223> OTHER INFORMATION: Description of Artificial Sequence: Synthetic
      vector sequence
<220> FEATURE:
<221> NAME/KEY: CDS
<222> LOCATION: (1)..(1245)

<400> SEQUENCE: 279

gaa ttc ggt ggt ggt gga tct gcg tgc gct gaa acg gtt gaa agt tgt       48
Glu Phe Gly Gly Gly Gly Ser Ala Cys Ala Glu Thr Val Glu Ser Cys
  1               5                  10                  15

tta gca aaa tcc cat aca gaa aat tca ttt act aac gtc tgg aaa gac       96
Leu Ala Lys Ser His Thr Glu Asn Ser Phe Thr Asn Val Trp Lys Asp
             20                  25                  30

gac aaa act tta gat cgt tac gct aac tat gag ggc tgt ctg tgg aat      144
Asp Lys Thr Leu Asp Arg Tyr Ala Asn Tyr Glu Gly Cys Leu Trp Asn
         35                  40                  45

gct aca ggc gtt gta gtt tgt act ggt gac gaa act cag tgt tac ggt      192
Ala Thr Gly Val Val Val Cys Thr Gly Asp Glu Thr Gln Cys Tyr Gly
     50                  55                  60

aca tgg gtt cct att ggg ctt gct atc cct gaa aat gag ggt ggt ggc      240
Thr Trp Val Pro Ile Gly Leu Ala Ile Pro Glu Asn Glu Gly Gly Gly
 65                  70                  75                  80

tct gag ggt ggc ggt tct gag ggt ggc ggt tct gag ggt ggc ggt act      288
Ser Glu Gly Gly Gly Ser Glu Gly Gly Gly Ser Glu Gly Gly Gly Thr
                 85                  90                  95

aaa cct cct gag tac ggt gat aca cct att ccg ggc tat act tat atc      336
Lys Pro Pro Glu Tyr Gly Asp Thr Pro Ile Pro Gly Tyr Thr Tyr Ile
            100                 105                 110

aac cct ctc gac ggc act tat ccg cct ggt act gag caa aac ccc gct      384
Asn Pro Leu Asp Gly Thr Tyr Pro Pro Gly Thr Glu Gln Asn Pro Ala
        115                 120                 125

aat cct aat cct tct ctt gag gag tct cag cct ctt aat act ttc atg      432
```

```
Asn Pro Asn Pro Ser Leu Glu Glu Ser Gln Pro Leu Asn Thr Phe Met
    130                 135                 140

ttt cag aat aat agg ttc cga aat agg cag ggg gca tta act gtt tat      480
Phe Gln Asn Asn Arg Phe Arg Asn Arg Gln Gly Ala Leu Thr Val Tyr
145                 150                 155                 160

acg ggc act gtt act caa ggc act gac ccc gtt aaa act tat tac cag      528
Thr Gly Thr Val Thr Gln Gly Thr Asp Pro Val Lys Thr Tyr Tyr Gln
                165                 170                 175

tac act cct gta tca tca aaa gcc atg tat gac gct tac tgg aac ggt      576
Tyr Thr Pro Val Ser Ser Lys Ala Met Tyr Asp Ala Tyr Trp Asn Gly
            180                 185                 190

aaa ttc aga gac tgc gct ttc cat tct ggc ttt aat gag gat tta ttt      624
Lys Phe Arg Asp Cys Ala Phe His Ser Gly Phe Asn Glu Asp Leu Phe
        195                 200                 205

gtt tgt gaa tat caa ggc caa tcg tct gac ctg cct caa cct cct gtc      672
Val Cys Glu Tyr Gln Gly Gln Ser Ser Asp Leu Pro Gln Pro Pro Val
    210                 215                 220

aat gct ggc ggc ggc tct ggt ggt ggt tct ggt ggc ggc tct gag ggt      720
Asn Ala Gly Gly Gly Ser Gly Gly Gly Ser Gly Gly Gly Ser Glu Gly
225                 230                 235                 240

ggt ggc tct gag ggt ggc ggt tct gag ggt ggc ggc tct gag gga ggc      768
Gly Gly Ser Glu Gly Gly Gly Ser Glu Gly Gly Gly Ser Glu Gly Gly
                245                 250                 255

ggt tcc ggt ggt ggc tct ggt tcc ggt gat ttt gat tat gaa aag atg      816
Gly Ser Gly Gly Gly Ser Gly Ser Gly Asp Phe Asp Tyr Glu Lys Met
            260                 265                 270

gca aac gct aat aag ggg gct atg acc gaa aat gcc gat gaa aac gcg      864
Ala Asn Ala Asn Lys Gly Ala Met Thr Glu Asn Ala Asp Glu Asn Ala
        275                 280                 285

cta cag tct gac gct aaa ggc aaa ctt gat tct gtc gct act gat tac      912
Leu Gln Ser Asp Ala Lys Gly Lys Leu Asp Ser Val Ala Thr Asp Tyr
    290                 295                 300

ggt gct gct atc gat ggt ttc att ggt gac gtt tcc ggc ctt gct aat      960
Gly Ala Ala Ile Asp Gly Phe Ile Gly Asp Val Ser Gly Leu Ala Asn
305                 310                 315                 320

ggt aat ggt gct act ggt gat ttt gct ggc tct aat tcc caa atg gct     1008
Gly Asn Gly Ala Thr Gly Asp Phe Ala Gly Ser Asn Ser Gln Met Ala
                325                 330                 335

caa gtc ggt gaa ggt gat aat tca cct tta atg aat aat ttc cgt caa     1056
Gln Val Gly Glu Gly Asp Asn Ser Pro Leu Met Asn Asn Phe Arg Gln
            340                 345                 350

tat tta cct tcc atc cct caa tcg gtt gaa tgt cgc cct ttt gtc ttt     1104
Tyr Leu Pro Ser Ile Pro Gln Ser Val Glu Cys Arg Pro Phe Val Phe
        355                 360                 365

ggc gct ggt aaa ccc tat gaa ttt tct att gat tgt gac aaa ata aac     1152
Gly Ala Gly Lys Pro Tyr Glu Phe Ser Ile Asp Cys Asp Lys Ile Asn
    370                 375                 380

tta ttc cgt ggt gtc ttt gcg ttt ctt tta tat gtt gcc acc ttt atg     1200
Leu Phe Arg Gly Val Phe Ala Phe Leu Leu Tyr Val Ala Thr Phe Met
385                 390                 395                 400

tat gta ttt tct acg ttt gct aac ata ctg cgt aat aag gag tct         1245
Tyr Val Phe Ser Thr Phe Ala Asn Ile Leu Arg Asn Lys Glu Ser
                405                 410                 415

tgataagctt                                                          1255
```

<210> SEQ ID NO 280
<211> LENGTH: 415
<212> TYPE: PRT
<213> ORGANISM: Artificial Sequence
<220> FEATURE:
<223> OTHER INFORMATION: Description of Artificial Sequence: Synthetic vector sequence

<400> SEQUENCE: 280

```
Glu Phe Gly Gly Gly Gly Ser Ala Cys Ala Glu Thr Val Glu Ser Cys
  1               5                  10                  15

Leu Ala Lys Ser His Thr Glu Asn Ser Phe Thr Asn Val Trp Lys Asp
             20                  25                  30

Asp Lys Thr Leu Asp Arg Tyr Ala Asn Tyr Glu Gly Cys Leu Trp Asn
         35                  40                  45

Ala Thr Gly Val Val Val Cys Thr Gly Asp Glu Thr Gln Cys Tyr Gly
     50                  55                  60

Thr Trp Val Pro Ile Gly Leu Ala Ile Pro Glu Asn Glu Gly Gly Gly
 65                  70                  75                  80

Ser Glu Gly Gly Gly Ser Glu Gly Gly Gly Ser Glu Gly Gly Gly Thr
                 85                  90                  95

Lys Pro Pro Glu Tyr Gly Asp Thr Pro Ile Pro Gly Tyr Thr Tyr Ile
            100                 105                 110

Asn Pro Leu Asp Gly Thr Tyr Pro Pro Gly Thr Glu Gln Asn Pro Ala
        115                 120                 125

Asn Pro Asn Pro Ser Leu Glu Glu Ser Gln Pro Leu Asn Thr Phe Met
    130                 135                 140

Phe Gln Asn Asn Arg Phe Arg Asn Arg Gln Gly Ala Leu Thr Val Tyr
145                 150                 155                 160

Thr Gly Thr Val Thr Gln Gly Thr Asp Pro Val Lys Thr Tyr Tyr Gln
                165                 170                 175

Tyr Thr Pro Val Ser Ser Lys Ala Met Tyr Asp Ala Tyr Trp Asn Gly
            180                 185                 190

Lys Phe Arg Asp Cys Ala Phe His Ser Gly Phe Asn Glu Asp Leu Phe
        195                 200                 205

Val Cys Glu Tyr Gln Gly Gln Ser Ser Asp Leu Pro Gln Pro Pro Val
    210                 215                 220

Asn Ala Gly Gly Gly Ser Gly Gly Gly Ser Gly Gly Gly Ser Glu Gly
225                 230                 235                 240

Gly Gly Ser Glu Gly Gly Gly Ser Glu Gly Gly Gly Ser Glu Gly Gly
                245                 250                 255

Gly Ser Gly Gly Gly Ser Gly Ser Gly Asp Phe Asp Tyr Glu Lys Met
            260                 265                 270

Ala Asn Ala Asn Lys Gly Ala Met Thr Glu Asn Ala Asp Glu Asn Ala
        275                 280                 285

Leu Gln Ser Asp Ala Lys Gly Lys Leu Asp Ser Val Ala Thr Asp Tyr
    290                 295                 300

Gly Ala Ala Ile Asp Gly Phe Ile Gly Asp Val Ser Gly Leu Ala Asn
305                 310                 315                 320

Gly Asn Gly Ala Thr Gly Asp Phe Ala Gly Ser Asn Ser Gln Met Ala
                325                 330                 335

Gln Val Gly Glu Gly Asp Asn Ser Pro Leu Met Asn Asn Phe Arg Gln
            340                 345                 350

Tyr Leu Pro Ser Ile Pro Gln Ser Val Glu Cys Arg Pro Phe Val Phe
        355                 360                 365

Gly Ala Gly Lys Pro Tyr Glu Phe Ser Ile Asp Cys Asp Lys Ile Asn
    370                 375                 380

Leu Phe Arg Gly Val Phe Ala Phe Leu Leu Tyr Val Ala Thr Phe Met
385                 390                 395                 400

Tyr Val Phe Ser Thr Phe Ala Asn Ile Leu Arg Asn Lys Glu Ser
```

405 410 415

<210> SEQ ID NO 281
<211> LENGTH: 502
<212> TYPE: DNA
<213> ORGANISM: Artificial Sequence
<220> FEATURE:
<223> OTHER INFORMATION: Description of Artificial Sequence: Synthetic
vector sequence
<220> FEATURE:
<221> NAME/KEY: CDS
<222> LOCATION: (4)..(492)

<400> SEQUENCE: 281

```
cgg gaa ttc gga ggc ggt tcc ggt ggt ggc tct ggt tcc ggt gat ttt       48
    Glu Phe Gly Gly Gly Ser Gly Gly Gly Ser Gly Ser Gly Asp Phe
      1               5                  10                  15

gat tat gaa aag atg gca aac gct aat aag ggg gct atg acc gaa aat       96
Asp Tyr Glu Lys Met Ala Asn Ala Asn Lys Gly Ala Met Thr Glu Asn
                 20                  25                  30

gcc gat gaa aac gcg cta cag tct gac gct aaa ggc aaa ctt gat tct      144
Ala Asp Glu Asn Ala Leu Gln Ser Asp Ala Lys Gly Lys Leu Asp Ser
             35                  40                  45

gtc gct act gat tac ggt gct gct atc gat ggt ttc att ggt gac gtt      192
Val Ala Thr Asp Tyr Gly Ala Ala Ile Asp Gly Phe Ile Gly Asp Val
         50                  55                  60

tcc ggc ctt gct aat ggt aat ggt gct act ggt gat ttt gct ggc tct      240
Ser Gly Leu Ala Asn Gly Asn Gly Ala Thr Gly Asp Phe Ala Gly Ser
     65                  70                  75

aat tcc caa atg gct caa gtc ggt gac ggt gat aat tca cct tta atg      288
Asn Ser Gln Met Ala Gln Val Gly Asp Gly Asp Asn Ser Pro Leu Met
 80                  85                  90                  95

aat aat ttc cgt caa tat tta cct tcc ctc cct caa tcg gtt gaa tgt      336
Asn Asn Phe Arg Gln Tyr Leu Pro Ser Leu Pro Gln Ser Val Glu Cys
                100                 105                 110

cgc cct ttt gtc ttt ggc gct ggt aaa cca tat gaa ttt tct att gat      384
Arg Pro Phe Val Phe Gly Ala Gly Lys Pro Tyr Glu Phe Ser Ile Asp
            115                 120                 125

tgt gac aaa ata aac tta ttc cgt ggt gtc ttt gcg ttt ctt tta tat      432
Cys Asp Lys Ile Asn Leu Phe Arg Gly Val Phe Ala Phe Leu Leu Tyr
        130                 135                 140

gtt gcc acc ttt atg tat gta ttt tct acg ttt gct aac ata ctg cgt      480
Val Ala Thr Phe Met Tyr Val Phe Ser Thr Phe Ala Asn Ile Leu Arg
    145                 150                 155

aat aag gag tct tgataagctt                                           502
Asn Lys Glu Ser
160
```

<210> SEQ ID NO 282
<211> LENGTH: 163
<212> TYPE: PRT
<213> ORGANISM: Artificial Sequence
<220> FEATURE:
<223> OTHER INFORMATION: Description of Artificial Sequence: Synthetic
vector sequence

<400> SEQUENCE: 282

```
Glu Phe Gly Gly Gly Ser Gly Gly Gly Ser Gly Ser Gly Asp Phe Asp
  1               5                  10                  15

Tyr Glu Lys Met Ala Asn Ala Asn Lys Gly Ala Met Thr Glu Asn Ala
             20                  25                  30

Asp Glu Asn Ala Leu Gln Ser Asp Ala Lys Gly Lys Leu Asp Ser Val
         35                  40                  45
```

```
Ala Thr Asp Tyr Gly Ala Ala Ile Asp Gly Phe Ile Gly Asp Val Ser
     50                  55                  60

Gly Leu Ala Asn Gly Asn Gly Ala Thr Gly Asp Phe Ala Gly Ser Asn
 65                  70                  75                  80

Ser Gln Met Ala Gln Val Gly Asp Gly Asp Asn Ser Pro Leu Met Asn
                 85                  90                  95

Asn Phe Arg Gln Tyr Leu Pro Ser Leu Pro Gln Ser Val Glu Cys Arg
            100                 105                 110

Pro Phe Val Phe Gly Ala Gly Lys Pro Tyr Glu Phe Ser Ile Asp Cys
        115                 120                 125

Asp Lys Ile Asn Leu Phe Arg Gly Val Phe Ala Phe Leu Leu Tyr Val
    130                 135                 140

Ala Thr Phe Met Tyr Val Phe Ser Thr Phe Ala Asn Ile Leu Arg Asn
145                 150                 155                 160

Lys Glu Ser


<210> SEQ ID NO 283
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 283

gcatgccata acttcgtata atgtacgcta tacgaagtta taagctt                   47


<210> SEQ ID NO 284
<211> LENGTH: 1163
<212> TYPE: DNA
<213> ORGANISM: Artificial Sequence
<220> FEATURE:
<223> OTHER INFORMATION: Description of Artificial Sequence: Synthetic
      gene cassette
<220> FEATURE:
<221> NAME/KEY: CDS
<222> LOCATION: (82)..(978)

<400> SEQUENCE: 284

gggggtgtac attcaaatat gtatccgctc atgagacaat aaccctgata aatgcttcaa      60

taatattgaa aaaggaagag t atg agt att caa cat ttc cgt gtc gcc ctt      111
                        Met Ser Ile Gln His Phe Arg Val Ala Leu
                         1               5                  10

att ccc ttt ttt gcg gca ttt tgc ctt cct gtt ttt gct cac cca gaa      159
Ile Pro Phe Phe Ala Ala Phe Cys Leu Pro Val Phe Ala His Pro Glu
                 15                  20                  25

acg ctg gtg aaa gta aaa gat gct gag gat cag ttg ggt gcg cga gtg      207
Thr Leu Val Lys Val Lys Asp Ala Glu Asp Gln Leu Gly Ala Arg Val
            30                  35                  40

ggt tac atc gaa ctg gat ctc aac agc ggt aag atc ctt gag agt ttt      255
Gly Tyr Ile Glu Leu Asp Leu Asn Ser Gly Lys Ile Leu Glu Ser Phe
        45                  50                  55

cgc ccc gaa gaa cgt ttt cca atg atg agc act ttt aaa gtt ctg cta      303
Arg Pro Glu Glu Arg Phe Pro Met Met Ser Thr Phe Lys Val Leu Leu
     60                  65                  70

tgt ggc gcg gta tta tcc cgt att gac gcc ggg caa gag caa ctc ggt      351
Cys Gly Ala Val Leu Ser Arg Ile Asp Ala Gly Gln Glu Gln Leu Gly
 75                  80                  85                  90

cgc cgc ata cac tat tct cag aat gac ttg gtt gag tac tca cca gtc      399
Arg Arg Ile His Tyr Ser Gln Asn Asp Leu Val Glu Tyr Ser Pro Val
                 95                 100                 105
```

```
aca gaa aag cat ctt acg gat ggc atg aca gta aga gaa tta tgc agt      447
Thr Glu Lys His Leu Thr Asp Gly Met Thr Val Arg Glu Leu Cys Ser
            110                 115                 120

gct gcc ata acc atg agt gat aac act gcg gcc aac tta ctt ctg aca      495
Ala Ala Ile Thr Met Ser Asp Asn Thr Ala Ala Asn Leu Leu Leu Thr
        125                 130                 135

acg atc gga gga ccg aag gag cta acc gct ttt ttg cac aac atg ggg      543
Thr Ile Gly Gly Pro Lys Glu Leu Thr Ala Phe Leu His Asn Met Gly
    140                 145                 150

gat cat gta act cgc ctt gat cgt tgg gaa ccg gag ctg aat gaa gcc      591
Asp His Val Thr Arg Leu Asp Arg Trp Glu Pro Glu Leu Asn Glu Ala
155                 160                 165                 170

ata cca aac gac gag cgt gac acc acg atg cct gta gca atg gca aca      639
Ile Pro Asn Asp Glu Arg Asp Thr Thr Met Pro Val Ala Met Ala Thr
                175                 180                 185

acg ttg cgc aaa cta tta act ggc gaa cta ctt act cta gct tcc cgg      687
Thr Leu Arg Lys Leu Leu Thr Gly Glu Leu Leu Thr Leu Ala Ser Arg
            190                 195                 200

caa cag tta ata gac tgg atg gag gcg gat aaa gtt gca gga cca ctt      735
Gln Gln Leu Ile Asp Trp Met Glu Ala Asp Lys Val Ala Gly Pro Leu
        205                 210                 215

ctg cgc tcg gcc ctt ccg gct ggc tgg ttt att gct gat aaa tct gga      783
Leu Arg Ser Ala Leu Pro Ala Gly Trp Phe Ile Ala Asp Lys Ser Gly
    220                 225                 230

gcc ggt gag cgt ggg tct cgc ggt atc att gca gca ctg ggg cca gat      831
Ala Gly Glu Arg Gly Ser Arg Gly Ile Ile Ala Ala Leu Gly Pro Asp
235                 240                 245                 250

ggt aag ccc tcc cgt atc gta gtt atc tac acg acg ggg agt cag gca      879
Gly Lys Pro Ser Arg Ile Val Val Ile Tyr Thr Thr Gly Ser Gln Ala
                255                 260                 265

act atg gat gaa cga aat aga cag atc gct gag ata ggt gcc tca ctg      927
Thr Met Asp Glu Arg Asn Arg Gln Ile Ala Glu Ile Gly Ala Ser Leu
            270                 275                 280

att aag cat tgg gta act gtc aga cca agt tta ctc ata tat act tta      975
Ile Lys His Trp Val Thr Val Arg Pro Ser Leu Leu Ile Tyr Thr Leu
        285                 290                 295

gat tgatttaaaa cttcattttt aatttaaaag gatctaggtg aagatccttt          1028
Asp

ttgataatct catgaccaaa atcccttaac gtgagttttc gttccactga gcgtcagacc   1088

ccgtagaaaa gatcaaagga tcttcttgag atcctttttg ataatggccg gcccccccc    1148

ttaattaagg ggggg                                                    1163
```

<210> SEQ ID NO 285
<211> LENGTH: 299
<212> TYPE: PRT
<213> ORGANISM: Artificial Sequence
<220> FEATURE:
<223> OTHER INFORMATION: Description of Artificial Sequence: Synthetic gene cassette

<400> SEQUENCE: 285

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60
```

```
Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

<210> SEQ ID NO 286
<211> LENGTH: 470
<212> TYPE: DNA
<213> ORGANISM: Artificial Sequence
<220> FEATURE:
<223> OTHER INFORMATION: Description of Artificial Sequence: Synthetic DNA cassette

<400> SEQUENCE: 286

```
gctagcacgc gccctgtagc ggcgcattaa gcgcggcggg tgtggtggtt acgcgcagcg      60

tgaccgctac acttgccagc gccctagcgc ccgctccttt cgctttcttc ccttcctttc     120

tcgccacgtt cgccggcttt ccccgtcaag ctctaaatcg ggggctccct ttagggttcc     180

gatttagtgc tttacggcac ctcgacccca aaaaacttga ttagggtgat ggttctcgta     240

gtgggccatc gccctgatag acggtttttc gccctttgac gttggagtcc acgttcttta     300

atagtggact cttgttccaa actggaacaa cactcaaccc tatctcggtc tattcttttg     360

atttataagg gattttgccg atttcggcct attggttaaa aaatgagctg atttaacaaa     420

aatttaacgc gaattttaac aaaatattaa cgtttacaat ttcatgtaca                470
```

<210> SEQ ID NO 287
<211> LENGTH: 832
<212> TYPE: DNA
<213> ORGANISM: Artificial Sequence
<220> FEATURE:
<223> OTHER INFORMATION: Description of Artificial Sequence: Synthetic DNA cassette

<400> SEQUENCE: 287
agatctaata agatgatctt cttgagatcg ttttggtctg cgcgtaatct cttgctctga 60
aaacgaaaaa accgccttgc agggcggttt ttcgtaggtt ctctgagcta ccaactcttt 120
gaaccgaggt aactggcttg gaggagcgca gtcactaaaa cttgtccttt cagtttagcc 180
ttaaccggcg catgacttca agactaactc ctctaaatca attaccagtg gctgctgcca 240
gtggtgcttt tgcatgtctt tccgggttgg actcaagacg atagttaccg gataaggcgc 300
agcggtcgga ctgaacgggg ggttcgtgca tacagtccag cttggagcga actgcctacc 360
cggaactgag tgtcaggcgt ggaatgagac aaacgcggcc ataacagcgg aatgacaccg 420
gtaaaccgaa aggcaggaac aggagagcgc aggagggagc cgccaggggg aaacgcctgg 480
tatctttata gtcctgtcgg gtttcgccac cactgatttg agcgtcagat ttcgtgatgc 540
ttgtcagggg ggcggagcct atggaaaaac ggctttgccg cggccctctc acttccctgt 600
taagtatctt cctggcatct tccaggaaat ctccgccccg ttcgtaagcc atttccgctc 660
gccgcagtcg aacgaccgag cgtagcgagt cagtgagcga ggaagcggaa tatatcctgt 720
atcacatatt ctgctgacgc accggtgcag cctttttct cctgccacat gaagcacttc 780
actgacaccc tcatcagtgc caacatagta agccagtata cactccgcta gc 832

<210> SEQ ID NO 288
<211> LENGTH: 49
<212> TYPE: DNA
<213> ORGANISM: Artificial Sequence
<220> FEATURE:
<223> OTHER INFORMATION: Description of Artificial Sequence: Synthetic
DNA cassette

<400> SEQUENCE: 288
agatctcata acttcgtata atgtatgcta tacgaagtta ttcagatct 49

<210> SEQ ID NO 289
<211> LENGTH: 96
<212> TYPE: DNA
<213> ORGANISM: Artificial Sequence
<220> FEATURE:
<223> OTHER INFORMATION: Description of Artificial Sequence: Synthetic
DNA cassette

<400> SEQUENCE: 289
tctagagcat gcgtaggaga aaataaaatg aaacaaagca ctattgcact ggcactctta 60
ccgttgctct tcacccctgt taccaaagcc gaattc 96

<210> SEQ ID NO 290
<211> LENGTH: 120
<212> TYPE: DNA
<213> ORGANISM: Artificial Sequence
<220> FEATURE:
<223> OTHER INFORMATION: Description of Artificial Sequence: Synthetic
DNA cassette

<400> SEQUENCE: 290
tctagagcat gcgtaggaga aaataaaatg aaacaaagca ctattgcact ggcactctta 60
ccgttgctct tcacccctgt taccaaagcc gactacaaag atgaagtgca attggaattc 120

<210> SEQ ID NO 291
<211> LENGTH: 96
<212> TYPE: DNA
<213> ORGANISM: Artificial Sequence
<220> FEATURE:

```
<223> OTHER INFORMATION: Description of Artificial Sequence: Synthetic
      DNA cassette

<400> SEQUENCE: 291

tctagaggtt gaggtgattt tatgaaaaag aatatcgcat ttcttcttgc atctatgttc      60

gtttttttcta ttgctacaaa tgcatacgct gaattc                              96


<210> SEQ ID NO 292
<211> LENGTH: 1221
<212> TYPE: DNA
<213> ORGANISM: Artificial Sequence
<220> FEATURE:
<223> OTHER INFORMATION: Description of Artificial Sequence: Synthetic
      gene cassette
<220> FEATURE:
<221> NAME/KEY: CDS
<222> LOCATION: (79)..(1158)

<400> SEQUENCE: 292

gctagcatcg aatggcgcaa aacctttcgc ggtatggcat gatagcgccc ggaagagagt      60

caattcaggg tggtgaat gtg aaa cca gta acg tta tac gat gtc gca gag      111
                    Val Lys Pro Val Thr Leu Tyr Asp Val Ala Glu
                     1               5                  10

tat gcc ggt gtc tct tat cag acc gtt tcc cgc gtg gtg aac cag gcc      159
Tyr Ala Gly Val Ser Tyr Gln Thr Val Ser Arg Val Val Asn Gln Ala
            15                  20                  25

agc cac gtt tct gcg aaa acg cgg gaa aaa gtg gaa gcg gcg atg gcg      207
Ser His Val Ser Ala Lys Thr Arg Glu Lys Val Glu Ala Ala Met Ala
        30                  35                  40

gag ctg aat tac att cct aac cgc gtg gca caa caa ctg gcg ggc aaa      255
Glu Leu Asn Tyr Ile Pro Asn Arg Val Ala Gln Gln Leu Ala Gly Lys
    45                  50                  55

cag tcg ttg ctg att ggc gtt gcc acc tcc agt ctg gcc ctg cac gcg      303
Gln Ser Leu Leu Ile Gly Val Ala Thr Ser Ser Leu Ala Leu His Ala
60                  65                  70                  75

ccg tcg caa att gtc gcg gcg att aaa tct cgc gcc gat caa ctg ggt      351
Pro Ser Gln Ile Val Ala Ala Ile Lys Ser Arg Ala Asp Gln Leu Gly
                80                  85                  90

gcc agc gtg gtc gtg tcg atg gta gaa cga agc ggc gtc gaa gcc tgt      399
Ala Ser Val Val Val Ser Met Val Glu Arg Ser Gly Val Glu Ala Cys
            95                  100                 105

aaa gcg gcg gtg cac aat ctt ctc gcg caa cgt gtc agt ggg ctg att      447
Lys Ala Ala Val His Asn Leu Leu Ala Gln Arg Val Ser Gly Leu Ile
        110                 115                 120

att aac tat ccg ctg gat gac cag gat gct att gct gtg gaa gct gcc      495
Ile Asn Tyr Pro Leu Asp Asp Gln Asp Ala Ile Ala Val Glu Ala Ala
    125                 130                 135

tgc act aat gtt ccg gcg tta ttt ctt gat gtc tct gac cag aca ccc      543
Cys Thr Asn Val Pro Ala Leu Phe Leu Asp Val Ser Asp Gln Thr Pro
140                 145                 150                 155

atc aac agt att att ttc tcc cat gag gac ggt acg cga ctg ggc gtg      591
Ile Asn Ser Ile Ile Phe Ser His Glu Asp Gly Thr Arg Leu Gly Val
                160                 165                 170

gag cat ctg gtc gca ttg ggc cac cag caa atc gcg ctg tta gct ggc      639
Glu His Leu Val Ala Leu Gly His Gln Gln Ile Ala Leu Leu Ala Gly
            175                 180                 185

cca tta agt tct gtc tcg gcg cgt ctg cgt ctg gct ggc tgg cat aaa      687
Pro Leu Ser Ser Val Ser Ala Arg Leu Arg Leu Ala Gly Trp His Lys
        190                 195                 200

tat ctc act cgc aat caa att cag ccg ata gcg gaa cgg gaa ggc gac      735
Tyr Leu Thr Arg Asn Gln Ile Gln Pro Ile Ala Glu Arg Glu Gly Asp
    205                 210                 215
```

-continued

```
tgg agt gcc atg tcc ggt ttt caa caa acc atg caa atg ctg aat gag      783
Trp Ser Ala Met Ser Gly Phe Gln Gln Thr Met Gln Met Leu Asn Glu
220                 225                 230                 235

ggc atc gtt ccc act gcg atg ctg gtt gcc aac gat cag atg gcg ctg      831
Gly Ile Val Pro Thr Ala Met Leu Val Ala Asn Asp Gln Met Ala Leu
                240                 245                 250

ggc gca atg cgt gcc att acc gag tcc ggg ctg cgc gtt ggt gcg gac      879
Gly Ala Met Arg Ala Ile Thr Glu Ser Gly Leu Arg Val Gly Ala Asp
            255                 260                 265

atc tcg gta gtg gga tac gac gat acc gag gac agc tca tgt tat atc      927
Ile Ser Val Val Gly Tyr Asp Asp Thr Glu Asp Ser Ser Cys Tyr Ile
        270                 275                 280

ccg ccg ctg acc acc atc aaa cag gat ttt cgc ctg ctg ggg caa acc      975
Pro Pro Leu Thr Thr Ile Lys Gln Asp Phe Arg Leu Leu Gly Gln Thr
    285                 290                 295

agc gtg gac cgc ttg ctg caa ctc tct cag ggc cag gcg gtg aag ggc     1023
Ser Val Asp Arg Leu Leu Gln Leu Ser Gln Gly Gln Ala Val Lys Gly
300                 305                 310                 315

aat cag ctg ttg ccc gtc tca ctg gtg aaa aga aaa acc acc ctg gct     1071
Asn Gln Leu Leu Pro Val Ser Leu Val Lys Arg Lys Thr Thr Leu Ala
                320                 325                 330

ccc aat acg caa acc gcc tct ccc cgc gcg ttg gcc gat tca ctg atg     1119
Pro Asn Thr Gln Thr Ala Ser Pro Arg Ala Leu Ala Asp Ser Leu Met
            335                 340                 345

cag ctg gca cga cag gtt tcc cga ctg gaa agc ggg cag tgaggctacc      1168
Gln Leu Ala Arg Gln Val Ser Arg Leu Glu Ser Gly Gln
        350                 355                 360

cgataaaagc ggcttcctga caggaggccg ttttgttttg cagcccactt aag          1221
```

<210> SEQ ID NO 293
<211> LENGTH: 360
<212> TYPE: PRT
<213> ORGANISM: Artificial Sequence
<220> FEATURE:
<223> OTHER INFORMATION: Description of Artificial Sequence: Synthetic gene cassette

<400> SEQUENCE: 293

```
Val Lys Pro Val Thr Leu Tyr Asp Val Ala Glu Tyr Ala Gly Val Ser
  1               5                  10                  15

Tyr Gln Thr Val Ser Arg Val Val Asn Gln Ala Ser His Val Ser Ala
             20                  25                  30

Lys Thr Arg Glu Lys Val Glu Ala Ala Met Ala Glu Leu Asn Tyr Ile
         35                  40                  45

Pro Asn Arg Val Ala Gln Gln Leu Ala Gly Lys Gln Ser Leu Leu Ile
     50                  55                  60

Gly Val Ala Thr Ser Ser Leu Ala Leu His Ala Pro Ser Gln Ile Val
 65                  70                  75                  80

Ala Ala Ile Lys Ser Arg Ala Asp Gln Leu Gly Ala Ser Val Val Val
                 85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160
```

```
Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360
```

<210> SEQ ID NO 294
<211> LENGTH: 2380
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 294

```
gatctagcac caggcgttta agggcaccaa taactgcctt aaaaaaatta cgccccgccc     60

tgccactcat cgcagtactg ttgtaattca ttaagcattc tgccgacatg gaagccatca    120

caaacggcat gatgaacctg aatcgccagc ggcatcagca ccttgtcgcc ttgcgtataa    180

tatttgccca tagtgaaaac gggggcgaag aagttgtcca tattggctac gtttaaatca    240

aaactggtga aactcaccca gggattggct gagacgaaaa acatattctc aataaaccct    300

ttagggaaat aggccaggtt ttcaccgtaa cacgccacat cttgcgaata tatgtgtaga    360

aactgccgga aatcgtcgtg gtattcactc cagagcgatg aaaacgtttc agtttgctca    420

tggaaaacgg tgtaacaagg gtgaacacta tcccatatca ccagctcacc gtctttcatt    480

gccatacgga actccgggtg agcattcatc aggcgggcaa gaatgtgaat aaaggccgga    540

taaaacttgt gcttattttt ctttacggtc tttaaaaagg ccgtaatatc cagctgaacg    600

gtctggttat aggtacattg agcaactgac tgaaatgcct caaaatgttc tttacgatgc    660

cattgggata tatcaacggt ggtatatcca gtgatttttt tctccatttt agcttcctta    720

gctcctgaaa atctcgataa ctcaaaaaat acgcccggta gtgatcttat ttcattatgg    780

tgaaagttgg aacctcaccc gacgtctaat gtgagttagc tcactcatta ggcaccccag    840

gctttacact ttatgcttcc ggctcgtatg ttgtgtggaa ttgtgagcgg ataacaattt    900
```

```
cacacaggaa acagctatga ccatgattac gaatttctag accccccccc cgcatgccat    960

aacttcgtat aatgtacgct atacgaagtt ataagcttga cctgtgaagt gaaaaatggc   1020

gcagattgtg cgacattttt tttgtctgcc gtttaattaa aggggggggg gggccggcct   1080

gggggggggt gtacatgaaa ttgtaaacgt taatattttg ttaaaattcg cgttaaattt   1140

ttgttaaatc agctcatttt ttaaccaata ggccgaaatc ggcaaaatcc cttataaatc   1200

aaaagaatag accgagatag ggttgagtgt tgttccagtt tggaacaaga gtccactatt   1260

aaagaacgtg gactccaacg tcaaagggcg aaaaaccgtc tatcagggcg atggcccact   1320

acgagaacca tcaccctaat caagtttttt ggggtcgagg tgccgtaaag cactaaatcg   1380

gaaccctaaa gggagccccc gatttagagc ttgacgggga aagccggcga acgtggcgag   1440

aaaggaaggg aagaaagcga aaggagcggg cgctagggcg ctggcaagtg tagcggtcac   1500

gctgcgcgta accaccacac ccgccgcgct taatgcgccg ctacagggcg cgtgctagcg   1560

gagtgtatac tggcttacta tgttggcact gatgagggtg tcagtgaagt gcttcatgtg   1620

gcaggagaaa aaaggctgca ccggtgcgtc agcagaatat gtgatacagg atatattccg   1680

cttcctcgct cactgactcg ctacgctcgg tcgttcgact gcggcgagcg gaaatggctt   1740

acgaacgggg cggagatttc ctggaagatg ccaggaagat acttaacagg gaagtgagag   1800

ggccgcggca aagccgtttt tccataggct ccgcccccct gacaagcatc acgaaatctg   1860

acgctcaaat cagtggtggc gaaacccgac aggactataa agataccagg cgtttccccc   1920

tggcggctcc ctcctgcgct ctcctgttcc tgcctttcgg tttaccggtg tcattccgct   1980

gttatggccg cgtttgtctc attccacgcc tgacactcag ttccgggtag gcagttcgct   2040

ccaagctgga ctgtatgcac gaaccccccg ttcagtccga ccgctgcgcc ttatccggta   2100

actatcgtct tgagtccaac ccggaaagac atgcaaaagc accactggca gcagccactg   2160

gtaattgatt tagaggagtt agtcttgaag tcatgcgccg gttaaggcta aactgaaagg   2220

acaagtttta gtgactgcgc tcctccaagc cagttacctc ggttcaaaga gttggtagct   2280

cagagaacct acgaaaaacc gccctgcaag gcggtttttt cgttttcaga gcaagagatt   2340

acgcgcagac caaaacgatc tcaagaagat catcttatta                         2380


<210> SEQ ID NO 295
<211> LENGTH: 219
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 295

Met Glu Lys Lys Ile Thr Gly Tyr Thr Thr Val Asp Ile Ser Gln Trp
  1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
```

```
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215
```

<210> SEQ ID NO 296
<211> LENGTH: 3488
<212> TYPE: DNA
<213> ORGANISM: Artificial Sequence
<220> FEATURE:
<223> OTHER INFORMATION: Description of Artificial Sequence: Synthetic vector sequence

<400> SEQUENCE: 296

```
gtacatgaaa ttgtaaacgt taatattttg ttaaaattcg cgttaaattt ttgttaaatc     60

agctcatttt ttaaccaata ggccgaaatc ggcaaaatcc cttataaatc aaaagaatag    120

accgagatag ggttgagtgt tgttccagtt tggaacaaga gtccactatt aaagaacgtg    180

gactccaacg tcaaagggcg aaaaaccgtc tatcagggcg atggcccact acgagaacca    240

tcaccctaat caagtttttt ggggtcgagg tgccgtaaag cactaaatcg gaaccctaaa    300

gggagccccc gatttagagc ttgacgggga aagccggcga acgtggcgag aaaggaaggg    360

aagaaagcga aaggagcggg cgctagggcg ctggcaagtg tagcggtcac gctgcgcgta    420

accaccacac ccgccgcgct taatgcgccg ctacagggcg cgtgctagcg gagtgtatac    480

tggcttacta tgttggcact gatgagggtg tcagtgaagt gcttcatgtg gcaggagaaa    540

aaaggctgca ccggtgcgtc agcagaatat gtgatacagg atatattccg cttcctcgct    600

cactgactcg ctacgctcgg tcgttcgact gcggcgagcg gaaatggctt acgaacgggg    660

cggagatttc ctggaagatg ccaggaagat acttaacagg gaagtgagag ggccgcggca    720

aagccgtttt tccataggct ccgcccccct gacaagcatc acgaaatctg acgctcaaat    780

cagtggtggc gaaacccgac aggactataa agataccagg cgtttccccc tggcggctcc    840

ctcctgcgct ctcctgttcc tgcctttcgg tttaccggtg tcattccgct gttatggccg    900

cgtttgtctc attccacgcc tgacactcag ttccgggtag gcagttcgct ccaagctgga    960

ctgtatgcac gaaccccccg ttcagtccga ccgctgcgcc ttatccggta actatcgtct   1020

tgagtccaac ccggaaagac atgcaaaagc accactggca gcagccactg gtaattgatt   1080

tagaggagtt agtcttgaag tcatgcgccg gttaaggcta aactgaaagg acaagtttta   1140

gtgactgcgc tcctccaagc cagttacctc ggttcaaaga gttggtagct cagagaacct   1200

acgaaaaacc gccctgcaag gcggtttttt cgttttcaga gcaagagatt acgcgcagac   1260

caaaacgatc tcaagaagat catcttatta gatctagcac caggcgttta agggcaccaa   1320

taactgcctt aaaaaaatta cgccccgccc tgccactcat cgcagtactg ttgtaattca   1380
```

-continued ttaagcattc tgccgacatg gaagccatca caaacggcat gatgaacctg aatcgccagc 1440
ggcatcagca ccttgtcgcc ttgcgtataa tatttgccca tagtgaaaac gggggcgaag 1500
aagttgtcca tattggctac gtttaaatca aaactggtga aactcaccca gggattggct 1560
gagacgaaaa acatattctc aataaaccct ttagggaaat aggccaggtt ttcaccgtaa 1620
cacgccacat cttgcgaata tatgtgtaga aactgccgga aatcgtcgtg gtattcactc 1680
cagagcgatg aaaacgtttc agtttgctca tggaaaacgg tgtaacaagg gtgaacacta 1740
tcccatatca ccagctcacc gtctttcatt gccatacgga actccgggtg agcattcatc 1800
aggcgggcaa gaatgtgaat aaaggccgga taaaacttgt gcttattttt ctttacggtc 1860
tttaaaaagg ccgtaatatc cagctgaacg gtctggttat aggtacattg agcaactgac 1920
tgaaatgcct caaaatgttc tttacgatgc cattgggata tatcaacggt ggtatatcca 1980
gtgatttttt tctccatttt agcttcctta gctcctgaaa atctcgataa ctcaaaaaat 2040
acgcccggta gtgatcttat ttcattatgg tgaaagttgg aacctcaccc gacgtctaat 2100
gtgagttagc tcactcatta ggcaccccag gctttacact ttatgcttcc ggctcgtatg 2160
ttgtgtggaa ttgtgagcgg ataacaattt cacacaggaa acagctatga ccatgattac 2220
gaatttctag accccccccc cgcatgccat aacttcgtat aatgtacgct atacgaagtt 2280
ataagcttga cctgtgaagt gaaaaatggc gcagattgtg cgacattttt tttgtctgcc 2340
gtttaattaa gggggggggc cggccattat caaaaaggat ctcaagaaga tcctttgatc 2400
ttttctacgg ggtctgacgc tcagtggaac gaaaactcac gttaagggat tttggtcatg 2460
agattatcaa aaaggatctt cacctagatc cttttaaatt aaaaatgaag ttttaaatca 2520
atctaaagta tatatgagta aacttggtct gacagttacc aatgcttaa tcagtgaggc 2580 acctatctca gcgatctgtc tatttcgttc atccatagtt gcctgactcc ccgtcgtgta 2640
gataactacg atacgggagg gcttaccatc tggccccagt gctgcaatga taccgcgaga 2700
cccacgctca ccggctccag atttatcagc aataaaccag ccagccggaa gggccgagcg 2760
cagaagtggt cctgcaactt tatccgcctc catccagtct attaactgtt gccgggaagc 2820
tagagtaagt agttcgccag ttaatagttt gcgcaacgtt gttgccattg ctacaggcat 2880
cgtggtgtca cgctcgtcgt ttggtatggc ttcattcagc tccggttccc aacgatcaag 2940
gcgagttaca tgatccccca tgttgtgcaa aaaagcggtt agctccttcg gtcctccgat 3000
cgttgtcaga agtaagttgg ccgcagtgtt atcactcatg gttatggcag cactgcataa 3060
ttctcttact gtcatgccat ccgtaagatg cttttctgtg actggtgagt actcaaccaa 3120
gtcattctga gaatagtgta tgcggcgacc gagttgctct tgcccggcgt caatacggga 3180
taataccgcg ccacatagca gaactttaaa agtgctcatc attggaaaac gttcttcggg 3240
gcgaaaactc tcaaggatct taccgctgtt gagatccagt tcgatgtaac ccactcgcgc 3300
acccaactga tcctcagcat cttttacttt caccagcgtt tctgggtgag caaaaacagg 3360
aaggcaaaat gccgcaaaaa agggaataag ggcgacacgg aaatgttgaa tactcatact 3420
cttccttttt caatattatt gaagcattta tcagggttat tgtctcatga gcggatacat 3480
atttgaat 3488

<210> SEQ ID NO 297
<211> LENGTH: 219
<212> TYPE: PRT
<213> ORGANISM: Artificial Sequence
<220> FEATURE:
<223> OTHER INFORMATION: Description of Artificial Sequence: Synthetic
vector sequence

<400> SEQUENCE: 297

Met Glu Lys Lys Ile Thr Gly Tyr Thr Thr Val Asp Ile Ser Gln Trp
1 5 10 15

His Arg Lys Glu His Phe Glu Ala Phe Gln Ser Val Ala Gln Cys Thr
20 25 30

Tyr Asn Gln Thr Val Gln Leu Asp Ile Thr Ala Phe Leu Lys Thr Val
35 40 45

Lys Lys Asn Lys His Lys Phe Tyr Pro Ala Phe Ile His Ile Leu Ala
50 55 60

Arg Leu Met Asn Ala His Pro Glu Phe Arg Met Ala Met Lys Asp Gly
65 70 75 80

Glu Leu Val Ile Trp Asp Ser Val His Pro Cys Tyr Thr Val Phe His
85 90 95

Glu Gln Thr Glu Thr Phe Ser Ser Leu Trp Ser Glu Tyr His Asp Asp
100 105 110

Phe Arg Gln Phe Leu His Ile Tyr Ser Gln Asp Val Ala Cys Tyr Gly
115 120 125

Glu Asn Leu Ala Tyr Phe Pro Lys Gly Phe Ile Glu Asn Met Phe Phe
130 135 140

Val Ser Ala Asn Pro Trp Val Ser Phe Thr Ser Phe Asp Leu Asn Val
145 150 155 160

Ala Asn Met Asp Asn Phe Phe Ala Pro Val Phe Thr Met Gly Lys Tyr
165 170 175

Tyr Thr Gln Gly Asp Lys Val Leu Met Pro Leu Ala Ile Gln Val His
180 185 190

His Ala Val Cys Asp Gly Phe His Val Gly Arg Met Leu Asn Glu Leu
195 200 205

Gln Gln Tyr Cys Asp Glu Trp Gln Gly Gly Ala
210 215

<210> SEQ ID NO 298
<211> LENGTH: 299
<212> TYPE: PRT
<213> ORGANISM: Artificial Sequence
<220> FEATURE:
<223> OTHER INFORMATION: Description of Artificial Sequence: Synthetic
vector sequence

<400> SEQUENCE: 298

Met Ser Ile Gln His Phe Arg Val Ala Leu Ile Pro Phe Phe Ala Ala
1 5 10 15

Phe Cys Leu Pro Val Phe Ala His Pro Glu Thr Leu Val Lys Val Lys
20 25 30

Asp Ala Glu Asp Gln Leu Gly Ala Arg Val Gly Tyr Ile Glu Leu Asp
35 40 45

Leu Asn Ser Gly Lys Ile Leu Glu Ser Phe Arg Pro Glu Glu Arg Phe
50 55 60

Pro Met Met Ser Thr Phe Lys Val Leu Leu Cys Gly Ala Val Leu Ser
65 70 75 80

Arg Ile Asp Ala Gly Gln Glu Gln Leu Gly Arg Arg Ile His Tyr Ser
85 90 95

Gln Asn Asp Leu Val Glu Tyr Ser Pro Val Thr Glu Lys His Leu Thr
100 105 110

Asp Gly Met Thr Val Arg Glu Leu Cys Ser Ala Ala Ile Thr Met Ser
115 120 125

```
Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

```
<210> SEQ ID NO 299
<211> LENGTH: 2728
<212> TYPE: DNA
<213> ORGANISM: Artificial Sequence
<220> FEATURE:
<223> OTHER INFORMATION: Description of Artificial Sequence: Synthetic
      vector sequence

<400> SEQUENCE: 299

gatctcataa cttcgtataa tgtatgctat acgaagttat gacgtctaat gtgagttagc      60

tcactcatta ggcaccccag gctttacact ttatgcttcc ggctcgtatg ttgtgtggaa     120

ttgtgagcgg ataacaattt cacacaggaa acagctatga ccatgattac gaatttctag     180

accccccccc cgcatgccat aacttcgtat aatgtacgct atacgaagtt ataagcttga     240

cctgtgaagt gaaaaatggc gcagattgtg cgacattttt tttgtctgcc gtttaattaa     300

gggggggggc cggccattat caaaaaggat ctcaagaaga tcctttgatc ttttctacgg     360

ggtctgacgc tcagtggaac gaaaactcac gttaagggat tttggtcatg agattatcaa     420

aaaggatctt cacctagatc cttttaaatt aaaaatgaag ttttaaatca atctaaagta     480

tatatgagta aacttggtct gacagttacc aatgcttaat cagtgaggc acctatctca     540

gcgatctgtc tatttcgttc atccatagtt gcctgactcc ccgtcgtgta gataactacg     600

atacgggagg gcttaccatc tggccccagt gctgcaatga taccgcgaga cccacgctca     660

ccggctccag atttatcagc aataaaccag ccagccggaa gggccgagcg cagaagtggt     720

cctgcaactt tatccgcctc catccagtct attaactgtt gccgggaagc tagagtaagt     780

agttcgccag ttaatagttt gcgcaacgtt gttgccattg ctacaggcat cgtggtgtca     840

cgctcgtcgt ttggtatggc ttcattcagc tccggttccc aacgatcaag gcgagttaca     900

tgatccccca tgttgtgcaa aaaagcggtt agctccttcg gtcctccgat cgttgtcaga     960

agtaagttgg ccgcagtgtt atcactcatg gttatggcag cactgcataa ttctcttact    1020

gtcatgccat ccgtaagatg cttttctgtg actggtgagt actcaaccaa gtcattctga    1080
```

```
gaatagtgta tgcggcgacc gagttgctct tgcccggcgt caatacggga taataccgcg   1140

ccacatagca gaactttaaa agtgctcatc attggaaaac gttcttcggg gcgaaaactc   1200

tcaaggatct taccgctgtt gagatccagt tcgatgtaac ccactcgcgc acccaactga   1260

tcctcagcat cttttacttt caccagcgtt tctgggtgag caaaaacagg aaggcaaaat   1320

gccgcaaaaa agggaataag ggcgacacgg aaatgttgaa tactcatact cttccttttt   1380

caatattatt gaagcattta tcagggttat tgtctcatga gcggatacat atttgaatgt   1440

acatgaaatt gtaaacgtta atattttgtt aaaattcgcg ttaaattttt gttaaatcag   1500

ctcatttttt aaccaatagg ccgaaatcgg caaaatccct tataaatcaa aagaatagac   1560

cgagataggg ttgagtgttg ttccagtttg gaacaagagt ccactattaa agaacgtgga   1620

ctccaacgtc aaagggcgaa aaaccgtcta tcagggcgat ggcccactac gagaaccatc   1680

accctaatca agttttttgg ggtcgaggtg ccgtaaagca ctaaatcgga accctaaagg   1740

gagcccccga tttagagctt gacggggaaa gccggcgaac gtggcgagaa aggaagggaa   1800

gaaagcgaaa ggagcgggcg ctagggcgct ggcaagtgta gcggtcacgc tgcgcgtaac   1860

caccacaccc gccgcgctta atgcgccgct acagggcgcg tgctagcgga gtgtatactg   1920

gcttactatg ttggcactga tgagggtgtc agtgaagtgc ttcatgtggc aggagaaaaa   1980

aggctgcacc ggtgcgtcag cagaatatgt gatacaggat atattccgct tcctcgctca   2040

ctgactcgct acgctcggtc gttcgactgc ggcgagcgga aatggcttac gaacggggcg   2100

gagatttcct ggaagatgcc aggaagatac ttaacaggga agtgagaggg ccgcggcaaa   2160

gccgtttttc cataggctcc gcccccctga caagcatcac gaaatctgac gctcaaatca   2220

gtggtggcga aacccgacag gactataaag ataccaggcg tttccccctg gcggctccct   2280

cctgcgctct cctgttcctg cctttcggtt taccggtgtc attccgctgt tatggccgcg   2340

tttgtctcat tccacgcctg acactcagtt ccgggtaggc agttcgctcc aagctggact   2400

gtatgcacga accccccgtt cagtccgacc gctgcgcctt atccggtaac tatcgtcttg   2460

agtccaaccc ggaaagacat gcaaaagcac cactggcagc agccactggt aattgattta   2520

gaggagttag tcttgaagtc atgcgccggt taaggctaaa ctgaaaggac aagttttagt   2580

gactgcgctc ctccaagcca gttacctcgg ttcaaagagt tggtagctca gagaacctac   2640

gaaaaaccgc cctgcaaggc ggtttttcg ttttcagagc aagagattac gcgcagacca   2700

aaacgatctc aagaagatca tcttatta                                      2728
```

```
<210> SEQ ID NO 300
<211> LENGTH: 299
<212> TYPE: PRT
<213> ORGANISM: Artificial Sequence
<220> FEATURE:
<223> OTHER INFORMATION: Description of Artificial Sequence: Synthetic
      vector sequence

<400> SEQUENCE: 300

Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
```

```
 65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp Val Thr
        275                 280                 285

Val Arg Pro Ser Leu Leu Ile Tyr Thr Leu Asp
    290                 295
```

<210> SEQ ID NO 301
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 301
tatgagatct cataacttcg tataatgtac gctatacgaa gttat 45

<210> SEQ ID NO 302
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 302
taataacttc gtatagcata cattatacga agttatgaga tctca 45

<210> SEQ ID NO 303
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303 catttttgc cctcgttatc tacgcatgcg ataacttcgt atagcgtaca ttatacgaag 60
ttattctaga catggtcata gctgtttcct g 91

<210> SEQ ID NO 304
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 304
ggggggaatt cggtggtggt ggatctgcgt gcgctgaaac ggttgaaagt tg 52

<210> SEQ ID NO 305
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
cccccccaag cttatcaaga ctccttatta cg 32

<210> SEQ ID NO 306
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 306 gggggggaa ttcggaggcg gttccggtgg tggc 34

<210> SEQ ID NO 307
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 307 gggggggaa ttcgagcaga agctgatctc tgaggaggat ctgtagggtg gtggctctgg 60
ttccggtgat tttg 74

<210> SEQ ID NO 308
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 308
ccataacttc gtataatgta cgctatacga agttata 37

<210> SEQ ID NO 309
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 309
agcttataac ttcgtatagc gtacattata cgaagttatg gcatg 45

<210> SEQ ID NO 310
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 310
agcttgacct gtgaagtgaa aaatggcgca gattgtgcga cattttttt gtctgccgtt 60 taattaaagg gggggt 76

<210> SEQ ID NO 311
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 311
gtacaccccc ccccaggccg gccccccccc ccctttaatt aaacggcaga caaaaaaaat 60
gtcgcacaat ctgcg 75

<210> SEQ ID NO 312
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 312
gggggggtgt acattcaaat atgtatccgc tcatg 35

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 313
gggttacatc gaactggatc tc 22

<210> SEQ ID NO 314
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 314
ccagttcgat gtaacccact cgcgcaccca actgatcctc agcatctttt actttcacc 59

<210> SEQ ID NO 315
<211> LENGTH: 43
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 315
actctagctt cccggcaaca gttaatagac tggatggagg cgg                        43

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ctgttgccgg gaagctagag taag                                             24

<210> SEQ ID NO 317
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ccccccctta attaggggg ggggccggcc attatcaaaa aggatctcaa gaagatcc         58

<210> SEQ ID NO 318
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318 gggggggct agcacgcgcc ctgtagcggc gcattaa                                37

<210> SEQ ID NO 319
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ccccccctgt acatgaaatt gtaaacgtta atattttg                              38

<210> SEQ ID NO 320
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gggcgatggc ccactacgag aaccatcacc ctaatc                                36

<210> SEQ ID NO 321
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
ggggggagat ctaataagat gatcttcttg ag    32

<210> SEQ ID NO 322
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gagttggtag ctcagagaac ctacgaaaaa ccgccctgca aggcg    45

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gtaggttctc tgagctacca actc    24

<210> SEQ ID NO 324
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gtttccccct ggcggctccc tcctgcgctc tcctgttcct gcc    43

<210> SEQ ID NO 325
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
aggagggagc cgccaggggg aaac    24

<210> SEQ ID NO 326
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gacatcagcg ctagcggagt gtatac    26

<210> SEQ ID NO 327
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gatctcataa cttcgtataa tgtatgctat acgaagttat tca 43

<210> SEQ ID NO 328
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 328
gatctgaata acttcgtata gcatacatta tacgaagtta tgaga 45

<210> SEQ ID NO 329
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 329
gggggggaga tctgaccaaa atcccttaac gtgag 35

<210> SEQ ID NO 330
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 330
ggtatctgcg ctctgctgta gccagttacc ttcgg 35

<210> SEQ ID NO 331
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 331
cccccccgct agccatgtga gcaaaaggcc agcaa 35

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 332
gggacgtcgg gtgaggttcc aac 23

<210> SEQ ID NO 333
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
ccatacggaa ctccgggtga gcattcatc 29

<210> SEQ ID NO 334
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 334
ccggagttcc gtatgg 16

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
acgtttaaat caaaactgg 19

<210> SEQ ID NO 336
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 336
ccagttttga tttaaacgta gccaatatgg acaacttctt cgcccccgtt ttcactatgg 60
gcaaatatt 69

<210> SEQ ID NO 337
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
ggaagatcta gcaccaggcg tttaag 26

<210> SEQ ID NO 338
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 338
gaggccggcc atcgaatggc gcaaaac 27

<210> SEQ ID NO 339
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 339
cgcgtaccgt cctcatggga gaaaataata c 31

<210> SEQ ID NO 340
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 340
ccatgaggac ggtacgcgac tgggcgtgga gcatctggtc gcattgggtc accagcaaat 60
ccgctgttag ctggcccatt aag 83

<210> SEQ ID NO 341
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
gtcagcggcg ggatataaca tgagctgtcc tcggtatcgt cg 42

<210> SEQ ID NO 342
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 342
gttatatccc gccgctgacc accatcaaac 30

<210> SEQ ID NO 343
<211> LENGTH: 65
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 343
catcagtgaa tcggccaacg cgcggggaga ggcggtttgc gtattgggag ccagggtggt 60
ttttc 65

<210> SEQ ID NO 344
<211> LENGTH: 73
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
ggttaattaa cctcactgcc cgctttccag tcgggaaacc tgtcgtgcca gctgcatcag 60
tgaatcggcc aac 73

<210> SEQ ID NO 345
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
ctagactagt gtttaaaccg gaccgggggg gggcttaagg gggggggggg 50

<210> SEQ ID NO 346
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 346
ctagcccccc ccccccttaa gccccccccc ggtccggttt aaacactagt 50

<210> SEQ ID NO 347
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 347
ctagactagt gtttaaaccg gaccgggggg gggcttaagg gggggggggg 50

<210> SEQ ID NO 348
<211> LENGTH: 82
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 348
ccccccctta agtgggctgc aaaacaaaac ggcctcctgt caggaagccg cttttatcgg 60
gtagcctcac tgcccgcttt cc 82

<210> SEQ ID NO 349
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
gttgttgtgc cacgcggtta ggaatgtaat tcagctccgc 40

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
aaccgcgtgg cacaacaac 19

<210> SEQ ID NO 351
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
cttcgttcta ccatcgacac gaccacgctg gcacccagtt g 41

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
gtgtcgatgg tagaacgaag 20

<210> SEQ ID NO 353
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
ccacagcaat agcatcctgg tcatccagcg gatagttaat aatcagccca ctgacacgtt 60
gcgcgag 67

<210> SEQ ID NO 354
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 354
gaccaggatg ctattgctgt gg 22

<210> SEQ ID NO 355
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 355
cagcgcgatt tgctggtggc ccaatgcgac cagatgc 37

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 356
caccagcaaa tcgcgctg 18

<210> SEQ ID NO 357
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 357
cccggactcg gtaatggcac gcattgcgcc cagcgcc 37

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 358
gccattaccg agtccggg 18

<210> SEQ ID NO 359
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 359
aattccacca tcatcaccat tgacgtcta 29

<210> SEQ ID NO 360
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
agcttagacg tcaatggtga tgatggtgg 29

<210> SEQ ID NO 361
<211> LENGTH: 1289
<212> TYPE: DNA
<213> ORGANISM: Artificial Sequence
<220> FEATURE:
<223> OTHER INFORMATION: Description of Artificial Sequence: Synthetic gene cassette

<400> SEQUENCE: 361
cgcgttaacc tcaggtgacc aagcccctgg ccaaggtccc gtacgttcga agattaccat 60
cacgtggatc cggtaccagg ccggccatta tcaaaaagga tctcaagaag atcctttgat 120
cttttctacg gggtctgacg ctcagtggaa cgaaaactca cgttaaggga ttttggtcat 180
gagattatca aaaaggatct tcacctagat ccttttaaat taaaaatgaa gttttaaatc 240
aatctaaagt atatatgagt aaacttggtc tgacagttac caatgcttaa tcagtgaggc 300
acctatctca gcgatctgtc tatttcgttc atccatagtt gcctgactcc ccgtcgtgta 360
gataactacg atacgggagg gcttaccatc tggccccagt gctgcaatga taccgcgaga 420
cccacgctca ccggctccag atttatcagc aataaaccag ccagccggaa gggccgagcg 480
cagaagtggt cctgcaactt tatccgcctc catccagtct attaactgtt gccgggaagc 540
tagagtaagt agttcgccag ttaatagttt gcgcaacgtt gttgccattg ctacaggcat 600
cgtggtgtca cgctcgtcgt ttggtatggc ttcattcagc tccggttccc aacgatcaag 660
gcgagttaca tgatccccca tgttgtgcaa aaaagcggtt agctccttcg gtcctccgat 720
cgttgtcaga agtaagttgg ccgcagtgtt atcactcatg gttatggcag cactgcataa 780

```
ttctcttact gtcatgccat ccgtaagatg cttttctgtg actggtgagt actcaaccaa    840

gtcattctga gaatagtgta tgcggcgacc gagttgctct tgcccggcgt caatacggga    900

taataccgcg ccacatagca gaactttaaa agtgctcatc attggaaaac gttcttcggg    960

gcgaaaactc tcaaggatct taccgctgtt gagatccagt tcgatgtaac ccactcgtgc   1020

acccaactga tcttcagcat cttttacttt caccagcgtt tctgggtgag caaaaacagg   1080

aaggcaaaat gccgcaaaaa agggaataag ggcgacacgg aaatgttgaa tactcatact   1140

cttccttttt caatattatt gaagcattta tcagggttat tgtctcatga gcggatacat   1200

atttgaatgt actcggccgc acgagctgca ggcgccatta atggctcgag cgcgcttcag   1260

cgctttgtct tccggatgta catgaaatt                                     1289
```

<210> SEQ ID NO 362
<211> LENGTH: 286
<212> TYPE: PRT
<213> ORGANISM: Artificial Sequence
<220> FEATURE:
<223> OTHER INFORMATION: Description of Artificial Sequence: Synthetic
      gene cassette

<400> SEQUENCE: 362

```
Met Ser Ile Gln His Phe Arg Val Ala Leu Ile Pro Phe Phe Ala Ala
  1               5                  10                  15

Phe Cys Leu Pro Val Phe Ala His Pro Glu Thr Leu Val Lys Val Lys
             20                  25                  30

Asp Ala Glu Asp Gln Leu Gly Ala Arg Val Gly Tyr Ile Glu Leu Asp
         35                  40                  45

Leu Asn Ser Gly Lys Ile Leu Glu Ser Phe Arg Pro Glu Glu Arg Phe
     50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270
```

```
Arg Gln Ile Ala Glu Ile Gly Ala Ser Leu Ile Lys His Trp
        275                 280                 285


<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363

gccctgcaag cggaagac                                                   18


<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364

ggctttcgaa tggccaaagg                                                 20


<210> SEQ ID NO 365
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys or Pro
<220> FEATURE:
<221> NAME/KEY: modified_base
<222> LOCATION: (52)..(54)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (58)..(60)
<223> OTHER INFORMATION: region represents a variable trinucleotide
      combination capable of coding any natural occurring amino acid
      other than Cys

<400> SEQUENCE: 365

gccctgcaag cggaagactt tgcgryttat tattgchwkc agnnndvtdv tnnnyctnnn     60

acctttggcc attcgaaagc c                                               81


<210> SEQ ID NO 366
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys or Pro
<220> FEATURE:
<221> NAME/KEY: modified_base
<222> LOCATION: (52)..(54)
```

```
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (58)..(60)
<223> OTHER INFORMATION: region represents a variable trinucleotide
      combination capable of coding any natural occurring amino acid
      other than Cys

<400> SEQUENCE: 366

gccctgcaag cggaagacgt gggcgtgtat tattgchwkc agnnndvtdv tnnnyctnnn     60

acctttggcc attcgaaagc c                                               81


<210> SEQ ID NO 367
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(45)
<223> OTHER INFORMATION: region represents a variable trinucleotide
      combination capable of coding any natural occurring amino acid
      other than Cys or Pro
<220> FEATURE:
<221> NAME/KEY: modified_base
<222> LOCATION: (52)..(54)
<223> OTHER INFORMATION: region represents a variable trinucleotide
      combination capable of coding any natural occurring amino acid
      other than Cys
<220> FEATURE:
<221> NAME/KEY: modified_base
<222> LOCATION: (58)..(60)
<223> OTHER INFORMATION: region represents a variable trinucleotide
      combination capable of coding any natural occurring amino acid
      other than Cys

<400> SEQUENCE: 367

gccctgcaag cggaagacgt ggcggtgtat tattgchwkc agnnndvtdv tnnnyctnnn     60

acctttggcc attcgaaagc c                                               81


<210> SEQ ID NO 368
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (47)..(49)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (50)..(52)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (53)..(55)
<223> OTHER INFORMATION: region represents a variable trinucleotide
      combination capable of coding any natural occurring amino acid
      other than Cys or Trp
<220> FEATURE:
<221> NAME/KEY: modified_base
<222> LOCATION: (56)..(58)
<223> OTHER INFORMATION: region represents a variable trinucleotide
      combination capable of coding any natural occurring amino acid
```

other than Cys or Trp
<220> FEATURE:
<221> NAME/KEY: modified_base
<222> LOCATION: (59)..(61)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (62)..(64)
<223> OTHER INFORMATION: region represents a variable trinucleotide combination capable of coding any natural occurring amino acid other than Cys

<400> SEQUENCE: 368
cctgcaagcg gaagacgaag cggattatta ttgccagagc yrkgacnnnn nnnnnnnnnn 60
nnnnggcggc ggcacgaagt taaccgttct tggccaggaa ttcgagcc 108

<210> SEQ ID NO 369
<211> LENGTH: 105
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (47)..(49)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (50)..(52)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (53)..(55)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (56)..(58)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (59)..(61)
<223> OTHER INFORMATION: region represents a variable trinucleotide combination capable of coding any natural occurring amino acid other than Cys

<400> SEQUENCE: 369
cctgcaagcg gaagacgaag cggattatta ttgccagagc yrkgacnnnn nnnnnnnnnn 60
nggcggcggc acgaagttaa ccgttcttgg ccaggaattc gagcc 105

<210> SEQ ID NO 370
<211> LENGTH: 102
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (47)..(49)
<223> OTHER INFORMATION: region represents a variable trinucleotide combination capable of coding any natural occurring amino acid other than Cys or Trp
<220> FEATURE:

<221> NAME/KEY: modified_base
<222> LOCATION: (50)..(52)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (53)..(55)
<223> OTHER INFORMATION: region represents a variable trinucleotide combination capable of coding any natural occurring amino acid other than Cys or Trp
<220> FEATURE:
<221> NAME/KEY: modified_base
<222> LOCATION: (56)..(58)
<223> OTHER INFORMATION: region represents a variable trinucleotide combination capable of coding any natural occurring amino acid other than Cys

<400> SEQUENCE: 370
cctgcaagcg gaagacgaag cggattatta ttgccagagc yrkgacnnnn nnnnnnnngg 60
cggcggcacg aagttaaccg ttcttggcca ggaattcgag cc 102

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 371
ggctcgaatt cctggcc 17

<210> SEQ ID NO 372
<211> LENGTH: 108
<212> TYPE: DNA
<213> ORGANISM: Artificial Sequence
<220> FEATURE:
<223> OTHER INFORMATION: Description of Artificial Sequence: Synthetic oligonucleotide template
<220> FEATURE:
<221> NAME/KEY: modified_base
<222> LOCATION: (21)..(23)
<223> OTHER INFORMATION: region represents a variable trinucleotide combination capable of coding any natural occurring amino acid other than Cys
<220> FEATURE:
<221> NAME/KEY: modified_base
<222> LOCATION: (27)..(29)
<223> OTHER INFORMATION: region represents a variable trinucleotide combination capable of coding any natural occurring amino acid other than Cys
<220> FEATURE:
<221> NAME/KEY: modified_base
<222> LOCATION: (30)..(32)
<223> OTHER INFORMATION: region represents a variable trinucleotide combination capable of coding any natural occurring amino acid other than Cys
<220> FEATURE:
<221> NAME/KEY: modified_base
<222> LOCATION: (33)..(35)
<223> OTHER INFORMATION: region represents a variable trinucleotide combination capable of coding any natural occurring amino acid other than Cys or not present
<220> FEATURE:
<221> NAME/KEY: modified_base
<222> LOCATION: (42)..(44)
<223> OTHER INFORMATION: region represents a variable trinucleotide combination capable of coding any natural occurring amino acid other than Cys
<220> FEATURE:
<221> NAME/KEY: modified_base
<222> LOCATION: (48)..(50)
<223> OTHER INFORMATION: region represents a variable trinucleotide combination capable of coding any natural occurring amino acid -continued

```
     other than Cys

<400> SEQUENCE: 372

agggtctcga gtgggtgagc nnnattnnnn nnnnnrvtrv tnnnaccnnn tatgcggata     60

gcgtgaaagg ccgttttacc atttcacgtg ataattcgaa aaacacca                 108
```

PROTEIN (POLY)PEPTIDES LIBRARIES

This application is a continuation of U.S. patent application Ser. No. 10/834,397, filed Apr. 29, 2004, which is a division of application Ser. No. 09/490,324, filed Jan. 24, 2000, now U.S. Pat. No. 6,828,422, which is a continuation of international application PCT/EP96/03647, filed Aug. 19, 1996, which claims priority to European Application No. 95 11 3021.0, filed Aug. 18, 1995. The contents of each of these application are hereby incorporated by reference in their entireties.

FIELD OF THE INVENTION

The present invention relates to synthetic DNA sequences which encode one or more collections of homologous proteins/(poly)peptides, and methods for generating and applying libraries of these DNA sequences. In particular, the invention relates to the preparation of a library of human-derived antibody genes by the use of synthetic consensus sequences which cover the structural repertoire of antibodies encoded in the human genome. Furthermore, the invention relates to the use of a single consensus antibody gene as a universal framework for highly diverse antibody libraries.

BACKGROUND TO THE INVENTION

All current recombinant methods which use libraries of proteins/(poly)peptides, e.g. antibodies, to screen for members with desired properties, e.g. binding a given ligand, do not provide the possibility to improve the desired properties of the members in an easy and rapid manner. Usually a library is created either by inserting a random oligonucleotide sequence into one or more DNA sequences cloned from an organism, or a family of DNA sequences is cloned and used as the library. The library is then screened, e.g. using phage display, for members which show the desired property. The sequences of one or more of these resulting molecules are then determined. There is no general procedure available to improve these molecules further on.

Winter (EP 0 368 684 B1) has provided a method for amplifying (by PCR), cloning, and expressing antibody variable region genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system.

However the Winter invention does not provide a method for optimizing the binding affinities of antibody fragments further on, a process which would be functionally equivalent to the naturally occurring phenomenon of "affinity maturation", which is provided by the present invention. Furthermore, the Winter invention does not provide for artificial variable region genes, which represent a whole family of structurally similar natural genes, and which can be assembled from synthetic DNA oligonucleotides. Additionally, Winter does not enable the combinatorial assembly of portions of antibody variable regions, a feature which is provided by the present invention. Furthermore, this approach has the disadvantage that the genes of all antibodies obtained in the screening procedure have to be completely sequenced, since, except for the PCR priming regions, no additional sequence information about the library members is available. This is time and labor intensive and potentially leads to sequencing errors.

The teaching of Winter as well as other approaches have tried to create large antibody libraries having high diversity in the complementarity determining regions (CDRs) as well as in the frameworks to be able to find antibodies against as many different antigens as possible. It has been suggested that a single universal framework may be useful to build antibody libraries, but no approach has yet been successful.

Another problem lies in the production of reagents derived from antibodies. Small antibody fragments show exciting promise for use as therapeutic agents, diagnostic reagents, and for biochemical research. Thus, they are needed in large amounts, and the expression of antibody fragments, e.g. Fv, single-chain Fv (scFv), or Fab in the periplasm of *E. coli* (Skerra & Plückthun, 1988; Better et al., 1988) is now used routinely in many laboratories. Expression yields vary widely, however. While some fragments yield up to several mg of functional, soluble protein per liter and OD of culture broth in shake flask culture (Carter et al., 1992, Plückthun et al. 1996), other fragments may almost exclusively lead to insoluble material, often found in so-called inclusion bodies. Functional protein may be obtained from the latter in modest yields by a laborious and time-consuming refolding process. The factors influencing antibody expression levels are still only poorly understood. Folding efficiency and stability of the antibody fragments, protease lability and toxicity of the expressed proteins to the host cells often severely limit actual production levels, and several attempts have been tried to increase expression yields. For example, Knappik & Plückthun (1995) could show that expression yield depends on the antibody sequence. They identified key residues in the antibody framework which influence expression yields dramatically. Similarly, Ullrich et al. (1995) found that point mutations in the CDRs can increase the yields in periplasmic antibody fragment expression. Nevertheless, these strategies are only applicable to a few antibodies. Since the Winter invention uses existing repertoires of antibodies, no influence on expressibility of the genes is possible.

Furthermore, the findings of Knappik & Plückthun and Ullrich demonstrate that the knowledge about antibodies, especially about folding and expression is still increasing. The Winter invention does not allow to incorporate such improvements into the library design.

The expressibility of the genes is important for the library quality as well, since the screening procedure relies in most cases on the display of the gene product on a phage surface, and efficient display relies on at least moderate expression of the gene.

These disadvantages of the existing methodologies are overcome by the present invention, which is applicable for all collections of homologous proteins. It has the following novel and useful features illustrated in the following by antibodies as an example:

Artificial antibodies and fragments thereof can be constructed based on known antibody sequences, which reflect the structural properties of a whole group of homologous antibody genes. Therefore it is possible to reduce the number of different genes without any loss in the structural repertoire. This approach leads to a limited set of artificial genes, which can be synthesized de novo, thereby allowing introduction of cleavage sites and removing unwanted cleavages sites. Furthermore, this approach enables (i), adapting the codon usage of the genes to that of highly expressed genes in any desired host cell and (ii), analyzing all possible pairs of antibody light (L) and heavy (H) chains in terms of interaction preference, antigen preference or recombinant expression titer, which is virtually impossible using the complete collection of antibody genes of an organism and all combinations thereof.

The use of a limited set of completely synthetic genes makes it possible to create cleavage sites at the boundaries of encoded structural sub-elements. Therefore, each gene is built up from modules which represent structural sub-elements on the protein/(poly)peptide level. In the case of antibodies, the modules consist of “framework” and “CDR” modules. By creating separate framework and CDR modules, different combinatorial assembly possibilities are enabled. Moreover, if two or more artificial genes carry identical pairs of cleavage sites at the boundaries of each of the genetic sub-elements, pre-built libraries of sub-elements can be inserted in these genes simultaneously, without any additional information related to any particular gene sequence. This strategy enables rapid optimization of, for example, antibody affinity, since DNA cassettes encoding libraries of genetic sub-elements can be (i), pre-built, stored and reused and (ii), inserted in any of these sequences at the right position without knowing the actual sequence or having to determine the sequence of the individual library member.

Additionally, new information about amino acid residues important for binding, stability, or solubility and expression could be integrated into the library design by replacing existing modules with modules modified according to the new observations.

The limited number of consensus sequences used for creating the library allows to speed up the identification of binding antibodies after screening. After having identified the underlying consensus gene sequence, which could be done by sequencing or by using fingerprint restriction sites, just those part(s) comprising the random sequence(s) have to be determined. This reduces the probability of sequencing errors and of false-positive results.

The above mentioned cleavage sites can be used only if they are unique in the vector system where the artificial genes have been inserted. As a result, the vector has to be modified to contain none of these cleavage sites. The construction of a vector consisting of basic elements like resistance gene and origin of replication, where cleavage sites have been removed, is of general interest for many cloning attempts. Additionally, these vector(s) could be part of a kit comprising the above mentioned artificial genes and pre-built libraries.

The collection of artificial genes can be used for a rapid humanization procedure of non-human antibodies, preferably of rodent antibodies. First, the amino acid sequence of the non-human, preferably rodent antibody is compared with the amino acid sequences encoded by the collection of artificial genes to determine the most homologous light and heavy framework regions. These genes are then used for insertion of the genetic sub-elements encoding the CDRs of the non-human, preferably rodent antibody.

Surprisingly, it has been found that with a combination of only one consensus sequence for each of the light and heavy chains of a scFv fragment an antibody repertoire could be created yielding antibodies against virtually every antigen. Therefore, one aspect of the present invention is the use of a single consensus sequence as a universal framework for the creation of useful (poly)peptide libraries and antibody consensus sequences useful therefor.

DETAILED DESCRIPTION OF THE INVENTION

The present invention enables the creation of useful libraries of (poly)peptides. In a first embodiment, the invention provides for a method of setting up nucleic acid sequences suitable for the creation of said libraries. In a first step, a collection of at least three homologous proteins is identified and then analyzed. Therefore, a database of the protein sequences is established where the protein sequences are aligned to each other. The database is used to define subgroups of protein sequences which show a high degree of similarity in both the sequence and, if information is available, in the structural arrangement. For each of the subgroups a (poly)peptide sequence comprising at least one consensus sequence is deduced which represents the members of this subgroup; the complete collection of (poly)peptide sequences represent therefore the complete structural repertoire of the collection of homologous proteins. These artificial (poly) peptide sequences are then analyzed, if possible, according to their structural properties to identify unfavorable interactions between amino acids within said (poly)peptide sequences or between said or other (poly)peptide sequences, for example, in multimeric proteins. Such interactions are then removed by changing the consensus sequence accordingly. The (poly) peptide sequences are then analyzed to identify sub-elements such as domains, loops, helices or CDRs. The amino acid sequence is backtranslated into a corresponding coding nucleic acid sequence which is adapted to the codon usage of the host planned for expressing said nucleic acid sequences. A set of cleavage sites is set up in a way that each of the sub-sequences encoding the sub-elements identified as described above, is flanked by two sites which do not occur a second time within the nucleic acid sequence. This can be achieved by either identifying a cleavage site already flanking a sub-sequence of by changing one or more nucleotides to create the cleavage site, and by removing that site from the remaining part of the gene. The cleavage sites should be common to all corresponding sub-elements or sub-sequences, thus creating a fully modular arrangement of the sub-sequences in the nucleic acid sequence and of the sub-elements in the corresponding (poly)peptide.

In a further embodiment, the invention provides for a method which sets up two or more sets of (poly)peptides, where for each set the method as described above is performed, and where the cleavage sites are not only unique within each set but also between any two sets. This method can be applied for the creation of (poly)peptide libraries comprising for example two α-helical domains from two different proteins, where said library is screened for novel hetero-association domains.

In yet a further embodiment, at least two of the sets as described above, are derived from the same collection of proteins or at least a part of it. This describes libraries comprising for example, but not limited to, two domains from antibodies such as VH and VL, or two extracellular loops of transmembrane receptors.

In another embodiment, the nucleic acid sequences set up as described above, are synthesized. This can be achieved by any one of several methods well known to the practitioner skilled in the art, for example, by total gene synthesis or by PCR-based approaches.

In one embodiment, the nucleic acid sequences are cloned into a vector. The vector could be a sequencing vector, an expression vector or a display (e.g. phage display) vector, which are well known to those skilled in the art. Any vector could comprise one nucleic acid sequence, or two or more nucleic sequences, either in different or the same operon. In the last case, they could either be cloned separately or as contiguous sequences.

In one embodiment, the removal of unfavorable interactions as described above, leads to enhanced expression of the modified (poly)peptides.

In a preferred embodiment, one or more sub-sequences of the nucleic acid sequences are replaced by different sequences. This can be achieved by excising the sub-sequences using the conditions suitable for cleaving the cleavage sites adjacent to or at the end of the sub-sequence, for example, by using a restriction enzyme at the corresponding restriction site under the conditions well known to those skilled in the art, and replacing the sub-sequence by a different sequence compatible with the cleaved nucleic acid sequence. In a further preferred embodiment, the different sequences replacing the initial sub-sequence(s) are genomic or rearranged genomic sequences, for example in grafting CDRs from non-human antibodies onto consensus antibody sequences for rapid humanization of non-human antibodies. In the most preferred embodiment, the different sequences are random sequences, thus replacing the sub-sequence by a collection of sequences to introduce variability and to create a library. The random sequences can be assembled in various ways, for example by using a mixture of mononucleotides or preferably a mixture of trinucleotides (Virnekäs et al., 1994) during automated oligonucleotide synthesis, by error-prone PCR or by other methods well known to the practitioner in the art. The random sequences may be completely randomized or biased towards or against certain codons according to the amino acid distribution at certain positions in known protein sequences. Additionally, the collection of random sub-sequences may comprise different numbers of codons, giving rise to a collection of sub-elements having different lengths.

In another embodiment, the invention provides for the expression of the nucleic acid sequences from a suitable vector and under suitable conditions well known to those skilled in the art.

In a further preferred embodiment, the (poly)peptides expressed from said nucleic acid sequences are screened and, optionally, optimized. Screening may be performed by using one of the methods well known to the practitioner in the art, such as phage-display, selectively infective phage, polysome technology to screen for binding, assay systems for enzymatic activity or protein stability. (Poly)peptides having the desired property can be identified by sequencing of the corresponding nucleic acid sequence or by amino acid sequencing or mass spectrometry. In the case of subsequent optimization, the nucleic acid sequences encoding the initially selected (poly)peptides can optionally be used without sequencing. Optimization is performed by repealing the replacement of sub-sequences by different sequences, preferably by random sequences, and the screening step one or more times.

The desired property the (poly)peptides are screened for is preferably, but not exclusively, selected from the group of optimized affinity or specificity for a target molecule, optimized enzymatic activity, optimized expression yields, optimized stability and optimized solubility.

In one embodiment, the cleavage sites flanking the sub-sequences are sites recognized and cleaved by restriction enzymes, with recognition and cleavage sequences being either identical or different, the restricted sites either having blunt or sticky ends.

The length of the sub-elements is preferably, but not exclusively ranging between 1 amino acid, such as one residue in the active site of an enzyme or a structure-determining residue, and 150 amino acids, as for whole protein domains. Most preferably, the length ranges between 3 and 25 amino acids, such as most commonly found in CDR loops of antibodies.

The nucleic acid sequences could be RNA or, preferably, DNA.

In one embodiment, the (poly)peptides have an amino acid pattern characteristic of a particular species. This can for example be achieved by deducing the consensus sequences from a collection of homologous proteins of just one species, most preferably from a collection of human proteins. Since the (poly)peptides comprising consensus sequences are artificial, they have to be compared to the protein sequence(s) having the closest similarity to ensure the presence of said characteristic amino acid pattern.

In one embodiment, the invention provides for the creation of libraries of (poly)peptides comprising at least part of members or derivatives of the immunoglobulin superfamily, preferably of member or derivatives of the immunoglobulins. Most preferably, the invention provides for the creation of libraries of human antibodies, wherein said (poly)peptides are or are derived from heavy or light chain variable regions wherein said structural sub-elements are framework regions (FR) 1, 2, 3, or 4 or complementary determining regions (CDR) 1, 2, or 3. In a first step, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed e.g. by total gene synthesis or by the use of synthetic genetic subunits. These genetic subunits correspond to structural sub-elements on the (poly)peptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. Most preferably, said (poly)peptides are or are derived from the HuCAL consensus genes: Vκ1, Vκ2, Vκ3, Vκ4, Vλ1, Vλ2, Vλ3, VH1A, VH1B, VH2, VH3, VH4, VH5, VH6, Cκ, Cλ, CH1 or any combination of said HuCAL consensus genes.

This collection of DNA molecules can then be used to create libraries of antibodies or antibody fragments, preferably Fv, disulphide-linked Fv, single-chain Fv (scFv), or Fab fragments, which may be used as sources of specificities against new target antigens. Moreover, the affinity of the antibodies can be optimized using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. Preferably, an scFv fragment library comprising the combination of HuCAL VH3 and HuCAL Vλ2 consensus genes and at least a random sub-sequence encoding the heavy chain CDR3 sub-element is screened for binding antibodies. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDRs) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are selected, collected and used as starting material for the next library. Here, one or more of the remaining genetic subunits are randomized as described above.

A further embodiment of the present invention relates to fusion proteins by providing for a DNA sequence which encodes both the (poly)peptide, as described above, as well as an additional moiety. Particularly preferred are moieties which have a useful therapeutic function. For example, the additional moiety may be a toxin molecule which is able to kill cells (Vitetta et al., 1993). There are numerous examples of such toxins, well known to the one skilled in the art, such as the bacterial toxins *Pseudomonas* exotoxin A, and diphtheria toxin, as well as the plant toxins ricin, abrin, modeccin, saporin, and gelonin. By fusing such a toxin for example to an antibody fragment, the toxin can be targeted to, for example, diseased cells, and thereby have a beneficial therapeutic effect. Alternatively, the additional moiety may be a cytokine, such as IL-2 (Rosenberg & Lotze, 1986), which has a particular effect (in this case a T-cell proliferative effect) on a family of cells. In a further embodiment, the additional moiety may confer on its (poly)peptide partner a means of detection and/or purification. For example, the fusion protein could comprise the modified antibody fragment and an enzyme commonly used for detection purposes, such as alkaline phosphatase (Blake et al., 1984). There are numerous other moieties which can be used as detection or purification tags, which are well known to the practitioner skilled in the art. Particularly preferred are peptides comprising at least five histidine residues (Hochuli et al., 1988), which are able to bind to metal ions, and can therefore be used for the purification of the protein to which they are fused (Lindner et al., 1992). Also provided for by the invention are additional moieties such as the commonly used C-myc and FLAG tags (Hopp et al., 1988; Knappik & Plückthun, 1994).

By engineering one or more fused additional domains, antibody fragments or any other (poly)peptide can be assembled into larger molecules which also fall under the scope of the present invention. For example, mini-antibodies (Pack, 1994) are dimers comprising two antibody fragments, each fused to a self-associating dimerization domain. Dimerization domains which are particularly preferred include those derived from a leucine zipper (Pack & Plückthun, 1992) or helix-turn-helix motif (Pack et al., 1993).

All of the above embodiments of the present invention can be effected using standard techniques of molecular biology known to anyone skilled in the art.

In a further embodiment, the random collection of sub-sequences (the library) is inserted into a singular nucleic acid sequence encoding one (poly)peptide, thus creating a (poly)peptide library based on one universal framework. Preferably a random collection of CDR sub-sequences is inserted into a universal antibody framework, for example into the HuCAL H3κ2 single-chain Fv fragment described above.

In further embodiments, the invention provides for nucleic acid sequence(s), vector(s) containing the nucleic acid sequence(s), host cell(s) containing the vector(s), and (poly)peptides, obtainable according to the methods described above.

In a further preferred embodiment, the invention provides for modular vector systems being compatible with the modular nucleic acid sequences encoding the (poly)peptides. The modules of the vectors are flanked by restriction sites unique within the vector system and essentially unique with respect to the restriction sites incorporated into the nucleic acid sequences encoding the (poly)peptides, except for example the restriction sites necessary for cloning the nucleic acid sequences into the vector. The list of vector modules comprises origins of single-stranded replication, origins of double-stranded replication for high- and low copy number plasmids, promotor/operator, repressor or terminator elements, resistance genes, potential recombination sites, gene III for display on filamentous phages, signal sequences, purification and detection tags, and sequences of additional moieties.

The vectors are preferably, but not exclusively, expression vectors or vectors suitable for expression and screening of libraries.

In another embodiment, the invention provides for a kit, comprising one or more of the list of nucleic acid sequence(s), recombinant vector(s), (poly)peptide(s), and vector(s) according to the methods described above, and suitable host cell(s) for producing the (poly)peptide(s).

In a preferred embodiment, the invention provides for the creation of libraries of human antibodies. In a first step, a database of published antibody sequences of human origin is established: The database is used to define subgroups of antibody sequences which show a high degree of similarity in both the sequence and the canonical fold (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed by the use of synthetic genetic subunits. These genetic subunits correspond to structural sub-elements on the protein level. On the DNA level, these genetic subunits are defined by cleavage sites at the start and the end of each of the subelements, which are unique in the vector system. All genes which are members of the collection of consensus sequences are constructed such that they contain a similar pattern of said genetic subunits.

This collection of DNA molecules can then be used to create libraries of antibodies which may be used as sources of specificities against new target antigens. Moreover, the affinity of the antibodies can be optimised using pre-built library cassettes and a general procedure. The invention provides a method for identifying one or more genes encoding one or more antibody fragments which binds to a target, comprising the steps of expressing the antibody fragments, and then screening them to isolate one or more antibody fragments which bind to a given target molecule. If necessary, the modular design of the genes can then be used to excise from the genes encoding the antibody fragments one or more genetic sub-sequences encoding structural sub-elements, and replacing them by one or more second sub-sequences encoding structural sub-elements. The expression and screening steps can then be repeated until an antibody having the desired affinity is generated.

Particularly preferred is a method in which one or more of the genetic subunits (e.g. the CDR's) are replaced by a random collection of sequences (the library) using the said cleavage sites. Since these cleavage sites are (i) unique in the vector system and (ii) common to all consensus genes, the same (pre-built) library can be inserted into all artificial antibody genes. The resulting library is then screened against any chosen antigen. Binding antibodies are eluted, collected and used as starting material for the next library. Here, one or more of the remaining genetic subunits are randomised as described above.

DEFINITIONS

Protein:

The term protein comprises monomeric polypeptide chains as well as homo- or heteromultimeric complexes of two or more polypeptide chains connected either by covalent interactions (such as disulphide bonds) or by non-covalent interactions (such as hydrophobic or electrostatic interactions).

Analysis of Homologous Proteins:

The amino acid sequences of three or more proteins are aligned to each other (allowing for introduction of gaps) in a way which maximizes the correspondence between identical or similar amino acid residues at all positions. These aligned sequences are termed homologous if the percentage of the sum of identical and/or similar residues exceeds a defined threshold. This threshold is commonly regarded by those skilled in the art as being exceeded when at least 15% of the amino acids in the aligned genes are identical, and at least 30% are similar. Examples for families of homologous proteins are: immunoglobulin superfamily, scavenger receptor superfamily, fibronectin superfamilies (e.g. type II and III), complement control protein superfamily, cytokine receptor superfamily, cystine knot proteins, tyrosine kinases, and numerous other examples well known to one of ordinary skill in the art.

Consensus Sequence:

Using a matrix of al least three aligned amino acid sequences, and allowing for gaps in the alignment, it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids.

Removing Unfavorable Interactions:

The consensus sequence is per se in most cases artificial and has to be analyzed in order to change amino acid residues which, for example, would prevent the resulting molecule to adapt a functional tertiary structure or which would block the interaction with other (poly)peptide chains in multimeric complexes. This can be done either by (i) building a three-dimensional model of the consensus sequence using known related structures as a template, and identifying amino acid residues within the model which may interact unfavorably with each other, or (ii) analyzing the matrix of aligned amino acid sequences in order to detect combinations of amino acid residues within the sequences which frequently occur together in one sequence and are therefore likely to interact with each other. These probable interaction-pairs are then tabulated and the consensus is compared with these "interaction maps". Missing or wrong interactions in the consensus are repaired accordingly by introducing appropriate changes in amino acids which minimize unfavorable interactions.

Identification of Structural Sub-Elements:

Structural sub-elements are stretches of amino acid residues within a protein/(poly)peptide which correspond to a defined structural or functional part of the molecule. These can be loops (e.g. CDR loops of an antibody) or any other secondary or functional structure within the protein/(poly) peptide (domains. α-helices, β-sheets, framework regions of antibodies, etc.). A structural sub-element can be identified using known structures of similar or homologous (poly)peptides, or by using the above mentioned matrices of aligned amino acid sequences. Here the variability at each position is the basis for determining stretches of amino acid residues which belong to a structural sub-element (e.g. hypervariable regions of an antibody).

Sub-Sequence:

A sub-sequence is defined as a genetic module which is flanked by unique cleavage sites and encodes at least one structural sub-element. It is not necessarily identical to a structural sub-element.

Cleavage Site:

A short DNA sequence which is used as a specific target for a reagent which cleaves DNA in a sequence-specific manner (e.g. restriction endonucleases).

Compatible Cleavage Sites:

Cleavage sites are compatible with each other, if they can be efficiently ligated without modification and, preferably, also without adding an adapter molecule.

Unique Cleavage Sites:

A cleavage site is defined as unique if it occurs only once in a vector containing at least one of the genes of interest, or if a vector containing at least one of the genes of interest could be treated in a way that only one of the cleavage sites could be used by the cleaving agent.

Corresponding (Poly)Peptide Sequences:

Sequences deduced from the same part of one group of homologous proteins are called corresponding (poly)peptide sequences.

Common Cleavage Sites:

A cleavage site in at least two corresponding sequences, which occurs at the same functional position (i.e. which flanks a defined sub-sequence), which can be hydrolyzed by the same cleavage tool and which yields identical compatible ends is termed a common cleavage site.

Excising Genetic Sub-Sequences:

A method which uses the unique cleavage sites and the corresponding cleavage reagents to cleave the target DNA at the specified positions in order to isolate, remove or replace the genetic sub-sequence flanked by these unique cleavage sites.

Exchanging Genetic Sub-Sequences:

A method by which an existing sub-sequence is removed using the flanking cleavage sites of this sub-sequence, and a new sub-sequence or a collection of sub-sequences, which contain ends compatible with the cleavage sites thus created, is inserted.

Expression of Genes:

The term expression refers to in vivo or in vitro processes, by which the information of a gene is transcribed into mRNA and then translated into a protein/(poly)peptide. Thus, the term expression refers to a process which occurs inside cells, by which the information of a gene is transcribed into mRNA and then into a protein. The term expression also includes all events of post-translational modification and transport, which are necessary for the (poly)peptide to be functional.

Screening of Protein/(Poly)Peptide Libraries:

Any method which allows isolation of one or more proteins/(poly)peptides having a desired property from other proteins/(poly)peptides within a library.

Amino Acid Pattern Characteristic for a Species:

A (poly)peptide sequence is assumed to exhibit an amino acid pattern characteristic for a species if it is deduced from a collection of homologous proteins from just this species.

Immunoglobulin Superfamily (IgSF):

The IgSF is a family of proteins comprising domains being characterized by the immunoglobulin fold. The IgSF comprises for example T-cell receptors and the immunoglobulins (antibodies).

Antibody Framework:

A framework of an antibody variable domain is defined by Kabat et al. (1991) as the part of the variable domain which serves as a scaffold for the antigen binding loops of this variable domain.

Antibody CDR:

The CDRs (complementarity determining regions) of an antibody consist of the antigen binding loops, as defined by Kabat et al. (1991). Each of the two variable domains of an antibody Fv fragment contain three CDRs.

HuCAL:

Acronym for Human Combinatorial Antibody Library. Antibody Library based on modular consensus genes according to the invention (see Example 1).

Antibody Fragment:

Any portion of an antibody which has a particular function, e.g. binding of antigen. Usually, antibody fragments are smaller than whole antibodies. Examples are Fv, disulphide-linked Fv, single-chain Fv (scFv), or Fab fragments. Additionally, antibody fragments are often engineered to include new functions or properties.

Universal Framework:

One single framework which can be used to create the full variability of functions, specificities or properties which is originally sustained by a large collection of different frameworks, is called universal framework.

Binding of an Antibody to its Target:

The process which leads to a tight and specific association between an antibody and a corresponding molecule or ligand is called binding. A molecule or ligand or any part of a molecule or ligand which is recognized by an antibody is called the target.

Replacing Genetic Sub-Sequences

A method by which an existing sub-sequence is removed using the flanking cleavage sites of this sub-sequence, and a new sub-sequence or collection of sub-sequences, which contains ends compatible with tow cleavage sites thus create, is inserted.

Assembling of Genetic Sequences:

Any process which is used to combine synthetic or natural genetic sequences in a specific manner in order to get longer genetic sequences which contain at least parts of the used synthetic or natural genetic sequences.

Analysis of Homologous Genes:

The corresponding amino acid sequences of two or more genes are aligned to each other in a way which maximizes the correspondence between identical or similar amino acid residues at all positions. These aligned sequences are termed homologous if the percentage of the gum of identical and/or similar residues exceeds a defined threshold. This threshold is commonly regarded by those skilled in the art as being exceeded when at least 15 percent of the amino acids in the aligned genes are identical, and at least 30 percent are similar.

LEGENDS TO FIGURES AND TABLES

FIGS. 2A-2G: Alignment of consensus sequences designed for each subgroup (amino acid residues are shown with their standard one-letter abbreviation). (A) (2A-2B) (SEQ ID NOS 28-31, respectively) kappa sequences, (B) (2C-2D) (SEQ ID NOS 32-34, respectively) lambda sequences and (C) (2E-2G) (SEQ ID NOS 35-41, respectively), heavy chain sequences. The positions are numbered according to Kabat (1991). In order to maximize homology in the alignment, gaps (–) have been introduced in the sequence at certain positions.

FIGS. 3A-3K: Gene sequences (SEQ ID NOS 42, 44, 46 and 48, respectively) of the synthetic V kappa consensus genes. The corresponding amino acid sequences (SEQ ID NOS 43, 45, 47 and 49, respectively) (see FIGS. 2A-2B) as well as the unique cleavage sites are also shown.

FIGS. 4A-4I: Gene sequences (SEQ ID NOS 50, 52 and 54, respectively) of the synthetic V lambda consensus genes. The corresponding amino acid sequences (SEQ ID NOS 51, 53 and 55, respectively) (see FIGS. 2C-2D) as well as the unique cleavage sites are also shown.

FIGS. 5A-5U: Gene sequences (SEQ ID NOS 56, 58, 60, 62, 64, 66 and 68, respectively) of the synthetic V heavy chain consensus genes. The corresponding amino acid sequences (SEQ ID NOS 57, 59, 61, 63, 65, 67 and 69, respectively) (see FIGS. 2E-2G) as well as the unique cleavage sites are also shown.

FIGS. 6A-6G: Oligonucleotides (SEQ ID NOS 70-164, respectively) used for construction of the consensus genes. The oligos are named according to the corresponding consensus gene, e.g. the gene Vκ1 was constructed using the six oligonucleotides OIK1 to OIK6. The oligonucleotides used for synthesizing the genes encoding the constant domains Cκ (OCLK1 to 8) and CH1 (OCH1 to 8) are also shown.

FIGS. 7A-7D: Sequences of the synthetic genes (SEQ ID NOS 165 and 167, respectively) encoding the constant domains Cκ (A) (7A-7B) and CH1 (B) (7C-7D). The corresponding amino acid sequences (SEQ ID NOS 166 and 168, respectively) as well as unique cleavage sites introduced in these genes are also shown.

FIGS. 7E-7H: Functional map and sequence (SEQ ID NOS 169-170, respectively) of module M24 comprising the synthetic CX gene segment (huCL lambda).

FIGS. 7I-7J: Oligonucleotides (SEQ ID NOS 171-176) used for synthesis of module M24.

FIGS. 8A-8E: Sequence (SEQ ID NOS 177-178, respectively) and restriction map of the synthetic gene encoding the consensus single-chain fragment VH3-Vκa. The signal sequence (amino acids 1 to 21) was derived from the *E. coli* phoA gene (Skerra & Pluckthun, 1988). Between the phoA signal sequence and the VH3 domain, a short sequence stretch encoding 4 amino acid residues (amino acid 22 to 25) has been inserted in order to allow detection of the single-chain fragment in Western blot or ELISA using the monoclonal antibody M1 (Knappik & PlÖckthun, 1994). The last 6 basepairs of the sequence were introduced for cloning purposes (EcoR1 site).

Figure 9:
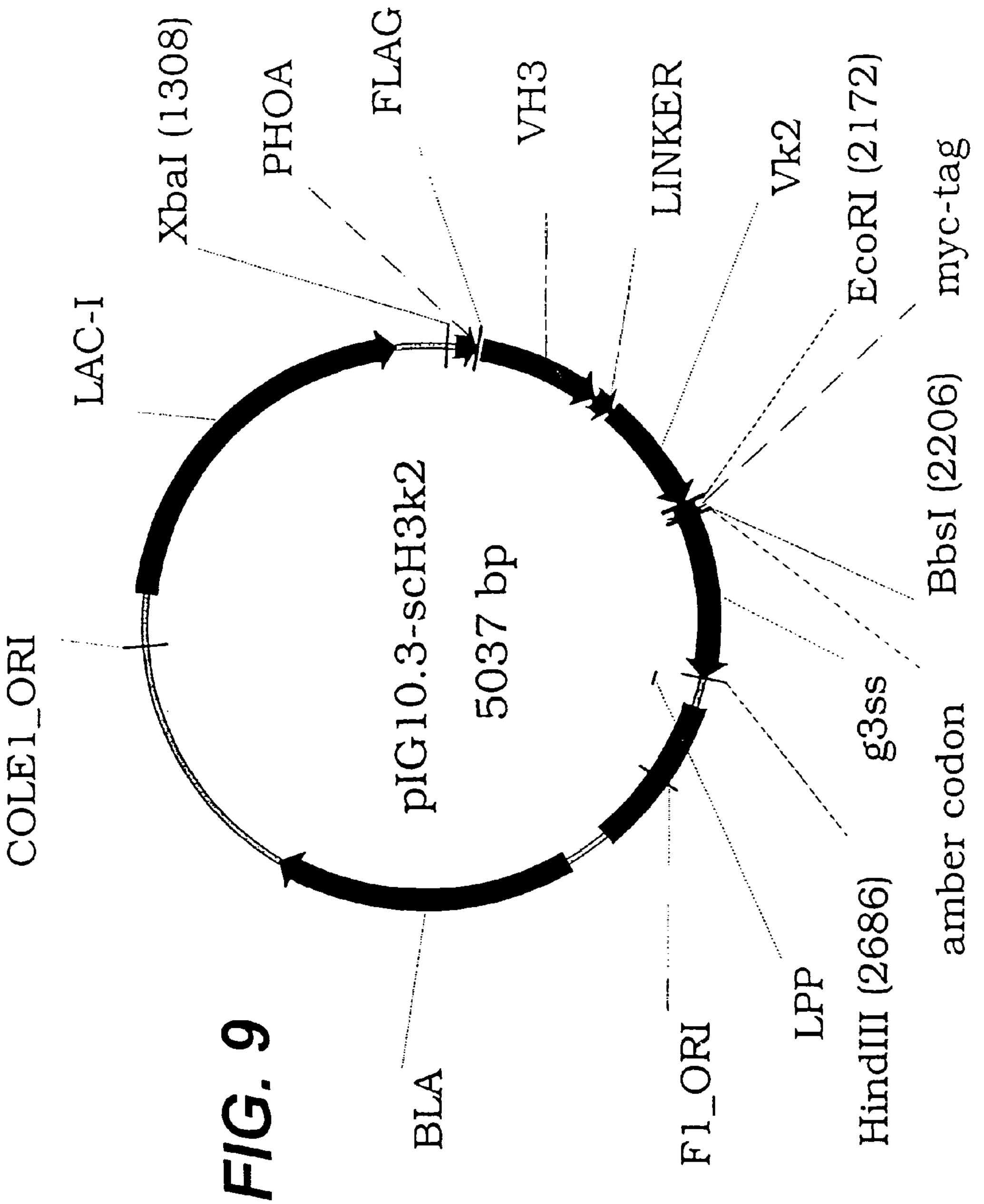

FIG. 9: Plasmid map of the vector pIG10.3 used for phage display of the $H3_K2$ scFv fragment. The vector is derived from pIG10 and contains the gene for the lac operon repressor, lacl, the artificial operon encoding the $H3_K2$-gene3ss fusion under control of the lac promoter, the lpp terminator of transcription, the single-strand replication origin of the *E. coli* phage f1 (F1_ORI), a gene encoding β-lactamase (bla) and the ColEI derived origin of replication.

FIGS. 10A-10B: Sequencing results of independent clones from the initial library, translated into the corresponding amino acid sequences. (A) (SEQ ID NO: 179) Amino acid sequence of the VH3 consensus heavy chain CDR3 (position 93 to 102, Kabat numbering). (B) (SEQ ID NOS 180-191, respectively) Amino acid sequences of 12 clones of the 10-mer library. (C) (SEQ ID NOS 192-202, respectively) Amino acid sequences of 11 clones of the 15-mer library, *: single base deletion.

Figure 11:
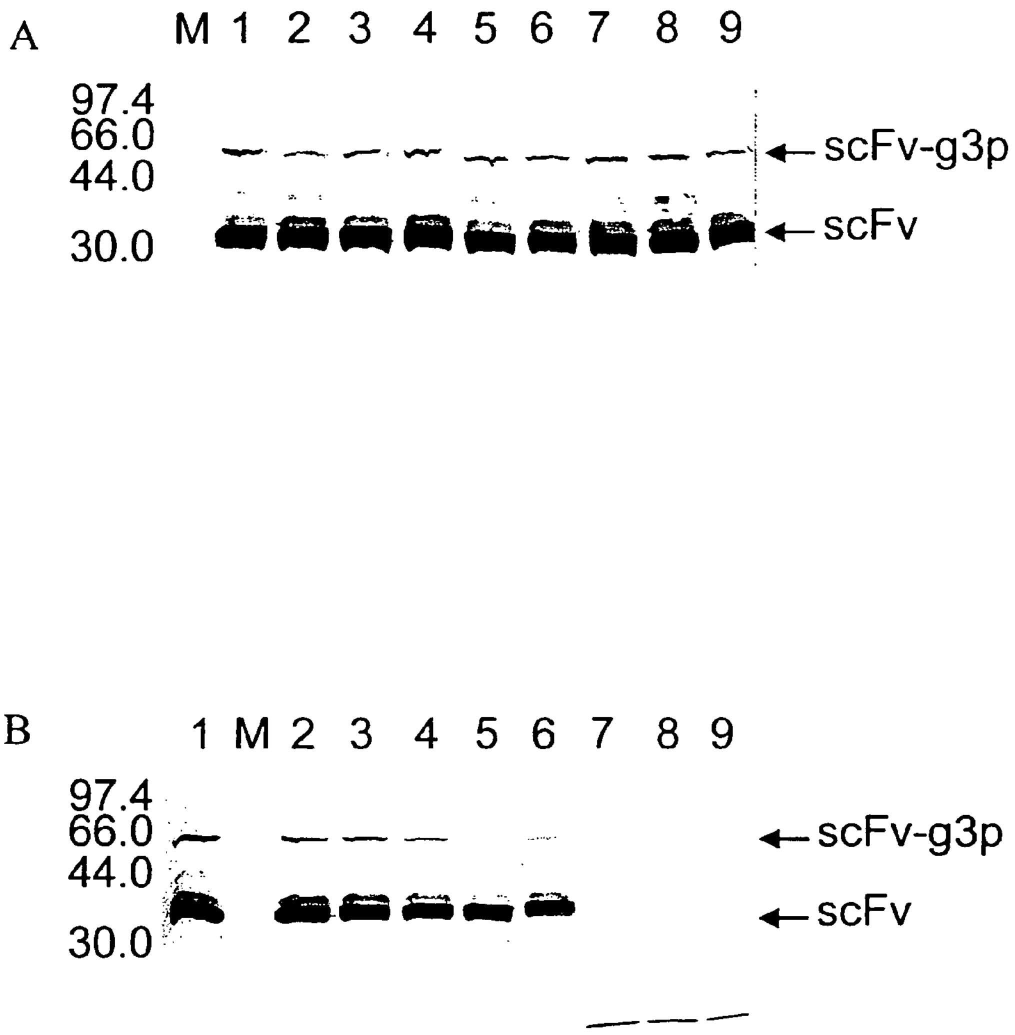

FIGS. 11A-11B: Expression test of individual library members. (A) Expression of 9 independent clones of the 10-mer library. (B) Expression of 9 independent clones of the 15-mer library. The lane designated with M contains the size marker. Both the gp3-scFv fusion and the scFv monomer are indicated.

Figure 12:
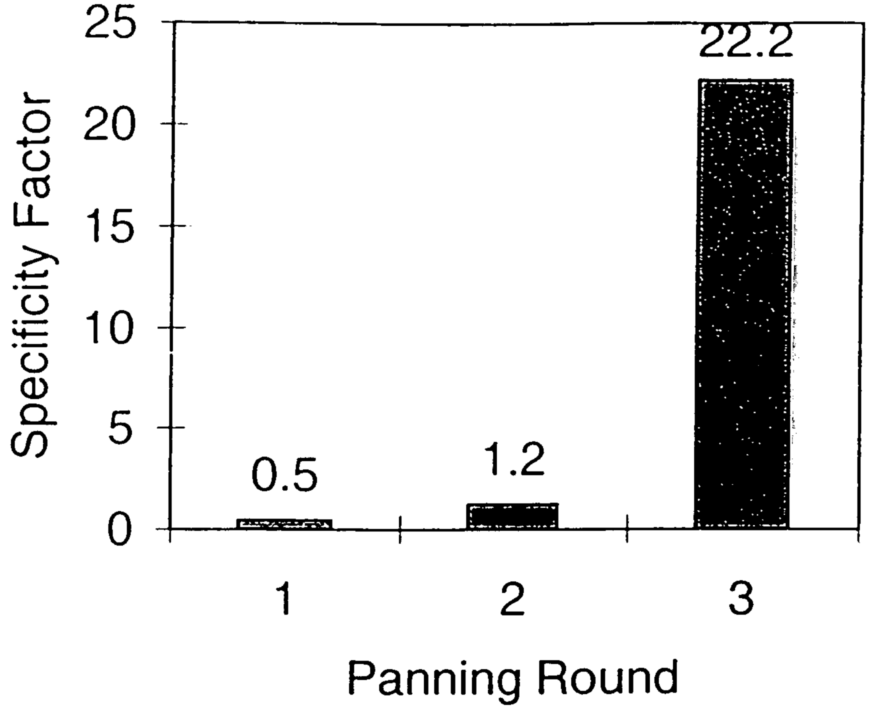

FIG. 12: Enrichment of specific phage antibodies during the panning against FITCBSA. The initial as well as the subsequent fluorescein-specific sub-libraries were panned against the blocking buffer and the ratio of the phage eluted from the FITC-BSA coated well vs. that from the powder milk coated well from each panning round is presented as the "specificity factor".

Figure 13:
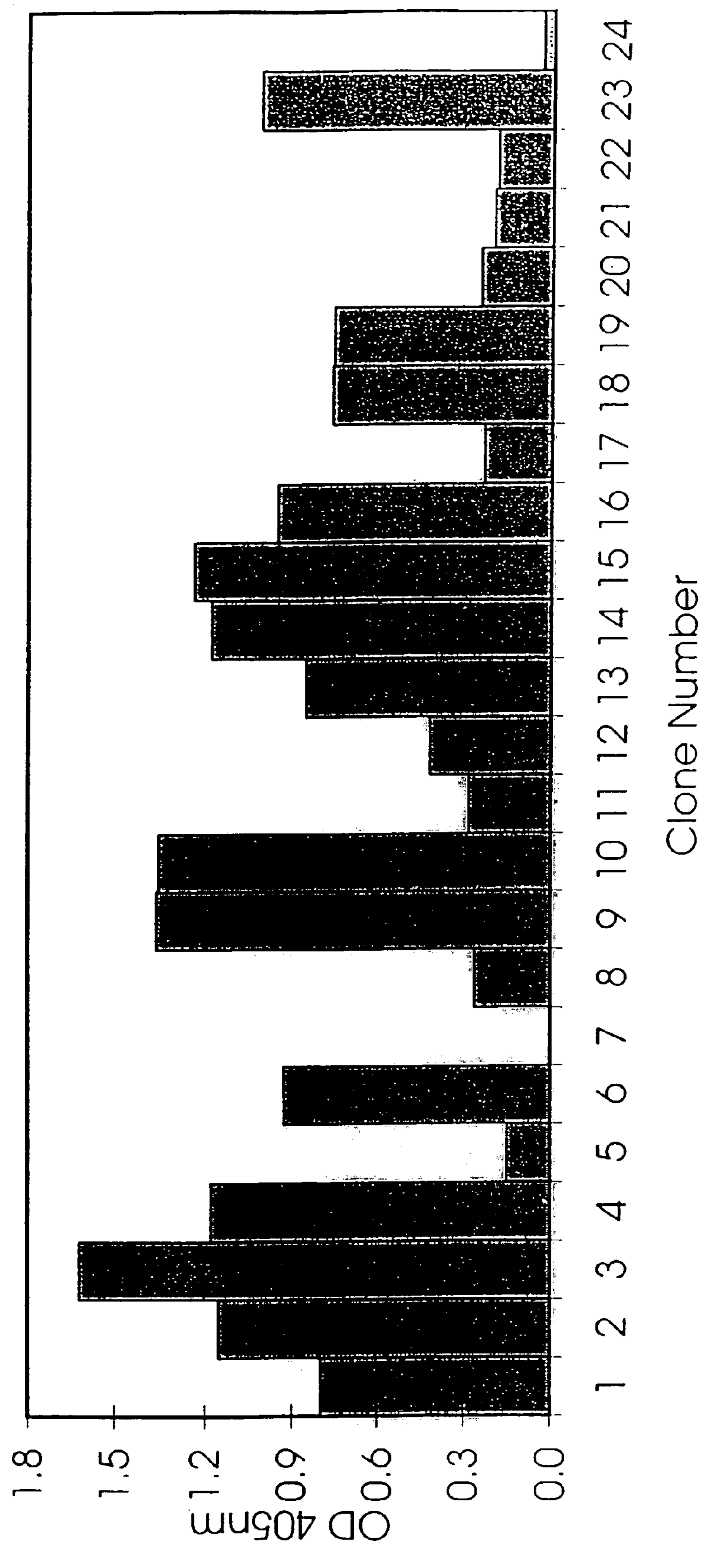

FIG. 13: Phage ELISA of 24 independent clones after the third round of panning tested for binding on FITC-BSA.

Figure 14:
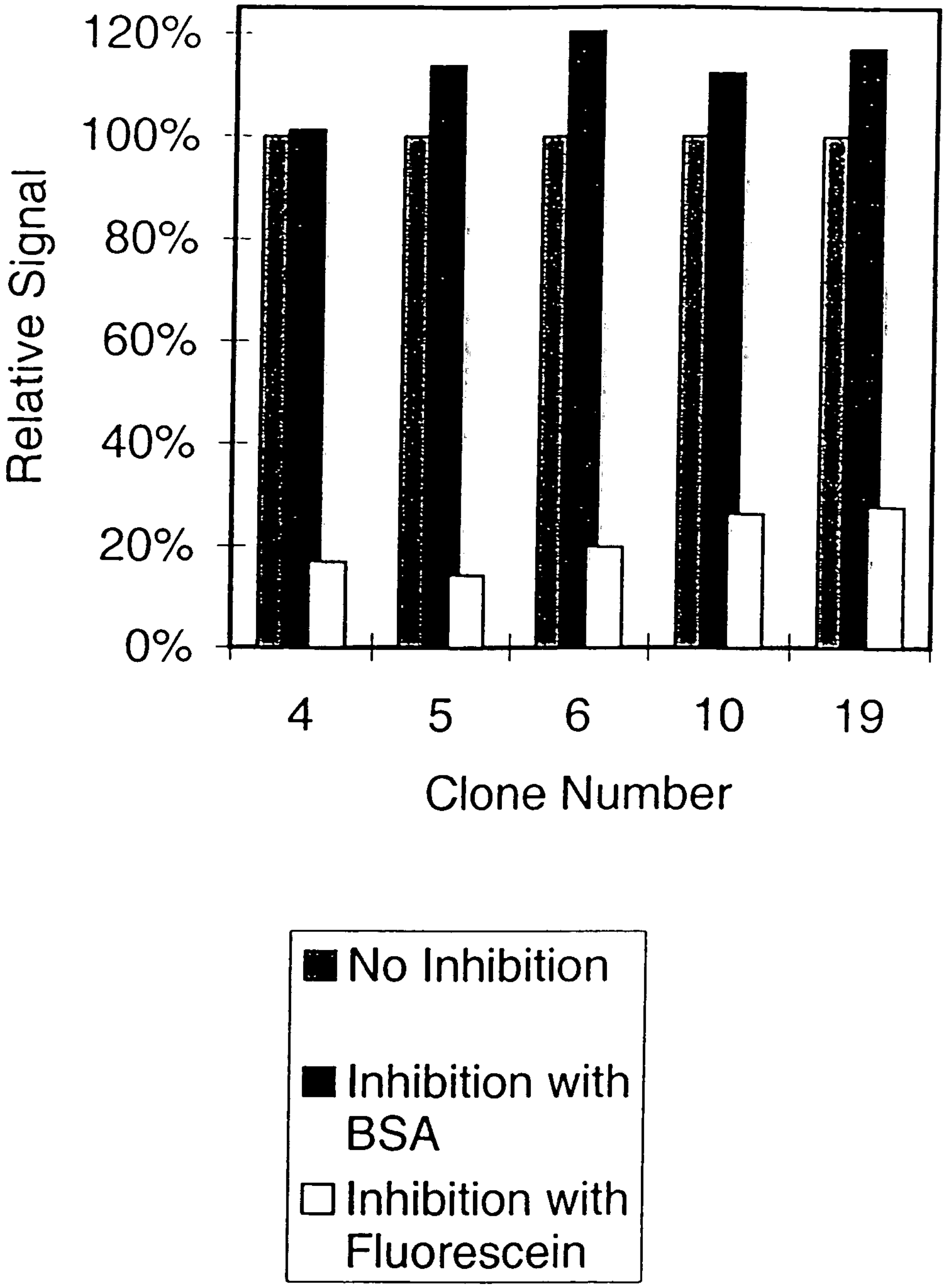

FIG. 14: Competition ELISA of selected FITC-BSA binding clones. The ELISA signals (OD.sub.405 nm) of scFv binding without inhibition are taken as 100%.

FIG. 15: Sequences results of the heavy chain CDR3s of independent clones after 3 rounds of planning against FITC-BSA, translated into the corresponding amino acid sequences (SEQ ID NOS 203-218, respectively) (position 93 to 102. Kabat numbering).

Figure 16:
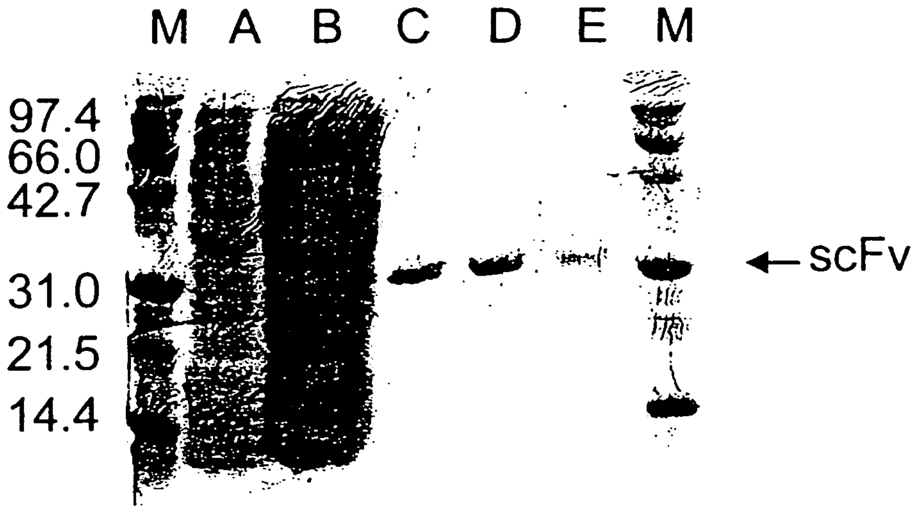

FIG. 16: Coomassie-Blue stained SDS-PAGE of the purified anti-fluorescein scFv fragments: M: molecular weight marker, A: total soluble cell extract after induction, B: fraction of the flow-through, C, D and E: purified scFv fragments 1HA-3E4, 1HA-3E5 and 1HA-3E10, respectively.

Figure 17:
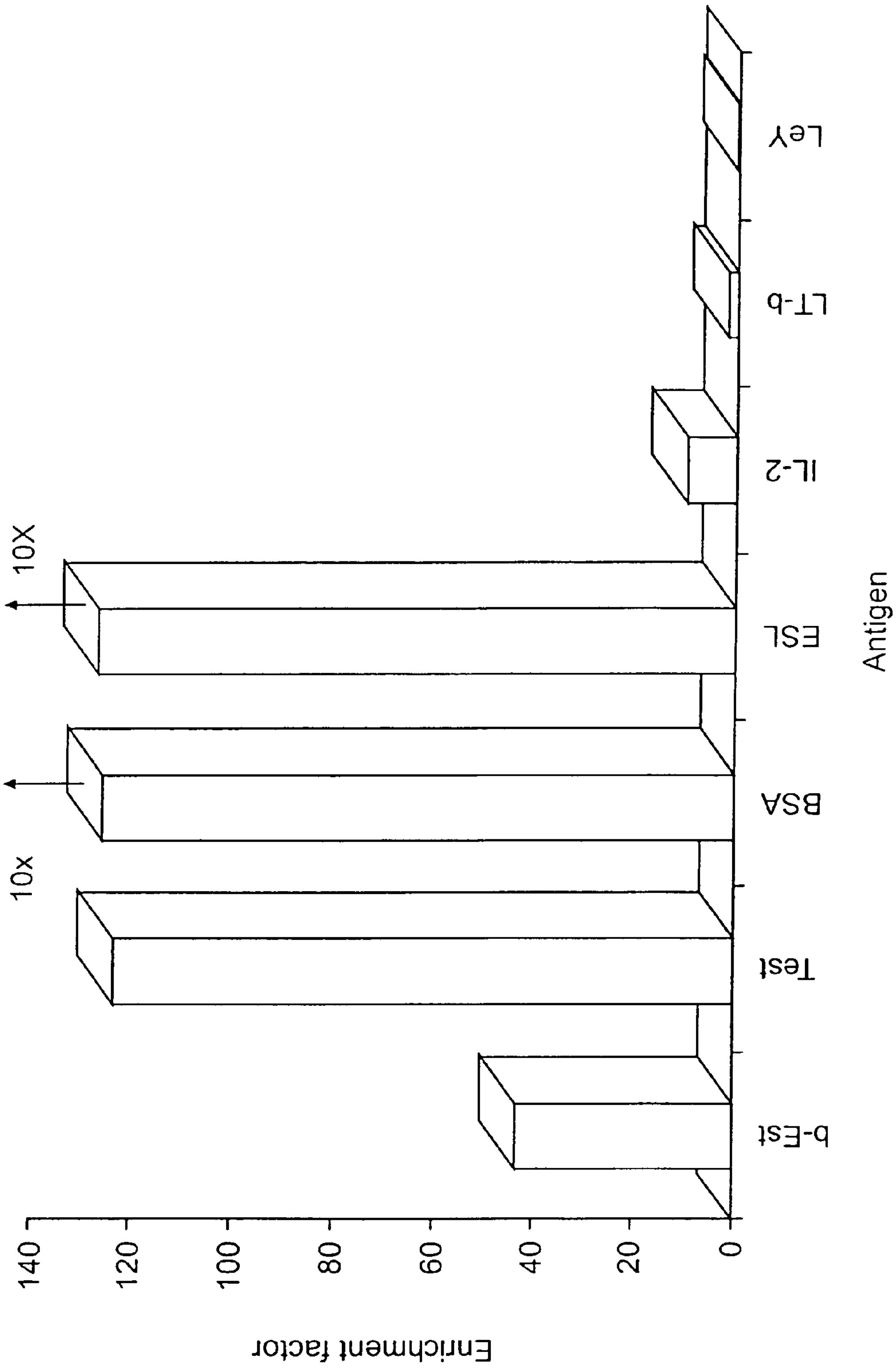

FIG. 17: Enrichment of specific phage antibodies during the panning against β-estradiol-BSA, testosterone-BSA, BSA, ESL-1, interleukin-2, lymphotoxin-β, and LeY-BSA after three rounds of panning.

Figure 18:
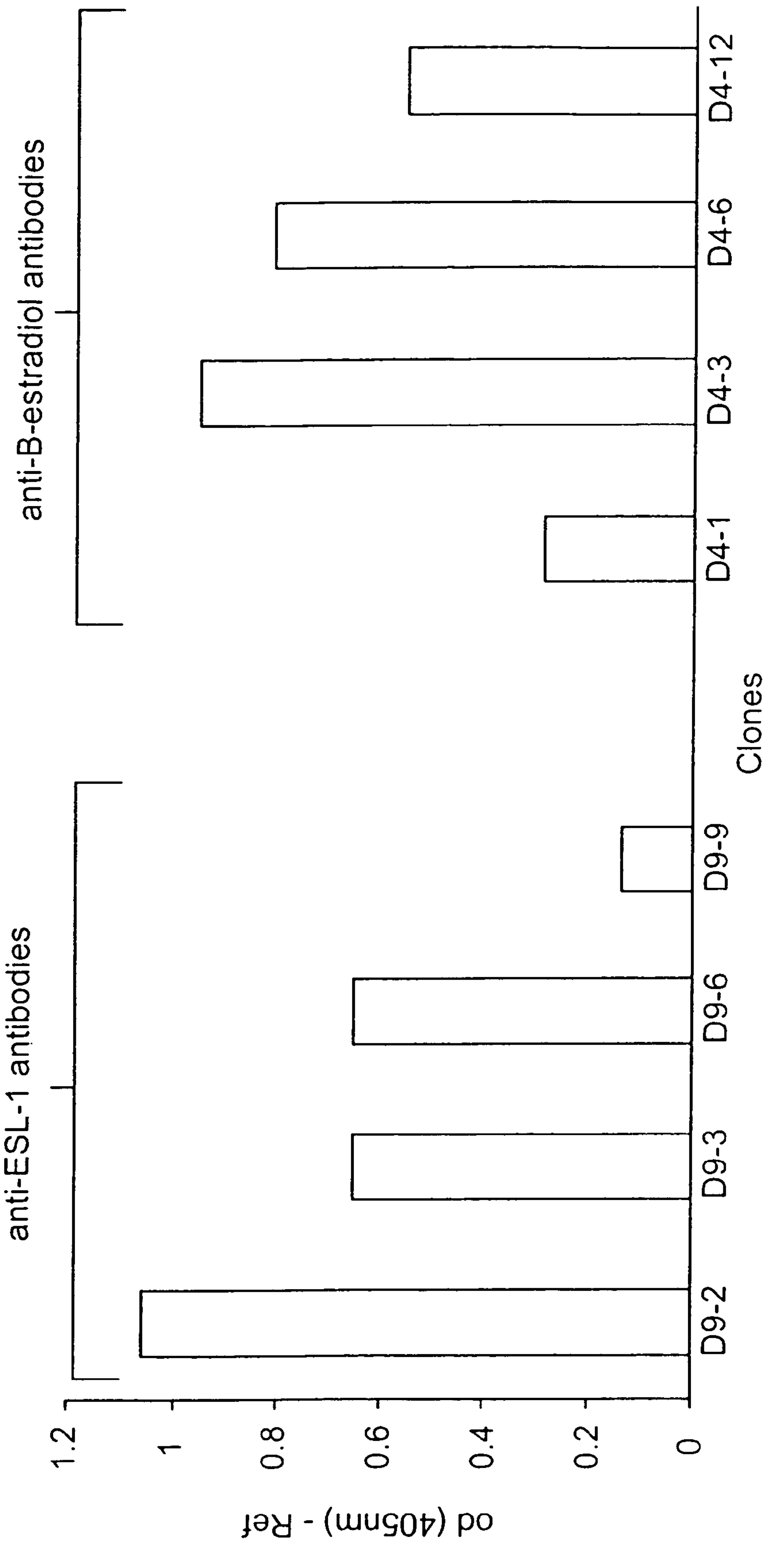

FIG. 18: ELISA of selected ESL-1 and .beta.-estradiol binding clones.

Figure 19:
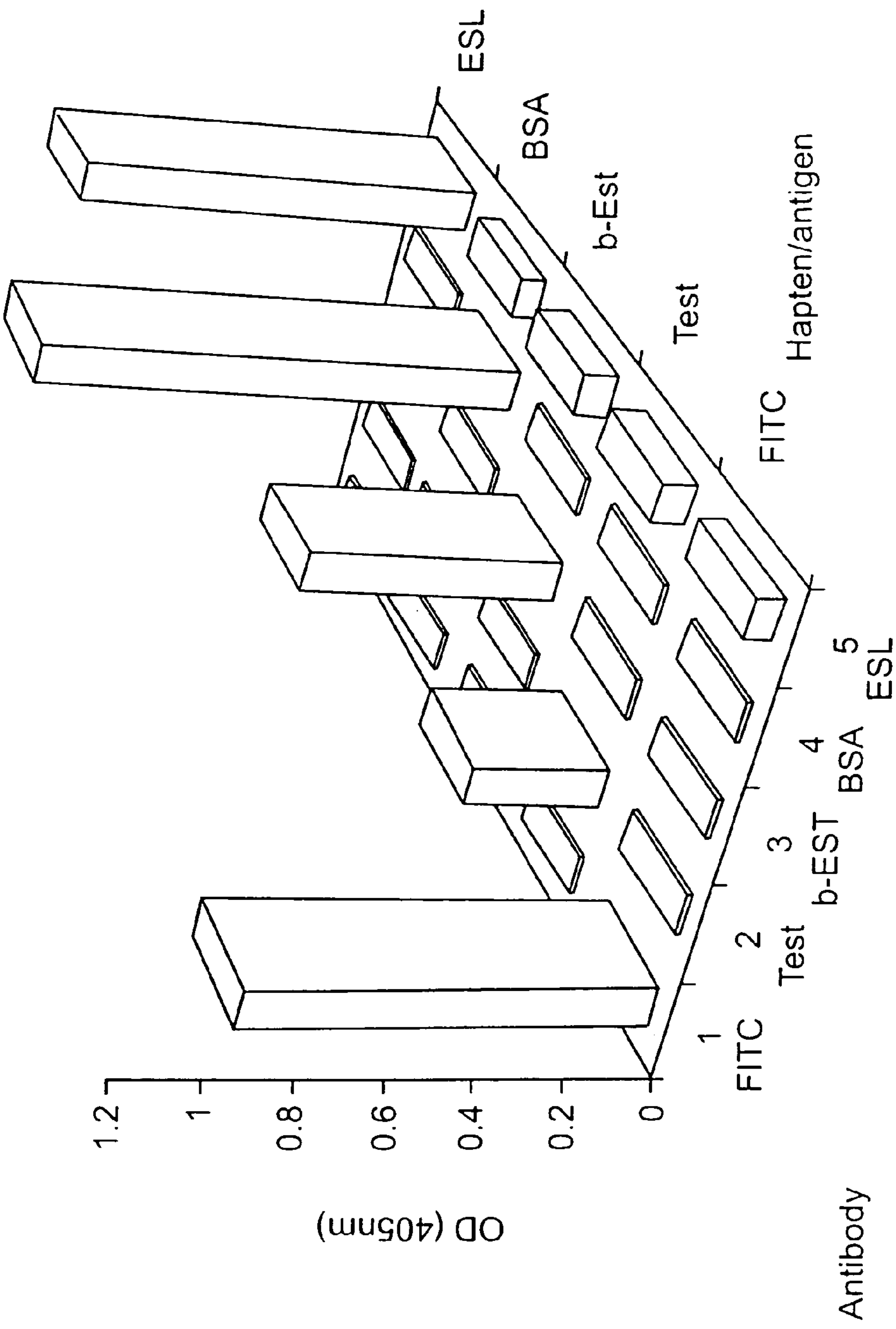

FIG. 19: Selectivity and cross-reactivity of HuCAL antibodies: in the diagonal specific binding of HuCAL antibodies can be seen, off-diagonal signals show non-specific cross-reactivity.

FIG. 20: Sequencing results of the heavy chain CDR3s of independent clones after 3 rounds of panning against p-estradiol-BSA, translated into the corresponding amino acid sequences (SEQ ID NOS 219-230 respectively) (position 93 to 102, Kabat numbering). One clone is derived from the 10mer library.

FIG. 21: Sequencing results of the heavy chain CDR3s of independent clones after 3 rounds of panning against testosterone-BSA, translated into the corresponding amino acid sequences (SEQ ID NOS 231-236, respectively) (position 93 to 102, Kabat numbering).

FIG. 22: Sequencing results of the heavy chain CDR3s of independent clones after 3 rounds of panning against lymphotoxin-p, translated into the corresponding amino acid sequences (SEQ ID NOS 237-244, respectively) (position 93 to 102, Kabat numbering). One clone comprises a 14mer CDR, presumably introduced by incomplete coupling of the trinucleotide mixture during oligonucleotide synthesis.

FIG. 23: Sequencing results of the heavy chain CDR3s of independent clones after 3 rounds of panning against ESL-1, translated into the corresponding amino acid sequences (SEQ ID NOS 245-256, respectively) (position 93 to 102, Kabat numbering). Two clones are derived from the 10mer library. One clone comprises a 16mer CDR, presumably introduced by chain elongation during oligonucleotide synthesis using trinucleotides.

FIG. 24: Sequencing results of the heavy chain CDR3s of independent clones after 3 rounds of panning against BSA, translated into the corresponding amino acid sequences (SEQ ID NOS 257-262, respectively) (position 93 to 102, Kabat numbering).

Figure 25A:
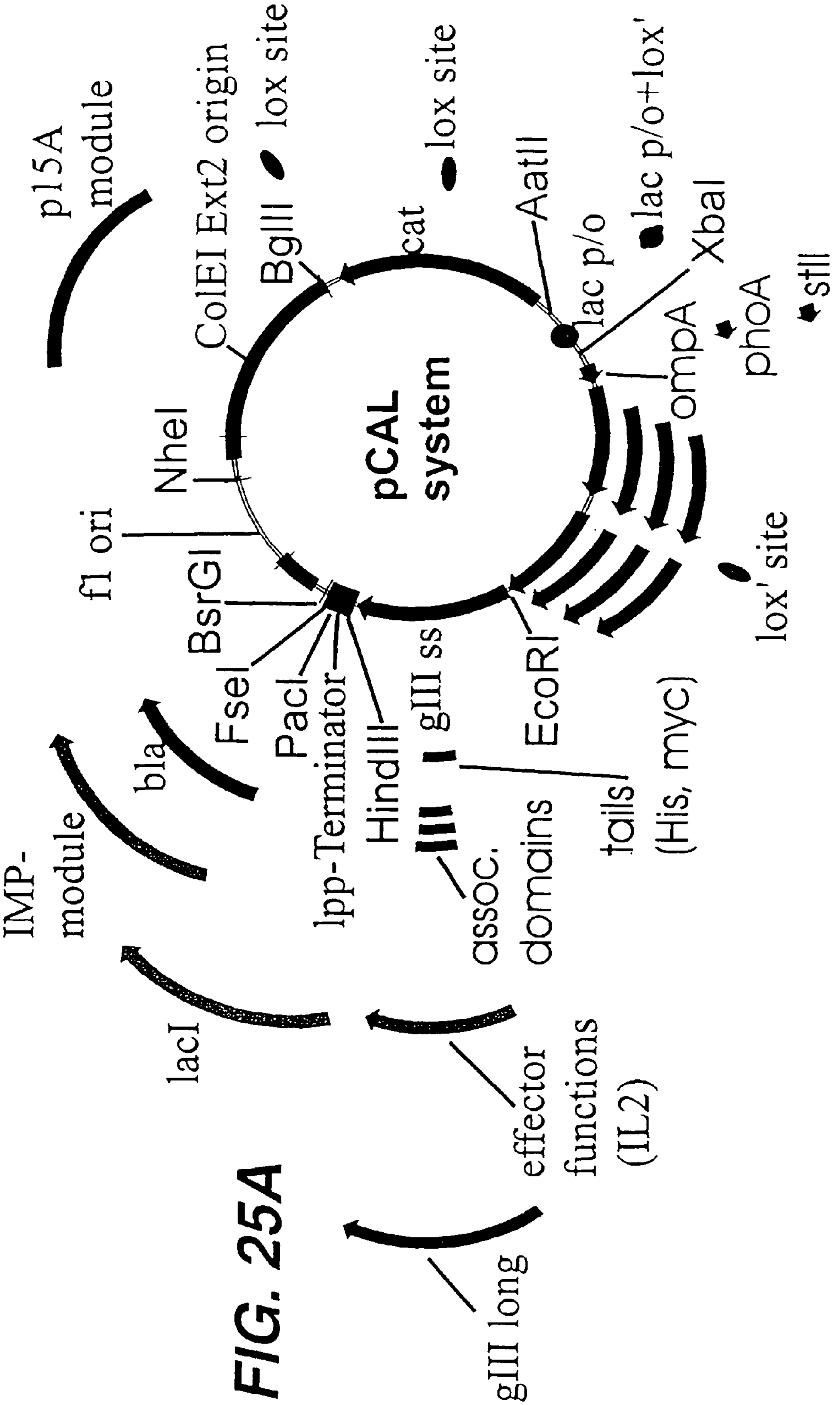

FIG. 25A: Schematic representation of the modular pCAL vector system.

FIGS. 25B-25C: List of restriction sites already used in or suitable for the modular HuCAL genes and pCAL vector system.

FIGS. 26A-26D: List of the modular vector elements for the pCAL vector series: shown are only those restriction sites which are part of the modular system.

Figure 27A:
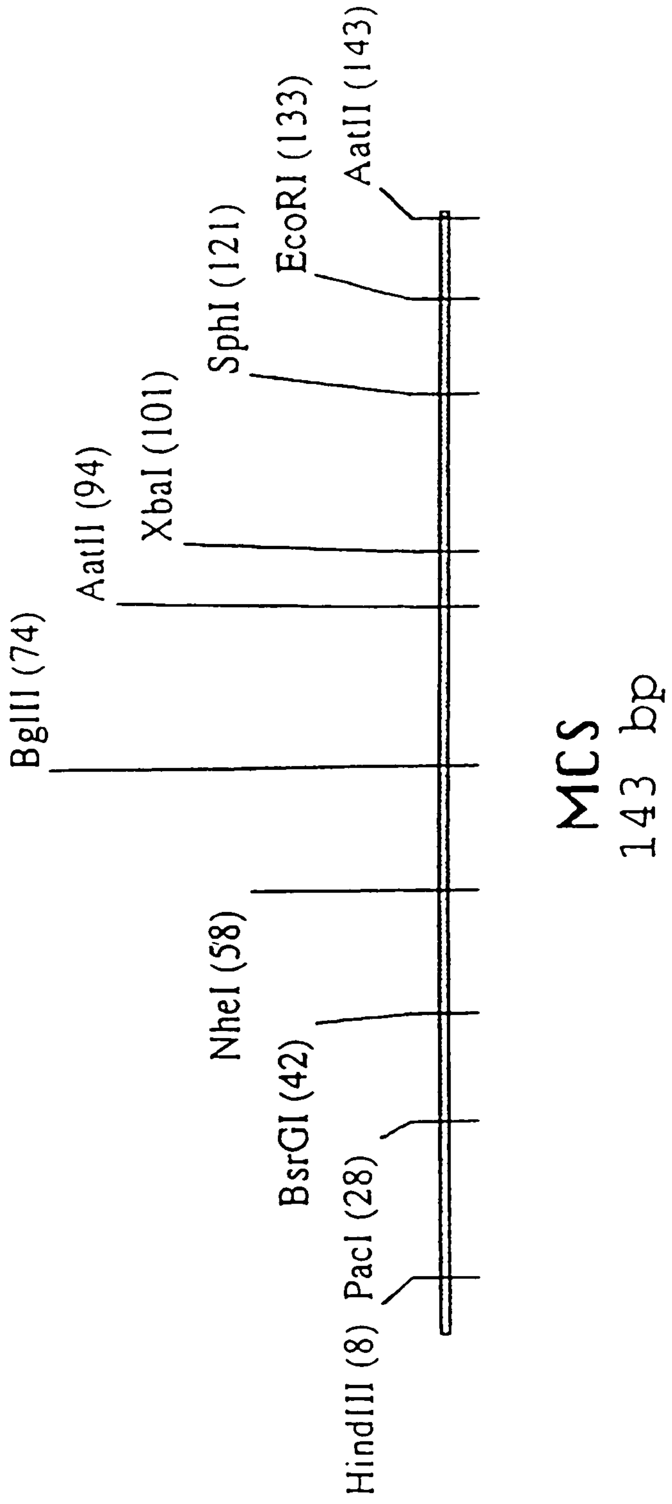
Figure 28A:
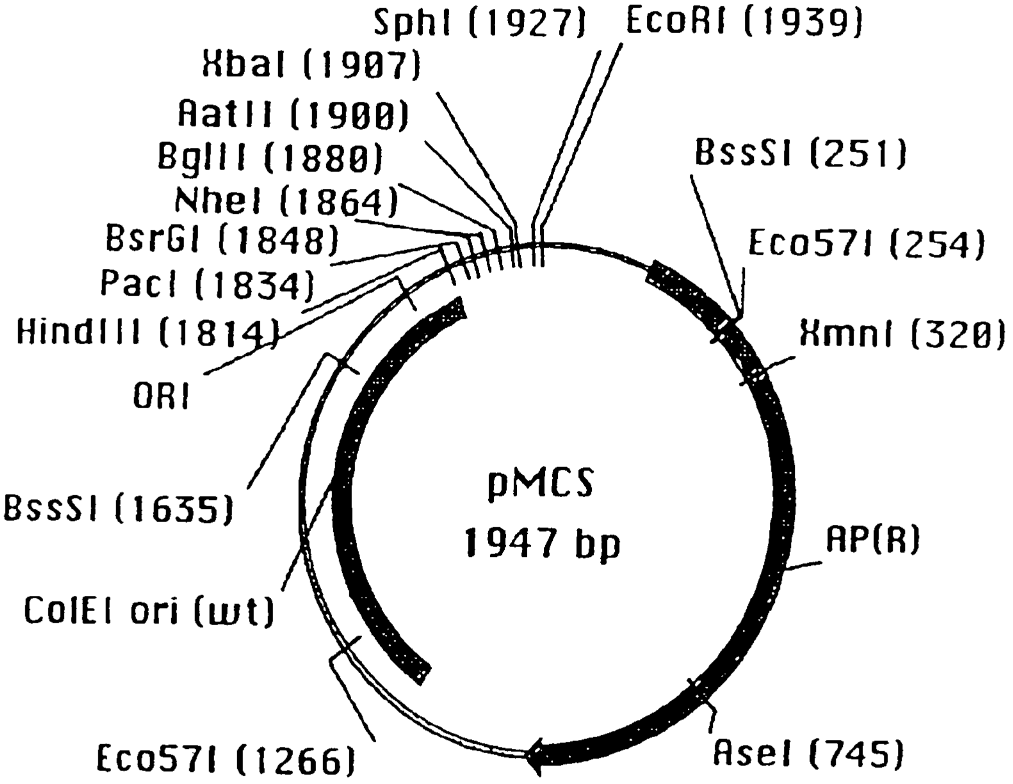

FIGS. 27A-27B: Functional map and sequence (SEQ ID NO: 263) of the multi-cloning site module (MCS).

FIGS. 28A-28G: Functional map and sequence (SEQ ID NO: 264-265, respectively) of the pMCS cloning vector series.

Figure 29A:
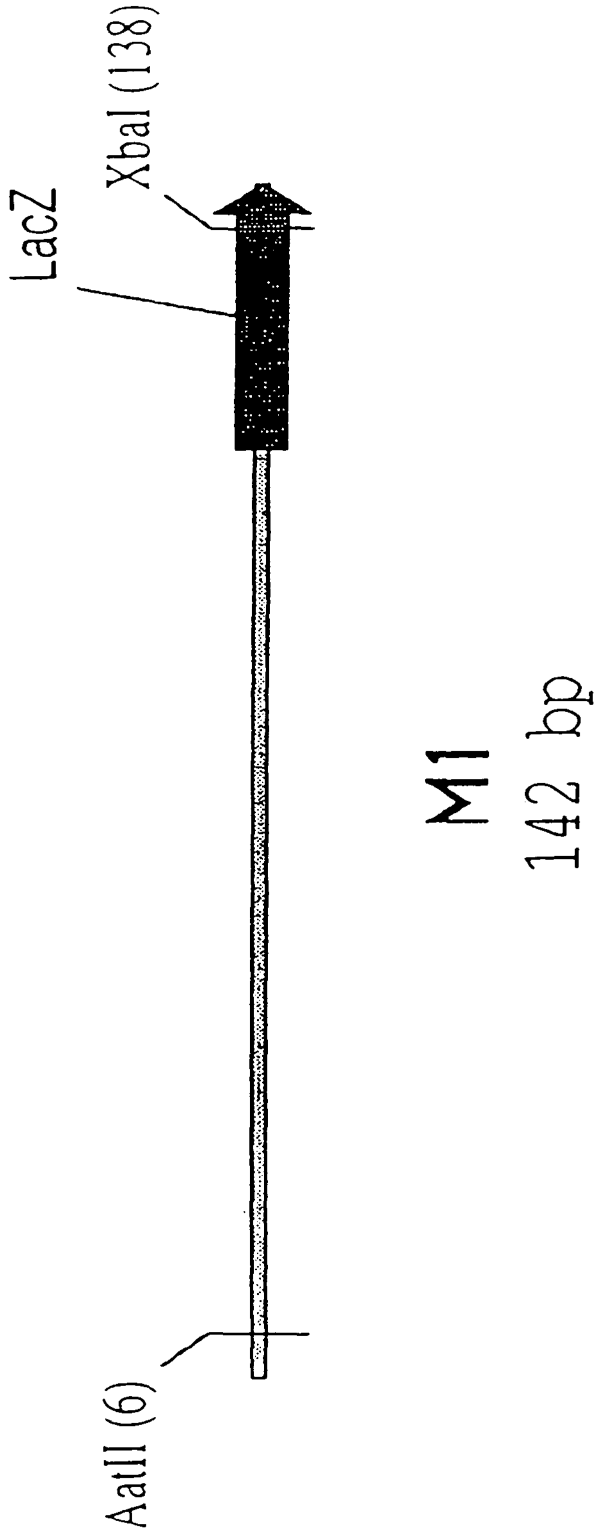

FIGS. 29A-29B: Functional map and sequence (SEQ ID NO: 266) of the pCAL module M1 (see FIGS. 26A-26D).

Figure 30A:
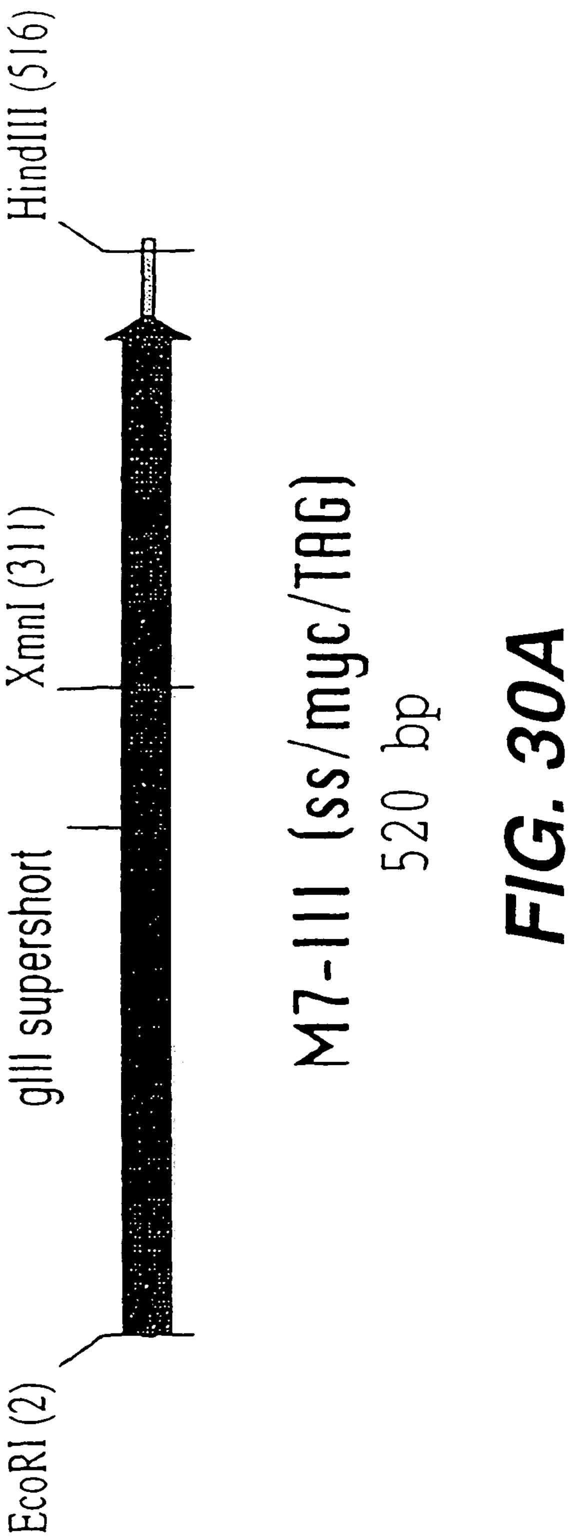

FIGS. 30A-30C: Functional map and sequence (SEQ ID NOS 267-268, respectively) of the pCAL module M7-III (see FIGS. 26A-26D).

Figure 31A:
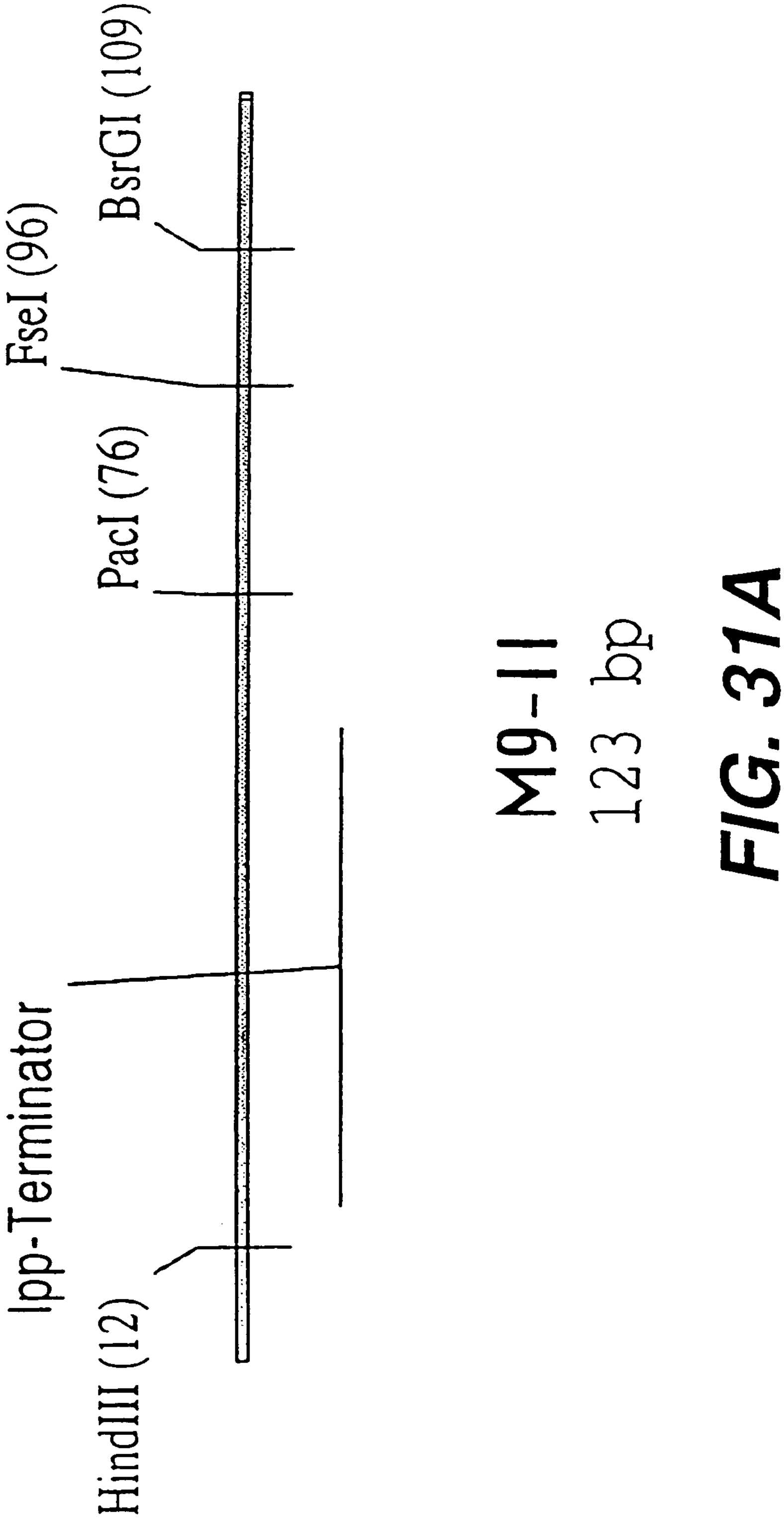

FIGS. 31A-31 B: Functional map and sequence (SEQ ID NO: 269) of the pCAL module M9-II (see FIGS. 26A-26D).

Figure 32A:
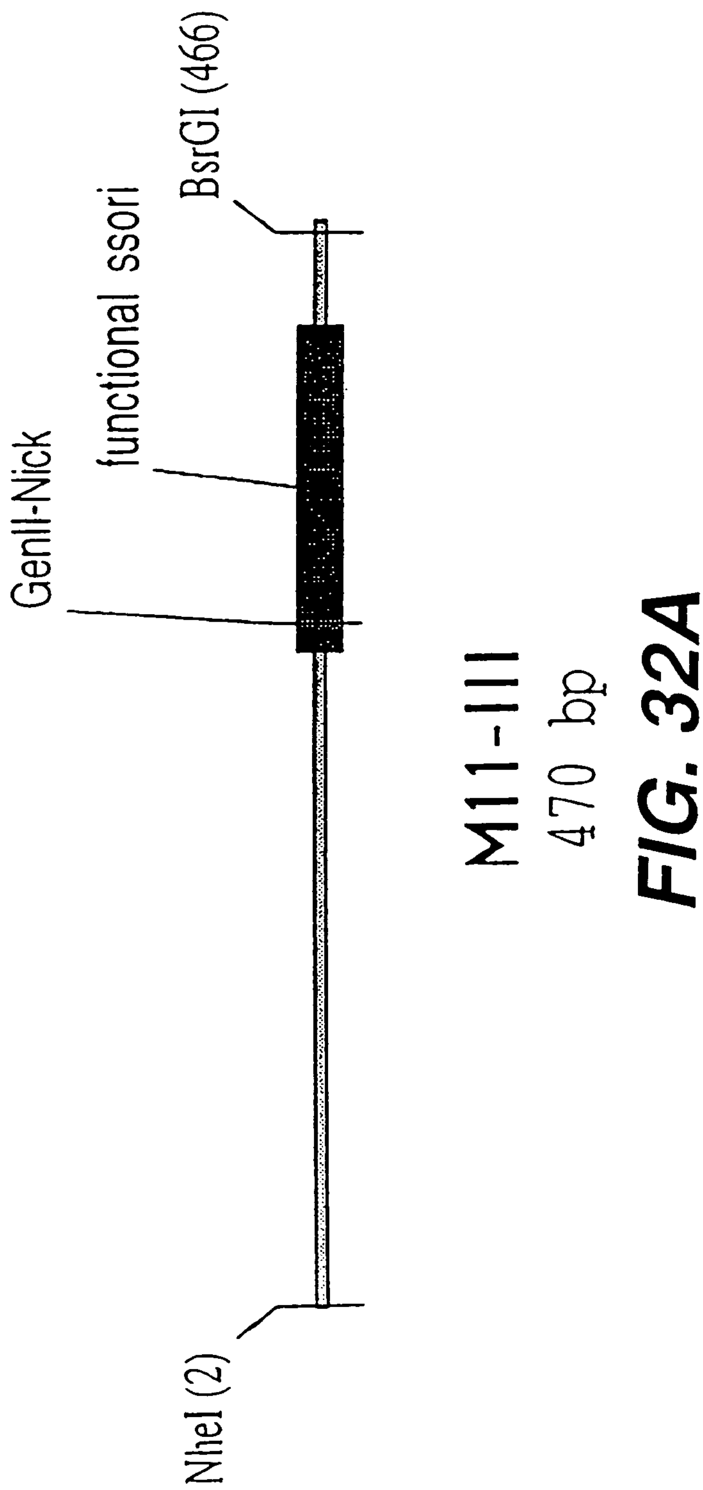
Figure 33A:
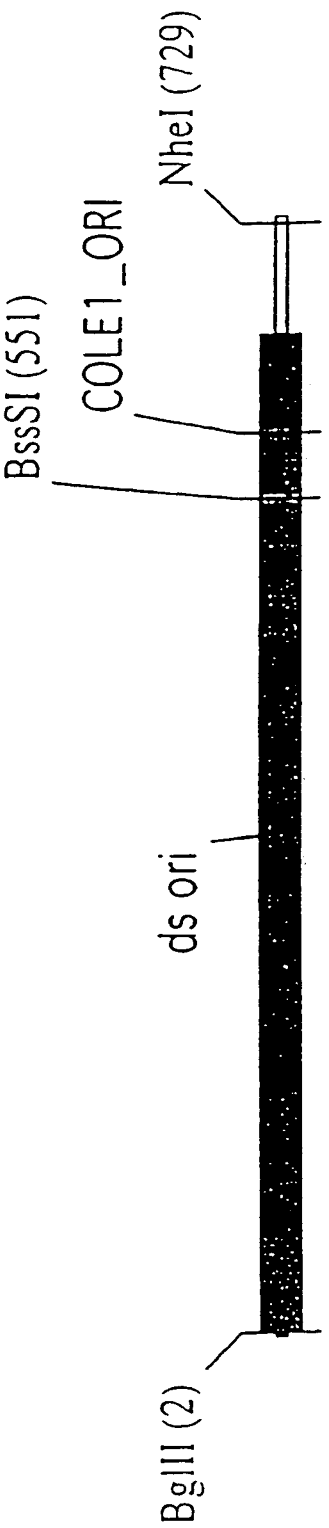
Figure 34A:
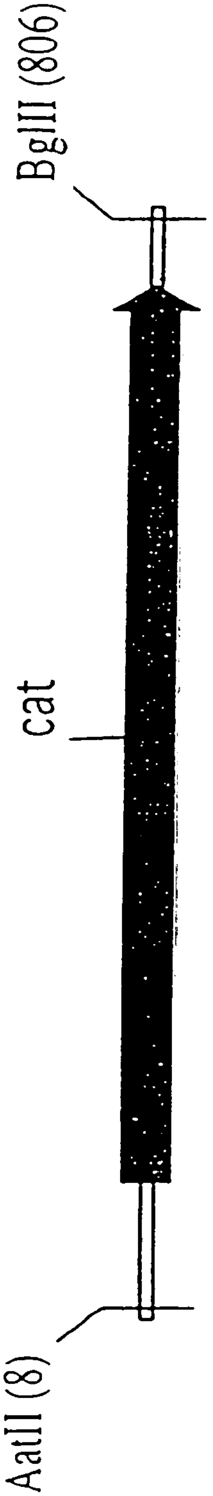

FIGS. 32A-32C: Functional map and sequence (SEQ ID NO: 270) of the pCAL module M11-II (see FIGS. 26A-26D).

FIGS. 33A-33D: Functional map and sequence (SEQ ID NO: 271) of the pCAL module M14-Ext2 (see FIGS. 26A-26D).

Figure 34D:
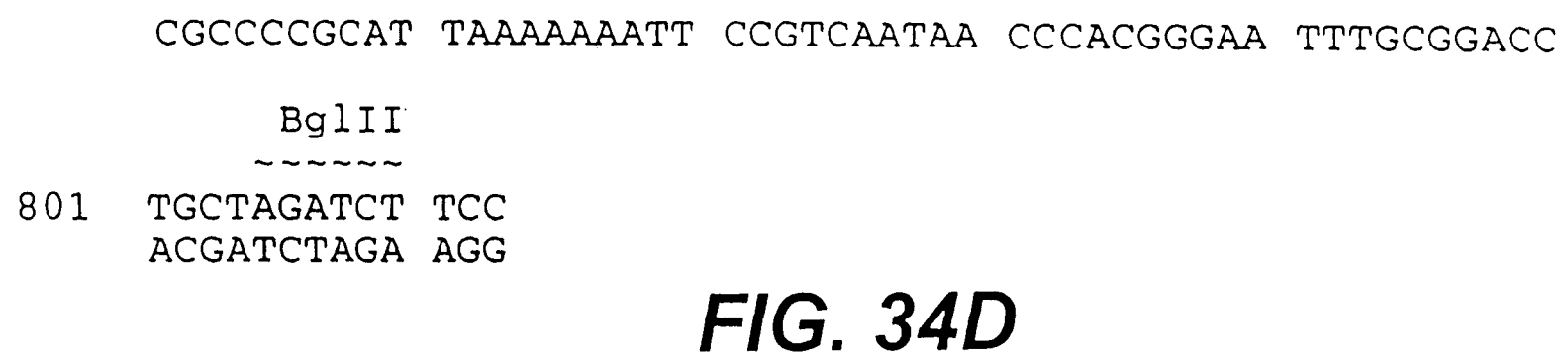

FIGS. 34A-34D: Functional map and sequence (SEQ ID NOS 272-273, respectively) of the pCAL module M17 (see FIGS. 26A-26D).

FIGS. 35A-35I: Functional map and sequence (SEQ ID NOS 274-276, respectively) module vector pCAL4.

FIGS. 35J-35XXX: Functional maps and sequences (SEQ ID NOS 277-300, respectively) of additional pCAL modules (M2, M3, M7I, M711, M8, M1011, M111I, M12, M13, M19, M20, M21, M41) and of low-copy number plasmid vectors (pCALO1 to pCALO3).

FIGS. 35YYY-35CCCC: List of oligonucleotides and primers (SEQ ID NOS 301-360, respectively) used for synthesis of pCAL vector modules.

FIGS. 36A-36F: Functional map and sequence (SEQ ID NOS 361-362, respectively) of the β-lactamase cassette for replacement of CDRs for CDR library cloning.

FIGS. 37A-37D: Oligo and primer (SEQ ID NOS 363-367, respectively) design for Vκ CDR3 libraries.

FIGS. 38A-38D: Oligo and primer (SEQ ID NOS 368-371, respectively) design for Vλ CDR3 libraries.

Figure 39:
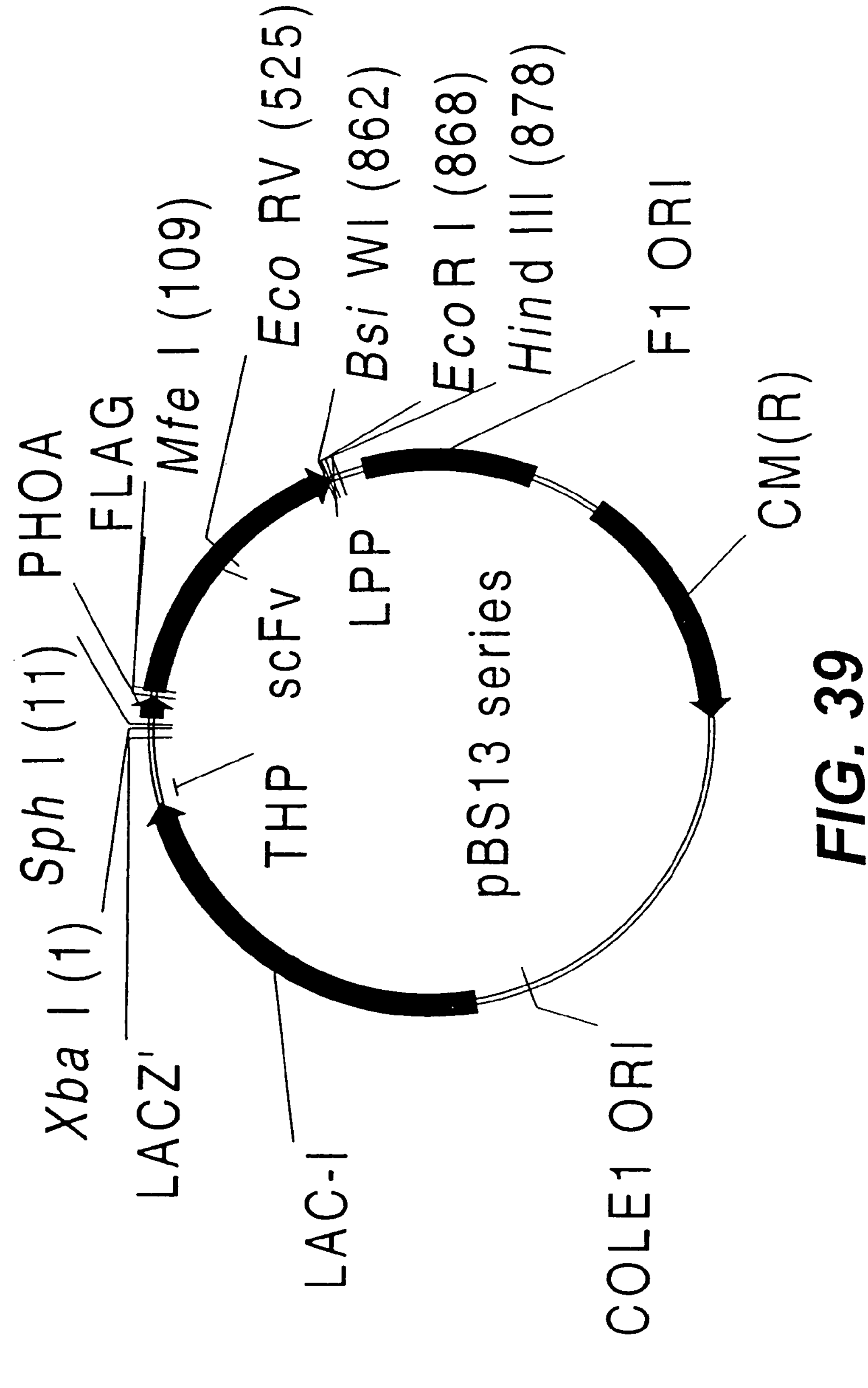

FIG. 39: Functional map of the pBS13 expression vector series.

FIGS. 40A-40B: Expression of all 49 HuCAL scFvs obtained by combining each of the 7 VH genes with each of the 7 VL genes (pBS 13, 30° C.): Values are given for the percentage of soluble vs. insoluble material, the total and the soluble amount compared to the combination H3P2, which was set to 100%. In addition, the corresponding values for the McPC603 scFv are given.

Table 1: Summary of human immunoglobulin germline sequences used for computing the germline membership of rearranged sequences. (A) kappa sequences, (B) lambda sequences and (C), heavy chain sequences. (1) The germline name used in the various calculations, (2) the references number for the corresponding sequence (see appendix for sequence related citations), (3) the family where each sequence belongs to and (4), the various names found in literature for germline genes with identical amino acid sequences Table 2: Rearranged human sequences used for the calculation of consensus sequences. (A) kappa sequences, (B) lambda sequences and (C), heavy chain sequences. The table summarized the name of the sequence (1), the length of the sequence in amino acids (2), the germline family (3) as well as the computed germline counterpart (4). The number of amino acid exchanges between the rearranged sequence and the germline sequence is tabulated in (5), and the percentage of different amino acids is given in (6). Column (7) gives the references number for the corresponding sequence (see appendix for sequence related citations).

Table 3: Assignment of rearranged V sequences to their germline counterparts. (A) kappa sequences, (B) lambda sequences and (C), heavy chain sequences. The germline genes are tabulated according to their family (1), and the number of rearranged genes found for every germline gene is given in (2).

Table 4: Computation of the consensus sequence of the rearranged V kappa sequences. (A) (SEQ ID NO: 14), V kappa subgroup 1, (B) (SEQ ID NO: 15), V kappa subgroup 2, (C) (SEQ ID NO: 16), V kappa subgroup 3 and (D) (SEQ ID NO: 17), V kappa subgroup 4. The number of each amino acid found at each position is tabulated together with the statistical analysis data. (1) Amino acids are given with their standard one-letter abbreviations (and B means D or N, Z means E or Q and X means any amino acid). The statistical analysis summarizes the number of sequences found at each position (2), the number of occurrences of the most common amino acid (3), the amino acid residue which is most common at this position (4), the relative frequency of the occurrence of the most common amino acid (5) and the number of different amino acids found at each position (6).

Table 5: Computation of the consensus sequence of the rearranged V lambda sequences. (A) (SEQ ID NO: 18), V lambda subgroup 1, (B) (SEQ ID NO: 19), V lambda subgroup 2, and (C) (SEQ ID NO: 20), V lambda subgroup 3. The number of each amino acid found at each position is tabulated together with the statistical analysis of the data. Abbreviations are the same as in Table 4.

Table 6: Computation of the consensus sequence of the rearranged V heavy chain sequences. (A) (SEQ ID NO: 21), V heavy chain subgroup 1A, (B) (SEQ ID NO: 22), V heavy chain subgroup 1 B, (C) (SEQ ID NO: 23), V heavy chain subgroup 2, (D) (SEQ ID NO: 24), V heavy chain subgroup 3, (E) (SEQ ID NO: 25), V heavy chain subgroup 4, (F) (SEQ ID NO: 26), V heavy chain subgroup 5, and (G) (SEQ ID NO: 27), V heavy chain subgroup 6. The number of each amino acid found at each position is tabulated together with the statistical analysis of the data. Abbreviations are the same as in Table 4.

EXAMPLES

Example 1

Design of a Synthetic Human Combinatorial Antibody Library (HuCAL)

The following example describes the design of a fully synthetic human combinatorial antibody library (HuCAL), based on consensus sequences of the human immunoglobulin repertoire, and the synthesis of the consensus genes. The general procedure is outlined in FIG. 1.

1.1 Sequence Database 1.1.1 Collection and Alignment of Human Immunoglobulin Sequences In a first step, sequences of variable domains of human immunoglobulins have been collected and divided into three sub bases: V heavy chain (VH), V kappa (Vκ) and V lambda (Vλ). For each sequence, the gene sequence was then translated into the corresponding amino acid sequence. Subsequently, all amino acid sequences were aligned according to Kabat et al. (1991). In the case of Vλ sequences, the numbering system of Chuchana et al. (1990) was used. Each of the three main databases was then divided into two further sub bases: the first sub base contained all sequences derived from rearranged V genes, where more than 70 positions of the sequence were known. The second sub base contained all germline gene segments (without the D- and J-minigenes; pseudogenes with internal stop codons were also removed). In all cases, where germline sequences with identical amino acid sequence but different names were found, only one sequence was used (see Table 1). The final databases of rearranged sequences contained 386, 149 and 674 entries for Vκ, Vλ and VH, respectively. The final databases of germline sequences contained 48, 20 and 141 entries for Vκ, Vλ and VH, respectively.

1.1.2 Assignment of Sequences to Subgroups

The sequences in the three germline databases where then grouped according to sequence homology (see also Tomlinson et al., 1992, Williams & Winter, 1993, and Cox et al., 1994). In the case of Vκ, 7 families could be established. Vλ was divided into 8 families and VH into 6 families. The VH germline genes of the VH7 family (Van Dijk et al., 1993) were grouped into the VH1 family, since the genes of the two families are highly homologous. Each family contained different numbers of germline genes, varying from 1 (for example VH6) to 47 (VH3).

1.2 Analysis of Sequences 1.2.1 Computation of Germline Membership

For each of the 1209 amino acid sequences in the databases of rearranged genes, the nearest germline counterpart, i.e. the germline sequence with the smallest number of amino acid differences was then calculated. After the germline counterpart was found, the number of somatic mutations which occurred in the rearranged gene and which led to amino acid exchanges could be tabulated. In 140 cases, the germline counterpart could not be calculated exactly, because more than one germline gene was found with an identical number of amino acid exchanges. These rearranged sequences were removed from the database. In a few cases, the number of amino acid exchanges was found to be unusually large (>20 for VL and >25 for VH), indicating either heavily mutated rearranged genes or derivation from germline genes not present in the database. Since it was not possible to distinguish between these two possibilities, these sequences were also removed from the database. Finally, 12 rearranged sequences were removed from the database because they were found to have very unusual CDR lengths and composition or unusual amino acids at canonical positions (see below). In summary, 1023 rearranged sequences out of 1209 (85%) could be clearly assigned to their germline counterparts (see Table 2).

After this calculation, every rearranged gene could be arranged in one of the families established for the germline genes. Now the usage of each germline gene, i.e. the number of rearranged genes which originate from each germline gene, could be calculated (see Table 2). It was found that the usage was strongly biased towards a subset of germline genes, whereas most of the germline genes were not present as rearranged genes in the database and therefore apparently not used in the immune system (Table 3). This observation had already been reported in the case of Vκ (Cox, et al., 1994). All germline gene families, where no or only very few rearranged counterparts could be assigned, were removed from the database, leaving 4 Vκ, 3 Vλ, and 6 VH families.

1.2.2 Analysis of CDR Conformations

The conformation of the antigen binding loops of antibody molecules, the CDRs, is strongly dependent on both the length of the CDRs and the amino acid residues located at the so-called canonical positions (Chothia & Lesk, 1987). It has been found that only a few canonical structures exist, which determine the structural repertoire of the immunoglobulin variable domains (Chothia et al., 1989). The canonical amino acid positions can be found in CDR as well as framework regions. The 13 used germline families defined above (7 VL and 6 VH) were now analyzed for their canonical structures in order to define the structural repertoire encoded in these families.

In 3 of the 4 Vκ families (Vκ1, 2 and 4), one different type of CDR1 conformation could be defined for every family. The family Vκ3 showed two types of CDR1 conformation: one type which was identical to Vκ1 and one type only found in Vκ3. All Vκ CDR2s used the same type of canonical structure. The CDR3 conformation is not encoded in the germline gene segments. Therefore, the 4 Vκ families defined by sequence homology and usage corresponded also to 4 types of canonical structures found in Vκ germline genes.

The 3 Vλ families defined above showed 3 types of CDR1 conformation, each family with one unique type. The Vλ1 family contained 2 different CDR1 lengths (13 and 14 amino acids), but identical canonical residues, and it is thought that both lengths adopt the same canonical conformation (Chothia & Lesk, 1987). In the CDR2 of the used Vλ germlines, only one canonical conformation exists, and the CDR3 conformation is not encoded in the germline gene segments. Therefore, the 3 Vλ families defined by sequence homology and usage corresponded also to 3 types of canonical structures.

The structural repertoire of the human VH sequences was analyzed in detail by Chothia et al., 1992. In total, 3 conformations of CDR1 (H1-1, H1-2 and H1-3) and 6 conformations of CDR2 (H2-1, H2-2, H2-3, H2-4, H2-5 and H2-x) could be defined. Since the CDR3 is encoded in the D- and J-minigene segments, no particular canonical residues are defined for this CDR.

All the members of the VH1 family defined above contained the CDR1 conformation H1-1, but differed in their CDR2 conformation: the H2-2 conformation was found in 6 germline genes, whereas the conformation H2-3 was found in 8 germline genes. Since the two types of CDR2 conformations are defined by different types of amino acid at the framework position 72, the VH1 family was divided into two subfamilies: VH1A with CDR2 conformation H2-2 and VH1B with the conformation H2-3. The members of the VH2 family all had the conformations H1-3 and H2-1 in CDR1 and CDR2, respectively. The CDR1 conformation of the VH3 members was found in all cases to be H1-1, but 4 different types were found in CDR2 (H2-1, H2-3, H2-4 and H2-x). In these CDR2 conformations, the canonical framework residue 71 is always defined by an arginine. Therefore, it was not necessary to divide the VH3 family into subfamilies, since the 4 types of CDR2 conformations were defined solely by the CDR2 itself. The same was true for the VH4 family. Here, all 3 types of CDR1 conformations were found, but since the CDR1 conformation was defined by the CDR itself (the canonical framework residue 26 was found to be glycine in all cases), no subdivisions were necessary. The CDR2 conformation of the VH4 members was found to be H2-1 in all cases. All members of the VH5 family were found to have the conformation H1-1 and H2-2, respectively. The single germline gene of the VH6 family had the conformations H1-3 and H2-5 in CDR1 and CDR2, respectively.

In summary, all possible CDR conformations of the Vκ and Vλ genes were present in the 7 families defined by sequence comparison. From the 12 different CDR conformations found in the used VH germline genes, 7 could be covered by dividing the family VH1 into two subfamilies, thereby creating 7 VH families. The remaining 5 CDR conformations (3 in the VH3 and 2 in the VH4 family) were defined by the CDRs themselves and could be created during the construction of CDR libraries. Therefore, the structural repertoire of the used human V genes could be covered by 49 (7×7) different frameworks.

1.2.3 Computation of Consensus Sequences

The 14 databases of rearranged sequences (4 Vκ, 3 Vλ and 7 VH) were used to compute the HuCAL consensus sequences of each subgroup (4 HuCAL-Vκ, 3 HuCAL-Vλ, 7 HuCAL-VH, see Table 4, 5 and 6). This was done by counting the number of amino acid residues used at each position (position variability) and subsequently identifying the amino acid residue most frequently used at each position. By using the rearranged sequences instead of the used germline sequences for the calculation of the consensus, the consensus was weighted according to the frequency of usage. Additionally, frequently mutated and highly conserved positions could be identified. The consensus sequences were cross-checked with the consensus of the germline families to see whether the rearranged sequences were biased at certain positions towards amino acid residues which do not occur in the collected germline sequences, but this was found not to be the case. Subsequently, the number of differences of each of the 14 consensus sequences to each of the germline sequences found in each specific family was calculated. The overall deviation from the most homologous germline sequence was found to be 2.4 amino acid residues (s.d.=2.7), ensuring that the "artificial" consensus sequences can still be considered as truly human sequences as far as immunogenicity is concerned.

1.3 Structural Analysis

So far, only sequence information was used to design the consensus sequences. Since it was possible that during the calculation certain artificial combinations of amino acid residues have been created, which are located far away in the sequence but have contacts to each other in the three dimensional structure, leading to destabilized or even misfolded frameworks, the 14 consensus sequences were analyzed according to their structural properties.

It was rationalized that all rearranged sequences present in the database correspond to functional and therefore correctly folded antibody molecules. Hence, the most homologous rearranged sequence was calculated for each consensus sequence. The positions where the consensus differed from the rearranged sequence were identified as potential "artificial residues" and inspected.

The inspection itself was done in two directions. First, the local sequence stretch around each potentially "artificial residue" was compared with the corresponding stretch of all the rearranged sequences. If this stretch was found to be truly artificial, i.e. never occurred in any of the rearranged sequences, the critical residue was converted into the second most common amino acid found at this position and analyzed again. Second, the potentially "artificial residues" were analyzed for their long range interactions. This was done by collecting all available structures of human antibody variable domains from the corresponding PDB files and calculating for every structure the number and type of interactions each amino acid residue established to each side-chain. These "interaction maps" were used to analyze the probable side-chain/side-chain interactions of the potentially "artificial residues". As a result of this analysis, the following residues were exchanged (given is the name of the gene, the position according to Kabat's numbering scheme, the amino acid found at this position as the most abundant one and the amino acid which was used instead):

VH2: $S_{65}T$

Vκ1: $N_{34}A$,

Vκ3: $G_9A$, $D_{60}A$, $R_{77}S$

Vλ3: V78T 1.4 Design of CDR Sequences

The process described above provided the complete consensus sequences derived solely from the databases of rearranged sequences. It was rationalized that the CDR1 and CDR2 regions should be taken from the databases of used germline sequences, since the CDRs of rearranged and mutated sequences are biased towards their particular antigens. Moreover, the germline CDR sequences are known to allow binding to a variety of antigens in the primary immune response, where only CDR3 is varied. Therefore, the consensus CDRs obtained from the calculations described above were replaced by germline CDRs in the case of VH and Vκ. In the case of Vλ, a few amino acid exchanges were introduced in some of the chosen germline CDRs in order to avoid possible protease cleavage sites as well as possible structural constraints.

The CDRs of following germline genes have been chosen:

| HuCAL gene | CDR1 | CDR2 |
|---|---|---|
| HuCAL-VH1A | VH1-12-1 | VH1-12-1 |
| HuCAL-VH1B | VH1-13-16 | VH1-13-6, -7, -8, -9 |
| HuCAL-VH2 | VH2-31-10, -11, -12, -13 | VH2-31-3, -4 |
| HuCAL-VH3 | VH3-13-8, -9, -10 | VH3-13-8, -9, -10 |
| HuCAL-VH4 | VH4-11-7 to -14 | VH4-11-8, -9, -11, -12, -14, -16 VH4-31-17, -18, -19, -20 |
| HuCAL-VH5 | VH5-12-1, -2 | VH5-12-1, -2 |
| HuCAL-VH6 | VH6-35-1 | VH6-35-1 |
| HuCAL-Vκ1 | Vκ1-14, -15 | Vκ1-2, -3, -4, -5, -7, -8, -12, -13, -18, -19 |
| HuCAL-Vκ2 | Vκ2-6 | Vκ2-6 |
| HuCAL-Vκ3 | Vκ3-1, -4 | Vκ3-4 |
| HuCAL-Vκ4 | Vκ4-1 | Vκ4-1 |
| HuCAL-Vλ1 | HUMLV117, DPL5 | DPL5 |
| HuCAL-Vλ2 | DPL11, DPL12 | DPL12 |
| HuCAL-Vλ3 | DPL23 | HUMLV318 |

In the case of the CDR3s, any sequence could be chosen since these CDRs were planned to be the first to be replaced by oligonucleotide libraries. In order to study the expression and folding behavior of the consensus sequences in *E. coli*, it would be useful to have all sequences with the same CDR3, since the influence of the CDR3s on the folding behavior would then be identical in all cases. The dummy sequences QQHYTTPP (see, for instance, positions 89-96 of SEQ ID NO: 28 and positions 88-95 of SEQ ID NO: 34) and ARWGGDGFYAMDY (positions 97-109 of SEQ ID NOS 35 & 36) were selected for the VL chains (kappa and lambda) and for the VH chains, respectively. These sequences are known to be compatible with antibody folding in *E. coli* (Carter et al., 1992).

1.5 Gene Design

The final outcome of the process described above was a collection of 14 HuCAL amino acid sequences, which represent the frequently used structural antibody repertoire of the human immune system (see FIG. 2). These sequences were back-translated into DNA sequences. In a first step, the back-translation was done using only codons which are known to be frequently used in *E. coli*. These gene sequences were then used for creating a database of all possible restriction endonuclease sites, which could be introduced without changing the corresponding amino acid sequences. Using this database, cleavage sites were selected which were located at the flanking regions of all sub-elements of the genes (CDRs and framework regions) and which could be introduced in all HuCAL VH, Vκ or Vλ genes simultaneously at the same position. In a few cases it was not possible to find cleavage sites for all genes of a subgroup. When this happened, the amino acid sequence was changed, if this was possible according to the available sequence and structural information. This exchange was then analyzed again as described above. In total, the following 6 amino acid residues were exchanged during this design (given is the name of the gene, the position according to Kabat's numbering scheme, the amino acid found at this position as the most abundant one and the amino acid which was used instead):

VH2: $T_3Q$

VH6: $S_{47}G$

Vκ3: $E_1D$, $I_{58}V$

Vκ4: $K_{24}R$

Vλ3: $T_{22}S$

In one case (5'-end of VH framework 3) it was not possible to identify a single cleavage site for all 7 VH genes. Two different type of cleavage sites were used instead: BstEII for HuCAL VH1A, VH1B, VH4 and VH5, and NspV for HuCAL VH2, VH3, VH4 and VH6.

Several restriction endonuclease sites were identified, which were not located at the flanking regions of the sub-elements but which could be introduced in every gene of a given group without changing the amino acid sequence. These cleavage sites were also introduced in order to make the system more flexible for further improvements. Finally, all but one remaining restriction endonuclease sites were removed in every gene sequence. The single cleavage site, which was not removed was different in all genes of a subgroup and could be therefore used as a "fingerprint" site to ease the identification of the different genes by restriction digest. The designed genes, together with the corresponding amino acid sequences and the group-specific restriction endonuclease sites are shown in FIGS. 3, 4 and 5, respectively.

1.6 Gene Synthesis and Cloning

The consensus genes were synthesized using the method described by Prodromou & Pearl, 1992, using the oligonucleotides shown in FIG. 6. Gene segments encoding the human constant domains Cκ, Cλ and CH1 were also synthesized, based on sequence information given by Kabat et al., 1991 (see FIG. 6 and FIG. 7). Since for both the CDR3 and the framework 4 gene segments identical sequences were chosen in all HuCAL Vκ, Vλ and VH genes, respectively, this part was constructed only once, together with the corresponding gene segments encoding the constant domains. The PCR products were cloned into pCR-Script KS(+) (Stratagene, Inc.) or pZErO-1 (Invitrogen, Inc.) and verified by sequencing.

Example 2

Cloning and Testing of a HuCAL-Based Antibody Library

A combination of two of the synthetic consensus genes was chosen after construction to test whether binding antibody fragments can be isolated from a library based on these two consensus frameworks. The two genes were cloned as a single-chain Fv (scFv) fragment, and a VH-CDR3 library was inserted. In order to test the library for the presence of functional antibody molecules, a selection procedure was carried out using the small hapten fluorescein bound to BSA (FITC-BSA) as antigen.

2.1 Cloning of the HuCAL VH3-Vk2 scFv Fragment

In order to test the design of the consensus genes, one randomly chosen combination of synthetic light and heavy gene (HuCAL-Vx2 and HuCAL-VH3) was used for the construction of a single-chain antibody (scFv) fragment. Briefly, the gene segments encoding the VH3 consensus gene and the CH1 gene segment including the CDR3-framework 4 region, as well as the VK2 consensus gene and the CK gene segment including the CDR3-framework 4 region were assembled yielding the gene for the VH3-CH1 Fd fragment and the gene encoding the VK2-Cκ light chain, respectively. The CH1 gene segment was then replaced by an oligonucleotide (SEQ ID NOS 2 & 3, respectively) cassette encoding a 20-mer peptide linker (SEQ ID NO: 1) with the sequence AGGGSGGGGSGGGGSGGGGS. The two oligonucleotides encoding this linker were 5'-TCAGCGGGTGGCG-GTTCTGGCGGCGGTGGGAGCGGTG GCGGTGGT-TCTGGCGGTGGTGGTTCCGATATCGGTCCACGTACGG-3' and 5'-AATTCCGTACGTGGACCGATATCGGAAC-CACCACCGCCAGA ACCACCGCCACCGCTCCCAC-CGCCGCCAGAACCGCCACCCGC-3', respectively. Finally, the HuCAL-Vκ2 gene was inserted via EcoRV and BsiWI into the plasmid encoding the HuCAL-VH3-linker fusion, leading to the final gene HuCAL-VH3-Vx2, which encoded the two consensus sequences in the single-chain format VH-linker-VL. The complete coding sequence is shown in FIG. 8.

2.2 Construction of a Monovalent Phage-Display Phagemid Vector pIG10.3

Phagemid pIG10.3 (FIG. 9) was constructed in order to create a phage-display system (Winter et al., 1994) for the H3κ2 scFv gene. Briefly, the EcoRI/HindIII restriction fragment in the phagemid vector pIG10 (Ge et al., 1995) was replaced by the c-myc followed by an amber codon (which encodes an glutamate in the amber-suppresser strain XL1 Blue and a stop codon in the non-suppresser strain JM83) and a truncated version of the gene III (fusion junction at codon 249, see Lowman et al., 1991) through PCR mutagenesis.

2.3 Construction of H-CDR3 Libraries

Heavy chain CDR3 libraries of two lengths (10 and 15 amino acids) were constructed using trinucleotide codon containing oligonucleotides (Virnekäs et al., 1994) as templates and the oligonucleotides complementing the flanking regions as primers. To concentrate only on the CDR3 structures that appear most often in functional antibodies, we kept the salt-bridge of $R_{H94}$ and $D_{H101}$ in the CDR3 loop. For the 15-mer library, both phenylalanine and methionine were introduced at position 100 since these two residues were found to occur quite often in human CDR3s of this length (not shown). For the same reason, valine and tyrosine were introduced at position 102. All other randomized positions contained codons for all amino acids except cystein, which was not used in the trinucleotide mixture.

The CDR3 libraries of lengths 10 and 15 were generated from the PCR fragments using oligonucleotide templates (SEQ ID NOS 4 & 5, respectively) 03HCDR103T (5'-GATACGGCCGTGTATTATTGCGCGCGT (TRI)6 GAT-TATTGGGGCCAAGGCACCCTG-3') and O3HCDR153T GATACGGCCGTGTATTATTGCGCGCGT$(TRI)_{10}$ (TTT/ATG)GAT(GTT/TAT)TGGGGCCAAGGCACCCTG-3'), and primers (SEQ ID NOS 6 & 7, respectively) O3HCDR35 (5'-GATACGGCCGTGTATTATTGC-3' and O3HCDR33 (5'-CAGGGTGCCTTGGCCCC-3'), where TRI are trinucleotide mixtures representing all amino acids without cystein, (TTT/ATG) and (GTT/TAT) are trinucleotide mixtures encoding the amino acids phenylalanine/methionine and valine/tyrosine, respectively. The potential diversity of these libraries was $4.7\times10^{7}$ and $3.4\times10^{10}$ for 10-mer and 15-mer library, respectively. The library cassettes were first synthesized from PCR amplification of the oligo templates in the presence of both primers: 25 pmol of the oligo template 03HCDR103T or 03HCDR153T, 50 pmol each of the primers O3HCDR35 and O3HCDR33, 20 nmol of dNTP, 10× buffer and 2.5 units of Pfu DNA polymerase (Stratagene) in a total volume of 100 ml for 30 cycles (1 minute at 92° C., 1 minute at 62° C. and 1 minute at 72° C.). A hot-start procedure was used. The resulting mixtures were phenol-extracted, ethanol-precipitated and digested overnight with EagI and StyI. The vector pIG10.3-sCH3κ2cat, where the EagI-StyI fragment in the vector pIG10.3-sCH3κ2 encoding the H-CDR3 was replaced by the chloramphenicol acetyltransferase gene (cat) flanked with these two sites, was similarly digested. The digested vector (35 μg) was gel-purified and ligated with 100 μg of the library cassette overnight at 16° C. The ligation mixtures were isopropanol precipitated, air-dried and the pellets were redissolved in 100 ml of ddH2O. The ligation was mixed with 1 ml of freshly prepared electrocompetent XL1 Blue on ice. 20 rounds of electroporation were performed and the transformants were diluted in SOC medium, shaken at 37° C. for 30 minutes and plated out on large LB plates (Amp/Tet/Glucose) at 37° C. for 6-9 hrs. The number of transformants (library size) was $3.2\times10^{7}$ and $2.3\times10^{7}$ for the 10-mer and the 15-mer library, respectively. The colonies were suspended in 2×YT medium (Amp/Tet/Glucose) and stored as glycerol culture. In order to test the quality of the initial library, phagemids from 24 independent colonies (12 from the 10-mer and 12 from the 15-mer library, respectively) were isolated and analyzed by restriction digestion and sequencing. The restriction analysis of the 24 phagemids indicated the presence of intact vector in all cases. Sequence analysis of these clones (see FIG. 10) indicated that 22 out of 24 contained a functional sequence in their heavy chain CDR3 regions. 1 out of 12 clones of the 10-mer library had a CDR3 of length 9 instead of 10, and 2 out of 12 clones of the 15-mer library had no open reading frame, thereby leading to a non-functional scFv; one of these two clones contained two consecutive inserts, but out of frame (data not shown). All codons introduced were presented in an even distribution.

Expression levels of individual library members were also measured. Briefly, 9 clones from each library were grown in 2×YT medium containing Amp/Tet/0.5% glucose at 37° C. overnight. Next day, the cultures were diluted into fresh medium with Amp/Tet. At an $OD_{600nm}$ of 0.4, the cultures were induced with 1 mM of IPTG and shaken at RT overnight. Then the cell pellets were suspended in 1 ml of PBS buffer+1 mM of EDTA. The suspensions were sonicated and the supernatants were separated on an SDS-PAGE under reducing conditions, blotted on nylon membrane and detected with anti-FLAG M1 antibody (see FIG. 11). From the nine clones of the 10-mer library, all express the scFv fragments. Moreover, the gene III/scFv fusion proteins were present in all cases. Among the nine clones from the 15-mer library analyzed, 6/9 (67%) led to the expression of both scFv and the gene III/scFv fusion proteins. More importantly, all clones expressing the scFvs and gene III/scFv fusions gave rise to about the same level of expression.

2.4 Biopanning

Phages displaying the antibody libraries were prepared using standard protocols. Phages derived from the 10-mer library were mixed with phages from the 15-mer library in a ratio of 20:1 ($1\times10^{10}$ cfu/well of the 10-mer and $5\times10^{8}$ cfu/well of the 15-mer phages, respectively). Subsequently, the phage solution was used for panning in ELISA plates (Maxisorp, Nunc) coated with FITC-BSA (Sigma) at concentration of 100 μg/ml in PBS at 4° C. overnight. The antigen-coated wells were blocked with 3% powder milk in PBS and the phage solutions in 1% powder milk were added to each well and the plate was shaken at RT for 1 hr. The wells were then washed with PBST and PBS (4 times each with shaking at RT for 5 minutes). The bound phages were eluted with 0.1 M triethylamine (TEA) at RT for 10 minutes. The eluted phage solutions were immediately neutralized with ½ the volume of 1 M Tris-Cl, pH 7.6. Eluted phage solutions (ca. 450 μl) were used to infect 5 ml of XL1 Blue cells at 37° C. for 30 min. The infected cultures were then plated out on large LB plates (Amp/Tet/Glucose) and allowed to grow at 37° C. until the colonies were visible. The colonies were suspended in 2×YT medium and the glycerol cultures were made as above described. This panning round was repeated twice, and in the third round elution was carried out with addition of fluorescein in a concentration of 100 μg/ml in PBS. The enrichment of specific phage antibodies was monitored by panning the initial as well as the subsequent fluorescein-specific sub-libraries against the blocking buffer (FIG. 12). Antibodies with specificity against fluorescein were isolated after 3 rounds of panning.

2.5 ELISA Measurements

One of the criteria for the successful biopanning is the isolation of individual phage clones that bind to the targeted antigen or hapten. We undertook the isolation of anti-FITC phage antibody clones and characterized them first in a phage ELISA format. After the 3rd round of biopanning (see above), 24 phagemid containing clones were used to inoculate 100 μl of 2×YT medium (Amp/Tet/Glucose) in an ELISA plate (Nunc), which was subsequently shaken at 37° C. for 5 hrs. 100 μl of 2×YT medium (Amp/Tet/1 mM IPTG) were added and shaking was continued for 30 minutes. A further 100 μl of 2×YT medium (Amp/Tet) containing the helper phage ($1\times10^{9}$ cfu/well) was added and shaking was done at RT for 3 hrs. After addition of kanamycin to select for successful helper phage infection, the shaking was continued overnight. The plates were then centrifuged and the supernatants were pipetted directly into ELISA wells coated with 100 μl FITC-BSA (100 μg/ml) and blocked with milk powder. Washing was performed similarly as during the panning procedure and the bound phages were detected with anti-M13 antibody-POD conjugate (Pharmacia) using soluble POD substrate (Boehringer-Mannheim). Of the 24 clones screened against FITC-BSA, 22 were active in the ELISA (FIG. 13). The initial libraries of similar titer gave rise to no detectable signal.

Specificity for fluorescein was measured in a competitive ELISA. Periplasmic fractions of five FITC specific scFvs were prepared as described above. Western blotting indicated that all clones expressed about the same amount of scFv fragment (data not shown). ELISA was performed as described above, but additionally, the periplasmic fractions were incubated 30 min at RT either with buffer (no inhibition), with 10 mg/ml BSA (inhibition with BSA) or with 10 mg/ml fluorescein (inhibition with fluorescein) before adding to the well. Binding scFv fragment was detected using the anti-FLAG antibody M1. The ELISA signal could only be inhibited, when soluble fluorescein was added, indicating binding of the scFvs was specific for fluorescein (FIG. 14).

2.6 Sequence Analysis

The heavy chain CDR3 region of 20 clones were sequenced in order to estimate the sequence diversity of fluorescein binding antibodies in the library (FIG. 15). In total, 16 of 20 sequences (80%) were different, showing that the constructed library contained a highly diverse repertoire of fluorescein binders. The CDR3s showed no particular sequence homology, but contained on average 4 arginine residues. This bias towards arginine in fluorescein binding antibodies had already been described by Barbas et al., 1992.

2.7 Production

*E. coli* JM83 was transformed with phagemid DNA of 3 selected clones and cultured in 0.5 L 2×YT medium. Induction was carried out with 1 mM IPTG at $OD_{600nm}$=0.4 and growth was continued with vigorous shaking at RT overnight. The cells were harvested and pellets were suspended in PBS buffer and sonicated. The supernatants were separated from the cell debris via centrifugation and purified via the BioLogic system (Bio-Rad) by with a POROS®MC 20 column (IMAC, PerSeptive Biosystems, Inc.) coupled with an ion-exchange chromatography column. The ion-exchange column was one of the POROS®HS, CM or HQ or PI 20 (PerSeptive Biosystems, Inc.) depended on the theoretical pI of the scFv being purified. The pH of all the buffers was adjusted to one unit lower or higher than the pI of the scFv being purified throughout. The sample was loaded onto the first IMAC column, washed with 7 column volumes of 20 mM sodium phosphate, 1 M NaCl and 10 mM imidazole. This washing was followed by 7 column volumes of 20 mM sodium phosphate and 10 mM imidazole. Then 3 column volumes of an imidazole gradient (10 to 250 mM) were applied and the eluent was connected directly to the ion-exchanger. Nine column volumes of isocratic washing with 250 mM imidazole was followed by 15 column volumes of 250 mM to 100 mM and 7 column volumes of an imidazole/NaCl gradient (100 to 10 mM imidazole, 0 to 1 M NaCl). The flow rate was 5 ml/min. The purity of scFv fragments was checked by SDS-PAGE Coomassie staining (FIG. 16). The concentration of the fragments was determined from the absorbance at 280 nm using the theoretically determined extinction coefficient (Gill & von Hippel, 1989). The scFv fragments could be purified to homogeneity (see FIG. 16). The yield of purified fragments ranged from 5 to 10 mg/L/OD.

Example 3

HuCAL H3κ2 Library Against a Collection of Antigens

In order to test the library used in Example 2 further, a new selection procedure was carried out using a variety of antigens comprising β-estradiol, testosterone, Lewis-Y epitope (LeY), interleukin-2 (IL-2), lymphotoxin-β (LT-β), E-selectin ligand-1 (ESL-1), and BSA.

3.1 Biopanning

The library and all procedures were identical to those described in Example 2. The ELISA plates were coated with β-estradiol-BSA (100 μg/ml), testosterone-BSA (100 μg/ml), LeY-BSA (20 μg/ml) IL-2 (20 μg/ml), ESL-1 (20 μg/ml) and BSA (100 μg/ml), LT-β (denatured protein, 20 μg/ml). In the first two rounds, bound phages were eluted with 0.1 M triethylamine (TEA) at RT for 10 minutes. In the case of BSA, elution after three rounds of panning was carried out with addition of BSA in a concentration of 100 μg/ml in PBS. In the case of the other antigens, third round elution was done with 0.1 M triethylamine. In all cases except LeY, enrichment of binding phages could be seen (FIG. 17). Moreover, a repetition of the biopanning experiment using only the 15-mer library resulted in the enrichment of LeY-binding phages as well (data not shown).

3.2. ELISA Measurements

Clones binding to β-estradiol, testosterone, LeY, LT-β, ESL-1 and BSA were further analyzed and characterized as described in Example 2 for FITC. ELISA data for anti-β-estradiol and anti-ESL-1 antibodies are shown in FIG. 18. In one experiment. selectivity and cross-reactivity of binding scFv fragments were tested. For this purpose, an ELISA plate was coated with FITC, testosterone, β-estradiol, BSA, and ESL-1, with 5 wells for each antigen arranged in 5 rows, and 5 antibodies, one against each of the antigens, were screened against each of the antigens. FIG. 19 shows the specific binding of the antibodies to the antigen it was selected for, and the low cross-reactivity with the other four antigens.

3.3 Sequence Analysis

The sequencing data of several clones against β-estradiol (34 clones), testosterone (12 clones), LT-β (23 clones), ESL-1 (34 clones), and BSA (10 clones) are given in FIGS. 20 to 24.

Example 4

Vector Construction

To be able to take advantage of the modularity of the consensus gene repertoire, a vector system had to be constructed which could be used in phage display screening of HuCAL libraries and subsequent optimization procedures. Therefore, all necessary vector elements such as origins of single-stranded or double-stranded replication, promotor/operator, repressor or terminator elements, resistance genes, potential recombination sites, gene III for display on filamentous phages, signal sequences, or detection tags had to be made compatible with the restriction site pattern of the modular consensus genes. FIG. 25 shows a schematic representation of the pCAL vector system and the arrangement of vector modules and restriction sites therein. FIG. 25*a* shows a list of all restriction sites which are already incorporated into the consensus genes or the vector elements as part of the modular system or which are not yet present in the whole system. The latter could be used in a later stage for the introduction of or within new modules.

4.1 Vector Modules

A series of vector modules was constructed where the restriction sites flanking the gene sub-elements of the HuCAL genes were removed, the vector modules themselves being flanked by unique restriction sites. These modules were constructed either by gene synthesis or by mutagenesis of templates. Mutagenesis was done by add-on PCR, by site-directed mutagenesis (Kunkel et al., 1991) or multisite oligonucleotide-mediated mutagenesis (Sutherland et al., 1995; Perlak, 1990) using a PCR-based assembly method.

FIG. 26 contains a list of the modules constructed. Instead of the terminator module M9 (HindIII-Ipp-PacI), a larger cassette M9II was prepared to introduce FseI as additional restriction site. M9II can be cloned via HindIII/BsrGI.

All vector modules were characterized by restriction analysis and sequencing. In the case of module M11-II, sequencing of the module revealed a two-base difference in positions 164/65 compared to the sequence database of the template. These two different bases (CA→GC) created an additional BanII site. Since the same two-base difference occurs in the 11 origin of other bacteriophages, it can be assumed that the two-base difference was present in the template and not created by mutagenesis during cloning. This BanII site was removed by site-directed mutagenesis, leading to module M11-III. The BssSI site of module M14 could initially not be removed without impact on the function of the CoIE1 origin, therefore M14-Ext2 was used for cloning of the first pCAL vector series. FIGS. 29 to 34 are showing the functional maps and sequences of the modules used for assembly of the modular vector pCAL4 (see below). The functional maps and sequences of additional modules can be found in FIG. 35*a*. FIG. 35*b* contains a list of oligonucleotides and primers used for the synthesis of the modules.

4.2 Cloning Vector pMCS

To be able to assemble the individual vector modules, a cloning vector pMCS containing a specific multi-cloning site (MCS) was constructed. First, an MCS cassette (FIG. 27) was made by gene synthesis. This cassette contains all those restriction sites in the order necessary for the sequential introduction of all vector modules and can be cloned via the 5'-HindIII site and a four base overhang at the 3'-end compatible with an AatII site. The vector pMCS (FIG. 28) was constructed by digesting pUC19 with AatII and HindIII, isolating the 2174 base pair fragment containing the bla gene and the CoIE1 origin, and ligating the MCS cassette.

4.3 Cloning of Modular Vector pCAL4

This was cloned step by step by restriction digest of pMCS and subsequent ligation of the modules M1 (via AatII/XbaI), M7III (via EcoRI/HindIII), and M9II (via HindIII/BsrGI), and M11-II (via BsrGI/NheI). Finally, the bla gene was replaced by the cat gene module M17 (via AatII/BglII), and the wild type CoIE1 origin by module M14-Ext2 (via BglII/NheI). FIG. 35 is showing the functional map and the sequence of pCAL4.

4.4 Cloning of Low-Copy Number Plasmid Vectors pCALO

A series of low-copy number plasmid vectors was constructed in a similar way using the p15A module M12 instead of the CoIE1 module M14-Ext2. FIG. 35*a* is showing the functional maps and sequences of the vectors pCALO1 to pCALO3.

Example 5

Construction of a HuCAL scFv Library 5.1. Cloning of all 49 HuCAL scFv Fragments All 49 combinations of the 7 HuCAL-VH and 7 HuCAL-VL consensus genes were assembled as described for the HuCAL VH3-VK2 scFv in Example 2 and inserted into the vector pBS12, a modified version of the pLisc series of antibody expression vectors (Skerra et al., 1991).

5.2 Construction of a CDR Cloning Cassette

For replacement of CDRs, a universal β-lactamase cloning cassette was constructed having a multi-cloning site at the 5'-end as well as at the 3'-end. The 5'-multi-cloning site comprises all restriction sites adjacent to the 5'-end of the HuCAL VH and VL CDRs, the 3'-multi-cloning site comprises all restriction sites adjacent to the 3' end of the HuCAL VH and VL CDRs. Both 5'- and 38'-multi-cloning site were prepared as cassettes via add-on PCR using synthetic oligonucleotides as 5'- and 3'-primers using wild type β-lactamase gene as template. FIG. 36 shows the functional map and the sequence of the cassette bla-MCS.

5.3. Preparation of VL-CDR3 Library Cassettes

The VL-CDR3 libraries comprising 7 random positions were generated from the PCR fragments using oligonucleotide templates Vκ1&Vκ3, Vκ2 and Vκ4 and primers O_K3L__5 and O_K3L__3 (FIG. 37) for the Vκ genes, and Vλ and primers O_L3L__5 (5'-GCAGAAGGCGAACGTCC-3') and O_L3LA__3 (FIG. 38) for the Vλ genes. Construction of the cassettes was performed as described in Example 2.3.

5.4 Cloning of HuCAL scFv Genes with VL-CDR3 Libraries

Each of the 49 single-chains was subcloned into pCAL4 via XbaI/EcoRI and the VL-CDR3 replaced by the β-lactamase cloning cassette via BbsI/MscI, which was then replaced by the corresponding VL-CDR3 library cassette synthesized as described above. This CDR replacement is described in detail in Example 2.3 where the cat gene was used.

5.5 Preparation of VH-CDR3 Library Cassette

The VH-CDR3 libraries were designed and synthesized as described in Example 2.3.

5.6 Cloning of HuCAL scFv Genes with VL- and VH-CDR3 Libraries

Each of the 49 single-chain VL-CDR3 libraries was digested with BssHII/StyI to replace VH-CDR3. The "dummy" cassette digested with BssHII/StyI was inserted, and was then replaced by a corresponding VH-CDR3 library cassette synthesized as described above.

Example 6

Expression Tests

Expression and toxicity studies were performed using the scFv format VH-linker-VL. All 49 combinations of the 7 HuCAL-VH and 7 HuCAL-VL consensus genes assembled as described in Example 5 were inserted into the vector pBS13, a modified version of the pLisc series of antibody expression vectors (Skerra et al., 1991). A map of this vector is shown in FIG. 39.

*E. coli* JM83 was transformed 49 times with each of the vectors and stored as glycerol stock. Between 4 and 6 clones were tested simultaneously, always including the clone H3κ2, which was used as internal control throughout. As additional control, the McPC603 scFv fragment (Knappik & Plückthun, 1995) in pBS13 was expressed under identical conditions. Two days before the expression test was performed, the clones were cultivated on LB plates containing 30 μg/ml chloramphenicol and 60 mM glucose. Using this plates an 3 ml culture (LB medium containing 90 μg chloramphenicol and 60 mM glucose) was inoculated overnight at 37° C. Next day the overnight culture was used to inoculate 30 ml LB medium containing chloramphenicol (30 μg/ml). The starting $OD_{600nm}$ was adjusted to 0.2 and a growth temperature of 30° C. was used. The physiology of the cells was monitored by measuring every 30 minutes for 8 to 9 hours the optical density at 600 nm. After the culture reached an $OD_{600nm}$ of 0.5, antibody expression was induced by adding IPTG to a final concentration of 1 mM. A 5 ml aliquot of the culture was removed after 2 h of induction in order to analyze the antibody expression. The cells were lysed and the soluble and insoluble fractions of the crude extract were separated as described in Knappik & Plückthun, 1995. The fractions were assayed by reducing SDS-PAGE with the samples normalized to identical optical densities. After blotting and immunostaining using the α-FLAG antibody M1 as the first antibody (see Ge et al., 1994) and an Fc-specific anti-mouse antiserum conjugated to alkaline phosphatase as the second antibody, the lanes were scanned and the intensities of the bands of the expected size (appr. 30 kDa) were quantified densitometrically and tabulated relative to the control antibody (see FIG. 40).

Example 7

Optimization of Fluorescein Binders 7.1. Construction of L-CDR3 and H-CDR2 Library Cassettes A L-CDR3 library cassette was prepared from the oligonucleotide (SEQ ID NO: 9) template CDR3L (5'-TGGAAGCTGAAGACGTGGGCGTGTATTATT GCCAGCAG(TR5)(TRI)$_4$CCG(TRI) TTTGGCCAGGGTACGAAAGTT-3') and primer (SEQ ID NO: 10) 5'-AATTTCGTACCCTGGCC-3' for synthesis of the complementary strand, where (TRI) was a trinucleotide mixture representing all amino acids except Cys, (TR5) comprised a trinucleotide mixture representing the 5 codons for Ala, Arg, His, Ser, and Tyr.

A H-CDR2 library cassette was prepared from the oligonucleotide template CDRsH (SEQ ID NOS 11 & 12, respectively) (5'-AGGGTCTCG AGIGGGTGAGC (TROATT (TRI)$_{2-3}$ (6)$_2$(TRI)ACC (TRI)TATGCG GATAGCGTGAAAGGCCGTTTTACCATTTCACGTGAT AATTCG AAAAA CACCA-3'), and primer (SEQ ID NO: 13) 5'-TGGTGTTTTTCGAATTATCA-3' for synthesis of the complementary strand, where (TRI) was a trinucleotide mixture representing all amino acids except Cys, (6) comprised the incorporation of (A/G)(A/C/G) T, resulting in the formation of 6 codons for Ala, Asn, Asp, Gly, Ser, and Thr, and the length distribution being obtained by performing one substoichiometric coupling of the (TRI) mixture during synthesis, omitting the capping step normally used in DNA synthesis.

DNA synthesis was performed on a 40 nmole scale, oligos were dissolved in TE buffer, purified via gel filtration using spin columns (S-200), and the DNA concentration determined by OD measurement at 260 nm (OD 1.0=40 μg/ml).

10 nmole of the oligonucleotide templates and 12 nmole of the corresponding primers were mixed and annealed at 80° C. for 1 min, and slowly cooled down to 37° C. within 20 to 30 min. The fill-in reaction was performed for 2 h at 37° C. using Klenow polymerase (2.0 μl) and 250 nmole of each dNTP. The excess of dNTPs was removed by gel filtration using Nick-Spin columns (Pharmacia), and the double-stranded DNA digested with BbsI/MscI (L-CDR3), or XhoI/SfuI (H-CDR2) over night at 37° C. The cassettes were purified via Nick-Spin columns (Pharmacia), the concentration determined by OD measurement, and the cassettes aliquoted (15 pmole) for being stored at −80° C.

7.2 Library Cloning:

DNA was prepared from the collection of FITC binding clones obtained in Example 2 (approx. $10^4$ to clones). The collection of scFv fragments was isolated via XbaI/EcoRI digest. The vector pCAL4 (100 fmole, 10 μg) described in Example 4.3 was similarly digested with XbaI/EcoRI, gel-purified and ligated with 300 fmole of the scFv fragment collection over night at 16° C. The ligation mixture was isopropanol precipitated, air-dried, and the pellets were redissolved in 100 μl of dd $H_2O$. The ligation mixture was mixed with 1 ml of freshly prepared electrocompetent SCS 101 cells (for optimization of L-CDR3), or XL1 Blue cells (for optimization of H-CDR2) on ice. One round of electroporation was performed and the transformants were eluted in SOC medium, shaken at 37° C. for 30 minutes, and an aliquot plated out on LB plates (Amp/Tet/Glucose) at 37° C. for 6-9 hrs. The number of transformants was $5\times10^4$.

Vector DNA (100 μg) was isolated and digested (sequence and restriction map of scH3κ2 see FIG. 8) with BbsI/MscI for optimization of L-CDR3, or XhoI/NspV for optimization of H-CDR2. 10 μg of purified vector fragments (5 pmole) were ligated with 15 pmole of the L-CDR3 or H-CDR2 library cassettes over night at 16° C. The ligation mixtures were isopropanol precipitated, air-dried, and the pellets were redissolved in 100 µl of dd $H_2O$. The ligation mixtures were mixed with 1 ml of freshly prepared electrocompetent XL1 Blue cells on ice. Electroporation was performed and the transformants were eluted in SOC medium and shaken at 37° C. for 30 minutes. An aliquot was plated out on LB plates (Amp/Tet/Glucose) at 37° C. for 6-9 hrs. The number of transformants (library size) was greater than $10^8$ for both libraries. The libraries were stored as glycerol cultures.

7.3. Biopanning

This was performed as described for the initial H3κ2 H-CDR3 library in Example 2.1. Optimized scFvs binding to FITC could be characterized and analyzed as described in Example 2.2 and 2.3, and further rounds of optimization could be made if necessary.

REFERENCES

Barbas III, C. F., Bain, J. D., Hoekstra, D. M. & Lerner, R. A., PNAS 8, 4457-4461 (1992).

Better, M., Chang, P., Robinson, R. & Horwitz, A. H., Science 240, 1041-1043 (1988).

Blake, M. S., Johnston, K. H., Russel-Jones, G. J. & Gotschlich, E. C., Anal. Biochem 136, 175-179 (1984).

Carter, P., Kelly, R. F., Rodrigues, M. L., Snedecor, B., Covrrubias, M., Velligan, M. D., Wong, W. L. T., Rowland, A. M., Kotts, C. E., Carver, M. E., Yang, M., Bourell, J. H., Shepard, H. M. & Henner, D., Bio/Technology 10, 163-167 (1992).

Chothia, C. & Lesk, A. M., J. Biol. Chem. 196, 910-917 (1987).

Chothia, C., Lesk, A. M., Gherardi, E., Tomlinson, I. A., Walter, G., Marks, J. D., Llewelyn, M. B. & Winter, G., J. Mol. Biol. 227, 799-817 (1992).

Chothia, C., Lesk, A. M., Tramontano, A., Levitt, M., Smith-Gill, S. J., Air, G., Sheriff, S., Padlan, E. A., Davies, D., Tulip, W. R., Colman, P. M., Spinelli, S., Alzari, P. M. & Poljak, R. J., Nature 342, 877-883 (1989).

Chuchana, P., Blancher, A., Brockly, F., Alexandre, D., Lefranc, G & Lefranc, M.-P., Eur. J. Immunol. 20, 1317-1325 (1990).

Cox. J. P. L., Tomlinson, I. M. & Winter, G., Eur. J. Immunol. 24, 827-836 (1994).

Ge, L., Knappik, A., Pack, P., Freund, C. & Plückthun, A., In: Antibody Engineering. Borrebaeck, C. A. K. (Ed.). p. 229-266 (1995), Oxford University Press, New York, Oxford.)

Gill, S. C. & von Hippel, P. H., Anal. Biochem. 182, 319.326 (1989).

Hochuli, E., Bannwarth, W., Döbeli, H., Gentz, R. & Stüber, D., Bio/Technology 6, 1321-1325 (1988).

Hopp, T. P., Prickett, K. S., Price, V. L., Libby, R. T., March, C. J., Cerretti, D. P., Urdal, D. L. & Conlon, P. J. Bio/Technology 6, 1204-1210 (1988).

Kabat, E. A., Wu, T. T., Perry, H. M., Gottesmann, K. S. & Foeller, C., Sequences of proteins of immunological interest, NIH publication 91-3242 (1991).

Knappik, A. & Plückthun, A., Biotechniques 17, 754-761 (1994).

Knappik, A. & Plückthun, A., Protein Engineering 8, 81-89 (1995).

Kunkel, T. A., Bebenek, K. & McClary, J., Methods in Enzymol. 204, 125-39 (1991).

Lindner, P., Guth, B., Wülfing, C., Krebber, C., Steipe, B., Müller, F. & Plückthun, A., Methods: A Companion to Methods Enzymol. 4, 41-56 (1992).

Lowman, H. B., Bass, S. H., Simpson, N. and Wells, J. A., Biochemistry 30, 10832-10838 (1991).

Pack, P. & Plückthun, A., Biochemistry 31, 1579-1584 (1992).

Pack, P., Kujau, M., Schroeckh, V., Knüpfer, U., Wenderoth, R., Riesenberg D. & Plückthun, A., Bio/Technology 11, 1271-1277 (1993).

Pack, P., Ph.D. thesis, Ludwig-Maximilians-Universität München (1994).

Perlak. F. J., Nuc. Acids Res. 18, 7457-7458 (1990).

Plückthun, A., Krebber, A., Krebber, C., Horn, U., Knüpfer, U., Wenderoth, R., Nieba, L., Proba, K. & Riesenberg, D., A practical approach. Antibody Engineering (Ed. J. McCafferty). IRL Press, Oxford, pp. 203-252 (1996).

Prodromou, C. & Pearl, L. H., Protein Engineering 5, 827-829 (1992).

Rosenberg, S. A. & Lotze, M. T., Ann. Rev. Immunol. 4, 681-709 (1986).

Skerra, A. & Plückthun, A., Science 240, 1038-1041 (1988).

Skerra, A., Pfitzinger, I. & Plückthun, A., Bio/Technology 2, 273-278 (1991).

Sutherland, L., Davidson, J., Glass, L. L., & Jacobs, H. T., BioTechniques 18, 458-464, 1995.

Tomlinson, I. M., Walter, G., Marks, J. D., Llewelyn, M. B. & Winter, G., J. Mol. Biol. 227, 776-798 (1992).

Ullrich, H. D., Patten, P. A., Yang, P. L., Romesberg, F. E. & Schultz, P. G., Proc. Natl. Acad. Sci. USA 92, 11907-11911 (1995).

Van Dijk, K. W., Mortari, F., Kirkham, P. M., Schroeder Jr., H. W. & Milner, E. C. B., Eur J. Immunol. 23, 832-839 (1993).

Virnekäs, B., Ge, L., Plückthun, A., Schneider, K. C., Wellnhofer, G. & Moroney, S. E., Nucleic Acids Research 22, 5600-5607 (1994).

Viletta, E. S., Thorpe, P. E. & Uhr, J., Immunol. Today 14, 253-259 (1993).

Williams, S. C. & Winter, G., Eur. J. Immunol. 23, 1456-1461 (1993).

Winter, G., Griffiths, A. D., Hawkins, R. E. & Hoogenboom, H. R., Ann. Rev. Immunol. 12, 433-455 (1994).

TABLE 1A

Human kappa germline gene segments

| Used Name[1] | Reference[2] | Family[3] | Germline genes[4] |
|---|---|---|---|
| Vk1-1 | 9 | 1 | O8; O18; DPK1 |
| Vk1-2 | 1 | 1 | L14; DPK2 |
| Vk1-3 | 2 | 1 | L15(1); HK101; HK146; HK189 |
| Vk1-4 | 9 | 1 | L11 |
| Vk1-5 | 2 | 1 | A30 |
| Vk1-6 | 1 | 1 | LFVK5 |
| Vk1-7 | 1 | 1 | LFVK431 |
| Vk1-8 | 1 | 1 | L1; HK137 |
| Vk1-9 | 1 | 1 | A20; DPK4 |
| Vk1-10 | 1 | 1 | L18; Va" |
| Vk1-11 | 1 | 1 | L4; L18; Va'; V4a |
| Vk1-12 | 2 | 1 | L5; L19(1); Vb; Vb4; DPK5; L19(2); Vb"; DPK6 |
| Vk1-13 | 2 | 1 | L15(2); HK134; HK166; DPK7 |
| Vk1-14 | 8 | 1 | L8; Vd; DPK8 |
| Vk1-15 | 8 | 1 | L9; Ve |
| Vk1-16 | 1 | 1 | L12(1); HK102; V1 |
| Vk1-17 | 2 | 1 | L12(2) |
| Vk1-18 | 1 | 1 | O12a (V3b) |
| Vk1-19 | 6 | 1 | O2; O12; DPK9 |
| Vk1-20 | 2 | 1 | L24; Ve"; V13; DPK10 |
| Vk1-21 | 1 | 1 | O4; O14 |
| Vk1-22 | 2 | 1 | L22 |
| Vk1-23 | 2 | 1 | L23 |
| Vk2-1 | 1 | 2 | A2; DPK12 |
| Vk2-2 | 6 | 2 | O1; O11(1); DPK13 |

TABLE 1A-continued

Human kappa germline gene segments

| Used Name[1] | Reference[2] | Family[3] | Germline genes[4] |
|---|---|---|---|
| Vk2-3 | 6 | 2 | O12(2); V3a |
| Vk2-4 | 2 | 2 | L13 |
| Vk2-5 | 1 | 2 | DPK14 |
| Vk2-6 | 4 | 2 | A3; A19; DPK15 |
| Vk2-7 | 4 | 2 | A29; DPK27 |
| Vk2-8 | 4 | 2 | A13 |
| Vk2-9 | 1 | 2 | A23 |
| Vk2-10 | 4 | 2 | A7; DPK17 |
| Vk2-11 | 4 | 2 | A17; DPK18 |
| Vk2-12 | 4 | 2 | A1; DPK19 |
| Vk3-1 | 11 | 3 | A11; humkv305; DPK20 |
| Vk3-2 | 1 | 3 | L20; Vg" |
| Vk3-3 | 2 | 3 | L2; L16; humkv328; humkv328h2; humkv328h5; DPK21 |
| Vk3-4 | 11 | 3 | A27; humkv325; VkRF; DPK22 |
| Vk3-5 | 2 | 3 | L25; DPK23 |
| Vk3-6 | 2 | 3 | L10(1) |
| Vk3-7 | 7 | 3 | L10(2) |
| Vk3-8 | 7 | 3 | L6; Vg |
| Vk4-1 | 3 | 4 | B3; VkIV; DPK24 |
| Vk5-1 | 10 | 5 | B2; EV15 |
| Vk6-1 | 12 | 6 | A14; DPK25 |
| Vk6-2 | 12 | 6 | A10; A26; DPK26 |
| Vk7-1 | 5 | 7 | B1 |

TABLE 1B

Human lambda germline gene segments

| Used Name[1] | Reference[2] | Family[3] | Germline genes[4] |
|---|---|---|---|
| DPL1 | 1 | 1 | |
| DPL2 | 1 | 1 | HUMLV1L1 |
| DPL3 | 1 | 1 | HUMLV122 |
| DPL4 | 1 | 1 | VLAMBDA 1.1 |
| HUMLV117 | 2 | 1 | |
| DPL5 | 1 | 1 | HUMLV117D |
| DPL6 | 1 | 1 | |
| DPL7 | 1 | 1 | IGLV1S2 |
| DPL8 | 1 | 1 | HUMLV1042 |
| DPL9 | 1 | 1 | HUMLV101 |
| DPL10 | 1 | 2 | |
| VLAMBDA 2.1 | 3 | 2 | |
| DPL11 | 1 | 2 | |
| DPL12 | 1 | 2 | |
| DPL13 | 1 | 2 | |
| DPL14 | 1 | 2 | |
| DPL16 | 1 | 3 | Humlv418; IGLV3S1 |
| DPL23 | 1 | 3 | VI III.1 |
| Humlv318 | 4 | 3 | |
| DPL18 | 1 | 7 | 4A; HUMIGLVA |
| DPL19 | 1 | 7 | |
| DPL21 | 1 | 8 | VL8.1 |
| HUMLV801 | 5 | 8 | |
| DPL22 | 1 | 9 | |
| DPL24 | 1 | unassigned | VLAMBDA N.2 |
| gVLX-4.4 | 6 | 10 | |

TABLE 1C

Human heavy chain germline gene segments

| Used Name[1] | Reference[2] | Family[3] | Germline genes[4] |
|---|---|---|---|
| VH1-12-1 | 19 | 1 | DP10; DA-2; DA-6 |
| VH1-12-8 | 22 | 1 | RR.VH1.2 |
| VH1-12-2 | 6 | 1 | hv1263 |
| VH1-12-9 | 7 | 1 | YAC-7; RR.VH1.1; 1-69 |
| VH1-12-3 | 19 | 1 | DP3 |
| VH1-12-4 | 19 | 1 | DP21; 4d275a; VH7a |
| VH1-12-5 | 18 | 1 | I-4.1b; V1-4.1b |

TABLE 1C-continued

Human heavy chain germline gene segments

| Used Name[1] | Reference[2] | Family[3] | Germline genes[4] |
|---|---|---|---|
| VH1-12-6 | 21 | 1 | 1D37; VH7b; 7-81; YAC-10 |
| VH1-12-7 | 19 | 1 | DP14; VH1GRR; V1-18 |
| VH1-13-1 | 10 | 1 | 71-5; DP2 |
| VH1-13-2 | 10 | 1 | E3-10 |
| VH1-13-3 | 19 | 1 | DP1 |
| VH1-13-4 | 12 | 1 | V35 |
| VH1-13-5 | 8 | 1 | V1-2b |
| VH1-13-6 | 18 | 1 | I-2; DP75 |
| VH1-13-7 | 21 | 1 | V1-2 |
| VH1-13-8 | 19 | 1 | DP8 |
| VH1-13-9 | 3 | 1 | 1-1 |
| VH1-13-10 | 19 | 1 | DP12 |
| VH1-13-11 | 15 | 1 | V13C |
| VH1-13-12 | 18 | 1 | I-3b; DP25; V1-3b |
| VH1-13-13 | 3 | 1 | 1-92 |
| VH1-13-14 | 18 | 1 | I-3; V1-3 |
| VH1-13-15 | 19 | 1 | DP15; V1-8 |
| VH1-13-16 | 3 | 1 | 21-2; 3-1; DP7; V1-46 |
| VH1-13-17 | 16 | 1 | HG3 |
| VH1-13-18 | 19 | 1 | DP4; 7-2; V1-45 |
| VH1-13-19 | 27 | 1 | COS 5 |
| VH1-1X-1 | 19 | 1 | DP5; 1-24P |
| VH2-21-1 | 18 | 2 | II-5b |
| VH2-31-1 | 2 | 2 | VH2S12-1 |
| VH2-31-2 | 2 | 2 | VH2S12-7 |
| VH2-31-3 | 2 | 2 | VH2S12-9; DP27 |
| VH2-31-4 | 2 | 2 | VH2S12-10 |
| VH2-31-5 | 14 | 2 | V2-26; DP26; 2-26 |
| VH2-31-6 | 15 | 2 | VF2-26 |
| VH2-31-7 | 19 | 2 | DP28; DA-7 |
| VH2-31-14 | 7 | 2 | YAC-3; 2-70 |
| VH2-31-8 | 2 | 2 | VH2S12-5 |
| VH2-31-9 | 2 | 2 | VH2S12-12 |
| VH2-31-10 | 18 | 2 | II-5; V2-5 |
| VH2-31-11 | 2 | 2 | VH2S12-2; VH2S12-8 |
| VH2-31-12 | 2 | 2 | VH2S12-4; VH2S12-6 |
| VH2-31-13 | 2 | 2 | VH2S12-14 |
| VH3-11-1 | 13 | 3 | v65-2; DP44 |
| VH3-11-2 | 19 | 3 | DP45 |
| VH3-11-3 | 3 | 3 | 13-2; DP48 |
| VH3-11-4 | 19 | 3 | DP52 |
| VH3-11-5 | 14 | 3 | v3-13 |
| VH3-11-6 | 19 | 3 | DP42 |
| VH3-11-7 | 3 | 3 | 8-1B; YAC-5; 3-66 |
| VH3-11-8 | 14 | 3 | V3-53 |
| VH3-13-1 | 3 | 3 | 22-2B; DP35; V3-11 |
| VH3-13-5 | 19 | 3 | DP59; VH19; V3-35 |
| VH3-13-6 | 25 | 3 | f1-p1; DP61 |
| VH3-13-7 | 19 | 3 | DP46; GL-SJ2; COS 8; hv3005; hv3005f3; 3d21b; 56p1 |
| VH3-13-8 | 24 | 3 | VH26 |
| VH3-13-9 | 5 | 3 | vh26c |
| VH3-13-10 | 19 | 3 | DP47; VH26; 3-23 |
| VH3-13-11 | 3 | 3 | 1-91 |
| VH3-13-12 | 19 | 3 | DP58 |
| VH3-13-13 | 3 | 3 | 1-9III; DP49; 3-30; 3d28.1 |
| VH3-13-14 | 24 | 3 | 3019B9; DP50; 3-33; 3d277 |
| VH3-13-15 | 27 | 3 | COS 3 |
| VH3-13-16 | 19 | 3 | DP51 |
| VH3-13-17 | 16 | 3 | H11 |
| VH3-13-18 | 19 | 3 | DP53; COS 6; 3-74; DA-8 |
| VH3-13-19 | 19 | 3 | DP54; VH3-11; V3-7 |
| VH3-13-20 | 14 | 3 | V3-64; YAC-6 |
| VH3-13-21 | 14 | 3 | V3-48 |
| VH3-13-22 | 14 | 3 | V3-43; DP33 |
| VH3-13-23 | 14 | 3 | V3-33 |
| VH3-13-24 | 14 | 3 | V3-21; DP77 |
| VH3-13-25 | 14 | 3 | V3-20; DP32 |
| VH3-13-26 | 14 | 3 | V3-9; DP31 |
| VH3-14-1 | 3 | 3 | 12-2; DP29; 3-72; DA-3 |
| VH3-14-4 | 7 | 3 | YAC-9; 3-73; MTGL |
| VH3-14-2 | 4 | 3 | VHD26 |
| VH3-14-3 | 19 | 3 | DP30 |
| VH3-1X-1 | 1 | 3 | LSG8.1; LSG9.1; LSG10.1; HUM12IGVH; HUM13IGVH |
| VH3-1X-2 | 1 | 3 | LSG11.1; HUM4IGVH |

TABLE 1C-continued

| Human heavy chain germline gene segments | | | |
|---|---|---|---|
| Used Name[1] | Reference[2] | Family[3] | Germline genes[4] |
| VH3-1X-3 | 3 | 3 | 9-1; DP38; LSG7.1; RCG1.1; LSG1.1; LSG3.1; LSG5.1; HUM15IGVH; HUM2IGVH; HUM9IGVH |
| VH3-1X-4 | 1 | 3 | LSG4.1 |
| VH3-1X-5 | 1 | 3 | LSG2.1 |
| VH3-1X-6 | 1 | 3 | LSG6.1; HUM10IGVH |
| VH3-1X-7 | 18 | 3 | 3-15; V3-15 |
| VH3-1X-8 | 1 | 3 | LSG12.1; HUM5IGVH |
| VH3-1X-9 | 14 | 3 | V3-49 |
| VH4-11-1 | 22 | 4 | Tou-VH4.21 |
| VH4-11-2 | 17 | 4 | VH4.21; DP63; VH5; 4d76; V4-34 |
| VH4-11-3 | 23 | 4 | 4.44 |
| VH4-11-4 | 23 | 4 | 4.44.3 |
| VH4-11-5 | 23 | 4 | 4.36 |
| VH4-11-6 | 23 | 4 | 4.37 |
| VH4-11-7 | 18 | 4 | IV-4; 4.35; V4-4 |
| VH4-11-8 | 17 | 4 | VH4.11; 3d197d; DP71; 58p2 |
| VH4-11-9 | 20 | 4 | H7 |
| VH4-11-10 | 20 | 4 | H8 |
| VH4-11-11 | 20 | 4 | H9 |
| VH4-11-12 | 17 | 4 | VH4.16 |
| VH4-11-13 | 23 | 4 | 4.38 |
| VH4-11-14 | 17 | 4 | VH4.15 |
| VH4-11-15 | 11 | 4 | 58 |
| VH4-11-16 | 10 | 4 | 71-4; V4-59 |
| VH4-21-1 | 11 | 4 | 11 |
| VH4-21-2 | 17 | 4 | VH4.17; VH4.23; 4d255; 4.40; DP69 |
| VH4-21-3 | 17 | 4 | VH4.19; 79; V4-4b |
| VH4-21-4 | 19 | 4 | DP70; 4d68; 4.41 |
| VH4-21-5 | 19 | 4 | DP67; VH4-4B |
| VH4-21-6 | 17 | 4 | VH4.22; VHSP; VH-JA |
| VH4-21-7 | 17 | 4 | VH4.13; 1-9II; 12G-1; 3d28d; 4.42; DP68; 4-28 |
| VH4-21-8 | 26 | 4 | hv4005; 3d24d |
| VH4-21-9 | 17 | 4 | VH4.14 |
| VH4-31-1 | 23 | 4 | 4.34; 3d230d; DP78 |
| VH4-31-2 | 23 | 4 | 4.34.2 |
| VH4-31-3 | 19 | 4 | DP64; 3d216d |
| VH4-31-4 | 19 | 4 | DP65; 4-31; 3d277d |
| VH4-31-5 | 23 | 4 | 4.33; 3d75d |
| VH4-31-6 | 20 | 4 | H10 |
| VH4-31-7 | 20 | 4 | H11 |
| VH4-31-8 | 23 | 4 | 4.31 |
| VH4-31-9 | 23 | 4 | 4.32 |
| VH4-31-10 | 20 | 4 | 3d277d |
| VH4-31-11 | 20 | 4 | 3d216d |
| VH4-31-12 | 20 | 4 | 3d279d |
| VH4-31-13 | 17 | 4 | VH4.18; 4d154; DP79 |
| VH4-31-14 | 8 | 4 | V4-39 |
| VH4-31-15 | 11 | 4 | 2-1; DP79 |
| VH4-31-16 | 23 | 4 | 4.30 |
| VH4-31-17 | 17 | 4 | VH4.12 |
| VH4-31-18 | 10 | 4 | 71-2; DP66 |
| VH4-31-19 | 23 | 4 | 4.39 |
| VH4-31-20 | 8 | 4 | V4-61 |
| VH5-12-1 | 9 | 5 | VH251; DP73; VHVCW; 51-R1; VHVLB; VHVCH; VHVTT; VHVAU; VHVBLK; VhAU; V5-51 |
| VH5-12-2 | 17 | 5 | VHVJB |
| VH5-12-3 | 3 | 5 | 1-v; DP80; 5-78 |
| VH5-12-4 | 9 | 5 | VH32; VHVRG; VHVMW; 5-2R1 |
| VH6-35-1 | 4 | 6 | VHVI; VH6; VHVIIS; VHVITE; VHVIJB; VHVICH; VHVICW; VHVIBLK; VHVIMW; DP74; 6-1G1; V6-1 |

TABLE 2A

| rearranged human kappa sequences | | | | | | |
|---|---|---|---|---|---|---|
| Name[1] | aa[2] | Computed family[3] | Germline gene[4] | Diff. to germline[5] | % diff. to germline[6] | Reference[7] |
| III-3R | 108 | 1 | O8 | 1 | 1.1% | 70 |
| No. 86 | 109 | 1 | O8 | 3 | 3.2% | 80 |
| AU | 108 | 1 | O8 | 6 | 6.3% | 103 |
| ROY | 108 | 1 | O8 | 6 | 6.3% | 43 |
| IC4 | 108 | 1 | O8 | 6 | 6.3% | 70 |
| HIV-B26 | 106 | 1 | O8 | 3 | 3.2% | 8 |
| GRI | 108 | 1 | O8 | 8 | 8.4% | 30 |
| AG | 106 | 1 | O8 | 8 | 8.6% | 116 |
| REI | 108 | 1 | O8 | 9 | 9.5% | 86 |
| CLL PATIENT 16 | 88 | 1 | O8 | 2 | 2.3% | 122 |
| CLL PATIENT 14 | 87 | 1 | O8 | 2 | 2.3% | 122 |
| CLL PATIENT 15 | 88 | 1 | O8 | 2 | 2.3% | 122 |
| GM4672 | 108 | 1 | O8 | 11 | 11.6% | 24 |
| HUM. YFC51.1 | 108 | 1 | O8 | 12 | 12.6% | 110 |
| LAY | 108 | 1 | O8 | 12 | 12.6% | 48 |
| HIV-b13 | 106 | 1 | O8 | 9 | 9.7% | 8 |
| MAL-NaCl | 108 | 1 | O8 | 13 | 13.7% | 102 |
| STRAb SA-1A | 108 | 1 | O2 | 0 | 0.0% | 120 |
| HuVHCAMP | 108 | 1 | O8 | 13 | 13.7% | 100 |
| CRO | 108 | 1 | O2 | 10 | 10.5% | 30 |
| Am 107 | 108 | 1 | O2 | 12 | 12.6% | 108 |
| WALKER | 107 | 1 | O2 | 4 | 4.2% | 57 |
| III-2R | 109 | 1 | A20 | 0 | 0.0% | 70 |
| FOG1-A4 | 107 | 1 | A20 | 4 | 4.2% | 41 |
| HK137 | 95 | 1 | L1 | 0 | 0.0% | 10 |
| CEA4-8A | 107 | 1 | O2 | 7 | 7.4% | 41 |
| Va' | 95 | 1 | L4 | 0 | 0.0% | 90 |
| TR1.21 | 108 | 1 | O2 | 4 | 4.2% | 92 |
| HAU | 108 | 1 | O2 | 6 | 6.3% | 123 |
| HK102 | 95 | 1 | L12(1) | 0 | 0.0% | 9 |
| H20C3K | 108 | 1 | L12(2) | 3 | 3.2% | 125 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| CHEB | 108 | 1 | O2 | 7 | 7.4% | 5 |
| HK134 | 95 | 1 | L15(2) | 0 | 0.0% | 10 |
| TEL9 | 108 | 1 | O2 | 9 | 9.5% | 73 |
| TR1.32 | 103 | 1 | O2 | 3 | 3.2% | 92 |
| RF-KES1 | 97 | 1 | A20 | 4 | 4.2% | 121 |
| WES | 108 | 1 | L5 | 10 | 10.5% | 61 |
| DILp1 | 95 | 1 | O4 | 1 | 1.1% | 70 |
| SA-4B | 107 | 1 | L12(2) | 8 | 8.4% | 120 |
| HK101 | 95 | 1 | L15(1) | 0 | 0.0% | 9 |
| TR1.23 | 108 | 1 | O2 | 5 | 5.3% | 92 |
| HF2-1/17 | 108 | 1 | A30 | 0 | 0.0% | 4 |
| 2E7 | 108 | 1 | A30 | 1 | 1.1% | 62 |
| 33.C9 | 107 | 1 | L12(2) | 7 | 7.4% | 126 |
| 3D6 | 105 | 1 | L12(2) | 2 | 2.1% | 34 |
| I-2a | 108 | 1 | L8 | 8 | 8.4% | 70 |
| RF-KL1 | 97 | 1 | L8 | 4 | 4.2% | 121 |
| TNF-E7 | 108 | 1 | A30 | 9 | 9.5% | 41 |
| TR1.22 | 108 | 1 | O2 | 7 | 7.4% | 92 |
| HIV-B35 | 106 | 1 | O2 | 2 | 2.2% | 8 |
| HIV-b22 | 106 | 1 | O2 | 2 | 2.2% | 8 |
| HIV-b27 | 106 | 1 | O2 | 2 | 2.2% | 8 |
| HIV-B8 | 107 | 1 | O2 | 10 | 10.8% | 8 |
| HIV-b3 | 107 | 1 | O2 | 10 | 10.8% | 8 |
| RF-SJ5 | 95 | 1 | A30 | 5 | 5.3% | 113 |
| GAL(I) | 108 | 1 | A30 | 6 | 6.3% | 64 |
| R3.5H5G | 108 | 1 | O2 | 6 | 6.3% | 70 |
| HIV-b14 | 106 | 1 | A20 | 2 | 2.2% | 8 |
| TNF-E1 | 105 | 1 | L5 | 8 | 8.4% | 41 |
| WEA | 108 | 1 | A30 | 8 | 8.4% | 37 |
| EU | 108 | 1 | L12(2) | 5 | 5.3% | 40 |
| FOG1-G8 | 108 | 1 | L8 | 11 | 11.6% | 41 |
| 1X7RG1 | 108 | 1 | L1 | 8 | 8.4% | 70 |
| BLI | 108 | 1 | L8 | 3 | 3.2% | 72 |
| KUE | 108 | 1 | L12(2) | 11 | 11.6% | 32 |
| LUNm01 | 108 | 1 | L12(2) | 10 | 10.5% | 6 |
| HIV-b1 | 106 | 1 | A20 | 4 | 4.3% | 8 |
| HIV-s4 | 103 | 1 | O2 | 2 | 2.2% | 8 |
| CAR | 107 | 1 | L12(2) | 11 | 11.7% | 79 |
| BR | 107 | 1 | L12(2) | 11 | 11.6% | 50 |
| CLL PATIENT 10 | 88 | 1 | O2 | 0 | 0.0% | 122 |
| CLL PATIENT 12 | 88 | 1 | O2 | 0 | 0.0% | 122 |
| KING | 108 | 1 | L12(2) | 12 | 12.6% | 30 |
| V13 | 95 | 1 | L24 | 0 | 0.0% | 46 |
| CLL PATIENT 11 | 87 | 1 | O2 | 0 | 0.0% | 122 |
| CLL PATIENT 13 | 87 | 1 | O2 | 0 | 0.0% | 122 |
| CLL PATIENT 9 | 88 | 1 | O12 | 1 | 1.1% | 122 |
| HIV-B2 | 106 | 1 | A20 | 9 | 9.7% | 8 |
| HIV-b2 | 106 | 1 | A20 | 9 | 9.7% | 8 |
| CLL PATIENT 5 | 88 | 1 | A20 | 1 | 1.1% | 122 |
| CLL PATIENT 1 | 88 | 1 | L8 | 2 | 2.3% | 122 |
| CLL PATIENT 2 | 88 | 1 | L8 | 0 | 0.0% | 122 |
| CLL PATIENT 7 | 88 | 1 | L5 | 0 | 0.0% | 122 |
| CLL PATIENT 8 | 88 | 1 | L5 | 0 | 0.0% | 122 |
| HIV-b5 | 105 | 1 | L5 | 11 | 12.0% | 8 |
| CLL PATIENT 3 | 87 | 1 | L8 | 1 | 1.1% | 122 |
| CLL PATIENT 4 | 88 | 1 | L9 | 0 | 0.0% | 122 |
| CLL PATIENT 18 | 85 | 1 | L9 | 6 | 7.1% | 122 |
| CLL PATIENT 17 | 86 | 1 | L12(2) | 7 | 8.1% | 122 |
| HIV-b20 | 107 | 3 | A27 | 11 | 11.7% | 8 |
| 2C12 | 108 | 1 | L12(2) | 20 | 21.1% | 68 |
| 1B11 | 108 | 1 | L12(2) | 20 | 21.1% | 68 |
| 1H1 | 108 | 1 | L12(2) | 21 | 22.1% | 68 |
| 2A12 | 108 | 1 | L12(2) | 21 | 22.1% | 68 |
| CUR | 109 | 3 | A27 | 0 | 0.0% | 66 |
| GLO | 109 | 3 | A27 | 0 | 0.0% | 16 |
| RF-TS1 | 96 | 3 | A27 | 0 | 0.0% | 121 |
| GAR' | 109 | 3 | A27 | 0 | 0.0% | 67 |
| FLO | 109 | 3 | A27 | 0 | 0.0% | 66 |
| PIE | 109 | 3 | A27 | 0 | 0.0% | 91 |
| HAH 14.1 | 109 | 3 | A27 | 1 | 1.0% | 51 |
| HAH 14.2 | 109 | 3 | A27 | 1 | 1.0% | 51 |
| HAH 16.1 | 109 | 3 | A27 | 1 | 1.0% | 51 |
| NOV | 109 | 3 | A27 | 1 | 1.0% | 52 |
| 33.F12 | 108 | 3 | A27 | 1 | 1.0% | 126 |
| 8E10 | 110 | 3 | A27 | 1 | 1.0% | 25 |

TABLE 2A-continued rearranged human kappa sequences

| Name[1] | aa[2] | Computed family[3] | Germline gene[4] | Diff. to germline[5] | % diff. to germline[6] | Reference[7] |
|---|---|---|---|---|---|---|
| TH3 | 109 | 3 | A27 | 1 | 1.0% | 25 |
| HIC (R) | 108 | 3 | A27 | 0 | 0.0% | 51 |
| SON | 110 | 3 | A27 | 1 | 1.0% | 67 |
| PAY | 109 | 3 | A27 | 1 | 1.0% | 66 |
| GOT | 109 | 3 | A27 | 1 | 1.0% | 67 |
| mAbA6H4C5 | 109 | 3 | A27 | 1 | 1.0% | 12 |
| BOR' | 109 | 3 | A27 | 2 | 2.1% | 84 |
| RF-SJ3 | 96 | 3 | A27 | 2 | 2.1% | 121 |
| SIE | 109 | 3 | A27 | 2 | 2.1% | 15 |
| ESC | 109 | 3 | A27 | 2 | 2.1% | 98 |
| HEW' | 110 | 3 | A27 | 2 | 2.1% | 98 |
| YES8c | 109 | 3 | A27 | 3 | 3.1% | 33 |
| TI | 109 | 3 | A27 | 3 | 3.1% | 114 |
| mAb113 | 109 | 3 | A27 | 3 | 3.1% | 71 |
| HEW | 107 | 3 | A27 | 0 | 0.0% | 94 |
| BRO | 106 | 3 | A27 | 0 | 0.0% | 94 |
| ROB | 106 | 3 | A27 | 0 | 0.0% | 94 |
| NG9 | 96 | 3 | A27 | 4 | 4.2% | 11 |
| NEU | 109 | 3 | A27 | 4 | 4.2% | 66 |
| WOL | 109 | 3 | A27 | 4 | 4.2% | 2 |
| 35G6 | 109 | 3 | A27 | 4 | 4.2% | 59 |
| RF-SJ4 | 109 | 3 | A11 | 0 | 0.0% | 88 |
| KAS | 109 | 3 | A27 | 4 | 4.2% | 84 |
| BRA | 106 | 3 | A27 | 1 | 1.1% | 94 |
| HAH | 106 | 3 | A27 | 1 | 1.1% | 94 |
| HIC | 105 | 3 | A27 | 0 | 0.0% | 94 |
| FS-2 | 109 | 3 | A27 | 6 | 6.3% | 87 |
| JH' | 107 | 3 | A27 | 6 | 6.3% | 38 |
| EV1-15 | 109 | 3 | A27 | 6 | 6.3% | 83 |
| SCA | 108 | 3 | A27 | 6 | 6.3% | 65 |
| mAb112 | 109 | 3 | A27 | 6 | 6.3% | 71 |
| SIC | 103 | 3 | A27 | 3 | 3.3% | 94 |
| SA-4A | 109 | 3 | A27 | 6 | 6.3% | 120 |
| SER | 108 | 3 | A27 | 6 | 6.3% | 98 |
| GOL' | 109 | 3 | A27 | 7 | 7.3% | 82 |
| B5G10K | 105 | 3 | A27 | 9 | 9.7% | 125 |
| HG2B10K | 110 | 3 | A27 | 9 | 9.4% | 125 |
| Taykv322 | 105 | 3 | A27 | 5 | 5.4% | 52 |
| CLL PATIENT 24 | 89 | 3 | A27 | 1 | 1.1% | 122 |
| HIV-b24 | 107 | 3 | A27 | 7 | 7.4% | 8 |
| HIV-b6 | 107 | 3 | A27 | 7 | 7.4% | 8 |
| Taykv310 | 99 | 3 | A27 | 1 | 1.1% | 52 |
| KA3D1 | 108 | 3 | L6 | 0 | 0.0% | 85 |
| 19.E7 | 107 | 3 | L6 | 0 | 0.0% | 126 |
| rsv6L | 109 | 3 | A27 | 12 | 12.5% | 7 |
| Taykv320 | 98 | 3 | A27 | 1 | 1.2% | 52 |
| Vh | 96 | 3 | L10(2) | 0 | 0.0% | 89 |
| LS8 | 108 | 3 | L6 | 1 | 1.1% | 109 |
| LS1 | 108 | 3 | L6 | 1 | 1.1% | 109 |
| LS2S3-3 | 107 | 3 | L6 | 2 | 2.1% | 99 |
| LS2 | 108 | 3 | L6 | 1 | 1.1% | 109 |
| LS7 | 108 | 3 | L6 | 1 | 1.1% | 109 |
| LS2S3-4d | 107 | 3 | L6 | 2 | 2.1% | 99 |
| LS2S3-4a | 107 | 3 | L6 | 2 | 2.1% | 99 |
| LS4 | 108 | 3 | L6 | 1 | 1.1% | 109 |
| LS6 | 108 | 3 | L6 | 1 | 1.1% | 109 |
| LS2S3-10a | 107 | 3 | L6 | 2 | 2.1% | 99 |
| LS2S3-8c | 107 | 3 | L6 | 2 | 2.1% | 99 |
| LS5 | 108 | 3 | L6 | 1 | 1.1% | 109 |
| LS2S3-5 | 107 | 3 | L6 | 3 | 3.2% | 99 |
| LUNm03 | 109 | 3 | A27 | 13 | 13.5% | 6 |
| IARC/BL41 | 108 | 3 | A27 | 13 | 13.7% | 55 |
| slkv22 | 99 | 3 | A27 | 3 | 3.5% | 13 |
| POP | 108 | 3 | L6 | 4 | 4.2% | 111 |
| LS2S3-10b | 107 | 3 | L6 | 3 | 3.2% | 99 |
| LS2S3-8f | 107 | 3 | L6 | 3 | 3.2% | 99 |
| LS2S3-12 | 107 | 3 | L6 | 3 | 3.2% | 99 |
| HIV-B30 | 107 | 3 | A27 | 11 | 11.7% | 8 |
| HIV-B20 | 107 | 3 | A27 | 11 | 11.7% | 8 |
| HIV-b3 | 108 | 3 | A27 | 11 | 11.7% | 8 |
| HIV-s6 | 104 | 3 | A27 | 9 | 9.9% | 8 |
| YSE | 107 | 3 | L2/L16 | 1 | 1.1% | 72 |
| POM | 109 | 3 | L2/L16 | 9 | 9.4% | 53 |
| Humkv328 | 95 | 3 | L2/L16 | 1 | 1.1% | 19 |
| CLL | 109 | 3 | L2/L16 | 3 | 3.2% | 47 |

TABLE 2A-continued

| rearranged human kappa sequences | | | | | | |
|---|---|---|---|---|---|---|
| Name[1] | aa[2] | Computed family[3] | Germline gene[4] | Diff. to germline[5] | % diff. to germline[6] | Reference[7] |
| LES | 96 | 3 | L2/L16 | 3 | 3.2% | 38 |
| HIV-s5 | 104 | 3 | A27 | 11 | 12.1% | 8 |
| HIV-s7 | 104 | 3 | A27 | 11 | 12.1% | 8 |
| slkv1 | 99 | 3 | A27 | 7 | 8.1% | 13 |
| Humka31es | 95 | 3 | L2/L16 | 4 | 4.2% | 18 |
| slkv12 | 101 | 3 | A27 | 8 | 9.2% | 13 |
| RF-TS2 | 95 | 3 | L2/L16 | 3 | 3.2% | 121 |
| II-1 | 109 | 3 | L2/L16 | 4 | 4.2% | 70 |
| HIV-s3 | 105 | 3 | A27 | 13 | 14.3% | 8 |
| RF-TMC1 | 96 | 3 | L6 | 10 | 10.5% | 121 |
| GER | 109 | 3 | L2/L16 | 7 | 7.4% | 75 |
| GF4/1.1 | 109 | 3 | L2/L16 | 8 | 8.4% | 36 |
| mAb114 | 109 | 3 | L2/L16 | 6 | 6.3% | 71 |
| HIV-loop13 | 109 | 3 | L2/L16 | 7 | 7.4% | 8 |
| bkv16 | 86 | 3 | L6 | 1 | 1.2% | 13 |
| CLL PATIENT 29 | 86 | 3 | L6 | 1 | 1.2% | 122 |
| slkv9 | 98 | 3 | L6 | 3 | 3.5% | 13 |
| bkv17 | 99 | 3 | L6 | 1 | 1.2% | 13 |
| slkv14 | 99 | 3 | L6 | 1 | 1.2% | 13 |
| slkv16 | 101 | 3 | L6 | 2 | 2.3% | 13 |
| bkv33 | 101 | 3 | L6 | 4 | 4.7% | 13 |
| slkv15 | 99 | 3 | L6 | 2 | 2.3% | 13 |
| bkv6 | 100 | 3 | L6 | 3 | 3.5% | 13 |
| R6B8K | 108 | 3 | L2/L16 | 12 | 12.6% | 125 |
| AL 700 | 107 | 3 | L2/L16 | 9 | 9.5% | 117 |
| slkv11 | 100 | 3 | L2/L16 | 3 | 3.5% | 13 |
| slkv4 | 97 | 3 | L6 | 4 | 4.8% | 13 |
| CLL PATIENT 26 | 87 | 3 | L2/L16 | 1 | 1.1% | 122 |
| AL Se124 | 103 | 3 | L2/L16 | 9 | 9.5% | 117 |
| slkv13 | 100 | 3 | L2/L16 | 6 | 7.0% | 13 |
| bkv7 | 100 | 3 | L2/L16 | 5 | 5.8% | 13 |
| bkv22 | 100 | 3 | L2/L16 | 6 | 7.0% | 13 |
| CLL PATIENT 27 | 84 | 3 | L2/L16 | 0 | 0.0% | 122 |
| bkv35 | 100 | 3 | L6 | 8 | 9.3% | 13 |
| CLL PATIENT 25 | 87 | 3 | L2/L16 | 4 | 4.6% | 122 |
| slkv3 | 86 | 3 | L2/L16 | 7 | 8.1% | 13 |
| slkv7 | 99 | 1 | O2 | 7 | 8.1% | 13 |
| HuFd79 | 111 | 3 | L2/L16 | 24 | 24.2% | 21 |
| RAD | 99 | 3 | A27 | 9 | 10.3% | 78 |
| CLL PATIENT 28 | 83 | 3 | L2/L16 | 4 | 4.8% | 122 |
| REE | 104 | 3 | L2/L16 | 25 | 27.2% | 95 |
| FR4 | 99 | 3 | A27 | 8 | 9.2% | 77 |
| MD3.3 | 92 | 3 | L6 | 1 | 1.3% | 54 |
| MD3.1 | 92 | 3 | L6 | 0 | 0.0% | 54 |
| GA3.6 | 92 | 3 | L6 | 2 | 2.6% | 54 |
| M3.5N | 92 | 3 | L6 | 3 | 3.8% | 54 |
| WEI' | 82 | 3 | A27 | 0 | 0.0% | 65 |
| MD3.4 | 92 | 3 | L2/L16 | 1 | 1.3% | 54 |
| MD3.2 | 91 | 3 | L6 | 3 | 3.8% | 54 |
| VER | 97 | 3 | A27 | 19 | 22.4% | 20 |
| CLL PATIENT 30 | 78 | 3 | L6 | 3 | 3.8% | 122 |
| M3.1N | 92 | 3 | L2/L16 | 1 | 1.3% | 54 |
| MD3.6 | 91 | 3 | L2/L16 | 0 | 0.0% | 54 |
| MD3.8 | 91 | 3 | L2/L16 | 0 | 0.0% | 54 |
| GA3.4 | 92 | 3 | L6 | 7 | 9.0% | 54 |
| M3.6N | 92 | 3 | A27 | 0 | 0.0% | 54 |
| MD3.10 | 92 | 3 | A27 | 0 | 0.0% | 54 |
| MD3.13 | 91 | 3 | A27 | 0 | 0.0% | 54 |
| MD3.7 | 93 | 3 | A27 | 0 | 0.0% | 54 |
| MD3.9 | 93 | 3 | A27 | 0 | 0.0% | 54 |
| GA3.1 | 93 | 3 | A27 | 6 | 7.6% | 54 |
| bkv32 | 101 | 3 | A27 | 5 | 5.7% | 13 |
| GA3.5 | 93 | 3 | A27 | 5 | 6.3% | 54 |
| GA3.7 | 92 | 3 | A27 | 7 | 8.9% | 54 |
| MD3.12 | 92 | 3 | A27 | 2 | 2.5% | 54 |
| M3.2N | 90 | 3 | L6 | 6 | 7.8% | 54 |
| MD3.5 | 92 | 3 | A27 | 1 | 1.3% | 54 |
| M3.4N | 91 | 3 | L2/L16 | 8 | 10.3% | 54 |
| M3.8N | 91 | 3 | L2/L16 | 7 | 9.0% | 54 |
| M3.7N | 92 | 3 | A27 | 3 | 3.8% | 54 |
| GA3.2 | 92 | 3 | A27 | 9 | 11.4% | 54 |
| GA3.8 | 93 | 3 | A27 | 4 | 5.1% | 54 |
| GA3.3 | 92 | 3 | A27 | 8 | 10.1% | 54 |
| M3.3N | 92 | 3 | A27 | 5 | 6.3% | 54 |
| B6 | 83 | 3 | A27 | 8 | 11.3% | 78 |

TABLE 2A-continued

| rearranged human kappa sequences | | | | | | |
|---|---|---|---|---|---|---|
| Name[1] | aa[2] | Computed family[3] | Germline gene[4] | Diff. to germline[5] | % diff. to germline[6] | Reference[7] |
| E29.1 KAPPA | 78 | 3 | L2/L16 | 0 | 0.0% | 22 |
| SCW | 108 | 1 | O8 | 12 | 12.6% | 31 |
| REI-based CAMPATH-9 | 107 | 1 | O8 | 14 | 14.7% | 39 |
| RZ | 107 | 1 | O8 | 14 | 14.7% | 50 |
| BI | 108 | 1 | O8 | 14 | 14.7% | 14 |
| AND | 107 | 1 | O2 | 13 | 13.7% | 69 |
| 2A4 | 109 | 1 | O2 | 12 | 12.6% | 23 |
| KA | 108 | 1 | O8 | 19 | 20.0% | 107 |
| MEV | 109 | 1 | O2 | 14 | 14.7% | 29 |
| DEE | 106 | 1 | O2 | 13 | 14.0% | 76 |
| OU(IOC) | 108 | 1 | O2 | 18 | 18.9% | 60 |
| HuRSV19VK | 111 | 1 | O8 | 21 | 21.0% | 115 |
| SP2 | 108 | 1 | O2 | 17 | 17.9% | 93 |
| BJ26 | 99 | 1 | O8 | 21 | 24.1% | 1 |
| NI | 112 | 1 | O8 | 24 | 24.2% | 106 |
| BMA 0310EUCIV2 | 106 | 1 | L12(1) | 21 | 22.3% | 105 |
| CLL PATIENT 6 | 71 | 1 | A20 | 0 | 0.0% | 122 |
| BJ19 | 85 | 1 | O8 | 16 | 21.9% | 1 |
| GM 607 | 113 | 2 | A3 | 0 | 0.0% | 58 |
| R5A3K | 114 | 2 | A3 | 1 | 1.0% | 125 |
| R1C8K | 114 | 2 | A3 | 1 | 1.0% | 125 |
| VK2.R149 | 113 | 2 | A3 | 2 | 2.0% | 118 |
| TR1.6 | 109 | 2 | A3 | 4 | 4.0% | 92 |
| TR1.37 | 104 | 2 | A3 | 5 | 5.0% | 92 |
| FS-1 | 113 | 2 | A3 | 6 | 6.0% | 87 |
| TR1.8 | 110 | 2 | A3 | 6 | 6.0% | 92 |
| NIM | 113 | 2 | A3 | 8 | 8.0% | 28 |
| Inc | 112 | 2 | A3 | 11 | 11.0% | 35 |
| TEW | 107 | 2 | A3 | 6 | 6.4% | 96 |
| CUM | 114 | 2 | O1 | 7 | 6.9% | 44 |
| HRF1 | 71 | 2 | A3 | 4 | 5.6% | 124 |
| CLL PATIENT 19 | 87 | 2 | A3 | 0 | 0.0% | 122 |
| CLL PATIENT 20 | 87 | 2 | A3 | 0 | 0.0% | 122 |
| MIL | 112 | 2 | A3 | 16 | 16.2% | 26 |
| FR | 113 | 2 | A3 | 20 | 20.0% | 101 |
| MAL-Urine | 83 | 1 | O2 | 6 | 8.6% | 102 |
| Taykv306 | 73 | 3 | A27 | 1 | 1.6% | 52 |
| Taykv312 | 75 | 3 | A27 | 1 | 1.6% | 52 |
| HIV-b29 | 93 | 3 | A27 | 14 | 17.5% | 8 |
| 1-185-37 | 110 | 3 | A27 | 0 | 0.0% | 119 |
| 1-187-29 | 110 | 3 | A27 | 0 | 0.0% | 119 |
| TT117 | 110 | 3 | A27 | 9 | 9.4% | 63 |
| HIV-loop8 | 108 | 3 | A27 | 16 | 16.8% | 8 |
| rsv23L | 108 | 3 | A27 | 16 | 16.8% | 7 |
| HIV-b7 | 107 | 3 | A27 | 14 | 14.9% | 8 |
| HIV-b11 | 107 | 3 | A27 | 15 | 16.0% | 8 |
| HIV-LC1 | 107 | 3 | A27 | 19 | 20.2% | 8 |
| HIV-LC7 | 107 | 3 | A27 | 20 | 21.3% | 8 |
| HIV-LC22 | 107 | 3 | A27 | 21 | 22.3% | 8 |
| HIV-LC13 | 107 | 3 | A27 | 21 | 22.3% | 8 |
| HIV-LC3 | 107 | 3 | A27 | 21 | 22.3% | 8 |
| HIV-LC5 | 107 | 3 | A27 | 21 | 22.3% | 8 |
| HIV-LC28 | 107 | 3 | A27 | 21 | 22.3% | 8 |
| HIV-b4 | 107 | 3 | A27 | 22 | 23.4% | 8 |
| CLL PATIENT 31 | 87 | 3 | A27 | 15 | 17.2% | 122 |
| HIV-loop2 | 108 | 3 | L2/L16 | 17 | 17.9% | 8 |
| HIV-loop35 | 108 | 3 | L2/L16 | 17 | 17.9% | 8 |
| HIV-LC11 | 107 | 3 | A27 | 23 | 24.5% | 8 |
| HIV-LC24 | 107 | 3 | A27 | 23 | 24.5% | 8 |
| HIV-b12 | 107 | 3 | A27 | 24 | 25.5% | 8 |
| HIV-LC25 | 107 | 3 | A27 | 24 | 25.5% | 8 |
| HIV-b21 | 107 | 3 | A27 | 24 | 25.5% | 8 |
| HIV-LC26 | 107 | 3 | A27 | 26 | 27.7% | 8 |
| G3D10K | 108 | 1 | L12(2) | 12 | 12.6% | 125 |
| TT125 | 108 | 1 | L5 | 8 | 8.4% | 63 |
| HIV-s2 | 103 | 3 | A27 | 28 | 31.1% | 8 |
| 265-695 | 108 | 1 | L5 | 7 | 7.4% | 3 |
| 2-115-19 | 108 | 1 | A30 | 2 | 2.1% | 119 |
| rsv13L | 107 | 1 | O2 | 20 | 21.1% | 7 |
| HIV-b18 | 106 | 1 | O2 | 14 | 15.1% | 8 |
| RF-KL5 | 98 | 3 | L6 | 36 | 36.7% | 97 |
| ZM1-1 | 113 | 2 | A17 | 7 | 7.0% | 3 |
| HIV-s8 | 103 | 1 | O8 | 16 | 17.8% | 8 |
| K-EV15 | 95 | 5 | B2 | 0 | 0.0% | 112 |
| RF-TS3 | 100 | 2 | A23 | 0 | 0.0% | 121 |

TABLE 2A-continued

| rearranged human kappa sequences | | | | | | |
|---|---|---|---|---|---|---|
| Name[1] | aa[2] | Computed family[3] | Germline gene[4] | Diff. to germline[5] | % diff. to germline[6] | Reference[7] |
| HF-21/28 | 111 | 2 | A17 | 1 | 1.0% | 17 |
| RPMI6410 | 113 | 2 | A17 | 1 | 1.0% | 42 |
| JC11 | 113 | 2 | A17 | 1 | 1.0% | 49 |
| O-81 | 114 | 2 | A17 | 5 | 5.0% | 45 |
| FK-001 | 113 | 4 | B3 | 0 | 0.0% | 81 |
| CD5+.28 | 101 | 4 | B3 | 1 | 1.0% | 27 |
| LEN | 114 | 4 | B3 | 1 | 1.0% | 104 |
| UC | 114 | 4 | B3 | 1 | 1.0% | 111 |
| CD5+.5 | 101 | 4 | B3 | 1 | 1.0% | 27 |
| CD5+.26 | 101 | 4 | B3 | 1 | 1.0% | 27 |
| CD5+.12 | 101 | 4 | B3 | 2 | 2.0% | 27 |
| CD5+.23 | 101 | 4 | B3 | 2 | 2.0% | 27 |
| CD5+.7 | 101 | 4 | B3 | 2 | 2.0% | 27 |
| VJI | 113 | 4 | B3 | 3 | 3.0% | 56 |
| LOC | 113 | 4 | B3 | 3 | 3.0% | 72 |
| MAL | 113 | 4 | B3 | 3 | 3.0% | 72 |
| CD5+.6 | 101 | 4 | B3 | 3 | 3.0% | 27 |
| H2F | 113 | 4 | B3 | 3 | 3.0% | 70 |
| PB17IV | 114 | 4 | B3 | 4 | 4.0% | 74 |
| CD5+.27 | 101 | 4 | B3 | 4 | 4.0% | 27 |
| CD5+.9 | 101 | 4 | B3 | 4 | 4.0% | 27 |
| CD5−.28 | 101 | 4 | B3 | 5 | 5.0% | 27 |
| CD5−.26 | 101 | 4 | B3 | 6 | 5.9% | 27 |
| CD5+.24 | 101 | 4 | B3 | 6 | 5.9% | 27 |
| CD5+.10 | 101 | 4 | B3 | 6 | 5.9% | 27 |
| CD5−.19 | 101 | 4 | B3 | 6 | 5.9% | 27 |
| CD5−.18 | 101 | 4 | B3 | 7 | 6.9% | 27 |
| CD5−.16 | 101 | 4 | B3 | 8 | 7.9% | 27 |
| CD5−.24 | 101 | 4 | B3 | 8 | 7.9% | 27 |
| CD5−.17 | 101 | 4 | B3 | 10 | 9.9% | 27 |
| MD4.1 | 92 | 4 | B3 | 0 | 0.0% | 54 |
| MD4.4 | 92 | 4 | B3 | 0 | 0.0% | 54 |
| MD4.5 | 92 | 4 | B3 | 0 | 0.0% | 54 |
| MD4.6 | 92 | 4 | B3 | 0 | 0.0% | 54 |
| MD4.7 | 92 | 4 | B3 | 0 | 0.0% | 54 |
| MD4.2 | 92 | 4 | B3 | 1 | 1.3% | 54 |
| MD4.3 | 92 | 4 | B3 | 5 | 6.3% | 54 |
| CLL PATIENT 22 | 87 | 2 | A17 | 2 | 2.3% | 122 |
| CLL PATIENT 23 | 84 | 2 | A17 | 2 | 2.4% | 122 |

TABLE 2B

| rearranged human lambda sequences | | | | | | |
|---|---|---|---|---|---|---|
| Name[1] | aa[2] | Computed family[3] | Germline gene[4] | Diff. to germline[5] | % diff. to germline[6] | Reference[7] |
| WAH | 110 | 1 | DPL3 | 7 | 7% | 68 |
| 1B9/F2 | 112 | 1 | DPL3 | 7 | 7% | 9 |
| DIA | 112 | 1 | DPL2 | 7 | 7% | 36 |
| mAb67 | 89 | 1 | DPL3 | 0 | 0% | 29 |
| HiH2 | 110 | 1 | DPL3 | 12 | 11% | 3 |
| NIG-77 | 112 | 1 | DPL2 | 9 | 9% | 72 |
| OKA | 112 | 1 | DPL2 | 7 | 7% | 84 |
| KOL | 112 | 1 | DPL2 | 12 | 11% | 40 |
| T2:C5 | 111 | 1 | DPL5 | 0 | 0% | 6 |
| T2:C14 | 110 | 1 | DPL5 | 0 | 0% | 6 |
| PR-TS1 | 110 | 1 | DPL5 | 0 | 0% | 55 |
| 4G12 | 111 | 1 | DPL5 | 1 | 1% | 35 |
| KIM46L | 112 | 1 | HUMLV117 | 0 | 0% | 8 |
| Fog-B | 111 | 1 | DPL5 | 3 | 3% | 31 |
| 9F2L | 111 | 1 | DPL5 | 3 | 3% | 79 |
| mAb111 | 110 | 1 | DPL5 | 3 | 3% | 48 |
| PHOX15 | 111 | 1 | DPL5 | 4 | 4% | 49 |
| BL2 | 111 | 1 | DPL5 | 4 | 4% | 74 |
| NIG-64 | 111 | 1 | DPL5 | 4 | 4% | 72 |
| RF-SJ2 | 100 | 1 | DPL5 | 6 | 6% | 78 |
| AL EZI | 112 | 1 | DPL5 | 7 | 7% | 41 |
| ZIM | 112 | 1 | HUMLV117 | 7 | 7% | 18 |
| RF-SJ1 | 100 | 1 | DPL5 | 9 | 9% | 78 |
| IGLV1.1 | 98 | 1 | DPL4 | 0 | 0% | 1 |
| NEW | 112 | 1 | HUMLV117 | 11 | 10% | 42 |

TABLE 2B-continued

| rearranged human lambda sequences | | | | | | |
|---|---|---|---|---|---|---|
| Name[1] | aa[2] | Computed family[3] | Germline gene[4] | Diff. to germline[5] | % diff. to germline[6] | Reference[7] |
| CB-201 | 87 | 1 | DPL2 | 1 | 1% | 62 |
| MEM | 109 | 1 | DPL2 | 6 | 6% | 50 |
| H210 | 111 | 2 | DPL10 | 4 | 4% | 45 |
| NOV | 110 | 2 | DPL10 | 8 | 8% | 25 |
| NEI | 111 | 2 | DPL10 | 8 | 8% | 24 |
| AL MC | 110 | 2 | DPL11 | 6 | 6% | 28 |
| MES | 112 | 2 | DPL11 | 8 | 8% | 84 |
| FOG1-A3 | 111 | 2 | DPL11 | 9 | 9% | 27 |
| AL NOV | 112 | 2 | DPL11 | 7 | 7% | 28 |
| HMST-1 | 110 | 2 | DPL11 | 4 | 4% | 82 |
| HBW4-1 | 108 | 2 | DPL12 | 9 | 9% | 52 |
| WH | 110 | 2 | DPL11 | 11 | 11% | 34 |
| 11-50 | 110 | 2 | DPL11 | 7 | 7% | 82 |
| HBp2 | 110 | 2 | DPL12 | 8 | 8% | 3 |
| NIG-84 | 113 | 2 | DPL11 | 12 | 11% | 73 |
| VIL | 112 | 2 | DPL11 | 9 | 9% | 58 |
| TRO | 111 | 2 | DPL12 | 10 | 10% | 61 |
| ES492 | 108 | 2 | DPL11 | 15 | 15% | 76 |
| mAb216 | 89 | 2 | DPL12 | 1 | 1% | 7 |
| BSA3 | 109 | 3 | DPL16 | 0 | 0% | 49 |
| THY-29 | 110 | 3 | DPL16 | 0 | 0% | 27 |
| PR-TS2 | 108 | 3 | DPL16 | 0 | 0% | 55 |
| E29.1 LAMBDA | 107 | 3 | DPL16 | 1 | 1% | 13 |
| mAb63 | 109 | 3 | DPL16 | 2 | 2% | 29 |
| TEL14 | 110 | 3 | DPL16 | 6 | 6% | 49 |
| 6H-3C4 | 108 | 3 | DPL16 | 7 | 7% | 39 |
| SH | 109 | 3 | DPL16 | 7 | 7% | 70 |
| AL GIL | 109 | 3 | DPL16 | 8 | 8% | 23 |
| H6-3C4 | 108 | 3 | DPL16 | 8 | 8% | 83 |
| V-lambda-2.DS | 111 | 2 | DPL11 | 3 | 3% | 15 |
| 8.12 ID | 110 | 2 | DPL11 | 3 | 3% | 81 |
| DSC | 111 | 2 | DPL11 | 3 | 3% | 56 |
| PV11 | 110 | 2 | DPL11 | 1 | 1% | 56 |
| 33.H11 | 110 | 2 | DPL11 | 4 | 4% | 81 |
| AS17 | 111 | 2 | DPL11 | 7 | 7% | 56 |
| SD6 | 110 | 2 | DPL11 | 7 | 7% | 56 |
| KS3 | 110 | 2 | DPL11 | 9 | 9% | 56 |
| PV6 | 110 | 2 | DPL12 | 5 | 5% | 56 |
| NGD9 | 110 | 2 | DPL11 | 7 | 7% | 56 |
| MUC1-1 | 111 | 2 | DPL11 | 11 | 10% | 27 |
| A30c | 111 | 2 | DPL10 | 6 | 6% | 56 |
| KS6 | 110 | 2 | DPL12 | 6 | 6% | 56 |
| TEL13 | 111 | 2 | DPL11 | 11 | 10% | 49 |
| AS7 | 110 | 2 | DPL12 | 6 | 6% | 56 |
| MCG | 112 | 2 | DPL12 | 12 | 11% | 20 |
| U266L | 110 | 2 | DPL12 | 13 | 12% | 77 |
| PR-SJ2 | 110 | 2 | DPL12 | 14 | 13% | 55 |
| BOH | 112 | 2 | DPL12 | 11 | 10% | 37 |
| TOG | 111 | 2 | DPL11 | 19 | 18% | 53 |
| TEL16 | 111 | 2 | DPL11 | 19 | 18% | 49 |
| No. 13 | 110 | 2 | DPL10 | 14 | 13% | 52 |
| BO | 112 | 2 | DPL12 | 18 | 17% | 80 |
| WIN | 112 | 2 | DPL12 | 17 | 16% | 11 |
| BUR | 104 | 2 | DPL12 | 15 | 15% | 46 |
| NIG-58 | 110 | 2 | DPL12 | 20 | 19% | 69 |
| WEIR | 112 | 2 | DPL11 | 26 | 25% | 21 |
| THY-32 | 111 | 1 | DPL8 | 8 | 8% | 27 |
| TNF-H9G1 | 111 | 1 | DPL8 | 9 | 9% | 27 |
| mAb61 | 111 | 1 | DPL3 | 1 | 1% | 29 |
| LV1L1 | 98 | 1 | DPL2 | 0 | 0% | 54 |
| HA | 113 | 1 | DPL3 | 14 | 13% | 63 |
| LA1L1 | 111 | 1 | DPL2 | 3 | 3% | 54 |
| RHE | 112 | 1 | DPL1 | 17 | 16% | 22 |
| K1B12L | 113 | 1 | DPL8 | 17 | 16% | 79 |
| LOC | 113 | 1 | DPL2 | 15 | 14% | 84 |
| NIG-51 | 112 | 1 | DPL2 | 12 | 11% | 67 |
| NEWM | 104 | 1 | DPL8 | 23 | 22% | 10 |
| MD3-4 | 106 | 3 | DPL23 | 14 | 13% | 4 |
| COX | 112 | 1 | DPL2 | 13 | 12% | 84 |
| HiH10 | 106 | 3 | DPL23 | 13 | 12% | 3 |
| VOR | 112 | 1 | DPL2 | 16 | 15% | 16 |
| AL POL | 113 | 1 | DPL2 | 16 | 15% | 57 |
| CD4-74 | 111 | 1 | DPL2 | 19 | 18% | 27 |
| AMYLOID MOL | 102 | 3 | DPL23 | 15 | 15% | 30 |
| OST577 | 108 | 3 | Humlv318 | 10 | 10% | 4 |

TABLE 2B-continued rearranged human lambda sequences

| Name[1] | aa[2] | Computed family[3] | Germline gene[4] | Diff. to germline[5] | % diff. to germline[6] | Reference[7] |
|---|---|---|---|---|---|---|
| NIG-48 | 113 | 1 | DPL3 | 42 | 40% | 66 |
| CARR | 108 | 3 | DPL23 | 18 | 17% | 19 |
| mAb60 | 108 | 3 | DPL23 | 14 | 13% | 29 |
| NIG-68 | 99 | 3 | DPL23 | 25 | 26% | 32 |
| KERN | 107 | 3 | DPL23 | 26 | 25% | 59 |
| ANT | 106 | 3 | DPL23 | 17 | 16% | 19 |
| LEE | 110 | 3 | DPL23 | 18 | 17% | 85 |
| CLE | 94 | 3 | DPL23 | 17 | 17% | 19 |
| VL8 | 98 | 8 | DPL21 | 0 | 0% | 81 |
| MOT | 110 | 3 | Humlv318 | 23 | 22% | 38 |
| GAR | 108 | 3 | DPL23 | 26 | 25% | 33 |
| 32.B9 | 98 | 8 | DPL21 | 5 | 5% | 81 |
| PUG | 108 | 3 | Humlv318 | 24 | 23% | 19 |
| T1 | 115 | 8 | HUMLV801 | 52 | 50% | 6 |
| RF-TS7 | 96 | 7 | DPL18 | 4 | 4% | 60 |
| YM-1 | 116 | 8 | HUMLV801 | 51 | 49% | 75 |
| K6H6 | 112 | 8 | HUMLV801 | 20 | 19% | 44 |
| K5C7 | 112 | 8 | HUMLV801 | 20 | 19% | 44 |
| K5B8 | 112 | 8 | HUMLV801 | 20 | 19% | 44 |
| K5G5 | 112 | 8 | HUMLV801 | 20 | 19% | 44 |
| K4B8 | 112 | 8 | HUMLV801 | 19 | 18% | 44 |
| K6F5 | 112 | 8 | HUMLV801 | 17 | 16% | 44 |
| HIL | 108 | 3 | DPL23 | 22 | 21% | 47 |
| KIR | 109 | 3 | DPL23 | 20 | 19% | 19 |
| CAP | 109 | 3 | DPL23 | 19 | 18% | 84 |
| 1B8 | 110 | 3 | DPL23 | 22 | 21% | 43 |
| SHO | 108 | 3 | DPL23 | 19 | 18% | 19 |
| HAN | 108 | 3 | DPL23 | 20 | 19% | 19 |
| cML23 | 96 | 3 | DPL23 | 3 | 3% | 12 |
| PR-SJ1 | 96 | 3 | DPL23 | 7 | 7% | 55 |
| BAU | 107 | 3 | DPL23 | 9 | 9% | 5 |
| TEX | 99 | 3 | DPL23 | 8 | 8% | 19 |
| X(PET) | 107 | 3 | DPL23 | 9 | 9% | 51 |
| DOY | 106 | 3 | DPL23 | 9 | 9% | 19 |
| COT | 106 | 3 | DPL23 | 13 | 12% | 19 |
| Pag-1 | 111 | 3 | Humlv318 | 5 | 5% | 31 |
| DIS | 107 | 3 | Humlv318 | 2 | 2% | 19 |
| WIT | 108 | 3 | Humlv318 | 7 | 7% | 19 |
| I.RH | 108 | 3 | Humlv318 | 12 | 11% | 19 |
| S1-1 | 108 | 3 | Humlv318 | 12 | 11% | 52 |
| DEL | 108 | 3 | Humlv318 | 14 | 13% | 17 |
| TYR | 108 | 3 | Humlv318 | 11 | 10% | 19 |
| J.RH | 109 | 3 | Humlv318 | 13 | 12% | 19 |
| THO | 112 | 2 | DPL13 | 38 | 36% | 26 |
| LBV | 113 | 1 | DPL3 | 38 | 36% | 2 |
| WLT | 112 | 1 | DPL3 | 33 | 31% | 14 |
| SUT | 112 | 2 | DPL12 | 37 | 35% | 65 |

TABLE 2C rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| 21/28 | 119 | 1 | VH1-13-12 | 0 | 0.0% | 31 |
| 8E10 | 123 | 1 | VH1-13-12 | 0 | 0.0% | 31 |
| MUC1-1 | 118 | 1 | VH1-13-6 | 4 | 4.1% | 42 |
| gF1 | 98 | 1 | VH1-13-12 | 10 | 10.2% | 75 |
| VHGL 1.2 | 98 | 1 | VH1-13-6 | 2 | 2.0% | 26 |
| HV1L1 | 98 | 1 | VH1-13-6 | 0 | 0.0% | 81 |
| RF-TS7 | 104 | 1 | VH1-13-6 | 3 | 3.1% | 96 |
| E55 1.A15 | 106 | 1 | VH1-13-15 | 1 | 1.0% | 26 |
| HA1L1 | 126 | 1 | VH1-13-6 | 7 | 7.1% | 81 |
| UC | 123 | 1 | VH1-13-6 | 5 | 5.1% | 105 |
| WIL2 | 123 | 1 | VH1-13-6 | 6 | 6.1% | 55 |
| R3.5H5G | 122 | 1 | VH1-13-6 | 10 | 10.2% | 70 |
| N89P2 | 123 | 1 | VH1-13-16 | 11 | 11.2% | 77 |
| mAb113 | 126 | 1 | VH1-13-6 | 10 | 10.2% | 71 |
| LS2S3-3 | 125 | 1 | VH1-12-7 | 5 | 5.1% | 98 |
| LS2S3-12a | 125 | 1 | VH1-12-7 | 5 | 5.1% | 98 |
| LS2S3-5 | 125 | 1 | VH1-12-7 | 5 | 5.1% | 98 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| LS2S3-12e | 125 | 1 | VH1-12-7 | 5 | 5.1% | 98 |
| LS2S3-4 | 125 | 1 | VH1-12-7 | 5 | 5.1% | 98 |
| LS2S3-10 | 125 | 1 | VH1-12-7 | 5 | 5.1% | 98 |
| LS2S3-12d | 125 | 1 | VH1-12-7 | 6 | 6.1% | 98 |
| LS2S3-8 | 125 | 1 | VH1-12-7 | 5 | 5.1% | 98 |
| LS2 | 125 | 1 | VH1-12-7 | 6 | 6.1% | 113 |
| LS4 | 105 | 1 | VH1-12-7 | 6 | 6.1% | 113 |
| LS5 | 125 | 1 | VH1-12-7 | 6 | 6.1% | 113 |
| LS1 | 125 | 1 | VH1-12-7 | 6 | 6.1% | 113 |
| LS6 | 125 | 1 | VH1-12-7 | 6 | 6.1% | 113 |
| LS8 | 125 | 1 | VH1-12-7 | 7 | 7.1% | 113 |
| THY-29 | 122 | 1 | VH1-12-7 | 0 | 0.0% | 42 |
| 1B9/F2 | 122 | 1 | VH1-12-7 | 10 | 10.2% | 21 |
| 51P1 | 122 | 1 | VH1-12-1 | 0 | 0.0% | 105 |
| NEI | 127 | 1 | VH1-12-1 | 0 | 0.0% | 55 |
| AND | 127 | 1 | VH1-12-1 | 0 | 0.0% | 55 |
| L7 | 127 | 1 | VH1-12-1 | 0 | 0.0% | 54 |
| L22 | 124 | 1 | VH1-12-1 | 0 | 0.0% | 54 |
| L24 | 127 | 1 | VH1-12-1 | 0 | 0.0% | 54 |
| L26 | 116 | 1 | VH1-12-1 | 0 | 0.0% | 54 |
| L33 | 119 | 1 | VH1-12-1 | 0 | 0.0% | 54 |
| L34 | 117 | 1 | VH1-12-1 | 0 | 0.0% | 54 |
| L36 | 118 | 1 | VH1-12-1 | 0 | 0.0% | 54 |
| L39 | 120 | 1 | VH1-12-1 | 0 | 0.0% | 54 |
| L41 | 120 | 1 | VH1-12-1 | 0 | 0.0% | 54 |
| L42 | 125 | 1 | VH1-12-1 | 0 | 0.0% | 54 |
| VHGL 1.8 | 101 | 1 | VH1-12-1 | 0 | 0.0% | 26 |
| 783c | 127 | 1 | VH1-12-1 | 0 | 0.0% | 22 |
| X17115 | 127 | 1 | VH1-12-1 | 0 | 0.0% | 37 |
| L25 | 124 | 1 | VH1-12-1 | 0 | 0.0% | 54 |
| L17 | 120 | 1 | VH1-12-1 | 1 | 1.0% | 54 |
| L30 | 127 | 1 | VH1-12-1 | 1 | 1.0% | 54 |
| L37 | 120 | 1 | VH1-12-1 | 1 | 1.0% | 54 |
| TNF-E7 | 116 | 1 | VH1-12-1 | 2 | 2.0% | 42 |
| mAb111 | 122 | 1 | VH1-12-1 | 7 | 7.1% | 71 |
| III-2R | 122 | 1 | VH1-12-9 | 3 | 3.1% | 70 |
| KAS | 121 | 1 | VH1-12-1 | 7 | 7.1% | 79 |
| YES8c | 122 | 1 | VH1-12-1 | 8 | 8.2% | 34 |
| RF-TS1 | 123 | 1 | VH1-12-1 | 8 | 8.2% | 82 |
| BOR' | 121 | 1 | VH1-12-8 | 7 | 7.1% | 79 |
| VHGL 1.9 | 101 | 1 | VH1-12-1 | 8 | 8.2% | 26 |
| mAb410.30F305 | 117 | 1 | VH1-12-9 | 5 | 5.1% | 52 |
| EV1-15 | 127 | 1 | VH1-12-8 | 10 | 10.2% | 78 |
| mAb112 | 122 | 1 | VH1-12-1 | 11 | 11.2% | 71 |
| EU | 117 | 1 | VH1-12-1 | 11 | 11.2% | 28 |
| H210 | 127 | 1 | VH1-12-1 | 12 | 12.2% | 66 |
| TRANSGENE | 104 | 1 | VH1-12-1 | 0 | 0.0% | 111 |
| CLL2-1 | 93 | 1 | VH1-12-1 | 0 | 0.0% | 30 |
| CLL10 13-3 | 97 | 1 | VH1-12-1 | 0 | 0.0% | 29 |
| LS7 | 99 | 1 | VH1-12-7 | 4 | 4.1% | 113 |
| ALL7-1 | 87 | 1 | VH1-12-7 | 0 | 0.0% | 30 |
| CLL3-1 | 91 | 1 | VH1-12-7 | 1 | 1.0% | 30 |
| ALL56-1 | 85 | 1 | VH1-13-8 | 0 | 0.0% | 30 |
| ALL1-1 | 87 | 1 | VH1-13-6 | 1 | 1.0% | 30 |
| ALL4-1 | 94 | 1 | VH1-13-8 | 0 | 0.0% | 30 |
| ALL56 15-4 | 85 | 1 | VH1-13-8 | 5 | 5.1% | 29 |
| CLL4-1 | 88 | 1 | VH1-13-1 | 1 | 1.0% | 30 |
| Au92.1 | 98 | 1 | VH1-12-5 | 0 | 0.0% | 49 |
| RF-TS3 | 120 | 1 | VH1-12-5 | 1 | 1.0% | 82 |
| Au4.1 | 98 | 1 | VH1-12-5 | 1 | 1.0% | 49 |
| HP1 | 121 | 1 | VH1-13-6 | 13 | 13.3% | 110 |
| BLI | 127 | 1 | VH1-13-15 | 5 | 5.1% | 72 |
| No. 13 | 127 | 1 | VH1-12-2 | 19 | 19.4% | 76 |
| TR1.23 | 122 | 1 | VH1-13-2 | 23 | 23.5% | 88 |
| S1-1 | 125 | 1 | VH1-12-2 | 18 | 18.4% | 76 |
| TR1.10 | 119 | 1 | VH1-13-12 | 14 | 14.3% | 88 |
| E55 1.A2 | 102 | 1 | VH1-13-15 | 3 | 3.1% | 26 |
| SP2 | 119 | 1 | VH1-13-6 | 15 | 15.3% | 89 |
| TNF-H9G1 | 111 | 1 | VH1-13-18 | 2 | 2.0% | 42 |
| G3D10H | 127 | 1 | VH1-13-16 | 19 | 19.4% | 127 |
| TR1.9 | 118 | 1 | VH1-13-12 | 14 | 14.3% | 88 |
| TR1.8 | 121 | 1 | VH1-12-1 | 24 | 24.5% | 88 |
| LUNm01 | 127 | 1 | VH1-13-6 | 22 | 22.4% | 9 |
| K1B12H | 127 | 1 | VH1-12-7 | 23 | 23.5% | 127 |
| L3B2 | 99 | 1 | VH1-13-6 | 2 | 2.0% | 46 |

TABLE 2C-continued

| rearranged human heavy chain sequences | | | | | | |
|---|---|---|---|---|---|---|
| Name[1] | aa[2] | Computed family[3] | Germline gene[4] | Diff. to germline[5] | % diff. to germline[6] | Reference[7] |
| ss2 | 100 | 1 | VH1-13-6 | 2 | 2.0% | 46 |
| No. 86 | 124 | 1 | VH1-12-1 | 20 | 20.4% | 76 |
| TR1.6 | 124 | 1 | VH1-12-1 | 19 | 19.4% | 88 |
| ss7 | 99 | 1 | VH1-12-7 | 3 | 3.1% | 46 |
| s5B7 | 102 | 1 | VH1-12-1 | 0 | 0.0% | 46 |
| s6A3 | 97 | 1 | VH1-12-1 | 0 | 0.0% | 46 |
| ss6 | 99 | 1 | VH1-12-1 | 0 | 0.0% | 46 |
| L2H7 | 103 | 1 | VH1-13-12 | 0 | 0.0% | 46 |
| s6BG8 | 93 | 1 | VH1-13-12 | 0 | 0.0% | 46 |
| s6C9 | 107 | 1 | VH1-13-12 | 0 | 0.0% | 46 |
| HIV-b4 | 124 | 1 | VH1-13-12 | 21 | 21.4% | 12 |
| HIV-b12 | 124 | 1 | VH1-13-12 | 21 | 21.4% | 12 |
| L3G5 | 98 | 1 | VH1-13-6 | 1 | 1.0% | 46 |
| 22 | 115 | 1 | VH1-13-6 | 11 | 11.2% | 118 |
| L2A12 | 99 | 1 | VH1-13-15 | 3 | 3.1% | 46 |
| PHOX15 | 124 | 1 | VH1-12-7 | 20 | 20.4% | 73 |
| LUNm03 | 127 | 1 | VH1-1X-1 | 18 | 18.4% | 9 |
| CEA4-8A | 129 | 1 | VH1-12-7 | 1 | 1.0% | 42 |
| M60 | 121 | 2 | VH2-31-3 | 3 | 3.0% | 103 |
| HiH10 | 127 | 2 | VH2-31-5 | 9 | 9.0% | 4 |
| COR | 119 | 2 | VH2-31-2 | 11 | 11.0% | 91 |
| 2-115-19 | 124 | 2 | VH2-31-11 | 8 | 8.1% | 124 |
| OU | 125 | 2 | VH2-31-14 | 20 | 25.6% | 92 |
| HE | 120 | 2 | VH2-31-13 | 19 | 19.0% | 27 |
| CLL33 40-1 | 78 | 2 | VH2-31-5 | 2 | 2.0% | 29 |
| E55 3.9 | 88 | 3 | VH3-11-5 | 7 | 7.2% | 26 |
| MTFC3 | 125 | 3 | VH3-14-4 | 21 | 21.0% | 131 |
| MTFC11 | 125 | 3 | VH3-14-4 | 21 | 21.0% | 131 |
| MTFJ1 | 114 | 3 | VH3-14-4 | 21 | 21.0% | 131 |
| MTFJ2 | 114 | 3 | VH3-14-4 | 21 | 21.0% | 131 |
| MTFUJ4 | 100 | 3 | VH3-14-4 | 21 | 21.0% | 131 |
| MTFUJ5 | 100 | 3 | VH3-14-4 | 21 | 21.0% | 131 |
| MTFUJ2 | 100 | 3 | VH3-14-4 | 22 | 22.0% | 131 |
| MTFC8 | 125 | 3 | VH3-14-4 | 23 | 23.0% | 131 |
| TD e Vq | 113 | 3 | VH3-14-4 | 0 | 0.0% | 16 |
| rMTF | 114 | 3 | VH3-14-4 | 5 | 5.0% | 131 |
| MTFUJ6 | 100 | 3 | VH3-14-4 | 10 | 10.0% | 131 |
| RF-KES | 107 | 3 | VH3-14-4 | 9 | 9.0% | 85 |
| N51P8 | 126 | 3 | VH3-14-1 | 9 | 9.0% | 77 |
| TEI | 119 | 3 | VH3-13-8 | 21 | 21.4% | 20 |
| 33.H11 | 115 | 3 | VH3-13-19 | 10 | 10.2% | 129 |
| SB1/D8 | 101 | 3 | VH3-1X-8 | 14 | 14.0% | 2 |
| 38P1 | 119 | 3 | VH3-11-3 | 0 | 0.0% | 104 |
| BRO'IGM | 119 | 3 | VH3-11-3 | 13 | 13.4% | 19 |
| NIE | 119 | 3 | VH3-13-7 | 15 | 15.3% | 87 |
| 3D6 | 126 | 3 | VH3-13-26 | 5 | 5.1% | 35 |
| ZM1-1 | 112 | 3 | VH3-11-3 | 8 | 8.2% | 5 |
| E55 3.15 | 110 | 3 | VH3-13-26 | 0 | 0.0% | 26 |
| gF9 | 108 | 3 | VH3-13-8 | 15 | 15.3% | 75 |
| THY-32 | 120 | 3 | VH3-13-26 | 3 | 3.1% | 42 |
| RF-KL5 | 100 | 3 | VH3-13-26 | 5 | 5.1% | 96 |
| OST577 | 122 | 3 | VH3-13-13 | 6 | 6.1% | 5 |
| BO | 113 | 3 | VH3-13-19 | 15 | 15.3% | 10 |
| TT125 | 121 | 3 | VH3-13-10 | 15 | 15.3% | 64 |
| 2-115-58 | 127 | 3 | VH3-13-10 | 11 | 11.2% | 124 |
| KOL | 126 | 3 | VH3-13-14 | 16 | 16.3% | 102 |
| mAb60 | 118 | 3 | VH3-13-17 | 14 | 14.3% | 45 |
| RF-AN | 106 | 3 | VH3-13-26 | 8 | 8.2% | 85 |
| BUT | 115 | 3 | VH3-11-6 | 13 | 13.4% | 119 |
| KOL-based CAMPATH-9 | 118 | 3 | VH3-13-13 | 16 | 16.3% | 41 |
| B1 | 119 | 3 | VH3-13-19 | 13 | 13.3% | 53 |
| N98P1 | 127 | 3 | VH3-13-1 | 13 | 13.3% | 77 |
| TT117 | 107 | 3 | VH3-13-10 | 12 | 12.2% | 64 |
| WEA | 114 | 3 | VH3-13-12 | 15 | 15.3% | 40 |
| HIL | 120 | 3 | VH3-13-14 | 14 | 14.3% | 23 |
| s5A10 | 97 | 3 | VH3-13-14 | 0 | 0.0% | 46 |
| s5D11 | 98 | 3 | VH3-13-7 | 0 | 0.0% | 46 |
| s6C8 | 100 | 3 | VH3-13-7 | 0 | 0.0% | 46 |
| s6H12 | 98 | 3 | VH3-13-7 | 0 | 0.0% | 46 |
| VH10.7 | 119 | 3 | VH3-13-14 | 16 | 16.3% | 128 |
| HIV-loop2 | 126 | 3 | VH3-13-7 | 16 | 16.3% | 12 |
| HIV-loop35 | 126 | 3 | VH3-13-7 | 16 | 16.3% | 12 |
| TRO | 122 | 3 | VH3-13-1 | 13 | 13.3% | 61 |
| SA-4B | 123 | 3 | VH3-13-1 | 15 | 15.3% | 125 |
| L2B5 | 98 | 3 | VH3-13-13 | 0 | 0.0% | 46 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| s6E11 | 95 | 3 | VH3-13-13 | 0 | 0.0% | 46 |
| s6H7 | 100 | 3 | VH3-13-13 | 0 | 0.0% | 46 |
| ss1 | 102 | 3 | VH3-13-13 | 0 | 0.0% | 46 |
| ss8 | 94 | 3 | VH3-13-13 | 0 | 0.0% | 46 |
| DOB | 120 | 3 | VH3-13-26 | 21 | 21.4% | 116 |
| THY-33 | 115 | 3 | VH3-13-15 | 20 | 20.4% | 42 |
| NOV | 118 | 3 | VH3-13-19 | 14 | 14.3% | 38 |
| rsv13H | 120 | 3 | VH3-13-24 | 20 | 20.4% | 11 |
| L3G11 | 98 | 3 | VH3-13-20 | 2 | 2.0% | 46 |
| L2E8 | 99 | 3 | VH3-13-19 | 0 | 0.0% | 46 |
| L2D10 | 101 | 3 | VH3-13-10 | 1 | 1.0% | 46 |
| L2E7 | 98 | 3 | VH3-13-10 | 1 | 1.0% | 46 |
| L3A10 | 100 | 3 | VH3-13-24 | 0 | 0.0% | 46 |
| L2E5 | 97 | 3 | VH3-13-2 | 1 | 1.0% | 46 |
| BUR | 119 | 3 | VH3-13-7 | 21 | 21.4% | 67 |
| s4D5 | 107 | 3 | VH3-11-3 | 1 | 1.0% | 46 |
| 19 | 116 | 3 | VH3-13-16 | 4 | 4.1% | 118 |
| s5D4 | 99 | 3 | VH3-13-1 | 0 | 0.0% | 46 |
| s6A8 | 100 | 3 | VH3-13-1 | 0 | 0.0% | 46 |
| HIV-loop13 | 123 | 3 | VH3-13-12 | 17 | 17.3% | 12 |
| TR1.32 | 112 | 3 | VH3-11-8 | 18 | 18.6% | 88 |
| L2B10 | 97 | 3 | VH3-11-3 | 1 | 1.0% | 46 |
| TR1.5 | 114 | 3 | VH3-11-8 | 21 | 21.6% | 88 |
| s6H9 | 101 | 3 | VH3-13-25 | 0 | 0.0% | 46 |
| 8 | 112 | 3 | VH3-13-1 | 6 | 6.1% | 118 |
| 23 | 115 | 3 | VH3-13-1 | 6 | 6.1% | 118 |
| 7 | 115 | 3 | VH3-13-1 | 4 | 4.1% | 118 |
| TR1.3 | 120 | 3 | VH3-11-8 | 20 | 20.6% | 88 |
| 18/2 | 125 | 3 | VH3-13-10 | 0 | 0.0% | 32 |
| 18/9 | 125 | 3 | VH3-13-10 | 0 | 0.0% | 31 |
| 30P1 | 119 | 3 | VH3-13-10 | 0 | 0.0% | 106 |
| HF2-1/17 | 125 | 3 | VH3-13-10 | 0 | 0.0% | 8 |
| A77 | 109 | 3 | VH3-13-10 | 0 | 0.0% | 44 |
| B19.7 | 108 | 3 | VH3-13-10 | 0 | 0.0% | 44 |
| M43 | 119 | 3 | VH3-13-10 | 0 | 0.0% | 103 |
| 1/17 | 125 | 3 | VH3-13-10 | 0 | 0.0% | 31 |
| 18/17 | 125 | 3 | VH3-13-10 | 0 | 0.0% | 31 |
| E54 3.4 | 109 | 3 | VH3-13-10 | 0 | 0.0% | 26 |
| LAMBDA-VH26 | 98 | 3 | VH3-13-10 | 1 | 1.0% | 95 |
| E54 3.8 | 111 | 3 | VH3-13-10 | 1 | 1.0% | 26 |
| GL16 | 106 | 3 | VH3-13-10 | 1 | 1.0% | 44 |
| 4G12 | 125 | 3 | VH3-13-10 | 1 | 1.0% | 56 |
| A73 | 106 | 3 | VH3-13-10 | 2 | 2.0% | 44 |
| AL1.3 | 111 | 3 | VH3-13-10 | 3 | 3.1% | 117 |
| 3.A290 | 118 | 3 | VH3-13-10 | 2 | 2.0% | 108 |
| Ab18 | 127 | 3 | VH3-13-8 | 2 | 2.0% | 100 |
| E54 3.3 | 105 | 3 | VH3-13-10 | 3 | 3.1% | 26 |
| 35G6 | 121 | 3 | VH3-13-10 | 3 | 3.1% | 57 |
| A95 | 107 | 3 | VH3-13-10 | 5 | 5.1% | 44 |
| Ab25 | 128 | 3 | VH3-13-10 | 5 | 5.1% | 100 |
| N87 | 126 | 3 | VH3-13-10 | 4 | 4.1% | 77 |
| ED8.4 | 99 | 3 | VH3-13-10 | 6 | 6.1% | 2 |
| RF-KL1 | 122 | 3 | VH3-13-10 | 6 | 6.1% | 82 |
| AL1.1 | 112 | 3 | VH3-13-10 | 2 | 2.0% | 117 |
| AL3.11 | 102 | 3 | VH3-13-10 | 1 | 1.0% | 117 |
| 32.B9 | 127 | 3 | VH3-13-8 | 6 | 6.1% | 129 |
| TK1 | 109 | 3 | VH3-13-10 | 2 | 2.0% | 117 |
| POP | 123 | 3 | VH3-13-10 | 8 | 8.2% | 115 |
| 9F2H | 127 | 3 | VH3-13-10 | 9 | 9.2% | 127 |
| VD | 115 | 3 | VH3-13-10 | 9 | 9.2% | 10 |
| Vh38Cl.10 | 121 | 3 | VH3-13-10 | 8 | 8.2% | 74 |
| Vh38Cl.9 | 121 | 3 | VH3-13-10 | 8 | 8.2% | 74 |
| Vh38Cl.8 | 121 | 3 | VH3-13-10 | 8 | 8.2% | 74 |
| 63P1 | 120 | 3 | VH3-11-8 | 0 | 0.0% | 104 |
| 60P2 | 117 | 3 | VH3-11-8 | 0 | 0.0% | 104 |
| AL3.5 | 90 | 3 | VH3-13-10 | 2 | 2.0% | 117 |
| GF4/1.1 | 123 | 3 | VH3-13-10 | 10 | 10.2% | 39 |
| Ab21 | 126 | 3 | VH3-13-10 | 12 | 12.2% | 100 |
| TD d Vp | 118 | 3 | VH3-13-17 | 2 | 2.0% | 16 |
| Vh38Cl.4 | 119 | 3 | VH3-13-10 | 8 | 8.2% | 74 |
| Vh38Cl.5 | 119 | 3 | VH3-13-10 | 8 | 8.2% | 74 |
| AL3.4 | 104 | 3 | VH3-13-10 | 1 | 1.0% | 117 |
| FOG1-A3 | 115 | 3 | VH3-13-19 | 2 | 2.0% | 42 |
| HA3D1 | 117 | 3 | VH3-13-21 | 1 | 1.0% | 81 |
| E54 3.2 | 112 | 3 | VH3-13-24 | 0 | 0.0% | 26 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| mAb52 | 128 | 3 | VH3-13-12 | 2 | 2.0% | 51 |
| mAb53 | 128 | 3 | VH3-13-12 | 2 | 2.0% | 51 |
| mAb56 | 128 | 3 | VH3-13-12 | 2 | 2.0% | 51 |
| mAb57 | 128 | 3 | VH3-13-12 | 2 | 2.0% | 51 |
| mAb58 | 128 | 3 | VH3-13-12 | 2 | 2.0% | 51 |
| mAb59 | 128 | 3 | VH3-13-12 | 2 | 2.0% | 51 |
| mAb105 | 128 | 3 | VH3-13-12 | 2 | 2.0% | 51 |
| mAb107 | 128 | 3 | VH3-13-12 | 2 | 2.0% | 51 |
| E55 3.14 | 110 | 3 | VH3-13-19 | 0 | 0.0% | 26 |
| F13-28 | 106 | 3 | VH3-13-19 | 1 | 1.0% | 94 |
| mAb55 | 127 | 3 | VH3-13-18 | 4 | 4.1% | 51 |
| YSE | 117 | 3 | VH3-13-24 | 6 | 6.1% | 72 |
| E55 3.23 | 106 | 3 | VH3-13-19 | 2 | 2.0% | 26 |
| RF-TS5 | 101 | 3 | VH3-13-1 | 3 | 3.1% | 85 |
| N42P5 | 124 | 3 | VH3-13-2 | 7 | 7.1% | 77 |
| FOG1-H6 | 110 | 3 | VH3-13-16 | 7 | 7.1% | 42 |
| O-81 | 115 | 3 | VH3-13-19 | 11 | 11.2% | 47 |
| HIV-s8 | 122 | 3 | VH3-13-12 | 11 | 11.2% | 12 |
| mAb114 | 125 | 3 | VH3-13-19 | 12 | 12.2% | 71 |
| 33.F12 | 116 | 3 | VH3-13-2 | 4 | 4.1% | 129 |
| 4B4 | 119 | 3 | VH3-1X-3 | 0 | 0.0% | 101 |
| M26 | 123 | 3 | VH3-1X-3 | 0 | 0.0% | 103 |
| VHGL 3.1 | 100 | 3 | VH3-1X-3 | 0 | 0.0% | 26 |
| E55 3.13 | 113 | 3 | VH3-1X-3 | 1 | 1.0% | 26 |
| SB5/D6 | 101 | 3 | VH3-1X-6 | 3 | 3.0% | 2 |
| RAY4 | 101 | 3 | VH3-1X-6 | 3 | 3.0% | 2 |
| 82-D V-D | 106 | 3 | VH3-1X-3 | 5 | 5.0% | 112 |
| MAL | 129 | 3 | VH3-1X-3 | 5 | 5.0% | 72 |
| LOC | 123 | 3 | VH3-1X-6 | 5 | 5.0% | 72 |
| LSF2 | 101 | 3 | VH3-1X-6 | 11 | 11.0% | 2 |
| HIB RC3 | 100 | 3 | VH3-1X-6 | 11 | 11.0% | 1 |
| 56P1 | 119 | 3 | VH3-13-7 | 0 | 0.0% | 104 |
| M72 | 122 | 3 | VH3-13-7 | 0 | 0.0% | 103 |
| M74 | 121 | 3 | VH3-13-7 | 0 | 0.0% | 103 |
| E54 3.5 | 105 | 3 | VH3-13-7 | 0 | 0.0% | 26 |
| 2E7 | 123 | 3 | VH3-13-7 | 0 | 0.0% | 63 |
| 2P1 | 117 | 3 | VH3-13-7 | 0 | 0.0% | 104 |
| RF-SJ2 | 127 | 3 | VH3-13-7 | 1 | 1.0% | 83 |
| PR-TS1 | 114 | 3 | VH3-13-7 | 1 | 1.0% | 85 |
| KIM46H | 127 | 3 | VH3-13-13 | 0 | 0.0% | 18 |
| E55 3.6 | 108 | 3 | VH3-13-7 | 2 | 2.0% | 26 |
| E55 3.10 | 107 | 3 | VH3-13-13 | 1 | 1.0% | 26 |
| 3.B6 | 114 | 3 | VH3-13-13 | 1 | 1.0% | 108 |
| E54 3.6 | 110 | 3 | VH3-13-13 | 1 | 1.0% | 26 |
| FL2-2 | 114 | 3 | VH3-13-13 | 1 | 1.0% | 80 |
| RF-SJ3 | 112 | 3 | VH3-13-7 | 2 | 2.0% | 85 |
| E55 3.5 | 105 | 3 | VH3-13-14 | 1 | 1.0% | 26 |
| BSA3 | 121 | 3 | VH3-13-13 | 1 | 1.0% | 73 |
| HMST-1 | 119 | 3 | VH3-13-7 | 3 | 3.1% | 130 |
| RF-TS2 | 126 | 3 | VH3-13-13 | 4 | 4.1% | 82 |
| E55 3.12 | 109 | 3 | VH3-13-15 | 0 | 0.0% | 26 |
| 19.E7 | 126 | 3 | VH3-13-14 | 3 | 3.1% | 129 |
| 11-50 | 119 | 3 | VH3-13-13 | 6 | 6.1% | 130 |
| E29.1 | 120 | 3 | VH3-13-15 | 2 | 2.0% | 25 |
| E55 3.16 | 108 | 3 | VH3-13-7 | 6 | 6.1% | 26 |
| TNF-E1 | 117 | 3 | VH3-13-7 | 7 | 7.1% | 42 |
| RF-SJ1 | 127 | 3 | VH3-13-13 | 6 | 6.1% | 83 |
| FOG1-A4 | 116 | 3 | VH3-13-7 | 8 | 8.2% | 42 |
| TNF-A1 | 117 | 3 | VH3-13-15 | 4 | 4.1% | 42 |
| PR-SJ2 | 107 | 3 | VH3-13-14 | 8 | 8.2% | 85 |
| HN.14 | 124 | 3 | VH3-13-13 | 10 | 10.2% | 33 |
| CAM' | 121 | 3 | VH3-13-7 | 12 | 12.2% | 65 |
| HIV-B8 | 125 | 3 | VH3-13-7 | 9 | 9.2% | 12 |
| HIV-b27 | 125 | 3 | VH3-13-7 | 9 | 9.2% | 12 |
| HIV-b8 | 125 | 3 | VH3-13-7 | 9 | 9.2% | 12 |
| HIV-s4 | 125 | 3 | VH3-13-7 | 9 | 9.2% | 12 |
| HIV-B26 | 125 | 3 | VH3-13-7 | 9 | 9.2% | 12 |
| HIV-B35 | 125 | 3 | VH3-13-7 | 10 | 10.2% | 12 |
| HIV-b18 | 125 | 3 | VH3-13-7 | 10 | 10.2% | 12 |
| HIV-b22 | 125 | 3 | VH3-13-7 | 11 | 11.2% | 12 |
| HIV-b13 | 125 | 3 | VH3-13-7 | 12 | 12.2% | 12 |
| 333 | 117 | 3 | VH3-14-4 | 24 | 24.0% | 24 |
| 1H1 | 120 | 3 | VH3-14-4 | 24 | 24.0% | 24 |
| 1B11 | 120 | 3 | VH3-14-4 | 23 | 23.0% | 24 |
| CLL30 2-3 | 86 | 3 | VH3-13-19 | 1 | 1.0% | 29 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| GA | 110 | 3 | VH3-13-7 | 19 | 19.4% | 36 |
| JeB | 99 | 3 | VH3-13-14 | 3 | 3.1% | 7 |
| GAL | 110 | 3 | VH3-13-19 | 10 | 10.2% | 126 |
| K6H6 | 119 | 3 | VH3-1X-6 | 18 | 18.0% | 60 |
| K4B8 | 119 | 3 | VH3-1X-6 | 18 | 18.0% | 60 |
| K5B8 | 119 | 3 | VH3-1X-6 | 18 | 18.0% | 60 |
| K5C7 | 119 | 3 | VH3-1X-6 | 19 | 19.0% | 60 |
| K5G5 | 119 | 3 | VH3-1X-6 | 19 | 19.0% | 60 |
| K6F5 | 119 | 3 | VH3-1X-6 | 19 | 19.0% | 60 |
| AL3.16 | 98 | 3 | VH3-13-10 | 1 | 1.0% | 117 |
| N86P2 | 98 | 3 | VH3-13-10 | 3 | 3.1% | 77 |
| N54P6 | 95 | 3 | VH3-13-16 | 7 | 7.1% | 77 |
| LAMBDA HT112-1 | 126 | 4 | VH4-11-2 | 0 | 0.0% | 3 |
| HY18 | 121 | 4 | VH4-11-2 | 0 | 0.0% | 43 |
| mAb63 | 126 | 4 | VH4-11-2 | 0 | 0.0% | 45 |
| FS-3 | 105 | 4 | VH4-11-2 | 0 | 0.0% | 86 |
| FS-5 | 111 | 4 | VH4-11-2 | 0 | 0.0% | 86 |
| FS-7 | 107 | 4 | VH4-11-2 | 0 | 0.0% | 86 |
| FS-8 | 110 | 4 | VH4-11-2 | 0 | 0.0% | 86 |
| PR-TS2 | 105 | 4 | VH4-11-2 | 0 | 0.0% | 85 |
| RF-TMC | 102 | 4 | VH4-11-2 | 0 | 0.0% | 85 |
| mAb216 | 122 | 4 | VH4-11-2 | 1 | 1.0% | 15 |
| mAb410.7.F91 | 122 | 4 | VH4-11-2 | 1 | 1.0% | 52 |
| mAbA6H4C5 | 124 | 4 | VH4-11-2 | 1 | 1.0% | 15 |
| Ab44 | 127 | 4 | VH4-11-2 | 2 | 2.1% | 100 |
| 6H-3C4 | 124 | 4 | VH4-11-2 | 3 | 3.1% | 59 |
| FS-6 | 108 | 4 | VH4-11-2 | 6 | 6.2% | 86 |
| FS-2 | 114 | 4 | VH4-11-2 | 6 | 6.2% | 84 |
| HIG1 | 126 | 4 | VH4-11-2 | 7 | 7.2% | 62 |
| FS-4 | 105 | 4 | VH4-11-2 | 8 | 8.2% | 86 |
| SA-4A | 123 | 4 | VH4-11-2 | 9 | 9.3% | 125 |
| LES-C | 119 | 4 | VH4-11-2 | 10 | 10.3% | 99 |
| DI | 78 | 4 | VH4-11-9 | 16 | 16.5% | 58 |
| Ab26 | 126 | 4 | VH4-31-4 | 8 | 8.1% | 100 |
| TS2 | 124 | 4 | VH4-31-12 | 15 | 15.2% | 110 |
| 265-695 | 115 | 4 | VH4-11-7 | 16 | 16.5% | 5 |
| WAH | 129 | 4 | VH4-31-13 | 19 | 19.2% | 93 |
| 268-D | 122 | 4 | VH4-11-8 | 22 | 22.7% | 6 |
| 58P2 | 118 | 4 | VH4-11-8 | 0 | 0.0% | 104 |
| mAb67 | 128 | 4 | VH4-21-4 | 1 | 1.0% | 45 |
| 4.L39 | 115 | 4 | VH4-11-8 | 2 | 2.1% | 108 |
| mF7 | 111 | 4 | VH4-31-13 | 3 | 3.0% | 75 |
| 33.C9 | 122 | 4 | VH4-21-5 | 7 | 7.1% | 129 |
| Pag-1 | 124 | 4 | VH4-11-16 | 5 | 5.2% | 50 |
| B3 | 123 | 4 | VH4-21-3 | 8 | 8.2% | 53 |
| IC4 | 120 | 4 | VH4-11-8 | 6 | 6.2% | 70 |
| C6B2 | 127 | 4 | VH4-31-12 | 4 | 4.0% | 48 |
| N78 | 118 | 4 | VH4-11-9 | 11 | 11.3% | 77 |
| B2 | 109 | 4 | VH4-11-8 | 12 | 12.4% | 53 |
| WRD2 | 123 | 4 | VH4-11-12 | 6 | 6.2% | 90 |
| mAb426.4.2F20 | 126 | 4 | VH4-11-8 | 2 | 2.1% | 52 |
| E54 4.58 | 115 | 4 | VH4-11-8 | 1 | 1.0% | 26 |
| WRD6 | 123 | 4 | VH4-11-12 | 10 | 10.3% | 90 |
| mAb426.12.3F1.4 | 122 | 4 | VH4-11-9 | 4 | 4.1% | 52 |
| E54 4.2 | 108 | 4 | VH4-21-6 | 2 | 2.0% | 26 |
| WIL | 127 | 4 | VH4-31-13 | 0 | 0.0% | 90 |
| COF | 126 | 4 | VH4-31-13 | 0 | 0.0% | 90 |
| LAR | 122 | 4 | VH4-31-13 | 2 | 2.0% | 90 |
| WAT | 125 | 4 | VH4-31-13 | 4 | 4.0% | 90 |
| mAb61 | 123 | 4 | VH4-31-13 | 5 | 5.1% | 45 |
| WAG | 127 | 4 | VH4-31-4 | 0 | 0.0% | 90 |
| RF-SJ4 | 108 | 4 | VH4-31-12 | 2 | 2.0% | 85 |
| E54 4.4 | 110 | 4 | VH4-11-7 | 0 | 0.0% | 26 |
| E55 4.A1 | 108 | 4 | VH4-11-7 | 0 | 0.0% | 26 |
| PR-SJ1 | 103 | 4 | VH4-11-7 | 1 | 1.0% | 85 |
| E54 4.23 | 111 | 4 | VH4-11-7 | 1 | 1.0% | 26 |
| CLL7 7-2 | 97 | 4 | VH4-11-12 | 0 | 0.0% | 29 |
| 37P1 | 95 | 4 | VH4-11-12 | 0 | 0.0% | 104 |
| ALL52 30-2 | 91 | 4 | VH4-31-12 | 4 | 4.0% | 29 |
| EBV-21 | 98 | 5 | VH5-12-1 | 0 | 0.0% | 13 |
| CB-4 | 98 | 5 | VH5-12-1 | 0 | 0.0% | 13 |
| CLL-12 | 98 | 5 | VH5-12-1 | 0 | 0.0% | 13 |
| L3-4 | 98 | 5 | VH5-12-1 | 0 | 0.0% | 13 |
| CLL11 | 98 | 5 | VH5-12-1 | 0 | 0.0% | 17 |
| CORD3 | 98 | 5 | VH5-12-1 | 0 | 0.0% | 17 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| CORD4 | 98 | 5 | VH5-12-1 | 0 | 0.0% | 17 |
| CORD8 | 98 | 5 | VH5-12-1 | 0 | 0.0% | 17 |
| CORD9 | 98 | 5 | VH5-12-1 | 0 | 0.0% | 17 |
| CD+1 | 98 | 5 | VH5-12-1 | 0 | 0.0% | 17 |
| CD+3 | 98 | 5 | VH5-12-1 | 0 | 0.0% | 17 |
| CD+4 | 98 | 5 | VH5-12-1 | 0 | 0.0% | 17 |
| CD−1 | 98 | 5 | VH5-12-1 | 0 | 0.0% | 17 |
| CD−5 | 98 | 5 | VH5-12-1 | 0 | 0.0% | 17 |
| VERG14 | 98 | 5 | VH5-12-1 | 0 | 0.0% | 17 |
| PBL1 | 98 | 5 | VH5-12-1 | 0 | 0.0% | 17 |
| PBL10 | 98 | 5 | VH5-12-1 | 0 | 0.0% | 17 |
| STRAb SA-1A | 127 | 5 | VH5-12-1 | 0 | 0.0% | 125 |
| DOB' | 122 | 5 | VH5-12-1 | 0 | 0.0% | 97 |
| VERG5 | 98 | 5 | VH5-12-1 | 0 | 0.0% | 17 |
| PBL2 | 98 | 5 | VH5-12-1 | 1 | 1.0% | 17 |
| Tu16 | 119 | 5 | VH5-12-1 | 1 | 1.0% | 49 |
| PBL12 | 98 | 5 | VH5-12-1 | 1 | 1.0% | 17 |
| CD+2 | 98 | 5 | VH5-12-1 | 1 | 1.0% | 17 |
| CORD10 | 98 | 5 | VH5-12-1 | 1 | 1.0% | 17 |
| PBL9 | 98 | 5 | VH5-12-1 | 1 | 1.0% | 17 |
| CORD2 | 98 | 5 | VH5-12-1 | 2 | 2.0% | 17 |
| PBL6 | 98 | 5 | VH5-12-1 | 2 | 2.0% | 17 |
| CORD5 | 98 | 5 | VH5-12-1 | 2 | 2.0% | 17 |
| CD−2 | 98 | 5 | VH5-12-1 | 2 | 2.0% | 17 |
| CORD1 | 98 | 5 | VH5-12-1 | 2 | 2.0% | 17 |
| CD−3 | 98 | 5 | VH5-12-1 | 3 | 3.1% | 17 |
| VERG4 | 98 | 5 | VH5-12-1 | 3 | 3.1% | 17 |
| PBL13 | 98 | 5 | VH5-12-1 | 3 | 3.1% | 17 |
| PBL7 | 98 | 5 | VH5-12-1 | 3 | 3.1% | 17 |
| HAN | 119 | 5 | VH5-12-1 | 3 | 3.1% | 97 |
| VERG3 | 98 | 5 | VH5-12-1 | 3 | 3.1% | 17 |
| PBL3 | 98 | 5 | VH5-12-1 | 3 | 3.1% | 17 |
| VERG7 | 98 | 5 | VH5-12-1 | 3 | 3.1% | 17 |
| PBL5 | 94 | 5 | VH5-12-1 | 0 | 0.0% | 17 |
| CD−4 | 98 | 5 | VH5-12-1 | 4 | 4.1% | 17 |
| CLL10 | 98 | 5 | VH5-12-1 | 4 | 4.1% | 17 |
| PBL11 | 98 | 5 | VH5-12-1 | 4 | 4.1% | 17 |
| CORD6 | 98 | 5 | VH5-12-1 | 4 | 4.1% | 17 |
| VERG2 | 98 | 5 | VH5-12-1 | 5 | 5.1% | 17 |
| 83P2 | 119 | 5 | VH5-12-1 | 0 | 0.0% | 103 |
| VERG9 | 98 | 5 | VH5-12-1 | 6 | 6.1% | 17 |
| CLL6 | 98 | 5 | VH5-12-1 | 6 | 6.1% | 17 |
| PBL8 | 98 | 5 | VH5-12-1 | 7 | 7.1% | 17 |
| Ab2022 | 120 | 5 | VH5-12-1 | 3 | 3.1% | 100 |
| CAV | 127 | 5 | VH5-12-4 | 0 | 0.0% | 97 |
| HOW' | 120 | 5 | VH5-12-4 | 0 | 0.0% | 97 |
| PET | 127 | 5 | VH5-12-4 | 0 | 0.0% | 97 |
| ANG | 121 | 5 | VH5-12-4 | 0 | 0.0% | 97 |
| KER | 121 | 5 | VH5-12-4 | 0 | 0.0% | 97 |
| 5.M13 | 118 | 5 | VH5-12-4 | 0 | 0.0% | 107 |
| Au2.1 | 118 | 5 | VH5-12-4 | 1 | 1.0% | 49 |
| WS1 | 126 | 5 | VH5-12-1 | 9 | 9.2% | 110 |
| TD Vn | 98 | 5 | VH5-12-4 | 1 | 1.0% | 16 |
| TEL13 | 116 | 5 | VH5-12-1 | 9 | 9.2% | 73 |
| E55 5.237 | 112 | 5 | VH5-12-4 | 2 | 2.0% | 26 |
| VERG1 | 98 | 5 | VH5-12-1 | 10 | 10.2% | 17 |
| CD4-74 | 117 | 5 | VH5-12-1 | 10 | 10.2% | 42 |
| 257-D | 125 | 5 | VH5-12-1 | 11 | 11.2% | 6 |
| CLL4 | 98 | 5 | VH5-12-1 | 11 | 11.2% | 17 |
| CLL8 | 98 | 5 | VH5-12-1 | 11 | 11.2% | 17 |
| Ab2 | 124 | 5 | VH5-12-1 | 12 | 12.2% | 120 |
| Vh383ex | 98 | 5 | VH5-12-1 | 12 | 12.2% | 120 |
| CLL3 | 98 | 5 | VH5-12-2 | 11 | 11.2% | 17 |
| Au59.1 | 122 | 5 | VH5-12-1 | 12 | 12.2% | 49 |
| TEL16 | 117 | 5 | VH5-12-1 | 12 | 12.2% | 73 |
| M61 | 104 | 5 | VH5-12-1 | 0 | 0.0% | 103 |
| Tu0 | 99 | 5 | VH5-12-1 | 5 | 5.1% | 49 |
| P2-51 | 122 | 5 | VH5-12-1 | 13 | 13.3% | 121 |
| P2-54 | 122 | 5 | VH5-12-1 | 11 | 11.2% | 121 |
| P1-56 | 119 | 5 | VH5-12-1 | 9 | 9.2% | 121 |
| P2-53 | 122 | 5 | VH5-12-1 | 10 | 10.2% | 121 |
| P1-51 | 123 | 5 | VH5-12-1 | 19 | 19.4% | 121 |
| P1-54 | 123 | 5 | VH5-12-1 | 3 | 3.1% | 121 |
| P3-69 | 127 | 5 | VH5-12-1 | 4 | 4.1% | 121 |
| P3-9 | 119 | 5 | VH5-12-1 | 4 | 4.1% | 121 |

TABLE 2C-continued rearranged human heavy chain sequences

| Name[1] | aa[2] | Computed family[3] | Germline gene[4] | Diff. to germline[5] | % diff. to germline[6] | Reference[7] |
|---|---|---|---|---|---|---|
| 1-185-37 | 125 | 5 | VH5-12-4 | 0 | 0.0% | 124 |
| 1-187-29 | 125 | 5 | VH5-12-4 | 0 | 0.0% | 124 |
| P1-58 | 128 | 5 | VH5-12-4 | 10 | 10.2% | 121 |
| P2-57 | 118 | 5 | VH5-12-4 | 3 | 3.1% | 121 |
| P2-55 | 123 | 5 | VH5-12-1 | 5 | 5.1% | 121 |
| P2-56 | 123 | 5 | VH5-12-1 | 20 | 20.4% | 121 |
| P2-52 | 122 | 5 | VH5-12-1 | 11 | 11.2% | 121 |
| P3-60 | 122 | 5 | VH5-12-1 | 8 | 8.2% | 121 |
| P1-57 | 123 | 5 | VH5-12-1 | 4 | 4.1% | 121 |
| P1-55 | 122 | 5 | VH5-12-1 | 14 | 14.3% | 121 |
| MD3-4 | 128 | 5 | VH5-12-4 | 12 | 12.2% | 5 |
| P1-52 | 121 | 5 | VH5-12-1 | 11 | 11.2% | 121 |
| CLL5 | 98 | 5 | VH5-12-1 | 13 | 13.3% | 17 |
| CLL7 | 98 | 5 | VH5-12-1 | 14 | 14.3% | 17 |
| L2F10 | 100 | 5 | VH5-12-1 | 1 | 1.0% | 46 |
| L3B6 | 98 | 5 | VH5-12-1 | 1 | 1.0% | 46 |
| VH6.A12 | 119 | 6 | VH6-35-1 | 13 | 12.9% | 122 |
| s5A9 | 102 | 6 | VH6-35-1 | 1 | 1.0% | 46 |
| s6G4 | 99 | 6 | VH6-35-1 | 1 | 1.0% | 46 |
| ss3 | 99 | 6 | VH6-35-1 | 1 | 1.0% | 46 |
| 6-1G1 | 101 | 6 | VH6-35-1 | 0 | 0.0% | 14 |
| F19L16 | 107 | 6 | VH6-35-1 | 0 | 0.0% | 68 |
| L16 | 120 | 6 | VH6-35-1 | 0 | 0.0% | 69 |
| M71 | 121 | 6 | VH6-35-1 | 0 | 0.0% | 103 |
| ML1 | 120 | 6 | VH6-35-1 | 0 | 0.0% | 69 |
| F19ML1 | 107 | 6 | VH6-35-1 | 0 | 0.0% | 68 |
| 15P1 | 127 | 6 | VH6-35-1 | 0 | 0.0% | 104 |
| VH6.N1 | 121 | 6 | VH6-35-1 | 0 | 0.0% | 122 |
| VH6.N11 | 123 | 6 | VH6-35-1 | 0 | 0.0% | 122 |
| VH6.N12 | 123 | 6 | VH6-35-1 | 0 | 0.0% | 122 |
| VH6.N2 | 125 | 6 | VH6-35-1 | 0 | 0.0% | 122 |
| VH6.N5 | 125 | 6 | VH6-35-1 | 0 | 0.0% | 122 |
| VH6.N6 | 127 | 6 | VH6-35-1 | 0 | 0.0% | 122 |
| VH6.N7 | 126 | 6 | VH6-35-1 | 0 | 0.0% | 122 |
| VH6.N8 | 123 | 6 | VH6-35-1 | 0 | 0.0% | 122 |
| VH6.N9 | 123 | 6 | VH6-35-1 | 0 | 0.0% | 122 |
| VH6.N10 | 123 | 6 | VH6-35-1 | 0 | 0.0% | 122 |
| VH6.A3 | 123 | 6 | VH6-35-1 | 0 | 0.0% | 122 |
| VH6.A1 | 124 | 6 | VH6-35-1 | 0 | 0.0% | 122 |
| VH6.A4 | 120 | 6 | VH6-35-1 | 0 | 0.0% | 122 |
| E55 6.16 | 116 | 6 | VH6-35-1 | 0 | 0.0% | 26 |
| E55 6.17 | 120 | 6 | VH6-35-1 | 0 | 0.0% | 26 |
| E55 6.6 | 120 | 6 | VH6-35-1 | 0 | 0.0% | 26 |
| VHGL 6.3 | 102 | 6 | VH6-35-1 | 0 | 0.0% | 26 |
| CB-201 | 118 | 6 | VH6-35-1 | 0 | 0.0% | 109 |
| VH6.N4 | 122 | 6 | VH6-35-1 | 0 | 0.0% | 122 |
| E54 6.4 | 109 | 6 | VH6-35-1 | 1 | 1.0% | 26 |
| VH6.A6 | 126 | 6 | VH6-35-1 | 1 | 1.0% | 122 |
| E55 6.14 | 120 | 6 | VH6-35-1 | 1 | 1.0% | 26 |
| E54 6.6 | 107 | 6 | VH6-35-1 | 1 | 1.0% | 26 |
| E55 6.10 | 112 | 6 | VH6-35-1 | 1 | 1.0% | 26 |
| E54 6.1 | 107 | 6 | VH6-35-1 | 2 | 2.0% | 26 |
| E55 6.13 | 120 | 6 | VH6-35-1 | 2 | 2.0% | 26 |
| E55 6.3 | 120 | 6 | VH6-35-1 | 2 | 2.0% | 26 |
| E55 6.7 | 116 | 6 | VH6-35-1 | 2 | 2.0% | 26 |
| E55 6.2 | 120 | 6 | VH6-35-1 | 2 | 2.0% | 26 |
| E55 6.X | 111 | 6 | VH6-35-1 | 2 | 2.0% | 26 |
| E55 6.11 | 111 | 6 | VH6-35-1 | 3 | 3.0% | 26 |
| VH6.A11 | 118 | 6 | VH6-35-1 | 3 | 3.0% | 122 |
| A10 | 107 | 6 | VH6-35-1 | 3 | 3.0% | 68 |
| E55 6.1 | 120 | 6 | VH6-35-1 | 4 | 4.0% | 26 |
| FK-001 | 124 | 6 | VH6-35-1 | 4 | 4.0% | 65 |
| VH6.A5 | 121 | 6 | VH6-35-1 | 4 | 4.0% | 122 |
| VH6.A7 | 123 | 6 | VH6-35-1 | 4 | 4.0% | 122 |
| HBp2 | 119 | 6 | VH6-35-1 | 4 | 4.0% | 4 |
| Au46.2 | 123 | 6 | VH6-35-1 | 5 | 5.0% | 49 |
| A431 | 106 | 6 | VH6-35-1 | 5 | 5.0% | 68 |
| VH6.A2 | 120 | 6 | VH6-35-1 | 5 | 5.0% | 122 |
| VH6.A9 | 125 | 6 | VH6-35-1 | 8 | 7.9% | 122 |
| VH6.A8 | 118 | 6 | VH6-35-1 | 10 | 9.9% | 122 |
| VH6-FF3 | 118 | 6 | VH6-35-1 | 2 | 2.0% | 123 |
| VH6.A10 | 126 | 6 | VH6-35-1 | 12 | 11.9% | 122 |
| VH6-EB10 | 117 | 6 | VH6-35-1 | 3 | 3.0% | 123 |
| VH6-E6 | 119 | 6 | VH6-35-1 | 6 | 5.9% | 123 |
| VH6-FE2 | 121 | 6 | VH6-35-1 | 6 | 5.9% | 123 |

TABLE 2C-continued

| rearranged human heavy chain sequences | | | | | | |
|---|---|---|---|---|---|---|
| Name[1] | aa[2] | Computed family[3] | Germline gene[4] | Diff. to germline[5] | % diff. to germline[6] | Reference[7] |
| VH6-EE6 | 116 | 6 | VH6-35-1 | 6 | 5.9% | 123 |
| VH6-FD10 | 118 | 6 | VH6-35-1 | 6 | 5.9% | 123 |
| VH6-EX8 | 113 | 6 | VH6-35-1 | 6 | 5.9% | 123 |
| VH6-FG9 | 121 | 6 | VH6-35-1 | 8 | 7.9% | 123 |
| VH6-E5 | 116 | 6 | VH6-35-1 | 9 | 8.9% | 123 |
| VH6-EC8 | 122 | 6 | VH6-35-1 | 9 | 8.9% | 123 |
| VH6-E10 | 120 | 6 | VH6-35-1 | 10 | 9.9% | 123 |
| VH6-FF11 | 122 | 6 | VH6-35-1 | 11 | 10.9% | 123 |
| VH6-FD2 | 115 | 6 | VH6-35-1 | 11 | 10.9% | 123 |
| CLL10 17-2 | 88 | 6 | VH6-35-1 | 4 | 4.0% | 29 |
| VH6-BB11 | 94 | 6 | VH6-35-1 | 4 | 4.0% | 123 |
| VH6-B4I | 93 | 6 | VH6-35-1 | 7 | 6.9% | 123 |
| JU17 | 102 | 6 | VH6-35-1 | 3 | 3.0% | 114 |
| VH6-BD9 | 96 | 6 | VH6-35-1 | 11 | 10.9% | 123 |
| VH6-BB9 | 94 | 6 | VH6-35-1 | 12 | 11.9% | 123 |

TABLE 3A

| assignment of rearranged V kappa sequences to their germline counterparts | | | |
|---|---|---|---|
| Family[1] | Name | Rearranged[2] | Sum |
| 1 | Vk1-1 | 28 | |
| 1 | Vk1-2 | 0 | |
| 1 | Vk1-3 | 1 | |
| 1 | Vk1-4 | 0 | |
| 1 | Vk1-5 | 7 | |
| 1 | Vk1-6 | 0 | |
| 1 | Vk1-7 | 0 | |
| 1 | Vk1-8 | 2 | |
| 1 | Vk1-9 | 9 | |
| 1 | Vk1-10 | 0 | |
| 1 | Vk1-11 | 1 | |
| 1 | Vk1-12 | 7 | |
| 1 | Vk1-13 | 1 | |
| 1 | Vk1-14 | 7 | |
| 1 | Vk1-15 | 2 | |
| 1 | Vk1-16 | 2 | |
| 1 | Vk1-17 | 16 | |
| 1 | Vk1-18 | 1 | |
| 1 | Vk1-19 | 33 | |
| 1 | Vk1-20 | 1 | |
| 1 | Vk1-21 | 1 | |
| 1 | Vk1-22 | 0 | |
| 1 | Vk1-23 | 0 | 119 entries |
| 2 | Vk2-1 | 0 | |
| 2 | Vk2-2 | 1 | |
| 2 | Vk2-3 | 0 | |
| 2 | Vk2-4 | 0 | |
| 2 | Vk2-5 | 0 | |
| 2 | Vk2-6 | 16 | |
| 2 | Vk2-7 | 0 | |
| 2 | Vk2-8 | 0 | |
| 2 | Vk2-9 | 1 | |
| 2 | Vk2-10 | 0 | |
| 2 | Vk2-11 | 7 | |
| 2 | Vk2-12 | 0 | 25 entries |
| 3 | Vk3-1 | 1 | |
| 3 | Vk3-2 | 0 | |
| 3 | Vk3-3 | 35 | |
| 3 | Vk3-4 | 115 | |
| 3 | Vk3-5 | 0 | |
| 3 | Vk3-6 | 0 | |
| 3 | Vk3-7 | 1 | |
| 3 | Vk3-8 | 40 | 192 entries |
| 4 | Vk4-1 | 33 | 33 entries |
| 5 | Vk5-1 | 1 | 1 entry |
| 6 | Vk6-1 | 0 | |
| 6 | Vk6-2 | 0 | 0 entries |
| 7 | Vk7-1 | 0 | 0 entries |

TABLE 3B

| assignment of rearranged V lambda sequences to their germline counterparts | | | |
|---|---|---|---|
| Family[1] | Name | Rearranged[2] | Sum |
| 1 | DPL1 | 1 | |
| 1 | DPL2 | 14 | |
| 1 | DPL3 | 6 | |
| 1 | DPL4 | 1 | |
| 1 | HUMLV117 | 4 | |
| 1 | DPL5 | 13 | |
| 1 | DPL6 | 0 | |
| 1 | DPL7 | 0 | |
| 1 | DPL8 | 3 | |
| 1 | DPL9 | 0 | 42 entries |
| 2 | DPL10 | 5 | |
| 2 | VLAMBDA 2.1 | 0 | |
| 2 | DPL11 | 23 | |
| 2 | DPL12 | 15 | |
| 2 | DPL13 | 0 | |
| 2 | DPL14 | 0 | 43 entries |
| 3 | DPL16 | 10 | |
| 3 | DPL23 | 19 | |
| 3 | Humlv318 | 9 | 38 entries |
| 7 | DPL18 | 1 | |
| 7 | DPL19 | 0 | 1 entries |
| 8 | DPL21 | 2 | |
| 8 | HUMLV801 | 6 | 8 entries |
| 9 | DPL22 | 0 | 0 entries |
| unassigned | DPL24 | 0 | 0 entries |
| 10 | gVLX-4.4 | 0 | 0 entries |

TABLE 3C

| assignment of rearranged V heavy chain sequences to their germline counterparts | | | |
|---|---|---|---|
| Family[1] | Name | Rearranged[2] | Sum |
| 1 | VH1-12-1 | 38 | |
| 1 | VH1-12-8 | 2 | |
| 1 | VH1-12-2 | 2 | |
| 1 | VH1-12-9 | 2 | |
| 1 | VH1-12-3 | 0 | |
| 1 | VH1-12-4 | 0 | |
| 1 | VH1-12-5 | 3 | |
| 1 | VH1-12-6 | 0 | |
| 1 | VH1-12-7 | 23 | |
| 1 | VH1-13-1 | 1 | |
| 1 | VH1-13-2 | 1 | |
| 1 | VH1-13-3 | 0 | |
| 1 | VH1-13-4 | 0 | |

TABLE 3C-continued

| assignment of rearranged V heavy chain sequences to their germline counterparts | | | |
|---|---|---|---|
| Family[1] | Name | Rearranged[2] | Sum |
| 1 | VH1-13-5 | 0 | |
| 1 | VH1-13-6 | 17 | |
| 1 | VH1-13-7 | 0 | |
| 1 | VH1-13-8 | 3 | |
| 1 | VH1-13-9 | 0 | |
| 1 | VH1-13-10 | 0 | |
| 1 | VH1-13-11 | 0 | |
| 1 | VH1-13-12 | 10 | |
| 1 | VH1-13-13 | 0 | |
| 1 | VH1-13-14 | 0 | |
| 1 | VH1-13-15 | 4 | |
| 1 | VH1-13-16 | 2 | |
| 1 | VH1-13-17 | 0 | |
| 1 | VH1-13-18 | 1 | |
| 1 | VH1-13-19 | 0 | |
| 1 | VH1-1X-1 | 1 | 110 entries |
| 2 | VH2-21-1 | 0 | |
| 2 | VH2-31-1 | 0 | |
| 2 | VH2-31-2 | 1 | |
| 2 | VH2-31-3 | 1 | |
| 2 | VH2-31-4 | 0 | |
| 2 | VH2-31-5 | 2 | |
| 2 | VH2-31-6 | 0 | |
| 2 | VH2-31-7 | 0 | |
| 2 | VH2-31-14 | 1 | |
| 2 | VH2-31-8 | 0 | |
| 2 | VH2-31-9 | 0 | |
| 2 | VH2-31-10 | 0 | |
| 2 | VH2-31-11 | 1 | |
| 2 | VH2-31-12 | 0 | |
| 2 | VH2-31-13 | 1 | 7 entries |
| 3 | VH3-11-1 | 0 | |
| 3 | VH3-11-2 | 0 | |
| 3 | VH3-11-3 | 5 | |
| 3 | VH3-11-4 | 0 | |
| 3 | VH3-11-5 | 1 | |
| 3 | VH3-11-6 | 1 | |
| 3 | VH3-11-7 | 0 | |
| 3 | VH3-11-8 | 5 | |
| 3 | VH3-13-1 | 9 | |
| 3 | VH3-13-2 | 3 | |
| 3 | VH3-13-3 | 0 | |
| 3 | VH3-13-4 | 0 | |
| 3 | VH3-13-5 | 0 | |
| 3 | VH3-13-6 | 0 | |
| 3 | VH3-13-7 | 32 | |
| 3 | VH3-13-8 | 4 | |
| 3 | VH3-13-9 | 0 | |
| 3 | VH3-13-10 | 46 | |
| 3 | VH3-13-11 | 0 | |
| 3 | VH3-13-12 | 11 | |
| 3 | VH3-13-13 | 17 | |
| 3 | VH3-13-14 | 8 | |
| 3 | VH3-13-15 | 4 | |
| 3 | VH3-13-16 | 3 | |
| 3 | VH3-13-17 | 2 | |
| 3 | VH3-13-18 | 1 | |
| 3 | VH3-13-19 | 13 | |
| 3 | VH3-13-20 | 1 | |
| 3 | VH3-13-21 | 1 | |
| 3 | VH3-13-22 | 0 | |
| 3 | VH3-13-23 | 0 | |
| 3 | VH3-13-24 | 4 | |
| 3 | VH3-13-25 | 1 | |
| 3 | VH3-13-26 | 6 | |
| 3 | VH3-14-1 | 1 | |
| 3 | VH3-14-4 | 15 | |
| 3 | VH3-14-2 | 0 | |
| 3 | VH3-14-3 | 0 | |
| 3 | VH3-1X-1 | 0 | |
| 3 | VH3-1X-2 | 0 | |
| 3 | VH3-1X-3 | 6 | |
| 3 | VH3-1X-4 | 0 | |
| 3 | VH3-1X-5 | 0 | |
| 3 | VH3-1X-6 | 11 | |

TABLE 3C-continued

| assignment of rearranged V heavy chain sequences to their germline counterparts | | | |
|---|---|---|---|
| Family[1] | Name | Rearranged[2] | Sum |
| 3 | VH3-1X-7 | 0 | |
| 3 | VH3-1X-8 | 1 | |
| 3 | VH3-1X-9 | 0 | 212 entries |
| 4 | VH4-11-1 | 0 | |
| 4 | VH4-11-2 | 20 | |
| 4 | VH4-11-3 | 0 | |
| 4 | VH4-11-4 | 0 | |
| 4 | VH4-11-5 | 0 | |
| 4 | VH4-11-6 | 0 | |
| 4 | VH4-11-7 | 5 | |
| 4 | VH4-11-8 | 7 | |
| 4 | VH4-11-9 | 3 | |
| 4 | VH4-11-10 | 0 | |
| 4 | VH4-11-11 | 0 | |
| 4 | VH4-11-12 | 4 | |
| 4 | VH4-11-13 | 0 | |
| 4 | VH4-11-14 | 0 | |
| 4 | VH4-11-15 | 0 | |
| 4 | VH4-11-16 | 1 | |
| 4 | VH4-21-1 | 0 | |
| 4 | VH4-21-2 | 0 | |
| 4 | VH4-21-3 | 1 | |
| 4 | VH4-21-4 | 1 | |
| 4 | VH4-21-5 | 1 | |
| 4 | VH4-21-6 | 1 | |
| 4 | VH4-21-7 | 0 | |
| 4 | VH4-21-8 | 0 | |
| 4 | VH4-21-9 | 0 | |
| 4 | VH4-31-1 | 0 | |
| 4 | VH4-31-2 | 0 | |
| 4 | VH4-31-3 | 0 | |
| 4 | VH4-31-4 | 2 | |
| 4 | VH4-31-5 | 0 | |
| 4 | VH4-31-6 | 0 | |
| 4 | VH4-31-7 | 0 | |
| 4 | VH4-31-8 | 0 | |
| 4 | VH4-31-9 | 0 | |
| 4 | VH4-31-10 | 0 | |
| 4 | VH4-31-11 | 0 | |
| 4 | VH4-31-12 | 4 | |
| 4 | VH4-31-13 | 7 | |
| 4 | VH4-31-14 | 0 | |
| 4 | VH4-31-15 | 0 | |
| 4 | VH4-31-16 | 0 | |
| 4 | VH4-31-17 | 0 | |
| 4 | VH4-31-18 | 0 | |
| 4 | VH4-31-19 | 0 | |
| 4 | VH4-31-20 | 0 | 57 entries |
| 5 | VH5-12-1 | 82 | |
| 5 | VH5-12-2 | 1 | |
| 5 | VH5-12-3 | 0 | |
| 5 | VH5-12-4 | 14 | 97 entries |
| 6 | VH6-35-1 | 74 | 74 entries |

TABLE 4A

Analysis of V kappa subgroup 1

| | Framework I | | | | | | | | | | | | | | | |
|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 |
| A | | 1 | | | | | | | 1 | | | | 102 | | 1 | |
| B | | | 1 | | | 1 | | | | | | | | | | |
| C | | | | | | | | | | | | | | 1 | | |
| D | 64 | | | | | | | | | | | | | | | |
| E | 8 | | 14 | | | | | | | | | | | | 1 | |
| F | | | | | | | | | 1 | 6 | | | | 1 | | |
| G | | | | | | | | | | | | | | | | 105 |
| H | | | | | | | | | | | | | | | | |
| I | | 65 | | | | | | | | | | | | | 4 | |
| K | | | 1 | | | | | | | | | | | | | |
| L | | 6 | | 21 | | | | | | | 96 | | 1 | | | |
| M | 1 | | | 66 | | | | | | | | | | | | |
| N | | | | | | | | | | | | | | | | |
| P | | | | | | | | 103 | | 1 | | 2 | | | 1 | |
| Q | | | 62 | | | 88 | | | | | 1 | | | | | |
| R | | | | | | | | | | | | | | | | |
| S | | | | | | | 89 | | 102 | 80 | | 103 | | 103 | | |
| T | | 1 | | | 88 | | | | | 18 | | | | | | |
| V | | 1 | 9 | | | | | | | | 8 | | 2 | | 98 | |
| W | | | | | | | | | | | | | | | | |
| X | 1 | | | | | | | | | | | | | | | |
| Y | | | | | | | | | | | | | | | | |
| — | | | | | | | | | | | | | | | | |
| unknown (?) | | | | | | | | | | | | | | | | |
| not sequenced | 31 | 31 | 18 | 18 | 17 | 16 | 16 | 2 | 1 | | | | | | | |
| sum of seq[2] | 74 | 74 | 87 | 87 | 88 | 89 | 89 | 103 | 104 | 105 | 105 | 105 | 105 | 105 | 105 | 105 |
| oomcaa[3] | 64 | 65 | 62 | 66 | 88 | 88 | 89 | 103 | 102 | 80 | 96 | 103 | 102 | 103 | 98 | 105 |
| mcaa[4] | D | I | Q | M | T | Q | S | P | S | S | L | S | A | S | V | G |
| rel. oomcaa[5] | 86% | 88% | 71% | 76% | 100% | 99% | 100% | 100% | 98% | 76% | 91% | 98% | 97% | 98% | 93% | 100% |
| pos occupied[6] | 4 | 5 | 5 | 2 | 1 | 2 | 1 | 1 | 3 | 4 | 3 | 2 | 3 | 3 | 5 | 1 |

| amino acid[1] | 17 | 18 | 19 | 20 | 21 | 22 | 23 | 24 | 25 | 26 | 27 | A | B | C | D |
|---|---|---|---|---|---|---|---|---|---|---|---|---|---|---|---|
| A | | | 1 | 1 | | 1 | | | 103 | | | | | | |
| B | | | | | | | | | | | 1 | | | | |
| C | | | | | | | 105 | | | | | | | | |
| D | 101 | | | | | | | | | | | | | | |
| E | 2 | | | | | | | 1 | 1 | | 2 | | | | |
| F | | | | | 2 | | | | | | | | | | |
| G | | | | | | | | | | 1 | | | | | |
| H | | | | | | | | | | | 1 | | | | |
| I | | | 6 | 4 | 101 | 1 | | | | | | | | | |
| K | | | | | | | | 2 | | | 1 | | | | |
| L | | | | | | | | 1 | | | | | | | |
| M | | | | | | | | | | | | | | | |

TABLE 4A-continued

Analysis of V kappa subgroup 1

| | | | | | | | | | | | | | | | |
|---|---|---|---|---|---|---|---|---|---|---|---|---|---|---|---|
| N | | | | | | | | | | 1 | | | | | |
| P | | | | | | | | | | | | | | | |
| Q | | | | | | | | | 20 | | 100 | | | | |
| R | | 94 | | | | | | | 81 | | | | | | |
| S | | 5 | | 1 | | | | | | 102 | | | | | |
| T | | 6 | | 99 | | 103 | | | 1 | 1 | | | | | |
| V | | | 98 | | 2 | | | | | | | | | | |
| W | | | | | | | | | | | | | | | |
| X | 1 | | | | | | | | | | | | | | |
| Y | 1 | | | | | | | | | | | | | | |
| — | | | | | | | | | | | | 105 | 105 | 105 | 105 |
| unknown (?) | | | | | | | | | | | | | | | |
| not sequenced | | | | | | | | | | | | | | | |
| sum of seq[2] | 105 | 105 | 105 | 105 | 105 | 105 | 105 | 105 | 105 | 105 | 105 | 105 | 105 | 105 | 105 |
| oomcaa[3] | 101 | 94 | 98 | 99 | 101 | 103 | 105 | 81 | 103 | 102 | 100 | 105 | 105 | 105 | 105 |
| mcaa[4] | D | R | V | T | I | T | C | R | A | S | Q | — | — | — | — |
| rel. oomcaa[5] | 96% | 90% | 93% | 94% | 96% | 98% | 100% | 77% | 98% | 97% | 95% | 100% | 100% | 100% | 100% |
| pos occupied[6] | 4 | 3 | 3 | 4 | 3 | 3 | 1 | 5 | 3 | 4 | 5 | 1 | 1 | 1 | 1 |

| | CDRI | | | | | | | | | | | | | | |
|---|---|---|---|---|---|---|---|---|---|---|---|---|---|---|---|
| amino acid[1] | E | F | 28 | 29 | 30 | 31 | 32 | 33 | 34 | 35 | 36 | 37 | 38 | 39 | 40 |
| A | | | | | 1 | 1 | | 1 | 42 | | | | | | |
| B | | | | | | | | | | | | 1 | 1 | | |
| C | | | | | | | 1 | | | | | | | | |
| D | | | 25 | | 1 | 5 | 7 | | | | | 1 | | | |
| E | | | | | | | 1 | | | | | 2 | | | |
| F | | | | 1 | 1 | | 7 | | | | 6 | | | | |
| G | | | 25 | | 7 | 3 | | | 4 | | | | | | |
| H | | | | | 1 | 2 | 2 | | 1 | | | 2 | | | |
| I | | | | 98 | 1 | 4 | | | 1 | | | | | | |
| K | | | | | | 7 | | | | | | | | 95 | |
| L | | | | | 2 | 1 | | 101 | | | | | | | |
| M | | | | | | | | | | | | | | | |
| N | | | 6 | | 16 | 42 | | | 50 | | | | | | |
| P | | | | | | | | | | | | | | | 102 |
| Q | | | | | | | | | | | | 98 | 103 | 2 | |
| R | | | | | 16 | 3 | 2 | | | | | | | 3 | 1 |
| S | | | 41 | 2 | 57 | 32 | 3 | 1 | 1 | | | | | | 1 |
| T | | | 7 | | | 4 | | | 4 | | | | | 1 | |
| V | | | 1 | 4 | 1 | | | 1 | | | | | | | |
| W | | | | | | | 21 | | | 104 | | | | | |
| X | | | | | | | | | 1 | | | | | | |
| Y | | | | | 1 | | 60 | | | | 98 | | | | |
| — | 105 | 105 | | | | | | | | | | | | | |
| unknown (?) | | | | | | | | | | | | | | 3 | |
| not sequenced | | | | | | 1 | 1 | 1 | 1 | 1 | 1 | 1 | 1 | 1 | 1 |
| sum of seq[2] | 105 | 105 | 105 | 105 | 105 | 104 | 104 | 104 | 104 | 104 | 104 | 104 | 104 | 104 | 104 |
| oomcaa[3] | 105 | 105 | 41 | 98 | 57 | 42 | 60 | 101 | 50 | 104 | 98 | 98 | 103 | 95 | 102 |
| mcaa[4] | — | — | S | I | S | N | Y | L | N | W | Y | Q | Q | K | P |
| rel. oomcaa[5] | 100% | 100% | 39% | 93% | 54% | 40% | 58% | 97% | 48% | 100% | 94% | 94% | 99% | 91% | 98% |
| pos occupied[6] | 1 | 1 | 6 | 4 | 12 | 11 | 9 | 4 | 8 | 1 | 2 | 5 | 2 | 4 | 3 |

TABLE 4A-continued

Analysis of V kappa subgroup 1

| | Framework II | | | | | | | | | CDR Ii | | | | | |
|---|---|---|---|---|---|---|---|---|---|---|---|---|---|---|---|
| amino acid[1] | 41 | 42 | 43 | 44 | 45 | 46 | 47 | 48 | 49 | 50 | 51 | 52 | 53 | 54 | 55 |
| A | | | 94 | | | | | | | 50 | 95 | | | | |
| B | | | | | | | | | | | | | | | |
| C | | | | | | | | | | | | | | | |
| D | | | | | | | | | | 21 | 1 | 1 | 1 | | |
| E | 1 | 3 | | | 1 | 1 | | | | 1 | | 1 | | | 33 |
| F | | | | | | 1 | | | 3 | | | 1 | | | |
| G | 100 | | 1 | | | | | | | 9 | 2 | | | | |
| H | | | | | | | | | 2 | | | | | | 1 |
| I | | 1 | | | | 1 | | 100 | | | | | 1 | | |
| K | | 95 | | | 86 | | | | | 16 | | | 2 | | 5 |
| L | | 1 | | | | 89 | 103 | | | | | | | 101 | |
| M | | | | | | | | 2 | | | | | | | |
| N | | | | | 10 | | | | | 2 | | 1 | 25 | | |
| P | | | | 104 | | | | | | 1 | | | | | 1 |
| Q | | 1 | | | 1 | | | | | | | | | | 62 |
| R | | | | | 3 | 3 | | | | | | | 1 | 1 | 2 |
| S | | | | | 1 | | | | 5 | 1 | 1 | 99 | 41 | 2 | |
| T | | 3 | | | 1 | | | | | 1 | 4 | 1 | 31 | | |
| V | | | 9 | | | 9 | | | | | 1 | | 1 | | |
| W | | | | | | | | | | | | | | | |
| X | | | | | 1 | | | | | | | | 1 | | |
| Y | | | | | | | | | 92 | 1 | | | | | |
| — | | | | | | | | | | | | | | | |
| unknown (?) | 3 | | | | | | | | | | | | | | |
| not sequenced | 1 | 1 | 1 | 1 | 1 | 1 | 2 | 3 | 3 | 2 | 1 | 1 | 1 | 1 | 1 |
| sum of seq[2] | 104 | 104 | 104 | 104 | 104 | 104 | 103 | 102 | 102 | 103 | 104 | 104 | 104 | 104 | 104 |
| oomcaa[3] | 100 | 95 | 94 | 104 | 86 | 89 | 103 | 100 | 92 | 50 | 95 | 99 | 41 | 101 | 62 |
| mcaa[4] | G | K | A | P | K | L | L | I | Y | A | A | S | S | L | Q |
| rel. oomcaa[5] | 96% | 91% | 90% | 100% | 83% | 86% | 100% | 98% | 90% | 49% | 91% | 95% | 39% | 97% | 60% |
| pos occupied[6] | 2 | 6 | 3 | 1 | 8 | 6 | 1 | 2 | 4 | 10 | 6 | 6 | 9 | 3 | 6 |

| amino acid[1] | 56 | 57 | 58 | 59 | 60 | 61 | 62 | 63 | 64 | 65 | 66 | 67 | 68 | 69 | 70 |
|---|---|---|---|---|---|---|---|---|---|---|---|---|---|---|---|
| A | 3 | | | | | | | | | | 2 | 1 | 1 | 1 | |
| B | | | | 1 | | | | | | | | | | | |
| C | | | | | | | | | | | | | | | |
| D | 1 | | | | | | | | | | | | | | 67 |
| E | | | | | | | | | | | | | 1 | | 30 |
| F | | | 1 | | | | 103 | | | | | 3 | | | |
| G | 2 | 105 | | | | | | | 105 | 4 | 101 | | 102 | | |
| H | | | | | | | | | | | | | | | 3 |
| I | 3 | 4 | | | | | 1 | 3 | | | | | | | |
| K | 1 | | | | | 1 | | | | | | | | | 1 |
| L | | | | | | | | 1 | | | | | | | |
| M | | | | | | | | | | | | | | 1 | |

TABLE 4A-continued

Analysis of V kappa subgroup 1

| | | | | | | | | | | | | | | | |
|---|---|---|---|---|---|---|---|---|---|---|---|---|---|---|---|
| N | 6 | | | | | | | | | | | | | | |
| P | 1 | | | 101 | 2 | | | | | | | | | | |
| Q | | | | | | | | | | 1 | | | | | |
| R | 1 | | | | | 103 | | 1 | | 1 | 1 | | | 2 | |
| S | 68 | | | 2 | 103 | | | 98 | | 96 | | 100 | | | |
| T | 19 | | | 1 | | 1 | | 2 | | 3 | | | | 101 | |
| V | | | 99 | | | | 1 | | | | | | | | 1 |
| W | | | | | | | | | | | | | | | |
| X | | | 1 | | | | | | | | 1 | | 1 | | 2 |
| Y | | | | | | | | | | | | 1 | | | 1 |
| — | | | | | | | | | | | | | | | |
| unknown (?) | | | | | | | | | | | | | | | |
| not sequenced | | | | | | | | | | | | | | | |
| sum of seq[2] | 105 | 105 | 105 | 105 | 105 | 105 | 105 | 105 | 105 | 105 | 105 | 105 | 105 | 105 | 105 |
| oomcaa[3] | 68 | 105 | 99 | 101 | 103 | 103 | 103 | 98 | 105 | 96 | 101 | 100 | 102 | 101 | 67 |
| mcaa[4] | S | G | V | P | S | R | F | S | G | S | G | S | G | T | D |
| rel. oomcaa[5] | 65% | 100% | 94% | 96% | 98% | 98% | 98% | 93% | 100% | 91% | 96% | 95% | 97% | 96% | 64% |
| pos occupied[6] | 10 | 1 | 4 | 4 | 2 | 3 | 3 | 5 | 1 | 5 | 4 | 4 | 4 | 4 | 7 |

| | Framework III | | | | | | | | | | | | | | |
|---|---|---|---|---|---|---|---|---|---|---|---|---|---|---|---|
| amino acid[1] | 71 | 72 | 73 | 74 | 75 | 76 | 77 | 78 | 79 | 80 | 81 | 82 | 83 | 84 | 85 |
| A | | 3 | | | | 1 | | | | 2 | | | | 101 | 1 |
| B | | | | | 1 | | | | 3 | | 2 | | | | |
| C | | | | | | | | | | | | | | | |
| D | | | | | | 1 | | | | | 16 | 101 | | | |
| E | | | | | | | | | | | 83 | | | | |
| F | 102 | 1 | 21 | | | | | | | | | | 73 | | |
| G | | | | | | | 4 | | | | 1 | | | 2 | |
| H | | | | | | | | | | | | | | | |
| I | | | | | 99 | 5 | | | | | | | 17 | | |
| K | | | | | | | | | | | | | | | |
| L | | | 81 | | | | | 103 | 1 | | | | 1 | | |
| M | | | | | | | | | | | | | | | 1 |
| N | | | | | | 7 | 4 | | | | | | | | 1 |
| P | | | | | | | | | | 97 | | | | | 1 |
| Q | | | | | | | | | 97 | | | | | | |
| R | | | | | | 2 | 1 | | 2 | | | | | | |
| S | | 2 | | 1 | | 86 | 94 | | | 4 | | | 1 | | |
| T | | 98 | | 102 | | 2 | 1 | | | | | | | | 97 |
| V | 1 | | 2 | | 4 | | | 1 | | | | | 11 | | 1 |
| W | | | | | | | | | | | | | | | |
| X | | | | 1 | | | | | | | 1 | 2 | | | |
| Y | 1 | | | | | | | | | | | | | | |
| — | | | | | | | | | | | | | | | |
| unknown (?) | | | | | | | | | | | | | | | |
| not sequenced | 1 | 1 | 1 | 1 | 1 | 1 | 1 | 1 | 2 | 2 | 2 | 2 | 2 | 2 | 3 |
| sum of seq[2] | 104 | 104 | 104 | 104 | 104 | 104 | 104 | 104 | 103 | 103 | 103 | 103 | 103 | 103 | 102 |
| oomcaa[3] | 102 | 98 | 81 | 102 | 99 | 86 | 94 | 103 | 97 | 97 | 83 | 101 | 73 | 101 | 97 |
| mcaa[4] | F | T | L | T | I | S | S | L | Q | P | E | D | F | A | T |
| rel. oomcaa[5] | 98% | 94% | 78% | 98% | 95% | 83% | 90% | 99% | 94% | 94% | 81% | 98% | 71% | 98% | 95% |
| pos occupied[6] | 3 | 4 | 3 | 3 | 3 | 7 | 5 | 2 | 4 | 3 | 5 | 2 | 5 | 2 | 6 |

TABLE 4A-continued

Analysis of V kappa subgroup 1

| amino acid[1] | 86 | 87 | 88 | 89 | 90 | 91 | 92 | 93 | 94 | 95 | A | B | C | D | E | F |
|---|---|---|---|---|---|---|---|---|---|---|---|---|---|---|---|---|
| | | | | CDR III | | | | | | | | | | | | |
| A | | | | | 1 | 7 | 1 | | 5 | 1 | | | | | | |
| B | | | | 2 | 3 | | | | | | | | | | | |
| C | | | 102 | | | | | | | | | | | | | |
| D | | | | | | | 23 | 5 | 1 | | | | | | | |
| E | | | | | | | 1 | 1 | | 1 | 1 | | | | | |
| F | | 7 | | | | 3 | | | 13 | | | | | | | |
| G | | | | | | 1 | | 1 | 2 | 1 | 1 | | | | | |
| H | | 1 | | 4 | 6 | 7 | 3 | 1 | | | | | | | | |
| I | | | | | | | 4 | 1 | 2 | 1 | | | | | | |
| K | 1 | | | | 7 | | 1 | | | | | | | | | |
| L | | | | 7 | | 6 | 2 | | 18 | 2 | | | | | | |
| M | | | | | | | | | | | | | | | | |
| N | | | | | | 6 | 31 | 19 | 1 | | | | | | | |
| P | | | | | | | | | 1 | 82 | 6 | | | | | |
| Q | | | | 90 | 86 | 1 | 2 | | | | | | | | | |
| R | | | | | | 1 | | 2 | 2 | | | | | | | |
| S | 1 | | | | | 27 | 3 | 58 | 5 | 10 | | | | | | |
| T | | | | | | 3 | 1 | 15 | 25 | | | | | | | |
| V | | | | | | | | | 5 | | | | | | | |
| W | | | | | | | | | 1 | | | | | | | |
| X | | | | | | | | | | | | | | | | |
| Y | 101 | 93 | | | | 42 | 32 | 1 | 23 | | | | | | | |
| — | | | | | | | | | | 3 | 82 | 88 | 89 | 89 | 89 | 89 |
| unknown (?) | | 1 | | | | | | | | | | | | | | |
| not sequenced | 2 | 3 | 3 | 2 | 2 | 1 | 1 | 1 | 1 | 4 | 16 | 16 | 16 | 16 | 16 | 16 |
| sum of seq[2] | 103 | 102 | 102 | 103 | 103 | 104 | 104 | 104 | 104 | 101 | 89 | 89 | 89 | 89 | 89 | 89 |
| oomcaa[3] | 101 | 93 | 102 | 90 | 86 | 42 | 32 | 58 | 25 | 82 | 82 | 88 | 89 | 89 | 89 | 89 |
| mcaa[4] | Y | Y | C | Q | Q | Y | Y | S | T | P | — | — | — | — | — | — |
| rel. oomcaa[5] | 98% | 91% | 100% | 87% | 83% | 40% | 31% | 56% | 24% | 81% | 92% | 99% | 100% | 100% | 100% | 100% |
| pos occupied[6] | 3 | 3 | 1 | 4 | 5 | 11 | 12 | 10 | 14 | 8 | 3 | 2 | 1 | 1 | 1 | 1 |

| amino acid[1] | 96 | 97 | 98 | 99 | 100 | 101 | 102 | 103 | 104 | 105 | 106 | A | 107 | 108 | sum |
|---|---|---|---|---|---|---|---|---|---|---|---|---|---|---|---|
| | | | Framework IV | | | | | | | | | | | | |
| A | 1 | | | | | | | | | | | | | | 627 |
| B | | | | | 1 | | | | | 1 | | | | | 19 |
| C | | | | | | | | | | | | | | | 209 |
| D | 1 | | | | | | | | | 15 | | | | | 459 |
| E | | | | | 2 | | | | | 65 | | | | | 258 |
| F | 6 | | 86 | | | | | | | | 2 | | | | 451 |
| G | | | | 87 | 29 | 87 | | | | | | | | 2 | 894 |
| H | 2 | 1 | | | | | | | | | | | | | 40 |
| I | 5 | | | | | | | | 1 | | 72 | | | | 606 |
| K | 1 | 1 | | | | | | 77 | | | | | 79 | | 480 |
| L | 18 | 1 | 1 | | | | | | 22 | 4 | 2 | | | | 793 |
| M | | 1 | | | | | | | | | 5 | | | | 77 |

TABLE 4A-continued

Analysis of V kappa subgroup 1

| | | | | | | | | | | | | | | | |
|---|---|---|---|---|---|---|---|---|---|---|---|---|---|---|---|
| N | 1 | | | | | | | | | | 1 | | 2 | | 232 |
| P | 6 | | | | 7 | | | | | | | | | 1 | 620 |
| Q | 1 | | | | 48 | | | | | 1 | | | | | 865 |
| R | 6 | | | | | | | 6 | | | | | 2 | 70 | 413 |
| S | 2 | 2 | | | | | | | | | | | | | 1636 |
| T | 2 | 82 | | | | | 87 | 3 | | | | | 2 | | 1021 |
| V | 2 | | | | | | | 1 | 63 | | 3 | | | | 440 |
| W | 15 | | | | | | | | | | | | | | 141 |
| X | | | | | | | | | | | | | | | 14 |
| Y | 16 | | | | | | | | | | | | | | 564 |
| — | 4 | 1 | | | | | | | | | | 85 | | 1 | 1250 |
| unknown (?) | | | | | | | | | | | | | | | 7 |
| not sequenced | 16 | 16 | 18 | 18 | 18 | 18 | 18 | 18 | 19 | 19 | 20 | 20 | 20 | 31 | 589 |
| sum of seq[2] | 89 | 89 | 87 | 87 | 87 | 87 | 87 | 87 | 86 | 86 | 85 | 85 | 85 | 74 | |
| oomcaa[3] | 18 | 82 | 86 | 87 | 48 | 87 | 87 | 77 | 63 | 65 | 72 | 85 | 79 | 70 | |
| mcaa[4] | L | T | F | G | G | G | T | K | V | E | I | — | K | R | |
| rel. oomcaa[5] | 20% | 92% | 99% | 100% | 55% | 100% | 100% | 89% | 73% | 76% | 85% | 100% | 93% | 95% | |
| pos occupied[6] | 17 | 7 | 2 | 1 | 5 | 1 | 1 | 4 | 3 | 5 | 6 | 1 | 4 | 4 | |

TABLE 4B

Analysis of V kappa subgroup 2

| | Framework I | | | | | | | | | | | | | | | | | | | | |
|---|---|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 | 20 | 21 |
| A | | | | | | | | | | | | | | | | | | | 22 | | |
| B | | | | | | | | | | | | | | | | | | | | | |
| C | | | | | | | | | | | | | | | | | | | | | |
| D | 14 | | | | | | | | | | | | | | | | | | | | |
| E | 3 | | | | | | | | | | | | | | | | 15 | | | | |
| F | | | | | | | | | 1 | 1 | | | | | | | | | | | |
| G | | | | | | | | | | | | | | | | 22 | | | | | |
| H | | | | | | | | | | | | | | | | | | | | | |
| I | | 8 | | | | | | | | | | | | | | | | | | | 22 |
| K | | | | | | | | | | | | | | | | | | | | | |
| L | | 3 | | 1 | | | | | 17 | | 18 | | | | 6 | | | | | | |
| M | | | | 15 | | | | | | | | | | | | | | | | | |
| N | | | | | | | | | | | | | | | | | | | | | |
| P | | | | | | | | 18 | | | | 18 | | 15 | | | 22 | | | | |
| Q | | | | | | 18 | | | | | | | | | | 7 | | | | | |
| R | | | | | | | | | | | | | | | | | | | | | |
| S | | | | | | | 18 | | | 17 | | | | | | | | | | 22 | |
| T | | | | | 17 | | | | | | | | 21 | | | | | | | | |
| V | | 6 | 17 | 1 | | | | | | | | 18 | | | | | | | | | |
| W | | | | | | | | | | | | | | | | | | | | | |
| X | | | | | | | | | | | | | | | | | | | | | |
| Y | | | | | | | | | | | | | | | | | | | | | |
| — | | | | | | | | | | | | | | | | | | | | | |
| unknown (?) | | | | | 1 | | | | | | | | | | | | | | | | |
| not sequenced | 5 | 5 | 5 | 5 | 4 | 4 | 4 | 4 | 4 | 4 | 4 | 4 | 4 | 1 | 1 | | | | | | |
| sum of seq[2] | 17 | 17 | 17 | 17 | 18 | 18 | 18 | 18 | 18 | 18 | 18 | 18 | 18 | 21 | 21 | 22 | 22 | 22 | 22 | 22 | 22 |
| oomcaa[3] | 14 | 8 | 17 | 15 | 17 | 18 | 18 | 18 | 17 | 17 | 18 | 18 | 18 | 21 | 15 | 22 | 15 | 22 | 22 | 22 | 22 |
| mcaa[4] | D | I | V | M | T | Q | S | P | L | S | L | P | V | T | P | G | E | P | A | S | I |
| rel. oomcaa[5] | 82% | 47% | 100% | 88% | 94% | 100% | 100% | 100% | 94% | 94% | 100% | 100% | 100% | 100% | 71% | 100% | 68% | 100% | 100% | 100% | 100% |
| pos occupied[6] | 2 | 3 | 1 | 3 | 1 | 1 | 1 | 1 | 2 | 2 | 1 | 1 | 1 | 1 | 2 | 1 | 2 | 1 | 1 | 1 | 1 |

TABLE 4B-continued

Analysis of V kappa subgroup 2

| | | | CDRI | | | | | | | | | | | | | | | | | | |
|---|---|---|---|---|---|---|---|---|---|---|---|---|---|---|---|---|---|---|---|---|---|
| amino acid[1] | 22 | 23 | 24 | 25 | 26 | 27 | A | B | C | D | E | F | 28 | 29 | 30 | 31 | 32 | 33 | 34 | 35 | 36 |
| A | | | | | | | | | | | | | | | | | | | | | |
| B | | | | | | | | | | | | | | | | | | | | | |
| C | | 22 | | | | | | | | | | | | | | | | | | | |
| D | | | | | | | | | | 1 | | | 9 | | 1 | 1 | | | 11 | | |
| E | | | | | | | | | | | | | | | | | | | | | |
| F | | | | | | | | | | | | | | | 2 | | | | | | 7 |
| G | | | | | | | | | | | 1 | | | 22 | | | | | | | |
| H | | | | | | | | | | 16 | | | | | | | 1 | | 1 | | |
| I | | | | | | | | | | | | | | | | | | | | | |
| K | | | 1 | | | | | | | | | | | | | 1 | | | | | |
| L | | | | | | 1 | | 22 | 13 | | | | | | | | | 22 | | | |
| M | | | | | | | | | 1 | | | | | | | | | | | | |
| N | | | | | | | | | | | | | 10 | | 7 | 12 | | | 9 | | |
| P | | | | | | | | | | | | | | | | | | | | | |
| Q | 1 | | | | | 21 | | | | | | | | | | | | | | | |
| R | | | 21 | | | | | | | | 2 | | | | | | | | | | |
| S | 21 | | | 22 | 22 | | 22 | | | | 19 | | 1 | | | | | | | | |
| T | | | | | | | | | | | | | | | | 8 | | | | | |
| V | | | | | | | | | 8 | | | | | | | | | | | | |
| W | | | | | | | | | | 1 | | | | | | | | | | 22 | |
| X | | | | | | | | | | | | | 1 | | 1 | | | | 1 | | |
| Y | | | | | | | | | | 4 | | | 1 | | 11 | | 21 | | | | 15 |
| — | | | | | | | | | | | | 22 | | | | | | | | | |
| unknown (?) | | | | | | | | | | | | | | | | | | | | | |
| not sequenced | | | | | | | | | | | | | | | | | | | | | |
| sum of seq[2] | 22 | 22 | 22 | 22 | 22 | 22 | 22 | 22 | 22 | 22 | 22 | 22 | 22 | 22 | 22 | 22 | 22 | 22 | 22 | 22 | 22 |
| oomcaa[3] | 21 | 22 | 21 | 22 | 22 | 21 | 22 | 22 | 13 | 16 | 19 | 22 | 10 | 22 | 11 | 12 | 21 | 22 | 11 | 22 | 15 |
| mcaa[4] | S | C | R | S | S | Q | S | L | L | H | S | — | N | G | Y | N | Y | L | D | W | Y |
| rel. oomcaa[5] | 95% | 100% | 95% | 100% | 100% | 95% | 100% | 100% | 59% | 73% | 86% | 100% | 45% | 100% | 50% | 55% | 95% | 100% | 50% | 100% | 68% |
| pos occupied[6] | 2 | 1 | 2 | 1 | 1 | 2 | 1 | 1 | 3 | 4 | 3 | 1 | 5 | 1 | 5 | 4 | 2 | 1 | 4 | 1 | 2 |

| | Framework II | | | | | | | | | | | | | CDR II | | | | | | | |
|---|---|---|---|---|---|---|---|---|---|---|---|---|---|---|---|---|---|---|---|---|---|
| amino acid[1] | 37 | 38 | 39 | 40 | 41 | 42 | 43 | 44 | 45 | 46 | 47 | 48 | 49 | 50 | 51 | 52 | 53 | 54 | 55 | 56 | 57 |
| A | | | | | | | | | | | | | | | | | | | 14 | | |
| B | | | | | | | | | | | | | | | | | | | | | |
| C | | | | | | | | | | | | | | | | | | | | | |
| D | | | | | | | | | | | | | | | | | | | 7 | | |
| E | | | | | | | | | 1 | | | | | | | | | | | | |
| F | | | | | | | | | | | | | | | | | | | | | |
| G | | | | | 22 | | | | | | | | | | 12 | | | | 1 | | 22 |
| H | | | | | | | | | | | | | | | | | | | | | |
| I | | | | | | | | | | 1 | | 22 | | | | | | | | | |
| K | | | 15 | | | | | | | | | | | 5 | | | | | | | |
| L | 16 | | | | | | | | | 14 | 21 | | | 14 | 1 | | | | | | |
| M | | | | | | | | | | | | | | | | | | | | | |
| N | | | | | | | | | | | | | | | | | 18 | | | | |
| P | | | | 22 | | | | 21 | | | | | | | | | | | | | |
| Q | 6 | 22 | | | | 22 | | | 12 | | | | | 1 | | | | | | | |
| R | | | 7 | | | | | | 8 | 7 | | | | 1 | | | | 22 | | | |
| S | | | | | | | 21 | | | | | | | | 2 | 22 | 2 | | | 22 | |
| T | | | | | | | | | | | | | | | | | 1 | | | | |
| V | | | | | | | | | | | 1 | | | | 6 | | | | | | |
| W | | | | | | | | | | | | | | | | | | | | | |
| X | | | | | | | | | | | | | | | | | | | | | |
| Y | | | | | | | | | | | | | 21 | | | | 1 | | | | |
| — | | | | | | | | | | | | | | | | | | | | | |
| unknown (?) | | | | | | | | | | | | | | | | | | | | | |
| not sequenced | | | | | | | 1 | 1 | 1 | | | | 1 | 1 | 1 | | | | | | |
| sum of seq[2] | 22 | 22 | 22 | 22 | 22 | 22 | 21 | 21 | 21 | 22 | 22 | 22 | 21 | 21 | 21 | 22 | 22 | 22 | 22 | 22 | 22 |
| oomcaa[3] | 16 | 22 | 15 | 22 | 22 | 22 | 21 | 21 | 12 | 14 | 21 | 22 | 21 | 14 | 12 | 22 | 18 | 22 | 14 | 22 | 22 |
| mcaa[4] | L | Q | K | P | G | Q | S | P | Q | L | L | I | Y | L | G | S | N | R | A | S | G |
| rel. oomcaa[5] | 73% | 100% | 68% | 100% | 100% | 100% | 100% | 100% | 57% | 64% | 95% | 100% | 100% | 67% | 57% | 100% | 82% | 100% | 64% | 100% | 100% |
| pos occupied[6] | 2 | 1 | 2 | 1 | 1 | 1 | 1 | 1 | 3 | 3 | 2 | 1 | 1 | 4 | 4 | 1 | 4 | 1 | 3 | 1 | 1 |

TABLE 4B-continued

Analysis of V kappa subgroup 2

| | Framework III | | | | | | | | | | | | | | | | | | | | |
|---|---|---|---|---|---|---|---|---|---|---|---|---|---|---|---|---|---|---|---|---|---|
| amino acid[1] | 58 | 59 | 60 | 61 | 62 | 63 | 64 | 65 | 66 | 67 | 68 | 69 | 70 | 71 | 72 | 73 | 74 | 75 | 76 | 77 | 78 |
| A | | | | | | | | | | | | | | | | | | | | | |
| B | | | | | | | | | | | | | | | | | | | | | |
| C | | | | | | | | | | | | | | | | | | | | | |
| D | | | 22 | | | | 1 | | | | 1 | | 22 | | | | | | | | |
| E | | | | | | | | | | | | | | | | | | | | | |
| F | | | | | 21 | | | | | | | | | 22 | | | | | | | |
| G | | | | | | | 21 | | 22 | | 21 | | | | | | | | | | |
| H | | | | | | | | | | | | | | | | | | | | | |
| I | | | | | | | | | | | | | | | | | 1 | 21 | | | |
| K | | | | | | | | | | | | | | | | | 19 | | | | |
| L | | | | | | | | | | | | | | | | 21 | 1 | | | | |
| M | | | | | | | | | | | | | | | | | | | | | |
| N | | | | | | | | | | | | | | | | | | | | | |
| P | | 22 | | | | | | | | | | | | | | | | | | | |
| Q | | | | | | | | | | | | | | | | | | | | | |
| R | | | | 20 | | | | 1 | | | | | | | | | | | | 20 | |
| S | | | | 1 | | 22 | | 21 | | 22 | | | | | | | | | 20 | 1 | |
| T | | | | 1 | | | | | | | | 22 | | | 21 | | | | 1 | | |
| V | 22 | | | | 1 | | | | | | | | | | | | | | | | 21 |
| W | | | | | | | | | | | | | | | | | | | | | |
| X | | | | | | | | | | | | | | | | | | | | | |
| Y | | | | | | | | | | | | | | | | | | | | | |
| — | | | | | | | | | | | | | | | | | | | | | |
| unknown (?) | | | | | | | | | | | | | | | 1 | | | | | | |
| not sequenced | | | | | | | | | | | | | | | | 1 | 1 | 1 | 1 | 1 | 1 |
| sum of seq[2] | 22 | 22 | 22 | 22 | 22 | 22 | 22 | 22 | 22 | 22 | 22 | 22 | 22 | 22 | 22 | 21 | 21 | 21 | 21 | 21 | 21 |
| oomcaa[3] | 22 | 22 | 22 | 20 | 21 | 22 | 21 | 21 | 22 | 22 | 21 | 22 | 22 | 22 | 21 | 21 | 19 | 21 | 20 | 20 | 21 |
| mcaa[4] | V | P | D | R | F | S | G | S | G | S | G | T | D | F | T | L | K | I | S | R | V |
| rel. oomcaa[5] | 100% | 100% | 100% | 91% | 95% | 100% | 95% | 95% | 100% | 100% | 95% | 100% | 100% | 100% | 95% | 100% | 90% | 100% | 95% | 95% | 100% |
| pos occupied[6] | 1 | 1 | 1 | 3 | 2 | 1 | 2 | 2 | 1 | 1 | 2 | 1 | 1 | 1 | 1 | 1 | 3 | 1 | 2 | 2 | 1 |

| | | | | | | | | | | | CDR III | | | | | | | | | | |
|---|---|---|---|---|---|---|---|---|---|---|---|---|---|---|---|---|---|---|---|---|---|
| amino acid[1] | 79 | 80 | 81 | 82 | 83 | 84 | 85 | 86 | 87 | 88 | 89 | 90 | 91 | 92 | 93 | 94 | 95 | A | B | C | D |
| A | | 20 | | | | | | | | | | | 14 | | | 1 | | | | | |
| B | | | | | | | | | | | | 1 | | | 1 | | | | | | |
| C | | | | | | | | | | 21 | | | | | | | | | | | |
| D | | | 1 | 21 | | | | | | | | | | | | | | | | | |
| E | 19 | | 20 | | | | | | | | | | | | | | | | | | |
| F | | | | | | | | | | | | | | | | | | | | | |
| G | 1 | | | | | 21 | | | | | | | 6 | | | 1 | | 2 | | | |
| H | | | | | | | | | | | | | 1 | | 7 | | | | | | |
| I | | | | | | | 1 | | | | | | | | | 1 | | | | | |
| K | | | | | | | | | | | | | | | | | | | | | |
| L | | | | | | | 1 | | | | | | | 12 | | | 2 | | | | |
| M | | | | | | | | | | | 21 | | | | | | | | | | |
| N | | | | | | | | | | | | | | | | | | | | | |
| P | | 1 | | | | | | | | | | | | | | 2 | 16 | 1 | | | |
| Q | 1 | | | | | | | | | | | 20 | | | 13 | | | | | | |
| R | | | | | | | | | | | | | | 1 | | | | | | | |
| S | | | | | | | | | | | | | | | | 3 | 2 | | | | |
| T | | | | | | | | | | | | | | 8 | | 7 | | | | | |
| V | | | | | 21 | | 19 | | | | | | | | | | | | | | |
| W | | | | | | | | | | | | | | | | 6 | | | | | |
| X | | | | | | | | | | | | | | | | | | | | | |
| Y | | | | | | | | 21 | 21 | | | | | | | | | | | | |
| — | | | | | | | | | | | | | | | | | | 14 | 17 | 17 | 17 |
| unknown (?) | | | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 2 | 5 | 5 | 5 | 5 |
| sum of seq[2] | 21 | 21 | 21 | 21 | 21 | 21 | 21 | 21 | 21 | 21 | 21 | 21 | 21 | 21 | 21 | 21 | 20 | 17 | 17 | 17 | 17 |
| oomcaa[3] | 19 | 20 | 20 | 21 | 21 | 21 | 19 | 21 | 21 | 21 | 21 | 20 | 14 | 12 | 13 | 7 | 16 | 14 | 17 | 17 | 17 |
| mcaa[4] | E | A | E | D | V | G | V | Y | Y | C | M | Q | A | L | Q | T | P | — | — | — | — |
| rel. oomcaa[5] | 90% | 95% | 95% | 100% | 100% | 100% | 90% | 100% | 100% | 100% | 100% | 95% | 67% | 57% | 62% | 33% | 80% | 82% | 100% | 100% | 100% |
| pos occupied[6] | 3 | 2 | 2 | 1 | 1 | 1 | 3 | 1 | 1 | 1 | 1 | 2 | 3 | 3 | 3 | 7 | 3 | 3 | 1 | 1 | 1 |

TABLE 4B-continued

Analysis of V kappa subgroup 2

| amino acid[1] | E | F | 96 | 97 | 98 | 99 | 100 | 101 | 102 | 103 | 104 | 105 | 106 | A | 107 | 108 | sum |
|---|---|---|---|---|---|---|---|---|---|---|---|---|---|---|---|---|---|
| | | | | | Framework IV | | | | | | | | | | | | |
| A | | | | | | | | | | | | | | | | | 71 |
| B | | | | | | | | | | | | | | | | | 3 |
| C | | | | | | | | | | | | 1 | | | | | 43 |
| D | | | | | | | | | | | | | | | | | 112 |
| E | | | | | | | | | | | | 13 | | | | | 71 |
| F | | | 1 | | 17 | | | | | | | | | | | | 72 |
| G | | | | | | 17 | 2 | 16 | | | | 1 | | | | | 233 |
| H | | | | | | | | | | | | | | | | | 26 |
| I | | | 3 | | | | | | | | | | 14 | | | | 94 |
| K | | | | | | | | | | 12 | | | | | 13 | | 66 |
| L | | | 2 | | | | | | | | 11 | | | | | | 219 |
| M | | | | | | | | | | | | | | | | | 37 |
| N | | | | | | | | | | | | | | | | | 56 |
| P | | | 1 | | | | | | | | | | | | | | 159 |
| Q | | | 1 | | | | 14 | | | | | | | | | | 159 |
| R | | | | | | | | | | 4 | | | | | | 12 | 126 |
| S | | | | | | | | | | | | | | | | | 325 |
| T | | | | 17 | | | | | 16 | | | | | | | | 140 |
| V | | | | | | | | | | | 5 | | | | | | 146 |
| W | | | 2 | | | | | | | | | | | | | | 31 |
| X | | | | | | | | | | | | | | | | | 3 |
| Y | | | 7 | | | | | | | | | | | | | | 123 |
| — | 17 | 17 | | | | | | | | | | | | 13 | | | 134 |
| unknown (?) | | | | | | | | | | | | | | | | | 2 |
| not sequenced | 5 | 5 | 5 | 5 | 5 | 5 | 6 | 6 | 6 | 6 | 6 | 7 | 8 | 9 | 9 | 10 | 211 |
| sum of seq[2] | 17 | 17 | 17 | 17 | 17 | 17 | 16 | 16 | 16 | 16 | 16 | 15 | 14 | 13 | 13 | 12 | |
| oomcaa[3] | 17 | 17 | 7 | 17 | 17 | 17 | 14 | 16 | 16 | 12 | 11 | 13 | 14 | 13 | 13 | 12 | |
| mcaa[4] | — | — | Y | T | F | G | Q | G | T | K | L | E | I | — | K | R | |
| rel. oomcaa[5] | 100% | 100% | 41% | 100% | 100% | 100% | 88% | 100% | 100% | 75% | 69% | 87% | 100% | 100% | 100% | 100% | |
| pos occupied[6] | 1 | 1 | 7 | 1 | 1 | 1 | 2 | 1 | 1 | 2 | 2 | 3 | 1 | 1 | 1 | 1 | |

TABLE 4C

Analysis of V kappa subgroup 3

| amino acid[1] | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | Framework I | | | | | | | | | | | | | | | |
| A | | 5 | | | | | 2 | | 27 | | | | | | 1 | |
| B | 1 | | | | | | | | | | | | | | | |
| C | | | | | | | | | | | | 2 | | | | |
| D | 2 | | | | | | | | 14 | | | | | | | |
| E | 76 | | 27 | | | | | | | | | | | | | |
| F | | 1 | | | | | | | | | | | | 1 | | |
| G | 1 | | | | | | | | 82 | | | | | | 1 | 152 |
| H | | | | | | | | | | 1 | | | | | | |
| I | | 75 | | | | | | | | | | | | | | |
| K | 3 | | | | | | | | | | | | | | | |
| L | | 4 | 1 | 104 | | | 1 | | | | 150 | | 129 | | 1 | |
| M | 5 | | | 13 | | | | | | | | | | | | |

TABLE 4C-continued

Analysis of V kappa subgroup 3

| | | | | | | | | | | | | | | | | |
|---|---|---|---|---|---|---|---|---|---|---|---|---|---|---|---|---|
| N | | | | | | | | | | | | | | 5 | | |
| P | | | | | | | | 124 | | | | | | | 147 | |
| Q | | | | | | 123 | | | | | | | | | | |
| R | | | | | 1 | | | | | | | | | | | |
| S | | | | | | | 119 | | 3 | 1 | | 150 | 1 | 141 | | |
| T | | 2 | | | 117 | | | | | 147 | | | | 5 | 1 | |
| V | | 1 | 89 | 1 | | | 1 | | | | 1 | | 22 | | 1 | |
| W | | | | | | | | | | | | | | | | |
| X | | | | | | | | | | | | | | | | |
| Y | | | | | | | | | | | | | | | | |
| — | | | | | | | | | | | | | | | | |
| unknown (?) | | | | | | | | | | | | | | | | |
| not sequenced | 88 | 88 | 117 | 118 | 118 | 123 | 123 | 124 | 126 | 149 | 151 | 152 | 152 | 152 | 152 | 152 |
| sum of seq[2] | 76 | 75 | 89 | 104 | 117 | 123 | 119 | 124 | 82 | 147 | 150 | 150 | 129 | 141 | 147 | 152 |
| oomcaa[3] | 64 | 65 | 62 | 66 | 88 | 88 | 89 | 103 | 102 | 80 | 96 | 103 | 102 | 103 | 98 | 105 |
| mcaa[4] | E | I | V | L | T | Q | S | P | G | T | L | S | L | S | P | G |
| rel. oomcaa[5] | 86% | 85% | 76% | 88% | 99% | 100% | 97% | 100% | 65% | 99% | 99% | 99% | 85% | 93% | 97% | 100% |
| pos occupied[6] | 6 | 6 | 3 | 3 | 2 | 1 | 4 | 1 | 4 | 3 | 2 | 2 | 3 | 4 | 6 | 1 |

| | | | | | | | | | | | | | | | | |
|---|---|---|---|---|---|---|---|---|---|---|---|---|---|---|---|---|
| | | | | | | | | | | | | | | | | CDRI |
| amino acid[1] | 17 | 18 | 19 | 20 | 21 | 22 | 23 | 24 | 25 | 26 | 27 | A | B | C | D | E |
| A | | | 178 | 2 | | | | | 166 | 1 | | | | | | |
| B | | | | | | | | | | | | | | | | |
| C | | | | | | | 181 | | | 1 | | | | | | |
| D | 6 | | | | | | | | | | | | | | | |
| E | 146 | 1 | | | | | | | | | 1 | | | | | |
| F | | | | | 7 | 1 | | | | | | | | | | |
| G | 1 | 1 | | | | | | | 1 | 1 | | 1 | | | | |
| H | | | | | | | | | | | 17 | | | | | |
| I | | 1 | | 5 | 2 | | | | | | | | | | | |
| K | | 1 | | | | | | 5 | | | | | | | | |
| L | | | | | 173 | | | | | | 1 | 1 | | | | |
| M | | | | | | | | | | | | | | | | |
| N | | | | | | | | | | | | 9 | | | | |
| P | | | | | | | | | | | | | | | | |
| Q | | | | | | | | | | | 159 | | | | | |
| R | | 175 | | | | | | 176 | | 1 | 1 | 10 | | | | |
| S | | | | | | 180 | | | 7 | 175 | | 87 | | | | |
| T | | 1 | | 174 | | | | | 7 | 2 | | 1 | | | | |
| V | | 1 | 4 | 1 | | | | | 1 | | | 1 | | | | |
| W | | | | | | | | 1 | | | | | | | | |
| X | | | | | | | | | | | | | | | | |
| Y | | | | | | 1 | | | | | 1 | | | | | |
| — | | | | | | | | | | | | 72 | 182 | 182 | 182 | 182 |
| unknown (?) | | | | | | | | | | | 1 | | | | | |
| not sequenced | | | | | | | | | | | | | | | | |
| sum of seq[2] | 153 | 181 | 182 | 182 | 182 | 182 | 181 | 182 | 182 | 181 | 181 | 182 | 182 | 182 | 182 | 182 |
| oomcaa[3] | 146 | 175 | 178 | 174 | 173 | 180 | 181 | 176 | 166 | 175 | 159 | 87 | 182 | 182 | 182 | 182 |
| mcaa[4] | E | R | A | T | L | S | C | R | A | S | Q | S | — | — | — | — |
| rel. oomcaa[5] | 95% | 97% | 98% | 96% | 95% | 99% | 100% | 97% | 91% | 97% | 88% | 48% | 100% | 100% | 100% | 100% |
| pos occupied[6] | 3 | 7 | 2 | 4 | 3 | 3 | 1 | 3 | 5 | 6 | 6 | 8 | 1 | 1 | 1 | 1 |

TABLE 4C-continued

Analysis of V kappa subgroup 3

| | | | | | | | | | | | | | | | | |
|---|---|---|---|---|---|---|---|---|---|---|---|---|---|---|---|---|
| | | | | | | | | | | | | | | | | Framewo |
| amino acid[1] | F | 28 | 29 | 30 | 31 | 32 | 33 | 34 | 35 | 36 | 37 | 38 | 39 | 40 | 41 | 42 |
| A | | | | 1 | 1 | | | 181 | | | | | | | | |
| B | | | | | | | | | | | | | | | | |
| C | | | | | | | | | | | | | | | | |
| D | | | 1 | 1 | 2 | 1 | | | | | | | | | | |
| E | | | | | | 1 | | | | | | | 1 | | | 1 |
| F | | 1 | | | | 7 | | | | 1 | | | | | | |
| G | | | 2 | 7 | 3 | 1 | | 2 | | | | | | 1 | 184 | |
| H | | | 1 | | | 2 | | | | 1 | | 12 | 1 | 1 | | |
| I | | 24 | 4 | 1 | 1 | | | | | | | | | | | |
| K | | | | 1 | 1 | | | | | | | | 153 | | | |
| L | | 8 | 1 | | | 1 | 176 | | | | | 3 | | | | 2 |
| M | | | | | | | | | | | | | | | | |
| N | | | 3 | 12 | 25 | 32 | | | | | | | | | | |
| P | | | | | 1 | | | | | | | | | 170 | | |
| Q | | | | | 1 | 1 | | | | | 183 | 167 | 1 | | | 181 |
| R | | | 10 | 3 | 18 | 16 | | 1 | | | 1 | | 27 | 5 | | |
| S | | 72 | 86 | 151 | 118 | 4 | | | | | | | | 5 | | |
| T | | 1 | 1 | 3 | 8 | 1 | | | | | | | 1 | | | |
| V | | 76 | 68 | | 1 | | 7 | | | | | 3 | | 2 | | |
| W | | | 5 | | | | | | 185 | | | | | | | |
| X | | | | | | | | | | | | | | | | |
| Y | | | | 1 | 1 | 115 | | | | 183 | | | | | | |
| — | 182 | | | | | | | | | | | | | | | |
| unknown (?) | | | | | | | | | | | 1 | | | | | |
| not sequenced | | | | | | | | | | | | | | | | |
| sum of seq[2] | 182 | 182 | 182 | 181 | 181 | 182 | 183 | 184 | 185 | 185 | 185 | 185 | 184 | 184 | 184 | 184 |
| oomcaa[3] | 182 | 76 | 86 | 151 | 118 | 115 | 176 | 181 | 185 | 183 | 183 | 167 | 153 | 170 | 184 | 181 |
| mcaa[4] | — | V | S | S | S | Y | L | A | W | Y | Q | Q | K | P | G | Q |
| rel. oomcaa[5] | 100% | 42% | 47% | 83% | 65% | 63% | 96% | 98% | 100% | 99% | 99% | 90% | 83% | 92% | 100% | 98% |
| pos occupied[6] | 1 | 6 | 11 | 10 | 13 | 12 | 2 | 3 | 1 | 3 | 2 | 4 | 6 | 6 | 1 | 3 |

| | | | | | | | | | | | | | | | | |
|---|---|---|---|---|---|---|---|---|---|---|---|---|---|---|---|---|
| | rk II | | | | | | | CDR II | | | | | | | | |
| amino acid[1] | 43 | 44 | 45 | 46 | 47 | 48 | 49 | 50 | 51 | 52 | 53 | 54 | 55 | 56 | 57 | 58 |
| A | 176 | | | | | | | 4 | 147 | | | | 176 | 1 | | |
| B | | | | | | | | | | | | | | | | |
| C | | | | | | | | | 1 | | | | | | | |
| D | | | | | | | | 43 | | | | | 2 | | 4 | |
| E | | | | | | | | | | | | | | | | |
| F | | | | 1 | | 1 | 4 | | | | | | | | | |
| G | | | | | | | | 125 | | | | | 2 | 10 | 179 | |
| H | | | | | | | 9 | | 1 | | | | | | | |
| I | | | | | | 178 | | | | | | | | 1 | | 168 |
| K | | | 1 | | | | | | | | 7 | 1 | | | | |
| L | | 1 | | 179 | 174 | 1 | | | | | | | | | | |
| M | | | | | | 3 | | | | | 1 | | | | | |

TABLE 4C-continued

Analysis of V kappa subgroup 3

| amino acid | | | | | | | | | | | | | | | | |
|---|---|---|---|---|---|---|---|---|---|---|---|---|---|---|---|---|
| N | | | 1 | | | | | 1 | | | 53 | | | 2 | | |
| P | 5 | 184 | | | | | | | | 2 | | | 2 | 2 | | |
| Q | | | | | | | 1 | | | | | | | | | |
| R | | | 182 | | | | | 1 | | | 4 | 180 | | | | |
| S | | | | | | | 3 | 6 | 4 | 179 | 74 | 1 | | 5 | | |
| T | 3 | | | | | | | | 11 | 2 | 44 | | | 164 | | 2 |
| V | | | | 3 | 9 | | | 3 | 19 | | | | 3 | | | 15 |
| W | | | | | | | 1 | | | | | 1 | | | | |
| X | | | | | | | | | | | | | | | | |
| Y | | | | | | | 165 | | | | | | | | 2 | |
| — | | | | | | | | | | | | | | | | |
| unknown (?) | | | 1 | | | | | | | | | | | | | |
| not sequenced | | | | | | | | | | | | | | | | |
| sum of seq[2] | 184 | 185 | 185 | 183 | 183 | 183 | 183 | 183 | 183 | 183 | 183 | 183 | 185 | 185 | 185 | 185 |
| oomcaa[3] | 176 | 184 | 182 | 179 | 174 | 178 | 165 | 125 | 147 | 179 | 74 | 180 | 176 | 164 | 179 | 168 |
| mcaa[4] | A | P | R | L | L | I | Y | G | A | S | S | R | A | T | G | I |
| rel. oomcaa[5] | 96% | 99% | 98% | 98% | 95% | 97% | 90% | 68% | 80% | 98% | 40% | 98% | 95% | 89% | 97% | 91% |
| pos occupied[6] | 3 | 2 | 3 | 3 | 2 | 4 | 6 | 7 | 6 | 3 | 6 | 4 | 5 | 7 | 3 | 3 |

| | | | | | | | | | | | | | | Framework III | | |
|---|---|---|---|---|---|---|---|---|---|---|---|---|---|---|---|---|
| amino acid[1] | 59 | 60 | 61 | 62 | 63 | 64 | 65 | 66 | 67 | 68 | 69 | 70 | 71 | 72 | 73 | 74 |
| A | | 68 | | | | | | 3 | | 5 | 3 | 1 | | 3 | | |
| B | | | | | | | | | | | | | | | | |
| C | | | | | | | | | | | | | | | | |
| D | | 112 | | | | 1 | | | | | | 152 | | | | |
| E | | | | | | | | 1 | | 1 | | 30 | | | | |
| F | | | | 183 | | | | | | | | | 183 | | 2 | |
| G | | | | | | 184 | 3 | 178 | | 177 | | | | | | |
| H | | 1 | | | | | | | | | | | | | | |
| I | | | | 1 | | | | | | | | | | 1 | | 3 |
| K | | | 1 | | | | | | | | | | | | | |
| L | | | | 1 | | | | | | | | | | | 182 | |
| M | | | | | | | | 1 | | | | | | | | |
| N | | 1 | | | | | | | | | | | | 1 | | |
| P | 177 | | | | | | | | | | | | | | | |
| Q | | | | | | | | | | | | 1 | | | | |
| R | | | 182 | | 2 | | 1 | | | | 2 | | | | | |
| S | 7 | | | | 180 | | 179 | | 185 | | 3 | | | 7 | | 2 |
| T | 1 | | 2 | | 3 | | 2 | | | | 177 | | | 172 | | 179 |
| V | | 3 | | | | | | 1 | | 1 | | | | | | |
| W | | | | | | | | | | 1 | | | | | | |
| X | | | | | | | | | | | | | | | | |
| Y | | | | | | | | | | | | | 1 | | | |
| — | | | | | | | | | | | | | | | | |
| unknown (?) | | | | | | | | 1 | | | | | | | | |
| not sequenced | | | | | | | | | | | | | | | | |
| sum of seq[2] | 185 | 185 | 185 | 185 | 185 | 185 | 185 | 185 | 185 | 185 | 185 | 184 | 184 | 184 | 184 | 184 |
| oomcaa[3] | 177 | 112 | 182 | 183 | 180 | 184 | 179 | 178 | 185 | 177 | 177 | 152 | 183 | 172 | 182 | 179 |
| mcaa[4] | P | D | R | F | S | G | S | G | S | G | T | D | F | T | L | T |
| rel. oomcaa[5] | 96% | 61% | 98% | 99% | 97% | 99% | 97% | 96% | 100% | 96% | 96% | 83% | 99% | 93% | 99% | 97% |
| pos occupied[6] | 3 | 5 | 3 | 3 | 3 | 2 | 4 | 5 | 1 | 5 | 4 | 4 | 2 | 5 | 2 | 3 |

TABLE 4C-continued

Analysis of V kappa subgroup 3

| amino acid[1] | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|
| A | | | | | | | 3 | | | 174 | | | | | | |
| B | | | | | 1 | | | | | | | | | | | |
| C | | | | | | | | | 2 | | | | 1 | 182 | | |
| D | | | 1 | | | | 3 | 182 | | | | | | | | |
| E | | | | | 149 | | 175 | | | | | | | | | 2 |
| F | | 1 | | | | | | | 178 | | 2 | 1 | 4 | | | |
| G | | | 3 | | | | | 1 | | 2 | | | | | | |
| H | | | | | | | | | | | 1 | | | | 1 | 7 |
| I | 178 | | | | | | | 1 | 1 | | 9 | | | | | |
| K | | | | | | | 1 | | | | | | | | | |
| L | | | | 178 | | 1 | | | 1 | | 7 | | 1 | | | 1 |
| M | | | | | | | | | | 1 | 5 | | | | | |
| N | 1 | 5 | | | | | | | | | | | | | | |
| P | | | | | | 149 | | | | | | | | | | |
| Q | | | | | 34 | | | | | | | | | 1 | 181 | 155 |
| R | | 1 | 111 | | | | | | | 3 | | | | | | 1 |
| S | | 169 | 65 | | | 34 | | | 1 | | | | 2 | | | |
| T | | 8 | 4 | | | | | | | 1 | | | | | | 8 |
| V | 4 | | | 6 | | | | | 1 | 3 | 159 | | | | | 7 |
| W | | | | | | | | | | | | | | | | |
| X | | | | | | | | | | | | | | | | |
| Y | 1 | | | | | | | | | | 1 | 183 | 176 | | 1 | 2 |
| — | | | | | | | | | | | | | | | | |
| unknown (?) | | | | | | | | | | | | | | | | |
| not sequenced | | | | | | | | | | | | | | | | |
| sum of seq[2] | 184 | 184 | 184 | 184 | 184 | 184 | 182 | 184 | 184 | 184 | 184 | 184 | 184 | 183 | 183 | 183 |
| oomcaa[3] | 178 | 169 | 111 | 178 | 149 | 149 | 175 | 182 | 178 | 174 | 159 | 183 | 176 | 182 | 181 | 155 |
| mcaa[4] | I | S | R | L | E | P | E | D | F | A | V | Y | Y | C | Q | Q |
| rel. oomcaa[5] | 97% | 92% | 60% | 97% | 81% | 81% | 96% | 99% | 97% | 95% | 86% | 99% | 96% | 96% | 99% | 85% |
| pos occupied[6] | 4 | 5 | 5 | 2 | 3 | 3 | 4 | 3 | 6 | 6 | 7 | 2 | 5 | 2 | 3 | 8 |

| | CDR III | | | | | | | | | | | | | | | |
|---|---|---|---|---|---|---|---|---|---|---|---|---|---|---|---|---|
| amino acid[1] | 91 | 92 | 93 | 94 | 95 | A | B | C | D | E | F | 96 | 97 | 98 | 99 | 100 |
| A | | 1 | 8 | 3 | 3 | | | | | | | | | | | 1 |
| B | | | | | | | | | | | | | | | | |
| C | 2 | | | 1 | | | | | | | | 2 | | | | |
| D | | 8 | 5 | | | | | | | | | | 1 | | | |
| E | | 2 | | | | | | | | | | 1 | | | | |
| F | 5 | | 2 | | | | | | | | | 7 | | 166 | | |
| G | 1 | 104 | 15 | | 1 | 1 | 2 | | | | | 1 | | | 166 | 41 |
| H | 4 | 1 | | | | | | | | | | 2 | | | | |
| I | | | 1 | | | 1 | | | | | | 4 | | | | |
| K | | | 2 | | | 1 | | | | | | 1 | | | | 1 |
| L | | | | 2 | 7 | 5 | | | | | | 42 | | | | |
| M | | 1 | | | 1 | 2 | | | | | | | | | | |

TABLE 4C-continued

Analysis of V kappa subgroup 3

| | | | | | | | | | | | | | | | | |
|---|---|---|---|---|---|---|---|---|---|---|---|---|---|---|---|---|
| N | | 28 | 71 | | | | | | | | | 1 | | | | |
| P | | | | 1 | 139 | 24 | | | | | | 7 | 2 | | | 9 |
| Q | 1 | | 1 | | 3 | 1 | | | | | | 3 | | | | 114 |
| R | 34 | 2 | 3 | | 2 | 2 | | | | | | 19 | | | | |
| S | 2 | 33 | 58 | 102 | 15 | 2 | | | | | | 1 | 8 | | | |
| T | | 2 | 13 | 1 | 1 | 2 | | | | | | 1 | 154 | | | |
| V | | | | | 3 | 1 | | | | | | 2 | | | | |
| W | | | | 69 | | | | | | | | 24 | | | | |
| X | | | | | | | | | | | | | | | | |
| Y | 134 | 1 | 1 | | | | | | | | | 43 | | | | |
| — | | | 3 | 3 | 7 | 127 | 167 | 169 | 169 | 169 | 169 | 8 | 1 | 1 | 1 | 1 |
| unknown (?) | | | | | | | | | | | | | | | | |
| not sequenced | | | | | | 14 | 14 | 14 | 14 | 14 | 14 | 14 | 17 | 16 | 16 | 16 |
| sum of seq[2] | 183 | 183 | 183 | 182 | 182 | 169 | 169 | 169 | 169 | 169 | 169 | 169 | 166 | 167 | 167 | 167 |
| oomcaa[3] | 134 | 104 | 71 | 102 | 139 | 127 | 167 | 169 | 169 | 169 | 169 | 43 | 154 | 166 | 166 | 114 |
| mcaa[4] | Y | G | N | S | P | — | — | — | — | — | — | Y | T | F | G | Q |
| rel. oomcaa[5] | 73% | 57% | 39% | 56% | 76% | 75% | 99% | 100% | 100% | 100% | 100% | 25% | 93% | 99% | 99% | 68% |
| pos occupied[6] | 8 | 11 | 13 | 8 | 11 | 12 | 2 | 1 | 1 | 1 | 1 | 18 | 5 | 2 | 2 | 6 |

| | Framework IV | | | | | | | | | |
|---|---|---|---|---|---|---|---|---|---|---|
| amino acid[1] | 101 | 102 | 103 | 104 | 105 | 106 | A | 107 | 108 | sum |
| A | | | | | | | | | | 1345 |
| B | | | | | | | | | | 2 |
| C | | | | | | | | | | 375 |
| D | | | | | 23 | | | | | 564 |
| E | | | 3 | | 141 | | | | | 759 |
| F | | | | | | 6 | | | | 765 |
| G | 166 | | | | | | | | 1 | 1804 |
| H | | | | | 1 | | | | | 64 |
| I | | | | | | 143 | | | | 803 |
| K | | | 152 | | | | | 157 | | 489 |
| L | | | | 54 | | 1 | | | 2 | 1596 |
| M | | | | | | 3 | | | | 36 |
| N | | 1 | | | | | | 3 | | 255 |
| P | | 1 | | 1 | | | | | | 1147 |
| Q | | | 1 | | 1 | | | | | 1314 |
| R | | | 9 | | | 2 | | 4 | 134 | 1326 |
| S | | 2 | | | | | | | | 2629 |
| T | | 162 | 1 | | | | | 1 | | 1593 |
| V | | | | 111 | | 11 | | | | 646 |
| W | | | | | | | | | | 287 |
| X | | | | | | | | | | |
| Y | | | 1 | | | | | | | 1014 |
| — | 1 | 1 | 1 | 1 | 1 | 1 | 166 | 1 | 1 | 2151 |
| unknown (?) | | | | | | | | | | |
| not sequenced | 16 | 16 | 15 | 16 | 16 | 16 | 17 | 17 | 45 | 337 |
| sum of seq[2] | 167 | 167 | 168 | 167 | 167 | 167 | 166 | 166 | 138 | |
| oomcaa[3] | 166 | 162 | 152 | 111 | 141 | 143 | 166 | 157 | 134 | |
| mcaa[4] | G | T | K | V | E | I | — | K | R | |
| rel. oomcaa[5] | 99% | 97% | 90% | 66% | 84% | 86% | 100% | 95% | 97% | |
| pos occupied[6] | 2 | 5 | 7 | 4 | 5 | 7 | 1 | 5 | 4 | |

TABLE 4D

Analysis of V kappa subgroup 4

| | Framework I | | | | | | | | | | | | | | | | | |
|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 |
| A | | | | | | | | | | | | 24 | | | | | 1 | |
| B | | | | | | | | | | | | | | | | | | |
| C | | | | | | | | | | 1 | | | | | | 1 | | |
| D | 25 | | | | | | | | 26 | | | | | | | | | |
| E | | | | | | | | | | | | | | | | | 25 | |
| F | | | | | | | | | | | | | | | | | | |
| G | | | | | | | | | | | | 1 | | | | 24 | | |
| H | | | | | | | | | | | | | | | | | | |
| I | | 26 | | | | | | | | | | | | | | | | |
| K | | | | | | 1 | | | | | | | | | | | | |
| L | | | | 1 | | | | | | | 26 | | | | | 26 | | |
| M | | | | 24 | | | | | | | | | | | | | | |
| N | 1 | | | | | | | | | | | | | | | | | |
| P | | | | | | | | 26 | | | | 1 | | | | | | |
| Q | | | 1 | | | 25 | | | | | | | | | | | | |
| R | | | | | | | | | | | | | | | | | | 26 |
| S | | | | | | | 26 | | | 25 | | | | 26 | | 1 | | |
| T | | | | | 26 | | | | | | | | | | | | | |
| V | | | 25 | 1 | | | | | | | | | 26 | | | | | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | 7 | 7 | 7 | 7 | 7 | 7 | 7 | 7 | 7 | 7 | 7 | 7 | 7 | 7 | 7 | 7 | 7 | 7 |
| sum of seq[2] | 26 | 26 | 26 | 26 | 26 | 26 | 26 | 26 | 26 | 26 | 26 | 26 | 26 | 26 | 26 | 26 | 26 | 26 |
| oomcaa[3] | 25 | 26 | 25 | 24 | 26 | 25 | 26 | 26 | 26 | 25 | 26 | 24 | 26 | 26 | 26 | 24 | 25 | 26 |
| mcaa[4] | D | I | V | M | T | Q | S | P | D | S | L | A | V | S | L | G | E | R |
| rel. oomcaa[5] | 96% | 100% | 96% | 92% | 100% | 96% | 100% | 100% | 100% | 96% | 100% | 92% | 100% | 100% | 100% | 92% | 96% | 100% |
| pos occupied[6] | 2 | 1 | 2 | 3 | 1 | 2 | 1 | 1 | 1 | 2 | 1 | 3 | 1 | 1 | 1 | 3 | 2 | 1 |

| | | | | | | CDRI | | | | | | | | | | | | |
|---|---|---|---|---|---|---|---|---|---|---|---|---|---|---|---|---|---|---|
| amino acid[1] | 19 | 20 | 21 | 22 | 23 | 24 | 25 | 26 | 27 | A | B | C | D | E | F | 28 | 29 | 30 |
| A | 26 | | | | | | 1 | | | | 1 | | | | | | | |
| B | | | | | | | | | | | | | | | | | | |
| C | | | | | 33 | | | | | | | | | | | | | |
| D | | | | | | | | | | | 1 | | 1 | | | 1 | | |
| E | | | | | | | | | | | | | | | | | | |
| F | | | | | | | | | | | | | | | | | | |
| G | | | | | | | | | | | | | | | | | | |
| H | | | | | | | | | | | | | | | | | | |
| I | | | 26 | | | | | | | | 1 | | | | | | | |
| K | | | | | | 33 | | | | | | | | | | 2 | | 30 |
| L | | | | | | | | | | | 2 | 31 | | | | | | |
| M | | | | | | | | | | | | | | | | | | |

TABLE 4D-continued

Analysis of V kappa subgroup 4

| | | | | | | | | | | | | | | | | | | |
|---|---|---|---|---|---|---|---|---|---|---|---|---|---|---|---|---|---|---|
| N | | | | 26 | | | | | | | | | | | | 30 | 31 | 1 |
| P | | | | | | | 1 | | | | | | | | 1 | | | |
| Q | | | | | | | | | 32 | | | | | | | | | 1 |
| R | | | | | | | | | 1 | | | | | | | | 1 | 1 |
| S | | | | | | | 31 | 33 | | 33 | | | | 32 | 32 | | 1 | |
| T | | 26 | | | | | | | | | | | | 1 | | | | |
| V | | | | | | | | | | | 28 | 2 | | | | | | |
| W | | | | | | | | | | | | | | | | | | |
| X | | | | | | | | | | | | | | | | | | |
| Y | | | | | | | | | | | | | 32 | | | | | |
| — | | | | | | | | | | | | | | | | | | |
| unknown (?) | | | | | | | | | | | | | | | | | | |
| not sequenced | 7 | 7 | 7 | 7 | | | | | | | | | | | | | | |
| sum of seq[2] | 26 | 26 | 26 | 26 | 33 | 33 | 33 | 33 | 33 | 33 | 33 | 33 | 33 | 33 | 33 | 33 | 33 | 33 |
| oomcaa[3] | 26 | 26 | 26 | 26 | 33 | 33 | 31 | 33 | 32 | 33 | 28 | 31 | 32 | 32 | 32 | 30 | 31 | 30 |
| mcaa[4] | A | T | I | N | C | K | S | S | Q | S | V | L | Y | S | S | N | N | K |
| rel. oomcaa[5] | 100% | 100% | 100% | 100% | 100% | 100% | 94% | 100% | 97% | 100% | 85% | 94% | 97% | 97% | 97% | 91% | 91% | 91% |
| pos occupied[6] | 1 | 1 | 1 | 1 | 1 | 1 | 3 | 1 | 2 | 1 | 5 | 2 | 2 | 2 | 2 | 3 | 3 | 4 |

| | | | | | Framework II | | | | | | | | | | | | | |
|---|---|---|---|---|---|---|---|---|---|---|---|---|---|---|---|---|---|---|
| amino acid[1] | 31 | 32 | 33 | 34 | 35 | 36 | 37 | 38 | 39 | 40 | 41 | 42 | 43 | 44 | 45 | 46 | 47 | 48 |
| A | | | | 32 | | | | | | 2 | | | | | | | | |
| B | | | | | | | | | | | | | | | | | | |
| C | | | | | | | | | | | | | | | | | | |
| D | | | | | | | | | | | | | | | | | | |
| E | | | | | | | | | | | 1 | | | | | | | |
| F | | | | | | | | | | | | | | | | | | |
| G | | | | | | | | | | | 32 | | | | | | | |
| H | | | | | | 2 | | | | | | | | | | | | |
| I | | | | | | | | | | | | | | | | | | 32 |
| K | | | | | | | | | 33 | | | | | | 32 | | | |
| L | | | 33 | | | | | | | | | | | | | 29 | 33 | |
| M | | | | | | | | | | | | | | | | | | 1 |
| N | 33 | | | | | | | | | | | | | | | | | |
| P | | | | | | | | | | 31 | | | 31 | 33 | | | | |
| Q | | | | | | | 32 | 33 | | | | 32 | | | | | | |
| R | | | | | | | 1 | | | | | 1 | | | 1 | | | |
| S | | | | | | | | | | | | | 2 | | | | | |
| T | | | | 1 | | | | | | | | | | | | | | |
| V | | | | | | | | | | | | | | | | 4 | | |
| W | | | | | 33 | | | | | | | | | | | | | |
| X | | | | | | | | | | | | | | | | | | |
| Y | | 33 | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 32 | 33 | 31 | 32 | 33 | 33 | 31 | 32 | 32 | 32 | 31 | 32 | 29 | 33 | 32 |
| mcaa[4] | N | Y | L | A | W | Y | Q | Q | K | P | G | Q | P | P | K | L | L | I |
| rel. oomcaa[5] | 100% | 100% | 100% | 97% | 100% | 94% | 97% | 100% | 100% | 94% | 97% | 97% | 94% | 100% | 97% | 88% | 100% | 97% |
| pos occupied[6] | 1 | 1 | 1 | 2 | 1 | 2 | 2 | 1 | 1 | 2 | 2 | 2 | 2 | 1 | 2 | 2 | 1 | 2 |

TABLE 4D-continued

Analysis of V kappa subgroup 4

| | | CDR II | | | | | | | | | | | | | | | | |
|---|---|---|---|---|---|---|---|---|---|---|---|---|---|---|---|---|---|---|
| amino acid[1] | 49 | 50 | 51 | 52 | 53 | 54 | 55 | 56 | 57 | 58 | 59 | 60 | 61 | 62 | 63 | 64 | 65 | 66 |
| A | | | 30 | | | | | | | | | | | | | | | |
| B | | | | | | | | | | | | | | | | | | |
| C | | | | | | | | | | | | | | | | | | |
| D | | | | | | | | | | | | 33 | | | | | | |
| E | | | | | | | 32 | | | | | | | | | | | |
| F | | | | | | | | | | | | | | 33 | | | | |
| G | | | | | | | | | 33 | | | | | | 1 | 33 | | 33 |
| H | | | | | | | | | | | | | | | | | | |
| I | | | | | 1 | | | | | | | | | | | | | |
| K | | | | | | | | | | | | | | | | | | |
| L | | | | | | | | | | | | | | | | | | |
| M | | | | | | | | | | | | | | | | | | |
| N | | | | | 2 | | | | | | | | | | | | | |
| P | | | | 1 | | | | | | | 33 | | 1 | | | | | |
| Q | | | | | | | | | | | | | | | | | | |
| R | | | | | | 33 | | | | | | | 32 | | | | | |
| S | | | 1 | 31 | 1 | | | 33 | | | | | | | 32 | | 33 | |
| T | | | 2 | 1 | 29 | | | | | | | | | | | | | |
| V | | | | | | | 1 | | | 33 | | | | | | | | |
| W | | 33 | | | | | | | | | | | | | | | | |
| X | | | | | | | | | | | | | | | | | | |
| Y | 33 | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 30 | 31 | 29 | 33 | 32 | 33 | 33 | 33 | 33 | 33 | 32 | 33 | 32 | 33 | 33 | 33 |
| mcaa[4] | Y | W | A | S | T | R | E | S | G | V | P | D | R | F | S | G | S | G |
| rel. oomcaa[5] | 100% | 100% | 91% | 94% | 88% | 100% | 97% | 100% | 100% | 100% | 100% | 100% | 97% | 100% | 97% | 100% | 100% | 100% |
| pos occupied[6] | 1 | 1 | 3 | 3 | 4 | 1 | 2 | 1 | 1 | 1 | 1 | 1 | 2 | 1 | 2 | 1 | 1 | 1 |

| | Framework III | | | | | | | | | | | | | | | | | |
|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 |
| A | | | | | | | | | | | | | | 33 | | | | 32 |
| B | | | | | | | | | | | | | | | | | | |
| C | | | | | | | | | | | | | | | | | | |
| D | | | | 32 | | | | | | | | | | | | 33 | | |
| E | | | | | | | | | | | | | | | 33 | | | |
| F | | | | | 32 | | | | | | | | | | | | | |
| G | | 33 | | 1 | | | | | | | | | | | | | | 1 |
| H | | | | | | | | | | | | | | | | | | |
| I | | | | | | | | | 33 | | | | | | | | | |
| K | | | | | | | | | | | | | | | | | | |
| L | | | | | | | 33 | | | | | 32 | | | | | | |
| M | | | | | | | | | | | | 1 | | | | | | |

TABLE 4D-continued

Analysis of V kappa subgroup 4

| | | | | | | | | | | | | | | | | | | |
|---|---|---|---|---|---|---|---|---|---|---|---|---|---|---|---|---|---|---|
| N | | | | | | | | | | 2 | 1 | | | | | | | |
| P | | | | | | | | | | | | | | | | | | |
| Q | | | | | | | | | | | | | | 32 | | | | |
| R | | | | | | | | | | | | | | 1 | | | | |
| S | 33 | | | | | | | | | 30 | 32 | | | | | | | |
| T | | | 33 | | | 33 | | 33 | | 1 | | | | | | | | |
| V | | | | | 1 | | | | | | | | | | | | 33 | |
| W | | | | | | | | | | | | | | | | | | |
| X | | | | | | | | | | | | | | | | | | |
| Y | | | | | | | | | | | | | | | | | | |
| — | | | | | | | | | | | | | | | | | | |
| unknown (?) | | | | | | | | | | | | | | | | | | |
| not sequenced | | | | | | | | | | | | | | | | | | |
| sum of seq[2] | 33 | 33 | 33 | 33 | 33 | 33 | 33 | 33 | 33 | 33 | 33 | 33 | 33 | 33 | 33 | 33 | 33 | 33 |
| oomcaa[3] | 33 | 33 | 33 | 32 | 32 | 33 | 33 | 33 | 33 | 30 | 32 | 32 | 32 | 33 | 33 | 33 | 33 | 32 |
| mcaa[4] | S | G | T | D | F | T | L | T | I | S | S | L | Q | A | E | D | V | A |
| rel. oomcaa[5] | 100% | 100% | 100% | 97% | 97% | 100% | 100% | 100% | 100% | 91% | 97% | 97% | 97% | 100% | 100% | 100% | 100% | 97% |
| pos occupied[6] | 1 | 1 | 1 | 2 | 2 | 1 | 1 | 1 | 1 | 3 | 2 | 2 | 2 | 1 | 1 | 1 | 1 | 2 |

| | | | | | CDR III | | | | | | | | | | | | | |
|---|---|---|---|---|---|---|---|---|---|---|---|---|---|---|---|---|---|---|
| amino acid[1] | 85 | 86 | 87 | 88 | 89 | 90 | 91 | 92 | 93 | 94 | 95 | A | B | C | D | E | F | 96 |
| A | | | | | | | | | | 1 | | | | | | | | |
| B | | | | | | | | | | | | | | | | | | |
| C | | | | 33 | | | | | | | | | | | | | | |
| D | | | | | | | | 1 | 1 | | | | | | | | | |
| E | | | | | | | | | | | | | | | | | | |
| F | | | 1 | | | | | 1 | | | | | | | | | | |
| G | | | | | | | | | 2 | | | | | | | | | |
| H | | | 1 | | 3 | | | | | | | | | | | | | |
| I | | | | | | | | | | 2 | | | | | | | | |
| K | | | | | | | | | | | | | | | | | | |
| L | | | | | | 1 | | 2 | | 1 | 3 | | | | | | | 1 |
| M | | | | | | | | | | | | | | | | | | |
| N | | | | | | | | | 4 | 4 | | | | | | | | |
| P | | | | | | | | | | 1 | 29 | 1 | | | | | | 4 |
| Q | | | | | 30 | 32 | | | | | 1 | | | | | | | 1 |
| R | | | | | | | | | 1 | | | 1 | | | | | | 2 |
| S | | | | | | | 2 | | 23 | 2 | | | | | | | | 1 |
| T | | | | | | | | | 2 | 22 | | | | | | | | |
| V | 33 | | | | | | | | | | | | | | | | | |
| W | | | | | | | | | | | | | | | | | | 2 |
| X | | | | | | | | | | | | | | | | | | |
| Y | | 33 | 31 | | | | 31 | 29 | | | | | | | | | | 1 |
| — | | | | | | | | | | | | 13 | 15 | 15 | 15 | 15 | 15 | 3 |
| unknown (?) | | | | | | | | | | | | | | | | | | |
| not sequenced | | | | | | | | | | | | 18 | 18 | 18 | 18 | 18 | 18 | 18 |
| sum of seq[2] | 33 | 33 | 33 | 33 | 33 | 33 | 33 | 33 | 33 | 33 | 33 | 15 | 15 | 15 | 15 | 15 | 15 | 15 |
| oomcaa[3] | 33 | 33 | 31 | 33 | 30 | 32 | 31 | 29 | 23 | 22 | 29 | 13 | 15 | 15 | 15 | 15 | 15 | 4 |
| mcaa[4] | V | Y | Y | C | Q | Q | Y | Y | S | T | P | — | — | — | — | — | — | R |
| rel. oomcaa[5] | 100% | 100% | 94% | 100% | 91% | 97% | 94% | 88% | 70% | 67% | 88% | 87% | 100% | 100% | 100% | 100% | 100% | 27% |
| pos occupied[6] | 1 | 1 | 3 | 1 | 2 | 2 | 2 | 4 | 6 | 7 | 3 | 3 | 1 | 1 | 1 | 1 | 1 | 8 |

TABLE 4D-continued

Analysis of V kappa subgroup 4

| | Framework IV | | | | | | | | | | | | | |
|---|---|---|---|---|---|---|---|---|---|---|---|---|---|---|
| amino acid[1] | 97 | 98 | 99 | 100 | 101 | 102 | 103 | 104 | 105 | 106 | A | 107 | 108 | sum |
| A | | | | | | | | | | | | | | 183 |
| B | | | | | | | | | | | | | | |
| C | | | | | | | | | | | | | | 68 |
| D | | | | | | | | | | | | | | 154 |
| E | | | | | | | | | 14 | | | | | 105 |
| F | | 15 | | | | | | | | | | | | 82 |
| G | | | 15 | 4 | 15 | | | | | | | | | 228 |
| H | | | | | | | | | | | | | | 6 |
| I | | | | | | | | | | 14 | | | | 135 |
| K | | | | | | | 14 | | | | | 13 | | 158 |
| L | | | | | | | | 4 | | | | | | 258 |
| M | | | | | | | | | | | | | | 27 |
| | 1 | | | | | | | | | | | | | |
| N | | | | | | | | | | | | 1 | | 136 |
| P | | | | | | 1 | | | | | | | | 195 |
| Q | | | | 11 | | | | 1 | | | | | | 264 |
| R | | | | | | | 1 | | 1 | | | 1 | 11 | 116 |
| S | 2 | | | | | | | | | 1 | | | | 499 |
| T | 12 | | | | | 14 | | | | | | | | 236 |
| V | | | | | | | | 9 | | | | | | 196 |
| W | | | | | | | | 1 | | | | | | 69 |
| X | | | | | | | | | | | | | | |
| Y | | | | | | | | | | | | | | 254 |
| — | | | | | | | | | | | 15 | | | 106 |
| unknown (?) | | | | | | | | | | | | | | |
| not sequenced | 18 | 18 | 18 | 18 | 18 | 18 | 18 | 18 | 18 | 18 | 18 | 18 | 22 | 518 |
| sum of seq[2] | 15 | 15 | 15 | 15 | 15 | 15 | 15 | 15 | 15 | 15 | 15 | 15 | 11 | |
| oomcaa[3] | 12 | 15 | 15 | 11 | 15 | 14 | 14 | 9 | 14 | 14 | 15 | 13 | 11 | |
| mcaa[4] | T | F | G | Q | G | T | K | V | E | I | — | K | R | |
| rel. oomcaa[5] | 80% | 100% | 100% | 73% | 100% | 93% | 93% | 60% | 93% | 93% | 100% | 87% | 100% | |
| pos occupied[6] | 3 | 1 | 1 | 2 | 1 | 2 | 2 | 4 | 2 | 2 | 1 | 3 | 1 | |

TABLE 5A

Analysis of V lambda subgroup 1

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | | | | | | | 19 | | 18 | 20 | | | | | |
| B | | | | | | | | | | | | | | | | | | | |
| C | | | | | | | | | | | | | | | | | | | |
| D | | | | | | | | | | | | | | | | | | | |
| E | | | | | | | | | | | | | | | | | | 1 | |
| F | | | | | | | | | | | | | | | | | | | |
| G | | | | | | | | | | | | | | | | | | | |
| H | 2 | | | | | | | | | | | | | | | | | | |
| I | | | 1 | | | | | | | | 1 | | | | | | | | |
| K | | | | | | | | | | | | | | | | | | 14 | |
| L | | | 1 | 41 | | | | | | | 1 | | | | | | | | |
| M | | | | | | | | | | | | | | | | | | | |

TABLE 5A-continued

Analysis of V lambda subgroup 1

| | | | | | | | | | | | | | | | | | | | |
|---|---|---|---|---|---|---|---|---|---|---|---|---|---|---|---|---|---|---|---|
| N | | | | | | | | | | | | | | | | | | | |
| P | | | | | | | 41 | 41 | | | | | | 1 | 41 | | | | |
| Q | 22 | | 1 | | | 41 | | | | | | | | | | | 42 | | |
| R | | | | | | | | | | | | | | | | | | 25 | |
| S | | 39 | | | | | | | 41 | | | 41 | | | 1 | | | 1 | |
| T | | | | | 41 | | | | | | | | | 19 | | | | 1 | |
| V | | 1 | 38 | | | | | | | | 20 | | 1 | 1 | | | | | 42 |
| W | | | | | | | | | | | | | | | | | | | |
| X | | | | | | | | | | | | | | | | | | | |
| Y | | | | | | | | | | | | | | | | | | | |
| Z | 16 | | | | | | | | | | | | | | | | | | |
| — | | | | | | | | | | 41 | | | | | | | | | |
| unknown (?) | | | | | | | | | | | | | | | | | | | |
| not sequenced | 2 | 2 | 1 | 1 | 1 | 1 | 1 | 1 | 1 | 1 | 1 | 1 | 1 | 1 | | | | | |
| sum of seq[2] | 40 | 40 | 41 | 41 | 41 | 41 | 41 | 41 | 41 | 41 | 41 | 41 | 41 | 41 | 42 | 42 | 42 | 42 | 42 |
| oomcaa[3] | 22 | 39 | 38 | 41 | 41 | 41 | 41 | 41 | 41 | 41 | 20 | 41 | 22 | 20 | 41 | 42 | 42 | 25 | 42 |
| mcaa[4] | Q | S | V | L | T | Q | P | P | S | — | V | S | G | A | P | G | Q | R | V |
| rel. oomcaa[5] | 55% | 98% | 93% | 100% | 100% | 100% | 100% | 100% | 100% | 100% | 49% | 100% | 54% | 49% | 98% | 100% | 100% | 60% | 100% |
| pos occupied[6] | 3 | 2 | 4 | 1 | 1 | 1 | 1 | 1 | 1 | 1 | 4 | 1 | 3 | 4 | 2 | 1 | 1 | 5 | 1 |

| | | | | | CDRI | | | | | | | | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 | 35 |
| A | 2 | | | | | | | 1 | | | | 2 | 2 | | | 1 | | | |
| B | | | | | | | | | | | | | | | | | | | |
| C | | | | 42 | | | | | | | | | | | | | | | |
| D | | | | | | | | | | 3 | | | 3 | 1 | | 3 | | 1 | |
| E | | | | | | | | | | | | | 1 | | | | | | |
| F | | | | | 1 | | | | 1 | | | | | | 1 | 1 | | | |
| G | | | | | | 42 | 3 | 1 | | | 2 | 39 | 4 | 2 | | | | | |
| H | | | | | | | | | | | | | | 2 | | 2 | | 2 | |
| I | 1 | 41 | | | | | | | | 1 | 37 | | | | | | | 1 | |
| K | | | | | | | | | | 1 | | | 1 | | | | | | |
| L | | 1 | | | | | | | | | 1 | | | | | | | | |
| M | | | | | | | | | | | 1 | | | | | | | | |
| N | | | | | | | | 2 | 1 | 37 | | | 13 | 31 | 2 | | 1 | 9 | |
| P | | | | | | | | | | | | | | | | 1 | | | |
| Q | | | | | | | | | | | | | | | | 1 | | | |
| R | | | | | | | 1 | 1 | | | | | 5 | | | | | | |
| S | 1 | | 42 | | 38 | | 34 | 34 | 38 | | | | 13 | 1 | 1 | 3 | | 19 | |
| T | 38 | | | | 3 | | 4 | 3 | 2 | | | 1 | | 1 | | 7 | | 2 | |
| V | | | | | | | | | | | 1 | | | | | 2 | 40 | | |
| W | | | | | | | | | | | | | | | | | | | 42 |
| X | | | | | | | | | | | | | | | | | | | |
| Y | | | | | | | | | | | | | | 4 | 1 | 20 | | 7 | |
| Z | | | | | | | | | | | | | | | | | | | |
| — | | | | | | | | | | | | | | | 36 | | | | |
| unknown (?) | | | | | | | | | | | | | | | | | | | |
| not sequenced | | | | | | | | | | | | | | | 1 | 1 | 1 | 1 | |
| sum of seq[2] | 42 | 42 | 42 | 42 | 42 | 42 | 42 | 42 | 42 | 42 | 42 | 42 | 42 | 42 | 41 | 41 | 41 | 41 | 42 |
| oomcaa[3] | 38 | 41 | 42 | 42 | 38 | 42 | 34 | 34 | 38 | 37 | 37 | 39 | 13 | 31 | 36 | 20 | 40 | 19 | 42 |
| mcaa[4] | T | I | S | C | S | G | S | S | S | N | I | G | N | N | — | Y | V | S | W |
| rel. oomcaa[5] | 90% | 98% | 100% | 100% | 90% | 100% | 81% | 81% | 90% | 88% | 88% | 93% | 31% | 74% | 88% | 49% | 98% | 46% | 100% |
| pos occupied[6] | 4 | 2 | 1 | 1 | 3 | 1 | 4 | 6 | 4 | 4 | 5 | 3 | 8 | 7 | 5 | 10 | 2 | 7 | 1 |

TABLE 5A-continued

Analysis of V lambda subgroup 1

| | Framework II | | | | | | | | | | | | | | | | | | |
|---|---|---|---|---|---|---|---|---|---|---|---|---|---|---|---|---|---|---|---|
| amino acid[1] | 36 | 37 | 38 | 39 | 40 | 41 | 42 | 43 | 44 | 45 | 46 | 47 | 48 | 49 | 50 | 51 | 52 | 53 | 54 |
| A | | | | | | | 4 | 40 | | | | | | | | | 1 | | |
| B | | | | | | | | | | | | | | | | | | | |
| C | | | | | | | | | | | | | | | | | | | |
| D | | | | | | 1 | | | | | | | | | 13 | 10 | 8 | | |
| E | | | | | | | | | | 2 | | | | | 5 | | | 1 | |
| F | 1 | | | 4 | | | | | | | | | | 1 | | | | | |
| G | | | | | | 39 | | | | | | | | | 1 | | | | |
| H | 1 | 1 | 6 | 1 | | | | | | | | | | 1 | | | | 1 | |
| I | | | | | | | | | | | | | 40 | | 1 | | | | |
| K | | | | | | | 1 | | | 35 | | | | | 1 | 1 | | 18 | |
| L | | | 1 | 31 | | | | | | | 41 | 40 | | | | | | 1 | 1 |
| M | | | | | | | 1 | | | | | | 1 | | | | | 1 | |
| N | | | | | | | | | | 1 | | | | | 3 | 28 | 30 | 2 | |
| P | | | | | 42 | 1 | | | 42 | | | | | | | | | | |
| Q | | 39 | 34 | | | | | | | | | | | | | | | 15 | |
| R | | 2 | | 1 | | 1 | | | | 4 | | | | | 7 | | | 2 | 40 |
| S | | | | | | | | 1 | | | | | | | 9 | 2 | 3 | 1 | |
| T | | | | | | | 36 | 1 | | | | | | | 1 | | | | |
| V | | | 1 | 5 | | | | | | | 1 | 2 | 1 | | | | | | |
| W | | | | | | | | | | | | | | | | | | | 1 |
| X | | | | | | | | | | | | | | | | | | | |
| Y | 40 | | | | | | | | | | | | | 40 | 1 | 1 | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 40 | 40 | 42 | 42 | 42 | 42 | 42 | 42 | 42 | 42 | 42 | 42 | 42 | 42 | 42 | 42 | 42 | 42 | 42 |
| oomcaa[3] | 40 | 39 | 34 | 31 | 42 | 39 | 36 | 40 | 42 | 35 | 41 | 40 | 40 | 40 | 13 | 28 | 30 | 18 | 40 |
| mcaa[4] | Y | Q | Q | L | P | G | T | A | P | K | L | L | I | Y | D | N | N | K | R |
| rel. oomcaa[5] | 95% | 93% | 81% | 74% | 100% | 93% | 86% | 95% | 100% | 83% | 98% | 95% | 95% | 95% | 31% | 67% | 71% | 43% | 95% |
| pos occupied[6] | 3 | 3 | 4 | 5 | 1 | 4 | 4 | 3 | 1 | 4 | 2 | 2 | 3 | 3 | 10 | 5 | 4 | 9 | 3 |

| | CDR II | | | | | | | | | | | | | | | | | | |
|---|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | 1 | | | | | | | | | | | | | | 5 | | | | |
| B | | | | | | | | | | | | | | | | | | | |
| C | | | | | | | | | | | | | | | | | | | |
| D | | | | | | | | | | | 38 | | | | | | | | |
| E | | | | | | | | | | | | | | | | | | | |
| F | | | | | | | | | | | | | 38 | | | | | | |
| G | | | | | | | | 41 | | | 2 | | | | 36 | | | | |
| H | | | | | | | | | | | 1 | | | | | | | | |
| I | | | | | | | | | 17 | | | | 3 | | | | | | |
| K | | | | | | | | | | | | | | | | | 38 | | |
| L | | 1 | | | | | | | | 1 | | | | | | | | | |
| M | | | | | | | | | | | | | | | | | | | |

TABLE 5A-continued

Analysis of V lambda subgroup 1

| | | | | | | | | | | | | | | | | | | | |
|---|---|---|---|---|---|---|---|---|---|---|---|---|---|---|---|---|---|---|---|
| N | | | | | | | | | | | | | | | | | | | |
| P | 38 | | | | | | | | | 38 | | | | | | | | | |
| Q | | | | | | | | | | | | | | | | | | | |
| R | | | | | | | | | | | | 42 | | | | | 4 | | |
| S | 2 | 40 | | | | | | | | 2 | | | | 42 | | 42 | | | |
| T | | | | | | | | | | | | | | | 1 | | | | |
| V | | | | | | | | | 24 | | | | 1 | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | 41 | 41 | 41 | 41 | 42 | | | | | | | | | | | 42 | 42 |
| unknown (?) | | | | | | | | | | | | | | | | | | | |
| not sequenced | 1 | 1 | | | | | | 1 | 1 | 1 | 1 | | | | | | | | |
| sum of seq[2] | 41 | 41 | 41 | 41 | 41 | 41 | 42 | 41 | 41 | 41 | 41 | 42 | 42 | 42 | 42 | 42 | 42 | 42 | 42 |
| oomcaa[3] | 38 | 40 | 41 | 41 | 41 | 41 | 42 | 41 | 24 | 38 | 38 | 42 | 38 | 42 | 36 | 42 | 38 | 42 | 42 |
| mcaa[4] | P | S | — | — | — | — | — | G | V | P | D | R | F | S | G | S | K | — | — |
| rel. oomcaa[5] | 93% | 98% | 100% | 100% | 100% | 100% | 100% | 100% | 59% | 93% | 93% | 100% | 90% | 100% | 86% | 100% | 90% | 100% | 100% |
| pos occupied[6] | 3 | 2 | 1 | 1 | 1 | 1 | 1 | 1 | 2 | 3 | 3 | 1 | 3 | 1 | 3 | 1 | 2 | 1 | 1 |

| | Framework III | | | | | | | | | | | | | | | | | | |
|---|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 | 85 |
| A | | 1 | 3 | | 41 | | | 24 | | | | | | 2 | | | | 38 | 1 |
| B | | | | | | | | | | | | | | | | | | | |
| C | | | | | | | | | | | | | | | | | | | |
| D | | 1 | | | | | | | | | | | | | 1 | 41 | | | 37 |
| E | | | | | | | | | | | | | 1 | | 24 | | 42 | | 1 |
| F | | | | | | | | | | | | | | | | | | | |
| G | | 40 | | | | | | 17 | | 1 | 42 | | | | 15 | | | | |
| H | | | | | | | | | | | | | 1 | | | | | | 2 |
| I | | | | | | | | | 41 | | | | | | | | | | 1 |
| K | | | | | | | | | | | | | | | | | | | |
| L | | | | | | | 42 | | | | | 41 | | | | | | | |
| M | | | | | | | | | | | | | | | | | | | |
| N | | | | | | | | | | | | | | | | | 1 | | |
| P | | | | | | | | | | | | | | 2 | | | | | |
| Q | | | | | | | | | | | | | 31 | | | | | | |
| R | | | | | | | | | | | | | 8 | | | | | | |
| S | 42 | | 1 | 42 | | 24 | | | | 20 | | | | 20 | | | | 1 | |
| T | | | 38 | | | 18 | | | | 21 | | | | 17 | | | | 3 | |
| V | | | | | 1 | | | 1 | 1 | | | 1 | | 1 | | | | | |
| W | | | | | | | | | | | | | 1 | | 2 | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 42 | 42 | 42 | 42 | 42 | 42 | 42 | 42 | 42 | 42 | 42 | 42 | 42 | 42 | 42 | 42 | 42 | 42 | 42 |
| oomcaa[3] | 42 | 40 | 38 | 42 | 41 | 24 | 42 | 24 | 41 | 21 | 42 | 41 | 31 | 20 | 24 | 41 | 42 | 38 | 37 |
| mcaa[4] | S | G | T | S | A | S | L | A | I | T | G | L | Q | S | E | D | E | A | D |
| rel. oomcaa[5] | 100% | 95% | 99% | 100% | 98% | 57% | 100% | 57% | 98% | 50% | 100% | 98% | 74% | 48% | 57% | 98% | 100% | 90% | 88% |
| pos occupied[6] | 1 | 3 | 3 | 1 | 2 | 2 | 1 | 3 | 2 | 3 | 1 | 2 | 5 | 5 | 4 | 2 | 1 | 3 | 5 |

TABLE 5A-continued

Analysis of V lambda subgroup 1

| | | | | CDR III | | | | | | | | | | | | | | |
|---|---|---|---|---|---|---|---|---|---|---|---|---|---|---|---|---|---|---|
| amino acid[1] | 86 | 87 | 88 | 89 | 90 | 91 | 92 | 93 | 94 | 95 | A | B | C | D | E | F | 96 | 97 | 98 |
| A | | | | 22 | 15 | | | 1 | | | | 16 | | | | | 4 | 1 | |
| B | | | | | | | | | | | | | | | | | | | |
| C | | | 42 | | | | | | | | | | | | | | | | |
| D | | | | | | | 39 | 17 | | | 7 | | | | | | | | |
| E | | | | | | | | | | | | 1 | | | | | 1 | | |
| F | | 2 | | | | | | | | 1 | | | | | | | | | 36 |
| G | | | | 14 | | | | 1 | | | | 17 | 1 | | | | 5 | 1 | |
| H | | 1 | | | | | | | | | | | 1 | | | | | | |
| I | | | | | | | | | | | 1 | | | | | | | 1 | |
| K | | | | | | | | | | | 1 | | | | | | | | |
| L | | | | 1 | | | | | | 37 | | | 1 | | | | | 1 | |
| M | | | | | | | | | | | | | | | | | | 1 | |
| N | | | | | | | 2 | 2 | | | 9 | 1 | | | | | | | |
| P | | | | | | | | | | 1 | | | | | | | 6 | | |
| Q | | | | 3 | | | | | | | | | | | | | | | |
| R | | | | | | | | | 5 | 1 | 2 | | | | | | 2 | | |
| S | | | | | 4 | | | 17 | 35 | | 18 | | 1 | | | | 1 | | |
| T | | | | | 22 | | | 1 | 1 | | 1 | | | | | | | | |
| V | | | | 1 | | | | 1 | | 1 | | 2 | | | | | 9 | 34 | |
| W | | | | | | 38 | | | | | | | | | | | 7 | | |
| X | | | | | | | | | | | | | | | | | | | |
| Y | 42 | 39 | | | | 3 | | 1 | | | | | | | | | 3 | | |
| Z | | | | | | | | | | | | | | | | | | | |
| — | | | | | | | | | | | 2 | 4 | 35 | 39 | 38 | 38 | 1 | | |
| unknown (?) | | | | | | | | | | | | | | | | | | | |
| not sequenced | | | | 1 | 1 | 1 | 1 | 1 | 1 | 1 | 1 | 1 | 3 | 3 | 3 | 3 | 3 | 3 | 4 |
| sum of seq[2] | 42 | 42 | 42 | 41 | 41 | 41 | 41 | 41 | 41 | 41 | 41 | 41 | 39 | 39 | 38 | 38 | 39 | 39 | 36 |
| oomcaa[3] | 42 | 39 | 42 | 22 | 22 | 38 | 39 | 17 | 35 | 37 | 18 | 17 | 35 | 39 | 38 | 38 | 9 | 34 | 36 |
| mcaa[4] | Y | Y | C | A | T | W | D | D | S | L | S | G | — | — | — | — | V | V | F |
| rel. oomcaa[5] | 100% | 93% | 100% | 54% | 54% | 93% | 95% | 41% | 85% | 90% | 44% | 41% | 90% | 100% | 100% | 100% | 23% | 87% | 100% |
| pos occupied[6] | 1 | 3 | 1 | 5 | 3 | 2 | 2 | 8 | 3 | 5 | 8 | 6 | 5 | 1 | 1 | 1 | 10 | 6 | 1 |

| | Framework IV | | | | | | | | | | | |
|---|---|---|---|---|---|---|---|---|---|---|---|---|
| amino acid[1] | 99 | 100 | 101 | 102 | 103 | 104 | 105 | 106 | A | 107 | 108 | sum |
| A | | | | | | | | | | | | 285 |
| B | | | | | | | | | | | | |
| C | | | | | | | | | | | | 84 |
| D | | | | | | | | | | | | 224 |
| E | | 1 | | | | | | | | | | 81 |
| F | | | | | | | | | | | | 87 |
| G | 36 | 31 | 36 | | | | | | | 26 | | 559 |
| H | | | | | | | | | | | | 25 |
| I | | | | | | | | | | | | 188 |
| K | | | | | 30 | | | | | | | 141 |
| L | | | | | | 25 | | | 34 | | | 344 |
| M | | | | | | | | | | | | 5 |

TABLE 5A-continued

Analysis of V lambda subgroup 1

| | | | | | | | | | | | | |
|---|---|---|---|---|---|---|---|---|---|---|---|---|
| N | | | | | 1 | | | | | | | 176 |
| P | | | | | | | | | | | 1 | 296 |
| Q | | | | | 3 | | | | 1 | | 18 | 251 |
| R | | | | | 1 | | | | | 2 | | 156 |
| S | | 1 | | | | | | | | 2 | | 720 |
| T | | 3 | | 36 | 1 | | 36 | | | | | 359 |
| V | | | | | | 11 | | 36 | 1 | | | 282 |
| W | | | | | | | | | | 1 | | 92 |
| X | | | | | | | | | | | | |
| Y | | | | | | | | | | | | 202 |
| Z | | | | | | | | | | | | 16 |
| — | | | | | | | | | | | | 524 |
| unknown (?) | | | | | | | | | | | | |
| not sequenced | 4 | 6 | 6 | 6 | 6 | 6 | 6 | 6 | 6 | 10 | 22 | 141 |
| sum of seq[2] | 36 | 36 | 36 | 36 | 36 | 36 | 36 | 36 | 36 | 31 | 19 | |
| oomcaa[3] | 36 | 31 | 36 | 36 | 30 | 25 | 36 | 36 | 34 | 26 | 18 | |
| mcaa[4] | G | G | G | T | K | L | T | V | L | G | O | |
| rel. oomcaa[5] | 100% | 86% | 100% | 100% | 83% | 69% | 100% | 100% | 94% | 84% | 95% | |
| pos occupied[6] | 1 | 4 | 1 | 1 | 5 | 2 | 1 | 1 | 3 | 4 | 2 | |

TABLE 5B

Analysis of V lambda subgroup 2

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | 35 | | | | | 30 | | | 6 | | 1 | 1 | | | | | |
| B | | | | | | | | | | | | | | | | | | | |
| C | | | | | | | | | | | | | | | | | | | |
| D | | | | | | | | | | | | | | | | 1 | | | |
| E | | | | | | | | | | | | | | | | | | | |
| F | | | | | | | | | | | | | | | | | | | |
| G | | | | | | | | | | | | | 42 | | | 42 | | | |
| H | 2 | | | | | | | | | | | | | | | | 1 | | |
| I | | | 1 | | | | | | | | | | | | | | | | 28 |
| K | | | | | | | | | | | | | | | | | | | |
| L | | | | 40 | | | | | | | | | | | 3 | | | | 1 |
| M | | | | | | | | | | | | | | | | | | | |
| N | | | | | | | | | | | | | | | | | | | |
| P | | | | | | | 42 | 6 | | | | | | | 40 | | | | |
| Q | 22 | | 4 | | | 41 | | | | | | | | | | | 42 | | |
| R | | | | | | | | 6 | 1 | | | | | | | | | | |
| S | | 41 | | | | | | | 40 | | | 42 | | 42 | | | | 43 | |
| T | | | | | 42 | | | | 1 | | | | | | | | | | |
| V | | 1 | 2 | | | | | | | | 36 | | | | | | | | 14 |
| W | | | | | | | | | | | | | | | | | | | |
| X | | | | | | | | | | | | | | | | | | | |
| Y | | | | | | | | | | | | | | | | | | | |
| Z | 16 | | | | | | | | | | | | | | | | | | |
| — | | | | | | | | | | 42 | | | | | | | | | |
| unknown (?) | | | | | | 1 | | | | | | | | | | | | | |
| not sequenced | 3 | 1 | 1 | 3 | 1 | 1 | 1 | 1 | 1 | 1 | 1 | 1 | | | | | | | |
| sum of seq[2] | 40 | 42 | 42 | 40 | 42 | 42 | 42 | 42 | 42 | 42 | 42 | 42 | 43 | 43 | 43 | 43 | 43 | 43 | 43 |
| oomcaa[3] | 22 | 41 | 35 | 40 | 42 | 41 | 42 | 30 | 40 | 42 | 36 | 42 | 42 | 42 | 40 | 42 | 42 | 43 | 28 |
| mcaa[4] | Q | S | A | L | T | Q | P | A | S | — | V | S | G | S | P | G | Q | S | I |
| rel. oomcaa[5] | 55% | 98% | 83% | 100% | 100% | 98% | 100% | 71% | 95% | 100% | 86% | 100% | 98% | 98% | 93% | 98% | 98% | 100% | 65% |
| pos occupied[6] | 3 | 2 | 4 | 1 | 1 | 1 | 1 | 3 | 3 | 1 | 2 | 1 | 2 | 2 | 2 | 2 | 2 | 1 | 3 |

TABLE 5B-continued

Analysis of V lambda subgroup 2

| | | | | | CDRI | | | | | | | | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 | 35 |
| A | | | | | 3 | | 1 | | | | | | 1 | | | 1 | | | |
| B | | | | | | | | | | | | | | | | | | | |
| C | | | | 42 | | | | | 1 | | | | | 1 | | | | | |
| D | | | | | | | | | | 39 | 1 | | 4 | | 5 | | | | |
| E | | | | | | | | | | | | | | | 1 | | | | |
| F | | 1 | | | | | | | | | | | 1 | | | 4 | | | |
| G | | | | | | 43 | | 1 | | | | 39 | 26 | | | | | | |
| H | | | | | | | | 1 | | | | | | | 1 | 1 | | | |
| I | | 41 | | | 1 | | | | | | 6 | | | | | | | | |
| K | | | | | | | | | | | | | | | 4 | | | | |
| L | | 1 | | | | | | | | | | | | | | 4 | | | |
| M | | | | | | | | | | | | | | | | | | | |
| N | | | | | | | | 1 | 3 | 4 | | 1 | 4 | 3 | 28 | | | | |
| P | | | | | | | | 1 | | | | | | | | | | | |
| Q | | | | | | | | | | | | | | | | | | | |
| R | | | | | | | | | 1 | | | | 2 | | | | | | |
| S | | | 42 | | 3 | | 3 | 35 | 38 | | | | 5 | 1 | 2 | 4 | 1 | 42 | |
| T | 43 | | | | 36 | | 39 | 3 | | | | 1 | | 1 | | | | | |
| V | | | | | | | | | | | 37 | | | | | | 41 | | |
| W | | | | | | | | | | | | | | | | | | | 43 |
| X | | | | | | | | | | | | | | | | | | | |
| Y | | | | | | | | 1 | | | | 1 | | 37 | | 29 | | | |
| Z | | | | | | | | | | | | | | | | | | | |
| — | | | | | | | | | | | | | | | 1 | | | | |
| unknown (?) | | | | | | | | | | | | | | | 1 | | | | |
| not sequenced | | | 1 | 1 | | | | | | | | | | | | | 1 | 1 | |
| sum of seq[2] | 43 | 43 | 42 | 42 | 43 | 43 | 43 | 43 | 43 | 43 | 43 | 43 | 43 | 43 | 43 | 43 | 42 | 42 | 43 |
| oomcaa[3] | 43 | 41 | 42 | 42 | 36 | 43 | 39 | 35 | 38 | 39 | 37 | 39 | 26 | 37 | 28 | 29 | 41 | 42 | 43 |
| mcaa[4] | T | I | S | C | T | G | T | S | S | D | V | G | G | Y | N | Y | V | S | W |
| rel. oomcaa[5] | 100% | 95% | 100% | 100% | 84% | 100% | 91% | 81% | 88% | 91% | 86% | 91% | 60% | 86% | 65% | 67% | 98% | 100% | 100% |
| pos occupied[6] | 1 | 3 | 1 | 1 | 4 | 1 | 3 | 7 | 4 | 2 | 2 | 5 | 7 | 5 | 7 | 6 | 2 | 1 | 1 |

| | Framework II | | | | | | | | | | | | | | | | | | |
|---|---|---|---|---|---|---|---|---|---|---|---|---|---|---|---|---|---|---|---|
| amino acid[1] | 36 | 37 | 38 | 39 | 40 | 41 | 42 | 43 | 44 | 45 | 46 | 47 | 48 | 49 | 50 | 51 | 52 | 53 | 54 |
| A | | | | | 1 | 4 | | 40 | | | | | | | | | | | |
| B | | | | | | | | | | | | | | | | | | | |
| C | | | | | | | | | | | | | | | | | | | |
| D | | | | 1 | | 2 | | | | | | | | | 20 | 1 | 2 | 1 | |
| E | | | | | | | | | | | | | | | 20 | | | 2 | |
| F | 2 | | | | | | | | | | | | | 7 | | 1 | | | |
| G | | | | | | 36 | | | | | | | | | 2 | 2 | | 1 | |
| H | | | 2 | 34 | | | | | | | | | | | | | | 1 | |
| I | | | | | | | 1 | | | | 1 | 9 | 43 | | | | 1 | | |
| K | | | | | | | 40 | | | 41 | | | | | | | 1 | 21 | |
| L | | | 1 | 1 | | | | | | | 38 | 6 | | | | | | | |
| M | | | | | | | | | | | | 26 | | | | | 1 | | |

TABLE 5B-continued

Analysis of V lambda subgroup 2

| | | | | | | | | | | | | | | | | | | | |
|---|---|---|---|---|---|---|---|---|---|---|---|---|---|---|---|---|---|---|---|
| N | | | | 2 | | | | | | | | | | | 1 | | 8 | 12 | |
| P | | | | | 41 | | | | 43 | | | | | | | | | | |
| Q | | 41 | 39 | | | | | | | 2 | | | | | | | | | |
| R | | 1 | | | | | 1 | | | | | | | | | | 2 | | 43 |
| S | | | | | 1 | | | | | | | | | 2 | | | 21 | 3 | |
| T | | | | | | | 1 | | | | | | | | | | 7 | | |
| V | | | | | | 1 | | 3 | | | 4 | 2 | | | | 39 | | | |
| W | | | | | | | | | | | | | | | | | | | |
| X | | | | | | | | | | | | | | | | | | | |
| Y | 41 | | 5 | | | | | | | | | | | 34 | | | | | |
| Z | | | | | | | | | | | | | | | | | | | |
| — | | | | | | | | | | | | | | | | | | | |
| unknown (?) | | 1 | 1 | | | | | | | | | | | | | | | | |
| not sequenced | | | | | | | | | | | | | | | | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 41 | 41 | 39 | 34 | 41 | 36 | 40 | 40 | 43 | 41 | 38 | 26 | 43 | 34 | 20 | 39 | 21 | 21 | 43 |
| mcaa[4] | Y | Q | Q | H | P | G | K | A | P | K | L | M | I | Y | D | V | S | K | R |
| rel. oomcaa[5] | 95% | 95% | 91% | 79% | 95% | 84% | 93% | 93% | 100% | 95% | 88% | 60% | 100% | 79% | 47% | 91% | 49% | 49% | 100% |
| pos occupied[6] | 2 | 2 | 3 | 5 | 3 | 4 | 4 | 2 | 1 | 2 | 3 | 4 | 1 | 3 | 4 | 4 | 8 | 8 | 1 |

| | CDR II | | | | | | | | | | | | | | | | | | |
|---|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | | | | | | | | | | | | | | | 2 | | | | |
| B | | | | | | | | | | | | | | | | | | | |
| C | | | | | | | | | | | | | | | | 1 | | | |
| D | | | | | | | | | | | 17 | | | | | | | | |
| E | | | | | | | | | | | | | | | | | | | |
| F | | | | | | | | | | | | | 42 | | | | | | |
| G | | | | | | | | 43 | 1 | | | | | | 41 | | | | |
| H | | | | | | | | | | | 2 | | | | | | | | |
| I | | | | | | | | | 3 | | | | | | | | | | |
| K | | | | | | | | | | | | | | | | | 42 | | |
| L | | | | | | | | | | | 1 | | 1 | | | | | | |
| M | | | | | | | | | | | | | | | | | | | |
| N | | | | | | | | | | | 19 | | | | | | | | |
| P | 43 | | | | | | | | | 15 | | | | | | | | | |
| Q | | | | | | | | | | | | | | | | | | | |
| R | | | | | | | | | | | | 43 | | | | | 1 | | |
| S | | 43 | | | | | | | | 28 | 2 | | | 43 | | 42 | | | |
| T | | | | | | | | | | | | | | | | | | | |
| V | | | | | | | | | 39 | | | | | | | | | | |
| W | | | | | | | | | | | | | | | | | | | |
| X | | | | | | | | | | | | | | | | | | | |
| Y | | | | | | | | | | | 2 | | | | | | | | |
| Z | | | | | | | | | | | | | | | | | | | |
| — | | | 43 | 43 | 43 | 43 | 43 | | | | | | | | | | | 43 | 43 |
| unknown (?) | | | | | | | | | | | | | | | | | | | |
| not sequenced | | | | | | | | | | | | | | | | | | | |
| sum of seq[2] | 43 | 43 | 43 | 43 | 43 | 43 | 43 | 43 | 43 | 43 | 43 | 43 | 43 | 43 | 43 | 43 | 43 | 43 | 43 |
| oomcaa[3] | 43 | 43 | 43 | 43 | 43 | 43 | 43 | 43 | 39 | 28 | 19 | 43 | 42 | 43 | 41 | 42 | 42 | 43 | 43 |
| mcaa[4] | P | S | — | — | — | — | — | G | V | S | N | R | F | S | G | S | K | — | — |
| rel. oomcaa[5] | 100% | 100% | 100% | 100% | 100% | 100% | 100% | 100% | 91% | 65% | 44% | 100% | 98% | 100% | 95% | 98% | 98% | 100% | 100% |
| pos occupied[6] | 1 | 1 | 1 | 1 | 1 | 1 | 1 | 1 | 3 | 2 | 6 | 1 | 2 | 1 | 2 | 2 | 2 | 1 | 1 |

TABLE 5B-continued

Analysis of V lambda subgroup 2

| | Framework III | | | | | | | | | | | | | | | | | | |
|---|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 | 85 |
| A | | 3 | | 1 | 43 | | | | | | | | | 36 | | | | 43 | |
| B | | | | | | | | | | | | | | | | | | | |
| C | | | | | | | | | | | | | | | | | | | |
| D | | 1 | 2 | | | | | | | | | | | | 3 | 42 | | | 39 |
| E | | | | | | | | | | | 1 | | | | 38 | | 43 | | |
| F | | | | | | | | | | | | | | | | | | | |
| G | | 39 | | | | | | | | | 42 | | | | 1 | | | | |
| H | | | | | | | | | | | | | | | | | | | 2 |
| I | | | | | | | | | 35 | | | | | | | | | | |
| K | | | 1 | | | | | | | | | | | | | | | | |
| L | | | | | | | 43 | | | | | 43 | | | | | | | |
| M | | | | | | | | | | | | | | | | | | | |
| N | | | 38 | | | | | | | | | | | | 1 | 1 | | | 1 |
| P | | | | | | | | | | | | | | 2 | | | | | |
| Q | | | | | | | | | | | | | 41 | | | | | | |
| R | | | | | | | | | | | | | 2 | | | | | | |
| S | 42 | | | 1 | | 43 | | | | 42 | | | | | | | | | |
| T | | | 1 | 41 | | | | 43 | | 1 | | | | 2 | | | | | |
| V | | | | | | | | | 8 | | | | | 3 | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | 1 | | | | | | | | | | | | | | | | |
| not sequenced | 1 | | | | | | | | | | | | | | | | | | |
| sum of seq[2] | 42 | 43 | 43 | 43 | 43 | 43 | 43 | 43 | 43 | 43 | 43 | 43 | 43 | 43 | 43 | 43 | 43 | 43 | 43 |
| oomcaa[3] | 42 | 39 | 38 | 41 | 43 | 43 | 43 | 43 | 35 | 42 | 42 | 43 | 41 | 36 | 38 | 42 | 43 | 43 | 39 |
| mcaa[4] | S | G | N | T | A | S | L | T | I | S | G | L | Q | A | E | D | E | A | D |
| rel. oomcaa[5] | 100% | 91% | 88% | 95% | 100% | 100% | 100% | 100% | 81% | 98% | 98% | 100% | 95% | 84% | 88% | 98% | 100% | 100% | 91% |
| pos occupied[6] | 1 | 3 | 4 | 3 | 1 | 1 | 1 | 1 | 2 | 2 | 2 | 1 | 2 | 4 | 4 | 2 | 1 | 1 | 3 |

| | | | | CDR III | | | | | | | | | | | | | | | |
|---|---|---|---|---|---|---|---|---|---|---|---|---|---|---|---|---|---|---|---|
| amino acid[1] | 86 | 87 | 88 | 89 | 90 | 91 | 92 | 93 | 94 | 95 | A | B | C | D | E | F | 96 | 97 | 98 |
| A | | | | 2 | 1 | | 21 | | 1 | | | | | | | | 1 | 1 | |
| B | | | | | | | | | | | | | | | | | | | |
| C | | | 43 | 11 | | | | | | | | | | | | | | | |
| D | | | | | | | | 3 | 1 | 2 | | | | | | | 1 | | |
| E | | | | | | | 1 | 1 | | | | | | | | | | | |
| F | | 3 | | | | 3 | | | | 1 | | 1 | | | | | 5 | | 42 |
| G | | | | | | | 1 | 21 | 3 | 4 | | | | | | | 1 | | |
| H | | | | | | 1 | | | | | | | | | | | | | |
| I | | | | | | | 1 | 1 | | 1 | 2 | | | | | | 1 | 7 | |
| K | | | | | | | | | | 3 | | | | | | | | | |
| L | | | | | | | | | | | | 1 | 1 | | | | 6 | 5 | |
| M | | | | | | | | | | | | | | | | | 1 | 1 | |

TABLE 5B-continued

Analysis of V lambda subgroup 2

| | | | | | | | | | | | | | | | | | | | |
|---|---|---|---|---|---|---|---|---|---|---|---|---|---|---|---|---|---|---|---|
| N | | | | | | | | | 5 | 7 | 5 | | | | | | 1 | | |
| P | | | | | | | | 1 | | | | 4 | | | | | | | |
| Q | | | | | | | | | | 1 | 2 | | | | | | | | |
| R | | | | | | | 2 | | 3 | | | 1 | | | | | 5 | | |
| S | | 1 | | 30 | 41 | | | 12 | 23 | 14 | 9 | | | | | | 1 | | |
| T | | | | | | | 16 | 4 | 4 | 3 | 21 | | | | | | | | |
| V | | | | | | | 1 | | | | | | | | | | 11 | 28 | |
| W | | | | | | | | | | | | | | | | | 5 | | |
| X | | | | | | | | | | | | | | | | | | | |
| Y | 43 | 39 | | | | 39 | | | 1 | 6 | | | | | | | 4 | | |
| Z | | | | | | | | | | | | | | | | | | | |
| — | | | | | | | | | | 1 | 3 | 36 | 42 | 43 | 43 | 43 | | | |
| unknown (?) | | | | | | | | | 2 | | | | | | | | | | |
| not sequenced | | | | | 1 | | | | | | 1 | | | | | | | 1 | 1 |
| sum of seq[2] | 43 | 43 | 43 | 43 | 42 | 43 | 43 | 43 | 43 | 43 | 42 | 43 | 43 | 43 | 43 | 43 | 43 | 42 | 42 |
| oomcaa[3] | 43 | 39 | 43 | 30 | 41 | 39 | 21 | 21 | 23 | 14 | 21 | 36 | 42 | 43 | 43 | 43 | 11 | 28 | 42 |
| mcaa[4] | Y | Y | C | S | S | Y | A | G | S | S | T | — | — | — | — | — | V | V | F |
| rel. oomcaa[5] | 100% | 91% | 100% | 70% | 98% | 91% | 49% | 49% | 53% | 33% | 50% | 84% | 98% | 100% | 100% | 100% | 26% | 67% | 100% |
| pos occupied[6] | 1 | 3 | 1 | 3 | 2 | 3 | 7 | 7 | 8 | 11 | 6 | 5 | 2 | 1 | 1 | 1 | 13 | 5 | 1 |

| | Framework IV | | | | | | | | | | | |
|---|---|---|---|---|---|---|---|---|---|---|---|---|
| amino acid[1] | 99 | 100 | 101 | 102 | 103 | 104 | 105 | 106 | A | 107 | 108 | sum |
| A | | 1 | | | | | | | | | | 280 |
| B | | | | | | | | | | | | |
| C | | | | | | | | | | | | 99 |
| D | | | | | | | | | | | | 188 |
| E | | | | | | | | | | | | 107 |
| F | | | | | | | | | | | | 113 |
| G | 42 | 33 | 42 | | | | | | | 19 | | 567 |
| H | | | | | | | | | | | | 48 |
| I | | | | | | | 1 | | | | | 184 |
| K | | | | | 36 | | | | | | | 189 |
| L | | | | | | 28 | | | 40 | | | 264 |
| M | | | | | | | | | | | | 29 |
| N | | | | | 1 | | | | | | | 146 |
| P | | | | | | | | | | | | 238 |
| Q | | | | | 1 | | | | | | 14 | 250 |
| R | | 1 | | | 2 | | | | | 4 | | 121 |
| S | | | | | | | 1 | | | 2 | | 831 |
| T | | 7 | | 41 | | | 40 | | | | | 398 |
| V | | | | | | 14 | | 42 | 1 | | | 327 |
| W | | | | | | | | | | | | 48 |
| X | | | | | | | | | | | | |
| Y | | | | | 1 | | | | | | | 285 |
| Z | | | | | | | | | | | | 16 |
| — | | | | | | | | | | | | 555 |
| unknown (?) | | | | | | | | | | | | 8 |
| not sequenced | 1 | 1 | 1 | 2 | 2 | 1 | 1 | 1 | 2 | 15 | 28 | 80 |
| sum of seq[2] | 42 | 42 | 42 | 41 | 41 | 42 | 42 | 42 | 41 | 25 | 14 | |
| oomcaa[3] | 42 | 33 | 42 | 41 | 36 | 28 | 40 | 42 | 40 | 19 | 14 | |
| mcaa[4] | G | G | G | T | K | L | T | V | L | G | Q | |
| rel. oomcaa[5] | 100% | 79% | 100% | 100% | 88% | 67% | 95% | 100% | 98% | 76% | 100% | |
| pos occupied[6] | 1 | 4 | 1 | 1 | 5 | 2 | 3 | 1 | 2 | 3 | 1 | |

TABLE 5C

Analysis of V lambda subgroup 3

| | Framework I | | | | | | | | | | | | | | | | | | |
|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 |
| A | | | | | 1 | | 1 | 2 | 7 | | | | | 20 | 1 | | | | 27 |
| B | | | | | | | | | | | | | | | | | | | |
| C | | | | | | | | | | | | | | | | | | | |
| D | | | 5 | | | | 10 | | | | | | | | | | | | |
| E | | | 20 | | | | | | | | | | 1 | | | 1 | | | |
| F | 1 | 1 | | | | | | | | | | 1 | | | 1 | | | | |
| G | | | 1 | | | | | | | | | | | | | 37 | | | |
| H | | | | | | | | | | | | | | | | | | | |
| I | | | | | | | | | | | | | | | | | | | |
| K | | | | | | | | | | | | | | | | | 2 | | |
| L | | | | 37 | | | | | | | 4 | | 1 | | 9 | | | | |
| M | | | | | | | | | | | | | | | | | | | |
| N | | | | | | | | | | | | | | | | | | | |
| P | | | | | | | 26 | 35 | 1 | | | | | | 27 | | | | 1 |
| Q | 4 | | 4 | | | 38 | | | | | | | | | | | 36 | | |
| R | | | | | | | | | | | | | | | | | | | |
| S | 13 | 14 | | | 1 | | 1 | | 28 | | | 37 | | 18 | | | | | |
| T | | | | | 36 | | | 1 | | | | | | | | | | 38 | |
| V | | | 8 | 1 | | | | | 2 | | 34 | | 36 | | | | | | 10 |
| W | | | | | | | | | | | | | | | | | | | |
| X | | | | | | | | | | | | | | | | | | | |
| Y | | 23 | | | | | | | | | | | | | | | | | |
| Z | | | | | | | | | | | | | | | | | | | |
| — | 20 | | | | | | | | | 38 | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 20 | 23 | 20 | 37 | 36 | 38 | 26 | 35 | 28 | 38 | 34 | 37 | 36 | 20 | 27 | 37 | 36 | 38 | 27 |
| mcaa[4] | — | Y | E | L | T | Q | P | P | S | — | V | S | V | A | P | G | Q | T | A |
| rel. oomcaa[5] | 53% | 61% | 53% | 97% | 95% | 100% | 68% | 92% | 74% | 100% | 89% | 97% | 95% | 53% | 71% | 97% | 95% | 100% | 71% |
| pos occupied[6] | 4 | 3 | 5 | 2 | 3 | 1 | 4 | 3 | 4 | 1 | 2 | 2 | 3 | 2 | 4 | 2 | 2 | 1 | 3 |

| | | | | | CDRI | | | | | | | | | | | | | | |
|---|---|---|---|---|---|---|---|---|---|---|---|---|---|---|---|---|---|---|---|
| amino acid[1] | 20 | 21 | 22 | 23 | 24 | 25 | 26 | 27 | D | E | 28 | 29 | 30 | 31 | A | 32 | 33 | 34 | 35 |
| A | | | 1 | | | | | 5 | | | | | 1 | 1 | | | 21 | 3 | |
| B | | | | | | | | | | | | | | | | | | | |
| C | | | | 38 | | | | | | | | | | | | | | 5 | |
| D | | | | | | | 30 | 1 | | | | | 10 | | | 3 | | 1 | |
| E | | | | | | | 2 | 2 | | | | 1 | 3 | 6 | | | | | |
| F | | | | | | | | | | | | | | 1 | | 2 | | | |
| G | | | | | 9 | 38 | | 1 | | | | 23 | 4 | | | | | | |
| H | | | | | | | 1 | | | | | | | | | 2 | | 9 | |
| I | | 38 | | | | | | | | | 9 | | | 1 | | | | | |
| K | | | | | | | | 7 | | | | | 2 | 13 | | | | | |
| L | | | | | | | | | | | 28 | | | | | | | | |
| M | 1 | | | | | | | | | | | | | 1 | | | | | |

TABLE 5C-continued

Analysis of V lambda subgroup 3

| | | | | | | | | | | | | | | | | | | | |
|---|---|---|---|---|---|---|---|---|---|---|---|---|---|---|---|---|---|---|---|
| N | | | 2 | | | | 4 | 9 | | | 1 | | 2 | | | 1 | | 2 | |
| P | | | 1 | | | | | | | | | 3 | | | | | | | |
| Q | | | | | 10 | | | | | | | | | 4 | | | | | |
| R | 25 | | | | | | | 2 | | | | 10 | 1 | | | | 1 | | |
| S | 9 | | 1 | | 19 | | | 10 | | | | | 11 | 2 | | 8 | | 14 | |
| T | 3 | | 33 | | | | | 1 | | | | 1 | 4 | | | | | | |
| V | | | | | | | | | | | | | | | | 1 | 15 | | |
| W | | | | | | | | | | | | | | | | | | | 38 |
| X | | | | | | | | | | | | | | | | | | | |
| Y | | | | | | | 1 | | | | | | | 8 | | 20 | 1 | 4 | |
| Z | | | | | | | | | | | | | | | | | | | |
| — | | | | | | | | | 38 | 38 | | | | | 37 | | | | |
| unknown (?) | | | | | | | | | | | | | | | | | | | |
| not sequenced | | | | | | | | | | | | | | | 1 | 1 | | | |
| sum of seq[2] | 38 | 38 | 38 | 38 | 38 | 38 | 38 | 38 | 38 | 38 | 38 | 38 | 38 | 37 | 37 | 37 | 38 | 38 | 38 |
| oomcaa[3] | 25 | 38 | 33 | 38 | 19 | 38 | 30 | 10 | 38 | 38 | 28 | 23 | 11 | 13 | 37 | 20 | 21 | 14 | 38 |
| mcaa[4] | R | I | T | C | S | G | D | S | — | — | L | G | S | K | — | Y | A | S | W |
| rel. oomcaa[5] | 66% | 100% | 87% | 100% | 50% | 100% | 79% | 26% | 100% | 100% | 74% | 61% | 29% | 35% | 100% | 54% | 55% | 37% | 100% |
| pos occupied[6] | 4 | 1 | 5 | 1 | 3 | 1 | 5 | 9 | 1 | 1 | 3 | 5 | 9 | 9 | 1 | 7 | 4 | 7 | 1 |

| | Framework II | | | | | | | | | | | | | | | | | | |
|---|---|---|---|---|---|---|---|---|---|---|---|---|---|---|---|---|---|---|---|
| amino acid[1] | 36 | 37 | 38 | 39 | 40 | 41 | 42 | 43 | 44 | 45 | 46 | 47 | 48 | 49 | 50 | 51 | 52 | 53 | 54 |
| A | | | | | | | | 23 | | | | | | | | 1 | | 1 | |
| B | | | | | | | | | | | | | | | | | | | |
| C | | | | | | | | | | | | | | | | | | | |
| D | | | | | | | | | | | | | | | 9 | 22 | 2 | 8 | |
| E | | | 1 | | | | | | | | | | | | 5 | 3 | | 3 | |
| F | 3 | | | | | | | | | | | | | 2 | | | 1 | | |
| G | | | | | | 36 | | | | | | | | | 9 | 2 | | | |
| H | | | | | | | 1 | | | | | | | 1 | 3 | | | 1 | |
| I | | | | | | | | | | 1 | | | 28 | | | | 1 | | |
| K | | | | 32 | | | | | | | | | | | 2 | 6 | 1 | 13 | |
| L | | | 2 | | | | | | | 6 | 33 | 1 | | | | | | | |
| M | | | | | | | | | | | 1 | | 1 | | | | | | |
| N | | | | | | | | | | | | | | | | 1 | 19 | 9 | |
| P | | | | 36 | | 1 | | 38 | | | | | | | | | | | |
| Q | | 37 | 35 | 1 | | | 36 | | | | | | | | 9 | | | 1 | |
| R | | 1 | | 4 | | 2 | | | | | | | | | 1 | 1 | | 1 | 38 |
| S | | | | 1 | 2 | | | 14 | | | | | | | | | 10 | 1 | |
| T | | | | | | | | | | | | | | | | 2 | 4 | | |
| V | | | | | | | | 1 | | 31 | 4 | 37 | 9 | | | | | | |
| W | | | | | | | | | | | | | | | | | | | |
| X | | | | | | | | | | | | | | | | | | | |
| Y | 35 | | | | | | | | | | | | | 35 | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 35 | 37 | 35 | 32 | 36 | 36 | 36 | 23 | 38 | 31 | 33 | 37 | 28 | 35 | 9 | 22 | 19 | 13 | 38 |
| mcaa[4] | Y | Q | Q | K | P | G | Q | A | P | V | L | V | I | Y | D | D | N | K | R |
| rel. oomcaa[5] | 92% | 97% | 92% | 84% | 95% | 95% | 95% | 61% | 100% | 82% | 87% | 97% | 74% | 92% | 24% | 58% | 50% | 34% | 100% |
| pos occupied[6] | 2 | 2 | 3 | 4 | 2 | 2 | 3 | 3 | 1 | 3 | 3 | 2 | 3 | 3 | 7 | 8 | 7 | 9 | 1 |

TABLE 5C-continued

Analysis of V lambda subgroup 3

| | CDR II | | | | | | | | | | | | | | | | | | |
|---|---|---|---|---|---|---|---|---|---|---|---|---|---|---|---|---|---|---|---|
| amino acid[1] | 55 | 56 | A | B | C | D | E | 57 | 58 | 59 | 60 | 61 | 62 | 63 | 64 | 65 | 66 | A | B |
| A | | 1 | | | | | | | | | | | | | | | | | |
| B | | | | | | | | | | | | | | | | | | | |
| C | | | | | | | | | | | | | | | | | | | |
| D | | | | | | | | | | | 9 | | | | | | | | |
| E | | | | | | | | | | | 27 | | | | | | | | |
| F | | | | | | | | | | | | | 38 | | | | | | |
| G | | | | | | | | 38 | | | | | | | 38 | | | | |
| H | | | | | | | | | | | | | | | | | | | |
| I | | | | | | | | | 37 | | | | | | | | | | |
| K | | | | | | | | | | | | | | | | | | | |
| L | | | | | | | | | | | | | | | | | | | |
| M | | | | | | | | | | | | | | | | | | | |
| N | | | | | | | | | | | | | | | | | 21 | | |
| P | 37 | 1 | | | | | | | | 36 | | | | | | | | | |
| Q | | | | | | | | | | | | | | | | | | | |
| R | | | | | | | | | | | | 38 | | | | | | | |
| S | 1 | 36 | | | | | | | | 1 | | | | 38 | | 38 | 12 | | |
| T | | | | | | | | | | | | | | | | | 5 | | |
| V | | | | | | | | | | | | | | | | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | 38 | 38 | 38 | 38 | 38 | | | | | | | | | | | 38 | 38 |
| unknown (?) | | | | | | | | | | | 1 | | | | | | | | |
| not sequenced | | | | | | | | | 1 | 1 | 1 | | | | | | | | |
| sum of seq[2] | 38 | 38 | 38 | 38 | 38 | 38 | 38 | 38 | 37 | 37 | 37 | 38 | 38 | 38 | 38 | 38 | 38 | 38 | 38 |
| oomcaa[3] | 37 | 36 | 38 | 38 | 38 | 38 | 38 | 38 | 37 | 36 | 27 | 38 | 38 | 38 | 38 | 38 | 21 | 38 | 38 |
| mcaa[4] | P | S | — | — | — | — | — | G | I | P | E | R | F | S | G | S | N | — | — |
| rel. oomcaa[5] | 97% | 95% | 100% | 100% | 100% | 100% | 100% | 100% | 100% | 97% | 73% | 100% | 100% | 100% | 100% | 100% | 55% | 100% | 100% |
| pos occupied[6] | 2 | 3 | 1 | 1 | 1 | 1 | 1 | 1 | 1 | 2 | 2 | 1 | 1 | 1 | 1 | 1 | 3 | 1 | 1 |

| | Framework III | | | | | | | | | | | | | | | | | | |
|---|---|---|---|---|---|---|---|---|---|---|---|---|---|---|---|---|---|---|---|
| amino acid[1] | 67 | 68 | 69 | 70 | 71 | 72 | 73 | 74 | 75 | 76 | 77 | 78 | 79 | 80 | 81 | 82 | 83 | 84 | 85 |
| A | | | | 1 | 36 | 1 | | 1 | | | | 11 | 1 | 34 | | | | 38 | |
| B | | | | | | | | | | | | | | | | | | | |
| C | | | | | | | | | | | | | | | | | | | |
| D | | | | | | | | | | | | | | | | 38 | | | 37 |
| E | | | | | | | | | | | | | 10 | | 14 | | 38 | | 1 |
| F | | | | | | | | | | | | | | | | | | | |
| G | | 37 | | | | | | | | | 28 | | | | 10 | | | | |
| H | | | 1 | | | | | | | | | | | | | | | | |
| I | | | | | | 1 | | 1 | 37 | 1 | | | | | 1 | | | | |
| K | | | 1 | | | | | | | | | | | | | | | | |
| L | | | | | | | 38 | | | | | | | | 2 | | | | |
| M | | | | | | | | | | | | | | | 10 | | | | |

TABLE 5C-continued

Analysis of V lambda subgroup 3

| | | | | | | | | | | | | | | | | | | | |
|---|---|---|---|---|---|---|---|---|---|---|---|---|---|---|---|---|---|---|---|
| N | | | 28 | | | | | | | 1 | | | | | | | | | |
| P | | | | | | | | | | | | | | | | | | | |
| Q | | 1 | | | | | | | | | | | 25 | | | | | | |
| R | | | | | | | | | | 1 | 10 | | 1 | | | | | | |
| S | 37 | | 2 | | | 11 | | | | 23 | | | | 1 | | | | | |
| T | 1 | | 6 | 37 | | 25 | | 36 | | 12 | | 13 | | 2 | | | | | |
| V | | | | | 2 | | | | 1 | | | 14 | 1 | 1 | 1 | | | | |
| W | | | | | | | | | | | | | | | | | | | |
| X | | | | | | | | | | | | | | | | | | | |
| Y | | | | | | | | | | | | | | | | | | | |
| Z | | | | | | | | | | | | | | | | | | | |
| — | | | | | | | | | | | | | | | | | | | |
| unknown (?) | | | | | | | | | | | | | | | | | | | |
| not sequenced | | | | | | | | | | | | | | | | | | | |
| sum of seq[2] | 38 | 38 | 38 | 38 | 38 | 38 | 38 | 38 | 38 | 38 | 38 | 38 | 38 | 38 | 38 | 38 | 38 | 38 | 38 |
| oomcaa[3] | 37 | 37 | 28 | 37 | 36 | 25 | 38 | 36 | 37 | 23 | 28 | 14 | 25 | 34 | 14 | 38 | 38 | 38 | 37 |
| mcaa[4] | S | G | N | T | A | T | L | T | I | S | G | V | Q | A | E | D | E | A | D |
| rel. oomcaa[5] | 97% | 97% | 74% | 97% | 95% | 66% | 100% | 95% | 97% | 61% | 74% | 37% | 66% | 89% | 37% | 100% | 100% | 100% | 97% |
| pos occupied[6] | 2 | 2 | 5 | 2 | 2 | 4 | 1 | 3 | 2 | 5 | 2 | 3 | 5 | 4 | 6 | 1 | 1 | 1 | 2 |

| | | | | CDR III | | | | | | | | | | | | | | | |
|---|---|---|---|---|---|---|---|---|---|---|---|---|---|---|---|---|---|---|---|
| amino acid[1] | 86 | 87 | 88 | 89 | 90 | 91 | 92 | 93 | 94 | 95 | A | B | C | D | E | F | 96 | 97 | 98 |
| A | | | | | 13 | 3 | 2 | | | 1 | 2 | | | | | | 4 | | |
| B | | | | | | | | | | | | | | | | | | | |
| C | | | 38 | | | | | | | | | | | | | | | | |
| D | | | | | | | 32 | 1 | 1 | | 6 | | | | | | | | |
| E | | | | 1 | | | | | | | | 2 | | | | | 2 | | |
| F | | 2 | | | | | | 2 | | | | | | | | | | | 35 |
| G | | | | | | | | | 3 | 14 | 3 | | | 1 | | | 3 | 1 | |
| H | | | | | | | | | | | | 12 | 1 | | | | | | |
| I | | | | | | | | | | | | | | | | | | 4 | |
| K | | | | | | | | | | | 1 | | | | | | | | |
| L | | | | 1 | | | | 1 | | 1 | | 1 | 1 | | | | 4 | 2 | |
| M | | | | | | | | | 1 | | | | | | | | 1 | 1 | |
| N | | | | 10 | | | 2 | 1 | 2 | | 10 | 1 | | | | | | | |
| P | | | | | | | | | 1 | | | | 3 | | | | 1 | | |
| Q | | | | 25 | | | | | | 1 | 1 | | | | | | | | |
| R | | | | | | 10 | | 1 | 2 | | | 2 | | | | | | | |
| S | | | | 1 | 14 | 1 | | 28 | 26 | 13 | | 1 | | | | 1 | | | |
| T | | | | | | 1 | | 3 | | 7 | 2 | | | | | | | | |
| V | | | | | 11 | | | | | | | | | | | | 18 | 28 | |
| W | | | | | | 23 | | | | | | | | | | | 1 | | |
| X | | | | | | | | | | | | | | | | | | | |
| Y | 38 | 36 | | | | | 1 | | 1 | | 1 | 3 | 1 | | | | 3 | | |
| Z | | | | | | | | | | | | | | | | | | | |
| — | | | | | | | | | | | 10 | 15 | 31 | 36 | 37 | 36 | | 1 | |
| unknown (?) | | | | | | | | | | | | | | | | | | | |
| not sequenced | | | | | | | 1 | 1 | 1 | 1 | 2 | 1 | 1 | 1 | 1 | 1 | 1 | 1 | 3 |
| sum of seq[2] | 38 | 38 | 38 | 38 | 38 | 38 | 37 | 37 | 37 | 37 | 36 | 37 | 37 | 37 | 37 | 37 | 37 | 37 | 35 |
| oomcaa[3] | 38 | 36 | 38 | 25 | 14 | 23 | 32 | 28 | 26 | 14 | 10 | 15 | 31 | 36 | 37 | 36 | 18 | 28 | 36 |
| mcaa[4] | Y | Y | C | Q | S | W | D | S | S | G | N | — | — | — | — | — | V | V | F |
| rel. oomcaa[5] | 100% | 95% | 100% | 66% | 37% | 61% | 86% | 76% | 70% | 38% | 28% | 41% | 84% | 97% | 100% | 97% | 49% | 76% | 100% |
| pos occupied[6] | 1 | 2 | 1 | 5 | 3 | 5 | 4 | 7 | 8 | 6 | 9 | 8 | 5 | 2 | 1 | 2 | 9 | 6 | 1 |

TABLE 5C-continued

Analysis of V lambda subgroup 3

| amino acid[1] | Framework IV | | | | | | | | | | | sum |
|---|---|---|---|---|---|---|---|---|---|---|---|---|
| | 99 | 100 | 101 | 102 | 103 | 104 | 105 | 106 | A | 107 | 108 | |
| A | | | | | | | | | | | | 285 |
| B | | | | | | | | | | | | |
| C | | | | | | | | | | 1 | | 82 |
| D | | | | | | | | | | | | 225 |
| E | | | | | 2 | | | | | | | 145 |
| F | | | | | | | | | | | | 90 |
| G | 35 | 31 | 35 | | | | | | | 24 | | 461 |
| H | | | | | | | | | | | | 32 |
| I | | | | | | | | | | | | 160 |
| K | | | | | 30 | | | | | | | 110 |
| L | | | | | | 28 | | | 33 | | | 233 |
| M | | | | | | | | | | | | 17 |
| N | | | | | | | | | | | | 126 |
| P | | | | | | | | | 1 | | | 249 |
| Q | | | | | | | | | | | 7 | 275 |
| R | | | | | 2 | | | | | | | 154 |
| S | | | | | | | | | | 2 | | 501 |
| T | | 4 | | 35 | | | 35 | | | | | 347 |
| V | | | | | | 7 | | 35 | | | | 308 |
| W | | | | | | | | | | | | 62 |
| X | | | | | | | | | | | | |
| Y | | | | | | | | | | | | 211 |
| Z | | | | | | | | | | | | |
| — | | | | | | | | | | | | 603 |
| unknown (?) | | | | | | | | | | | | 1 |
| not sequenced | 3 | 3 | 3 | 3 | 4 | 3 | 3 | 3 | 4 | 11 | 28 | 89 |
| sum of seq[2] | 35 | 35 | 35 | 35 | 34 | 35 | 35 | 35 | 34 | 27 | 7 | |
| oomcaa[3] | 35 | 31 | 35 | 35 | 30 | 28 | 35 | 35 | 33 | 24 | 7 | |
| mcaa[4] | G | G | G | T | K | L | T | V | L | G | Q | |
| rel. oomcaa[5] | 100% | 89% | 100% | 100% | 88% | 80% | 100% | 100% | 97% | 89% | 100% | |
| pos occupied[6] | 1 | 2 | 1 | 1 | 3 | 2 | 1 | 1 | 2 | 3 | 1 | |

TABLE 6A

Analysis of V heavy chain subgroup 1A

| amino acid[1] | Framework I | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| A | | | | | 1 | 14 | | | 60 | | | | | | | 24 | 1 | | | |
| B | | | | | | | | | | | | | | | | | | | | |
| C | | | | | | | | | | | | | | | | | | | | |
| D | | | | | | | | | | | | | | | | | | | | |
| E | 1 | | | | 2 | 1 | | 2 | | 64 | | | | | | | | | | |
| F | | | | | | | | | | | | | | | | | | | | |
| G | | | | | | | | 58 | 1 | | | | | | 64 | | | | | |
| H | | | 2 | | | | | | | | | | | | | | | | | |
| I | | 2 | | | | | | | | | | | | | | | | | | |
| K | | 2 | | | | | | | | | | 57 | 64 | | | | | | 60 | |
| L | | | 2 | 59 | | | | | | | 3 | | | | | | | | | |
| M | | 1 | | | | | | | | | | | | | | | | | | |

TABLE 6A-continued

Analysis of V heavy chain subgroup 1A

| | | | | | | | | | | | | | | | | | | | | |
|---|---|---|---|---|---|---|---|---|---|---|---|---|---|---|---|---|---|---|---|---|
| N | | | | | | | | | | | | 6 | | | | | | | | |
| P | | | | | | | | | | | | | | 63 | | | | | | |
| Q | 53 | 56 | | 2 | 45 | | | | | | | | | | | | | | | |
| R | | | | | | | | | | | | 1 | | | | | | | 3 | |
| S | | | | | | 60 | | 3 | | | | | | 1 | | 40 | 63 | | | |
| T | | | | | | | | | | | | | | | | | | | 1 | |
| V | 2 | 55 | | | 55 | | | | | 61 | | | | | | | | 64 | | 64 |
| W | | | | | | | | | | | | | | | | | | | | |
| X | | | | | | | | | | | | | | | | | | | | |
| Y | | | | | | | | | | | | | | | | | | | | |
| Z | 3 | | | | | | | | | | | | | | | | | | | |
| — | | | | | | | | | | | | | | | | | | | | |
| unknown (?) | | | | | | | | | | | | | | | | | | | | |
| not sequenced | 11 | 10 | 10 | 10 | 10 | 10 | 10 | 10 | 6 | 6 | 6 | 6 | 6 | 6 | 6 | 6 | 6 | 6 | 6 | 6 |
| sum of seq[2] | 59 | 60 | 60 | 60 | 60 | 60 | 60 | 60 | 64 | 64 | 64 | 64 | 64 | 64 | 64 | 64 | 64 | 64 | 64 | 64 |
| oomcaa[3] | 53 | 55 | 56 | 59 | 55 | 45 | 60 | 58 | 60 | 64 | 61 | 57 | 64 | 63 | 64 | 40 | 63 | 64 | 60 | 64 |
| mcaa[4] | Q | V | Q | L | V | Q | S | G | A | E | V | K | K | P | G | S | S | V | K | V |
| rel. oomcaa[5] | 90% | 92% | 93% | 98% | 92% | 75% | 100% | 97% | 94% | 100% | 95% | 89% | 100% | 98% | 100% | 63% | 98% | 100% | 94% | 100% |
| pos occupied[6] | 4 | 4 | 3 | 2 | 4 | 3 | 1 | 2 | 3 | 1 | 2 | 3 | 1 | 2 | 1 | 2 | 2 | 1 | 3 | 1 |

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | | | | 62 | | | | 1 | | | | | | | 41 | | | | | |
| B | | | | | | | | | | | | | | | | | | | | |
| C | | 63 | | | | | | | | | | | | | | | | | | |
| D | | | | | | | 1 | | | | | | | | | | | | | |
| E | | | | | | | | | | | | | | | | | | | | |
| F | | | | | | | | | 69 | | | | | 3 | | 3 | | | | |
| G | | | | 1 | | 69 | 41 | | 1 | | | | | | 23 | | | | | |
| H | | | | | | | | | | 1 | | | | 1 | | | 1 | | | |
| I | | | | | | | | 1 | | | | | | | | 61 | 1 | | 1 | |
| K | | | 63 | | | | | | | 1 | 1 | | | | | | | | | |
| L | | | | | | | | | | | | | | | 1 | 2 | | | | |
| M | | | | | | | | | | | | | | | | 4 | | | | |
| N | | | | | | | | | | 2 | 5 | | | | | | 4 | | | |
| P | | | | | | | | | | | | | | | 1 | | | | | |
| Q | | | | | | | | | | | | | | | | | | | | |
| R | | 1 | 1 | | | | | | | 1 | 1 | | | | | | | | | 70 |
| S | 63 | | | | 68 | | 1 | | | 40 | 60 | | | 2 | | | 60 | | | |
| T | 1 | | | 2 | | | | 68 | | 25 | 3 | | | | 3 | | 4 | | | |
| V | | | | | | | | | | | | | | | 1 | | | | 69 | |
| W | | | | | | | | | | | | | | | | | | 70 | | |
| X | | | | | | | | | | | | | | | | | | | | |
| Y | | | | | | | 27 | | | | | | | 64 | | | | | | |
| Z | | | | | | | | | | | | 70 | 70 | | | | | | | |
| — | | | | | | | | | | | | | | | | | | | | |
| unknown (?) | | | | | | | | | | | | | | | | | | | | |
| not sequenced | 6 | 6 | 6 | 5 | 2 | 1 | | | | | | | | | | | | | | |
| sum of seq[2] | 64 | 64 | 64 | 65 | 68 | 69 | 70 | 70 | 70 | 70 | 70 | 70 | 70 | 70 | 70 | 70 | 70 | 70 | 70 | 70 |
| oomcaa[3] | 63 | 63 | 63 | 62 | 68 | 69 | 41 | 68 | 69 | 40 | 60 | 70 | 70 | 64 | 41 | 61 | 60 | 70 | 69 | 70 |
| mcaa[4] | S | C | K | A | S | G | G | T | F | S | S | — | — | Y | A | I | S | W | V | R |
| rel. oomcaa[5] | 98% | 98% | 98% | 95% | 100% | 100% | 59% | 97% | 99% | 57% | 86% | 100% | 100% | 91% | 59% | 87% | 86% | 100% | 99% | 100% |
| pos occupied[6] | 2 | 2 | 2 | 3 | 1 | 1 | 4 | 3 | 2 | 6 | 5 | 1 | 1 | 4 | 6 | 4 | 5 | 1 | 2 | 1 |

TABLE 6A-continued

Analysis of V heavy chain subgroup 1A

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | 70 | | | | | | | | | 1 | | | | 5 | | | | | |
| B | | | | | | | | | | | | | | | | | | | | |
| C | | | | | | | | | | | | | | | | | | | | |
| D | | | | | | | | 1 | | | | | | | | | | | | |
| E | | | | | | | | 69 | | | | | | | | | | | | |
| F | | | | | | | | | | | | | 2 | | | | | 3 | 39 | |
| G | | | 1 | 68 | | 69 | | | 1 | | 69 | 39 | | | 1 | | | | | 68 |
| H | | | 1 | | | | | | | | | | | | | | | | | |
| I | | | | | | | | | | | | | 65 | 38 | | | | 34 | | |
| K | | | | | | | | | | | | | | | | | | | | |
| L | | | | 1 | | | 68 | | | 1 | | 1 | | | | | | 2 | 4 | |
| M | | | | | | | | | | 67 | | | | 2 | | | | 4 | | |
| N | | | | | | | | | | | | | | 4 | | | | 3 | 22 | |
| P | | | 68 | | | | 1 | | | | | | | | 44 | | | | | |
| Q | 69 | | | | 69 | | | | | | | | | | | | | 1 | 1 | 1 |
| R | 1 | | | 1 | | 1 | | | | | | 4 | | | | | | 1 | | |
| S | | | | | 1 | | | | 1 | 1 | | | | 22 | | | | | 1 | 1 |
| T | | | | | | | | | | | | | 1 | 2 | 4 | | | 1 | 3 | |
| V | | | | | | | | | | 1 | | | 2 | 2 | 16 | | | 1 | | |
| W | | | | | | | 1 | | 67 | | | 26 | | | | | | | | |
| X | | | | | | | | | | | | | | | | | | | | |
| Y | | | | | | | | | 1 | | | | | | | | | 20 | | |
| Z | | | | | | | | | | | | | | | | | | | | |
| — | | | | | | | | | | | | | | | | 70 | 70 | | | |
| unknown (?) | | | | | | | | | | | | | | | | | | | | |
| not sequenced | | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 | 70 |
| oomcaa[3] | 69 | 70 | 68 | 68 | 69 | 69 | 68 | 69 | 67 | 67 | 69 | 39 | 65 | 38 | 44 | 70 | 70 | 34 | 39 | 68 |
| mcaa[4] | Q | A | P | G | Q | G | L | E | W | M | G | G | I | I | P | — | — | I | F | G |
| rel. oomcaa[5] | 99% | 100% | 97% | 97% | 99% | 99% | 97% | 99% | 96% | 96% | 99% | 56% | 93% | 54% | 63% | 100% | 100% | 49% | 56% | 97% |
| pos occupied[6] | 2 | 1 | 3 | 3 | 2 | 2 | 3 | 2 | 4 | 4 | 2 | 4 | 4 | 6 | 5 | 1 | 1 | 10 | 6 | 3 |

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | 1 | 34 | | | 69 | | | | | | | | | | | 43 | | | | |
| B | | | | | | | | | | | | | | | | | | | | |
| C | | | | | | | | | | | | | | | | | | | | |
| D | 15 | | 1 | | | | | | | 2 | | | | | | | 70 | | | |
| E | | | | | | | | | 1 | | | | | | | | | 33 | | |
| F | | | | 1 | | | | 48 | | | | 3 | | 4 | | | | | | |
| G | 1 | | | | | | 3 | | | 67 | | | | | | | | | | |
| H | | | 1 | | | | | | | | | | | | | | | | | |
| I | 4 | | | | | | | | | | | | 1 | 44 | | | | 1 | | |
| K | 1 | | 2 | 1 | | | 47 | | 1 | | 1 | | | | | | | 8 | | |
| L | 1 | 1 | | | | | | 22 | | | | 2 | | 1 | | 3 | | | | |
| M | | | | | | | | | | | | | | 21 | | | | | | |

TABLE 6A-continued

Analysis of V heavy chain subgroup 1A

| | | | | | | | | | | | | | | | | | | | | |
|---|---|---|---|---|---|---|---|---|---|---|---|---|---|---|---|---|---|---|---|---|
| N | 9 | | 59 | | | | 18 | | | | | | | | | | | | | |
| P | 1 | 7 | | | | | | | | | | | | | | | | | | |
| Q | 1 | 1 | | | | 70 | | | 64 | | | | | | | | | | | |
| R | 2 | | | | | | 2 | | 1 | | 69 | | | | | | | 1 | | |
| S | | 1 | 2 | | 1 | | | | | | | | | | 5 | | | | 70 | |
| T | 34 | 26 | 4 | | | | | | 3 | | | | 66 | | 65 | 24 | | 27 | | 67 |
| V | | | | | | | | | | 1 | | 65 | 3 | | | | | | | 3 |
| W | | | | | | | | | | | | | | | | | | | | |
| X | | | | | | | | | | | | | | | | | | | | |
| Y | | | 1 | 68 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 | 70 |
| oomcaa[3] | 34 | 34 | 59 | 68 | 69 | 70 | 47 | 48 | 64 | 67 | 69 | 65 | 66 | 44 | 65 | 43 | 70 | 33 | 70 | 67 |
| mcaa[4] | T | A | N | Y | A | Q | K | F | Q | G | R | V | T | I | T | A | D | E | S | T |
| rel. oomcaa[5] | 49% | 49% | 84% | 97% | 99% | 100% | 67% | 69% | 91% | 96% | 99% | 93% | 94% | 63% | 93% | 61% | 100% | 47% | 100% | 96% |
| pos occupied[6] | 11 | 6 | 7 | 3 | 2 | 1 | 4 | 2 | 5 | 3 | 2 | 3 | 3 | 4 | 2 | 3 | 1 | 5 | 1 | 2 |

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | | 64 | | | 1 | | | | | | 3 | | | 1 | 70 | | | | |
| B | | | | | | | | | | | | | | | | | | | | |
| C | | | | | | | | | | | | | | | | | | | | 70 |
| D | | | | | | 2 | | | | | | | 26 | 70 | | | | | | |
| E | | | | | | 64 | | | | | | | 44 | | | | | | | |
| F | | | | | | | | | | | | | | | | | 1 | 1 | 2 | |
| G | | | | | | | | | 1 | | | | | | | | | | | |
| H | | | | 1 | | | | 1 | | | | | | | | | | | | |
| I | | 1 | | | | | 3 | 1 | 1 | | | | | | | | 2 | | | |
| K | | | | | | | | | | | 3 | | | | | | | | | |
| L | | | | | 3 | | 63 | | | 70 | | | | | | | 2 | | | |
| M | | | | | 67 | | | | | | | | | | 1 | | 1 | | | |
| N | 4 | | | | | | | 1 | 16 | | | | | | | | | | | |
| P | | | | | | | | | | | | | | | | | | | | |
| Q | | | | 1 | | 3 | | | | | | | | | | | | | | |
| R | 3 | | | | | | | 23 | 1 | | 62 | | | | | | | | | |
| S | 62 | | 1 | | | | | 41 | 49 | | | 67 | | | 1 | | | | | |
| T | 1 | 69 | 2 | | | | | 3 | 2 | | 4 | | | | 67 | | | | | |
| V | | | 3 | | | | 4 | | | | 1 | | | | | | 64 | | | |
| W | | | | | | | | | | | | | | | | | | | | |
| X | | | | | | | | | | | | | | | | | | | | |
| Y | | | | 68 | | | | | | | | | | | | | | 69 | 68 | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 70 | 70 | 70 | 70 | 70 | 70 | 70 | 70 | 70 | 70 | 70 | 70 | 70 | 70 | 70 | 70 | 70 | 70 | 70 | 70 |
| oomcaa[3] | 62 | 69 | 64 | 68 | 67 | 64 | 63 | 41 | 49 | 70 | 62 | 67 | 44 | 70 | 67 | 70 | 64 | 69 | 68 | 70 |
| mcaa[4] | S | T | A | Y | M | E | L | S | S | L | R | S | E | D | T | A | V | Y | Y | C |
| rel. oomcaa[5] | 89% | 99% | 91% | 97% | 96% | 91% | 90% | 59% | 70% | 100% | 89% | 96% | 63% | 100% | 96% | 100% | 91% | 99% | 97% | 100% |
| pos occupied[6] | 4 | 2 | 4 | 3 | 2 | 4 | 3 | 6 | 6 | 1 | 4 | 2 | 2 | 1 | 4 | 1 | 5 | 2 | 2 | 1 |

TABLE 6A-continued

Analysis of V heavy chain subgroup 1A

| | CDR III | | | | | | | | | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 66 | 2 | 16 | | 1 | 1 | 1 | 4 | 1 | 2 | 2 | 1 | 1 | | 1 | 1 | 1 | 2 | | 1 |
| B | | | | | | | | | | | | | | | | | | | | |
| C | | | | | 1 | 1 | 16 | 2 | | 1 | 1 | 7 | 2 | 1 | | | | | | |
| D | | | 16 | 5 | 3 | | 3 | 5 | 4 | 3 | 4 | | | 1 | 1 | 14 | | | | 59 |
| E | | | 9 | | | | 2 | | | 1 | | | 1 | | | 1 | | | | |
| F | | | | | 1 | 3 | | 2 | | 3 | 1 | 2 | | 2 | 1 | | | | 28 | 2 |
| G | | 2 | 14 | 13 | 20 | 10 | 14 | 5 | 20 | 15 | 16 | 3 | 3 | 4 | 15 | 1 | 1 | 7 | | |
| H | | | | | | | | | | 1 | 1 | 1 | | 1 | | | | | | |
| I | | | | 2 | 5 | 2 | 2 | | 2 | 2 | 1 | 1 | | | 1 | | | | | |
| K | | 5 | | | 2 | 1 | | | 1 | | | | | | | | | | | |
| L | | 1 | 4 | 4 | 2 | 5 | 2 | 1 | 1 | | 4 | 2 | | 1 | | | 1 | | 1 | |
| M | | | 1 | | 2 | | 1 | | 1 | | | 1 | 1 | | | | | | 10 | |
| N | | | | 2 | 2 | 1 | 2 | 1 | 2 | 2 | 2 | 2 | | | 1 | 1 | 4 | | | |
| P | | | | 20 | 3 | | 1 | 3 | 2 | 2 | 2 | 4 | 2 | 1 | 4 | 1 | | 1 | | 1 |
| Q | | | | 1 | | | 1 | | 1 | 1 | 1 | | | | | | | | | |
| R | | 55 | 1 | 5 | 7 | 8 | 1 | 4 | | 2 | | 1 | | 16 | | | | | | |
| S | | 1 | 1 | 5 | 5 | 5 | 5 | 21 | 5 | 11 | 8 | 4 | 3 | | 2 | 1 | | 2 | | 1 |
| T | 1 | 3 | 3 | 5 | 4 | 1 | 3 | 4 | 2 | 5 | 2 | | 1 | | | 1 | 1 | | | |
| V | 3 | | 3 | 2 | 4 | 3 | 3 | 3 | 4 | 2 | 2 | 2 | 1 | 2 | 1 | | | | | |
| W | | | | 1 | 1 | 3 | 1 | 1 | | | 2 | | 3 | | | | 1 | 5 | 1 | |
| X | | | | | | | | | | | | | | | | | | | | |
| Y | | 1 | | 2 | 3 | 20 | 5 | 4 | 9 | 1 | 2 | 11 | 20 | 10 | 6 | 9 | 10 | 7 | 1 | |
| Z | | | | | | | | | | | | | | | | | | | | |
| — | | | | 1 | 2 | 2 | 3 | 6 | 11 | 11 | 14 | 23 | 26 | 26 | 31 | 34 | 46 | 39 | 21 | 1 |
| unknown (?) | | | | | | | | | | | | | 1 | | 1 | 1 | | 2 | 3 | |
| not sequenced | | | 2 | 2 | 2 | 4 | 4 | 4 | 4 | 5 | 5 | 5 | 5 | 5 | 5 | 5 | 5 | 5 | 5 | 5 |
| sum of seq[2] | 70 | 70 | 68 | 68 | 66 | 66 | 66 | 66 | 65 | 65 | 65 | 65 | 65 | 65 | 65 | 65 | 65 | 65 | 65 | 65 |
| oomcaa[3] | 66 | 55 | 16 | 20 | 20 | 20 | 16 | 21 | 20 | 15 | 16 | 23 | 26 | 26 | 31 | 34 | 46 | 39 | 28 | 59 |
| mcaa[4] | A | R | A | P | G | Y | C | S | G | — | — | — | — | — | — | — | — | — | F | D |
| rel. oomcaa[5] | 94% | 79% | 24% | 29% | 29% | 30% | 24% | 32% | 30% | 23% | 25% | 35% | 40% | 40% | 48% | 52% | 71% | 60% | 43% | 91% |
| pos occupied[6] | 3 | 8 | 10 | 14 | 18 | 15 | 18 | 15 | 15 | 17 | 17 | 15 | 12 | 11 | 11 | 10 | 8 | 7 | 6 | 6 |

| | Framework IV | | | | | | | | | | | | |
|---|---|---|---|---|---|---|---|---|---|---|---|---|---|
| amino acid[1] | 102 | 103 | 104 | 105 | 106 | 107 | 108 | 109 | 110 | 111 | 112 | 113 | sum |
| A | | | | | | | | | | | | | 670 |
| B | | | | | | | | | | | | | |
| C | | | | | | | | | | | | | 165 |
| D | | 1 | 1 | | | | | | | | | | 308 |
| E | 1 | 1 | | | | | | | | | | | 297 |
| F | 2 | | | | | | | | | | | | 226 |
| G | | | 58 | | 59 | 1 | 1 | | | | | | 928 |
| H | | | | 1 | | | | | | | | | 14 |
| I | 3 | | | | | | | | 4 | | | | 286 |
| K | | | | 3 | | 1 | | | | | | | 325 |
| L | 3 | | | 1 | | | 40 | 1 | | | | | 386 |
| M | 1 | | | | | | 3 | | | | | | 189 |

TABLE 6A-continued

Analysis of V heavy chain subgroup 1A

| | | | | | | | | | | | | | |
|---|---|---|---|---|---|---|---|---|---|---|---|---|---|
| N | | | | 1 | | | | | | | | | 176 |
| P | 5 | | | | | | | | | | | 1 | 238 |
| Q | | | | 52 | | | | | | | | | 494 |
| R | | | | 1 | | | | | | | | | 351 |
| S | | | | | | | | | | | 53 | 51 | 972 |
| T | | | | | | 54 | 11 | 1 | 51 | | 1 | | 736 |
| V | 15 | | 1 | | | | 1 | 54 | | 54 | | 1 | 699 |
| W | | 59 | | 1 | | | | | | | | | 243 |
| X | | | | | | | | | | | | | |
| Y | 34 | | 1 | | | | | | | | | | 542 |
| Z | | | | | | | | | | | | | 3 |
| — | 1 | | | | | | | | | | | | 578 |
| unknown (?) | | | | | | | | | | | | | 8 |
| not sequenced | 5 | 9 | 9 | 10 | 11 | 14 | 14 | 14 | 15 | 16 | 16 | 17 | 406 |
| sum of seq[2] | 65 | 61 | 61 | 60 | 59 | 56 | 56 | 56 | 55 | 54 | 54 | 53 | |
| oomcaa[3] | 34 | 59 | 58 | 52 | 59 | 54 | 40 | 54 | 51 | 54 | 53 | 51 | |
| mcaa[4] | Y | W | G | Q | G | T | L | V | T | V | S | S | |
| rel. oomcaa[5] | 52% | 97% | 95% | 87% | 100% | 96% | 71% | 96% | 93% | 100% | 98% | 96% | |
| pos occupied[6] | 9 | 3 | 4 | 7 | 1 | 3 | 5 | 3 | 2 | 1 | 2 | 3 | |

TABLE 6B

Analysis of V heavy chain subgroup 1B

| | Framework I | | | | | | | | | | | | | | | | | | | |
|---|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 | 20 |
| A | | | | | | | | | 32 | | | | | | | 34 | | | | |
| B | | | | | | | | | | | | | | | | | | | | |
| C | | | | | | | | | | | | | | | | | | | | |
| D | | | | | | | | | | | | | | | | | | | | |
| E | | 1 | | | 5 | 1 | | | | 35 | | | | | | | | | | |
| F | | | | | | | | | | | | | | | | | | | | |
| G | | | | | | | | 27 | | | | | | | 35 | | | | | |
| H | | | 1 | | | | | | | | | | | 1 | | | | | | |
| I | | | | | | | | | | | | | | | | | | | | 1 |
| K | | 3 | 1 | | | | | | | | | 34 | 33 | | | | | | 33 | |
| L | | | 3 | 26 | 1 | | | | | | | | | | | | | | | |
| M | | | | 1 | 1 | | | | | | | | | | | | | | | |
| N | | | | | | | | | | | | | | | | | | | | |
| P | | | | | | | | | 1 | | | | | 33 | | | 1 | | | |
| Q | 21 | | 20 | | | 26 | | | | | | | | | | | | | | |
| R | 1 | | | | | | | | | | | 1 | 2 | | | | | | | |
| S | | | | | | | 27 | | | | | | | | | 1 | 34 | | | |
| T | | | | | | | | | 1 | | | | | 1 | | | | | 2 | |
| V | 3 | 21 | | | 20 | | | | | | 35 | | | | | | | 35 | | 34 |
| W | | | | | | | | | | | | | | | | | | | | |
| X | | | | | | | | | | | | | | | | | | | | |
| Y | | | | | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | 15 | 15 | 15 | 13 | 13 | 13 | 13 | 13 | 6 | 5 | 5 | 5 | 5 | 5 | 5 | 5 | 5 | 5 | 5 | 5 |
| sum of seq[2] | 25 | 25 | 25 | 27 | 27 | 27 | 27 | 27 | 34 | 35 | 35 | 35 | 35 | 35 | 35 | 35 | 35 | 35 | 35 | 35 |
| oomcaa[3] | 21 | 21 | 20 | 26 | 20 | 26 | 27 | 27 | 32 | 35 | 35 | 34 | 33 | 33 | 35 | 34 | 34 | 35 | 33 | 34 |
| mcaa[4] | Q | V | Q | L | V | Q | S | G | A | E | V | K | K | P | G | A | S | V | K | V |
| rel. oomcaa[5] | 84% | 84% | 80% | 96% | 74% | 96% | 100% | 100% | 94% | 100% | 100% | 97% | 94% | 94% | 100% | 97% | 97% | 100% | 94% | 97% |
| pos occupied[6] | 3 | 3 | 4 | 2 | 4 | 2 | 1 | 1 | 3 | 1 | 1 | 2 | 2 | 3 | 1 | 2 | 2 | 1 | 2 | 2 |

TABLE 6B-continued

Analysis of V heavy chain subgroup 1B

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | | | | 30 | | | | | | | 2 | | | | 6 | | | | | |
| B | | | | | | | | | | | | | | | | | | | | |
| C | | 35 | | | | | | | | | | | | | | | | | | |
| D | | | | | | | | | | | 1 | | | | 5 | | 1 | | | 1 |
| E | | | 3 | | | | | | | | 1 | | | | | | | | | |
| F | | | | | | | 2 | | 39 | | | | | 2 | 2 | | | | | |
| G | | | | 1 | | 40 | | | | 1 | 14 | | | | 1 | | | | | 1 |
| H | | | | | | | | | | | | | | 3 | 1 | | 34 | | | |
| I | | | | | | | | 1 | | 1 | | | | | | 9 | | | | |
| K | | | 28 | | | | | | | | | | | | | | | | | |
| L | | | | | | | | | 1 | | 1 | | | | | 5 | | | 2 | |
| M | | | | | | | | | | | | | | | | 23 | | | | |
| N | | | | | | | 1 | | | 1 | 3 | | | | | 1 | 3 | | | |
| P | | | | | | | | | | | | | | | 1 | | | | | |
| Q | | | 2 | | | | | | | | 1 | | | | 1 | | 1 | | | 1 |
| R | | | 2 | | | | | 2 | | | | | | 1 | | | | | | 37 |
| S | 35 | | | | 40 | | | 5 | | 2 | 15 | | | 2 | 1 | | | | | |
| T | | | | 3 | | | | 32 | | 34 | | | | | 1 | | | | | |
| V | | | | 1 | | | 1 | | | 1 | 1 | | | | 2 | 2 | | | 38 | |
| W | | | | | | | | | | | | | | | | | | 40 | | |
| X | | | | | | | | | | | | | | | | | | | | |
| Y | | | | | | | 36 | | | | 1 | | | 32 | 19 | | 1 | | | |
| Z | | | | | | | | | | | | | | | | | | | | |
| — | | | | | | | | | | | | 40 | 40 | | | | | | | |
| unknown (?) | | | | | | | | | | | | | | | | | | | | |
| not sequenced | 5 | 5 | 5 | 5 | | | | | | | | | | | | | | | | |
| sum of seq[2] | 35 | 35 | 35 | 35 | 40 | 40 | 40 | 40 | 40 | 40 | 40 | 40 | 40 | 40 | 40 | 40 | 40 | 40 | 40 | 40 |
| oomcaa[3] | 35 | 35 | 28 | 30 | 40 | 40 | 36 | 32 | 39 | 34 | 15 | 40 | 40 | 32 | 19 | 23 | 34 | 40 | 38 | 37 |
| mcaa[4] | S | C | K | A | S | G | Y | T | F | T | S | — | — | Y | Y | M | H | W | V | R |
| rel. oomcaa[5] | 100% | 100% | 80% | 86% | 100% | 100% | 90% | 80% | 98% | 85% | 38% | 100% | 100% | 80% | 48% | 58% | 85% | 100% | 95% | 93% |
| pos occupied[6] | 1 | 1 | 4 | 4 | 1 | 1 | 4 | 4 | 2 | 6 | 10 | 1 | 1 | 5 | 11 | 5 | 5 | 1 | 2 | 4 |

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | 39 | | | | 1 | | | | | 1 | | | | 7 | | | 1 | | |
| B | | | | | | | | | | | | | | | | | | | | |
| C | | | | | | | | | | | | | | | | | | | | |
| D | | | | | | | | | | | | | | 1 | | | | | 1 | |
| E | | | | 1 | | | | 39 | | | | | | | | | | 1 | 1 | |
| F | | | | | | | 2 | | | | | | 1 | | | | | 1 | | |
| G | | | | 39 | | 28 | | | | | 39 | 1 | | | 1 | | | 9 | 1 | 39 |
| H | | | | | | | | | | | | | | | | | | 2 | | |
| I | | | | | | | | | | 3 | | | 34 | | | | | | | |
| K | | | | | 1 | | | | | | | | | | | | | | 1 | |
| L | | | 1 | | | | 37 | | | | | | 1 | | | | | | | |
| M | | | | | | | | | | 37 | | 2 | 4 | | | | | | | |

TABLE 6B-continued

Analysis of V heavy chain subgroup 1B

| | | | | | | | | | | | | | | | | | | | | |
|---|---|---|---|---|---|---|---|---|---|---|---|---|---|---|---|---|---|---|---|---|
| N | | | | | | | | | | | | | | 35 | | | | 20 | 12 | 1 |
| P | | 1 | 34 | | | | 1 | | | | | | | | 31 | | | | | |
| Q | 39 | | | | 39 | | | 1 | | | | | | | | | | | | |
| R | 1 | | | | | 10 | | | | | | 4 | | | | | | 3 | 1 | |
| S | | | 1 | | | 1 | | | | | | | | 2 | | | | 1 | 20 | |
| T | | | 4 | | | | | | | | | | | 1 | | | | | 3 | |
| V | | | | | | | | | | | | | | 1 | 1 | | | | | |
| W | | | | | | | | | 40 | | | 33 | | | | | | | | |
| X | | | | | | | | | | | | | | | | | | | | |
| Y | | | | | | | | | | | | | | | | | | 2 | | |
| Z | | | | | | | | | | | | | | | | 40 | 40 | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 | 40 |
| oomcaa[3] | 39 | 39 | 34 | 39 | 39 | 28 | 37 | 39 | 40 | 37 | 39 | 33 | 34 | 35 | 31 | 40 | 40 | 20 | 20 | 39 |
| mcaa[4] | Q | A | P | G | Q | G | L | E | W | M | G | W | I | N | P | — | — | N | S | G |
| rel. oomcaa[5] | 98% | 98% | 85% | 98% | 98% | 70% | 93% | 98% | 100% | 93% | 98% | 83% | 85% | 88% | 78% | 100% | 100% | 50% | 50% | 98% |
| pos occupied[6] | 2 | 2 | 4 | 2 | 2 | 4 | 3 | 2 | 1 | 2 | 2 | 4 | 4 | 5 | 4 | 1 | 1 | 9 | 8 | 2 |

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | 1 | 2 | | | 27 | 2 | | | | 1 | | 1 | | | | 2 | | | | 12 |
| B | | | | | | | | | | | | | | | | | | | | |
| C | | | | | | | | | | | | | | | | | | | | |
| D | 1 | | | | | | | | | 4 | | | | | | | 35 | | | |
| E | 2 | | 2 | | | 1 | | | | 1 | | | | | | 1 | | | | |
| F | | | | 4 | | | | 39 | | | | | | 3 | | | | | | |
| G | 15 | | 6 | | 1 | | | | | 34 | | | | | | | | | | |
| H | | | 1 | 1 | | | | | | | | | | | | | 1 | | | |
| I | | 1 | 1 | | | | | | | | | 1 | 1 | 13 | | | | | | 22 |
| K | 2 | 2 | 8 | | | | 36 | | 1 | | | | | | | 1 | | | | |
| L | | | | | | 1 | | 1 | | | | | | 1 | | | | | | |
| M | | | | | | | | | | | | | | 23 | | | | 1 | | 1 |
| N | 17 | | 18 | | | | 1 | | | | | | | | | | 4 | | | |
| P | | | | | | | | | | | | | | | | | | | 3 | |
| Q | | | | | | 36 | | | 37 | | | | | | | | | | | |
| R | | | 2 | | | | 1 | | 2 | | 37 | | | | | 34 | | 1 | | |
| S | 1 | | | 2 | 11 | | 1 | | | | | | | | | 1 | | | 37 | |
| T | | 35 | 2 | | 1 | | 1 | | | | | | 39 | | 40 | 1 | | 38 | | 5 |
| V | 1 | | | | | | | | | | | 38 | | | | | | | | |
| W | | | | | | | | | | | 3 | | | | | | | | | |
| X | | | | | | | | | | | | | | | | | | | | |
| Y | | | | 33 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 | 40 |
| oomcaa[3] | 17 | 35 | 18 | 33 | 27 | 36 | 36 | 39 | 37 | 34 | 37 | 38 | 39 | 23 | 40 | 34 | 35 | 38 | 37 | 22 |
| mcaa[4] | N | T | N | Y | A | Q | K | F | Q | G | R | V | T | M | T | R | D | T | S | I |
| rel. oomcaa[5] | 43% | 88% | 45% | 83% | 68% | 90% | 90% | 98% | 93% | 85% | 93% | 95% | 98% | 58% | 100% | 85% | 88% | 95% | 93% | 55% |
| pos occupied[6] | 8 | 4 | 8 | 4 | 4 | 4 | 5 | 2 | 3 | 4 | 2 | 3 | 2 | 4 | 1 | 6 | 3 | 3 | 2 | 4 |

TABLE 6B-continued

Analysis of V heavy chain subgroup 1B

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | | 35 | | | | | | | | | 1 | 2 | | | 40 | | | | |
| B | | | | | | | | | | | | | | | | | | | | |
| C | | | | | | | | | | | | | | | | | | | | 37 |
| D | 1 | | | | | 4 | | | | | | | 19 | 40 | | | 1 | | | |
| E | | | | | | 35 | | | | | | | 19 | | | | | | | |
| F | | | 1 | | | | | | | | | 2 | | | | | | | 2 | 1 |
| G | | | | | | 1 | | 1 | 2 | | | | | | | | | | | |
| H | | | | | | | | | | | | | | | | | | | | |
| I | | 1 | | | | | | | | | | | | | | | 1 | | | |
| K | | | | | | | | | | | 1 | | | | | | | | | |
| L | | | | | 2 | | 39 | | | 39 | | | | | | | 2 | | | 1 |
| M | | | | | 37 | | 1 | | | | | | | | | | 2 | | | |
| N | 7 | | | | | | | 1 | 2 | | | | | | | | | | | |
| P | | | | | | | | | | | | 1 | | | | | | | 1 | |
| Q | | | | | | | | | | | | | | | | | | | | |
| R | 4 | | | | | | | 2 | 16 | | 37 | | | | | | | | | |
| S | 27 | | | 1 | | | | 35 | 20 | | 1 | 36 | | | | | | 1 | 1 | |
| T | 1 | 39 | | | | | | 1 | | | 1 | | | | 40 | | | | | |
| V | | | 4 | | 1 | | | | | 1 | | | | | | | 33 | | | |
| W | | | | | | | | | | | | | | | | | | | | |
| X | | | | | | | | | | | | | | | | | | | | |
| Y | | | | 39 | | | | | | | | | | | | | | 38 | 35 | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 40 | 40 | 40 | 40 | 40 | 40 | 40 | 40 | 40 | 40 | 40 | 40 | 40 | 40 | 40 | 40 | 40 | 40 | 40 | 40 |
| oomcaa[3] | 27 | 39 | 35 | 39 | 37 | 35 | 39 | 35 | 20 | 39 | 37 | 36 | 19 | 40 | 40 | 40 | 33 | 38 | 35 | 37 |
| mcaa[4] | S | T | A | Y | M | E | L | S | S | L | R | S | D | D | T | A | V | Y | Y | C |
| rel. oomcaa[5] | 68% | 98% | 88% | 98% | 93% | 88% | 98% | 88% | 50% | 98% | 93% | 90% | 48% | 100% | 100% | 100% | 85% | 97% | 90% | 95% |
| pos occupied[6] | 5 | 2 | 3 | 2 | 3 | 3 | 2 | 5 | 4 | 2 | 4 | 4 | 3 | 1 | 1 | 1 | 5 | 2 | 4 | 3 |

| | CDR III | | | | | | | | | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 37 | 1 | 6 | | 1 | 1 | | 2 | 3 | 1 | 3 | | 1 | | | | | 5 | | |
| B | | | | | | | | | | | | | | | | | | | | |
| C | | 1 | | | | 3 | | | | 2 | 1 | | | | | | | | | |
| D | | | 7 | | 5 | 2 | 3 | 1 | 5 | 4 | | 1 | | 2 | 2 | 1 | 2 | | | 27 |
| E | | | 2 | | 1 | | | 1 | 1 | | 2 | | 1 | | 1 | | | | | |
| F | | | | 1 | 1 | 3 | | | 2 | 1 | 1 | 1 | 1 | | | | | 2 | 15 | |
| G | | 1 | 7 | 7 | 5 | 5 | 9 | 4 | 7 | 1 | 3 | | 2 | 2 | 1 | | 1 | 3 | | 1 |
| H | | | 1 | | | | 2 | | | 1 | 1 | | | | | | | | | |
| I | | 1 | | 1 | 1 | 3 | 1 | 1 | 1 | 1 | 1 | 1 | | | | | | | 1 | |
| K | | 1 | | | 1 | | | | 1 | 1 | | 1 | | 1 | | | 1 | | | |
| L | | | 2 | 4 | 4 | 4 | 3 | | | 1 | 2 | 1 | 1 | 2 | | 1 | | | 2 | |
| M | | | | 2 | | 1 | 1 | | | | | | | | 1 | | | | 4 | |

TABLE 6B-continued

Analysis of V heavy chain subgroup 1B

| | | | | | | | | | | | | | | | | | | | | |
|---|---|---|---|---|---|---|---|---|---|---|---|---|---|---|---|---|---|---|---|---|
| N | | | | | 1 | | | 1 | | 1 | 1 | 1 | | | 3 | | 1 | | | 1 |
| P | | | | 6 | 4 | | | | 1 | 1 | | 3 | 2 | | | | 1 | | | |
| Q | | | | | 1 | | | | | | | 1 | 2 | 1 | | | | | | |
| R | 1 | 31 | | 5 | 1 | 1 | 3 | | | | | 1 | | 1 | | | | 1 | | |
| S | | 1 | 3 | 3 | 1 | 4 | 3 | 6 | 3 | 2 | 2 | 1 | | 1 | | | | | | |
| T | | 2 | 1 | 1 | 2 | 2 | 1 | 5 | 1 | 1 | 1 | | 1 | | | 1 | | 1 | | |
| V | 1 | | 7 | 1 | 1 | | 1 | 3 | 1 | 2 | | 1 | | | 1 | 2 | 1 | | | 1 |
| W | | | 1 | | 1 | | 2 | 2 | | 1 | 1 | | | | | 1 | | 4 | | |
| X | | | | | | | | | | | | | | | | | | | | |
| Y | | | | 5 | 5 | 4 | 2 | 3 | | 4 | 3 | 3 | 2 | 1 | 2 | 5 | 6 | 2 | | |
| Z | | | | | | | | | | | | | | | | | | | | |
| — | | | | 1 | 1 | 4 | 6 | 8 | 10 | 11 | 14 | 20 | 23 | 25 | 25 | 25 | 23 | 18 | 11 | 6 |
| unknown (?) | | | | | | | | | | | | | | | | | | | 3 | |
| not sequenced | 1 | 1 | 3 | 3 | 3 | 3 | 3 | 3 | 4 | 4 | 4 | 4 | 4 | 4 | 4 | 4 | 4 | 4 | 4 | 4 |
| sum of seq[2] | 39 | 39 | 37 | 37 | 37 | 37 | 37 | 37 | 36 | 36 | 36 | 36 | 36 | 36 | 36 | 36 | 36 | 36 | 36 | 36 |
| oomcaa[3] | 37 | 31 | 7 | 7 | 5 | 5 | 9 | 8 | 10 | 11 | 14 | 20 | 23 | 25 | 25 | 25 | 23 | 18 | 15 | 27 |
| mcaa[4] | A | R | D | G | D | G | G | — | — | — | — | — | — | — | — | — | — | — | F | D |
| rel. oomcaa[5] | 95% | 79% | 19% | 19% | 14% | 14% | 24% | 22% | 28% | 31% | 39% | 56% | 64% | 69% | 69% | 69% | 64% | 50% | 42% | 75% |
| pos occupied[6] | 3 | 8 | 10 | 12 | 18 | 13 | 13 | 12 | 12 | 17 | 14 | 13 | 10 | 9 | 8 | 7 | 8 | 8 | 5 | 3 |

| | Framework IV | | | | | | | | | | | | |
|---|---|---|---|---|---|---|---|---|---|---|---|---|---|
| amino acid[1] | 102 | 103 | 104 | 105 | 106 | 107 | 108 | 109 | 110 | 111 | 112 | 113 | sum |
| A | | | | | | | | | | | | | 340 |
| B | | | | | | | | | | | | | |
| C | | | | | | | | | | | | | 79 |
| D | 2 | | | | | | | | | | | | 179 |
| E | | | | 1 | | | | | | | | | 159 |
| F | 2 | | | | | | | | | | | | 130 |
| G | | | 27 | | 26 | | | | | 1 | | | 450 |
| H | 1 | | | | | | | | | | | | 51 |
| I | 7 | | | | | | | | 3 | | | | 113 |
| K | | | | 2 | | | | | | | | | 194 |
| L | | | | | | | 12 | | | 1 | | | 204 |
| M | | | | | | | 2 | | | | | | 144 |
| N | 1 | | | | | | | | | | | | 138 |
| P | 1 | | | 1 | | | | | | | | | 128 |
| Q | | | | 23 | | | | | | | | | 253 |
| R | | | | | | | 1 | | | | | | 247 |
| S | 3 | | | | | | | | 1 | | 18 | 18 | 432 |
| T | | | | | | 21 | 6 | | 16 | | 1 | | 390 |
| V | 6 | | | | | | | 21 | | 18 | | | 342 |
| W | | 29 | | | | | | | | | | | 158 |
| X | | | | | | | | | | | | | |
| Y | 11 | | | | | | | | | | | | 284 |
| Z | | | | | | | | | | | | | |
| — | 3 | | | | | | | | | | | | 394 |
| unknown (?) | | | | | | | | | | | | | 3 |
| not sequenced | 4 | 11 | 13 | 13 | 14 | 19 | 19 | 19 | 20 | 20 | 21 | 22 | 458 |
| sum of seq[2] | 36 | 29 | 27 | 27 | 26 | 21 | 21 | 21 | 20 | 20 | 19 | 18 | |
| oomcaa[3] | 11 | 29 | 27 | 23 | 26 | 21 | 12 | 21 | 16 | 18 | 18 | 18 | |
| mcaa[4] | Y | W | G | Q | G | T | L | V | T | V | S | S | |
| rel. oomcaa[5] | 31% | 100% | 100% | 85% | 100% | 100% | 57% | 100% | 80% | 90% | 95% | 100% | |
| pos occupied[6] | 10 | 1 | 1 | 4 | 1 | 1 | 4 | 1 | 3 | 3 | 2 | 1 | |

TABLE 6C

Analysis of V heavy chain subgroup 2

| | Framework I | | | | | | | | | | | | | | | | | | | |
|---|---|---|---|---|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 | 16 | 17 | 18 | 19 | 20 |
| A | | | | | | | | | | 3 | | | | | | | | | | |
| B | | | | | | | | | | | | | | | | | | | | |
| C | | | | | | | | | | | | | | | | | | | | |
| D | | | | | | | | | | | | | | | | | | | | |
| E | 1 | | | | | 6 | | | | | | | | | | 2 | | | | |
| F | | | | | | | | | | | | | | | | | | | | |
| G | | | | | | | | 6 | | | | | | | | | | | | |
| H | | | | | | | | | | | | | | | | | | | | |
| I | | 1 | | | | | | | | | | | | | | | | | | |
| K | | | | | 3 | | | | | | | | 6 | | 1 | | | | | |
| L | | | | 6 | | | | | | | 6 | | | | | | | 6 | | 6 |
| M | | | | | | | | | | | | | | | | | | | | |
| N | | | | | | | 1 | | | | | | | | | | | | | |
| P | | | | | | | 1 | | 6 | | | | | 6 | | | 1 | | | |
| Q | 2 | | | | | | | | | | | | | | | 4 | | | | |
| R | | | | | 2 | | | | | | | | | | | | | | | |
| S | | | | | | | 4 | | | | | | | | | | | | | |
| T | | | 6 | | 1 | | | | | 2 | | | | | 5 | | 5 | | 6 | |
| V | | 5 | | | | | | | | 1 | | 6 | | | | | | | | |
| W | | | | | | | | | | | | | | | | | | | | |
| X | | | | | | | | | | | | | | | | | | | | |
| Y | | | | | | | | | | | | | | | | | | | | |
| Z | 3 | | | | | | | | | | | | | | | | | | | |
| — | | | | | | | | | | | | | | | | | | | | |
| unknown (?) | | | | | | | | | | | | | | | | | | | | |
| not sequenced | 1 | 1 | 1 | 1 | 1 | 1 | 1 | 1 | 1 | 1 | 1 | 1 | 1 | 1 | 1 | 1 | 1 | 1 | 1 | 1 |
| sum of seq[2] | 6 | 6 | 6 | 6 | 6 | 6 | 6 | 6 | 6 | 6 | 6 | 6 | 6 | 6 | 6 | 6 | 6 | 6 | 6 | 6 |
| oomcaa[3] | 3 | 5 | 6 | 6 | 3 | 6 | 4 | 6 | 6 | 3 | 6 | 6 | 6 | 6 | 5 | 4 | 5 | 6 | 6 | 6 |
| mcaa[4] | Z | V | T | L | K | E | S | G | P | A | L | V | K | P | T | Q | T | L | T | L |
| rel. oomcaa[5] | 50% | 83% | 100% | 100% | 50% | 100% | 67% | 100% | 100% | 50% | 100% | 100% | 100% | 100% | 83% | 67% | 83% | 100% | 100% | 100% |
| pos occupied[6] | 3 | 2 | 1 | 1 | 3 | 1 | 3 | 1 | 1 | 3 | 1 | 1 | 1 | 1 | 2 | 2 | 2 | 1 | 1 | 1 |

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | | | | | | | | 1 | | | | 1 | | | 1 | | | | | |
| B | | | | | | | | | | | | | | | | | | | | |
| C | | 7 | | | | | | | | | | | | | 2 | | | | | |
| D | | | | | | | | | | | | 1 | | | | | | | | |
| E | | | | | | | | | | | | | | | | | | | | |
| F | | | | 3 | | | 6 | | 1 | | | | | | | | | | | |
| G | | | | | | 7 | | | | | | | 4 | | 3 | | 3 | | | |
| H | | | | | | | | | | | | | | | | | | | | |
| I | | | | | | | | | | | | | 1 | | | | | | 7 | |
| K | | | | | | | | | | | | | | | | | | | | |
| L | | | | 2 | | | 1 | | 6 | | | | | | | | | | | |
| M | | | | | | | | | | | | | | 5 | | | | | | |

TABLE 6C-continued

Analysis of V heavy chain subgroup 2

| | | | | | | | | | | | | | | | | | | | | |
|---|---|---|---|---|---|---|---|---|---|---|---|---|---|---|---|---|---|---|---|---|
| N | | | | | | | | | | | 2 | | | | | | | | | |
| P | | | | | | | | | | | | | | | | | | | | |
| Q | | | | | | | | | | | | | | | | | | | | |
| R | | | | | | | | | | | | | 2 | | 1 | | | | | 7 |
| S | | | 1 | | 6 | | | 6 | | 6 | 2 | 4 | | | | | 4 | | | |
| T | 6 | | 6 | | | | | | | 1 | 3 | 1 | | | | | | | | |
| V | | | | 2 | | | | | | | | | | 2 | | 7 | | | | |
| W | | | | | | | | | | | | | | | | | | 7 | | |
| X | | | | | | | | | | | | | | | | | | | | |
| Y | | | | | 1 | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | 1 | | | | | | | | | | | | | | | | | | | |
| sum of seq[2] | 6 | 7 | 7 | 7 | 7 | 7 | 7 | 7 | 7 | 7 | 7 | 7 | 7 | 7 | 7 | 7 | 7 | 7 | 7 | 7 |
| oomcaa[3] | 6 | 7 | 6 | 3 | 6 | 7 | 6 | 6 | 6 | 6 | 3 | 4 | 4 | 5 | 3 | 7 | 4 | 7 | 7 | 7 |
| mcaa[4] | T | C | T | F | S | G | F | S | L | S | T | S | G | M | G | V | S | W | I | R |
| rel. oomcaa[5] | 100% | 100% | 86% | 43% | 86% | 100% | 86% | 86% | 86% | 86% | 43% | 57% | 57% | 71% | 43% | 100% | 57% | 100% | 100% | 100% |
| pos occupied[6] | 1 | 1 | 2 | 3 | 2 | 1 | 2 | 2 | 2 | 2 | 3 | 4 | 3 | 2 | 4 | 1 | 2 | 1 | 1 | 1 |

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | | | | | 6 | | | | | 7 | | | | | | | | | |
| B | | | | | | | | | | | | | | | | | | | | |
| C | | | | | | | | | | | | | | | | | | | | |
| D | | | | | | | | | | | | | | 2 | | | | | 3 | 6 |
| E | | | | | | | | 7 | | | | | | | | | | | | |
| F | | | | | | | | | | | | | | 2 | | | | | | |
| G | | 1 | | 7 | | 1 | | | | | | | | | | | | | | |
| H | | | | | | | | | | | | 2 | | | | | | | | 1 |
| I | | | | | | | | | | | | | 6 | | | | | | | |
| K | | | | | 6 | | | | | | | | | | | | | | | |
| L | | | | | | | 7 | | | 7 | | 2 | 1 | 1 | | | | | | |
| M | | | | | | | | | | | | | | | | | | | | |
| N | | | | | | | | | | | | | | | | | | | 3 | |
| P | | 5 | 7 | | | | | | | | | | | | | | | | | |
| Q | 6 | | | | | | | | | | | | | | | | | | | |
| R | 1 | | | | 1 | | | | | | | 2 | | | | | | | | |
| S | | 1 | | | | | | | | | | | | | | | | 2 | | |
| T | | | | | | | | | | | | | | | | | | | | |
| V | | | | | | | | | | | | | | | | | | | | |
| W | | | | | | | | | 7 | | | 1 | | | | | | 4 | | |
| X | | | | | | | | | | | | | | 1 | | | | 1 | 1 | |
| Y | | | | | | | | | | | | | | 1 | 1 | | | | | |
| Z | | | | | | | | | | | | | | | | | | | | |
| — | | | | | | | | | | | | | | | 6 | 7 | 7 | | | |
| unknown (?) | | | | | | | | | | | | | | | | | | | | |
| not sequenced | | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 | 7 |
| oomcaa[3] | 6 | 5 | 7 | 7 | 6 | 6 | 7 | 7 | 7 | 7 | 7 | 2 | 6 | 2 | 6 | 7 | 7 | 4 | 3 | 6 |
| mcaa[4] | Q | P | P | G | K | A | L | E | W | L | A | H | I | D | — | — | — | W | D | D |
| rel. oomcaa[5] | 86% | 71% | 100% | 100% | 86% | 86% | 100% | 100% | 100% | 100% | 100% | 29% | 86% | 29% | 86% | 100% | 100% | 57% | 43% | 86% |
| pos occupied[6] | 2 | 3 | 1 | 1 | 2 | 2 | 1 | 1 | 1 | 1 | 1 | 4 | 2 | 5 | 2 | 1 | 1 | 3 | 3 | 2 |

TABLE 6C-continued

Analysis of V heavy chain subgroup 2

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | | | | | | | | | | | | | | | | | | | | |
| B | | | | | | | | | | | | | | | | | | | | |
| C | | | | | | | | | | | | | | | | | | | | |
| D | 5 | | | | | | | | | | | | | | | | 6 | 1 | | |
| E | 1 | | | | | | | | 1 | | | | | | | | | | | |
| F | | 1 | | 1 | | | | | | | | | | | | | | | | |
| G | | | | | | | | | | | | | | | | | | | | |
| H | | | | 1 | | | | | | | | | | | | | | | | |
| I | | | | | | | | | | | | | | 6 | | | | | | |
| K | 1 | 6 | | | | | | | 4 | | | | | | | 6 | | | | 6 |
| L | | | | | | | | 7 | | | | 7 | | | | | | | | |
| M | | | | | | | | | | | | | | | | | | | | |
| N | | | | | | | | | | | | | | | | | 1 | | | |
| P | | | | | | 2 | | | | | | | | | | | | | | |
| Q | | | | | | | | | | | | | | | | | | | | |
| R | | | 2 | | | 1 | | | 2 | | 7 | | | | | 1 | | | | 1 |
| S | | | 2 | | 6 | | 7 | | | 4 | | | 1 | | 5 | | | | 7 | |
| T | | | | | | 4 | | | | 3 | | | 6 | | 2 | | | 6 | | |
| V | | | | | | | | | | | | | | 1 | | | | | | |
| W | | | | 1 | | | | | | | | | | | | | | | | |
| X | | | | | 1 | | | | | | | | | | | | | | | |
| Y | | | 3 | 4 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 | 7 |
| oomcaa[3] | 5 | 6 | 3 | 4 | 6 | 4 | 7 | 7 | 4 | 4 | 7 | 7 | 6 | 6 | 5 | 6 | 6 | 6 | 7 | 6 |
| mcaa[4] | D | K | Y | Y | S | T | S | L | K | S | R | L | T | I | S | K | D | T | S | K |
| rel. oomcaa[5] | 71% | 86% | 43% | 57% | 86% | 57% | 100% | 100% | 57% | 57% | 100% | 100% | 86% | 86% | 71% | 86% | 86% | 86% | 100% | 86% |
| pos occupied[6] | 3 | 2 | 3 | 4 | 2 | 3 | 1 | 1 | 3 | 2 | 1 | 1 | 2 | 2 | 2 | 2 | 2 | 2 | 1 | 2 |

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | | | | | | | | | | | | 1 | | | 5 | | | | |
| B | | | | | | | | | | | | | | | | | | | | |
| C | | | | | | | | | | | | | | | | | | | | 7 |
| D | | | | | | | | | | | 6 | | | 7 | | | | | | |
| E | | | | | | | | | | | | | | | | | | | | |
| F | | | | | 1 | | | | | | | | | | | | | | | |
| G | | | | | | | | | | | | | | | | 2 | | | | |
| H | | | | | | | | | | | | | | | | | | | | |
| I | | | | | | 2 | | 1 | | | | | | | | | | | | |
| K | | | | | | | | | | | | | | | | | | | | |
| L | | | | | 6 | | | | | | | | | | | | | | | |
| M | | | | | | | 7 | | | 5 | | | | | | | | | | |

TABLE 6C-continued

Analysis of V heavy chain subgroup 2

| | | | | | | | | | | | | | | | | | | | | |
|---|---|---|---|---|---|---|---|---|---|---|---|---|---|---|---|---|---|---|---|---|
| N | 5 | | | | | | | | 6 | | 1 | | | | | | | | | |
| P | | | | | | | | | | | | 7 | | | | | | | | |
| Q | | 7 | | | | | | | | | | | | | | | | | | |
| R | | | | | | | | | | | | | | | | | | | | |
| S | 2 | | | | | | | | | | | | | | | | | | | |
| T | | | | | | 5 | | 5 | | | | | | | 7 | | 7 | | | |
| V | | | 7 | 7 | | | | | | 1 | | | 6 | | | | | | | |
| W | | | | | | | | | | | | | | | | | | | | |
| X | | | | | | | | | | | | | | | | | | | | |
| Y | | | | | | | | | | | | | | | | | | 7 | 7 | |
| Z | | | | | | | | | | | | | | | | | | | | |
| — | | | | | | | | 1 | 1 | 1 | | | | | | | | | | |
| unknown (?) | | | | | | | | | | | | | | | | | | | | |
| not sequenced | | | | | | | | | | | | | | | | | | | | |
| sum of seq[2] | 7 | 7 | 7 | 7 | 7 | 7 | 7 | 7 | 7 | 7 | 7 | 7 | 7 | 7 | 7 | 7 | 7 | 7 | 7 | 7 |
| oomcaa[3] | 5 | 7 | 7 | 7 | 6 | 5 | 7 | 5 | 6 | 5 | 6 | 7 | 6 | 7 | 7 | 5 | 7 | 7 | 7 | 7 |
| mcaa[4] | N | Q | V | V | L | T | M | T | N | M | D | P | V | D | T | A | T | Y | Y | C |
| rel. oomcaa[5] | 71% | 100% | 100% | 100% | 86% | 71% | 100% | 71% | 86% | 71% | 86% | 100% | 86% | 100% | 100% | 71% | 100% | 100% | 100% | 100% |
| pos occupied[6] | 2 | 1 | 1 | 1 | 2 | 2 | 1 | 3 | 2 | 3 | 2 | 1 | 2 | 1 | 1 | 2 | 1 | 1 | 1 | 1 |

| | CDR III | | | | | | | | | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 5 | | | | | | | 1 | 2 | 1 | | | | | | | | | | |
| B | | | | | | | | | | | | | | | | | | | | |
| C | | | | | | | | | | | | | | | | | | | | |
| D | | | | | | | | | | | | | | | | | | | | 6 |
| E | | | | | | | | 2 | | | 1 | | | | | | | | | |
| F | | | | | | | | | | | | | | | | | | | 3 | |
| G | | | | | | 1 | 1 | | 1 | 2 | 1 | 1 | 1 | 1 | | | | | | |
| H | | 1 | | 1 | | | | | | | | | | | | | | | | |
| I | | | 3 | | | 2 | | | | | | | | | | | | | | |
| K | | | | | | | 1 | | | | | | | | | | | | | |
| L | | | | | | | | 1 | | 1 | | | | | | | | | 1 | |
| M | | | | | | | | 1 | | | | | | | | | | | 2 | |
| N | | | | 1 | 2 | | | | | | | | | | | | 1 | | | |
| P | | | | 1 | 1 | | 1 | | 1 | | | | | | | | | | | |
| Q | | | 1 | | | | | | | | | | | | | | | | | |
| R | | 6 | 1 | | | 1 | | | 1 | | | | | | | | | | | |
| S | | | | 1 | | 1 | 1 | | | | | | | | | | | | | |
| T | | | | 1 | | | 1 | | 1 | | | | | | | | | | | |
| V | 2 | | 1 | 1 | 1 | | 1 | 1 | | | 1 | | | | | | | | | |
| W | | | | | | 1 | | | | | | | | | 1 | | | 1 | | |
| X | | | | | | | | | | | | | | | | | | | | |
| Y | | | | | 2 | | | | | | 1 | 2 | 1 | 1 | 1 | | | 2 | | |
| Z | | | | | | | | | | | | | | | | | | | | |
| — | | | | | | | | | | 2 | 2 | 3 | 4 | 4 | 4 | 6 | 5 | 3 | | |
| unknown (?) | | | | | | | | | | | | | | | | | | | | |
| not sequenced | | | 1 | 1 | 1 | 1 | 1 | 1 | 1 | 1 | 1 | 1 | 1 | 1 | 1 | 1 | 1 | 1 | 1 | 1 |
| sum of seq[2] | 7 | 7 | 6 | 6 | 6 | 6 | 6 | 6 | 6 | 6 | 6 | 6 | 6 | 6 | 6 | 6 | 6 | 6 | 6 | 6 |
| oomcaa[3] | 5 | 6 | 3 | 1 | 2 | 2 | 1 | 2 | 2 | 2 | 2 | 3 | 4 | 4 | 4 | 6 | 5 | 3 | 3 | 6 |
| mcaa[4] | A | R | I | H | N | I | G | E | A | — | — | — | — | — | — | — | — | — | F | D |
| rel. oomcaa[5] | 71% | 86% | 50% | 17% | 33% | 33% | 17% | 33% | 33% | 33% | 33% | 50% | 67% | 67% | 67% | 100% | 83% | 50% | 50% | 100% |
| pos occupied[6] | 2 | 2 | 4 | 6 | 4 | 5 | 6 | 5 | 5 | 4 | 5 | 3 | 3 | 3 | 3 | 1 | 2 | 3 | 3 | 1 |

TABLE 6C-continued

Analysis of V heavy chain subgroup 2

| | Framework IV | | | | | | | | | | | | |
|---|---|---|---|---|---|---|---|---|---|---|---|---|---|
| amino acid[1] | 102 | 103 | 104 | 105 | 106 | 107 | 108 | 109 | 110 | 111 | 112 | 113 | sum |
| A | | | | | | | | | 1 | | | | 35 |
| B | | | | | | | | | | | | | |
| C | | | | | | | | | | | | | 16 |
| D | | | | | | | | | | | | | 43 |
| E | | | | | | | | | | | | | 21 |
| F | | | | | | | | | | | | | 18 |
| G | | | 6 | | 6 | | | | | | | | 55 |
| H | | | | | | | | | | | | | 6 |
| I | | | | | | | | | | | | | 29 |
| K | | | | 1 | | | 1 | | | | | | 42 |
| L | 1 | | | | | | 3 | | | | | | 78 |
| M | | | | | | | | | | | | | 20 |
| N | | | | | | | | | | | | | 23 |
| P | 1 | | | | | | 1 | | | | | | 41 |
| Q | | | | 3 | | | | | | | | | 23 |
| R | | | | 2 | | | | | | | | | 41 |
| S | | | | | | | | | | | 6 | 3 | 82 |
| T | | | | | | 6 | 1 | | 5 | | 1 | | 102 |
| V | 3 | | | | | | | 6 | | 6 | | | 68 |
| W | | 6 | | | | | | | | | | | 29 |
| X | | | | | | | | | | | | | 4 |
| Y | 1 | | | | | | | | | | | | 35 |
| Z | | | | | | | | | | | | | 3 |
| — | | | | | | | | | | | | | 56 |
| unknown (?) | | | | | | | | | | | | | |
| not sequenced | 1 | 1 | 1 | 1 | 1 | 1 | 1 | 1 | 1 | 1 | 1 | 4 | 54 |
| sum of seq[2] | 6 | 6 | 6 | 6 | 6 | 6 | 6 | 6 | 6 | 6 | 6 | 3 | |
| oomcaa[3] | 3 | 6 | 6 | 3 | 6 | 6 | 3 | 6 | 5 | 6 | 6 | 3 | |
| mcaa[4] | V | W | G | Q | G | T | L | V | T | V | S | S | |
| rel. oomcaa[5] | 50% | 100% | 100% | 50% | 100% | 100% | 50% | 100% | 83% | 100% | 100% | 100% | |
| pos occupied[6] | 4 | 1 | 1 | 3 | 1 | 1 | 4 | 1 | 2 | 1 | 1 | 1 | |

TABLE 6D

Analysis of V heavy chain subgroup 3

| | Frame | | | | | | | | | | | | | | |
|---|---|---|---|---|---|---|---|---|---|---|---|---|---|---|---|
| amino acid[1] | 1 | 2 | 3 | 4 | 5 | 6 | 7 | 8 | 9 | 10 | 11 | 12 | 13 | 14 | 15 |
| A | | | | | 1 | | 1 | | | 12 | | 1 | | 3 | 1 |
| B | | | 1 | | | 1 | | | | | | | 1 | | |
| C | | | | | | | | | | | | | | | |
| D | 1 | | | | | 1 | | | | 16 | | | | | |
| E | 110 | | 9 | | 15 | 166 | | | 9 | | | | 8 | | 2 |
| F | | | | | | | | | | | 4 | | | | |
| G | | | | | | | | 181 | 193 | 174 | | 1 | | | 202 |
| H | | | 5 | | | | | | | | | | 4 | | |
| I | | | | | | | | | | | | 9 | | | |
| K | | 5 | 3 | | | | | | | | | | 26 | | |
| L | | 1 | 5 | 176 | 43 | | | | | | 140 | | | 1 | |
| M | | 12 | | 1 | | | | | | | | | | | |

TABLE 6D-continued

Analysis of V heavy chain subgroup 3

| | | | | | | | | | | | | | | | |
|---|---|---|---|---|---|---|---|---|---|---|---|---|---|---|---|
| N | | | | | | | | | | 1 | | | | | |
| P | | | | | | | | | | | | | 1 | 194 | |
| Q | 41 | | 138 | 1 | 3 | 12 | | | | | | | 162 | | |
| R | | | 6 | | | | | | | | | | 4 | | |
| S | | | | | | | 178 | | | 2 | | | | 8 | |
| T | | | | | | | 1 | | | | | | | | |
| V | 5 | 147 | | 1 | 118 | | | | | | 62 | 195 | | | |
| W | | | | | | | | | | | | | | | 1 |
| X | | | | | | | | | | | | | | | |
| Y | | | | | | | | | | | | | | | |
| Z | 8 | | | | | | | | | | | | | | |
| — | | | | | | | | | | | | | | | |
| unknown (?) | | | | | | | | | | | | | | | |
| not sequenced | 47 | 47 | 45 | 33 | 32 | 32 | 32 | 31 | 10 | 7 | 6 | 6 | 6 | 6 | 6 |
| sum of seq$^2$ | 165 | 165 | 167 | 179 | 180 | 180 | 180 | 181 | 202 | 205 | 206 | 206 | 206 | 206 | 206 |
| oomcaa$^3$ | 110 | 147 | 138 | 176 | 118 | 166 | 178 | 181 | 193 | 174 | 140 | 195 | 162 | 194 | 202 |
| mcaa$^4$ | E | V | Q | L | V | E | S | G | G | G | L | V | Q | P | G |
| rel. oomcaa$^5$ | 67% | 89% | 83% | 98% | 66% | 92% | 99% | 100% | 96% | 85% | 68% | 95% | 79% | 94% | 98% |
| pos occupied$^6$ | 5 | 4 | 7 | 4 | 5 | 4 | 3 | 1 | 2 | 5 | 3 | 4 | 7 | 4 | 4 |

| | work I | | | | | | | | | | | | | | |
|---|---|---|---|---|---|---|---|---|---|---|---|---|---|---|---|
| amino acid$^1$ | 16 | 17 | 18 | 19 | 20 | 21 | 22 | 23 | 24 | 25 | 26 | 27 | 28 | 29 | 30 |
| A | | | | | | | | 183 | 192 | | 1 | | | | |
| B | | | | | | | | | | | | | | | |
| C | | | | | | 1 | 209 | | | | | | | | |
| D | | | | | | | | | | | | | | | 7 |
| E | 8 | | | | | | | 8 | | | 3 | | 1 | | |
| F | | 1 | 1 | | | 1 | | | | | | 201 | | 201 | |
| G | 134 | | | | | | | | 2 | | 207 | | | | 3 |
| H | | | | | | | | | | | | | | | 1 |
| I | | | | | | | | 2 | | | | 3 | 17 | 1 | |
| K | | | | 15 | | | | | | | | | | | 4 |
| L | | | 205 | | 201 | | | | | | | 6 | | 3 | |
| M | | | 1 | | | | | | | | | | 1 | | |
| N | | | | | | | | | | | | | 10 | | 10 |
| P | | | | | | | | 1 | | | | | 2 | | |
| Q | | | 1 | | | | | | | | | | | | |
| R | 62 | | | 191 | | | | | | | | | | | 11 |
| S | | 206 | | | | 207 | | 4 | 2 | 209 | | | 15 | | 174 |
| T | 4 | 1 | | 2 | | | | 4 | 4 | | | 1 | 163 | | |
| V | | | | | 8 | | | 7 | 9 | | | | 1 | 6 | |
| W | | | | | | | | | | | | | | | |
| X | | | | | | | | | | | | | | | |
| Y | | | | | | | | | | | | | | | |
| Z | | | | | | | | | | | | | | | |
| — | | | | | | | | | | | | | | | |
| unknown (?) | | | | | | | | | | | | | | | |
| not sequenced | 4 | 4 | 4 | 4 | 3 | 3 | 3 | 3 | 3 | 3 | 1 | 1 | 2 | 1 | 2 |
| sum of seq$^2$ | 208 | 208 | 208 | 208 | 209 | 209 | 209 | 209 | 209 | 209 | 211 | 211 | 210 | 211 | 210 |
| oomcaa$^3$ | 134 | 206 | 205 | 191 | 201 | 207 | 209 | 183 | 192 | 209 | 207 | 201 | 163 | 201 | 174 |
| mcaa$^4$ | G | S | L | R | L | S | C | A | A | S | G | F | T | F | S |
| rel. oomcaa$^5$ | 64% | 99% | 99% | 92% | 96% | 99% | 100% | 88% | 92% | 100% | 98% | 95% | 78% | 95% | 83% |
| pos occupied$^6$ | 4 | 3 | 4 | 3 | 2 | 3 | 1 | 7 | 5 | 1 | 3 | 4 | 8 | 4 | 7 |

TABLE 6D-continued

Analysis of V heavy chain subgroup 3

| | CDRI | | | | | | | | Frame | | | | | | |
|---|---|---|---|---|---|---|---|---|---|---|---|---|---|---|---|
| amino acid[1] | 31 | A | B | 32 | 33 | 34 | 35 | 36 | 37 | 38 | 39 | 40 | 41 | 42 | 43 |
| A | 1 | | | 17 | 80 | | 1 | | | 1 | | 187 | | 1 | |
| B | | | | | | | | | | | | | | | |
| C | | | | | | | | | | | | 1 | | 1 | |
| D | 26 | | | 3 | 7 | | 2 | | | | | | | | |
| E | 1 | | | | 10 | | | | | | | | | 1 | 1 |
| F | | | | 5 | | | | | | | | | | | |
| G | 13 | | | | 31 | | 1 | | | | | 2 | | 209 | |
| H | | | | 4 | | | 88 | | | | | | | | |
| I | 1 | | | 1 | | 15 | | | 12 | | | | | | |
| K | 7 | | | | | | | | | | 1 | | | | 202 |
| L | 3 | | | | | 3 | | | 2 | 3 | 1 | 2 | 1 | | |
| M | | | | | | 193 | | | | | | | | | |
| N | 35 | | | 8 | 3 | | 34 | | | | | | | | |
| P | | | | 1 | | | 1 | | | | | 4 | 191 | | |
| Q | | | | | | | | | | | 209 | | 1 | | 1 |
| R | 7 | | | | | | | | | 207 | | 7 | | | 8 |
| S | 103 | | | 17 | 8 | | 72 | | | | | 3 | 14 | | |
| T | 9 | | | | 15 | | 10 | | | | | 4 | 5 | | |
| V | 2 | | | | 7 | 1 | | | 197 | | | 2 | | | |
| W | | | | | 30 | | | 212 | | | | | | | |
| X | 1 | | | | | | | | | | | | | | |
| Y | 1 | | | 154 | 19 | | 3 | | | | | | | | |
| Z | | | | | | | | | | | | | | | |
| — | | 210 | 210 | | | | | | | | | | | | |
| unknown (?) | | | | | | | | | | | | | | | |
| not sequenced | 2 | | | 2 | 2 | | | | 1 | 1 | 1 | | | | |
| sum of seq[2] | 210 | 210 | 210 | 210 | 210 | 212 | 212 | 212 | 211 | 211 | 211 | 212 | 212 | 212 | 212 |
| oomcaa[3] | 103 | 210 | 210 | 154 | 80 | 193 | 88 | 212 | 197 | 207 | 209 | 187 | 191 | 209 | 202 |
| mcaa[4] | S | — | — | Y | A | M | H | W | V | R | Q | A | P | G | K |
| rel. oomcaa[5] | 49% | 100% | 100% | 73% | 38% | 91% | 42% | 100% | 93% | 98% | 99% | 88% | 90% | 99% | 95% |
| pos occupied[6] | 14 | 1 | 1 | 9 | 10 | 4 | 9 | 1 | 3 | 3 | 3 | 9 | 5 | 4 | 4 |

| | work II | | | | | | | | | | | | | | |
|---|---|---|---|---|---|---|---|---|---|---|---|---|---|---|---|
| amino acid[1] | 44 | 45 | 46 | 47 | 48 | 49 | 50 | 51 | 52 | A | B | C | 53 | 54 | 55 |
| A | 1 | | | | | 77 | 42 | | 1 | 2 | | 14 | | 7 | |
| B | | | 3 | | | | | | | 1 | | | | | |
| C | | | | | | | | | | | | | 1 | | |
| D | | | 1 | | | | | | | 7 | | | 94 | 8 | 3 |
| E | | | 198 | | | | | | 3 | 2 | 1 | | 2 | | 1 |
| F | | | | | | | 7 | 1 | 2 | 1 | | | | 1 | 6 |
| G | 207 | | | | | 33 | 11 | | 10 | 46 | | | 4 | 163 | 85 |
| H | | | | | | | 6 | | | 1 | | | | | |
| I | | | | | 3 | | 3 | 191 | | 1 | | | | | |
| K | | | | | | | | 1 | 37 | 2 | 1 | 30 | | 3 | 1 |
| L | | 211 | | | 5 | | 12 | 1 | | | | | | | |
| M | | | | | | | 1 | 1 | | | | | | | |

TABLE 6D-continued

Analysis of V heavy chain subgroup 3

| | | | | | | | | | | | | | | | |
|---|---|---|---|---|---|---|---|---|---|---|---|---|---|---|---|
| N | | | | | | | 13 | | 7 | 9 | 2 | | 13 | 11 | 1 |
| P | | 1 | | | | | | | | 1 | | | 1 | | |
| Q | | | 7 | | | | 7 | | | 10 | | | | | |
| R | 1 | | | | | | 24 | 1 | 17 | 5 | 1 | | 2 | | 16 |
| S | 3 | | | 1 | | 102 | 11 | 9 | 118 | 43 | | 1 | 74 | 17 | 82 |
| T | | | | | | | 3 | 5 | 4 | 2 | | 13 | 12 | 3 | 3 |
| V | | | 3 | | 204 | | 49 | 2 | | 1 | | 6 | | | |
| W | | | | 210 | | | 1 | | 8 | 6 | | | | | |
| X | | | | | | | | | | | | | 4 | | 3 |
| Y | | | | 1 | | | 22 | | 5 | 58 | | | | | 8 |
| Z | | | | | | | | | | | | | | | |
| — | | | | | | | | | | 14 | 178 | 178 | 2 | 1 | 1 |
| unknown (?) | | | | | | | | | | | | | | | |
| not sequenced | | | | | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 207 | 211 | 198 | 210 | 204 | 102 | 49 | 191 | 118 | 58 | 178 | 178 | 94 | 163 | 85 |
| mcaa[4] | G | L | E | W | V | S | V | I | S | Y | — | — | D | G | G |
| rel. oomcaa[5] | 98% | 100% | 93% | 99% | 96% | 48% | 23% | 90% | 56% | 27% | 84% | 84% | 44% | 77% | 40% |
| pos occupied[6] | 4 | 2 | 5 | 3 | 3 | 3 | 15 | 9 | 11 | 19 | 5 | 5 | 12 | 9 | 12 |

| | CDR II | | | | | | | | | | | | | | |
|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 |
| A | 9 | 1 | 2 | | 174 | 33 | | | | | | | 1 | | |
| B | 1 | 2 | | | | | | | | | | | | | |
| C | | | | | | | | | | | | | | | |
| D | 11 | | 17 | | | 160 | | | | | | | | | |
| E | 8 | 3 | 2 | | | 1 | | | 2 | | | | | | |
| F | 1 | | 3 | 2 | | | | | | | | 207 | | | |
| G | 5 | 1 | 5 | | 4 | 5 | | | | 212 | 1 | | | | |
| H | 1 | | 4 | | | | | | | | | | | | |
| I | 3 | 37 | 2 | | | | | 8 | | | | | 14 | 208 | |
| K | 1 | 61 | | | | | | | 199 | | 8 | | | | |
| L | 1 | 1 | 1 | | 1 | | | | | | | 1 | 1 | | |
| M | 8 | | 2 | | 1 | | | | | | | | | | |
| N | 51 | | 4 | | | 2 | | | 2 | | | | | | |
| P | 1 | 1 | | | 6 | 8 | 18 | | 1 | | | | | | |
| Q | 3 | 2 | | | | | | | 2 | | 2 | | | | |
| R | 5 | 4 | | | 5 | | | | 6 | | 201 | | | | |
| S | 48 | | 11 | | 4 | | 193 | | | | | 2 | 7 | | 211 |
| T | 42 | 97 | 5 | | 7 | | | | | | | | 189 | | 1 |
| V | | 2 | | | 10 | 2 | | 204 | | | | 1 | | 3 | |
| W | | | 2 | | | | | | | | | | | | |
| X | 4 | | 1 | | | 1 | | | | | | | | | |
| Y | 9 | | 151 | 210 | | | 1 | | | | | 1 | 1 | | |
| Z | | | | | | | | | | | | | | | |
| — | | | | | | | | | | | | | | | |
| unknown (?) | | | | | | | | | | | | | | | |
| not sequenced | | | | | | | | | | | | | | | |
| sum of seq[2] | 212 | 212 | 212 | 212 | 212 | 212 | 212 | 212 | 212 | 212 | 212 | 212 | 212 | 212 | 212 |
| oomcaa[3] | 51 | 97 | 151 | 210 | 174 | 160 | 193 | 204 | 199 | 212 | 201 | 207 | 189 | 208 | 211 |
| mcaa[4] | N | T | Y | Y | A | D | S | V | K | G | R | F | T | I | S |
| rel. oomcaa[5] | 24% | 46% | 71% | 99% | 82% | 75% | 91% | 96% | 94% | 100% | 95% | 98% | 89% | 98% | 100% |
| pos occupied[6] | 19 | 12 | 15 | 2 | 9 | 8 | 3 | 2 | 6 | 1 | 4 | 5 | 5 | 3 | 2 |

TABLE 6D-continued

Analysis of V heavy chain subgroup 3

| | Framework III | | | | | | | | | | | | | | |
|---|---|---|---|---|---|---|---|---|---|---|---|---|---|---|---|
| amino acid[1] | 71 | 72 | 73 | 74 | 75 | 76 | 77 | 78 | 79 | 80 | 81 | 82 | A | B | C |
| A | | | | 57 | | | 1 | 8 | | | | | | 1 | |
| B | | | | | | | | | | | 2 | | | | |
| C | | | | | | | | | | | | | | | |
| D | | 199 | 38 | | 2 | 2 | | | 1 | | | | 10 | | |
| E | | 6 | | | 4 | | | | | | 5 | | | | |
| F | | | | | | | | | 13 | | | | | | |
| G | | | | | | | | | | | | | 1 | 4 | |
| H | | | | | | 1 | | | 1 | | 2 | | 2 | | |
| I | | | 1 | | | | 2 | 2 | | | | 3 | 1 | 1 | |
| K | | | | | 186 | 6 | | | | | | | 3 | | |
| L | | | | | | | | 188 | | 209 | | 3 | 1 | | 212 |
| M | 1 | | | | 2 | | 10 | 3 | | 2 | | 205 | | | |
| N | | 5 | 170 | | 2 | 188 | | | | | 3 | | 181 | 10 | |
| P | | | | | | | 1 | | | | | | | | |
| Q | | | | | 7 | | | | | | 199 | | | | |
| R | 211 | | | | 1 | 1 | | | | | | | 2 | 8 | |
| S | | | | 153 | 8 | 10 | 56 | | 3 | | | | 6 | 186 | |
| T | | | | | | | 142 | | | | 1 | | 4 | 2 | |
| V | | | | 1 | | | | 11 | | 1 | | 1 | | | |
| W | | | | | | | | | | | | | | | |
| X | | 2 | 2 | | | 4 | | | | | | | 1 | | |
| Y | | | | | | | | | 194 | | | | | | |
| Z | | | | | | | | | | | | | | | |
| — | | | | | | | | | | | | | | | |
| unknown (?) | | | | | | | | | | | | | | | |
| not sequenced | | | 1 | 1 | | | | | | | | | | | |
| sum of seq[2] | 212 | 212 | 211 | 211 | 212 | 212 | 212 | 212 | 212 | 212 | 212 | 212 | 212 | 212 | 212 |
| oomcaa[3] | 211 | 199 | 170 | 153 | 186 | 188 | 142 | 188 | 194 | 209 | 199 | 205 | 181 | 186 | 212 |
| mcaa[4] | R | D | N | S | K | N | T | L | Y | L | Q | M | N | S | L |
| rel. oomcaa[5] | 100% | 94% | 81% | 73% | 88% | 89% | 67% | 89% | 92% | 99% | 94% | 97% | 85% | 88% | 100% |
| pos occupied[6] | 2 | 4 | 4 | 3 | 8 | 7 | 6 | 5 | 5 | 3 | 6 | 4 | 11 | 7 | 1 |

| amino acid[1] | 83 | 84 | 85 | 86 | 87 | 88 | 89 | 90 | 91 | 92 | 93 | 94 | 95 | 96 | 97 |
|---|---|---|---|---|---|---|---|---|---|---|---|---|---|---|---|
| A | | 149 | 1 | | 1 | 207 | | | | | 173 | 2 | 15 | 9 | 11 |
| B | | | | | | | | | | | | | | | |
| C | | | | | | | | | 1 | 210 | | 5 | 2 | | 1 |
| D | | 5 | 15 | 209 | | | | | | | | 2 | 54 | 7 | 6 |
| E | 1 | | 190 | | | | | | | | | | 11 | 2 | 11 |
| F | | | | | | | 1 | | 15 | | | 1 | | 9 | 6 |
| G | 1 | 1 | 6 | | | 4 | 1 | | | | 2 | 8 | 34 | 26 | 35 |
| H | | 1 | | | | | | | 1 | | | | | 3 | 11 |
| I | | 8 | | | | | 2 | | | | | | 4 | 15 | 10 |
| K | 30 | | | | | | | | | | | 60 | 4 | 3 | 5 |
| L | | | | | | | 18 | | | | | 1 | 6 | 11 | 7 |
| M | | | | | 2 | | 1 | | | | | | | 6 | 1 |

TABLE 6D-continued

Analysis of V heavy chain subgroup 3

| | | | | | | | | | | | | | | | |
|---|---|---|---|---|---|---|---|---|---|---|---|---|---|---|---|
| N | | 1 | | 1 | | | | | | | | 2 | 20 | 4 | 3 |
| P | | 9 | | | | | | | | | 1 | 3 | 4 | 29 | 10 |
| Q | | | | 1 | | | | | | | | 5 | 3 | 9 | 2 |
| R | 177 | | | | | | | | | | | 103 | 9 | 30 | 19 |
| S | | 1 | | | 1 | | | | | | | 3 | 9 | 8 | 11 |
| T | 3 | 28 | | | 207 | | 1 | | | | 25 | 15 | 7 | 6 | 20 |
| V | | 9 | | | | | 187 | | | | 10 | 1 | 7 | 7 | 15 |
| W | | | | | | | | | | 1 | | | 3 | 4 | 3 |
| X | | | | 1 | | | | | | | | | | | |
| Y | | | | | | | | 211 | 194 | | | | 12 | 9 | 8 |
| Z | | | | | | | | | | | | | | | |
| — | | | | | | | | | | | | | 1 | 3 | 4 |
| unknown (?) | | | | | | | | | | | | | | | |
| not sequenced | | | | | 1 | 1 | 1 | 1 | 1 | 1 | 1 | 1 | 7 | 12 | 13 |
| sum of seq[2] | 212 | 212 | 212 | 212 | 211 | 211 | 211 | 211 | 211 | 211 | 211 | 211 | 205 | 200 | 199 |
| oomcaa[3] | 177 | 149 | 190 | 209 | 207 | 207 | 187 | 211 | 194 | 210 | 173 | 103 | 54 | 30 | 35 |
| mcaa[4] | R | A | E | D | T | A | V | Y | Y | C | A | R | D | R | G |
| rel. oomcaa[5] | 83% | 70% | 90% | 99% | 98% | 98% | 89% | 100% | 92% | 100% | 82% | 49% | 26% | 15% | 18% |
| pos occupied[6] | 5 | 10 | 4 | 4 | 4 | 2 | 7 | 1 | 4 | 2 | 5 | 14 | 18 | 20 | 21 |

| | CDR III | | | | | | | | | | | | | | |
|---|---|---|---|---|---|---|---|---|---|---|---|---|---|---|---|
| amino acid[1] | 98 | 99 | 100 | A | B | C | D | E | F | G | H | I | J | K | 101 |
| A | 7 | 13 | 7 | 9 | 6 | 2 | 3 | 5 | 5 | | 9 | | 13 | | 2 |
| B | | | | | | | | | | | | | | | |
| C | 13 | 5 | | 1 | 2 | 11 | 3 | | 2 | | | | | 1 | |
| D | 11 | 7 | 10 | 4 | 2 | 3 | 10 | 3 | 3 | 1 | | 3 | 2 | | 146 |
| E | 6 | 3 | 1 | 13 | | 1 | 1 | | | | | | | | 1 |
| F | 3 | 5 | 4 | 5 | 5 | 6 | 3 | 5 | 7 | 2 | | 1 | 1 | 65 | 1 |
| G | 34 | 17 | 35 | 17 | 14 | 23 | 10 | 5 | 1 | 5 | 3 | 2 | 32 | | 6 |
| H | 3 | 4 | 3 | 2 | 9 | 2 | | 1 | 3 | 1 | 2 | 8 | 1 | | |
| I | 6 | 11 | 4 | 4 | 3 | 1 | 3 | 10 | 3 | 3 | 2 | | 1 | 2 | |
| K | 2 | 11 | | | 3 | 1 | | | | | | | | | |
| L | 26 | 13 | 4 | 12 | 8 | 2 | 6 | 3 | 10 | 3 | | | | 2 | 1 |
| M | | 1 | 2 | | | | | | | | 1 | | | 32 | |
| N | 4 | 6 | 4 | 3 | 2 | 2 | 6 | | | | 2 | 5 | | | 2 |
| P | 6 | 5 | 5 | 6 | 9 | 8 | 2 | 3 | 2 | 1 | | 3 | | 9 | |
| Q | 4 | | 1 | 1 | 1 | 1 | 1 | | | | | 1 | | | |
| R | 4 | 10 | 9 | 7 | 5 | 5 | 2 | 3 | 1 | | 1 | | 2 | | 4 |
| S | 16 | 28 | 27 | 25 | 24 | 8 | 11 | 9 | 3 | | 2 | 3 | 1 | 1 | 1 |
| T | 6 | 12 | 9 | 17 | 17 | 1 | 2 | 5 | 1 | 9 | 3 | 1 | | | |
| V | 13 | 7 | 15 | 4 | 3 | 6 | 2 | 12 | | 1 | 1 | 1 | 1 | | |
| W | 6 | 5 | 6 | 7 | 2 | 4 | | | | 1 | | 6 | 10 | | |
| X | | | | 1 | | | | | | | | | | | 1 |
| Y | 16 | 14 | 17 | 5 | 8 | 18 | 20 | 13 | 20 | 25 | 28 | 32 | 28 | | |
| Z | | | | | | | | | | | | | | | |
| — | 12 | 21 | 35 | 54 | 73 | 87 | 102 | 110 | 126 | 135 | 134 | 120 | 91 | 71 | 21 |
| unknown (?) | | | | | | | 3 | 2 | 1 | 1 | | | 3 | 2 | |
| not sequenced | 14 | 14 | 14 | 14 | 15 | 19 | 21 | 22 | 23 | 23 | 23 | 25 | 25 | 26 | 25 |
| sum of seq[2] | 198 | 198 | 198 | 197 | 196 | 192 | 190 | 189 | 188 | 188 | 188 | 186 | 186 | 185 | 186 |
| oomcaa[3] | 34 | 28 | 35 | 54 | 73 | 87 | 192 | 110 | 126 | 135 | 134 | 120 | 91 | 71 | 146 |
| mcaa[4] | G | S | G | — | — | — | — | — | — | — | — | — | — | — | D |
| rel. oomcaa[5] | 17% | 14% | 18% | 27% | 37% | 45% | 54% | 58% | 67% | 72% | 71% | 65% | 49% | 38% | 78% |
| pos occupied[6] | 20 | 20 | 19 | 20 | 19 | 20 | 17 | 14 | 14 | 12 | 12 | 13 | 12 | 8 | 11 |

TABLE 6D-continued

Analysis of V heavy chain subgroup 3

| amino acid[1] | Framework IV 102 | 103 | 104 | 105 | 106 | 107 | 108 | 109 | 110 | 111 | 112 | 113 | sum |
|---|---|---|---|---|---|---|---|---|---|---|---|---|---|
| A | 1 | | 1 | | | 2 | | | | | | | 1767 |
| B | | | | 1 | | | | | | | | | 13 |
| C | | | | | | | | | | | | | 470 |
| D | 2 | | | | | | | | | | | | 1121 |
| E | | | | | 1 | | | | | | | | 832 |
| F | 2 | | | | | | | | | | | | 807 |
| G | | | 140 | | 130 | | 1 | | | | | | 2743 |
| H | 4 | | | | | | | | | | | | 179 |
| I | 15 | | | | | | | | 1 | 1 | | | 651 |
| K | | | | 13 | | | | | | | | | 933 |
| L | 10 | | | 1 | | | 91 | | | | | 2 | 1881 |
| M | | | | | | | 6 | | | | | | 496 |
| N | 1 | | | | | 1 | | | | | | | 844 |
| P | 17 | | | | | 1 | 1 | | | | | | 568 |
| Q | | | | 111 | | | | | | | | | 949 |
| R | | | | 8 | | | | | | | | | 1413 |
| S | 7 | 1 | | | | | | | | | 118 | 110 | 3009 |
| T | | | | | | 123 | 27 | | 122 | | | 1 | 1426 |
| V | 34 | | 1 | | | 1 | | 125 | | 119 | | | 1851 |
| W | | 158 | | | | | | | | | | | 686 |
| X | | | | | | | | | | | | | 26 |
| Y | 82 | | | | | | | | | | | | 1598 |
| Z | | | | | | | | | | | | | 8 |
| — | 9 | 2 | 2 | 2 | 2 | 2 | 2 | 2 | 2 | 2 | 1 | 1 | 2023 |
| unknown (?) | | | | | | | | | | | | | 12 |
| not sequenced | 27 | 50 | 67 | 75 | 78 | 81 | 83 | 84 | 86 | 89 | 92 | 97 | 1650 |
| sum of seq[2] | 184 | 161 | 144 | 136 | 133 | 130 | 128 | 127 | 125 | 122 | 119 | 114 | |
| oomcaa[3] | 82 | 158 | 140 | 111 | 130 | 123 | 91 | 125 | 122 | 119 | 118 | 110 | |
| mcaa[4] | Y | W | G | Q | G | T | L | V | T | V | S | S | |
| rel. oomcaa[5] | 45% | 98% | 97% | 82% | 98% | 95% | 71% | 98% | 98% | 98% | 99% | 96% | |
| pos occupied[6] | 12 | 3 | 4 | 6 | 3 | 6 | 6 | 2 | 3 | 3 | 2 | 4 | |

TABLE 6E

Analysis of V heavy chain subgroup 4

| amino acid[1] | Framework I 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| A | | | | | | | | | 19 | | | | | 1 | | | 1 | | 1 | |
| B | | | | | | | | | | | | | | | | | | | | |
| C | | | | | | | | | | | | | | | | | | | | |
| D | | | | | | | | | | | | | | | | | | | | |
| E | | | | | | 32 | | | | | | | | | | 44 | | | | |
| F | | | | | | | | | | | | | | | | | | | | |
| G | | | | | | | | 54 | 1 | 53 | | | | | | 2 | | | | |
| H | | | 4 | | 2 | | | | | | | | | | | | | | | |
| I | | | | | | | | | | | | | | | | | | | | |
| K | | | | | | | | | | | | 1 | 54 | | | | | | 1 | |
| L | | 7 | | 54 | | | | | | | 53 | 19 | | 1 | | | | 53 | | 50 |
| M | | | | | | | | | | | | | | | | | | | | |

TABLE 6E-continued

Analysis of V heavy chain subgroup 4

| | | | | | | | | | | | | | | | | | | | | |
|---|---|---|---|---|---|---|---|---|---|---|---|---|---|---|---|---|---|---|---|---|
| N | | | | | | | | | | | | | | | | | | | | |
| P | | | | | | | | | 33 | | | | | 51 | 1 | | | | | 2 |
| Q | 52 | | 50 | | 51 | 20 | | | | | | | | | | 7 | | | | |
| R | 1 | | | | | | | | | | | | | | | | | | | |
| S | | | | | | | 33 | | | | | | | | 52 | | | | 52 | |
| T | | | | | | | | | 1 | | | | | | | | 52 | | | |
| V | | 47 | | | | 1 | | | | | | 34 | | | | | | | | 1 |
| W | | | | | | | 20 | | | | | | | | | | | | | |
| X | | | | | | | | | | | | | | | | | | | | |
| Y | | | | | | | | | | | | | | | | | | | | |
| Z | 1 | | | | | | | | | | | | | | | | | | | |
| — | | | | | | | | | | | | | | | | | | | | |
| unknown (?) | | | | | | | | | | | | | | | | | | | | |
| not sequenced | 3 | 3 | 3 | 3 | 4 | 4 | 4 | 3 | 3 | 4 | 4 | 3 | 3 | 4 | 4 | 4 | 4 | 4 | 3 | 4 |
| sum of seq[2] | 54 | 54 | 54 | 54 | 53 | 53 | 53 | 54 | 54 | 53 | 53 | 54 | 54 | 53 | 53 | 53 | 53 | 53 | 54 | 53 |
| oomcaa[3] | 52 | 47 | 50 | 54 | 51 | 32 | 33 | 54 | 33 | 53 | 53 | 34 | 54 | 51 | 52 | 44 | 52 | 53 | 52 | 50 |
| mcaa[4] | Q | V | Q | L | Q | E | S | G | P | G | L | V | K | P | S | E | T | L | S | L |
| rel. oomcaa[5] | 96% | 87% | 93% | 100% | 96% | 60% | 62% | 100% | 61% | 100% | 100% | 63% | 100% | 96% | 98% | 83% | 98% | 100% | 96% | 94% |
| pos occupied[6] | 3 | 2 | 2 | 1 | 2 | 3 | 2 | 1 | 4 | 1 | 1 | 3 | 1 | 3 | 2 | 3 | 2 | 1 | 3 | 3 |

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | | | 22 | | | | | | | | | | | 1 | | | | | | |
| B | | | | | | | | | | | | | | | | | | | | |
| C | | 53 | | | | | | | | | | | | | 1 | | | | | |
| D | | | 1 | | | | | | | | 4 | 1 | 1 | 1 | | | 1 | | | |
| E | | | | | | | | | | | | | | | | | | | | |
| F | | | | | 1 | | | | 22 | | | | | 1 | 1 | | | | 1 | |
| G | | | | | | 53 | 53 | | | | 21 | 3 | 4 | | | | 8 | | | |
| H | | | | | | | 1 | | | | | | | 2 | | | | | | |
| I | | | 1 | | | | | 1 | 32 | | | | | | | | | | 51 | |
| K | | | | | | | | | | | | | | | | | | | | |
| L | | | | | | | | | | | | | | | | | | | 1 | |
| M | | | | | | | | | | | | | | | | | | | | |
| N | | | | | | | | | | 1 | 1 | | 2 | 2 | | | 1 | | | |
| P | | | | | | | | 3 | | | | | | | | | | | | |
| Q | | | | | | | | | | | 1 | | | | | | | | | |
| R | | | | | | 1 | | | | 3 | 2 | | 1 | | | | | | | 57 |
| S | | | 2 | | 35 | | | 51 | 1 | 52 | 25 | 5 | 9 | 1 | | | 44 | | 1 | |
| T | 53 | | 29 | | | | | | | | 2 | 1 | | | | | 3 | | | |
| V | | | | 55 | | 1 | | | 1 | | | | | | | | | | 3 | |
| W | | | | | | | | | | | | 1 | | | 2 | 56 | | 57 | | |
| X | | | | | | | | | | | | | | | | | | | | |
| Y | | | | | 19 | | 1 | | | | | | | 48 | 52 | | | | | |
| Z | | | | | | | | | | | | | | | | | | | | |
| — | | | | | | | | | | | | 45 | 39 | | | | | | | |
| unknown (?) | | | | | | | | | | | | | | | | | | | | |
| not sequenced | 4 | 4 | 2 | 2 | 2 | 2 | 2 | 2 | 1 | 1 | 1 | | | 1 | 1 | 1 | | | | |
| sum of seq[2] | 53 | 53 | 55 | 55 | 55 | 55 | 55 | 55 | 56 | 56 | 56 | 56 | 56 | 56 | 56 | 56 | 57 | 57 | 57 | 57 |
| oomcaa[3] | 53 | 53 | 29 | 55 | 35 | 53 | 53 | 51 | 32 | 52 | 25 | 45 | 39 | 48 | 52 | 56 | 44 | 57 | 51 | 57 |
| mcaa[4] | T | C | T | V | S | G | G | S | I | S | S | — | — | Y | Y | W | S | W | I | R |
| rel. oomcaa[5] | 100% | 100% | 53% | 100% | 64% | 96% | 96% | 93% | 57% | 93% | 45% | 80% | 70% | 86% | 93% | 100% | 77% | 100% | 89% | 100% |
| pos occupied[6] | 1 | 1 | 5 | 1 | 3 | 3 | 3 | 3 | 4 | 3 | 7 | 6 | 6 | 7 | 4 | 1 | 5 | 1 | 5 | 1 |

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | | 8 | 1 | | | | | | | 1 | | | | | | | | | |
| B | | | | | | | | | | | | | | | | | | | | |
| C | | | | | | | | | | | | | | | | | | | | |
| D | | | | | | | | | | | | | | 1 | | | | 1 | | |
| E | | | | 1 | | | | 56 | | | | 22 | | | | | | | | |
| F | | | | | | | | | | | | 1 | | 1 | | | | | | |
| G | | | | 55 | | 55 | | | | | 56 | 1 | | | | | | 1 | | 57 |
| H | | 2 | | | | | | | | | | | | | | | | 24 | | |
| I | | | | | | | | | | 54 | | 1 | 54 | | | | | | | |
| K | | | | | 54 | | | | | | | | | | | | | | | |
| L | | 1 | | | | | 55 | | | 2 | | | | | | | | | | |
| M | | | | | | | | | | | | | | | | | | | | |

TABLE 6E-continued

Analysis of V heavy chain subgroup 4

| | | | | | | | | | | | | | | | | | | | | |
|---|---|---|---|---|---|---|---|---|---|---|---|---|---|---|---|---|---|---|---|---|
| N | | | | | | | | | | | | | | 21 | | | | | | |
| P | | 50 | 49 | | | | 2 | | | | | | | | | | | | | |
| Q | 56 | | | | | | | 1 | | | | 1 | | | | | | | | |
| R | | | | | 3 | 2 | | | | | | 9 | | 1 | | | | | | |
| S | | 3 | | | | | | | | | | 7 | | 1 | | | | | 52 | |
| T | 1 | 1 | | | | | | | | | | | | | | | | 8 | 5 | |
| V | | | | | | | | | | 1 | | | 3 | | | | | | | |
| W | | | | | | | | | 56 | | | | | | | | | | | |
| X | | | | | | | | | | | | | | | | | | | | |
| Y | | | | | | | | | 1 | | | 15 | | 32 | | | | 23 | | |
| Z | | | | | | | | | | | | | | | | | | | | |
| — | | | | | | | | | | | | | | | 57 | 57 | 57 | | | |
| unknown (?) | | | | | | | | | | | | | | | | | | | | |
| not sequenced | | | | | | | | | | | | | | | | | | | | |
| sum of seq[2] | 57 | 57 | 57 | 57 | 57 | 57 | 57 | 57 | 57 | 57 | 57 | 57 | 57 | 57 | 57 | 57 | 57 | 57 | 57 | 57 |
| oomcaa[3] | 56 | 50 | 49 | 55 | 54 | 55 | 55 | 56 | 56 | 54 | 56 | 22 | 54 | 32 | 57 | 57 | 57 | 24 | 52 | 57 |
| mcaa[4] | Q | P | P | G | K | G | L | E | W | I | G | E | I | Y | — | — | — | H | S | G |
| rel. oomcaa[5] | 98% | 88% | 86% | 96% | 95% | 96% | 96% | 98% | 98% | 95% | 98% | 39% | 95% | 56% | 100% | 100% | 100% | 42% | 91% | 100% |
| pos occupied[6] | 2 | 5 | 2 | 3 | 2 | 2 | 2 | 2 | 2 | 3 | 2 | 8 | 2 | 6 | 1 | 1 | 1 | 5 | 2 | 1 |

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | | 1 | | | | | | | | | 1 | | 1 | | | 1 | | | | 1 |
| B | | | | | | | | | | | | | | | | | | | | |
| C | | | | | | | | | | | | | | | | | | | | |
| D | | | 2 | | | | | | | | | 1 | | | | | 55 | | | |
| E | | | | | | | | | | | | | | | | | 1 | | | |
| F | | | | 3 | | | | | | | | | | | | | | 1 | | |
| G | 1 | | | | | | | | | 1 | | | | | | | | | | |
| H | | | 2 | | | | | | | | | | | | | | | | | |
| I | 1 | 1 | | | | | | | | | | 1 | 1 | 48 | | 3 | | | | |
| K | | | | | 1 | | | | 53 | | | | | | | | | 1 | | 51 |
| L | | | | | | 1 | | 55 | | | | | 1 | | | 3 | | | | 1 |
| M | | | | | | | | | | | | | | 7 | | | | 2 | | |
| N | 2 | | 40 | | 53 | | | | | | | | 2 | | | | | | | 1 |
| P | | | | | | 54 | | 1 | | | | | | | | | | | | |
| Q | | | | | | | | | | | | | | | | | 1 | | | |
| R | 2 | | | | | | | | 3 | | 56 | | | | | | | | | 2 |
| S | 49 | | 1 | | 2 | | 56 | | | 56 | | | 1 | | 56 | | | 1 | 57 | |
| T | 1 | 54 | 1 | | | 1 | | | 1 | | | | 51 | | 1 | | | 52 | | |
| V | 1 | 1 | | | | | | | | | | 53 | | 2 | | 50 | | | | 1 |
| W | | | | | | | | | | | | | | | | | | | | |
| X | | | | | | | | | | | | | | | | | | | | |
| Y | | | 11 | 54 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | 1 | 1 | 1 | 1 | | | | 1 | 1 | | | | | | | |
| sum of seq[2] | 57 | 57 | 57 | 57 | 56 | 56 | 56 | 56 | 57 | 57 | 57 | 56 | 56 | 57 | 57 | 57 | 57 | 57 | 57 | 57 |
| oomcaa[3] | 49 | 54 | 40 | 54 | 53 | 54 | 56 | 55 | 53 | 56 | 56 | 53 | 51 | 48 | 56 | 50 | 55 | 52 | 57 | 51 |
| mcaa[4] | S | T | N | Y | N | P | S | L | K | S | R | V | T | I | S | V | D | T | S | K |
| rel. oomcaa[5] | 86% | 95% | 70% | 95% | 95% | 96% | 100% | 98% | 93% | 98% | 98% | 95% | 91% | 84% | 98% | 88% | 96% | 91% | 100% | 89% |
| pos occupied[6] | 7 | 4 | 6 | 2 | 3 | 3 | 1 | 2 | 3 | 2 | 2 | 4 | 5 | 3 | 2 | 4 | 3 | 5 | 1 | 6 |

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | | | | | | | | | | | 55 | 57 | | | 57 | | | | |
| B | | | | | | | | | | | | | | | | | | | | |
| C | | | | | | | | | | | | | | | | | | | | 57 |
| D | | | | | 1 | | | | | | | | | 57 | | | | | | |
| E | | | | | | 1 | | | | | | | | | | | | | | |
| F | | | 54 | | | | | | 1 | | | | | | | | | | | |
| G | | | | | | | | 1 | | | | | | | | | | | | |
| H | | | | | | | | | | | | | | | | | | | | |
| I | | | 1 | | | | | 1 | | | 3 | | | | | | | | | |
| K | 3 | | | | | 46 | | 2 | | | | | | | | | | | | |
| L | | 3 | 1 | | 55 | | 53 | | | 2 | | | | | | | 1 | | | |
| M | | | | | | 1 | 1 | | | 1 | | | | | | | 1 | | | |

TABLE 6E-continued

Analysis of V heavy chain subgroup 4

| | | | | | | | | | | | | | | | | | | | | |
|---|---|---|---|---|---|---|---|---|---|---|---|---|---|---|---|---|---|---|---|---|
| N | 54 | | | | | 3 | | 3 | 1 | | | | | | | | | | | |
| P | | | | | | | | | | | | | | | | | | | | |
| Q | | 54 | | | 1 | 1 | | | | | | | | | | | | | | |
| R | | | | | | 2 | | 2 | | | | 1 | | | | | | | | |
| S | | | 1 | 57 | | 2 | 1 | 44 | 55 | | 1 | | | | 2 | | | | 1 | |
| T | | | | | | 1 | | 4 | | | 53 | | | | 55 | | | | | |
| V | | | | | | | 2 | | | 54 | | 1 | | | | | 55 | | | |
| W | | | | | | | | | | | | | | | | | | | | |
| X | | | | | | | | | | | | | | | | | | | | |
| Y | | | | | | | | | | | | | | | | | | 57 | 56 | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 57 | 57 | 57 | 57 | 57 | 57 | 57 | 57 | 57 | 57 | 57 | 57 | 57 | 57 | 57 | 57 | 57 | 57 | 57 | 57 |
| oomcaa[3] | 54 | 54 | 54 | 57 | 55 | 46 | 53 | 44 | 55 | 54 | 53 | 55 | 57 | 57 | 55 | 57 | 55 | 57 | 56 | 57 |
| mcaa[4] | N | Q | F | S | L | K | L | S | S | V | T | A | A | D | T | A | V | Y | Y | C |
| rel. oomcaa[5] | 95% | 95% | 95% | 100% | 96% | 81% | 93% | 77% | 96% | 95% | 93% | 96% | 100% | 100% | 96% | 100% | 96% | 100% | 98% | 100% |
| pos occupied[6] | 2 | 2 | 4 | 1 | 3 | 8 | 4 | 7 | 3 | 3 | 3 | 3 | 1 | 1 | 2 | 1 | 3 | 1 | 2 | 1 |

| | | | | | | | | | CDR III | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 56 | | 3 | 3 | 3 | 2 | 5 | 4 | 2 | 2 | 4 | | 2 | 1 | | 1 | 1 | 12 | | |
| B | | | | | | | | | | | | | | | | | | | | |
| C | | | | | 1 | | | | 1 | | | | | | | | | | | |
| D | | | 6 | | 5 | 5 | 5 | 4 | 3 | 2 | 4 | 3 | 1 | | 1 | 2 | 1 | | | 41 |
| E | | | 6 | 1 | 1 | 2 | 1 | | | 1 | 3 | 1 | 2 | 1 | | | | | | |
| F | | | | 4 | 1 | 1 | | 2 | 3 | 2 | 2 | | 1 | 1 | | | | | 31 | |
| G | | | 25 | 9 | 10 | 8 | 10 | 11 | 4 | 7 | 7 | 6 | 1 | 1 | 1 | 2 | 1 | 9 | | |
| H | | | 1 | | | | 1 | | | | | | 1 | | | 1 | | | | 2 |
| I | | | | 1 | | 2 | 4 | 1 | 3 | 2 | 3 | | 1 | | | | | | 1 | |
| K | | | 2 | 1 | | | | | | 2 | 2 | | | 1 | | | | | | |
| L | | | 2 | 6 | 7 | 3 | 5 | 3 | 2 | 4 | 1 | 5 | 3 | 3 | | 1 | | | | |
| M | | | | 1 | 4 | | 3 | 1 | | 2 | 1 | | | | | | | | 9 | |
| N | | | | 3 | | | | | 2 | 1 | 1 | 5 | 1 | 1 | | | 2 | | | |
| P | | | | 4 | 5 | 3 | 1 | 1 | 2 | 1 | 1 | 1 | 2 | 3 | 1 | 2 | 1 | | | |
| Q | | | | | 1 | 1 | | 1 | | | 1 | 1 | | | 3 | | | | | 1 |
| R | | 54 | 4 | 12 | 2 | 5 | 5 | 3 | 2 | 3 | 1 | 2 | | | 2 | 1 | | | | |
| S | | 1 | 1 | 4 | 8 | 8 | 1 | 2 | 5 | 7 | 4 | 2 | 1 | 1 | 1 | | | | | |
| T | | 1 | 1 | 2 | 1 | 3 | 4 | 4 | 3 | 3 | | | 1 | 1 | 1 | | | | | |
| V | 1 | 1 | 4 | 2 | 2 | 5 | 4 | 4 | 7 | 3 | 1 | 2 | 1 | | | | | | | |
| W | | | 1 | 2 | 1 | 2 | 2 | 4 | 5 | 1 | 1 | 2 | | 2 | 1 | | 3 | 2 | | |
| X | | | | | | | | | | | | | | | | | | | | |
| Y | | | | 1 | 4 | 5 | 3 | 6 | 4 | 2 | 3 | 4 | 8 | 4 | 8 | 3 | 5 | 8 | | 2 |
| Z | | | | | | | | | | | | | | | | | | | | |
| — | | | | | | 1 | 2 | 4 | 6 | 9 | 11 | 16 | 23 | 27 | 29 | 34 | 31 | 14 | 4 | |
| unknown (?) | | | | | | | | | | | | | | 1 | | | 1 | 1 | 1 | |
| not sequenced | | | 1 | 1 | 1 | 1 | 1 | 2 | 3 | 3 | 6 | 7 | 8 | 9 | 9 | 10 | 11 | 11 | 11 | 11 |
| sum of seq[2] | 57 | 57 | 56 | 56 | 56 | 56 | 56 | 55 | 54 | 54 | 51 | 50 | 49 | 48 | 48 | 47 | 46 | 46 | 46 | 46 |
| oomcaa[3] | 56 | 54 | 25 | 12 | 10 | 8 | 10 | 11 | 7 | 9 | 11 | 16 | 23 | 27 | 29 | 34 | 31 | 14 | 31 | 41 |
| mcaa[4] | A | R | G | R | G | G | G | G | V | — | — | — | — | — | — | — | — | — | F | D |
| rel. oomcaa[5] | 98% | 95% | 45% | 21% | 18% | 14% | 18% | 20% | 13% | 17% | 22% | 32% | 47% | 56% | 60% | 72% | 67% | 30% | 67% | 89% |
| pos occupied[6] | 2 | 4 | 12 | 16 | 16 | 16 | 16 | 16 | 16 | 18 | 18 | 13 | 15 | 13 | 10 | 9 | 8 | 5 | 4 | 4 |

TABLE 6E-continued

Analysis of V heavy chain subgroup 4

| amino acid[1] | Framework IV 102 | 103 | 104 | 105 | 106 | 107 | 108 | 109 | 110 | 111 | 112 | 113 | sum |
|---|---|---|---|---|---|---|---|---|---|---|---|---|---|
| A | | | | | | 1 | | | 1 | | | | 322 |
| B | | | | | | | | | | | | | |
| C | | | | | | | | | | | | | 113 |
| D | | | | | | | | | | | | | 210 |
| E | | | | | | | | | | | | | 176 |
| F | | | | | | | | | | | | | 135 |
| G | | | 41 | | 40 | 1 | | | | | | | 674 |
| H | 1 | | | | | | | | 1 | | | | 45 |
| I | 9 | | | | | 1 | | | | | | | 282 |
| K | | | | 3 | | | | | | | | | 278 |
| L | 4 | | | | | | 19 | | | | | | 540 |
| M | | | | | | | 9 | | | | | | 43 |
| N | | | | | | 1 | | | | | | | 204 |
| P | 3 | | | 2 | | | | | | | | 2 | 281 |
| Q | | | | 29 | | | | | | | | | 334 |
| R | 1 | | | 4 | | | 1 | | | | | | 250 |
| S | 1 | | | 1 | | | | | | | 36 | 33 | 986 |
| T | | | | 1 | | 33 | 8 | | 34 | | | | 532 |
| V | 12 | | | | | | | 36 | | 36 | | | 488 |
| W | | 46 | | | | | | | | | | | 267 |
| X | | | | | | | | | | | | | |
| Y | 16 | | | | | | | | | | | | 455 |
| Z | | | | | | | | | | | | | 1 |
| — | | | | | | | | | | | | | 466 |
| unknown (?) | | | | | | | | | | | | | 4 |
| not sequenced | 10 | 11 | 16 | 17 | 17 | 20 | 20 | 21 | 21 | 21 | 21 | 22 | 426 |
| sum of seq[2] | 47 | 46 | 41 | 40 | 40 | 37 | 37 | 36 | 36 | 36 | 36 | 35 | |
| oomcaa[3] | 16 | 46 | 41 | 29 | 40 | 33 | 19 | 36 | 34 | 36 | 36 | 33 | |
| mcaa[4] | Y | W | G | Q | G | T | L | V | T | V | S | S | |
| rel. oomcaa[5] | 34% | 100% | 100% | 73% | 100% | 89% | 51% | 100% | 94% | 100% | 100% | 94% | |
| pos occupied[6] | 8 | 1 | 1 | 6 | 1 | 5 | 4 | 1 | 3 | 1 | 1 | 2 | |

TABLE 6F

Analysis of V heavy chain subgroup 5

| amino acid[1] | Framework I 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| A | | | | | 1 | | | 1 | 89 | | 1 | | | 1 | | | | | | |
| B | | | | | | | | | | | | | | | | | | | | |
| C | | | | | | | 1 | | | | | | | | | | | | | |
| D | | | | | | | | | | 2 | | | | | | | | | | |
| E | 88 | 1 | | | 2 | | | | 4 | 93 | | | | | | 92 | | | | |
| F | | | | | | | | | | | | | | | | | 1 | | | |
| G | 1 | | | | | | | 92 | | | | | | | 94 | | | | | |
| H | | | | | | | | | | | | | | | | | | | | |
| I | | | | | | | | | | | | | | | | | | | | 96 |
| K | | | | | | | | | | | | 94 | 94 | | | | | | 77 | |
| L | | 1 | | 91 | | 2 | | | | | | | | | | | | 95 | | |
| M | | | | | | | | | | | 3 | | | | | | | | 1 | |

TABLE 6F-continued

Analysis of V heavy chain subgroup 5

| | | | | | | | | | | | | | | | | | | | | |
|---|---|---|---|---|---|---|---|---|---|---|---|---|---|---|---|---|---|---|---|---|
| N | | | | | | | | | | | | | | | | | | | | |
| P | | | | 1 | | | | | 1 | | | | | 94 | | | | | | |
| Q | 3 | | 92 | | 1 | 90 | | | | | | | | | | 3 | | | 1 | |
| R | | | | | | 1 | | | | | | 1 | 1 | | 1 | | | | 17 | |
| S | | | | | | | 92 | | | | | | | | | | 94 | | | |
| T | | | | | | | | | | | | | | | | | | | | |
| V | | 90 | | | 89 | | | | 1 | | 91 | | | | | | | | | |
| W | | | | | | | | | | | | | | | | | | | | |
| X | | | | | | | | | | | | | | | | | | | | |
| Y | | | | | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | 5 | 5 | 5 | 5 | 4 | 4 | 4 | 4 | 2 | 2 | 2 | 2 | 2 | 2 | 2 | 2 | 2 | 2 | 1 | 1 |
| sum of seq[2] | 92 | 92 | 92 | 92 | 93 | 93 | 93 | 93 | 95 | 95 | 95 | 95 | 95 | 95 | 95 | 95 | 95 | 95 | 96 | 96 |
| oomcaa[3] | 88 | 90 | 92 | 91 | 89 | 90 | 92 | 92 | 89 | 83 | 91 | 94 | 94 | 94 | 94 | 92 | 94 | 95 | 77 | 96 |
| mcaa[4] | E | V | Q | L | V | Q | S | G | A | E | V | K | K | P | G | E | S | L | K | I |
| rel. oomcaa[5] | 96% | 98% | 100% | 99% | 96% | 97% | 99% | 99% | 94% | 98% | 96% | 99% | 99% | 99% | 99% | 97% | 99% | 100% | 80% | 100% |
| pos occupied[6] | 3 | 3 | 1 | 2 | 4 | 3 | 2 | 2 | 4 | 2 | 3 | 2 | 2 | 2 | 2 | 2 | 2 | 1 | 4 | 1 |

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | | | | 3 | 2 | | | | | 4 | | | | | | | 8 | | 1 | |
| B | | | | | | | | | | | | | | | | | | | | |
| C | | 96 | | | | | | 1 | | | 1 | | | | | | | | | |
| D | | | | | | | | 2 | | | 2 | | | | | | 1 | | | |
| E | | | | | | 2 | | | | | 1 | | | | | | | | | |
| F | | | | | 3 | | 6 | | 97 | | | | | 2 | | | | | | |
| G | | | | 92 | | 93 | | | | | 1 | | | | | | 72 | | | |
| H | | | | | | | | | | | 1 | | | 4 | | | | | | 1 |
| I | | | | | | | | | | 4 | | | | | | 93 | | | | |
| K | | | 89 | | | | | 1 | | | | | | | | | | | | |
| L | | | | | | | | | | | | | | | 1 | | | | 2 | |
| M | | | 1 | | | | | | | | | | | | | 1 | | | 1 | |
| N | | | 1 | | | | | 2 | | 4 | 14 | | | 2 | | | | | | |
| P | | | | | 1 | | | | | | | | | | | | | | | 1 |
| Q | | | 4 | | | | | | | | | | | | | | | | | |
| R | | | 1 | | | 1 | | 2 | | | | | | | 1 | | | | | 95 |
| S | 94 | | | 1 | 90 | | | 84 | | 10 | 61 | | | 2 | 2 | | 15 | | | |
| T | 2 | | | | | | | 5 | | 75 | 16 | | | | | 2 | 1 | | | |
| V | | | | | | | | | | | | | | | | 1 | | | 93 | |
| W | | | | | | | | | | | | | | | 93 | | | 97 | | |
| X | | | | | | | | | | | | | | | | | | | | |
| Y | | | | | | | 90 | | | | | | | 87 | | | | | | |
| Z | | | | | | | | | | | | | | | | | | | | |
| — | | | | | | | | | | | | 97 | 97 | | | | | | | |
| unknown (?) | | | | | | | | | | | | | | | | | | | | |
| not sequenced | 1 | 1 | 1 | 1 | 1 | 1 | 1 | | | | | | | | | | | | | |
| sum of seq[2] | 96 | 96 | 96 | 96 | 96 | 96 | 96 | 97 | 97 | 97 | 97 | 97 | 97 | 97 | 97 | 97 | 97 | 97 | 97 | 97 |
| oomcaa[3] | 94 | 96 | 89 | 92 | 90 | 93 | 90 | 84 | 97 | 75 | 61 | 97 | 97 | 87 | 93 | 93 | 72 | 97 | 93 | 95 |
| mcaa[4] | S | C | K | G | S | G | Y | S | F | T | S | — | — | Y | W | I | G | W | V | R |
| rel. oomcaa[5] | 98% | 100% | 93% | 96% | 94% | 97% | 94% | 87% | 100% | 77% | 63% | 100% | 100% | 90% | 96% | 96% | 74% | 100% | 96% | 98% |
| pos occupied[6] | 2 | 1 | 5 | 3 | 4 | 3 | 2 | 7 | 1 | 5 | 8 | 1 | 1 | 5 | 4 | 4 | 5 | 1 | 4 | 3 |

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | | 1 | | | 1 | | | | | | | | | 1 | | | 2 | 1 | |
| B | | | | | | | | | | | | | | | | | | | | |
| C | | | | | | | | | | | | | | 1 | | | | 1 | | |
| D | | | | | | | | | | | | | | 14 | | | | 8 | 93 | |
| E | | | | | 3 | | | 97 | | | | | | | | | | | 2 | |
| F | | | | | | | | | | | | 1 | | 2 | | | | | | |
| G | | | | 97 | | 96 | | | | | 95 | | | | | | | 69 | 1 | |
| H | | | | | | | | | | | | | | 3 | 1 | | | | | |
| I | | | | | | | | | | 1 | | 75 | 92 | | | | | | | |
| K | | 1 | | | 94 | | | | | | | | | | | | | | | |
| L | | | | | | | 94 | | | 2 | | 2 | 1 | | | | | | | |
| M | | 92 | | | | | | | | 89 | | | 1 | | | | | | | |

TABLE 6F-continued

Analysis of V heavy chain subgroup 5

| | | | | | | | | | | | | | | | | | | | | |
|---|---|---|---|---|---|---|---|---|---|---|---|---|---|---|---|---|---|---|---|---|
| N | | | | | | | | | | | | | | | | | | | | |
| P | | | 96 | | | | 2 | | | | | | | 1 | 93 | | | | | 1 |
| Q | 97 | | | | | | 1 | | | | | | | | | | | | | |
| R | | 1 | | | | | | | | | 1 | 14 | | | | | | 1 | | |
| S | | | | | | | | | | | | 1 | | | 1 | | | 16 | | 96 |
| T | | 1 | | | | | | | | | | 3 | 1 | | 1 | | | | | |
| V | | 2 | | | | | | | | 5 | 1 | 1 | 2 | | | | | | | |
| W | | | | | | | | | 94 | | | | | | | | | | | |
| X | | | | | | | | | | | | | | | | | | | | |
| Y | | | | | | | | | 3 | | | | | 76 | | | | | | |
| Z | | | | | | | | | | | | | | | | | | | | |
| — | | | | | | | | | | | | | | | | 97 | 97 | | | |
| unknown (?) | | | | | | | | | | | | | | | | | | | | |
| not sequenced | | | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 | 97 | 97 |
| oomcaa[3] | 97 | 92 | 96 | 97 | 94 | 96 | 94 | 97 | 94 | 89 | 95 | 75 | 92 | 76 | 93 | 97 | 97 | 69 | 93 | 96 |
| mcaa[4] | Q | M | P | G | K | G | L | E | W | M | G | I | I | Y | P | — | — | G | D | S |
| rel. oomcaa[5] | 100% | 95% | 99% | 100% | 97% | 99% | 97% | 100% | 97% | 92% | 98% | 77% | 95% | 78% | 96% | 100% | 100% | 71% | 96% | 99% |
| pos occupied[6] | 1 | 5 | 2 | 1 | 2 | 2 | 3 | 1 | 2 | 4 | 3 | 7 | 5 | 6 | 5 | 1 | 1 | 6 | 4 | 2 |

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | | 6 | | | | | 1 | | | | | | | | | 88 | | | | |
| B | | | | | | | | | | | | | | | | | | | | |
| C | | | | | 1 | | | | | 1 | | | | | | | | | | |
| D | 77 | | | | | | | | | 2 | | | | | | | 97 | | | |
| E | 3 | | | | | | | | 2 | | | | | | | | | 2 | | |
| F | | | | 2 | | | | 91 | | | | 1 | | 3 | | | | | | |
| G | 1 | | | | | | | | | 94 | | | | | | | | | | |
| H | | | | | | | | | | | 15 | | | | | | | | | |
| I | | 4 | 1 | | | | | 1 | | | | 3 | | 88 | | | | | | 91 |
| K | | | 2 | | | | | | | | | | | | | | | 93 | | |
| L | | | | | | 1 | | 4 | | | | | | | 2 | | | | | |
| M | | | | | | | | | | | | | | 3 | | | | | | 1 |
| N | 2 | | 14 | 2 | | | | | | | | | | | | | | | | |
| P | | | | | | 95 | 1 | | 1 | | | | | | | | | | 1 | |
| Q | | | | | | | | | 91 | | 81 | | | | | | | 1 | | |
| R | | | 78 | | | | | | 3 | | 1 | | | 1 | | | | 1 | | |
| S | 2 | 2 | | | 95 | 1 | 95 | 1 | | | | | 1 | | 95 | | | | 96 | 1 |
| T | | 85 | 2 | | 1 | | | | | | | | 96 | | | | | | | 4 |
| V | | | | 1 | | | | | | | | 93 | | 2 | | 9 | | | | |
| W | | | | | | | | | | | | | | | | | | | | |
| X | | | | | | | | | | | | | | | | | | | | |
| Y | 12 | | | 92 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 97 | 97 | 97 | 97 | 97 | 97 | 97 | 97 | 97 | 97 | 97 | 97 | 97 | 97 | 97 | 97 | 97 | 97 | 97 | 97 |
| oomcaa[3] | 77 | 85 | 78 | 92 | 95 | 95 | 95 | 91 | 91 | 94 | 81 | 93 | 96 | 88 | 95 | 88 | 97 | 93 | 96 | 91 |
| mcaa[4] | D | T | R | Y | S | P | S | F | Q | G | Q | V | T | I | S | A | D | K | S | I |
| rel. oomcaa[5] | 79% | 88% | 80% | 95% | 98% | 98% | 98% | 94% | 94% | 97% | 84% | 86% | 99% | 91% | 98% | 91% | 100% | 96% | 99% | 94% |
| pos occupied[6] | 6 | 4 | 5 | 4 | 3 | 3 | 3 | 4 | 4 | 3 | 3 | 3 | 2 | 5 | 2 | 1 | 1 | 4 | 2 | 4 |

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | 1 | 91 | | | | | | | | 1 | 96 | | | | 93 | | | | |
| B | | | | | | | | | | | | | | | | | | | | |
| C | | | | | | | 1 | | | | | | | | | | | | | 95 |
| D | | | | 1 | | | | | | | | | | 96 | | | | | | |
| E | | | | | | 1 | | | | | 1 | | | | | | | | | |
| F | | | | 1 | | | | | | | | | | | | | | 2 | 6 | |
| G | | | | | | | | 3 | 1 | | | | | | | 4 | | | | |
| H | | | | | | 3 | | | | | | | | | | | | | | |
| I | | | | | | | | | | | | | | | 2 | | 9 | | | |
| K | | | | | | | | | | | 91 | | | | | | 1 | | | |
| L | | | | | 96 | | | | | 97 | | | | | | | 2 | | | |
| M | | | | | | | | | | | | | | | | | 84 | | | |

TABLE 6F-continued

Analysis of V heavy chain subgroup 5

| | | | | | | | | | | | | | | | | | | | | |
|---|---|---|---|---|---|---|---|---|---|---|---|---|---|---|---|---|---|---|---|---|
| N | 7 | | | | | | | 2 | 2 | | | | | | 2 | | | | | |
| P | | | 1 | | | | | | | | | | | | | | | | | |
| Q | | | | | | 93 | | | | | | | | | | | | | | |
| R | 1 | | | | | | 1 | 1 | 3 | | 3 | | | | | | | | | |
| S | 87 | 2 | 1 | 1 | | | | 90 | 91 | | | | 96 | | 5 | | | | | |
| T | 2 | 94 | 2 | | | | | 1 | | | 1 | 1 | 1 | | 88 | | 1 | | | |
| V | | | 2 | | 1 | | | | | | | | | 1 | | | | | | |
| W | | | | | | | 95 | | | | | | | | | | | | | |
| X | | | | | | | | | | | | | | | | | | | | |
| Y | | | | 94 | | | | | | | | | | | | | | 94 | 89 | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | 1 | 2 | 2 |
| sum of seq[2] | 97 | 97 | 97 | 97 | 97 | 97 | 97 | 97 | 97 | 97 | 97 | 97 | 97 | 97 | 97 | 97 | 97 | 96 | 95 | 95 |
| oomcaa[3] | 87 | 94 | 91 | 94 | 96 | 93 | 95 | 90 | 91 | 97 | 91 | 96 | 96 | 96 | 88 | 93 | 84 | 94 | 89 | 95 |
| mcaa[4] | S | T | A | Y | L | Q | W | S | S | L | K | A | S | D | T | A | M | Y | Y | C |
| rel. oomcaa[5] | 90% | 97% | 94% | 97% | 99% | 96% | 98% | 93% | 94% | 100% | 94% | 99% | 99% | 99% | 91% | 96% | 87% | 98% | 94% | 100% |
| pos occupied[6] | 4 | 3 | 5 | 4 | 2 | 3 | 3 | 5 | 4 | 1 | 5 | 2 | 2 | 2 | 4 | 2 | 5 | 2 | 2 | 1 |

| | CDR III | | | | | | | | | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 92 | | 1 | 1 | 2 | | 3 | 4 | 3 | 2 | | 1 | | | 1 | | | 4 | | 2 |
| B | | | | | | | | | | | | | | | | | | | | |
| C | | | | | | 1 | 1 | 1 | | | 2 | | 1 | | | | | | | |
| D | | | | 3 | 3 | 3 | 3 | 1 | 2 | 1 | 1 | 2 | | 2 | 1 | 1 | 2 | | | 37 |
| E | | | 1 | 1 | 1 | 2 | | | 1 | 1 | | | | 1 | | | 1 | | | |
| F | | | | | 1 | | 3 | | | 3 | 2 | | 1 | | | | | | 26 | |
| G | | | 1 | 9 | 11 | 12 | 12 | 5 | 2 | 4 | 3 | 10 | 2 | 1 | | | | 5 | | |
| H | | | 10 | 1 | | 2 | | | 1 | 1 | | 1 | | | | | | | | |
| I | | | | 3 | | 2 | 2 | 1 | 1 | 4 | 1 | 1 | | 1 | 1 | | | | | |
| K | | 1 | 1 | 1 | | 1 | 3 | 1 | | | | | | | | 2 | | | | |
| L | | | 11 | 2 | 3 | 1 | 1 | 2 | 5 | | 1 | | 1 | | 1 | | | | | |
| M | | | | | 2 | 1 | 1 | | 1 | 1 | 1 | 1 | | | | | | | 10 | |
| N | | | | 1 | | 2 | | 1 | 1 | 2 | | | 1 | | | | | 2 | | |
| P | | | 5 | 1 | 4 | 3 | 1 | 2 | | | | 1 | 1 | 1 | 1 | | | | | |
| Q | | 1 | 3 | 2 | | 1 | 1 | 4 | 2 | 1 | 2 | | | | | | | | | 3 |
| R | | 92 | 7 | 9 | 2 | 2 | | 2 | 1 | | 2 | | | | | | | | | |
| S | | 1 | 1 | 3 | 2 | 6 | 4 | 4 | 5 | 3 | 5 | 3 | 2 | 2 | | | 1 | | 1 | |
| T | 1 | | 1 | 3 | 2 | 1 | 2 | 6 | 3 | 3 | 6 | 1 | | 1 | | | | | | |
| V | 2 | | 2 | 4 | 4 | | 1 | | 1 | 2 | | | 1 | | | | | | | |
| W | | | 1 | | 2 | 1 | | | | | 1 | | 2 | | 1 | | 1 | 1 | | |
| X | | | | | | | | | | | | | | | | | | | | |
| Y | | | | 1 | 6 | 3 | 6 | 9 | 8 | 7 | 2 | 1 | 2 | 6 | 8 | 9 | 9 | 10 | | 1 |
| Z | | | | | | | | | | | | | | | | | | | | |
| — | | | | | | 1 | 1 | 2 | 8 | 10 | 16 | 23 | 30 | 30 | 31 | 32 | 30 | 22 | 7 | 2 |
| unknown (?) | | | | | | | | | | | | | 1 | | | 1 | 1 | 1 | | |
| not sequenced | 2 | 2 | 52 | 52 | 52 | 52 | 52 | 52 | 52 | 52 | 52 | 52 | 52 | 52 | 52 | 52 | 52 | 52 | 52 | 52 |
| sum of seq[2] | 95 | 95 | 45 | 45 | 45 | 45 | 45 | 45 | 45 | 45 | 45 | 45 | 45 | 45 | 45 | 45 | 45 | 45 | 45 | 45 |
| oomcaa[3] | 92 | 92 | 11 | 9 | 11 | 12 | 12 | 9 | 8 | 10 | 16 | 23 | 30 | 30 | 31 | 32 | 30 | 22 | 26 | 37 |
| mcaa[4] | A | R | L | G | G | G | G | Y | Y | — | — | — | — | — | — | — | — | — | F | D |
| rel. oomcaa[5] | 97% | 97% | 24% | 20% | 24% | 27% | 27% | 20% | 18% | 22% | 36% | 51% | 67% | 67% | 69% | 71% | 67% | 49% | 59% | 82% |
| pos occupied[6] | 3 | 4 | 13 | 16 | 14 | 18 | 16 | 15 | 16 | 15 | 14 | 11 | 11 | 9 | 8 | 4 | 6 | 6 | 4 | 5 |

TABLE 6F-continued

Analysis of V heavy chain subgroup 5

| amino acid[1] | 102 | 103 | 104 | 105 | 106 | 107 | 108 | 109 | 110 | 111 | 112 | 113 | sum |
|---|---|---|---|---|---|---|---|---|---|---|---|---|---|
| | Framework IV | | | | | | | | | | | | |
| A | | | | | | | | | | | | 1 | 611 |
| B | | | | | | | | | | | | | |
| C | | | | | | | | | | | | | 205 |
| D | 1 | | | | | | | | | | | | 458 |
| E | | | | 1 | | | | | | | | | 404 |
| F | 2 | | | | | | | | | | | | 256 |
| G | | | 41 | | 41 | | | | | | | | 1065 |
| H | | | | | | | | | | | | | 44 |
| I | 9 | | | | | | | | 2 | | | | 588 |
| K | | | | 3 | | | | | | | | | 650 |
| L | 2 | | | | | | 25 | 1 | | | | | 549 |
| M | | | | | | | 8 | | | | | | 303 |
| N | | | | | | | | | | | | | 64 |
| P | 2 | | | | | 1 | | | | | 1 | | 414 |
| Q | | | | 34 | | | | | | | | | 612 |
| R | | | | 3 | | | | | | | | | 351 |
| S | 2 | | | | | | | | | | 40 | 39 | 1545 |
| T | 1 | | | | | 40 | 8 | | 39 | | | | 604 |
| V | 11 | | | | | | | 40 | | 41 | | | 594 |
| W | | 43 | | | | | | | | | | | 432 |
| X | | | | | | | | | | | | | |
| Y | 13 | | | | | | | | | | | | 738 |
| Z | | | | | | | | | | | | | |
| — | 2 | | | | | | | | | | | | 635 |
| unknown (?) | | | | | | | | | | | | | 4 |
| not sequenced | 52 | 54 | 56 | 56 | 56 | 56 | 56 | 56 | 56 | 56 | 56 | 57 | 1678 |
| sum of seq[2] | 45 | 43 | 41 | 41 | 41 | 41 | 41 | 41 | 41 | 41 | 41 | 40 | |
| oomcaa[3] | 13 | 43 | 41 | 34 | 41 | 40 | 25 | 40 | 39 | 41 | 40 | 39 | |
| mcaa[4] | Y | W | G | Q | G | T | L | V | T | V | S | S | |
| rel. oomcaa[5] | 29% | 100% | 100% | 83% | 100% | 89% | 61% | 98% | 95% | 100% | 98% | 98% | |
| pos occupied[6] | 10 | 1 | 1 | 4 | 1 | 2 | 3 | 2 | 2 | 1 | 2 | 2 | |

TABLE 6G

Analysis of V heavy chain subgroup 6

| amino acid[1] | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | Framework I | | | | | | | | | | | | | | | | | | | |
| A | | | | | | | | | | | | 1 | | | | | | | | |
| B | | | | | | | | | | | | | | | | | | | | |
| C | | | | | | | | | | | | | | | | | | | | |
| D | | | | | | | | | | | | | | | | | | | | |
| E | | | | | | | | | | | | | | | | | | | | |
| F | | | | | | | | | | | | | | | | | | | | |
| G | | | | | | | | 52 | | 67 | | | | | | | | | | |
| H | | | | | | | | | | | | | | | | | | | | |
| I | | | | | | | | | | | | | | | | | | | | |
| K | | | | | | | | | | | | | 68 | | | | | | | |
| L | | | | 52 | | | | | | | 68 | 1 | | | | | | 67 | 1 | 68 |
| M | | | | | | | | | | | | | | | | | | | | |

TABLE 6G-continued

Analysis of V heavy chain subgroup 6

| | | | | | | | | | | | | | | | | | | | | |
|---|---|---|---|---|---|---|---|---|---|---|---|---|---|---|---|---|---|---|---|---|
| N | | | | | | | | | | | | | | | | | | | | |
| P | | | | | | | | | 68 | | | | | 67 | | | | | 1 | |
| Q | 52 | | 52 | | 51 | 52 | | | | | | | | | | 68 | | | | |
| R | | | | | 1 | | | | | 1 | | | | | | | | | | |
| S | | | | | | | 52 | | | | | | | 1 | 68 | | | | 66 | |
| T | | | | | | | | | | | | | | | | | 68 | | | |
| V | | 52 | | | | | | | | | | 66 | | | | | | 1 | | |
| W | | | | | | | | | | | | | | | | | | | | |
| X | | | | | | | | | | | | | | | | | | | | |
| Y | | | | | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | 22 | 22 | 22 | 22 | 22 | 22 | 22 | 22 | 6 | 6 | 6 | 6 | 6 | 6 | 6 | 6 | 6 | 6 | 6 | 6 |
| sum of seq[2] | 52 | 52 | 52 | 52 | 52 | 52 | 52 | 52 | 68 | 68 | 68 | 68 | 68 | 68 | 68 | 68 | 68 | 68 | 68 | 68 |
| oomcaa[3] | 52 | 52 | 52 | 52 | 51 | 52 | 52 | 52 | 68 | 67 | 68 | 66 | 68 | 67 | 68 | 68 | 68 | 67 | 66 | 68 |
| mcaa[4] | Q | V | Q | L | Q | Q | S | G | P | G | L | V | K | P | S | Q | T | L | S | L |
| rel. oomcaa[5] | 100% | 100% | 100% | 100% | 98% | 100% | 100% | 100% | 100% | 99% | 100% | 97% | 100% | 99% | 100% | 100% | 100% | 99% | 97% | 100% |
| pos occupied[6] | 1 | 1 | 1 | 1 | 2 | 1 | 1 | 1 | 1 | 2 | 1 | 3 | 1 | 2 | 1 | 1 | 1 | 2 | 3 | 1 |

| | | | | | | | | | | | CDRI | | | | | | | | | |
|---|---|---|---|---|---|---|---|---|---|---|---|---|---|---|---|---|---|---|---|---|
| amino acid[1] | 21 | 22 | 23 | 24 | 25 | 26 | 27 | 28 | 29 | 30 | 31 | A | B | 32 | 33 | 34 | 35 | 36 | 37 | 38 |
| A | 1 | | 67 | | | | | | | | | | | 66 | 67 | | | | | |
| B | | | | | | | | | | | | | | | | | | | | |
| C | | 68 | | | | | | | | | | | | | | | | | | |
| D | | | | | | | 68 | | | | 1 | | | | | | 1 | | | |
| E | | | | | | | | | | | | | | | | | | | | |
| F | | | | | | | | | | 2 | | | | 1 | 1 | | | | 1 | |
| G | | | 1 | | | 69 | | | | | | | 3 | 1 | 2 | | | | | |
| H | | | | | | | | | | | | | | | | | 1 | | | |
| I | | | | 64 | | | | | | | | 2 | | | | | 1 | | 70 | |
| K | | | | | | | | | | | | 3 | | | | | | | | |
| L | | | | | | | | | | | | | | | | | | | | |
| M | | | | | | | | | | | | | | | | | | | | |
| N | | | | | | | 1 | | | | 2 | 66 | | | | | 70 | | | |
| P | | | | | | | | | | | | | | | | | | | | |
| Q | | | | | | | | | | | | | | | | | | | | |
| R | | | | | | | | | | | 2 | 1 | | | | | | | | 74 |
| S | 1 | | | 1 | 69 | | | 69 | | 68 | 66 | | 67 | | 3 | | 1 | | | |
| T | 57 | | | | | | | | | | 2 | 1 | 4 | | 1 | | | | | |
| V | | | 1 | 4 | | | | | 70 | | | | | 6 | | | | | 2 | |
| W | | 1 | | | | | | | | | | | | | | 74 | | 74 | | |
| X | | | | | | | | | | | | | | | | | | | | |
| Y | | | | | | | | | | | | 1 | | | | | | | 1 | |
| Z | | | | | | | | | | | | | | | | | | | | |
| — | | | | | | | | | | | | | | | | | | | | |
| unknown (?) | | | | | | | | | | | 1 | | | | | | | | | |
| not sequenced | 5 | 5 | 5 | 5 | 5 | 5 | 5 | 5 | 4 | 4 | | | | | | | | | | |
| sum of seq[2] | 69 | 69 | 69 | 69 | 69 | 69 | 69 | 69 | 70 | 70 | 74 | 74 | 74 | 74 | 74 | 74 | 74 | 74 | 74 | 74 |
| oomcaa[3] | 67 | 68 | 67 | 64 | 69 | 69 | 68 | 69 | 70 | 68 | 66 | 66 | 67 | 66 | 67 | 74 | 70 | 74 | 70 | 74 |
| mcaa[4] | T | C | A | I | S | G | D | S | V | S | S | N | S | A | A | W | N | W | I | R |
| rel. oomcaa[5] | 97% | 99% | 97% | 93% | 100% | 100% | 99% | 100% | 100% | 97% | 89% | 89% | 91% | 89% | 91% | 100% | 95% | 100% | 95% | 100% |
| pos occupied[6] | 3 | 2 | 3 | 3 | 1 | 1 | 2 | 1 | 1 | 2 | 5 | 6 | 3 | 4 | 5 | 1 | 5 | 1 | 4 | 1 |

| | Framework II | | | | | | | | | | | | | | | | | | | |
|---|---|---|---|---|---|---|---|---|---|---|---|---|---|---|---|---|---|---|---|---|
| amino acid[1] | 39 | 40 | 41 | 42 | 43 | 44 | 45 | 46 | 47 | 48 | 49 | 50 | 51 | 52 | A | B | C | 53 | 54 | 55 |
| A | | | | 1 | | | | | | | | | 1 | | | | | 1 | | |
| B | | | | | | | | | | | | | | | | | | | | |
| C | | | | | | | | | | | | | | | | | | | | |
| D | | | | | | | | | | | | | | | | | | | | |
| E | | | | | | | | 74 | | | | | | | | | | | | |
| F | | | | | | | | | | | | | | 2 | 1 | | | 1 | | |
| G | | | | | | 74 | | | | | 74 | 1 | | | | | | | 1 | |
| H | | | | | | | | | | | | | | | 1 | | | | | |
| I | | | | | | | | | | | | | | | | | | | | |
| K | 1 | | | | 1 | | | | | | | | | | | 1 | | | 66 | |
| L | 1 | | | | | | 74 | | | 74 | | | | | | | | | | |
| M | | | | | | | | | | | | | | | | | | | | |

TABLE 6G-continued

Analysis of V heavy chain subgroup 6

| | | | | | | | | | | | | | | | | | | | | |
|---|---|---|---|---|---|---|---|---|---|---|---|---|---|---|---|---|---|---|---|---|
| N | | | | | | | | | | | | | | | | | | | 1 | |
| P | | | 73 | | | | | | | | | | | | | | | | | |
| Q | 72 | | | | | | | | | | | | | | | | | | | |
| R | | | | | 73 | | | | | | | 73 | | | | 72 | | | 1 | 1 |
| S | | 74 | 1 | 73 | | | | | | | | | | | | 1 | | 72 | | |
| T | | | | | | | | | | | | | 73 | | | | | | 5 | |
| V | | | | | | | | | | | | | | | | | | | | |
| W | | | | | | | | | 74 | | | | | | | | | | | 73 |
| X | | | | | | | | | | | | | | | | | | | | |
| Y | | | | | | | | | | | | | | 72 | 72 | | | | | |
| Z | | | | | | | | | | | | | | | | | | | | |
| — | | | | | | | | | | | | | | | | | 74 | | | |
| unknown (?) | | | | | | | | | | | | | | | | | | | | |
| not sequenced | | | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 | 74 | 74 |
| oomcaa[3] | 72 | 74 | 73 | 73 | 73 | 74 | 74 | 74 | 74 | 74 | 74 | 73 | 73 | 72 | 72 | 72 | 74 | 72 | 66 | 73 |
| mcaa[4] | Q | S | P | S | R | G | L | E | W | L | G | R | T | Y | Y | R | — | S | K | W |
| rel. oomcaa[5] | 97% | 100% | 99% | 99% | 99% | 100% | 100% | 100% | 100% | 100% | 100% | 99% | 99% | 97% | 97% | 97% | 100% | 97% | 89% | 99% |
| pos occupied[6] | 3 | 1 | 2 | 2 | 2 | 1 | 1 | 1 | 1 | 1 | 1 | 2 | 2 | 2 | 3 | 3 | 1 | 3 | 5 | 2 |

| | CDR II | | | | | | | | | | | | | | | | | | | |
|---|---|---|---|---|---|---|---|---|---|---|---|---|---|---|---|---|---|---|---|---|
| amino acid[1] | 56 | 57 | 58 | 59 | 60 | 61 | 62 | 63 | 64 | 65 | 66 | 67 | 68 | 69 | 70 | 71 | 72 | 73 | 74 | 75 |
| A | | | | | 73 | 1 | | | | | | | 2 | | | 6 | | 1 | | |
| B | | | | | | | | | | | | | | | | | | | | |
| C | | | | 1 | | | | | | | | | | | | | | | | |
| D | | | 68 | | | 1 | | | | | | | | | 2 | | 73 | | | |
| E | 1 | | 3 | | | 7 | | | 1 | | | | | | | | | | | 2 |
| F | 7 | | | | | | | | | | | | | | | | | | | |
| G | | | 1 | | | | 1 | | | 8 | | | | | | | | | | |
| H | 1 | | | | | | | | | | | | | | | | 1 | | | |
| I | | | | | | 1 | | | | | | 65 | 2 | 71 | | | | 1 | | |
| K | | 1 | | | | | | | 67 | | | | | | 1 | | | | | 70 |
| L | 1 | | | | | 5 | | 2 | | | | 4 | | | | | | 1 | | |
| M | | | | | | | | | | | | 1 | | | | | | | | |
| N | 2 | 65 | 1 | | | | | | 1 | | | | | 69 | | | | | | |
| P | | | | | 1 | 1 | | | | | | | | | 66 | | | | | |
| Q | | | | | | | | | 2 | | 1 | | | | | | | | | |
| R | | 1 | | | | | | | 3 | | 73 | | | | | | | | | |
| S | 2 | 2 | 1 | 1 | | | 73 | | | 66 | | | 1 | 2 | 1 | | | | 73 | |
| T | | 4 | | | | | | | | | | | 69 | 1 | | | | 71 | 1 | 2 |
| V | | | | | | 58 | | 72 | | | | 4 | | 2 | 1 | | | | | |
| W | | | | | | | | | | | | | | | | | | | | |
| X | | | | | | | | | | | | | | | | | | | | |
| Y | 60 | 1 | | 72 | | | | | | | | | | | | | | | | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | | | | | | | | | |
| sum of seq[2] | 74 | 74 | 74 | 74 | 74 | 74 | 74 | 74 | 74 | 74 | 74 | 74 | 74 | 74 | 74 | 74 | 74 | 74 | 74 | 74 |
| oomcaa[3] | 60 | 65 | 68 | 72 | 73 | 58 | 73 | 72 | 67 | 66 | 73 | 65 | 69 | 71 | 69 | 66 | 73 | 71 | 73 | 70 |
| mcaa[4] | Y | N | D | Y | A | V | S | V | K | S | R | I | T | I | N | P | D | T | S | K |
| rel. oomcaa[5] | 81% | 88% | 92% | 97% | 99% | 78% | 99% | 97% | 91% | 89% | 99% | 88% | 93% | 96% | 93% | 89% | 99% | 96% | 99% | 95% |
| pos occupied[6] | 7 | 6 | 5 | 3 | 2 | 7 | 2 | 2 | 5 | 2 | 2 | 4 | 4 | 3 | 4 | 4 | 2 | 4 | 2 | 3 |

| | Framework III | | | | | | | | | | | | | | | | | | | |
|---|---|---|---|---|---|---|---|---|---|---|---|---|---|---|---|---|---|---|---|---|
| amino acid[1] | 76 | 77 | 78 | 79 | 80 | 81 | 82 | A | B | C | 83 | 84 | 85 | 86 | 87 | 88 | 89 | 90 | 91 | 92 |
| A | | | | | | | | | | | | | 1 | | | 74 | | | | |
| B | | | | | | | | | | | | | | | | | | | | |
| C | | | | | | | | | | | | | | | | | | | | 73 |
| D | | | | | | | | 3 | | | | | | 73 | | | | | | |
| E | | | | | | | | | | | | | 73 | | | | | | | |
| F | | | 71 | | | | | | 1 | | | | | | | | | | 3 | |
| G | | | | | | | | | | | | | | 1 | | | | | | |
| H | | | | | | 2 | | 1 | | | | | | | | | | | | |
| I | | | 1 | | | | | | | | | | | | | | 2 | | | |
| K | | | | | | | | 4 | | | | | | | | | | | | |
| L | | 1 | | | 74 | | 72 | | | | | | | | | | | | | |
| M | | | | | | | 1 | | | 1 | | | | | | | 2 | | | |

TABLE 6G-continued

Analysis of V heavy chain subgroup 6

| | | | | | | | | | | | | | | | | | | | | |
|---|---|---|---|---|---|---|---|---|---|---|---|---|---|---|---|---|---|---|---|---|
| N | 74 | | | | | | | 63 | | | | | | | | | | | 1 | |
| P | | | | | | | | | | | | 70 | | | | | | | | |
| Q | | 72 | | | | 71 | | | | | | | | | | | | | | |
| R | | 1 | | | | 1 | | 1 | | | | | | | | | | | | 1 |
| S | | | | 74 | | | | 1 | 73 | | 1 | 3 | | | | | | | | |
| T | | | | | | | | 1 | | | 73 | | | | 74 | | | 1 | | |
| V | | | 2 | | | | 1 | | | 73 | | | | | | | 70 | | | |
| W | | | | | | | | | | | | | | | | | | | | |
| X | | | | | | | | | | | | | | | | | | | | |
| Y | | | | | | | | | | | | | | | | | | 73 | 70 | |
| Z | | | | | | | | | | | | | | | | | | | | |
| — | | | | | | | | | | | | | | | | | | | | |
| unknown (?) | | | | | | | | | | | | | | | | | | | | |
| not sequenced | | | | | | | | | | | | 1 | | | | | | | | |
| sum of seq[2] | 74 | 74 | 74 | 74 | 74 | 74 | 74 | 74 | 74 | 74 | 74 | 73 | 74 | 74 | 74 | 74 | 74 | 74 | 74 | 74 |
| oomcaa[3] | 74 | 72 | 71 | 74 | 74 | 71 | 72 | 63 | 73 | 73 | 73 | 70 | 73 | 73 | 74 | 74 | 70 | 73 | 70 | 73 |
| mcaa[4] | N | Q | F | S | L | Q | L | N | S | V | T | P | E | D | T | A | V | Y | Y | C |
| rel. oomcaa[5] | 100% | 97% | 96% | 100% | 100% | 96% | 97% | 85% | 99% | 99% | 99% | 96% | 99% | 99% | 100% | 100% | 95% | 99% | 95% | 99% |
| pos occupied[6] | 1 | 3 | 3 | 1 | 1 | 3 | 3 | 7 | 2 | 2 | 2 | 2 | 2 | 2 | 1 | 1 | 3 | 2 | 3 | 2 |

| | CDR III | | | | | | | | | | | | | | | | | | | |
|---|---|---|---|---|---|---|---|---|---|---|---|---|---|---|---|---|---|---|---|---|
| amino acid[1] | 93 | 94 | 95 | 96 | 97 | 98 | 99 | 100 | A | B | C | D | E | F | G | H | I | J | K | 101 |
| A | 69 | | 11 | 1 | 3 | 12 | 4 | 3 | 2 | 5 | | 8 | | | | | | 10 | 1 | |
| B | | | | | | | | | | | | | | | | | | | | |
| C | | | | | 1 | | 1 | | | 1 | | 1 | 1 | | | | | | | |
| D | | | 19 | 4 | 3 | 7 | 4 | 3 | 1 | 6 | 1 | 1 | 1 | | | | | | | 62 |
| E | | | 10 | 4 | 2 | 1 | 2 | 2 | 1 | 2 | | | | | | | 1 | | | |
| F | 1 | | 1 | 1 | 1 | | 1 | 2 | 3 | | 2 | | | 1 | | | | | 38 | 4 |
| G | 1 | | 16 | 4 | 15 | 15 | 11 | 8 | 6 | 2 | 5 | 1 | 8 | 6 | 1 | | | 17 | | |
| H | | | | 1 | | 1 | | | 1 | 1 | 1 | 1 | | | | 1 | 1 | 1 | | |
| I | | | | 1 | 2 | | 2 | | 5 | 1 | | | | | | | | | | |
| K | | 1 | 1 | 1 | 1 | 1 | 1 | 1 | | | | 1 | | | | | | | | |
| L | | | 1 | 8 | 4 | 2 | 3 | 2 | 1 | | | | | 1 | 5 | | | | 8 | |
| M | | | | 1 | | | | 1 | | | 5 | | | | | | | | 11 | |
| N | | | 1 | 3 | 1 | 2 | 1 | 1 | 1 | 3 | | 2 | | 1 | | 1 | 3 | | | |
| P | | | 5 | 10 | 4 | | 5 | 3 | | 5 | 1 | | 1 | | | | | | | |
| Q | | | 1 | 1 | 1 | 1 | | | | | 1 | | | | | | | | | 1 |
| R | | 69 | 1 | 7 | 8 | 1 | 8 | 8 | 3 | | 1 | 1 | 5 | | | | | | | 1 |
| S | | 3 | 5 | 5 | 5 | 7 | 6 | 7 | 3 | 4 | 2 | | | | | 1 | 1 | | | |
| T | | | 1 | 1 | 4 | 3 | 4 | 4 | 6 | 3 | 1 | | | 1 | | | | | | |
| V | 3 | 1 | 4 | 5 | 1 | 9 | | | 4 | | 9 | 5 | 1 | 1 | | | | | 2 | |
| W | | | 1 | 6 | 8 | | 3 | 2 | 4 | | | | | | | | 4 | 4 | | |
| X | | | | | | | | | | | | | | | | | | | | |
| Y | | | | 6 | 4 | 2 | 2 | 2 | 6 | 6 | 2 | 4 | 2 | 1 | 8 | 8 | 12 | 12 | | |
| Z | | | | | | | | | | | | | | | | | | | | |
| — | | | | 2 | 3 | 7 | 14 | 23 | 25 | 33 | 41 | 47 | 53 | 54 | 57 | 56 | 50 | 28 | 12 | 4 |
| unknown (?) | | | | | | | | | | | | | | 6 | 1 | 5 | | | | |
| not sequenced | | | | 1 | 2 | 2 | 1 | 1 | 1 | 1 | 1 | 1 | 1 | 1 | 1 | 1 | 1 | 1 | 1 | 1 |
| sum of seq[2] | 74 | 74 | 73 | 72 | 71 | 71 | 72 | 72 | 72 | 72 | 72 | 72 | 72 | 72 | 72 | 72 | 72 | 72 | 72 | 72 |
| oomcaa[3] | 69 | 69 | 19 | 10 | 15 | 15 | 14 | 23 | 25 | 33 | 41 | 47 | 53 | 54 | 57 | 56 | 50 | 28 | 38 | 62 |
| mcaa[4] | A | R | D | P | G | G | — | — | — | — | — | — | — | — | — | — | — | — | F | D |
| rel. oomcaa[5] | 93% | 93% | 26% | 14% | 21% | 21% | 19% | 32% | 35% | 46% | 57% | 65% | 74% | 75% | 79% | 78% | 69% | 39% | 53% | 86% |
| pos occupied[6] | 4 | 4 | 14 | 20 | 19 | 15 | 17 | 16 | 16 | 13 | 13 | 11 | 8 | 8 | 4 | 5 | 7 | 6 | 6 | 5 |

TABLE 6G-continued

Analysis of V heavy chain subgroup 6

| amino acid[1] | Framework IV 102 | 103 | 104 | 105 | 106 | 107 | 108 | 109 | 110 | 111 | 112 | 113 | sum |
|---|---|---|---|---|---|---|---|---|---|---|---|---|---|
| A | | | | | | | 2 | | | | | | 494 |
| B | | | | | | | | | | | | | |
| C | | | | | | | | | | | | | 147 |
| D | | | | | | | | 1 | | | | | 403 |
| E | | | | | | | | | | | | | 186 |
| F | 2 | | | | | | | | | | 2 | | 150 |
| G | | | 49 | | 50 | | | | | | | | 571 |
| H | 2 | | | | | | | | | | | | 18 |
| I | 9 | | | | | 3 | | 1 | | | | | 304 |
| K | | | | 1 | | | 1 | | | | | | 293 |
| L | 5 | | | | | | 26 | | | | | | 632 |
| M | | | | | | | 8 | | | | | | 31 |
| N | | | | | | | | | | | | | 436 |
| P | 4 | | | 6 | | | | | | | | 1 | 387 |
| Q | | | | 40 | | | | | | | | | 539 |
| R | | | | 2 | | | | | | | | | 495 |
| S | 4 | | 1 | | | 1 | | | | | 43 | 46 | 1271 |
| T | | | | | | 45 | 4 | | 45 | | | | 640 |
| V | 21 | | | | | | 2 | 46 | | 48 | | | 647 |
| W | | 65 | | | | | 5 | | | | | | 398 |
| X | | | | | | | | | | | | | |
| Y | 19 | | | | | | | | | | | | 518 |
| Z | | | | | | | | | | | | | |
| — | 2 | | | | | | | | | | | | 585 |
| unknown (?) | | | | | | | | | | | | | 13 |
| not sequenced | 5 | 8 | 23 | 24 | 23 | 24 | 25 | 25 | 28 | 25 | 28 | 26 | 580 |
| sum of seq[2] | 68 | 65 | 50 | 49 | 50 | 49 | 48 | 48 | 45 | 48 | 45 | 47 | |
| oomcaa[3] | 21 | 65 | 49 | 40 | 50 | 45 | 26 | 46 | 45 | 48 | 43 | 46 | |
| mcaa[4] | V | W | G | Q | G | T | L | V | T | V | S | S | |
| rel. oomcaa[5] | 31% | 100% | 98% | 82% | 100% | 92% | 54% | 96% | 100% | 100% | 96% | 98% | |
| pos occupied[6] | 9 | 1 | 2 | 4 | 1 | 3 | 7 | 3 | 1 | 1 | 2 | 2 | |

APPENDIX TO TABLES 1A-C

A. References of Rearranged Sequences

References of Rearranged Human Kappa Sequences Used for Alignment

1 Alescio-Zonta, L. & Baglioni, C. (1970) Eur. J. Biochem., 15, 450-463.

2 Andrews, D. W. & Capra, J. D. (1981) Biochemistry, 20, 5816-5822.

3 Andris, J. S., Ehrlich, P. H., Ostberg, L. & Capra, J. D. (1992) J. Immunol., 149, 4053-4059.

4 Atkinson, P. M., Lampman, G. W., Furie, B. C., Naparstek, Y., Schwartz, R. S., Stollar, B. D. & Furie, B. (1985) J. Clin. Invest., 75, 1138-1143.

5 Aucouturier, P., Bauwens, M., Khamlichi, A. A., Denoroy, L. Spinelli. S., Touchard, G., Preud'homme, J.-L. & Cogne, M. (1993) J. Immunol., 150, 3561-3568.

6 Avila, M. A., Vazques, J., Danielsson, L., Fernandez De Cossio, M. E. & Borrebaeck, C. A. K. (1993) Gene, 127, 273-274.

7 Barbas Iii, C. F., Crowe, Jr., J. E., Cababa, D., Jones, T. M., Zebedee, S. L. Murphy, B. R., Chanock, R. M. & Burton, D. R. (1992) Proc. Natl. Acad. Sci. Usa, 89, 10164-10168.

8 Barbas, C. F., Iii, et al. (1993) J-Mol-Biol., 230, 812-23.

9 Bentley, D. L. & Rabbitts, T. H. (1980) Nature, 288, 730-733.

10 Bentley, D. L. & Rabbitts, T. H. (1983) Cell, 32, 181-189.

11 Bentley, D. L. (1984) Nature, 307, 77-80.

12 Bhat, N. M., Bieber, M. M., Chapman, C. J., Stevenson, F. K. & Teng, N. N. H. (1993) J. Immunol., 151, 5011-5021.

13 Blaison, G., Kuntz, J.-L. & Pasquali, J.-L. (1991) Eur. J. Immunol., 21, 1221-1227.

14 Braun, H., Leibold, W., Barnikol, H. U. & Hilschmann, N. (1971) Z. Physiol. Chem., 352, 647-651; (1972) Z. Physiol. Chem., 353, 1284-1306.

15 Capra, J. D. & Kehoe, J. M. (1975) Adv. Immunology, 20, 1-40.; Andrews, D. W. & Capra, J. D. (1981) Proc. Nat. Acad. Sci. Usa, 78, 3799-3803.

16 Capra, J. D. & Kehoe, J. M. (1975) Adv. Immunology, 20, 1-40. Ledford, D. K., Goni, F., Pizzolato, M., Franklin, E. C., Solomon, A. & Frangione, B. (1983) J. Immunol., 131, 1322-1325.

17 Chastagner, P., Theze, J. & Zouali, M. (1991) Gene, 101, 305-306.

18 Chen. P. P., Robbins, D. L., Jirik, F. R., Kipps, T. J. & Carson, D. A. (1987) J. Exp. Med, 166, 1900-1905.

19 Chen. P. P., Robbins, D. L., Jirik, F. R., Kipps, T. J. & Carson, D. A. (1987) J. Exp. Med, 166, 1900-1905; Liu, M.-F., Robbins, D. L., Crowley, J. J., Sinha, S., Kozin, F., Kipps, T. J., Carson, D. A. & Chen. P. P. (1989) J. Immunol., 142, 688-694.

20 Chersi, A. & Natali, P. G. (1978) Immunochemistry, 15, 585-589.

21 Co, M. S., Deschamps, M., Whitley, R. J. & Queen, C. (1991) Proc. Natl. Acad. Sci. Usa, 88, 2869-2873.
22 Cuisinier, A.-M., Fumoux. F., Fougereau, M. & Tonnelle, C. (1992) Mol. Immunol., 29, 1363-1373.
23 Davidson, A., Manheimer-Lory, A., Aranow, C., Peterson, R., Hannigan, N. & Diamond, B. (1990) J. Clin. Invest., 85, 1401-1409.
24 Denomme, G. A., Mahmoudi, M., Edwards. J. Y., Massicotte. H., Cairns, E. & Bell. D. A. (1993) Hum. Antibod. Hybridomas, 4, 98-103.
25 Dersimonian, H., Mcadam, K. P. W. J., Mackworth-Young, C. & Stollar, B. D. (1989) J. Immunol., 142, 4027-4033.
26 Dreyer, W. J., Gray, W. R. & Hood, L. (1967) Cold Spring Harbor Symp. Quantitative Biol., 32, 353-367.
27 Ebeling, S. B., Schutte, M. E. M. & Logtenberg, T. (1993) Eur. J. Immunol., 23, 1405-1408.
28 Eulitz, M. & Kley, H.-P. (1977) Immunochem., 14, 289-297.
29 Eulitz, M. & Linke, R. P. (1982) Z. Physiol. Chem., 363, 1347-1358.
30 Eulitz, M., Breuer, M., Eblen, A., Weiss, D. T. & Solomon, A. (1990) In Amyloid And Amyloidosis. Eds. J. B. Natvig, O. Forre, G. Husby, A. Husebekk, B. Skogen, K. Sletten & P. Westermark, Kluwer Academic
31 Eulitz, M., Gotze, D. & Hilschmann, N. (1972) Z. Physiol. Chem., 353, 487-491: Eulitz, M. & Hilschmann, N. (1974) Z. Physiol. Chem., 355, 842-866.
32 Eulitz, M., Kley, H. P. & Zeitler, H. J. (1979) Z. Physiol. Chem., 360, 725-734.
33 Ezaki, I., Kanda, H., Sakai, K., Fukui, N., Shingu, M., Nobunaga, M. & Watanabe, T. (1991) Arthritis And Rheumatism, 34, 343-350.
34 Felgenhauer. M., Kohl, J. & Ruker, F. (1990) Nucl. Acids Res., 18, 4927.
35 Ferri, G., Stoppini, M., Iadarola, P., Bellotti, V. & Merlini, G. (1989) Biochim. Biophys. Acta, 995, 103-108.
36 Gillies, S. D., Dorai, H., Wesolowski, J., Majeau, G., Young, D., Boyd, J., Gardner, J. & James, K. (1989) Bio/Tech., 7, 799-804.
37 Goni, F. & Frangione, B. (1983) Proc. Nat Acad. Sci. Usa, 80, 4837-4841.
38 Goni, F. R., Chen, P. P., Mcginnis, D., Arjonilla, M. L., Fernandez, J., Carson, D., Solomon, A., Mendez, E. & Frangione, B. (1989) J. Immunol., 142, 3158-3163.
39 Gorman, S. D., Clark, M. R., Routledge, E. G., Cobbold, S. P. & Waldmann, H. (1991) Proc. Natl. Acad. Sci. Usa, 88, 4181-4185.
40 Gottlieb, P. D., Cunningham, B. A., Rutishauser, U. & Edelman, G. M. (1970) Biochemistry, 9, 3155-3161.
41 Griffiths, A. D., Malmqvist, M., Marks, J. D., Bye, J. M., Embleton, M. J., Mccafferty. J., Baier, M., Holliger, K. P., Gorick, B. D., Hughes-Jones, N. C., Hoogenboom, H. R. & Winter, G. (1993) Embo J., 12, 725-734.
42 Hieter, P. A., Max, E. E., Seidman, J. G., Maizel, J. V., Jr. & Leder, P. (1980) Cell, 22, 197-207; Klobeck, H. G, Meindl, A., Combriato, G., Solomon, A. & Zachau, H. G. (1985) Nucl. Acids Res., 13, 6499-6513; Weir, L. & Leder, P. (1986)
43 Hilschmann, N. & Craig, L. C. (1965) Proc. Nat. Acad. Sci. Usa, 53, 1403-1409; Hilschmann, N. (1967) Z. Physiol. Chem., 348, 1077-1080.
44 Hilschmann, N. & Craig, L. C. (1965) Proc. Nat. Acad. Sci. Usa, 53, 1403-1409; Hilschmann, N. (1967) Z. Physiol. Chem., 348, 1718-1722; Hilschmann, N. (1969) Naturwissenschaften, 56, 195-205.
45 Hirabayashi, Y., Munakata, Y., Sasaki, T. & Sano, H. (1992) Nucl. Acids Res., 20, 2601.
46 Jaenichen, H.-R., Pech, M., Lindenmaier, W., Wildgruber, N. & Zachau, H. G. (1984) Nuc. Acids Res., 12, 5249-5263.
47 Jirik, F. R., Sorge, J., Fong, S., Heitzmann, J. G., Curd, J. G., Chen, P. P., Goldfien, R. & Carson, D. A. (1986) Proc. Nat. Acad. Sci. Usa, 83, 2195-2199.
48 Kaplan, A. P. & Metzger, H. (1969) Biochemistry, 8, 3944-3951.; Klapper, D. G. & Capra, J. D. (1976) Ann. Immunol. (Inst. Pasteur), 127c, 261-271.
49 Kennedy, M. A. (1991) J. Exp. Med., 173, 1.033-1036.
50 Kim, H. S. & Deutsch, H. F. (1988) Immunol., 64, 573-579.
51 Kipps, T. J., Tomhave, E., Chen, P. P. & Carson, D. A. (1988) J. Exp. Med., 167, 840-852.
52 Kipps, T. J., Tomhave, E., Chen, P. P. & Fox, R. I. (1989) J. Immunol., 142, 4261-4268.
53 Klapper, D. G. & Capra, J. D. (1976) Ann. Immunol. (Inst. Pasteur), 127c, 261-271.
54 Klein, U., Kuppers, R. & Rajewsky, K. (1993) Eur. J. Immunol., 23, 3272-3277.
55 Klobeck, H. G, Meindl, A., Combriato, G., Solomon, A. & Zachau, H. G. (1985) Nucl. Acids Res., 13, 6499-6513.
56 Klobeck, H. G., Bornkammm, G. W., Combriato, G., Mocikat, R., Pohlenz, H. D. & Zachau, H. G. (1985) Nucl. Acids Res., 13, 6515-6529.
57 Klobeck, H. G., Combriato, G. & Zachau, H. G. (1984) Nuc. Acids Res., 12, 6995-7006.
58 Klobeck, H. G., Solomon, A. & Zachau, H. G. (1984) Nature, 309, 73-76.
59 Knight, G. B., Agnello, V., Bonagura, V., Barnes. J. L., Panka, D. J. & Zhang, Q.-X. (1993) J. Exp. Med., 178, 1903-1911.
60 Kohler, H., Shimizu, A., Paul, C. & Putnam, F. W. (1970) Science, 169, 56-59. (Kaplan, A. P. & Metzger, H. (1969) Biochemistry, 8, 3944-3951.)
61 Kratzin, H., Yang, C. Y., Krusche, J. U. & Hilschmann, N. (1980) Z. Physiol. Chem., 361, 1591-1598.
62 Kunicki, T. J., Annis, D. S., Gorski, J. & Nugent, D. J. (1991) J. Autoimmunity, 4, 433-446.
63 Larrick, J. W., Wallace, E. F., Coloma, M. J., Bruderer, U., Lang, A. B. & Fry, K. E. (1992) Immunological Reviews, 130, 69-85.
64 Laure, C. J., Watanabe, S. & Hilschmann, N. (1973) Z. Physiol. Chem., 354, 1503-1504.
65 Ledford, D. K., Goni, F., Pizzolato, M., Franklin. E. C., Solomon, A. & Frangione, B. (1983) J. Immunol., 131, 1322-1325.
66 Ledford, D. K., Goni, F., Pizzolato, M., Franklin, E. C., Solomon, A. & Frangione, B. (1983) J. Immunol., 131, 1322-1325.
67 Ledford, D. K., Goni, F., Pizzolato, M., Franklin, E. C., Solomon, A. & Frangione, B. (1983) J. Immunol., 131, 1322-1325. Pons-Estel, B., Goni, F., Solomon, A. & Frangione, B. (1984) J. Exp. Med., 160, 893.
68 Levy, S., Mendel, E., Kon, S., Avnur, Z. & Levy, R. (1988) J. Exp. Med., 168, 475-489.
69 Liepnieks, J. J., Dwulet, F. E. & Benson, M. D. (1990) Mol. Immunol., 27, 481-485.
70 Manheimer-Lory, A., Katz, J. B., Pillinger, M., Ghossein, C., Smith, A. & Diamond, B. (1991) J. Exp. Med., 174, 1639-1652.
71 Mantovani, L., Wilder, R. L. & Casali, P. (1993) J. Immunol., 151, 473-488.
72 Mariette, X., Tsapis, A. & Brouet, J.-C. (1993) Eur. J. Immunol., 23, 846-851.

73 Marks, J. D., Hoogenboom, H. R., Bonnert, T. P., Mccafferty, J., Griffiths, A. D. & Winter, G. (1991) J. Mol. Biol., 222, 581-597.
74 Marsh. P., Mills, F. & Gould, H. (1985) Nuc. Acids Res., 13, 6531-6544.
75 Middaugh, C. R. & Litman, G. W. (1987) J. Biol. Chem., 262, 3671-3673:
76 Milstein, C. & Deverson, E. V. (1971) Biochem. J., 123, 945-958.
77 Milstein, C. (1969) Febs Letters, 2, 301-304.
78 Milstein, C. (1969) Febs Letters, 2, 301-304.
79 Milstein, C. P. & Deverson, E. V. (1974) Eur. J. Biochem., 49, 377-391.
80 Moran, M. J., Andris, J. S., Matsumato, Y.-I., Capra, J. D. & Hersh, E. M. (1993) Mol. Immunol., 30, 1543-1551.
81 Nakatani, T., Nomura, N., Horigome, K., Ohtsuka, H. & Noguchi, H. (1989) Bio/Tech., 7, 805-810.
82 Newkirk, M., Chen, P. I., Carson, D., Posnett, D. & Capra, J. D. (1986) Mol. Immunol., 23, 239-244.
83 Newkirk, M. M., Gram, H., Heinrich, G. F., Ostberg, L., Capra, J. D. & Wasserman, R. L. (1988) J. Clin. Invest., 81, 1511-1518.
84 Newkirk, M. M., Mageed, R. A., Jefferis, R., Chen, P. P. & Capra, J. D. (1987) J. Exp. Med., 166, 550-564.
85 Olee. B. T., Lu, E. W., Huang, D.-F., Soto-Gil, R. W., Deftos. M., Kozin, F., Carson, D. A. & Chen, P. P. (1992) J. Exp. Med., 175, 831-842.
86 Palm, W. & Hilschmann, N. (1973) Z. Physiol. Chem., 354, 1651-1654: (1975) Z. Physiol. Chem., 356, 167-191.
87 Pascual, V., Victor, K., Lelsz, D., Spellerberg, M. B., Hamblin, T. J., Thompson, K. M., Randen, I., Natvig, J., Capra, J. D. & Stevenson, F. K. (1991) J. Immunol., 146, 4385-4391.
88 Pascual, V., Victor, K., Randen, I., Thompson, K., Steinitz, M., Forre, O., Fu, S.-M., Natvig, J. B. & Capra. J. D. (1992) Scand. J. Immunol., 36, 349-362.
89 Pech, M. & Zachau, H. G. (1984) Nuc. Acids Res., 12, 9229-9236.
90 Pech, M., Jaenichen. H.-R., Pohlenz, H.-D., Neumaier, P. S., Klobeck, H.-G. & Zachau, H. G. (1984) J. Mol. Biol., 176, 189-204.
91 Pons-Estel, B., Goni, F., Solomon, A. & Frangione, B. (1984) J. Exp. Med., 160, 893-904.
92 Portolano. S., Mclachlan, S. M. & Rapoport, B. (1993) J. Immunol., 151, 2839-2851.
93 Portolano, S., Seto, P., Chazenbalk, G. D., Nagayama, Y., Mclachlan, S. M. & Rapoport, B. (1991) Biochem. Biophys. Res. Commun., 179, 372-377.
94 Pratt. L. F., Rassenti, L., Larrick, J., Robbins, B., Banks, P. M. & Kipps, T. J. (1989) J. Immunol., 143, 699-705.
95 Prelli, F., Tummolo, D., Solomon, A. & Frangione, B. (1986) J. Immunol., 136, 4169-4173.
96 Putnam, F. W., Whitley, E. J., Jr., Paul, C. & Davidson, J. N. (1973) Biochemistry, 12, 3763-3780.
97 Randen, I., Pascual, V., Victor, K., Thompson, K. M., Forre, O., Capra, J. D. & Natvig, J. B. (1993) Eur. J. Immunol., 23, 1220-1225.
98 Rassenti, L. Z., Pratt, L. F., Chen, P. P., Carson, D. A. & Kipps, T. J. (1991) J. Immunol., 147, 1060-1066.
99 Reidl, L. S., Friedman, D. F., Goldman, J., Hardy, R. R., Jefferies, L. C. & Silberstein, L. E. (1991) J. Immunol., 147, 3623-3631.
100 Riechmann, L., Clark, M., Waldmann, H. & Winter, G. (1988) Nature, 332, 323-327.
101 Riesen, W., Rudikoff, S., Oriol, R. & Potter, M. (1975) Biochemistry, 14, 1052-1057; Riesen, W.-F., Braun, D. G. & Jaton. J. C. (1976) Proc. Nat. Acad. Sci. Usa, 73, 2096-2100; Riesen, W. F. & Jaton, J. C. (1976) Biochemistry, 15, 3829.
102 Rodilla Sala, E., Kratzin, D. H., Pick, A. I. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic
103 Schiechl, H. & Hilschmann, N. (1971) Z. Physiol. Chem., 352, 111-115; (1972) Z. Physiol. Chem., 353, 345-370.
104 Schneider, M. & Hilschmann, N. (1974) Z. Physiol. Chem., 355, 1164-1168.
105 Shearman, C. W., Pollock, D., White, G., Hehir, K., Moore, G. P., Kanzy, E. J. & Kurrle, R. (1991) J. Immunol., 147, 4366-4373.
106 Shinoda, T. (1973) J. Biochem., 73, 433-446.
107 Shinoda, T. (1975) J. Biochem., 77, 1277-1296.
108 Shinoda, T., Takenawa, T., Hoshi, A. & Isobe, T. (1990) In Amyloid And Amyloidosis, Eds. J. B. Natvig, O. Forre, G. Husby, A. Husebekk, B. Skogen, K. Sletten & P. Westermark, Kluwer Academic Publishers, Dordrecht/Boston/London, Pp. 157-
109 Silberstein, L. E., Litwin, S. & Carmack, C. E. (1989) J. Exp. Med., 169, 1631-1643.
110 Sims, M. J., Hassal, D. G., Brett, S., Rowan. W., Lockyer, M. J., Angel, A., Lewis, A. P., Hale, G., Waldmann, H. & Crowe, J. S. (1993) J. Immunol., 151, 2296-2308.
111 Spatz, L. A., Wong, K. K., Williams. M., Desai, R., Golier, J., Berman, J. E., Alt, F. W. & Latov. N. (1990) J. Immunol., 144, 2821-2828.
112 Stavnezer, J., Kekish, O., Batter, D., Grenier. J., Balazs. I., Henderson, E. & Zegers, B. J. M. (1985) Nucl. Acids Res., 13, 3495-3514.
113 Straubinger, B., Thiebe, R., Pech, M. & Zachau. H. G. (1988) Gene, 69, 209-214.
114 Suter, L., Barnikol, H. U., Watanabe, S. & Hilschmann, N. (1969) Z. Physiol. Chem., 350, 275-278; (1972) Z. Physiol. Chem., 353, 189-208.
115 Tempest, P. R., Bremner, P., Lambert M., Taylor, G., Furze, J. M., Carr, F. J. & Harris, W. J. (1991) Bio/Tech., 9, 266-271.
116 Titani, K., Shinoda, T. & Putnam, F. W. (1969) J. Biol. Chem., 244, 3550-3560.
117 Toft, K. G., Olstad, O. K., Sletten, K. & Westermark, P. (1990) In Amyloid And Amyloidosis, Eds. J. B. Natvig, O. Forre, G. Husby, A. Husebekk, B. Skogen, K. Sletten & P. Westermark, Kluwer Academic
118 Van Es, J. H., Aanstoot, H., Gmelig-Meyling, F. H. J., Derksen, R. H. W. M. & Logtenberg, T. (1992) J. Immunol., 149, 2234-2240.
119 Victor, K. D., Pascual, V., Lefvert, A. K. & Capra, J. D. (1992) Mol. Immunol., 29, 1501-1506.
120 Victor, K. D., Pascual, V., Williams, C. L. Lennon, V. A. & Capra, J. D. (1992) Eur. J. Immunol., 22, 2231-2236.
121 Victor, K. D., Randen, I., Thompson, K., Forre, O., Natvig, J. B., Fu, S. M. & Capra, J. D. (1991) J. Clin. Invest, 87, 1603-1613.
122 Wagner, S. D. & Luzzatto, L. (1993) Eur. J. Immunol., 23, 391-397.
123 Watanabe, S. & Hilschmann, N. (1970) Z. Physiol. Chem., 351, 1291-1295.
124 Weisbart, R. H., Wong, A. L., Noritake, D., Kacena, A., Chan, G., Ruland, C., Chin, E., Chen, I. S. Y. & Rosenblatt, J. D. (1991) J. Immunol., 147, 2795-2801.
125 Weng, N.-P., Yu-Lee, L.-Y., Sanz, I., Patten, B. M. & Marcus, D. M. (1992) J. Immunol., 149, 2518-2529.

126 Winkler, T. H., Fehr, H. & Kalden, J. R. (1992) Eur. J. Immunol., 22, 1719-1728.

References of Rearranged Human Lambda Sequences Used for Alignment

1 Alexandre, D., Chuchana, P., Brockly, F., Blancher, A., Lefranc, G. & Lefranc, M.-P. (1989) Nuc. Acids Res., 17, 3975.

2 Anderson, M. L. M., Brown, L., Mckenzie, E., Kellow, J. E. & Young, B. D. (1985) Nuc. Acids Re, 13, 2931-2941.

3 Andris. J. S., Brodeur, B. R. & Capra. J. D. (1993) Mol. Immunol., 30, 1601-1616.

4 Andris, J. S., Ehrlich, P. H., Ostberg, L. & Capra, J. D. (1992) J. Immunol., 149, 4053-4059.

5 Baczko. K., Braun, D. G., Hess, M. & Hilschmann, N. (1970) Z. Physiol. Chem., 351, 763-767; Baczko, K., Braun, D. G. & Hilschmann, N. (1974) Z. Physiol. Chem., 355, 131-154.

6 Berinstein, N., Levy. S. & Levy. R. (1989) Science, 244, 337-339.

7 Bhat, M. M., Bieber, M. M., Chapman, C. J., Stevenson, F. K. & Teng, N. N. H. (1993) J. Immunol., 151, 5011-5021.

8 Cairns, E., Kwong, P. C., Misener, V., Ip, P., Bell, D. A. & Siminovitch, K. A. (1989) J. Immunol., 143, 685-691.

9 Carroll, W. L., Yu, M., Link, M. P. & Korsmeyer, S. J. (1989) J. Immunol., 143, 692-698.

10 Chen, B. L. & Poljak, R. J. (1974) Biochemistry, 13, 1295-1302.

11 Chen, B. L., Chiu, Y. Y. H., Humphrey, R. L. & Poljak, R. J. (1978) Biochim. Biophys. Acta, 537, 9-21.

12 Combriato, G. & Klobeck, H. G. (1991) Eur. J. Immunol., 21, 1513-1522.

13 Cuisinier, A.-M., Fumoux. F., Fougereau, M. & Tonnelle, C. (1992) Mol. Immunol., 29, 1363-1373.

14 Dwulet, F. E., Strako, K. & Benson, M. D. (1985) Scand. J. Immunol., 22, 653-660.

15 Elahna, P., Livneh, A., Manheimer-Lory, A. J. & Diamond, B. (1991) J. Immunol., 147, 2771-2776.

16 Engelhard, M., Hess, M. & Hilschmann, N. (1974) Z. Physiol. Chem., 355, 85-88; Engelhard. M. & Hilschmann, N. (1975) Z. Physiol. Chem., 356, 1413-1444.

17 Eulitz, M. (1974) Eur. J. Biochem., 50, 49-69.

18 Eulitz, M., Breuer, M. & Linke, R. P. (1987) Biol. Che. Hoppe-Seyler, 368, 863-870.

19 Eulitz, M., Murphy, C., Weiss, D. T. & Solomon, A. (1991) J. Immunol., 146, 3091-3096.

20 Fett, J. W. & Deutsch, H. F. (1974) Biochemistry, 13, 4102-4114.

21 Fett, J. W. & Deutsch, H. F. (1976) Immunochem., 13, 149-155.; Jabusch, J. R. & Deutsch, H. F. (1982) Mol. Immunol., 19, 901-906.

22 Furey, W. Jr., Wang, B. C., Yoo, C. S. & Sax, M. (1983) J. Mol. Biol., 167, 661-692.

23 Fykse, E.-M., Sletten, K., Husby. G. & Cornwell. G. G., Iii (1988) Biochem. J., 256, 973-980.

24 Garver, F. A. & Hilschmann, N. (1971) Febs Letters, 16, 128-132; (1972) Eur. J. Biochem., 26, 10-32.

25 Gawinowicz, M. A., Merlini, G., Birken, S., Osserman, E. F. & Kabat, E. A. (1991) J. Immunol., 147, 915-920.

26 Ghiso, J., Solomon, A. & Frangione, B. (1986) J. Immunol., 136, 716-719.

27 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725-734.

28 Gullasken, N., Idso, H., Nilsen, R., Sletten, K., Husby, G. & Cornwell, G. G. (1990) In Amyloid And Amyloidosis, Eds. J. B. Natvig, O. Forre, G. Husby, A. Husebekk, B. Skogen, K. Sletten & P. Westermark, Kluwer Academic 29 Harindranath, N., Goldfarb, I. S., Ikematsu, H., Burastero, S. E., Wilder, R. L., Notkins, A. L. & Casali, P. (1991) Int. Immunol., 3, 865-875.

30 Holm, E., Sletten, K. & Husby, G. (1986) Biochem. J., 239, 545-551.

31 Hughes-Jones, N. C., Bye, J. M., Beale, D. & Coadwell, J. (1990) Biochem. J., 268, 135-140.

32 Kametani, F., Yoshimura, K., Tonoike, H., Hoshi, A., Shinoda, T. & Isobe, T. (1985) Biochem. Biophys. Res. Commun., 126, 848-852.

33 Kiefer, C. R., Mcquire, B. S., Jr., Osserman, E. F. & Garver, F. A. (1983) J. Immunol., 131, 1871-1875.

34 Kiefer, C. R., Patton, H. M., Jr., Mcquire, B. S., Jr. & Garver, F. A. (1980) J. Immunol., 124, 301-306.

35 Kishimoto, T., Okajima, H., Okumoto, T. & Taniguchi, M. (1989) Nucl. Acids Res., 17, 4385.

36 Klafki, H.-W., Kratzin, H. D., Pick. A. I., Eckart, K. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic 37 Kohler, H., Rudofsky, S. & Kluskens, L. (1975) J. Immunology, 114, 415-421.

38 Kojima, M., Odani, S. & Ikenaka, T. (1980) Mol. Immunol., 17, 1407-1414.

39 Komori, S., Yamasaki, N., Shigeta, M., Isojima. S. & Watanabe. T. (1988) Clin. Exp. Immunol., 71, 508-516.

40 Kratzin, H. D., Palm. W., Stangel. M., Schmidt, W. E., Friedrich, J. & Hilschmann, N. (1989) Biol. Chem. Hoppe-Seyler, 370, 263-272.

41 Kratzin, H. D., Pick, A. I., Stangel, M. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic Publishers, Dordrecht/Boston/London, Pp. 181-

42 Langer, B., Steinmetz-Kayne, M. & Hilschmann, N. (1968) Z. Physiol. Chem., 349, 945-951.

43 Larrick, J. W., Danielsson, L., Brenner, C. A., Wallace, E. F., Abrahamson, M., Fry, K. E. & Borrebaeck, C. A. K. (1989) Bio/Tech., 7, 934-938.

44 Levy, S., Mendel, E., Kon, S., Avnur, Z. & Levy. R. (1988) J. Exp. Med., 168, 475-489.

45 Lewis, A. P., Lemon, S. M., Barber, K. A., Murphy, P., Parry, N. R., Peakman, T. C., Sims, M. J., Worden, J. & Crowe, J. S. (1993) J. Immunol., 151, 2829-2838.

46 Liu, V. Y. S., Low, T. L. K., Infante, A. & Putnam, F. W. (1976) Science, 193, 1017-1020; Infante, A. & Putnam, F. W. (1979) J. Biol. Chem., 254, 9006-9016.

47 Lopez De Castro, J. A., Chiu, Y. Y. H. & Poljak, R. J. (1978) Biochemistry, 17, 1718-1723.

48 Mantovani, L., Wilder, R. L. & Casali, P. (1993) J. Immunol., 151, 473-488.

49 Marks, J. D., Hoogenboom, H. R., Bonnert, T. P., Mccafferty, J., Griffiths, A. D. & Winter, G. (1991) J. Mol. Biol., 222, 581-597.

50 Mihaesco, E., Roy. J.-P., Congy, N., Peran-Rivat, L. & Mihaesco, C. (1985) Eur. J. Biochem., 150, 349-357.

51 Milstein, C., Clegg, J. B. & Jarvis, J. M. (1968) Biochem. J., 110, 631-652.

52 Moran, M. J., Andris, J. S., Matsumato, Y.-I., Capra, J. D. & Hersh, E. M. (1993) Mol. Immunol., 30, 1543-1551.

53 Nabeshima, Y. & Ikenaka, T. (1979) Mol. Immunol., 16, 439-444.

54 Olee, B. T., Lu, E. W., Huang, D.-F., Soto-Gil, R. W., Deftos, M., Kozin, F., Carson, D. A. & Chen, P. P. (1992) J. Exp. Med., 175, 831-842.

55 Pascual, V., Victor, K., Randen, I., Thompson, K., Steinitz, M., Forre, O., Fu, S.-M., Natvig, J. B. & Capra, J. D. (1992) Scand. J. Immunol., 36, 349-362.

56 Paul, E., Iliev, A. A., Livneh, A. & Diamond, B. (1992) J. Immunol., 149, 3588-3595.

57 Pick, A. I., Kratzin, H. D., Barnikol-Watanabe, S. & Hilschmann, N. (1990) In Amyloid And Amyloidosis, Eds. J. B. Natvig, O. Forre, G. Husby, A. Husebekk, B. Skogen, K. Sletten & P. Westermark, Kluwer Academic 58 Ponstingl, H. & Hilschmann, N. (1969) Z. Physiol. Chem., 350, 1148-1152: (1971) Z. Physiol. Chem., 352, 859-877.

59 Ponstingl, H., Hess, M. & Hilschmann, N. (1968) Z. Physiol. Chem., 349, 867-871; (1971) Z. Physiol. Chem., 352, 247-266.

60 Randen, I., Pascual, V., Victor, K., Thompson, K. M., Forre, O., Capra, J. D. & Narvig, J. B. (1993) Eur. J. Immunol., 23, 1220-1225.

61 Scholz, R. & Hilschmann, N. (1975) Z. Physiol. Chem., 356, 1333-1335.

62 Settmacher, U., Jahn, S., Siegel, P., Von Baehr, R. & Hansen, A. (1993) Mol. Immunol., 30, 953-954.

63 Shinoda, T., Titani, K. & Putnam, F. W. (1970) J. Biol. Chem., 245, 4475-4487.

64 Sletten, K., Husby, G. & Natvig, J. B. (1974) Scand. J. Immunol., 3, 833-836.; Sletten, K., Natvig, J. B., Husby, G. & Juul, J. (1981) Biochem. J., 195, 561-572.

65 Solomon, A., Frangione, B. & Franklin, E. C. (1982) J. Clin. Invest, 70, 453-460.; Frangione, B., Moloshok, T. & Solomon, A. (1983) J. Immunol., 131, 2490-2493.

66 Takahashi, N., Takayasu, T., Isobe, T., Shinoda, T., Okuyama, T. & Shimizu, A. (1979) J. Biochem., 86, 1523-1535.

67 Takahashi, N., Takayasu, T., Shinoda, T., Ito, S., Okuyama, T. & Shimizu, A. (1980) Biomed. Res., 1, 321-333.

68 Takahashi, Y., Takahashi, N., Tetaert, D. & Putnam, F. W. (1983) Proc. Nat. Acad. Sci. Usa, 80, 3686-3690.

69 Takayasu, T., Takahashi, N., Shinoda, T., Okuyama, T. & Tomioka, H. (1980) J. Biochem., 89, 421-436.

70 Titani, K., Wikler, M., Shinoda, T. & Putnam, F. W. (1970) J. Biol. Chem., 245, 2171-2176.

71 Toft, K. G., Sletten, K. & Husby, G. (1985) Biol. Chem. Hoppe-Seyler, 366, 617-625.

72 Tonoike, H., Kametani, F., Hoshi, A., Shinoda, T. & Isobe, T. (1985) Biochem. Biophys. Res. Commun., 126, 1228-1234.

73 Tonoike, H., Kametani, F., Hoshi, A., Shinoda, T. & Isobe, T. (1985) Febs Letters, 185, 139-141.

74 Tsujimoto, Y. & Croce, C. M. (1984) Nucl. Acids Res., 12, 8407-8414.

75 Tsunetsugu-Yokota. Y., Minekawa, T., Shigemoto, K., Shirasawa, T. & Takemori, T. (1992) Mol. Immunol., 29, 723-728.

76 Tveteraas, T., Sletten, K. & Westermark. P. (1985) Biochem. J., 232, 183-190.

77 Vasicek, T. J. & Leder, P. (1990) J. Exp. Med., 172, 609-620.

78 Victor, K. D., Randen, I., Thompson, K., Forre, O., Natvig, J. B., Fu, S. M. & Capra, J. D. (1991) J. Clin. Invest., 87, 1603-1613.

79 Weng, N.-P., Yu-Lee, L.-Y., Sanz, I., Patten, B. M. & Marcus, D. M. (1992) J. Immunol., 149, 2518-2529.

80 Wikler, M. & Putnam, F. W. (1970) J. Biol. Chem., 245, 4488-4507.

81 Winkler, T. H., Fehr, H. & Kalden, J. R. (1992) Eur. J. Immunol., 22, 1719-1728.

82 Yago, K., Zenita, K., Ohwaki, I., Harada, Y., Nozawa, S., Tsukazaki, K., Iwamori, M., Endo, N., Yasuda, N., Okuma, M. & Kannagi, R. (1993) Mol. Immunol., 30, 1481-1489.

83 Yamasaki, N., Komori, S. & Watanabe, T. (1987) Mol. Immunol., 24, 981-985.

84 Zhu, D., Kim, H. S. & Deutsch, H. F. (1983) Mol. Immunol., 20, 1107-1116.

85 Zhu, D., Zhang, H., Zhu, N. & Luo, X. (1986) Scientia Sinica, 29, 746-755.

References of Rearranged Human Heavy Chain Sequences Used for Alignment

1 Adderson, E. E., Azmi, F. H., Wilson, P. M., Shackelford, P. G. & Carroll, W. L. (1993) J. Immunol., 151, 800-809.

2 Adderson, E. E., Shackelford, P. G., Quinn, A. & Carroll, W. L. (1991) J. Immunol., 147, 1667-1674.

3 Akahori, Y., Kurosawa, Y., Kamachi, Y., Torii, S. & Matsuoka, H. (1990) J. Clin. Invest., 85, 1722-1727.

4 Andris, J. S., Brodeur, B. R. & Capra, J. D. (1993) Mol. Immunol., 30, 1601-1616.

5 Andris, J. S., Ehrlich, P. H., Ostberg, L. & Capra, J. D. (1992) J. Immunol., 149, 4053-4059.

6 Andris, J. S., Johnson, S., Zolla-Pazner, S. & Capra, J. D. (1991) Proc. Natl. Acad. Sci. Usa, 88, 7783-7787.

7 Anker, R., Conley, M. E. & Pollok, B. A. (1989) J. Exp. Med., 169, 2109-2119.

8 Atkinson, P. M., Lampman, G. W., Furie, B. C., Naparstek, Y., Schwartz, R. S., Stollar, B. D. & Furie, B. (1985) J. Clin. Invest., 75, 1138-1143.; Lampman, G. W., Furie, B., Schwartz, R. S., Stollar, B. D. & Furie, B. C. (1989)

9 Avila, M. A., Vazques. J., Danielsson, L., Fernandez De Cossio, M. E. & Borrebaeck, C. A. K. (1993) Gene, 127, 273-274.

10 Bakkus, M. H. C., Heirman, C., Van Riet, I., Van Camp, B. & Thielemans. K. (1992) Blood, 80, 2326-2335.

11 Barbas Iii, C. F., Crowe, Jr., J. E., Cababa, D., Jones, T. M., Zebedee, S. L., Murphy, B. R., Chanock, R. M. & Burton. D. R. (1992) Proc. Natl. Acad. Sci. Usa, 89, 10164-10168.

12 Barbas, C. F., Iii, Collet, T. A., Amberg, W., Roben, P., Binley, J. M., Hoekstra, D., Cababa, D., Jones, T. M., Williamson, R. A., Pilkington, G. R., Haigwood, N. L., Cabezas, E., Satterthwait, A. C., Sanz, I. & Burton, D. R. (1993) J. Mol. Biol., 230, 812-823.

13 Berman, J. E., Humphries, C. G., Barth, J., Alt, F. W. & Tucker, P. W. (1991) J. Exp. Med., 173, 1529-1535.

14 Berman, J. E., Mellis, S. J., Pollock, R., Smith, C. L., Suh, H., Heinke, B., Kowal, C., Surti, U., Chess, L., Cantor, C. R. & Alt, F. W. (1988) Embo J., 7, 727-738.

15 Bhat, N. M., Bieber, M. M., Chapman, C. J., Stevenson, F. K. & Teng, N. N. H. (1993) J. Immunol., 151, 5011-5021.

16 Bird, J., Galili, N., Link, M., Stites, D. & Sklar, J. (1988) J. Exp. Med., 168, 229-245.

17 Cai, J., Humphries, C., Richardson, A. & Tucker, P. W. (1992) J. Exp. Med., 176, 1073-1081.

18 Cairns, E., Kwong, P. C., Misener, V., Ip, P., Bell, D. A. & Siminovitch, K. A. (1989) J. Immunol., 143, 685-691.

19 Capra, J. D. & Hopper, J. E. (1976) Immunochemistry, 13, 995-999; Hopper, J. E., Noyes, C., Heinrikson, R. & Kessel, J. W. (1976) J. Immunol., 116, 743-746.

20 Capra, J. D. & Kehoe, J. M. (1974) Proc. Nat. Acad. Sci. Usa, 71, 845-848.

21 Carroll, W. L., Yu, M., Link, M. P. & Korsmeyer, S. J. (1989) J. Immunol., 143, 692-698.

22 Chen, P. P., Liu, M.-F., Glass, C. A., Sinha, S., Kipps, T. J. & Carson, D. A. (1989) Arthritis & Rheumatism, 32, 72-76; Kipps, T. J., Tomhave, E., Pratt, L. F., Duffy, S., Chen, P. P. & Carson, D. A. (1989) Proc. Natl. Acad. Sci. Usa, 86, 5913-5917.
23 Chiu, Y. Y. H., Lopez De Castro, J. A. & Poljak, R. J. (1979) Biochemistry, 18, 553-560.
24 Cleary, M. L., Meeker, T. C., Levy, S., Lee, E., Trela, M., Sklar, J. & Levy, R. (1986) Cell, 44, 97-106.
25 Cuisinier, A.-M., Fumoux, F., Fougereau, M. & Tonnelle, C. (1992) Mol. Immunol., 29, 1363-1373.
26 Cuisinier, A.-M., Gauthier, L., Boubli, L., Fougereau, M. & Tonnelle, C. (1993) Eur. J. Immunol., 23, 110-118.
27 Cunningham, B. A., Gottlieb. P. D., Pflumm, M. N. & Edelman, G. M. (1971) Progress In Immunology (B. Amos, Ed.), Academic Press, N.Y., Pp. 3-24.
28 Cunningham. B. A., Rutishauser, U., Gall, W. E., Gottlieb, P. D., Waxdal, M. J. & Edelman, G. M. (1970) Biochemistry, 9, 3161-3170.
29 Deane, M. & Norton, J. D. (1990) Eur. J. Immunol., 20, 2209-2217.
30 Deane, M. & Norton, J. D. (1991) Leukemia, 5, 646-650.
31 Dersimonian, H., Schwartz. R. S., Barrett, K. J. & Stollar, B. D. (1987) J. Immunol., 139, 2496-2501.
32 Dersimonian, H., Schwartz, R. S., Barrett, K. J. & Stollar, B. D. (1987) J. Immunol., 139, 2496-2501; Chen, P. P., Liu, M.-F., Sinha, S. & Carson, D. A. (1988) Arth. Rheum., 31, 1429-1431.
33 Desai, R., Spatz, L., Matsuda, T., Ilyas, A. A., Berman, J. E., Alt, F. W., Kabat, E. A. & Latov, N. (1990) J. Neuroimmunol., 26, 35-41.
34 Ezaki, I., Kanda, H., Sakai, K., Fukui, N., Shingu, M., Nobunaga, M. & Watanabe, T. (1991) Arthritis And Rheumatism, 34, 343-350.
35 Felgenhauer, M., Kohl. J. & Ruker, F. (1990) Nucl. Acids Res., 18, 4927.
36 Florent, G., Lehman, D. & Putnam, F. W. (1974) Biochemistry, 13, 2482-2498.
37 Friedlander, R. M., Nussenzweig, M. C. & Leder, P. (1990) Nucl. Acids Res., 18, 4278.
38 Gawinowicz, M. A., Merlini, G., Birken, S., Osserman, E. F. & Kabat, E. A. (1991) J. Immunol., 147, 915-920.
39 Gillies, S. D., Dorai, H., Wesolowski, J., Majeau, G., Young, D., Boyd, J., Gardner, J. & James, K. (1989) Bio/Tech., 7, 799-804.
40 Goni, F. & Frangione, B. (1983) Proc. Nat. Acad. Sci. Usa, 80, 4837-4841.
41 Gorman, S. D., Clark, M. R., Routledge, E. G., Cobbold, S. P. & Waldmann, H. (1991) Proc. Natl. Acad. Sci. Usa, 88, 4181-4185.
42 Griffiths, A. D., Malmqvist, M., Marks, J. D., Bye, J. M., Embleton, M. J., Mccafferty, J., Baier, M., Holliger, K. P., Gorick, B. D., Hughes-Jones, N. C., Hoogenboom, H. R. & Winter, G. (1993) Embo J., 12, 725-734.
43 Grillot-Courvalin, C., Brouet, J.-C., Piller, F., Rassenti, L. Z., Labaume, S., Silverman, G. J., Silberstein, L. & Kipps, T. J. (1992) Eur. J. Immunol., 22, 1781-1788.
44 Guillaume, T., Rubinstein, D. B., Young, F., Tucker, L., Logtenberg, T., Schwartz, R. S. & Barrett, K. L. (1990) J. Immunol., 145, 1934-1945; Young, F., Tucker, L., Rubinstein, D., Guillaume, T., Andre-Schwartz, J., Barrett, K. J., Schwartz, R. S. & Logtenberg, T. (1990)
45 Harindranath, N., Goldfarb, I. S., Ikematsu, H., Burastero, S. E., Wilder, R. L., Notkins, A., & Casali, P. (1991) Int. Immunol., 3, 865-875.
46 Hillson, J. L., Oppliger, I. R., Sasso, E. H., Milner, E. C. B. & Wener, M. H. (1992) J. Immunol., 149, 3741-3752.
47 Hirabayashi. Y., Munakata, Y., Sasaki, T. & Sano, H. (1992) Nucl. Acids Res., 20, 2601.
48 Hoch, S. & Schwaber, J. (1987) J. Immunol., 139, 1689-1693.
49 Huang, C., Stewart, A. K., Schwartz, R. S. & Stollar, B. D. (1992) J. Clin. Invest., 89, 1331-1343.
50 Hughes-Jones, N. C., Bye. J. M., Beale, D. & Coadwell, J. (1990) Biochem. J., 268, 135-140.
51 Ikematsu, H., Harindranath, N., Ueki, Y., Notkins, A. L. & Casali, P. (1993) J. Immunol., 150, 1325-1337.
52 Ikematsu, H., Kasaian, M. T., Schettino, E. W. & Casali, P. (1993) J. Immunol., 151, 3604-3616.
53 Kelly, P. J., Pascual, V., Capra, J. D. & Lipsky, P. E. (1992) J. Immunol., 148, 1294-1301.
54 Kipps, T. J. & Duffy, S. F. (1991) J. Clin. Invest., 87, 2087-2096.
55 Kipps, T. J., Tomhave, E., Pratt, L. F., Duffy, S., Chen, P. P. & Carson, D. A. (1989) Proc. Natl. Acad. Sci. Usa, 86, 5913-5917.
56 Kishimoto, T., Okajima, H., Okumoto, T. & Taniguchi, M. (1989) Nucl. Acids Res., 17, 4385.
57 Knight, G. B., Agnello, V., Bonagura, V., Barnes, J. L., Panka, D. J. & Zhang, Q.-X. (1993) J. Exp. Med., 178, 1903-1911.
58 Kohler, H., Shimizu, A., Paul, C., Moore, V. & Putnam, F. W. (1970) Nature, 227, 1318-1320; Florent, G., Lehman, D. & Putnam, F. W. (1974) Biochemistry, 13, 2482-2498
59 Komori, S., Yamasaki, N., Shigeta, M., Isojima, S. & Watanabe, T. (1988) Clin. Exp. Immunol., 71, 508-516.
60 Kon, S., Levy. S. & Levy, R. (1987) Proc. Natl. Acad. Sci. Usa, 84, 5053-5057.
61 Kratzin, H., Altevogt, P., Ruban, E., Kortt, A., Staroscik, K. & Hilschmann, N. (1975) Z. Physiol. Chem., 356, 1337-1342; Kratzin, H., Altevogt, P., Kortt, A., Ruban, E. & Hilschmann, N. (1978) Z. Physiol. Chem., 359, 1717-1745.
62 Kudo. A., Ishihara, T., Nishimura, Y. & Watanabe, T. (1985) Gene, 33, 1B1-189.
63 Kunicki, T. J., Annis, D. S., Gorski, J. & Nugent, D. J. (1991) J. Autoimmunity, 4, 433-446.
64 Larrick, J. W., Wallace, E. F., Coloma, M. J., Bruderer, U., Lang, A. B. & Fry, K. E. (1992) Immunological Reviews, 130, 69-85.
65 Lehman, D. W. & Putnam, F. W. (1980) Proc. Nat. Acad. Sci. Usa, 77, 3239-3243.
66 Lewis, A. P., Lemon, S. M., Barber. K. A., Murphy, P., Parry, N. R., Peakman, T. C., Sims, M. J., Worden, J. & Crowe, J. S. (1993) J. Immunol., 151, 2829-2838.
67 Liu, V. Y. S., Low, T. L. K., Infante, A. & Putnam, F. W. (1976) Science, 193, 1017-1020.
68 Logtenberg, T., Young, F. M., Van Es, J., Gmelig-Meyling, F. H. J., Berman, J. E. & Alt, F. W. (1989) J. Autoimmunity, 2, 203-213.
69 Logtenberg, T., Young, F. M., Van Es, J. H., Gmelig-Meyling, F. H. J. & Alt, F. W. (1989) J. Exp. Med., 170, 1347-1355.
70 Manheimer-Lory, A., Katz, J. B., Pillinger, M., Ghossein, C., Smith, A. & Diamond, B. (1991) J. Exp. Med., 174, 1639-1652.
71 Mantovani, L., Wilder, R. L. & Casali, P. (1993) J. Immunol., 151, 473-488.
72 Mariette, X., Tsapis, A. & Brouet, J.-C. (1993) Eur. J. Immunol., 23, 846851.
73 Marks, J. D., Hoogenboom, H. R., Bonnert, T. P., Mccafferty, J., Griffiths, A. D. & Winter, G. (1991) J. Mol. Biol., 222, 581-597.

74 Meeker, T. C., Grimaldi, J., O'rourke, R., Loeb, J. Juliusson, G. & Einhorn, S. (1988) J. Immol., 141, 3994-3998.

75 Milili, M., Fougereau, M., Guglielmi, P. & Schiff, C. (1991) Mol. Immunol., 28, 753-761.

76 Moran, M. J., Andris, J. S., Matsumato, Y.-I., Capra, J. D. & Hersh, E. M. (1993) Mol. Immunol., 30, 1543-1551.

77 Mortari, F., Wang, J.-Y. & Schroeder, Jr., H. W. (1993) J. Immunol., 150, 1348-1357.

78 Newkirk, M. M., Gram, H., Heinrich, G. F., Ostberg, L., Capra, J. D. & Wasserman, R. L. (1988) J. Clin. Invest., 81, 1511-1518.

79 Newkirk, M. M., Mageed, R. A., Jefferis, R., Chen, P. P. & Capra, J. D. (1987) J. Exp. Med., 166, 550-564.

80 Nickerson, K. G., Berman, J., Glickman, E., Chess, L. & Alt, F. W. (1989) J. Exp. Med., 169, 1391-1403.

81 Olee, B. T., Lu, E. W., Huang, D.-F., Soto-Gil, R. W., Deftos, M., Kozin, F., Carson, D. A. & Chen, P. P. (1992) J. Exp. Med., 175, 831-842.

82 Pascual, V., Randen, I., Thompson, K., Sioud, M. Forre, O., Natvig, J. & Capra, J. D. (1990) J. Clin. Invest., 86, 1320-1328.

83 Pascual, V., Randen, I., Thompson, K., Sioud, M. Forre, O., Natvig, J. & Capra, J. D. (1990) J. Clin. Invest., 86, 1320-1328; Randen, I., Brown, D., Thompson, K. M., Hughes-Jones, N., Pascual, V., Victor, K., Capra, J. D., Forre, O. & Natvig, J. B. (1992)

84 Pascual, V., Victor, K., Lelsz, D., Spellerberg, M. B., Hamblin, T. J., Thompson, K. M., Randen, I., Natvig, J., Capra, J. D. & Stevenson, F. K. (1991) J. Immunol., 146, 4385-4391.

85 Pascual, V., Victor, K., Randen, I., Thompson, K., Steinitz, M., Forre, O., Fu, S.-M., Natvig, J. B. & Capra, J. D. (1992) Scand. J. Immunol., 36, 349-362.

86 Pascual, V., Victor. K., Spellerberg, M., Hamblin, T. J., Stevenson, F. K. & Capra. J. D. (1992) J. Immunol., 149, 2337-2344.

87 Ponstingl. H., Schwarz, J., Reichel, W. & Hilschmann, N. (1970) Z. Physiol. Chem., 351, 1591-1594.; Ponstingl, H. & Hilschmann, N. (1976) Z. Physiol. Chem., 357, 1571-1604.

88 Portolano, S., Mclachlan, S. M. & Rapoport, B. (1993) J. Immunol., 151, 2839-2851.

89 Portolano, S., Seto, P., Chazenbalk, G. D., Nagayama, Y., Mclachlan, S. M. & Rapoport, B. (1991) Biochem. Biophys. Res. Commun., 79, 372-377.

90 Pratt, L. F., Szubin, R., Carson, D. A. & Kipps, T. J. (1991) J. Immunol., 147, 2041-2046.

91 Press, E. M. & Hogg, N. M. (1970) Biochem. J., 117, 641-660.

92 Putnam, F. W., Shimizu, A., Paul., C., Shinoda, T. & Kohler, H. (1971) Ann. N.Y. Acad. Sci., 190, 83-103.

93 Putnam, F. W., Takahashi, N., Tetaert, D., Debuire, B. & Lin, L. C. (1981) Proc. Nat. Acad. Sci. Usa; 78, 6168-6172.; Takahashi, N., Tetaert, D., Debuire, B., Lin, L. & Putnam, F. W. (1982) Proc. Nat. Acad. Sci. Usa, 79, 2850-2854.

94 Raaphorst, F. M., Timmers, E., Kenter, M. J. H., Van Tol, M. J. D., Vossen, J. M. & Schuurman, R. K. B. (1992) Eur. J. Immunol., 22, 247-251.

95 Rabbitts, T. H., Bentley, D. L., Dunnick; W., Forster, A., Matthyssens, G. & Milstein, C. (1980) Cold Spring Harb. Symp. Quanti. Biol., 45, 867-878; Matthyssens, G. & Rabbitts, T. H. (1980) Proc. Nat. Acad. Sci. Usa, 77, 6561-6565.

96 Randen, I., Pascual, V., Victor, K., Thompson, K. M., Forre, O., Capra, J. D. & Natvig, J. B. (1993) Eur. J. Immunol, 23, 1220-1225.

97 Rassenti, L. Z. & Kipps, T. J. (1993) J. Exp. Med., 177, 1039-1046.

98 Reidl, L. S., Friedman, D. F., Goldman, J., Hardy, R. R., Jefferies, L. C. & Silberstein, L. E. (1991) J. Immunol., 147, 3623-3631.

99 Roudier, J., Silverman, G. J., Chen, P. P., Carson, D. A. & Kipps, T. J. (1990) J. Immunol., 144, 1526-1530.

100 Sanz, I., Casali, P., Thomas, J. W., Notkins, A. L. & Capra, J. D. (1989) J. Immunol., 142, 4054-4061.

101 Sanz. I., Dang. H., Takei, M., Talal, N. & Capra, J. D. (1989) J. Immunol., 142, 883-887.

102 Schmidt, W. E., Jung, H-.D., Palm, W. & Hilschmann, N. (1983) Z. Physiol. Chem., 364, 713-747.

103 Schroeder, H. W., Jr. & Wang, J. Y. (1990) Proc. Natl. Acad. Sci. Usa, 87, 6146-6150.

104. Schroeder, H. W., Jr., Hillson, J. L. & Perlmutter, R. M. (1987) Science, 238, 791-793.

105 Schroeder, H. W., Jr., Hillson, J. L. & Perlmutter, R. M. (1987) Science, 238, 791-793; Chen, P. P., Liu, M.-F., Glass, C. A., Sinha, S., Kipps, T. J. & Carson, D. A. (1989) Arthritis & Rheumatism, 32, 72-76.

106 Schroeder, H. W., Jr., Hillson, J. L. & Perlmutter, R. M. (1987) Science, 238, 791-793; Chen, P. P., Liu, M.-F., Sinha, S. & Carson, D. A. (1988) Arth. Rheum., 31, 1429-1431.

107 Schutte, M. E., Ebeling, S. B., Akkermans, K. E., Gmelig-Meyling, F. H. & Logtenberg, T. (1991) Eur. J. Immunol., 21, 1115-1121.

108 Schutte, M. E., Ebeling, S. B., Akkermans, K. E., Gmelig-Meyling, F. H. J. & Logtenberg, T. (1991) Eur. J. Immunol., 21, 1115-1121.

109 Settmacher, U., Jahn, S., Siegel, P., Von Baehr, R. & Hansen, A. (1993) Mol. Immunol., 30, 953-954.

110 Shen, A., Humphries, C., Tucker, P. & Blattner, F. (1987) Proc. Natl. Acad. Sci. Usa, 84, 8563-8567.

111 Shimizu, A., Nussenzweig, M. C., Mizuta, T.-R., Leder, P. & Honjo, T. (1989) Proc. Natl. Acad. Sci. Usa, 86, 8020-8023.

112 Shin, E. K., Matsuda, F., Fujikura, J., Akamizu, T., Sugawa, H., Mori, T. & Honjo, T. (1993) Eur. J. Immunol., 23, 2365-2367.

113 Silberstein, L. E., Litwin, S. & Carmack, C. E. (1989) J. Exp. Med., 169, 1631-1643.

114 Singal, D. P., Frame, B., Joseph, S., Blajchman, M. A. & Leber, B. F. (1993) Immunogenet., 38, 242.

115 Spatz, L. A., Wong, K. K., Williams, M., Desai, R., Golier, J., Berman, J. E., Alt, F. W. & Latov, N. (1990) J. Immunol., 144, 2821-2828.

116 Steiner, L. A., Garcia-Pardo. A. & Margolies. M. N. (1979) Biochemistry, 18, 4068-4080.

117 Stewart, A. K., Huang, C., Stollar, B. D. & Schwartz, R. S. (1993) J. Exp. Med., 177, 409-418.

118 Thomas, J. W. (1993) J. Immunol., 150, 1375-1382.

119 Torano, A. & Putnam, F. W. (1978) Proc. Nat. Acad. Sci. Usa, 75, 966-969.

120 Van Der Heijden, R. W. J., Bunschoten, H., Pascual, V., Uytdehaag, F. G. C. M., Osterhaus. A. D. M. E. & Capra, J. D. (1990) J. Immunol., 144, 2835-2839.

121 Van Der Stoep, N., Van Der Linden, J. & Logtenberg. T. (1993) J. Exp. Med., 177, 99-107.

122 Van Es, J. H., Gmelig-Meyling, F. H. J. & Logtenberg, T. (1992) Eur. J. Immunol., 22, 2761-2764.

123 Varade, W. S., Marin, E., Kittelberger, A. M. & Insel, R. A. (1993) J. Immunol., 150, 4985-4995.

124 Victor, K. D., Pascual, V., Lefvert, A. K. & Capra, J. D. (1992) Mol. Immunol., 29, 1501-1506.
125 Victor, K. D., Pascual, V., Williams, C. L., Lennon, V. A. & Capra, J. D. (1992) Eur. J. Immunol., 22, 2231-2236.
126 Watanabe, S., Barnikol, H. U., Horn, J., Bertram, J. & Hilschmann, N. (1973) Z. Physiol. Chem., 354, 1505-1509.
127 Weng, N.-P., Yu-Lee, L.-Y., Sanz, I., Patten, B. M. & Marcus, D. M. (1992) J. Immunol., 149, 2518-2529.
128 White, M. B., Word, C. J., Humphries, C. G., Blattner, F. R. & Tucker, P. W. (1990) Mol. Cell. Biol., 10, 3690-3699.
129 Winkler, T. H., Fehr, H. & Kalden, J. R. (1992) Eur. J. Immunol., 22, 1719-1728.
130 Yago, K., Zenita, K., Ohwaki, I., Harada, Y., Nozawa, S., Tsukazaki, K., Iwamori, M., Endo, N., Yasuda, N., Okuma, M. & Kannagi, R. (1993) Mol. Immunol., 30, 1481-1489.
131 Zelenetz, A. D., Chen, T. T. & Levy, R. (1992) J. Exp. Med., 176, 1137-1148.

B. References of Germline Sequences

References of Human Germline Kappa Sequences

1 Cox, J. P. L., Tomlinson, I. M. & Winter, G. (1994) Eur. J. Immunol., 24, 827-836.
2 Huber, C., & Al. (1993) Eur. J. Immunol., 23, 2868.
3 Klobeck. H. G., Bornkammm, G. W., Combriato, G., Mocikat, R., Pohlenz, H. D. & Zachau, H. G. (1985) Nucl. Acids Res., 13, 6515-6529.
4 Lautner-Rieske, A., Huber, C., Meindl, A., Pargent, W., Schäble, K. F., Thiebe, R., Zocher. I. & Zachau, H. G. (1992) Eur. J. Immunol. 22, 1023.
5 Lorenz, W., Schäble, K. F., Thiebe, R., Stavnezer, J. & Zachau, H. G. (1988) Mol. Immunol., 25, 479.
6 Pargent, W., Meindl, A., Thiebe, R., Mitzel, S. & Zachau, H. G. (1991) Eur. J. Immunol., 21, 1821-1827.
7 Pech, M. & Zachau, H. G. (1984) Nuc. Acids Res., 12, 9229-9236.
8 Pech, M., Jaenichen, H.-R., Pohlenz, H.-D., Neumaier, P. S., Klobeck, H.-G. & Zachau, H. G. (1984) J. Mol. Biol., 176, 189-204.
9 Scott, M. G., Crimmins, D. L., Mccourt, D. W., Chung, G., Schable, K. F., Thiebe, R., Quenzel, E.-M., Zachau, H. G. & Nahm, M. H. (1991) J. Immunol., 147, 4007-4013.
10 Stavnezer, J., Kekish, O., Batter, D., Grenier, J., Balazs, I., Henderson, E. & Zegers, B. J. M. (1985) Nucl. Acids Res., 13, 3495-3514.
11 Straubinger, B., Huber, E., Lorenz, W., Osterholzer, E., Pargent, W., Pech, M., Pohlenz, H.-D., Zimmer, F.-J. & Zachau, H. G. (1988) J. Mol. Biol., 199, 23-34.
12 Straubinger, B., Thiebe, R., Huber, C., Osterholzer, E. & Zachau, H. G. (1988) Biol. Chem. Hoppe-Seyer, 369, 601-607.

References of Human Germline Lambda Sequences

1 Williams, S. C. & Winter, G. (1993) Eur. J. Immunol., 23, 1456-1461.
2 Siminovitch, K. A., Misener, V., Kwong, P. C., Song, Q.-L. & Chen, P. P. (1989) J. Clin. Invest., 84, 1675-1678.
3 Brockly, F., Alexandre, D., Chuchana, P., Huck, S., Lefranc, G. & Lefranc, M.-P. (1989) Nuc. Acids. Res., 17, 3976.
4 Daley, M. D., Peng, H.-Q., Misener, V., Liu, X.-Y., Chen, P. P. & Siminovitch, K. A. (1992) Mol. Immunol., 29, 1515-1518.
5 Deftos, M., Soto-Gil, R., Quan, M., Olee, T. & Chen, P. P. (1994) Scand. J. Immunol., 39, 95.
6 Stiernholm, N. B. J., Kuzniar, B. & Berinstein, N. L. (1994) J. Immunol., 152, 4969-4975.
7 Combriato, G. & Klobeck, H. G. (1991) Eur. J. Immunol., 21, 1513-1522.
8 Anderson, M. L. M., Szajnert M. F., Kaplan, J. C., Mccoll, L. & Young, B. D. (1984) Nuc. Acids Res., 12, 6647-6661.

References of Human Germline Heavy Chain Sequences

1 Adderson, E. E., Azmi, F. H., Wilson, P. M., Shackelford, P. G. & Carroll, W. L. (1993) J. Immunol., 151, 800-809.
2 Andris. J. S., Brodeur, B. R. & Capra. J. D. (1993) Mol. Immunol., 30, 1601-1616.
3 Berman, J. E., Mellis, S. J., Pollock, R., Smith, C. L., Suh, H., Heinke, B., Kowal, C., Surti, U., Chess, L., Cantor. C. R & Alt F. W. (1988) Embo J., 7, 727-738.
4 Buluwela, L. & Rabbitts, T. H. (1988) Eur. J. Immunol., 18, 1843-1845.; Buluwela, L., Albertson. D. G., Sherrington, P., Rabbitts. P. H., Spurr, N. & Rabbitts. T. H. (1988) Embo J., 7, 2003-2010.
5 Chen. P. P., Liu. M.-F., Sinha, S. & Carson, D. A. (1988) Arth. Rheum., 31, 1429-1431.
6 Chen, P. P., Liu, M.-F., Glass, C. A., Sinha, S., Kipps, T. J. & Carson, D. A. (1989) Arthritis & Rheumatism, 32, 72-76.
7 Cook, G. P. et al. (1994) Nature Genetics 7, 162-168.
8 Haino, M. et al., (1994). J. Biol. Chem. 269, 2619-2626
9 Humphries, C. G., Shen, A., Kuziel, W. A. Capra, J. D., Blattner, F. R. & Tucker, P. W. (1988) Nature, 331, 446-449.
10 Kodaira, M., Kinashi, T., Umemura, I., Matsuda, F., Noma, T., Ono, Y. & Honjo, T. (1986) J. Mol. Biol., 190, 529-541.
11 Lee, K. H., Matsuda, F., Kinashi, T., Kodaira, M. & Honjo, T. (1987) J. Mol. Biol., 195, 761-768.
12 Matsuda, F., Lee, K. H., Nakai, S., Sato, T., Kodaira, M., Zong, S. Q., Ohno, H., Fukuhara. S. & Honjo, T. (1988) Embo J., 7, 1047-1051.
13 Matsuda, F., Shin, E. K., Hirabayashi, Y., Nagaoka, H., Yoshida, M. C. Zong, S. Q. & Honjo, T. (1990) Embo J., 9, 2501-2506.
14 Matsuda, F., Shin, E. K., Nagaoka, H., Matsumura, R., Haino, M., Fukita, Y., Taka-Ishi, S., Imai, T., Riley, J. H., Anand, R. &, Al. (1993) Nature Genet. 3, 88-94
15 Nagaoka, H., Ozawa, K., Matsuda, F., Hayashida, H., Matsumura, R., Haino, M., Shin, E. K., Fukita, Y., Imai, T., Anand, R., Yokoyama, K., Eki, T., Soeda, E. & Honjo, T. (1993). (Temporal)
16 Rechavi, G., Bienz, B., Ram, D., Ben-Neriah, Y., Cohen, J. B., Zakut. R. & Givol, D. (1982) Proc. Nat. Acad. Sci. Usa, 79, 4405-4409.
17 Sanz, I., Kelly, P., Williams, C., Scholl, S., Tucker, P. & Capra, J. D. (1989) Embo J., 8, 3741-3748.
18 Shin, E. K., Matsuda, F., Fujikura, J., Akamizu. T., Sugawa, H., Mori, T. & Honjo, T. (1993) Eur. J. Immunol., 23, 2365-2367.
19 Tomlinson, Im., Walter, G., Marks, Jd., Llewelyn, Mb. & Winter. G. (1992) J. Mol. Biol. 227, 776-798.
20 Van Der Maarel, S., Van Dijk, K. W., Alexander, C. M., Sasso, E. H., Bull, A. & Milner. E. C. B. (1993) J. Immunol., 150, 2858-2868.
21 Van Dijk, K. W., Mortari, F., Kirkham, P. M., Schroeder, Jr., H. W. & Milner, E. C. B. (1993) Eur. J. Immunol., 23, 832-839.
22 Van Es. J. H., Aanstool, H., Gmelig-Meyling, F. H. J., Derksen, R. H. W. M. & Logtenberg, T. (1992) J. Immunol., 149, 2234-2240.
23 Weng, N.-P., Snyder, J. G., Yu-Lee, L.-Y. & Marcus, D. M. (1992) Eur. J. Immunol., 22, 1075-1082.
24 Winkler, T. H., Fehr, H. & Kalden, J. R. (1992) Eur. J. Immunol., 22, 1719-1728.
25 Olee, T., Yang, P. M., Siminovitch, K. A., Olsen, N. J., Hillson, J. L., Wu, J., Kozin, F., Carson, D. A. E. Chen, P. P. (1991) J. Clin. Invest. 88, 193-203.

26 Chen, P. P. & Yang, P. M. (1990) Scand. J. Immunol. 31, 593-599.

27 Tomlinson, M., Walter, G., Cook & Winter, G. (Unpublished)

The invention claimed is:

1. A method of identifying at least one gene encoding one or more human antibodies or antibody fragments having an optimized affinity, comprising the steps of:

(a) expressing in a host cell a collection of genes encoding human antibodies or antibody fragments from a first library of genes, wherein said first library of genes comprises nucleic acids encoding a plurality of human VH and VL amino acid sequences, wherein each of said VH and VL amino acid sequences comprises four human consensus sequence framework regions interspaced by three complementary determining regions CDR1, CDR2, and CDR3, and wherein each of said nucleic acids encoding said VH and VL amino acid sequences contains DNA cleavage sites at the boundary between each consensus framework region and CDR region, wherein each of said cleavage sites is unique within said nucleic acid and is common to all nucleic acid sequences of said library at corresponding positions, wherein said first library of genes comprises nucleic acids encoding the human consensus sequence framework regions selected from the group consisting of VH1A (SEQ ID NO:56), VH1B (SEQ ID NO: 58), VH2 (SEQ ID NO: 60), VH3 (SEQ ID NO: 62), VH4 (SEQ ID NO: 64), VH5 (SEQ ID NO: 66), and VH6 (SEQ ID NO: 68);

(b) isolating a plurality of human antibodies or antibody fragments that specifically bind an antigen by screening said collection of antibodies or antibody fragments against said antigen;

(c) obtaining the genes encoding said plurality of human antibodies or antibody fragments isolated in step (b);

(d) replacing one or more sub-sequences encoding a complementarity determining region of each of said genes obtained in step (c) with a pre-built library of compatible sub-sequences encoding complementarity determining regions to prepare a second library of genes, wherein said replacing step is carried out without determining the sequences of the nucleic acids obtained in step (c);

(e) expressing in a host cell a collection of human antibodies or antibody fragments from said second, library of genes and screening said collection of human antibodies or antibody fragments against said antigen;

(f) identifying one or more antibodies or antibody fragments that specifically bind said antigen and that have an optimized affinity compared to the antibodies or antibody fragments identified in step (b).

2. The method according to claim 1, wherein said at least one CDR is a VH or VL CDR1.

3. The method according to claim 1, wherein said at least one CDR is a VH or VL CDR2.

4. The method according to claim 1, wherein said at least one CDR is a VH or VL CDR3.

5. The method according to claim 1, wherein said first library of genes comprises nucleic acids encoding the human consensus sequence framework regions selected from the group consisting of VK1 (SEQ ID NO:42), VK2 (SEQ ID NO: 44), VK3 (SEQ ID NO: 46), and VK4 (SEQ ID NO: 48).

6. The method according to claim 1, wherein said first library of genes comprises nucleic acids encoding, the human consensus sequence framework regions selected from the group consisting of Vλ1 (SEQ ID NO:50), Vλ2 (SEQ ID NO: 52), and Vλ3 (SEQ ID NO: 54).

7. The method according to claim 1, wherein the nucleic acid sequences in said first library of genes that encode said human antibodies or antibody fragments are adapted to the codon usage of said host cell.

8. The method according to claim 1, wherein said host cell is *E coli*.

* * * * *